(12) United States Patent
Jordis et al.

(10) Patent No.: US 7,166,588 B2
(45) Date of Patent: Jan. 23, 2007

(54) DERIVATIVES AND ANALOGS OF GALANTHAMINE

(75) Inventors: Ulrich Jordis, Vienna (AT); Johannes Frohlich, Dornbach im Wienerwald (AT); Matthias Treu, Vienna (AT); Manfred Hirnschall, Vienna (AT); Laszlo Czollner, Ebenfurth (AT); Beate Kälz, Steinbrunn (AT); Stefan Welzig, Vienna (AT)

(73) Assignee: Sanochemia Pharmazeutika Aktiengesellschaft, Vienna (AT)

( * ) Notice: Subject to any disclaimer, the term of this patent is extended or adjusted under 35 U.S.C. 154(b) by 585 days.

(21) Appl. No.: 09/980,025

(22) PCT Filed: May 22, 2001

(86) PCT No.: PCT/AT01/00082

§ 371 (c)(1),
(2), (4) Date: Mar. 18, 2002

(87) PCT Pub. No.: WO01/74820

PCT Pub. Date: Nov. 10, 2001

(65) Prior Publication Data

US 2003/0199493 A1    Oct. 23, 2003

(30) Foreign Application Priority Data

Mar. 31, 2000  (AT) ................................ A 546/2000
Feb. 15, 2001  (AT) ................................ A 238/2001

(51) Int. Cl.
A61K 31/55    (2006.01)
(52) U.S. Cl. ........................ 514/215; 514/216; 540/581
(58) Field of Classification Search ................ 514/215, 514/216; 540/581
See application file for complete search history.

(56) References Cited

U.S. PATENT DOCUMENTS

| 3,947,445 A | 3/1976 | Henry et al. |
| 5,153,193 A | 10/1992 | Flanagan et al. |
| 5,336,675 A | 8/1994 | Snorrason |
| 5,428,159 A | 6/1995 | Shieh et al. |
| 6,043,359 A | 3/2000 | Czollner et al. |
| 6,369,238 B1 | 4/2002 | Czollner et al. |
| 6,407,229 B1 | 6/2002 | Czollner et al. |
| 6,638,925 B1 | 10/2003 | Czollner et al. |
| 2004/0067974 A1 | 4/2004 | Czollner et al. |

FOREIGN PATENT DOCUMENTS

| AT | 401 058 B | 6/1996 |
| EP | 0 345 808 A1 | 12/1989 |
| EP | 0 236 684 B1 | 5/1992 |
| EP | 0 648 771 A1 | 4/1995 |
| EP | 0 653 427 A1 | 5/1995 |
| NL | 8800350 | 9/1989 |
| WO | 88/08708 | 11/1988 |
| WO | WO 95/27715 | 10/1995 |
| WO | WO 96/12692 | 5/1996 |
| WO | 97/11078 | 3/1997 |
| WO | WO 97/40049 | 10/1997 |
| WO | WO 00/32199 | 6/2000 |
| WO | WO 2005/030333 A2 | 4/2005 |

OTHER PUBLICATIONS

Pokorna, L et al 'Capillary zone electrophoresis determination of galanthamine in biological fluids and pharmaceutical preparatives: Experimental design and artificial neural network optimization' Electrophoresis 199, 20, 1993-1997.*
Poschalko, A et al 'Synthesis of (+)-6H-benzofuro[3a,3,2,ef][3]benazepine: an unnatural analog of (-)galanthamine' Tetrahedron 58 (2002) 1513-1518.*
Pilger,C et al 'Accurate prediction of the bound conformation of galanthamine in the active site of Torpedo californica acetylcholinesterase using molecular docking' J. Molecular Graphics and Modelling 19, 288-296, 2001.*
Coyle, Galanthamine, a cholinesterase inhibitor that allosterically modulates nicotinic receptors: effects on the course of Alzheimer's disease, Society of Biological Pysychiatry, (2001), 49:289-299.*
Sramek, Review of the acetylcholinesterase inhibitor galanthamine, Exp. Opin. Invest. Drugs (2000) 9(10), 2393-2402.*
R. Roques et al., "Structure of Norgalanthamine Hydrochloride", Acta Crystallogr., Sect. B (1980), vol. B36, No. 7, pp. 1589-1593 XP001009771.
Jaume Bastida et al., "Narcissus Alkaloids. Part 19, Alkaloids from Narcissus Leonensis", Phytochemistry, (1993), vol. 34, No. 6, pp. 1656-1658, XP001009775.
P. Remuzon, "Fluoronaphthyridines as Antibacterial Agents", J. Med. Chem., 1992, vol. 35, pp. 2898-2909.

* cited by examiner

Primary Examiner—Amelia A. Owens
(74) Attorney, Agent, or Firm—Popovich, Wiles & O'Connell, P.A.

(57) ABSTRACT

New compounds of general formula I

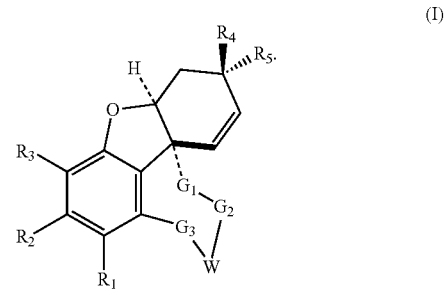

(I)

14 Claims, No Drawings

DERIVATIVES AND ANALOGS OF GALANTHAMINE

This invention relates to new substituted benzofuran derivatives, process for their production, their salts as well as the use for a) Treatment of Alzheimer's disease,
b) treatment of Parkinson's disease,
c) treatment of Huntington's disease (chorea),
d) treatment of multiple sclerosis,
e) treatment of amyotrophic lateral sclerosis,
f) treatment of epilepsy,
g) treatment of the sequelae of stroke,
h) treatment of the sequelae of cranio-cerebral trauma,
i) treatment and prophylaxis of the sequelae of diffuse oxygen and nutrient deficiency in the brain, as they are observed after hypoxia, anoxia, asphyxia, cardiac arrest, poisonings, as well as in the case of complications in difficult deliveries of infants or in the case of anesthesia,
j) especially also prophylactic treatment of apoptotic degeneration in neurons that were or are damaged by local radiotherapy or chemotherapy of brain tumors, and
k) treatment of bacterial meningitis and
l) treatment of diseases with apoptotic components, especially in the wake of an amyloid-associated cell degeneration,
m) treatment of diabetes mellitus, especially if the disease is accompanied by amyloid degeneration of islet cells.

The new derivatives and analogs of galanthamine according to the invention increase the muscular power and the perseverance of Alzheimer patients.

The new compounds according to the invention are those of general formula I

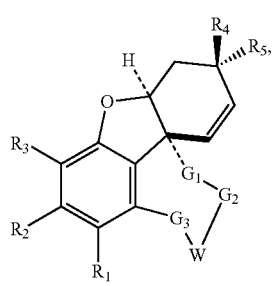

(I)

in which the substituents have the meanings that are explained below:

$R_1$ and $R_2$ are the same or different and mean:

a) hydrogen, F, Cl, Br, I, CN, NC, OH, SH, $NO_2$, $SO_3H$, $PO_3H$, $NH_2$, $CF_3$, $OSO_2(CH_2)_nCF_3$, in which n is equal to 0, 1 or 2), $OSO_2$-aryl, $OSO_2$-vinyl or $OSO_2$-ethinyl;

b) a low ($C_1$–$C_6$), optionally branched, optionally substituted (Ar)alkyl, (Ar)alkoxy group, cycloalkyl or cycloalkyloxy group;

c) an amino group, which optionally is substituted by one or two identical or different low ($C_1$–$C_6$), optionally branched, optionally substituted (Ar)alkyl or (Ar)alkylcarbonyl or (Ar)alkoxycarbonyl groups or an amino group which exhibits a cyclic substitution in the form of a pyrrolidine, piperidine, morpholine, thiomorpholine, piperazine, homopiperazine radical that is substituted in any case, d) a COOH, COO(Ar)alkyl, CO-amino, with the definition of the amino group as in the last paragraph under c) or a CHOH(Ar)alkyl group;

e) a —$(CH_2)nX$ (in which X=Br, Cl, F or I), —$(CH_2)_nOH$, —$(CH_2)_nCHO$, —$(CH_2)_nCOCH$, —$(CH_2)_nCN$, —$(CH_2)_nNC$, —$(CH_2)_nCOalkyl$, —$(CH_2)_nCOaryl$ group, in which n means 1–4;

f) a —$(CH_2)_n$vinyl, $(CH_2)_n$ethinyl group, or $(CH_2)_n$cycloalkyl group in which n describes 0, 1 or 2, and cycloalkyl describes an aliphatic ring of the ring size of 3–7;

g) a $C_3$–$C_6$-substituted alkenyl group (optionally substituted with H, F, Br, Cl, CN, $CO_2$alkyl, COalkyl, COaryl);

h) a $C_3$–$C_6$-substituted alkinyl group (optionally substituted with H, F, Br, Cl, CN, $CO_2$alkyl, Coalkyl, Coaryl); or i) $R^1$ and $R^2$ together mean —CH=CH—CH=CH—, —$O(CH_2)_nO$— (n=1 to 3), —CH=CH-A1 or —CH2—CH2-A1, whereby NH, O or S can stand for A1;

$R_3$ has the same meaning as $R_1$, especially OH and $OCH_3$ and in addition $R_2$ and $R_3$ together mean —$A_2(CH_2)_n A_2$, in which n is 1 to 3 and $A_2$ means two identical or different radicals that are selected from NH, O or S;

$R_4$ and $R_5$ are either a) both hydrogen, or
b) a combination of hydrogen or an (Ar)alkyl, (Ar)alkenyl or (Ar)alkinyl group with i) $OR_6$, in which $R_6$ means hydrogen, a low ($C_1$–$C_{10}$, optionally branched or substituted) alkyl group or cycloalkyl group, a $C_3$–$C_{10}$ substituted silyl group (for example, triethylsilyl, trimethylsilyl, t-butyldimethylsilyl or dimethylphenylsilyl), a $C_2$–$C_{10}$ α-alkoxyalkyl group, for example tetrahydropyranyl, tetrahydrofuranyl, methoxymethyl, ethoxymethyl, (2-methoxypropyl), ethoxyethyl, phenoxymethyl or (1-phenoxyethyl);

ii) O—CS—$NHR_6$ (thiourethane), in which $R_6$ has the above-mentioned meaning iii) O—CO—$NHR_7$ with the meaning below:

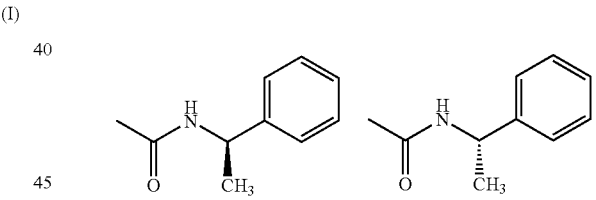

iv) O—CO—$HR_6$, in which $R_6$ has the above-mentioned meaning, especially ester with the substitution pattern of amino acids (both enantiomers), such as

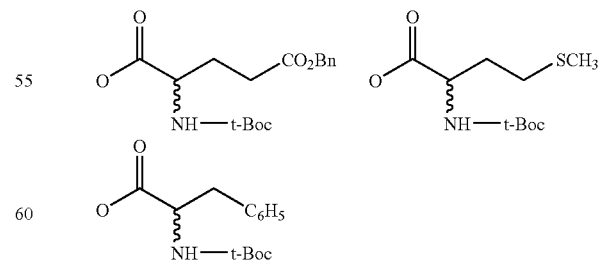

v) $NR_7R_7$, in which two substituents $R_7$ are the same or different and mean hydrogen, a low ($C_1$–$C_4$), optionally branched or cyclic alkyl group, or the two substituents $R_7$ together are —$(CH_2)_{n-}$, in which n is 3 to 5;

vi) NH—COR$_6$ (amide), in which R$_6$ has the above-mentioned meaning;

vii) S—R$_6$, in which R$_6$ is hydrogen or a low (C$_1$–C$_{10}$), optionally branched, optionally substituted (Ar)alkyl group, and in which R$_6$ has the above-mentioned meaning;

viii) SO$_n$R$_8$, in which n is 0, 1 or 2, in which R$_8$ is a (C$_1$–C$_{10}$), optionally branched or cyclic, optionally substituted (Ar)alkyl group.

If R$_4$ is hydrogen, R$_5$ can be OH, CN, CO$_2$-alkyl, CON-R$_a$R$_b$, in which R$_a$ is hydrogen, a low (C$_1$–C$_6$), optionally branched, cyclic alkyl group that is substituted in any case, and R$_b$ is hydrogen, a low (C$_1$–C$_6$), optionally branched or substituted alkyl group, or R$_a$+R$_b$ together are —(CH$_2$)$_n$—, in which n means 2 to 6, or —(CH$_2$)$_n$E(CH$_2$)$_n$—, in which E is the same as NH, N-alkyl, O, or S, and n is 0 to 5, aryl (phenyl or naphthyl), 6-π heterocycle, (such as, for example, imidazolyl, oxazolyl, isoxazolyl, triazolyl, tetrazolyl, oxadiazolyl, thiadiazolyl, pyridazinyl, pyrimidinyl, pyrazinyl and substituted variants thereof), or imidazolinyl, thiazolinyl or oxazolinyl.

For the case that R$_5$ is not hydrogen, R$_4$ can also be OH.

R$_4$ and R$_5$ together can be carbonyl (=O), hydrazone (=N—NH—R$_9$, =N—NR$_9$R$_{10}$ or oxime (=N—OR$_{10}$), in which R$_9$ is hydrogen, a low (C$_1$–C$_6$), optionally branched or cyclic, optionally substituted (Ar)alkyl- or (Ar)alkylcarbonyl-, (Ar)alkylcarbonyloxy group or a sulfonic acid group, such as tosyl or mesyl, and R$_{10}$ is hydrogen, a low (C$_1$–C$_6$), optionally branched or cyclic, optionally substituted (Ar) alkyl- or (Ar)alkylcarbonyl group, a sulfonic acid group, such as a tosyl group or mesyl group.

R$_4$ and R$_5$ together can be substituents of the type

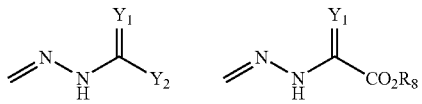

in which Y$_1$, Y$_2$ are the same or different and mean O, S, NH or N—R$_9$ (free valences are in any case hydrogen), or for the case that Y$_1$ is NH and Y$_2$ is N—R$_9$, R$_4$ and R$_5$ can be connected by —(CH$_2$)$_n$— (n=2, 3, or 4).

G$_1$: —(CH$_2$)$_x$—, in which x is 1 or 2;

G$_2$: —(CH$_2$)$_y$—, in which y is 0 to 2;

G$_3$: —(CH$_2$)$_z$—, in which z is 0 to 3, is carbonyl or thiocarbonyl, provided that x+y+z together are at least 2 and at most 4 or in which G$_3$ means —CH(OH)— or —C(OH)=.

G$_1$ and G$_2$ together or separately can also mean:

—C(R$_{11}$ R$_{12}$)—, in which R$_{11}$ and R$_{12}$ mean hydrogen, OH, a low, optionally branched or cyclic, optionally substituted (Ar)alkyl, aryl, (Ar)alkyloxy or aryloxy group or together an alkylspiro group (C$_3$–C$_7$ spiro ring)

or G$_1$ and G$_2$ together mean

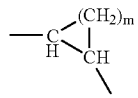

in which m is 1 to 7.

W can have the following meanings:

a) CR$_{13}$R$_{14}$, in which R$_{13}$ means hydrogen and R$_{14}$ means the radicals —(CH$_2$)$_n$NR$_7$R$_7$ or —CO—NR$_7$R$_7$ or —COOR$_7$, whereby n can assume the values 0 to 2 and R$_7$ is as defined above, or R$_7$R$_7$ form a ring by —(CH$_2$)$_n$ (in which n is 3 to 5), whereby substituents R$_{13}$ and R$_{14}$ can be exchanged.

b) N-Phenyl (whereby the phenyl radical optionally is substituted with fluorine, bromine, chlorine, (C$_1$–C$_4$) alkyl, CO$_2$ alkyl, CN, CONH$_2$, or alkoxy) or N-thien-2 or 3-yl, or N-fur-2 or 3-yl or N-1,3,5-triazinyl, whereby the triazine radical can then be substituted with Cl, OR$_6$ or NR$_7$R$_7$, and R$_6$ or R$_7$ have the meaning indicated above;

c) One of the substituents that is presented below

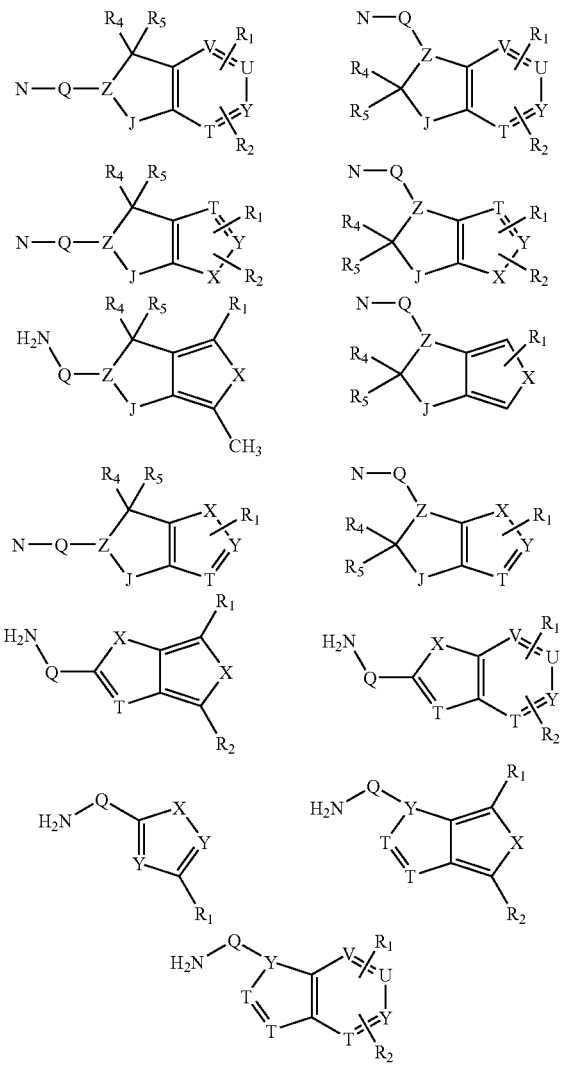

Y = CH or N
T = CH or N
U = CH or N
V = CH or N
X = NR$_6$, O or S
Z = CH or N in which I means no bond or —(CH$_2$)$_n$—, with n=0 to 3, carbonyl, thiocarbonyl O, S, —SO— or SO$_2$, R$_6$ has the meaning that is indicated above, and in addition, Q is defined as —$(CH_2)_n$-M*—$(CH_2)_m$, whereby n=0 to 4 and m=0 to 4 and M* represents alkinyl, alkenyl, disubstituted phenyl, disubstituted thiophene, disubstituted furan, disubstituted pyrazine, disubstituted pyridazine, a peptide spacer L or a heterocyclic spacer HS, whereby this definition of the spacer is defined in addition by the following graphic formulas

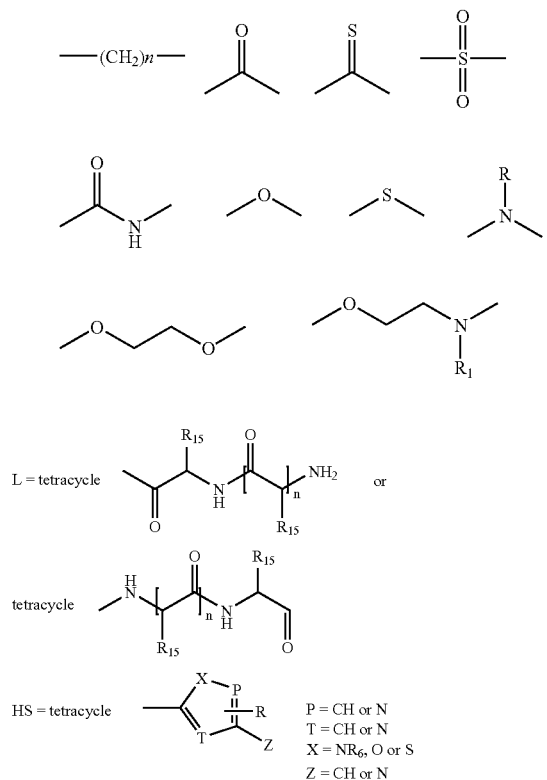

in which $R_{15}$ means the side chain of D-, L-, D, L-aminoacids or unnatural amino acids, and for the case of n>1, $R_{15}$ in the individual radicals in each case means the same or a different side chain of D-, L-, D, L-amino acids or unnatural amino acids, whereby these formulas are defined such that atom N in addition to Q is connected in each case to G2 and G3 of formula I;

d) W can also be connected to a tricyclic substituent (Tr) via spacer Q, whereby the tricyclic substituents are defined by the following graphic formulas,

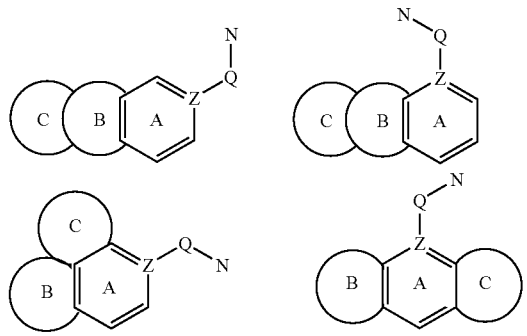

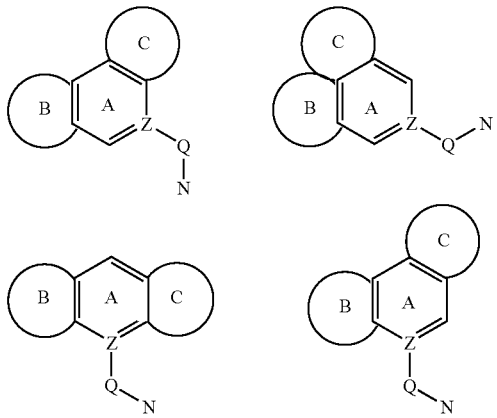

and these formulas are defined such that atom N in addition to Q is connected in each case with G2 and G3 of formula I, and Q and Z have the meaning indicated under c).

The tricyclic substituent (Tr) means a tricyclic ring system, with at least one heterocyclic ring as a ring component and a binding site to a carbon atom of an anellated benzene ring thereof, whereby Tr optionally is substituted at least in one place, in which ring A is an optionally substituted benzene ring and one of rings B and C is an optionally substituted heterocyclic ring and the other can contain a substituted 4- to 14-membered, preferably a 5- to 7-membered ring, which can contain one or more heteroatoms in the ring. The benzene ring is optionally further substituted in at least one place, whereby these substituents can be halogens, such as fluorine and chlorine, halo-$C_1$–$C_3$ alkyl groups, such as trifluoromethyl, $C_1$–$C_3$ alkyl groups, such as methyl, $C_1$–$C_3$ alkoxy groups, such as methoxy, and the hydroxy group, whereby halogens, such as fluorine, are preferred.

Heterocyclic ring B or C that is optionally substituted is, for example, a 4- to 14-membered ring, preferably a 5- to 7-membered ring. At least one heteroatom of the heterocyclic ring (1 to 3 heteroatoms are possible) can be nitrogen, oxygen, sulfur. In particular, rings B and C are pyridine, pyrazine, pyrimidine, imidazole, furan, thiophene, pyrrolidine, piperidine, hexamethylethylenimine, tetrahydrofuran, piperazine, morpholine and thiomorpholine, whereby 5- to 7-membered nonaromatic rings, which can have one or two heteroatoms that are the same or different, are preferred.

Ring B or C can also be a non-aromatic, heterocyclic ring that contains 1–3 heteroatoms, such as nitrogen, oxygen or sulfur, and nonaromatic heterocyclic rings with a nitrogen atom and another heteroatom, which is nitrogen, oxygen or sulfur.

"5- to 8-membered rings B or C" are 5- to 8-membered heterocyclic or alicyclic rings or carbon rings, which are substituted at least in one place. These 5- to 8-membered carbon rings can be a benzene ring or a saturated or unsaturated ring, for example, benzene, cyclopentane, cyclopentene, cyclohexane, cyclohexene, cyclohexadiene, cycloheptane, cycloheptene and cycloheptadiene.

If rings B or C contain at least one heteroatom (e.g., 1–3 heteroatoms, such as nitrogen, oxygen, sulfur, etc.), i.e., if ring B or C is a heterocyclic ring, it may or may not be aromatic. Such aromatic heterocyclic rings are, for example, pyridine, furan, thiophene. Preferred nonaromatic, heterocyclic rings are the above-indicated examples of rings B or C.

Accordingly, tricyclic substituent Tr can be a condensed benzene ring of general formula

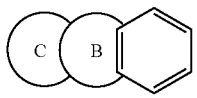

Examples in this respect are:
Carbazole,
1,2,3,4-4a,9a-hexahydrocarbazole,
9,10-dihydroacridine,
1,2,3,4-tetrahydroacridine,
10,11-dihydro-5H-dibenz[b,f]azepine,
5,6,11,12-tetrahydrodibenz[b,g]azocine,
6,11-dihydro-5H-dibenz[b,e,]azepine,
6,7-dihydro-5H-dibenz[c,e]azepine,
5,6,11,12-tetrahydrodibenz[b,f]azocine,
dibenzofuran,
9H-xanthene,
1-O-11-dihydrobenz[b,f]oxepin,
6,11-dihydrobenz[b,e]oxepin,
6,7-dihydro-5H-dibenz[b,g]oxacine,
dibenzothiophene,
9H-thioxanthene,
10,11-dihydrodibenzo[b,f]thiepin,
6,11-dihydrodibenzo[b,e]thiepin,
6,7-dihydro-5H-dibenzo[b,g]thiocin,
10H-phenothiazine,
10H-phenoxazine,
5,10-dihydrophenazine,
10,11-dibenzo[b,f]-[1,4]thiazepine,
2,3,5,6,11,11a-hexahydro-1H-pyrrolo[2,1-b][3]benzazepine,
1-O,11-dihydro-5H-dibenzo[b,e][1,4]diazepine,
5,11-dihdyrodibenz[b,e][1,4]oxazepine,
5,11-dihydrodibenzo[b,f][1,4]thiazepine,
10,11-dihydro-5H-dibenzo[b,e][1,4]diazepine,
1,2,3,3a,8,8a-hexahydropyrrolo[2,3b]indole.

Tricyclic substituent Tr can be a condensed benzene ring of general formula

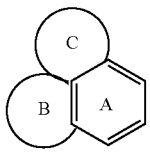

and can mean, for example:
1H,3H-Naphth[1,8-cd][1,2]oxazine,
naphth[1,8-de]-1,3-oxazine,
naphth[1,8-de]-1,2-oxazine,
1,2,2a,3,4,5-hexahydrobenz[cd]indole,
2,3,3a,4,5,6-hexahydro-1H-benzo[de]quinoline,
4H-pyrrolo[3,2,1-ij]quinoline,
1,2,5,6-tetrahydro-4H-pyrrolo[3,2,1-ij]quinoline,
5,6-dihydro-4H-pyrrolo[3,2,1-ij]quinoline,
1H,5H-benzo[ij]quinolizine,
2,3,6,7-tetrahydro-1H,5H-benzo[ij]quinolizine,
azepino[3,2,1-hi]indole,
1,2,4,5,6,7-hexahydroazepino[3,2,1-hi]indole,
1H-pyrido[3,2,1-jk][1]benzazepine,
5,6,7,8-tetrahydro-1H-pyrido[3,2,1-jk][1]benzazepine,
1,2,5,6,7,8-hexahydro-5H-pyrido[3,2,1-jk][1]benzazepine,
2,3-dihydro-1H-benz[de]isoquinoline,
1,2,3,4,4a,5,6,7-octahydronaphth[1,8-bc]azepine,
2,3,5,6,7,8-hexahydro-1H-pyrido[3,2,1-jk][1]benzazepine.

Tricyclic substituent Tr can be a condensed benzene ring of general formula

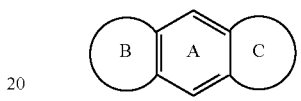

Examples of these compounds are:
1,2,3,5,6,7-Hexahydrobenzo[1,2-b:4,5b']dipyrrole,
1,2,3,5,6,7-hexahydrocyclopent[f]indole,
1,2,3,6,7,8-hexahydrocyclopentan[e]indole or
2,3,4,7,8-hexahydro-1H-cyclopenta[f]quinoline.

Tricyclic substituent Tr can be a condensed benzene ring of general formula

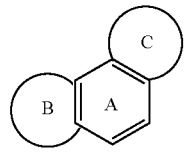

Examples of this are:
1,2,3,6,7,8-Hexahydrocyclopent[e]indole or
2,3,4,7,8,9-hexahydro-1H-cyclopenta[f]guinoline.

Additional examples of tricyclic substituents Tr are condensed benzene rings of the following formulas, whereby the binding site to Q can take up the space of any hydrogen atom:

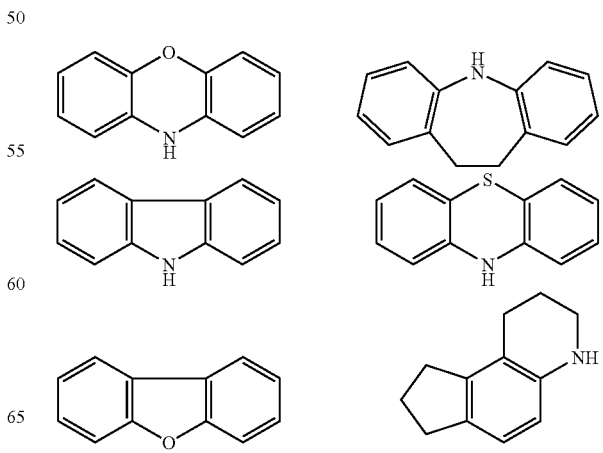

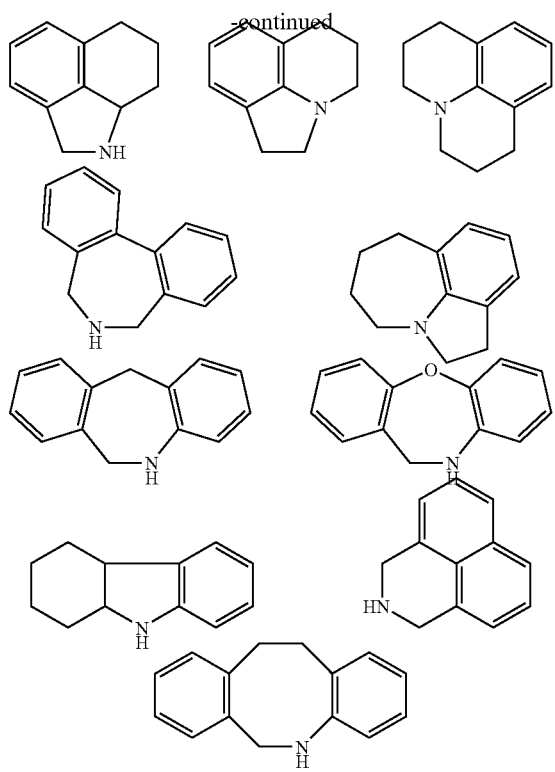

In addition, Tr can be a cyclic or bicyclic hydrocarbon which is referred to by the following formula:

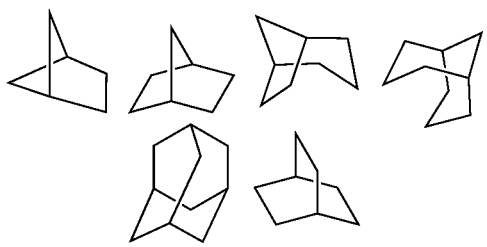

In addition, each substituent Tr can be substituted by one or more substituents $R_1$, whereby the definition of substituent $R_1$ is the same as in formula I.

e) In addition, W can mean —NH—, —S—, —SO— or —$SO_2$—.

In addition, the invention relates to compounds of general formula II

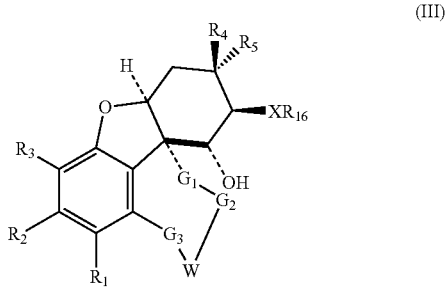

(II)

in which D stands for NH, N-alkyl, N-acyl, oxygen or sulfur, and in which substituents $R_1$ to $R_5$, $G_1$ to $G_3$ and W can have the meanings that are indicated above in general formula I.

In addition, the invention relates to compounds of general formula III

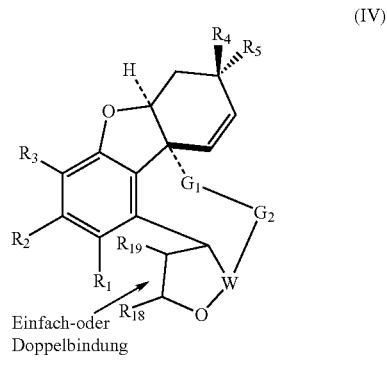

(III)

in which X—$R_{16}$ is a substituent in which X is oxygen or sulfur and $R_{16}$ is hydrogen or a low ($C_1$–$C_{10}$), optionally branched or cyclic, optionally substituted (Ar)alkyl group, and in which substituents $R_1$ to $R_5$, $G_1$ to $G_3$ and W can have the meanings that are indicated above in general formula I.

The invention extends to compounds of general formula IV

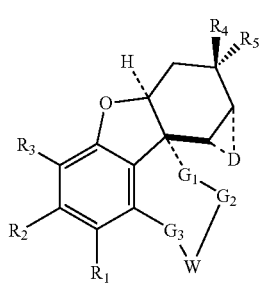

(IV)

Einfach-oder Doppelbindung
Single or double bond in which W represents CH or N, and $R_{18}$ and $R_{19}$ mean hydrogen, alkyl, aryl or aralkyl, and in which the C atoms that carry substituents $R_{18}$ and $R_{19}$ are linked to one another via a single bond or a double bond and in which substituents $R_1$ to $R_5$ as well as $G_1$ and $G_3$ have the meanings that are indicated above in general formula I.

It is preferred if in the compound of general formula IV substituent W is nitrogen and/or substituent $G_1$ is —$(CH_2)_x$—, in which x is equal to 1 or 2 and $G_2$ means —$(CH_2)_y$—, in which y is equal to 0 to 2, provided that x+y together mean at least 2 and at most 4.

Separation of Optical Isomers from rac. Norgalanthamine:

In addition, the invention includes a process for chiral separation of (GR)-3-methoxy-5,6,9,10,11,12-hexahydro-4aH[1]benzofuro[3a,3,2-ef][2benzazepin-6-ol (norgalanthamine)(4)

The separation of (+) and (−) isomers is carried out by fractionated crystallization in such a way that a solution or suspension of the optical isomer mixture in which 3 to 50× the amount is added to or introduced into a solvent, such as water, methanol, ethanol, propanol, isopropanol, acetone or mixtures of this solvent, mainly methanol with the equimolar amount or excess chiral acid (unsubstituted, (+) or (−) tartaric acid, citric acid, lactic acid, preferably (+)-O,O-di-p-toluoyl tartaric acid that is substituted in one or more places and that is dissolved in one of the above-mentioned solvents—and the solution or suspension of the optical isomer mixture is added, that the solution is inoculated with crystals produced from the natural (−) galanthamine derivatives and chiral organic acids, such as (+)-O,O-di-p-toluoyl tartaric acid, and is allowed to stand at −40 to +20 degrees, preferably 0 degrees for 2–24 hours or longer, that the formed crystals are filtered and dried, then mixed with excess $NH_4OH$ and extracted with an organic solvent, such as chloroform, methylene chloride, ethyl acetate, butyl acetate, diethyl ether, t-butyl-methyl ether, dibutyl ether, petroleum ether, xylene, benzene, toluene or similar solvents, and the corresponding (−) norgalanthamine is isolated by distillation of the solvent.

In this process, concentration by evaporation of the mother liquor, uptake of excess $NH_4OH$, extraction with an organic solvent (as indicated above) and concentration by evaporation yield additional fractions of norgalanthamine, from which in the same way as above, the (+) norgalanthamine can be produced with chiral organic acids, such as (−)-O,O-di-p-toluoyl tartaric acid.

The products that are obtained according to the invention can be purified by a suitable process, for example, sublimation, fractionated crystallization or chromatography.

Among the compounds according to the invention, especially the compounds that are mentioned below are considered:

In the survey below, "AchE" means acetylcholinesterase, "BchE" means butyrylcholinesterase, "hr" means human recombinant, "mE" means pre-incubation of the enzyme with inhibitor, and "$IC_{50}$" means concentration, in which 50% inhibition takes place.

| Substance Code | Structure | IC50 (AChE, mE, hr) | IC50 (BChE, mE, hr) | Laboratory Code | Patent Example Number |
|---|---|---|---|---|---|
| SPH-1118 | 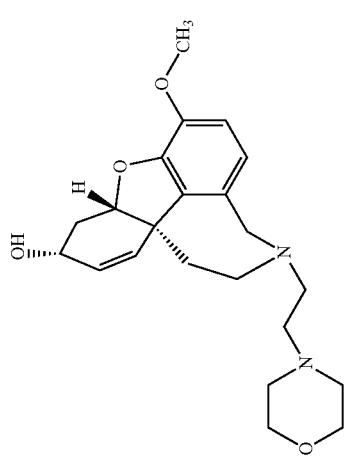 | 100 | 200 | Ro22 | 77 |
| SPH-1146 | 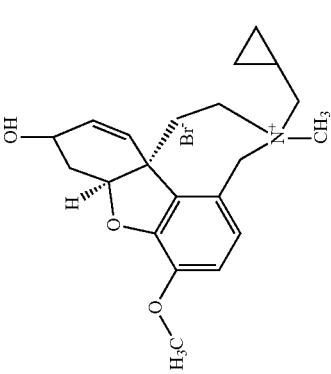 | 1.2 | 3.6 | TK 66/1 | 136 |

-continued
| Substance Code | Structure | IC50 (AChE, mE, hr) | IC50 (BChE, mE, hr) | Laboratory Code | Patent Example Number |
|---|---|---|---|---|---|
| SPH-1149 | 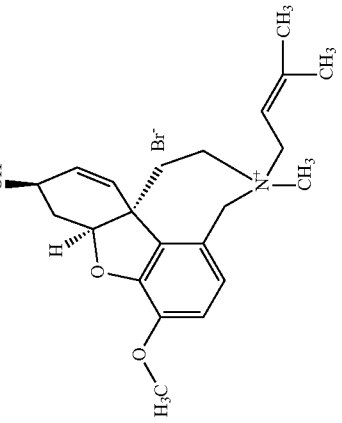 | 0.2 | 0.21 | HM 104 | 137 |
| SPH-1162 | 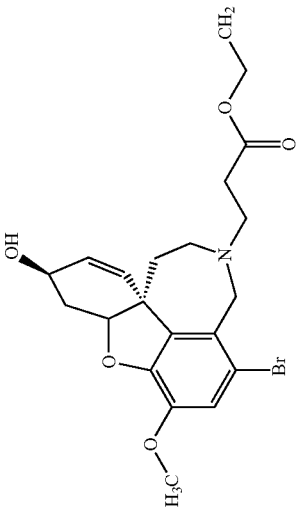 | 200 | | CI 2-1, CB 19 | 138 |

-continued
| Substance Code | Structure | IC50 (AChE, mE, hr) | IC50 (BChE, mE, hr) | Laboratory Code | Patent Example Number |
|---|---|---|---|---|---|
| SPH-1184 | 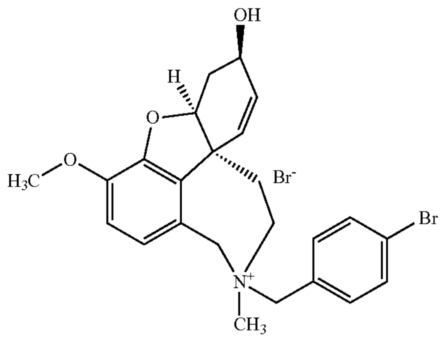 | 0.2 | 0.6 | LCz 225/1 | 139 |
| SPH-1191 | 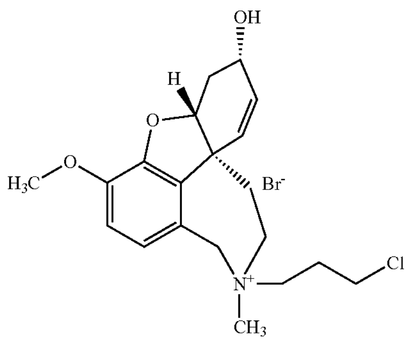 | 0.35 | 4.4 | LCz 205 | 140 |
| SPH-1196 | 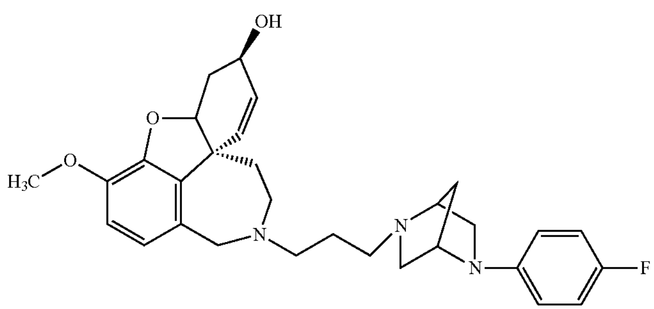 | 5.2 | 5 | TK 36-2 | 30 |

-continued
| Substance Code | Structure | IC50 (AChE, mE, hr) | IC50 (BChE, mE, hr) | Laboratory Code | Patent Example Number |
|---|---|---|---|---|---|
| SPH-1163 | 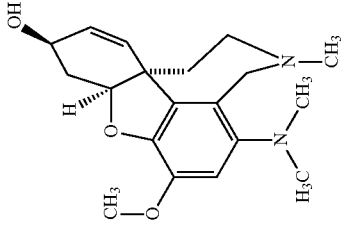 | 200 | 0.47 | MH 7-1-1 | 35 |
| SPH-1199 | 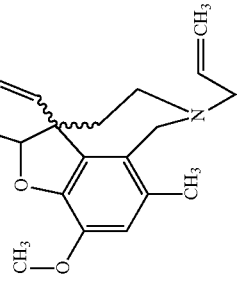 | 200 | 2.3 | MH 25-1 | 102 |

-continued

| Substance Code | Structure | IC50 (AChE, mE, hr) | IC50 (BChE, mE, hr) | Laboratory Code | Patent Example Number |
|---|---|---|---|---|---|
| SPH-1200 | 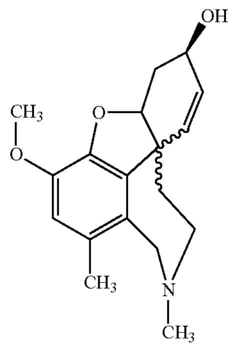 | 200 | 17 | MH 30-1 | 88 |
| SPH-1201 | 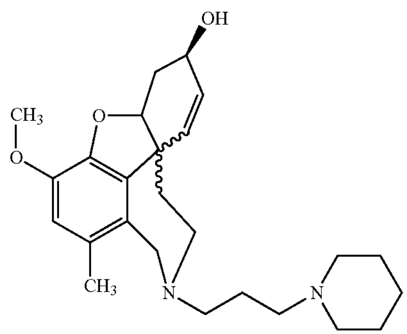 | 46 | 0.6 | MH-29-1 | 105 |

-continued
| Substance Code | Structure | IC50 (AChE, mE, hr) | IC50 (BChE, mE, hr) | Laboratory Code | Patent Example Number |
|---|---|---|---|---|---|
| SPH-1202 | 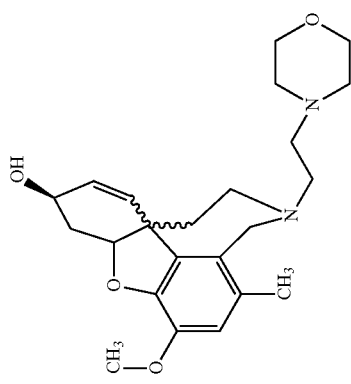 | 200 | 5.2 | MH-28-1 | 104 |
| SPH-1203 | 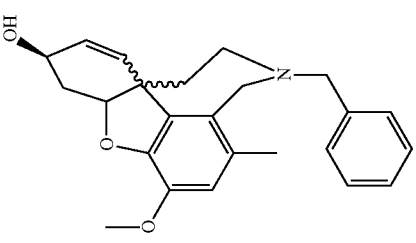 | | | MH-26-1 | 103 |

-continued

| Substance Code | Structure | IC50 (AChE, mE, hr) | IC50 (BChE, mE, hr) | Laboratory Code | Patent Example Number |
|---|---|---|---|---|---|
| SPH-1204 | 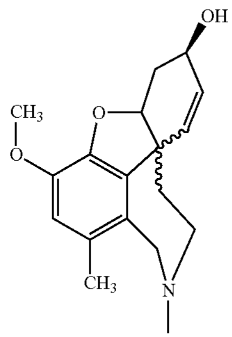 | 200 | 200 | MH 31-2 | 89 |
| SPH-1205 | 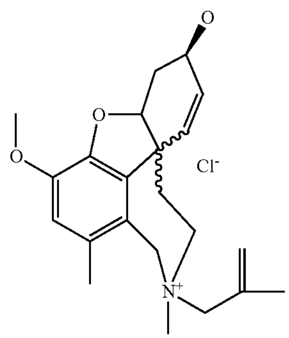 | 70 | 2.4 | MH 33 | 90 |

-continued

| Substance Code | Structure | IC50 (AChE, mE, hr) | IC50 (BChE, mE, hr) | Laboratory Code | Patent Example Number |
|---|---|---|---|---|---|
| SPH-1206 | 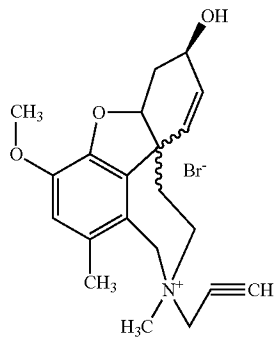 | 78 | 2.5 | MH 38-1 | 91 |
| SPH-1207 | 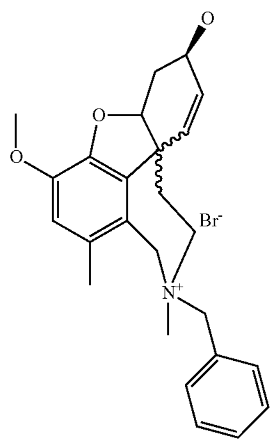 | 47 | 0.7 | MH 39-1 | 92 |

-continued

| Substance Code | Structure | IC50 (AChE, mE, hr) | IC50 (BChE, mE, hr) | Laboratory Code | Patent Example Number |
|---|---|---|---|---|---|
| SFH-1208 | 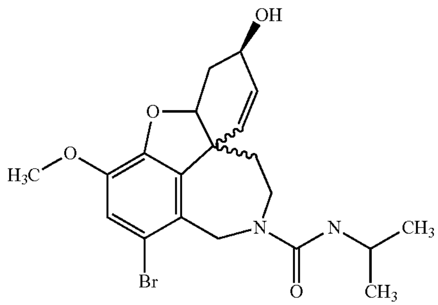 | 200 | 25 | CB 2 | 141 |
| SPH-1209 | 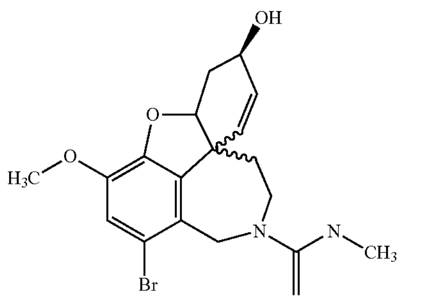 | 31 | 20 | CB 5 | 142 |
| SPH-1210 | 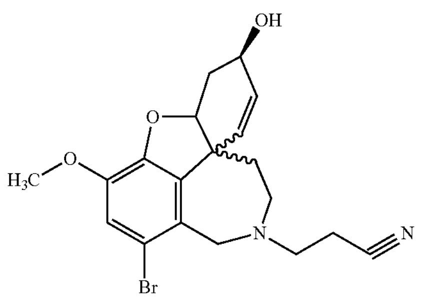 | 200 | 43 | CB 4 | 143 |

-continued

| Substance Code | Structure | IC50 (AChE, mE, hr) | IC50 (BChE, mE, hr) | Laboratory Code | Patent Example Number |
|---|---|---|---|---|---|
| SPH-1211 | 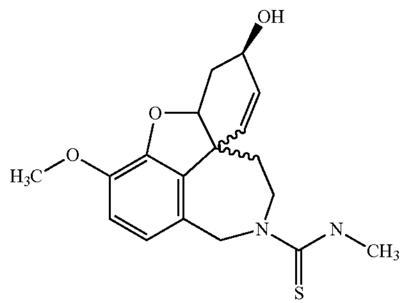 | 23 | 30 | CB 13, CB 29 | 27 |
| SPH-1213 | 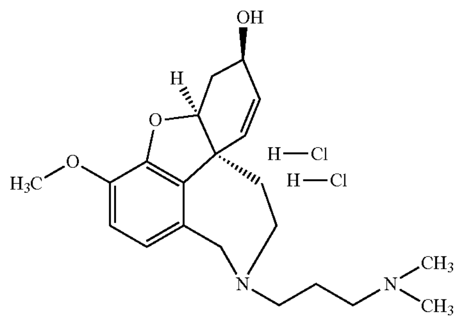 | 6 | 10 | TK 96/3 | 71 |
| SPH-1214 | 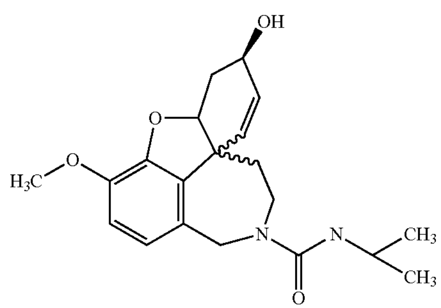 | 4.2 | 200 | CB 34, CB 34-2 | 19 |

-continued

| Substance Code | Structure | IC50 (AChE, mE, hr) | IC50 (BChE, mE, hr) | Laboratory Code | Patent Example Number |
|---|---|---|---|---|---|
| SPH-1215 | 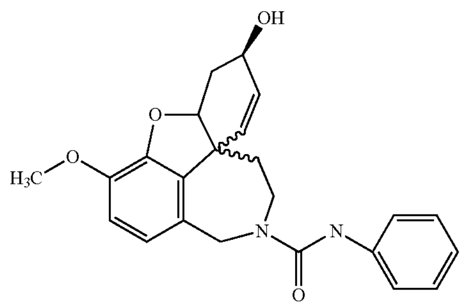 | 70 | 200 | CB 33 | 23 |
| SPH-1216 | 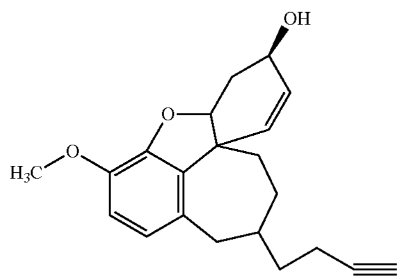 | 90 | 200 | CB 35 | 44 |
| SPH-1217 | 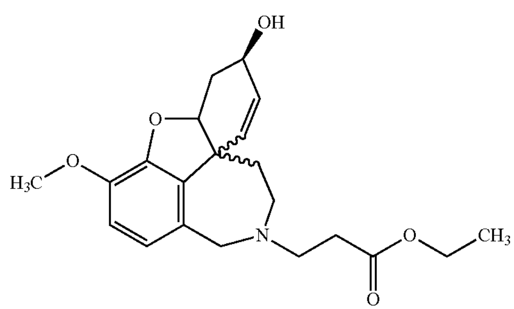 | 9.5 | 17 | CB 28 | 40 |

| Substance Code | Structure | IC50 (AChE, mE, hr) | IC50 (BChE, mE, hr) | Laboratory Code | Patent Example Number |
|---|---|---|---|---|---|
| SPH-1218 | 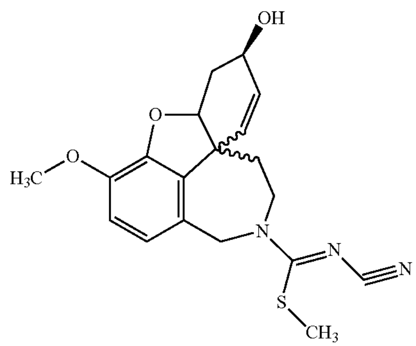 | 25 | 0.54 | CB 30 | 8 |
| SPH-1219 | 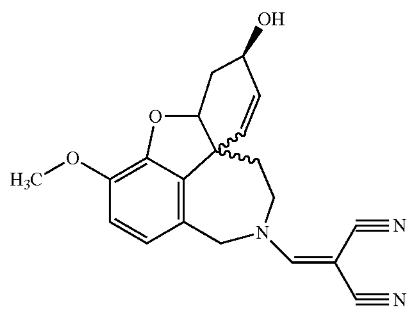 | 28.5 | 200 | CB 36 | 31 |
| SPH-1220 | 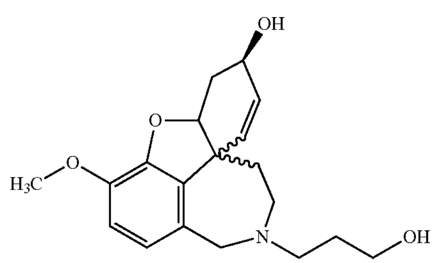 | 7.2 | 21 | CB 41 | 45 |

-continued

| Substance Code | Structure | IC50 (AChE, mE, hr) | IC50 (BChE, mE, hr) | Laboratory Code | Patent Example Number |
|---|---|---|---|---|---|
| SPH-1221 | 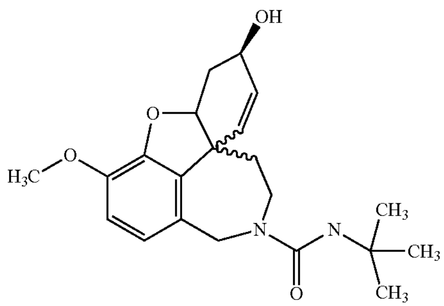 | 4.8 | 200 | CB 45 | 20 |
| SPH-1222 | | 6.7 | 200 | CB 46 | 22 |
| SPH-1227 | 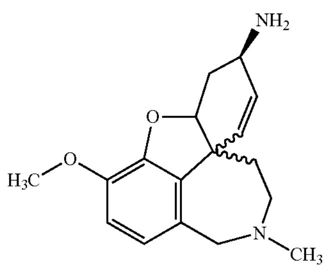 | 40 | 6 | HM 38 | 144 |
| SPH-1228 | 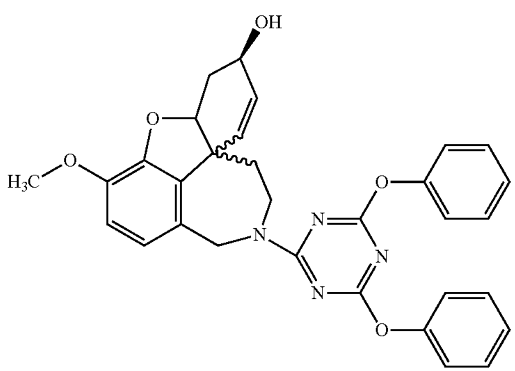 | 200 | 200 | CB 43 | 15 |

-continued

| Substance Code | Structure | IC50 (AChE, mE, hr) | IC50 (BChE, mE, hr) | Laboratory Code | Patent Example Number |
|---|---|---|---|---|---|
| SPH-1229 | 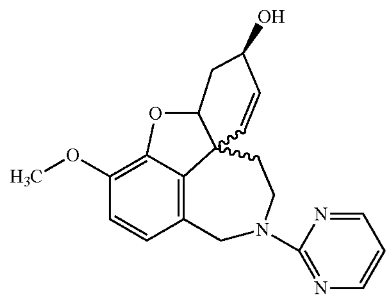 | 38 | 30 | CB 52 | 9 |
| SPH-1230 | 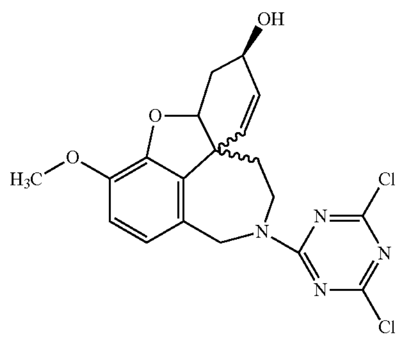 | | | CB 53 | 13 |
| SPH-1231 | 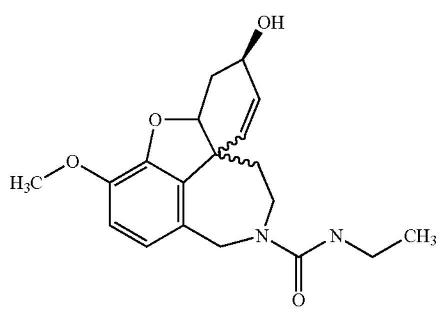 | 33 | 200 | CB 49 | 21 |

| Substance Code | Structure | IC50 (AChE, mE, hr) | IC50 (BChE, mE, hr) | Laboratory Code | Patent Example Number |
|---|---|---|---|---|---|
| SPH-1232 | 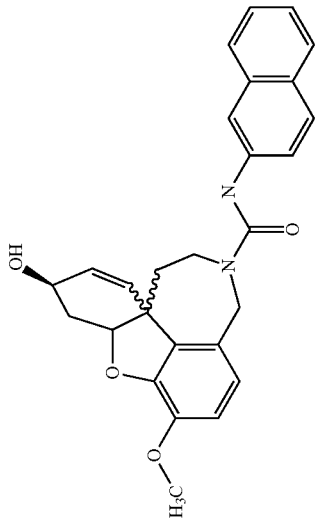 | 36 | 200 | CB 50 | 26 |
| SPH-1233 | 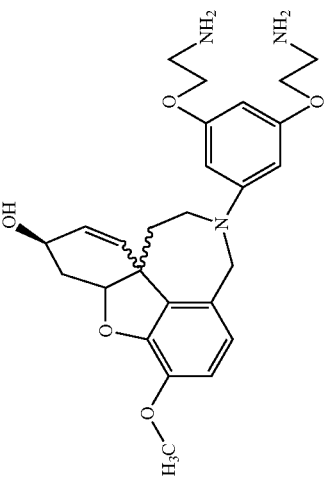 | 200 | 200 | CB 51 | 16 |
| SPH-1234 | 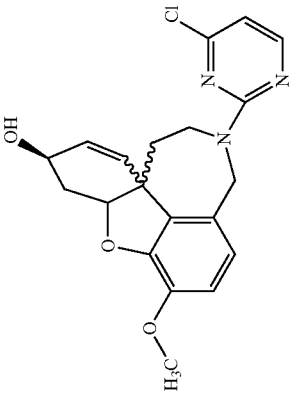 | 66 | 200 | CB 56 | 10 |

-continued

| Substance Code | Structure | IC50 (AChE, mE, hr) | IC50 (BChE, mE, hr) | Laboratory Code | Patent Example Number |
|---|---|---|---|---|---|
| SPH-1235 | 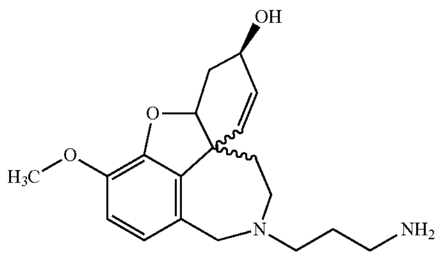 | 3.4 | 11 | CB 42 | 46 |
| SPH-1236 | 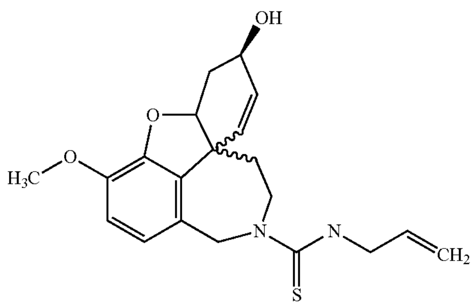 | 21 | 200 | CB 48 | 28 |
| SPH-1237 | 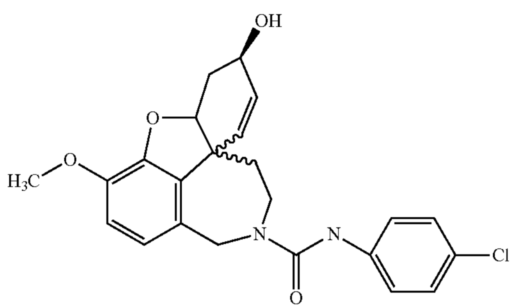 | 24 | 200 | CB 47 | 24 |

-continued

| Substance Code | Structure | IC50 (AChE, mE, hr) | IC50 (BChE, mE, hr) | Laboratory Code | Patent Example Number |
|---|---|---|---|---|---|
| SPH-1242 | 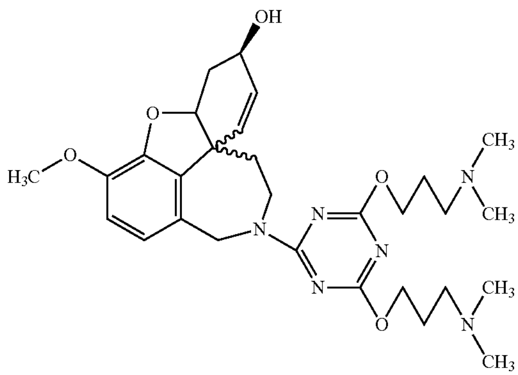 | 70 | 40 | CB 55 | 17 |
| SPH-1243 | 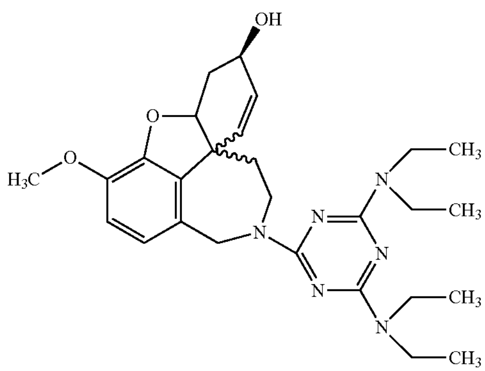 | 40 | 200 | CB 58 | 14 |

-continued

| Substance Code | Structure | IC50 (AChE, mE, hr) | IC50 (BChE, mE, hr) | Laboratory Code | Patent Example Number |
|---|---|---|---|---|---|
| SPH-1244 | 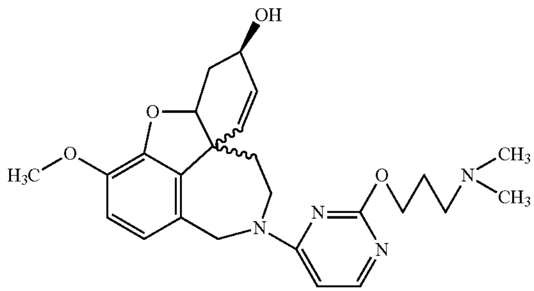 | 7.6 | 36 | CB 57 | 12 |
| SPH-1245 | 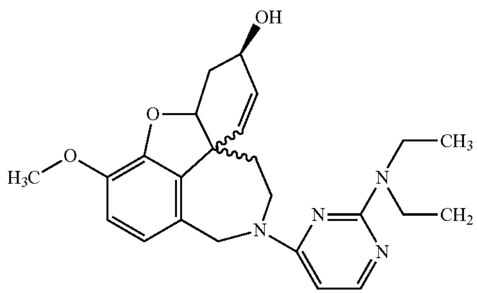 | 25 | 200 | CB 59 | 11 |
| SPH-1246 | 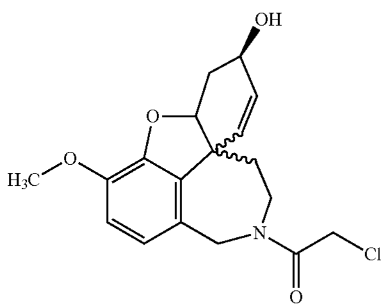 | 17.5 | 20 | MR 16 | 18 |

-continued

| Substance Code | Structure | IC50 (AChE, mE, hr) | IC50 (BChE, mE, hr) | Laboratory Code | Patent Example Number |
|---|---|---|---|---|---|
| SPH-1247 | 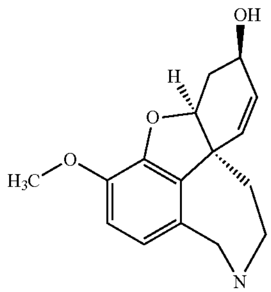 | 2.4 | 4 | MR 17 | 48-Stufe1 |
| SPH-1248 | 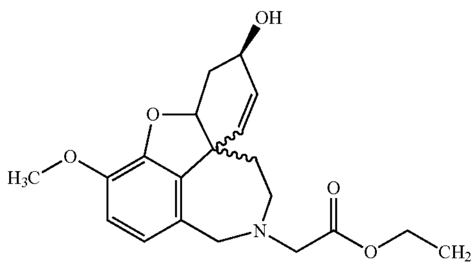 | 40 | 90 | MR 7 | 34 |
| SPH-1249 | 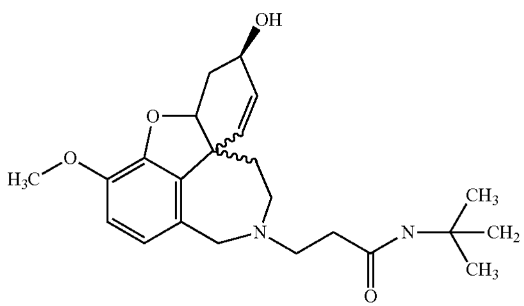 | 45 | 26 | MR 13 | 43 |
| SPH-1250 | | 200 | 95 | MH-66 | 94 |
| SPH-1251 | | 59 | 45 | MH-71 | 95 |

-continued

| Substance Code | Structure | IC50 (AChE, mE, hr) | IC50 (BChE, mE, hr) | Laboratory Code | Patent Example Number |
|---|---|---|---|---|---|
| SPH-1252 | 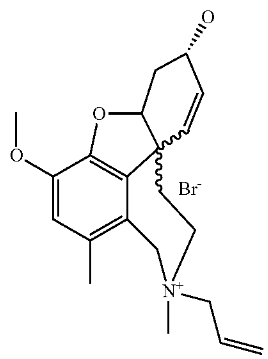 | 200 | 52 | MH-72 | 96 |
| SPH-1253 | 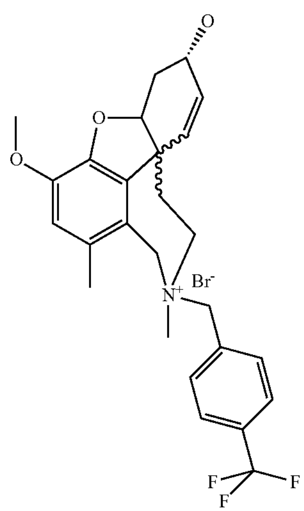 | 60 | 5.4 | MH-75 | 97 |

-continued

| Substance Code | Structure | IC50 (AChE, mE, hr) | IC50 (BChE, mE, hr) | Laboratory Code | Patent Example Number |
|---|---|---|---|---|---|
| SPH-1254 | 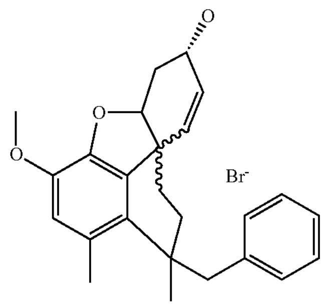 | 200 | 3 | MH-76 | 98 |
| SPH-1255 | 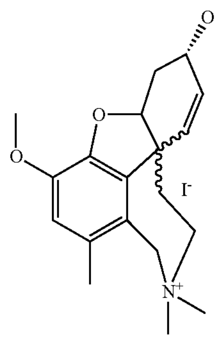 | 200 | 200 | MH-81 | 99 |
| SPH-1256 | 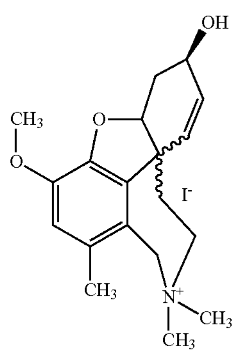 | 200 | 14 | MH-83 | 93 |

-continued

| Substance Code | Structure | IC50 (AChE, mE, hr) | IC50 (BChE, mE, hr) | Laboratory Code | Patent Example Number |
|---|---|---|---|---|---|
| SPH-1259 | 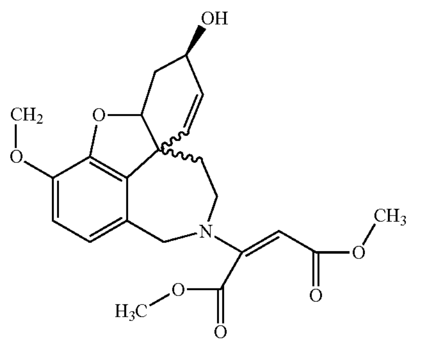 | 140 | 80 | HM 60 | 29 |
| SPH-1262 | 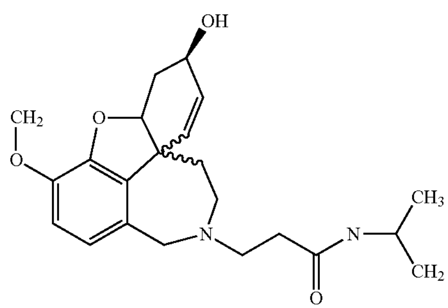 | 54.5 | 36 | MR 14 | 42 |
| SPH-1263 | 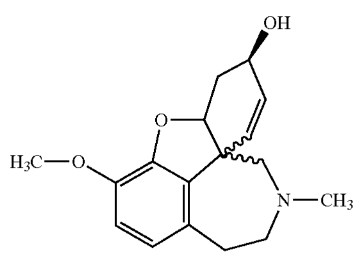 | 200 | 200 | Ap 74 | 1 |

| Substance Code | Structure | IC50 (AChE, mE, hr) | IC50 (BChE, mE, hr) | Laboratory Code | Patent Example Number |
|---|---|---|---|---|---|
| SPH-1264 | 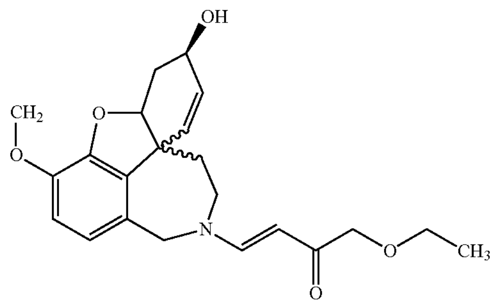 | 50 | 200 | HM 58 | 33 |
| SPH-1266 | 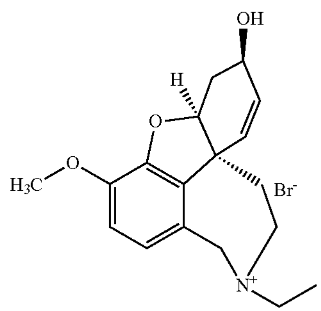 | 30 | 200 | CB 75 | 59 |
| SPH-1267 | 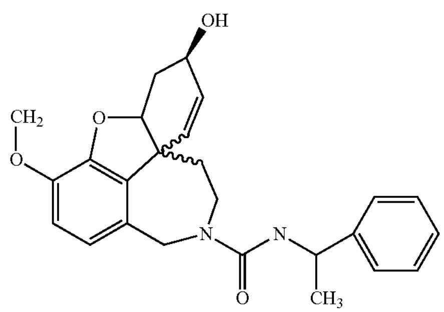 | 30 | 200 | CB 73 | 25 |

-continued

| Substance Code | Structure | IC50 (AChE, mE, hr) | IC50 (BChE, mE, hr) | Laboratory Code | Patent Example Number |
|---|---|---|---|---|---|
| SPH-1268 | 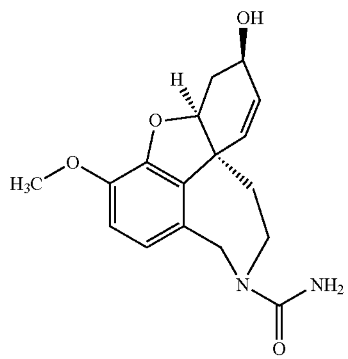 | 44 | 200 | CB 78 | 55 |
| SPH-1269 | 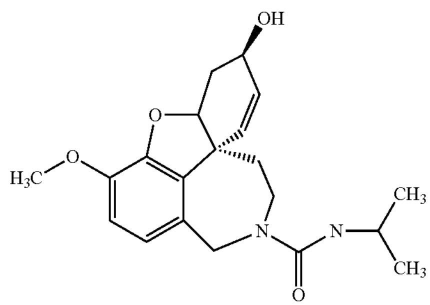 | 2.6 | 10 | CB 85 | 57 |
| SPH-1270 | 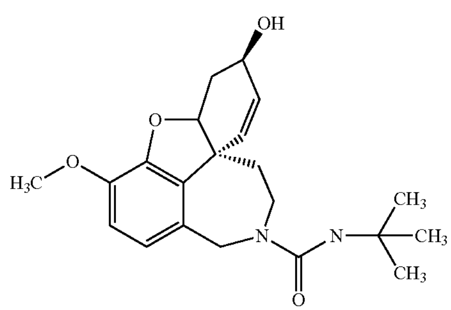 | 2.5 | 7 | CB 86 | 58 |

| Substance Code | Structure | IC50 (AChE, mE, hr) | IC50 (BChE, mE, hr) | Laboratory Code | Patent Example Number |
|---|---|---|---|---|---|
| SPH-1271 | 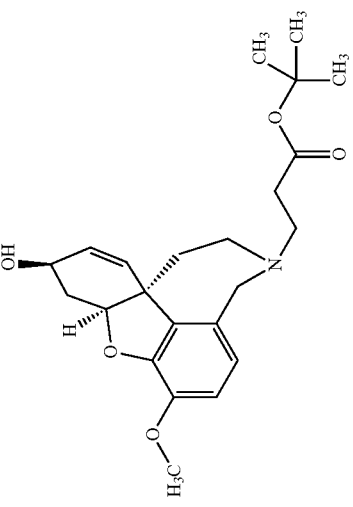 | 15 | 4 | CB 87 | 69 |
| SPH-1272 | 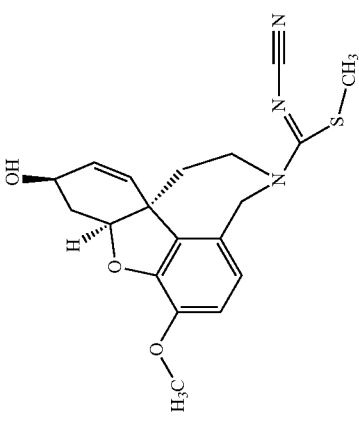 | 6.7 | 30 | CB 81 | 60 |

-continued
| Substance Code | Structure | IC50 (AChE, mE, hr) | IC50 (BChE, mE, hr) | Laboratory Code | Patent Example Number |
|---|---|---|---|---|---|
| SPH-1273 | 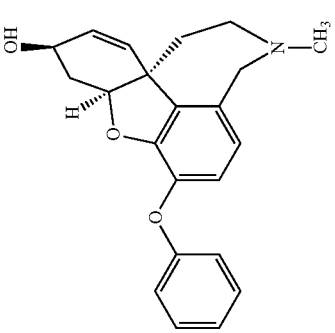 | 21 | 3.4 | CB 99, BK 10 | 145 |
| SPH-1276 | 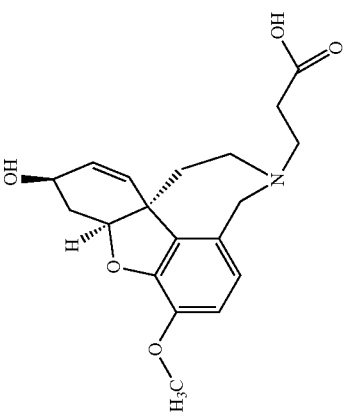 | 42 | 40 | CB 89 | 68 |
| SPH-1277 | | 33 | 7.3 | HM 57 | 41 |
| SPH-1278 | | 100 | 32 | HM 60 | 32 |

-continued
| Substance Code | Structure | IC50 (AChE, mE, hr) | IC50 (BChE, mE, hr) | Laboratory Code | Patent Example Number |
|---|---|---|---|---|---|
| SPH-1280 | 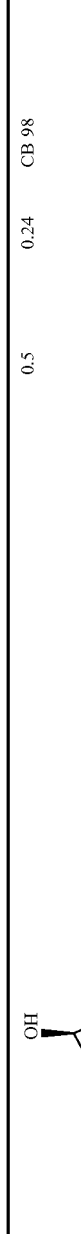 | 0.5 | 0.24 | CB 98 | 48 |
| SPH-1282 | 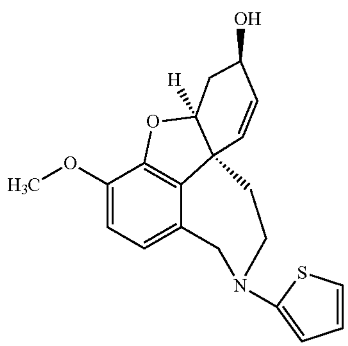 | 4 | 0.54 | CB 100, BK 11 | 49 |

-continued
| Substance Code | Structure | IC50 (AChE, mE, hr) | IC50 (BChE, mE, hr) | Laboratory Code | Patent Example Number |
|---|---|---|---|---|---|
| SPH-1283 | 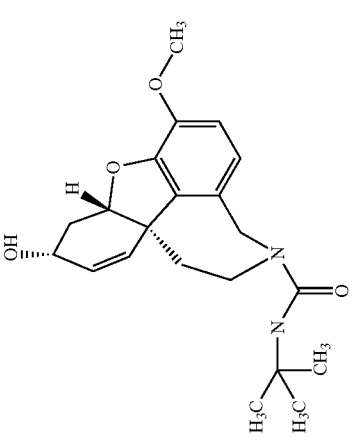 | 93 | 100 | DD 9 | 76 |
| SPH-1284 | 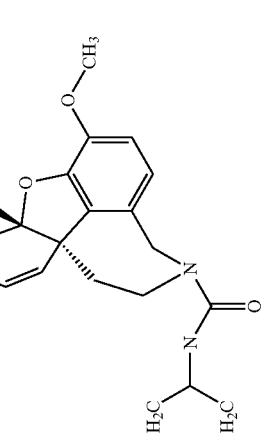 | 8 | 90 | DD 10 | 75 |

-continued
| Substance Code | Structure | IC50 (AChE, mE, hr) | IC50 (BChE, mE, hr) | Laboratory Code | Patent Example Number |
|---|---|---|---|---|---|
| SPH-1286 | 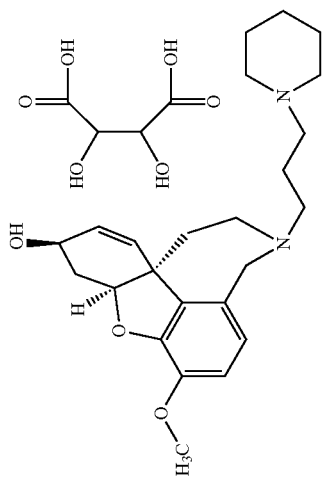 | 0.3 | 1.5 | BK-32-1-3, AH 8 | 72 |
| SPH-1287 | 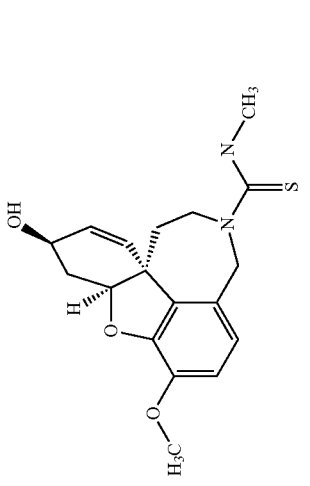 | 18.5 | 63 | HM 109 | 56 |
| SPH-1288 | 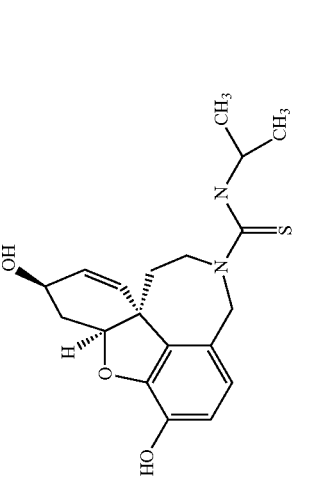 | 6.3 | 60 | HM 112, DD 13 | 146 |

-continued

| Substance Code | Structure | IC50 (AChE, mE, hr) | IC50 (BChE, mE, hr) | Laboratory Code | Patent Example Number |
|---|---|---|---|---|---|
| SPH-1289 | 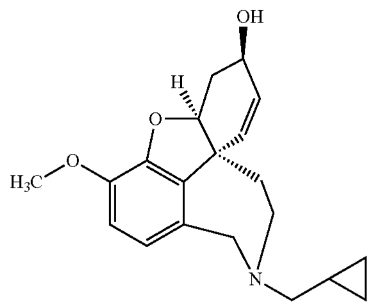 | 0.7 | 1.2 | HM 117 | 61 |
| SPH-1290 | 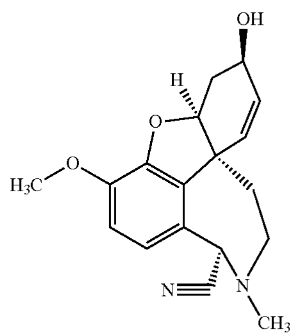 | 1.2 | 100 | MH 123-3, AH 11 | 110 |
| SPH-1291 | 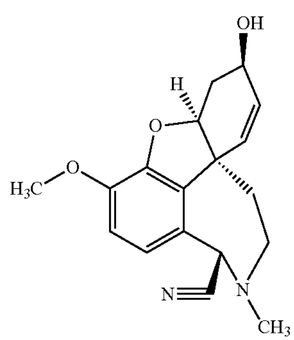 | 0.8 | 200 | MH 123-3, TT 33 | 110b |

-continued
| Substance Code | Structure | IC50 (AChE, mE, hr) | IC50 (BChE, mE, hr) | Laboratory Code | Patent Example Number |
|---|---|---|---|---|---|
| SPH-1292 | 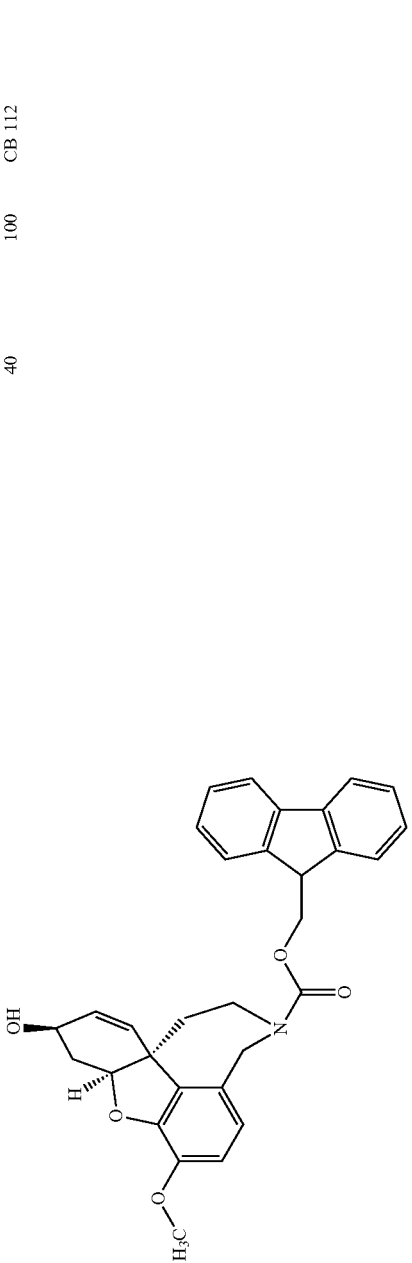 | 40 | 100 | CB 112 | 53 |
| SPH-1293 | 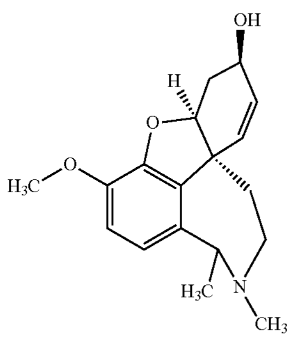 | 4.2 | 25 | MH 122-3, Pi-4 | 114 |

| Substance Code | Structure | IC50 (AChE, mE, hr) | IC50 (BChE, mE, hr) | Laboratory Code | Patent Example Number |
| --- | --- | --- | --- | --- | --- |
| SPH-1295 | 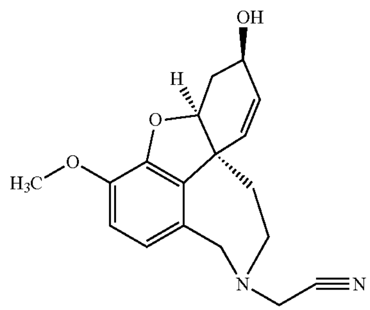 | 15 | 32 | BM 1 | 63 |
| SPH-1296 | 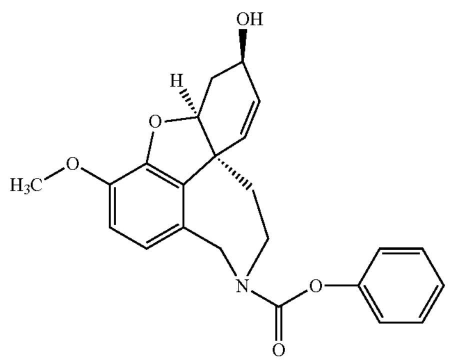 | 46 | 200 | CB 147, DD 16 | 51 |
| SPH-1298 | 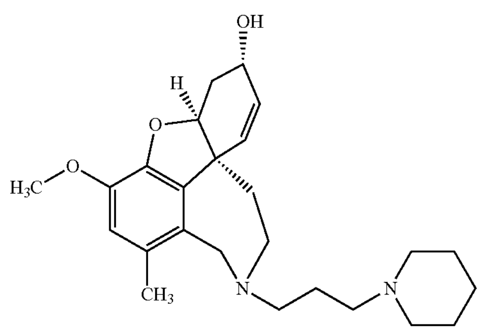 | 200 | 70 | MH-117 | 106 |

-continued

| Substance Code | Structure | IC50 (AChE, mE, hr) | IC50 (BChE, mE, hr) | Laboratory Code | Patent Example Number |
|---|---|---|---|---|---|
| SPH-1302 | 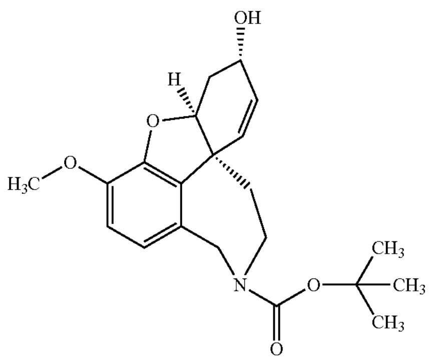 | 23 | 200 | HM 203 | 147 |
| SPH-1309 | 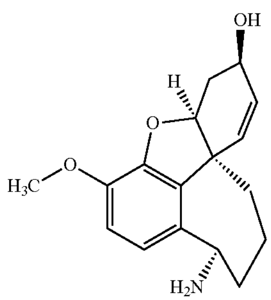 | 200 | 200 | MT 176 | 128d |
| SPH-1310 | 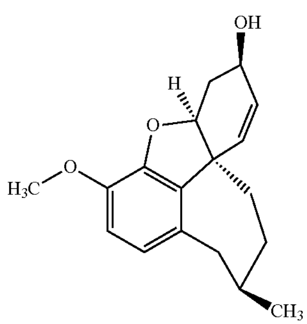 | 5.3 | 200 | MT 141 | 83 |

-continued

| Substance Code | Structure | IC50 (AChE, mE, hr) | IC50 (BChE, mE, hr) | Laboratory Code | Patent Example Number |
|---|---|---|---|---|---|
| SPH-1311 | (galantamine derivative with -NH2 side chain) | 1.3 | 2.1 | BM 4 | 65 |
| SPH-1312 | (galantamine derivative with 4-fluorophenyl azabicyclic side chain) | 3 | 2.4 | DD 24 | 73 |

-continued

| Substance Code | Structure | IC50 (AChE, mE, hr) | IC50 (BChE, mE, hr) | Laboratory Code | Patent Example Number |
|---|---|---|---|---|---|
| SPH-1314 | 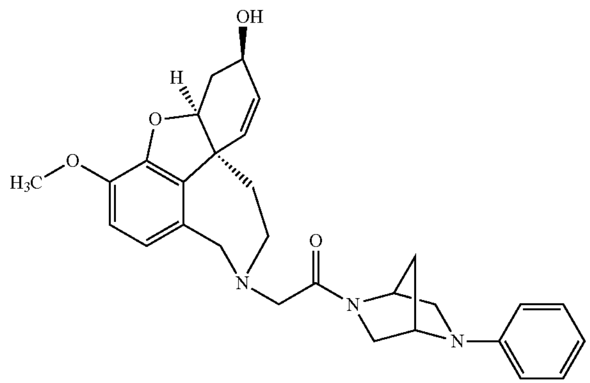 | 8.4 | 2.4 | DD 18 | 64 |
| SPH-1315 | 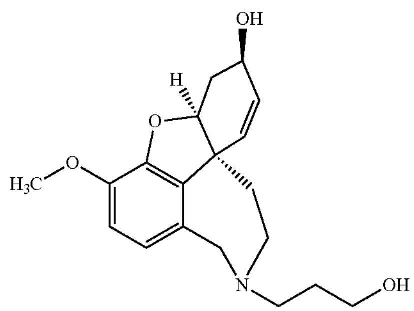 | 2.8 | 5 | | 70 |

-continued

| Substance Code | Structure | IC50 (AChE, mE, hr) | IC50 (BChE, mE, hr) | Laboratory Code | Patent Example Number |
|---|---|---|---|---|---|
| SPH-1317 | 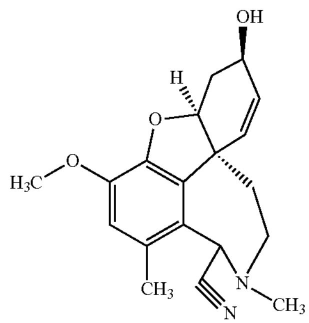 | 80 | 200 | PI 12 | 111 |
| SPH-1318 | 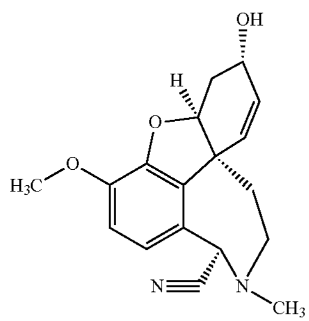 | 200 | 200 | PI 14 | 112 |
| SPH-1319 | 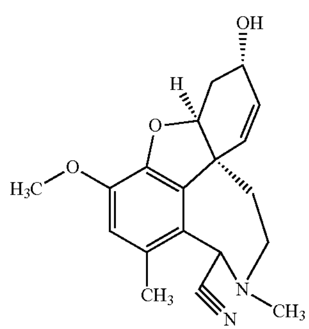 | 200 | 200 | PI 19 | 113 |

-continued

| Substance Code | Structure | IC50 (AChE, mE, hr) | IC50 (BChE, mE, hr) | Laboratory Code | Patent Example Number |
|---|---|---|---|---|---|
| SPH-1320 | | 83 | 30 | PI 21 | 116 |
| SPH-1326 | 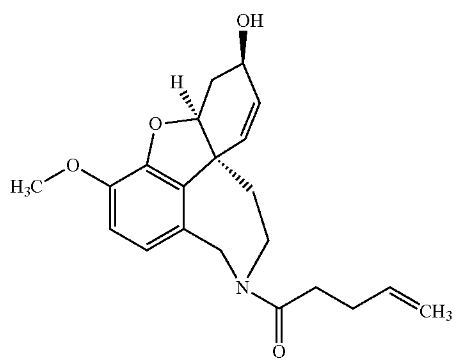 | 8.4 | 2.6 | CB 171 | 54 |
| SPH-1327 | 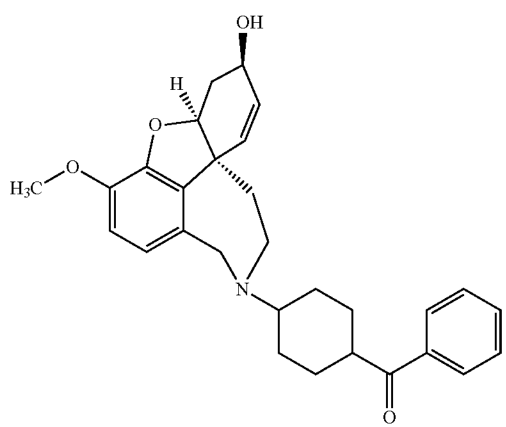 | 24 | 3 | WO 2 | 50 |

| Substance Code | Structure | IC50 (AChE, mE, hr) | IC50 (BChE, mE, hr) | Laboratory Code | Patent Example Number |
|---|---|---|---|---|---|
| SPH-1328 | 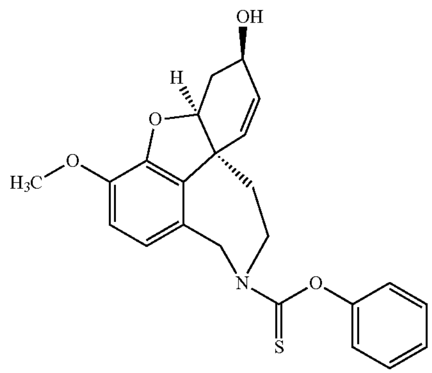 | 7.2 | 200 | CB 161 | 52 |
| SPH-1329 | | 2.9 | 0.85 | DD 26 | 67 |
| SPH-1330 | 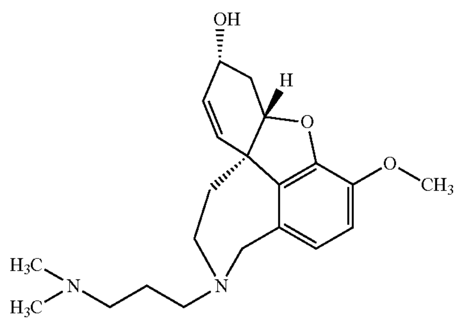 | 64 | 67 | RMA 15 | 78 |

-continued

| Substance Code | Structure | IC50 (AChE, mE, hr) | IC50 (BChE, mE, hr) | Laboratory Code | Patent Example Number |
|---|---|---|---|---|---|
| SPH-1331 | 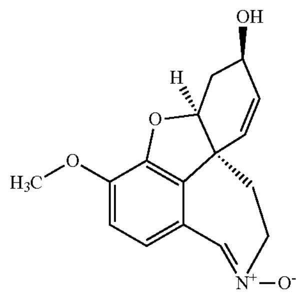 | 50 | 200 | MH 142 | 119 |
| SPH-1332 | 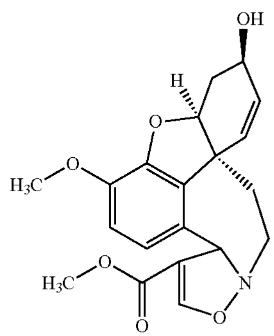 | 200 | 200 | MH 145 | 120 |
| SPH-1333 | 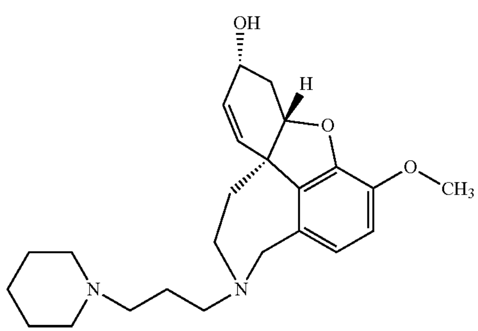 | 9 | 23 | RMA 14, DD 7 | 79 |

-continued
| Substance Code | Structure | IC50 (AChE, mE, hr) | IC50 (BChE, mE, hr) | Laboratory Code | Patent Example Number |
|---|---|---|---|---|---|
| SPH-1335 | 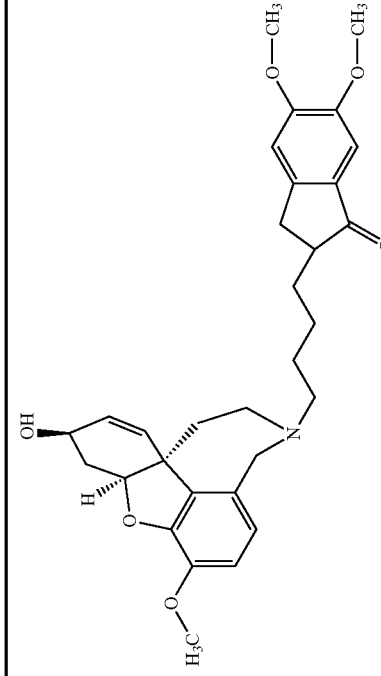 | 0.02 | 0.8 | CB 177, BK 6 | 6-Stufe3 |
| SPH-1339 | 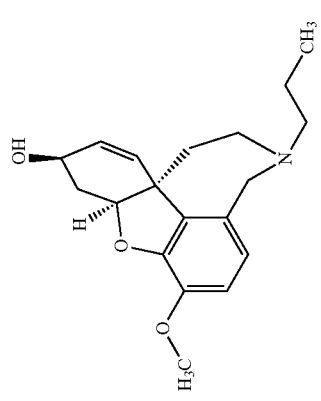 | 0.3 | 1.5 | HM 264-1 | 149 |

-continued

| Substance Code | Structure | IC50 (AChE, mE, hr) | IC50 (BChE, mE, hr) | Laboratory Code | Patent Example Number |
|---|---|---|---|---|---|
| SPH-1340 | 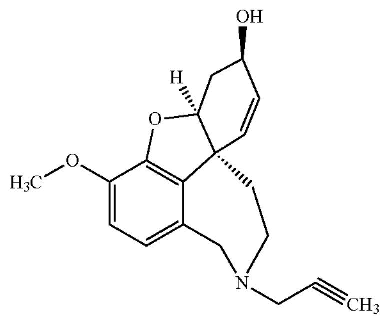 | 32 | 30 | HM 265-1 | 150 |
| SPH-1345 | 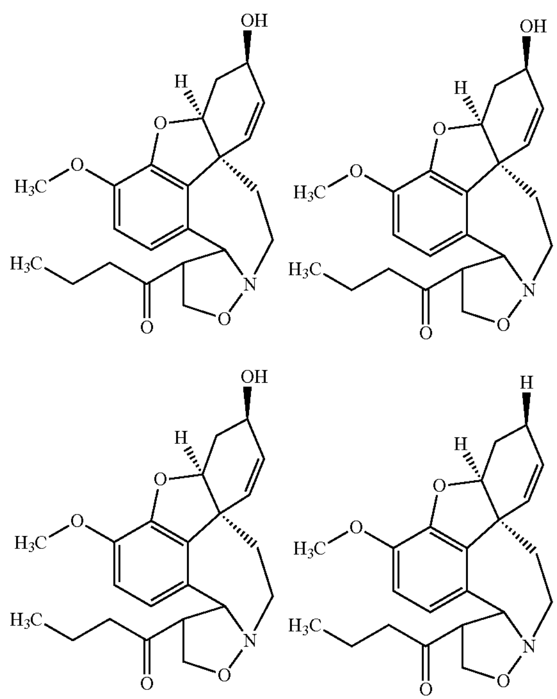 | 200 | 200 | MH143 | 119 |

-continued
| Substance Code | Structure | IC50 (AChE, mE, hr) | IC50 (BChE, mE, hr) | Laboratory Code | Patent Example Number |
|---|---|---|---|---|---|
| SPH-1357 | 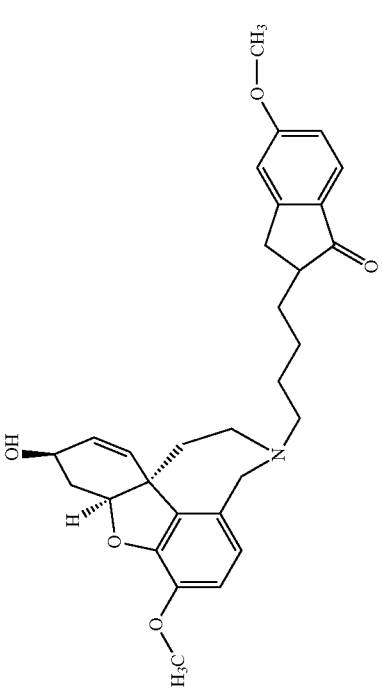 | 0.022 | 0.8 | MF 8 | 151 |
| SPH-1359 | 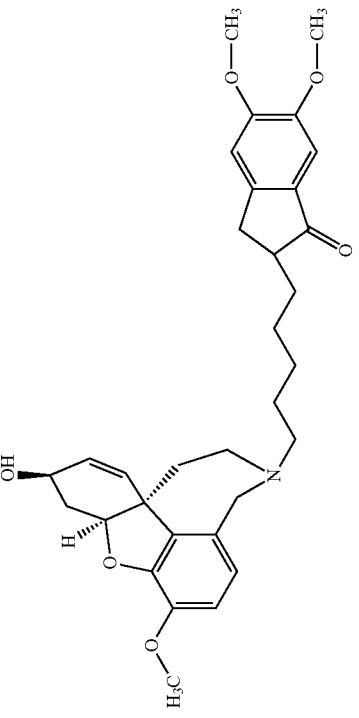 | 0.0052 | 0.24 | MF 19 | 7-Stufe3 |

-continued

| Substance Code | Structure | IC50 (AChE, mE, hr) | IC50 (BChE, mE, hr) | Laboratory Code | Patent Example Number |
|---|---|---|---|---|---|
| SPH-1362 | 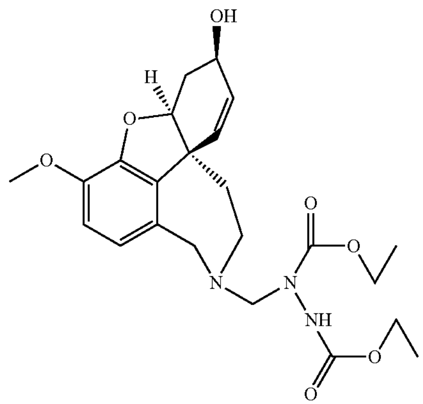 | 3 | 200 | MF-3, CK-21-3 | 181 |
| SPH-1363 | 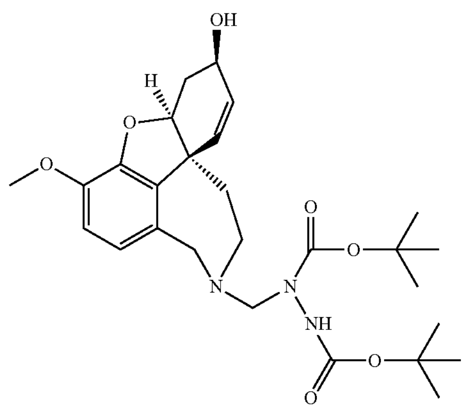 | 3.6 | 20 | MF-17, CK-24-2 | 180 |

-continued
| Substance Code | Structure | IC50 (AChE, mE, hr) | IC50 (BChE, mE, hr) | Laboratory Code | Patent Example Number |
|---|---|---|---|---|---|
| SPH-1369 | 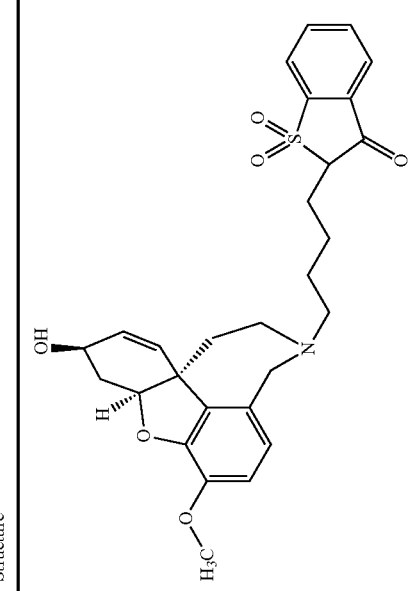 | 0.022 | 1.5 | MT 273 | 3 |
| SPH-1371 | 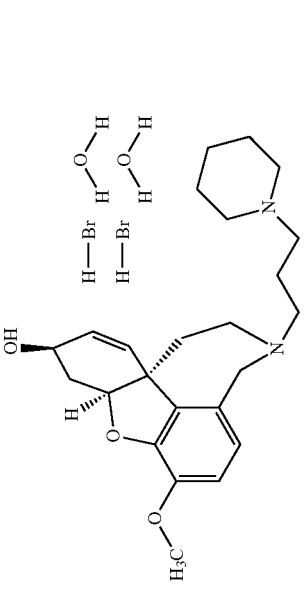 | 0.36 | | BK-32-2, BK-32-1-3 | 170 |

-continued

| Substance Code | Structure | IC50 (AChE, mE, hr) | IC50 (BChE, mE, hr) | Laboratory Code | Patent Example Number |
|---|---|---|---|---|---|
| SPH-1372 | 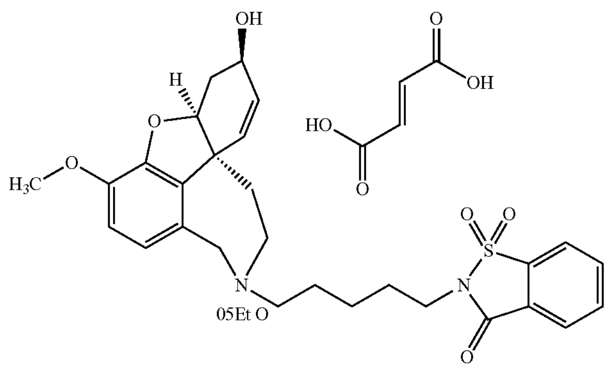 | 0.022 | | UJ-1682-2 | 4 |
| SPH-1373 | 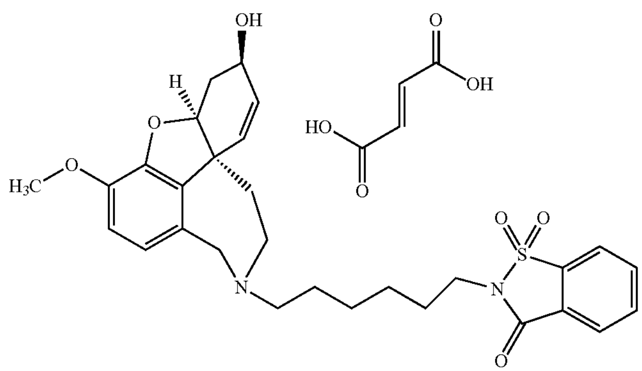 | 0.043 | | UJ-1685 | 5 |
| SPH-1374 | | 0.027 | | UJ-1686 | 3 |

-continued
| Substance Code | Structure | IC50 (AChE, mE, hr) | IC50 (BChE, mE, hr) | Laboratory Code | Patent Example Number |
|---|---|---|---|---|---|
| SPH-1375 | 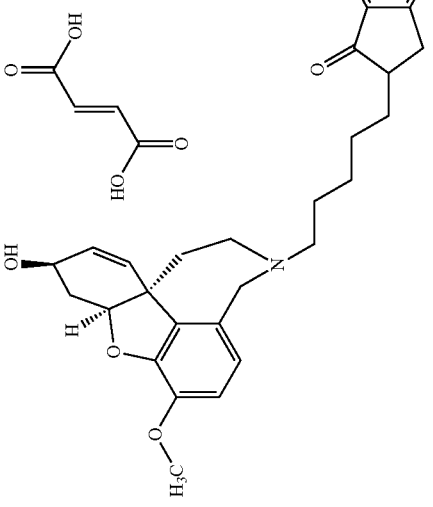 | 0.023 | | UJ-1683 | 7 |
| SPH-1376 | 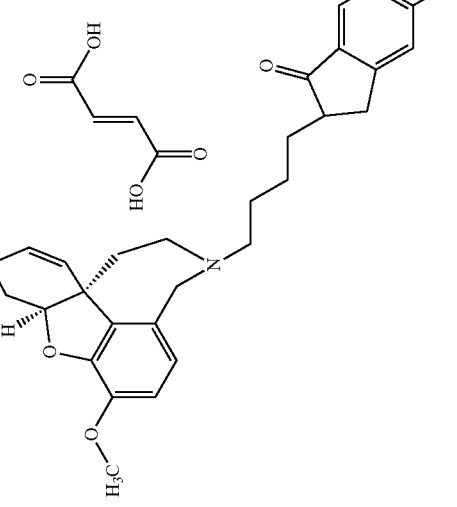 | 0.02 | | UJ-1684 | 6 |

-continued
| Substance Code | Structure | IC50 (AChE, mE, hr) | IC50 (BChE, mE, hr) | Laboratory Code | Patent Example Number |
|---|---|---|---|---|---|
| SPH-1377 | 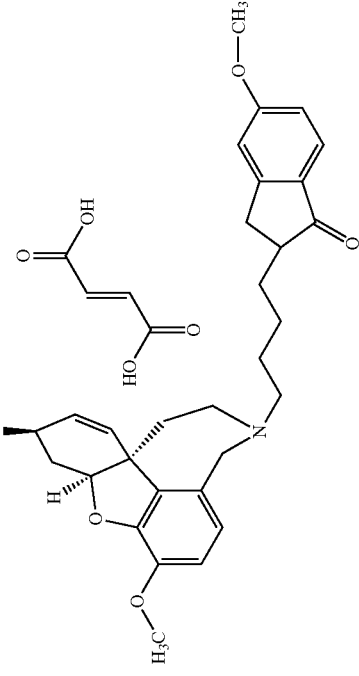 | 0.024 | | BK-34-2 | 155 |
| SPH-1490 | 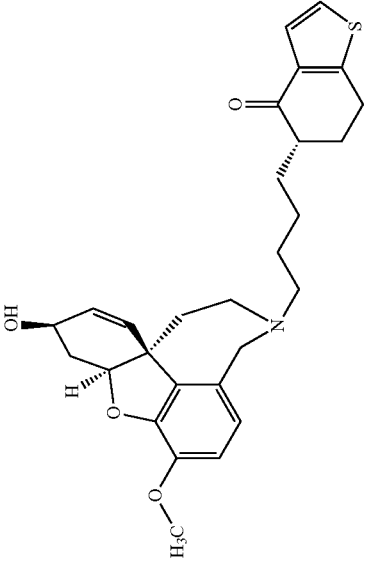 | | | MB-8 | 171 |

-continued

| Substance Code | Structure | IC50 (AChE, mE, hr) | IC50 (BChE, mE, hr) | Laboratory Code | Patent Example Number |
|---|---|---|---|---|---|
| SPH-1491 | 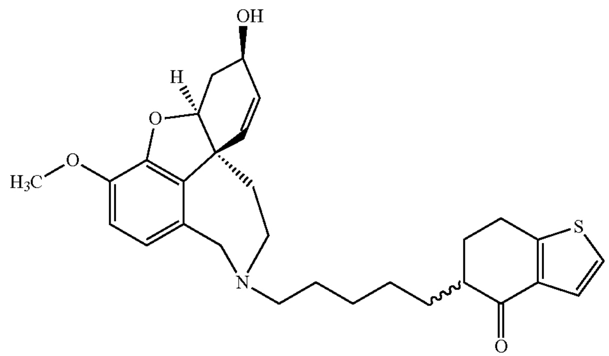 | | | MB-1 | 172 |
| SPH-1492 | 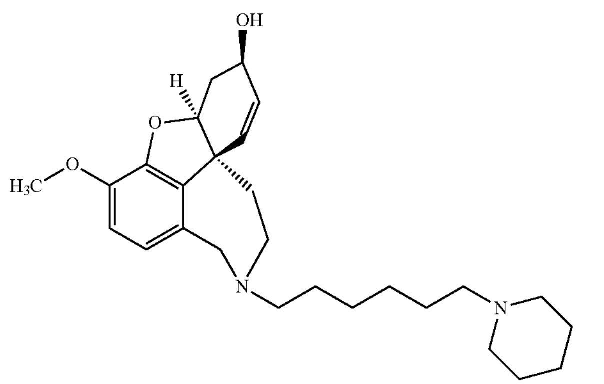 | | | MB-7 | 173 |

-continued

| Substance Code | Structure | IC50 (AChE, mE, hr) | IC50 (BChE, mE, hr) | Laboratory Code | Patent Example Number |
|---|---|---|---|---|---|
| SPH-1493 | 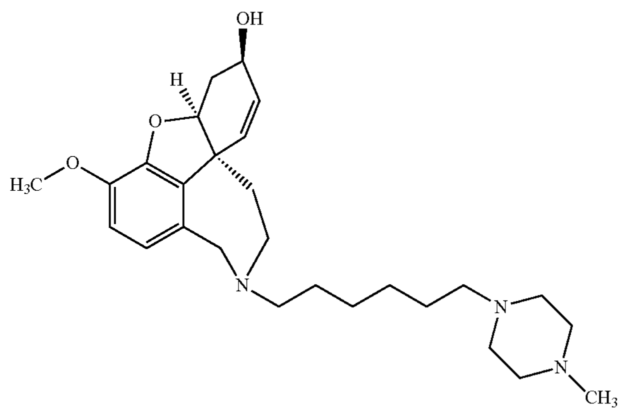 | | | MB-10 | 174 |
| SPH-1494 | 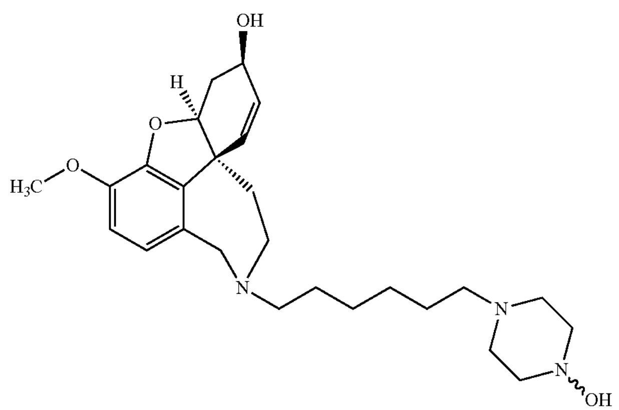 | | | MB-15 | 175 |

-continued

| Substance Code | Structure | IC50 (AChE, mE, hr) | IC50 (BChE, mE, hr) | Laboratory Code | Patent Example Number |
|---|---|---|---|---|---|
| SPH-1515 | 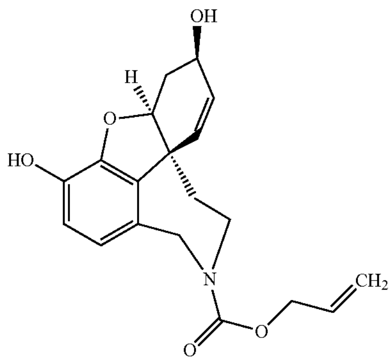 | | | ML-7 | 157 |
| SPH-1521 | | | | | 176 |
| SPH-1522 | 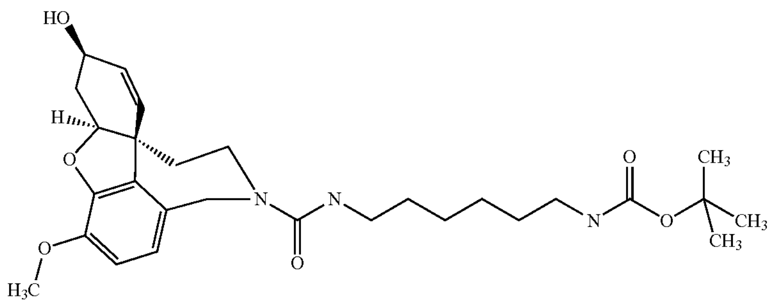 | | | CK-52-6 | 158 |

| Substance Code | Structure | IC50 (AChE, mE, hr) | IC50 (BChE, mE, hr) | Laboratory Code | Patent Example Number |
|---|---|---|---|---|---|
| SPH-1523 | 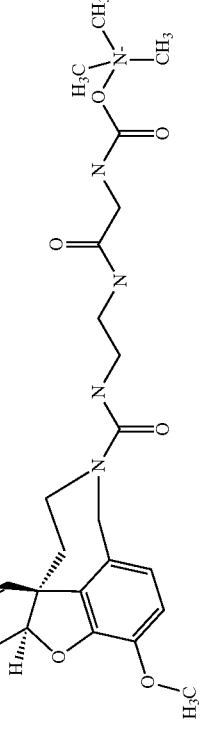 | | | CK-56-2 | 159 |
| SPH-1524 | 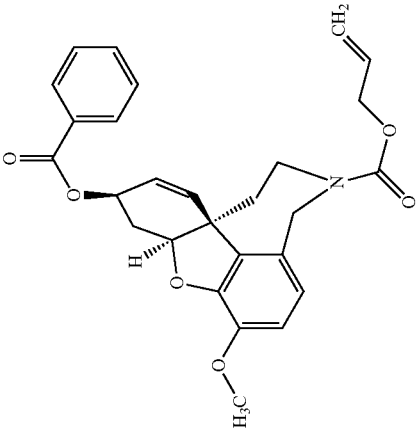 | | | CK-65-1 | 160 |

| Substance Code | Structure | IC50 (AChE, mE, hr) | IC50 (BChE, mE, hr) | Laboratory Code | Patent Example Number |
|---|---|---|---|---|---|
| SPH-1525 | 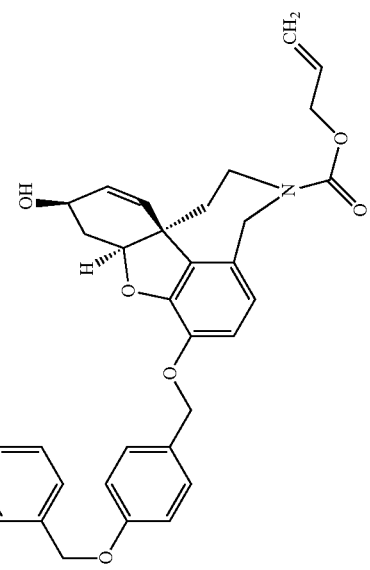 | | | CK-63 | 161 |
| SPH-1526 | 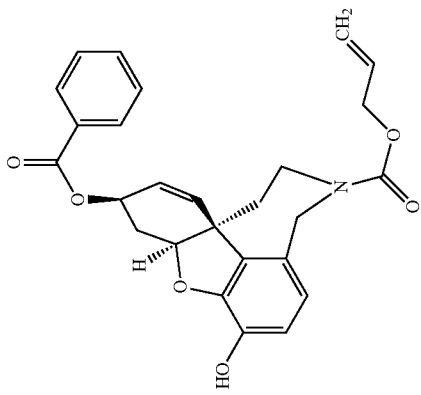 | | | CK-63 | 162 |

| Substance Code | Structure | IC50 (AChE, mE, hr) | IC50 (BChE, mE, hr) | Laboratory Code | Patent Example Number |
|---|---|---|---|---|---|
| SPH-1528 | 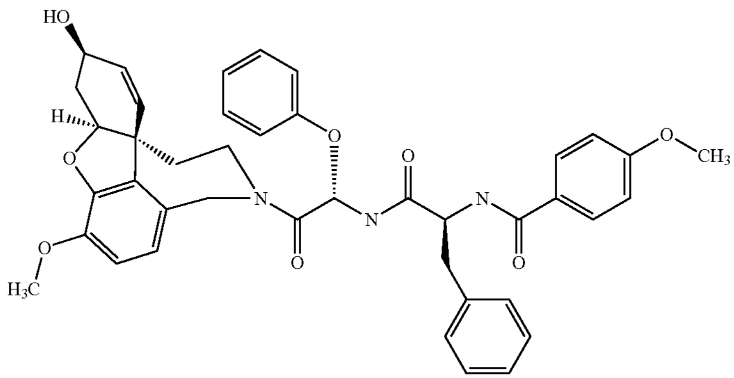 | | | CK-49-1-IPP-3-1 | 163 |
| SPH-1529 | 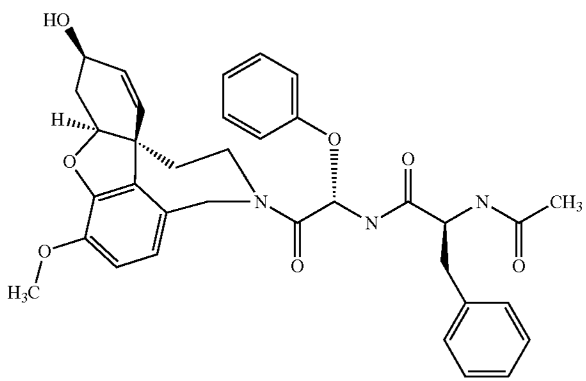 | | | CK-59-AcPP-3-1 | 164 |

| Substance Code | Structure | IC50 (AChE, mE, hr) | IC50 (BChE, mE, hr) | Laboratory Code | Patent Example Number |
|---|---|---|---|---|---|
| SPH-1530 | 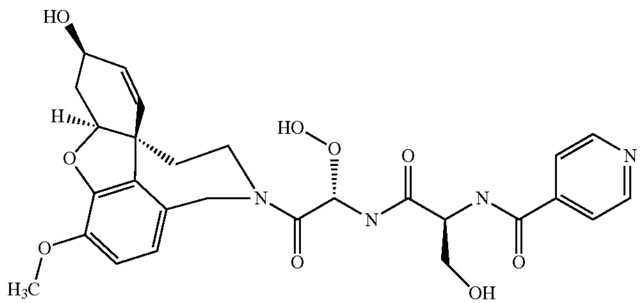 | | | CK-59-ISS-4-1 | 165 |
| SPH-1531 | 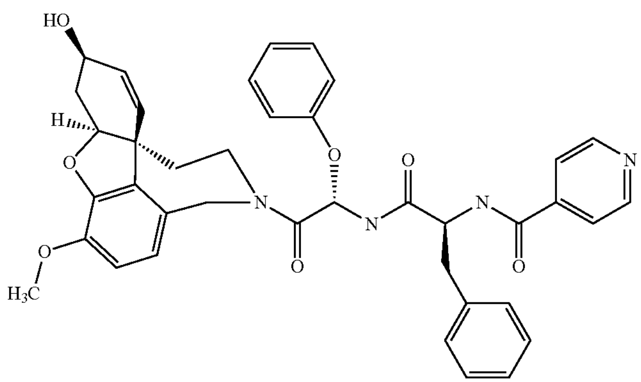 | | | CK-59-IPP-2-1 | 166 |
| SPH-1532 | | | | CK-59-MSS-5-1 | 167 |

-continued

| Substance Code | Structure | IC50 (AChE, mE, hr) | IC50 (BChE, mE, hr) | Laboratory Code | Patent Example Number |
|---|---|---|---|---|---|
| SPH-1534 | 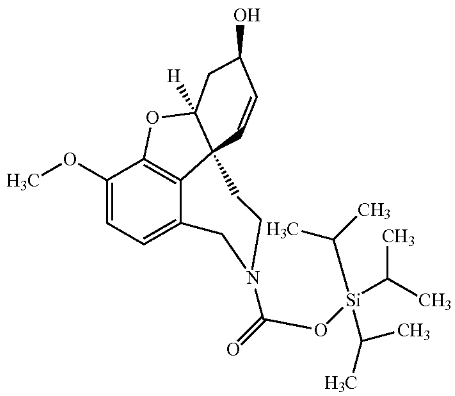 | | | CK-9-2 | 182 |
| SPH-1535 | 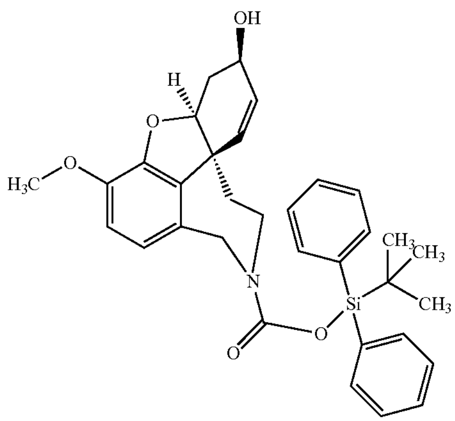 | | | CK-10 | 183 |

| Substance Code | Structure | IC50 (AChE, mE, hr) | IC50 (BChE, mE, hr) | Laboratory Code | Patent Example Number |
|---|---|---|---|---|---|
| SPH-1536 | 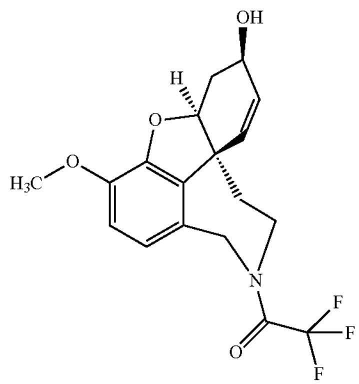 | | | CK-32 | 184 |
| SPH-1537 | 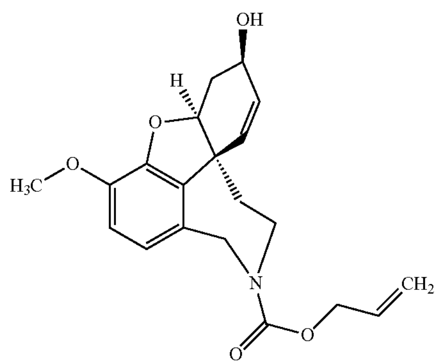 | | | CK-17 | 185 |

| Substance Code | Structure | IC50 (AChE, mE, hr) | IC50 (BChE, mE, hr) | Laboratory Code | Patent Example Number |
|---|---|---|---|---|---|
| SPH-1538 | 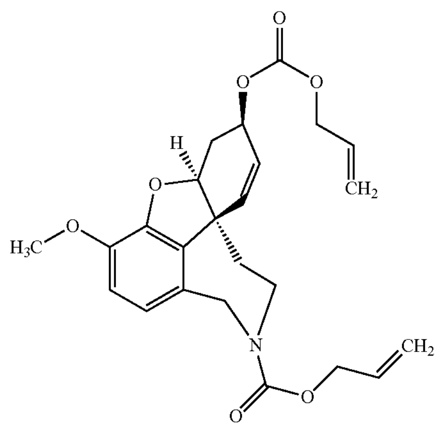 | | | CK-17-1 | 186 |
| SPH-1539 | 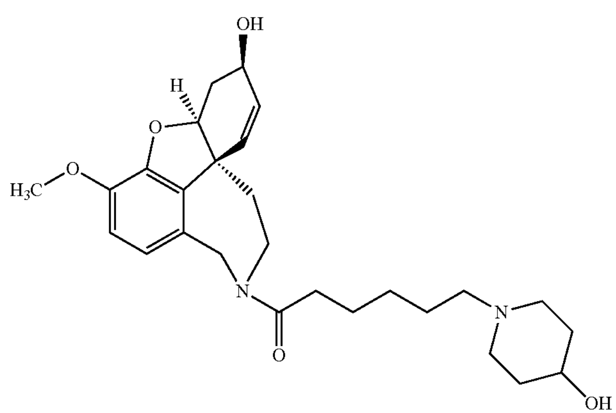 | | | CK-36 | 187 |

-continued

| Substance Code | Structure | IC50 (AChE, mE, hr) | IC50 (BChE, mE, hr) | Laboratory Code | Patent Example Number |
|---|---|---|---|---|---|
| SPH-1540 | 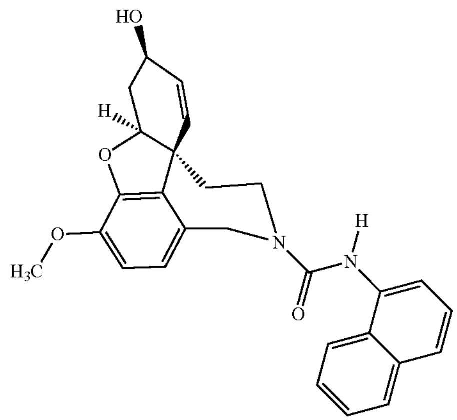 | | | CK-41 | 188 |
| SPH-1541 | 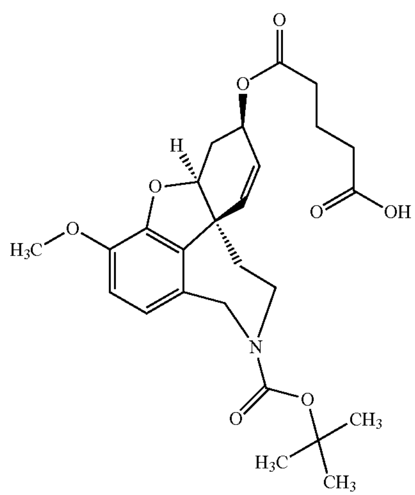 | | | CK-48 | 189 |

-continued
| Substance Code | Structure | IC50 (AChE, mE, hr) | IC50 (BChE, mE, hr) | Laboratory Code | Patent Example Number |
|---|---|---|---|---|---|
| SPH-1542 | 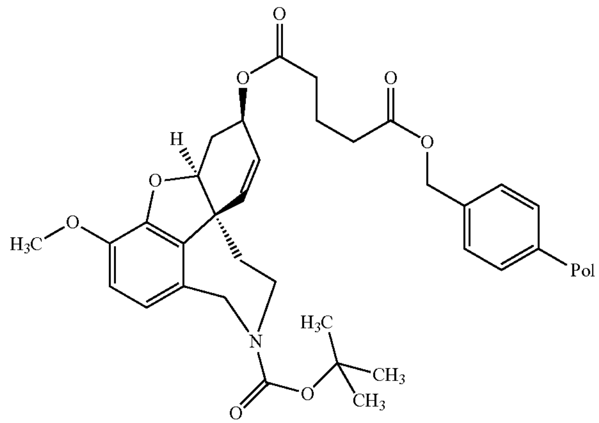 | | | CK-43-5 | 190 |
| SPH-1193 | 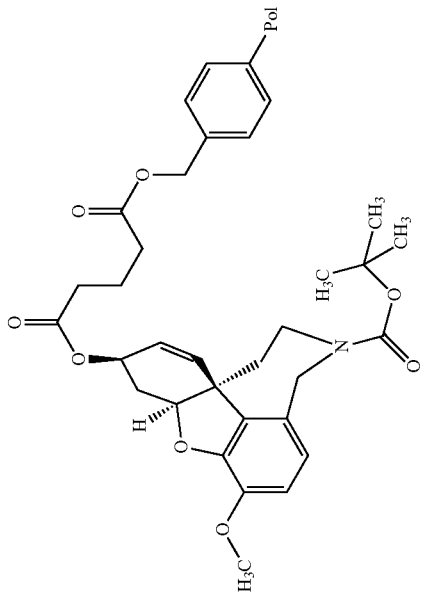 | 1.5 | 0.8 | | |

Within the scope of the invention, i.a., the compound (6R)-3-methoxy-5,6,9,10,11,12-hexahydro-4a[H1]benzo-furo[3a,3,2-ef][2]benzazepin-6-ol (norgalanthamine), specifically racemic norgalanthamine, (−) norgalanthamine and (+) norgalanthamine, is especially to be considered. Both racemic norgalanthamine and its (+)- and (−)-isomers can be used in pharmaceutical agents for treatment of the diseases mentioned above under a) to m) as active ingredients per se or in combination with other active ingredients.

The compounds according to the invention can be synthesized with proper use of the process and modes of operation for the production of galanthamine and galanthamine derivatives described in WO 96/12692 and WO 97/40049.

An addition to the above-mentioned synthesis methods, some of the compounds according to the invention can be produced with use of the combinatory (or parallel) synthesis technology. With this synthesis method, the skeleton of interest (or nuclear molecule) is immobilized in a solid phase (e.g., glass pellets, polymer pellets or another inert vehicle), which facilitates the separation of excess reactants from a modified skeleton. The solid phase that is used in each case depends on the concentration capacity, the reactants that are used and the reaction solvents. In particular, polymer pellets, such as, for example, Merriefield resin, Wang resin or TentaGel (Rapp) resin, are considered.

The immobilization of the skeleton is carried out by a functional group that can be recovered in the last step of the synthesis under suitable reaction conditions. The last step consists in the cleavage of the desired product from the solid phase. The selection of the linker unit, which couples the basic molecule to the solid phase, depends on the combination and/or the series of reactants and the reaction conditions that are necessary to obtain maximum yields and/or purity. Moreover, with different linkers, the products can be cleaved off from the same solid phase under different conditions. This technology allows a quick synthesis including automated syntheses of compounds according to the invention.

Relative to the combinatory and/or parallel synthesis, reference is made to the bibliographic references below, in which general process descriptions are included:

1) Abelson, J. N., Combinatorial Chemistry. Academic Press, San Diego (1996).

2) Epton, R., Innovation and Perspectives in Solid Phase Synthesis and Combinatorial Libraries, Mayflower Scientific Limited, Birmingham (1996).

3) Wilson, S. R. and Czarnik, A. W., Combinatorial Chemistry. Synthesis and Applications. John Wiley & Sons, Inc., New York (1997).

4) Gordon, E. M. and Kerwin, J. F. J., Combinatorial Chemistry and Molecular Diversity in Drug Discovery. John Wiley and Sons, Inc., New York (1998).

5) Thompson, L. A., Ellman, J. A. Chem. Rev. 96, 555 (1996).

6) Special Issue on Combinatorial Chemistry, cf., Acc. Chem. Res., 29, 111 (1996).

7) Fruchtel, J. S.; Jung, G. Angew. Chem. [Applied Chemistry] Int. Ed. Engl. 35, 17 (1996).

8) Cheng, S.; Comer, D. D.; Williams, J. P.; Myers, P. L.; Boger, D. L. J. Am. Chem. Soc., 118, 2567 (1996).

9) For additional information regarding this quickly developing field, see: A Dynamic Database of References in Molecular Diversity at http://www.5z.com.

10) Bayer, E.; Angew Chem. Int. Ed., 30, 113–129 (1991).

11) Mayer, J. P.; Zhang, J.; Bjergarde, K.; Lentz, D. M.; Gaudino, J. J.; Tetrahedron Letters, 37, 8081 (1996).

12) Bayer, E.; Angew. Chem. Int. Ed., 30, 113–129 (1991).

13) DE 19745628 A1.

In the example of a norgalanthamine skeleton ($G_1=G_2=G_3$=methylene; W=NH) or "homogalanthamine ($G_1=G_2=G_3$=methylene; W=CH—$NH_2$), a bond between the molecule and the solid phase can be obtained either via a carbon center (C-linked), a nitrogen center (N-linked) or an oxygen center (O-linked). The linkage points depend on the type of structural modification desired. In the reaction diagrams mentioned below by way of example, various transformations of skeletons linked by linkers to various solid phases are depicted.

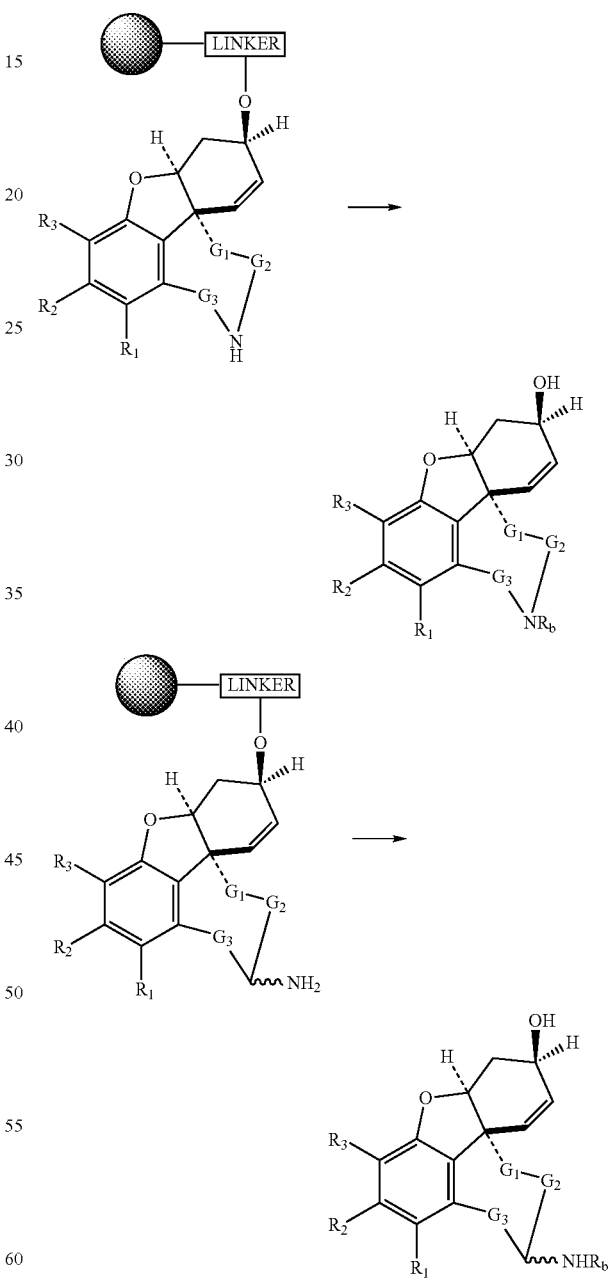

Linker = —$X(CH_2)_nCO$ (X = $CH_2$, CO, O, S, NH),
—$X(CH_2)_nOCO$ (X = $CH_2$, CO, O, S, NH),
—$XC_6H_4CH_2$— (X = $CH_2$, CO, O, S, NH), THP,
—$X(CH_2)_nSi(alkyl)_2$—, O-Linker Transformations of Skeletons of the Norganlanthamine Type and the "Homogalanthamine" Type
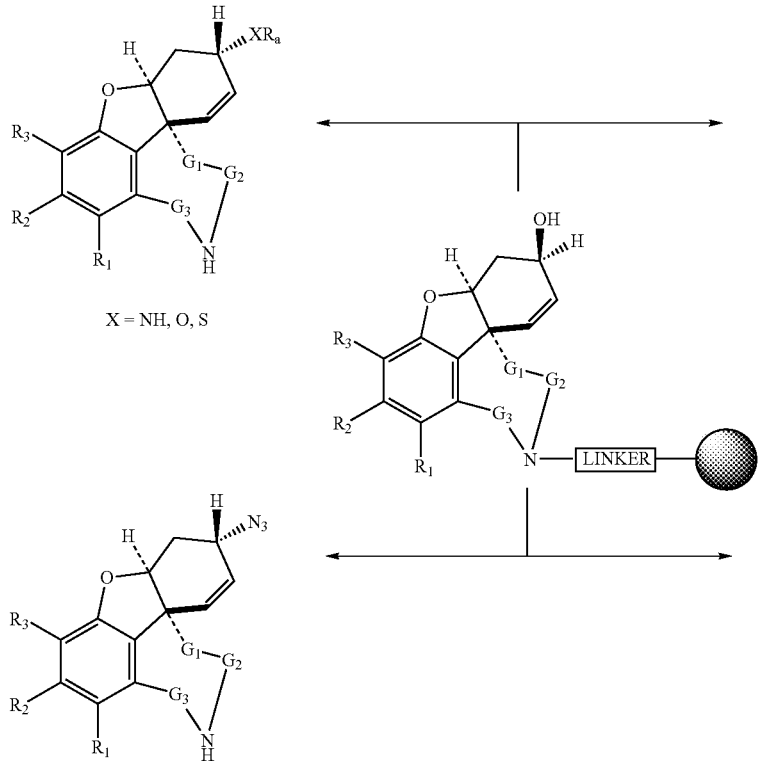
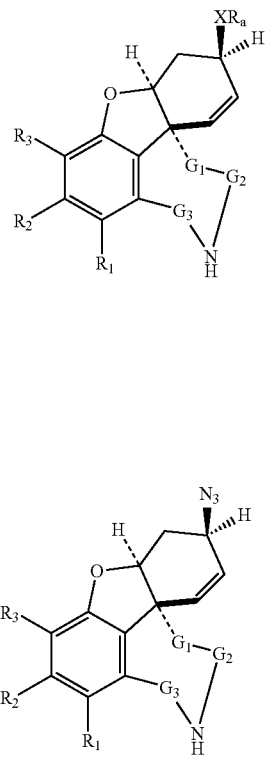
Linker = $X(CH_2)_nCO(X = CH_2, O, NH, SO_{0-2})$, $X(CH_2)_nCS(X = CH_2, O, NH, SO_{0-2})$, $X(CH_2)_nJCO(X = CH_2, O, NH, SO_{0-2}; J = NH, O, S)$, $XC_6H_4CH_2(X = CH_2, O, S)$,
N-Linker Transformations of a Molecule Skeleton of the Norgalathamine Type
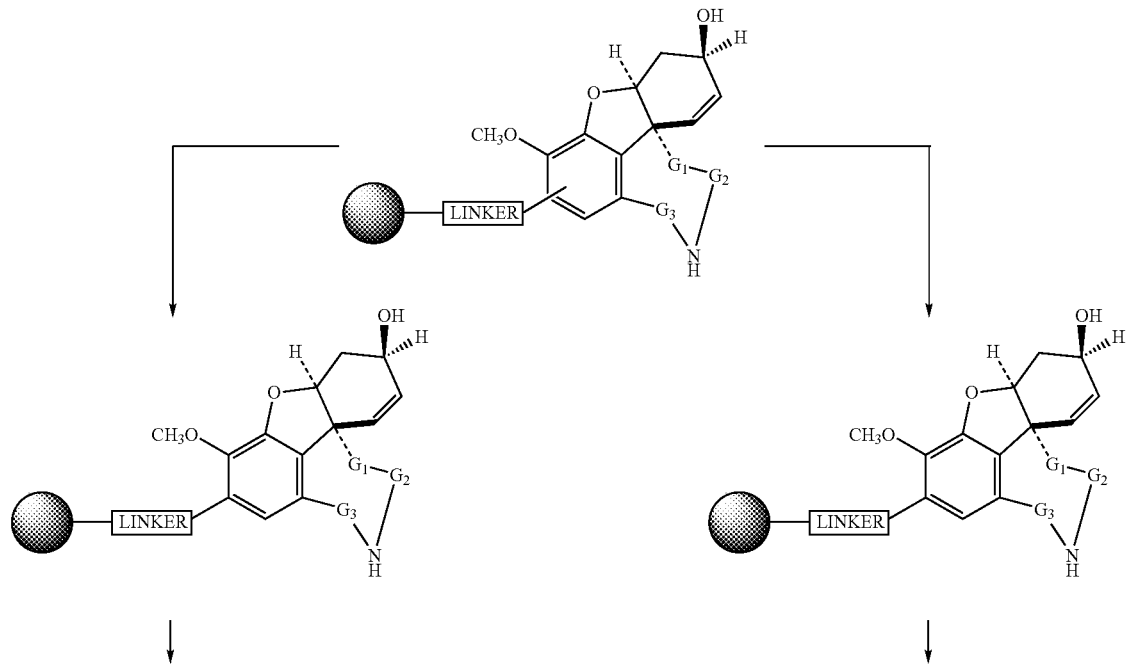

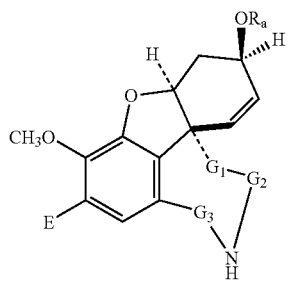

E = H, halogen, acyl, alkoxycarbonyl, NO$_2$

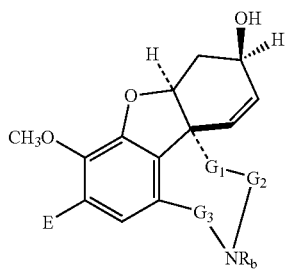

Linker = —(CH$_2$)$_n$Si(alkyl)$_2$—, —C$_6$H$_4$Si(alkyl)$_2$—,
—(CH$_2$)$_n$Sn(alkyl)$_2$—, —C$_6$H$_4$Sn(alkyl)$_2$—,
—(CH$_2$)$_n$S, —C$_6$H$_4$S C-Linker Transformations of a Skeleton of the Norgalanthamine Type

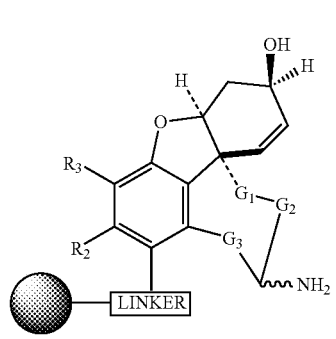

E = H, halogen, acyl, alkoxycarbonyl, NO$_2$

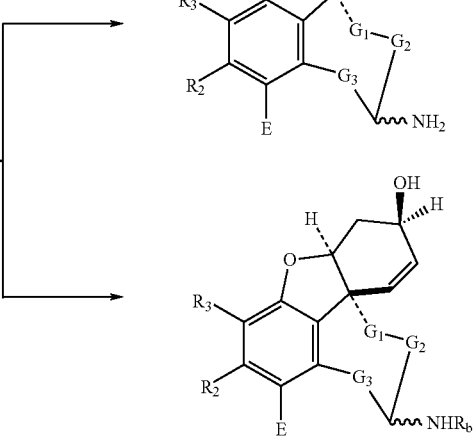

Linker = —(CH$_2$)$_n$Si(alkyl)$_2$—, —C$_6$H$_4$Si(alkyl)$_2$—,
—(CH$_2$)$_n$Sn(alkyl)$_2$—, —C$_6$H$_4$Sn(alkyl)$_2$—,
—(CH$_2$)$_n$S, —C$_6$H$_4$S C-Linker Transformations of the "Homogalanthamine Skeleton"

The compounds according to the invention, as well as pharmaceutically acceptable acid addition salts thereof can be used as active ingredients in pharmaceutical agents, for example for treating diseases with apoptotic components.

Neurodegenerative diseases of the human nervous system belong to the syndromes for which few or no causal treatment methods are now available. Neurological diseases of this type with chronic course are primarily defined as follows:

Primary degenerative dementias (primarily Alzheimer's disease),
Cerebral and spinal paralysis (amyotrophic lateral sclerosis, multiple sclerosis),
Centrally induced motor disturbances (Parkinson's disease and Huntington's disease) and
Diseases of the epileptic group.

Neurodegeneration, however, also plays a role in the immediate wake of acute neurological cases, among which primarily the following can be mentioned:

Ischemic stroke (obstruction of an artery supplying the brain),
hemorrhagic stroke (internal cerebral hemorrhage),
cranio-cerebral trauma, and
brain damage after cardiac failure or respiratory arrest (hypoxia/anoxia).

The compounds of the invention as well as pharmaceutically acceptable acid addition salts thereof can use active ingredients of pharmaceutical agents for treatment of neurodegenerative processes, whereby the primary aim is not to bring about an improvement of the acute symptoms and signs but rather a slowing and modification of the associated processes.

Within the framework of diabetes mellitus type II, there is increasing evidence of a role of amyloid fragments in the cell degeneration of the insulin-producing Langerhans' islet cells. The cell degeneration can be aggravated by a non-controlled calcium inflow.[1,2,3]

The compounds according to the invention as well as pharmaceutically acceptable acid addition salts thereof can be used as active ingredients in pharmaceutical agents, for example for treating degenerative diseases of the islet cells (such as, e.g., diabetes mellitus type II).

The compounds of the invention can be used as active ingredients in pharmaceutical agents that can be used as follows:

a) for treatment of Alzheimer's disease,
b) for treatment of Parkinson's disease,
c) for treatment of Huntington's disease (chorea),
d) for treatment of multiple sclerosis,
e) for treatment of amyotrophic lateral sclerosis,
f) for treatment of epilepsy,
g) for treatment of the sequelae of stroke,
h) for treatment of the sequelae of cranio-cerebral trauma,
i) for treatment and prophylaxis of the sequelae of diffuse oxygen and nutrient deficiency in the brain, as they are observed after hypoxia, anoxia, asphyxia, cardiac arrest, poisonings, as well as in the case of complications in difficult deliveries of infants or in the case of anesthesia,
j) especially also for prophylactic treatment of apoptotic degeneration in neurons that were or are damaged by local radiotherapy or chemotherapy of brain tumors, and
k) for treatment of bacterial meningitis and
l) for treatment of diseases with apoptotic components, especially in the wake of an amyloid-associated cell degeneration,
m) for treatment of diabetes mellitus, especially if it is accompanied by amyloid degeneration of islet cells.

The compounds according to the invention or their pharmaceutically acceptable acid addition salts, e.g., hydrobromide, hydrochloride, methyl sulfate, methiodide, tartrate, fumarate, oxalate, etc. (see table below) can be administered to patients orally, rectally or by subcutaneous, intramuscular, intravenous or intrathecal injection or infusion, or intracerebroventricularly, e.g., using an implanted container.

| English | Acid | Salt |
| --- | --- | --- |
| Sulfamic | Sulfamic acid | — |
|  | Amidosulfonic acid | Amidosulfonate |
| 1,2-ethanedisulfonic | 1,2-ethanedisulfonic acid | 1,2-ethanedisulfonate |
| 2-ethylsuccinic | 1,2-ethylsuccinic acid | 2-ethylsuccinate |
| 2-hydroxyethanesulfonic = isethionic | 2-hydroxyethanesulfonic acid | 2-hydroxyethanesulfonate |
| 3-hydroxynaphthoic | 3-hydroxynaphthoic acid | 3-hydroxynaphthoate |
| acetic | acetic acid | acetate |
| benzoic | benzoic acid | benzoate |
| benzenesulfonic | benzenesulfonic acid | benzenesulfonate |
| calcium dihydrogenedetic | calcium dihydrogen ethylenediamine tetraacetic acid | calcium ethylenediamine tetraacetate |
| camphorsulfonic | camphorsulfonic acid | camphorsulfonate |
| carbonic | carbonic acid | carbonate |
| citric | citric acid | citrate |
| dodecylsulfonic | dodecylsulfonic acid | dodecylsulfonate |
| ethanesulfonic | ethanesulfonic acid | ethanesulfonate |
| edetic | ethylenediamine tetraacetic acid | ethylenediamine tetraacetate |
| fumaric | fumaric acid | fumarate |
| glubionic | glubionic acid | glubionate |
| glucoheptonic | glucoheptonic acid | glucoheptonate |
| gluconic | gluconic acid | gluconate |
| glutamic | glutamic acid | glutamate |
| hexylresorcinic | hexylresorcylic acid | hexylresorcylate |
| HBr | hydrobromic acid | hydrobromide |
| HCl | hydrochloric acid | hydrochloride |
| bicarbonic | carbonic acid | bicarbonate |
| bitartaric | tartaric acid | hydrogen tartrate |
| hydriodic | hydriodic acid | hydriodide |
| lactic | lactic acid | lactate |
| lactobionic | lactobionic acid | lactobionate |
| laevulinic | laevulinic acid | laevulinate |
| estolic (laurylsulfuric) | laurylsulfuric acid | laurylsulfate |
| LIPOIC-(ALPHA) ACID | lipoic acid | liponate |
| malic | malic acid | malate |
| maleic | maleic acid | maleinate |
| malonic | malonic acid | malonate |
| methanesulfonic | methanesulfonic acid | methanesulfonate |
| naphthalenesulfonic | napththalenesulfonic acid | naphthalene sulfonate |
| nitric | nitric acid | nitrate |
| pantothenic | pantothenic acid | pantothenate |
| phosphoric | phosphoric acid | phosphate |
| polygalacturonic | polygalacturonic acid pectic acid | polygalacturonate |
| propionic | propionic acid | propionate |
| salicylic | salicylic acid | salicylate |
| succinic | succinic acid | succinate |
| sulfuric | sulfuric acid | sulfate |
| tartaric | tartaric acid | tartrate |

Typical dosage rates in administration of these active ingredients depend on the nature of the compound that is used and in intravenous administration are in the range of 0.01 to 2.0 mg per day and per kilogram of body weight based on the physical condition and other medications of the patient.

The following specific formulations can be used:

Tablets and capsules that contain 0.5 to 50 mg Solution for parenteral administration that contains 0.1 to 30 mg of active ingredient/ml Liquid formulations for oral administration at a concentration of 0.1 to 15 mg/ml Liquid formulations for intracerebroventricular administration, at a concentration of 1 or 5 mg of active ingredient/ml.

The compounds according to the invention can also be a transdermal system, in which 0.1 to 10 mg/day is released.

A transdermal dosage system consists of a storage layer that contains 0.1 to 30 mg of the active substance as a free base or salt in any case together with a penetration accelerator, e.g., dimethyl sulfoxide, or a carboxylic acid, e.g., octanoic acid, and a realistic-looking polyacrylate, e.g., hexylacrylate/vinyl acetate/acrylic acid copolymer including softeners, e.g., isopropylmyristat. As a covering, an active ingredient-impermeable outside layer, e.g., a metalcoated, siliconized polyethylene patch with a thickness of, for example, 0.35 mm, is used. To produce an adhesive layer, e.g., a dimethylaminomethacrylate/methacrylate copolymer in an organic solvent is used.

The invention also relates to pharmaceutical compositions that in a pharmaceutically acceptable adjuvant contains a therapeutically effective amount of at least one of the compounds that are proposed according to the invention.

The invention also extends to the use of these compounds for the production of pharmaceutical agents and processes for the production of such compounds.

In particular, the compounds according to the invention, which in many cases show a cholinesterase-inhibiting action, are suitable as therapeutic and/or prophylactic active ingredients for senile dementia, Alzheimer's disease, etc. The compounds that are proposed according to the invention are new tetracyclic, condensed, heterocyclic compounds.

In addition to the therapeutic and/or prophylactic properties, the compounds and compositions according to the invention can also be used in the diagnosis of disease conditions of the above-mentioned type.

Literature:
1) Kawahara, M.; Kuroda, Y.; Arispe, N.; Rojas, E.; "Alzheimer's Beta-Amyloid, Human Islet Amylin, and Prion Protein Fragment Evoke Intracellular Free Calcium Elevations by a Common Mechanism in a Hypothalamic BnRH Neuronal Cell Line." J Biol Chem 2000 May 12; 275 (19): 14077–83

2) Ma, Z.: Westermark, P.; Westermark, GT; "Amyloid in Human Islets of Langerhans: Immunologic Evidence that Islet Amyloid Polypeptide is Modified in Amyloidogenesis." Pancreas 2000 August; 21(2): 212–8

3) Rhoades, E.; Agarwal, J.; Gafni, A.; "Aggregation of an Amyloidogenic Fragment of Human Islet Amyloid Polypeptide." Biotin Biophys Acta 2000 Feb. 9; 1476(2): 230–8

Below, operating instructions and examples for the production of compounds according to the invention are indicated.

General Remarks

"Concentration" refers to the removal of solvents under reduced pressure by means of a rotary evaporator.

"MPLC" refers to a chromatographic purification on silica gel 20–60 μm with use of Büchi chromatography columns, a Shimadzu LC-8A pump and a Shimadzu 6AV UV detector.

EXAMPLE 1

Step 1:
4-Bromo-2-methoxy-5-(2-nitroethenyl)-phenol

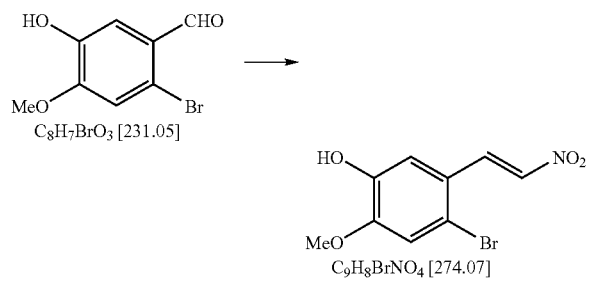

40.0 g (173 mmol) of 2-bromo-5-hydroxy-4-methoxybenzaldehyde and 13.3 g (173 mmol) of ammonium acetate are refluxed in 400 ml of nitromethane for 15 minutes. The reaction mixture is evaporated to the dry state, the residue is digested in about 70 ml of methanol and then suctioned off. To obtain a second fraction of the product, the methanol solution is concentrated by evaporation to about 30 ml and then poured onto 500 ml of water. The precipitated solid is filtered off by suction, washed with about 100 ml of water and dried together with the first fraction at 50° C./50 mbar, by which a total of 43.6 g (92% of theory) of yellow crystals is obtained on 4-bromo-2-methoxy-5-(2-nitroethenyl)-phenol with a melting point of 152–154° C.

TLC: $CH_2Cl_2$:MeOH=9:1 $^1$H-NMR ($CDCl_3$; δ (ppm): 3.85 (s, 3H, $OCH_3$); 7.30 (s, 1H, H-6); 7.38 (s, 1H, H-3); 8.03 (d, $^3J_{HH}$=13.41 Hz, 1H, ArCH=); 8.16 (d, $^3J_{HH}$=13.41 Hz, 1H, =$CHNO_2$); $^{13}$C-NMR ($CDCl_3$; δ (ppm): 56.3 (q, $OCH_3$); 114.7 (d, C-6); 116.1 (d, C-3); 116.6 (s, C-2); 121.4 (s, C-1); 136.8 (d, ArCH=); 137.6 (d, =$CHNO_2$); 146.5 (s, C-5); 152.2 (s, C-4)

Step 2:
4-Bromo-2-methoxy-5-(2-aminoethyl)-phenol

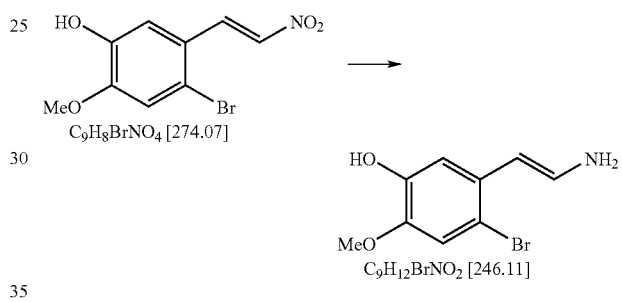

Method A:
7.2 g (74 mmol) of concentrated sulfuric acid is added in drops at 0° C. under nitrogen atmosphere to 168 ml (148 mmol) of a 0.88N lithium aluminum hydride solution in diethyl ether. 10.0 g (36.5 mmol) of 4-bromo-2-methoxy-5-(2-nitroethenyl)-phenol is partially dissolved in one liter of absolute diethyl ether in boiling heat, and then the supernatant solution is added with a transfer needle and dry nitrogen to the aluminum hydride solution at room temperature. After the addition is completed, 700 ml of diethyl ether from the reaction mixture is distilled in undissolved 4-bromo-2-methoxy-5-(2-nitroethenyl)-phenol in the receiving flask. By heating to reflux, a saturated solution is produced that is fed to the reaction mixture as above. This process is repeated (three to four times) until the addition of 4-bromo-2-methoxy-5-(2-nitroethenyl)-phenol is completed. Then, it is hydrolyzed with water at 0° C., and the ethereal phase is extracted twice with 300 ml each of 4N hydrochloric acid. The acid solution is mixed with 22.2 g (148 mmol) of L-(+)-tartaric acid, made basic with concentrated aqueous ammonia and exhaustively extracted with chloroform. The combined organic phases are washed with saturated aqueous sodium chloride solution, dried ($Na_2SO_4$), filtered and concentrated by evaporation, by which 2.20 g (24% of theory) of colorless crystals is obtained on 4-bromo-2-methoxy-5-(2-aminoethyl)-phenyl with a melting point of 170–172° C.

Method B:
A solution of 18.0 g (65.7 mmol) of 4-bromo-2-methoxy-5-(2-nitroethenyl)-phenol in 200 ml of absolute tetrahydrofuran is added in drops over the course of 2 hours under nitrogen to a reflux-heated solution of 15.0 g (394.2 mmol) of lithium aluminum hydride in 1 l of absolute tetrahydrofuran. Then, while being cooled with ice, the reaction mixture is hydrolyzed with about 20 ml of water and evaporated to the dry state. The residue is taken up in 500 ml of 2N hydrochloric acid and washed with 500 ml of ethyl acetate. The washing phase is shaken back with 200 ml of 2N hydrochloric acid, the combined aqueous phases are mixed with 70 g (467 mmol) of L-(+)-tartaric acid, made basic with concentrated aqueous ammonia and extracted three times with 800 ml of chloroform each. The combined organic phases are dried on sodium sulfate, filtered and concentrated by evaporation, by which 9.92 g (61% of theory) of colorless crystals is obtained on 4-bromo-2-methoxy-5-(2-aminoethyl)-phenol with a melting point of 170–172° C.

Step 3: 4-Bromo-5-{N-[(4-hydroxyphenyl)methyl]-2-aminoethyl}-2-methoxyphenol

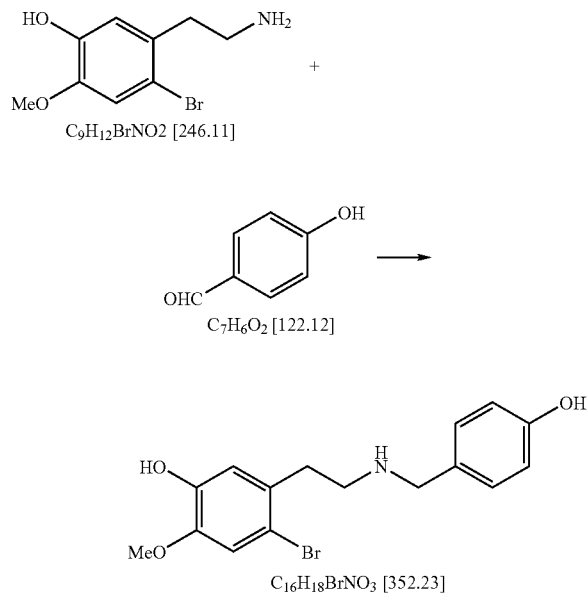

6.4 g (26.0 mmol) of 4-bromo-2-methoxy-5-(2-aminoethyl)-phenol and 3.2 g (26.0 mmol) of p-hydroxy-benzaldehyde are refluxed for 2 hours in 150 ml of absolute ethanol. Then, while being cooled with ice, 5.0 g (132.0 mmol) of sodium borohydride is added and refluxed for another half hour, the excess sodium borohydride is destroyed by adding approximately 1 ml of glacial acetic acid as well as 50 ml of water while being cooled with ice, and the solution is concentrated by evaporation. The residue is acidified with 2N hydrochloric acid and washed with 50 ml of chloroform. During hydrolysis, optionally larger solid fragments can form, which must be ground before extraction since they include large amounts of product. The washing phase is shaken back with 30 ml of 2N hydrochloric acid, the combined aqueous phases are made basic with concentrated aqueous ammonia and extracted three times with 80 ml each of ethyl acetate. The organic phases are combined, dried on sodium sulfate, filtered and concentrated by evaporation, by which 8.9 g (97% of theory) of colorless crystals is obtained on 4-bromo-5-{N-[(4-hydroxyphenyl)methyl]-2-aminoethyl}-2-methoxyphenol with a melting point of 69–72° C.

TLC: $CHCl_3$:MeOH=9:1+2% $NH_3$ $^1$H-NMR (DMSO; δ (ppm)): 2.55–2.78 (m, 4H, ArC$\underline{H}_2$C$\underline{H}_2$NH); 3.58 (s, 2H, NHC$\underline{H}_2$Ph); 3.73 (s, 3H, $OCH_3$); 6.60–6.76, 7.02–7.14 (2*m, 6H, 2*Ph); $^{13}$C-NMR (DMSO; δ (ppm)): 35.2 (t, ArCH$_2$); 48.7 (t, CH$_2$$\underline{C}$H$_2$NH); 52.2 (t, NHCH$_2$Ph); 55.9 (q, $OCH_3$); 111.3 (s, C-4); 114.8 (d, C-3'); 115.9 (d, C-6); 117.3 (d, C-3); 129.1 (d, C-2'); 130.7 (s, C-5); 131.4 (s, C-1'); 146.0 (s, C-2); 146.8 (s, C-1); 156.0 (s, C-4').

Step 4: N-[2-(2-Bromo-5-hydroxy-4-methoxyphenyl)ethyl]-N-[(4-hydroxyphenyl)methyl]formamide

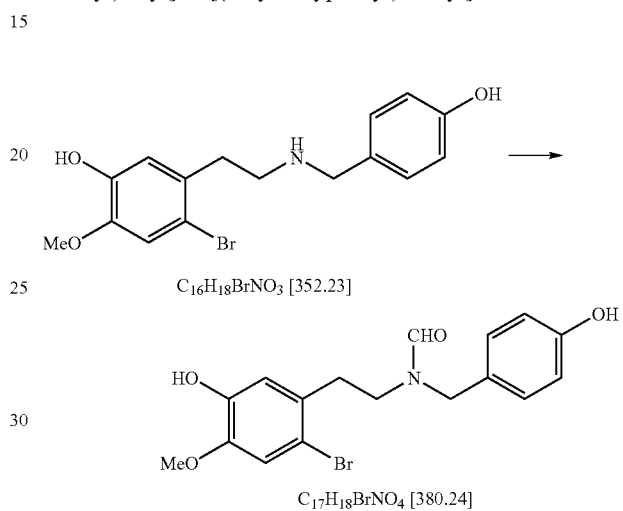

8.5 g (24.1 mmol) of 4-bromo-5-{N-[(4-hydroxyphenyl)methyl]-2-amninoethyl}-2-methoxyphenol and 10 ml (123.8 mmol) of ethyl formate are refluxed with 2.5 ml of formic acid, 10 ml of N,N-dimethylformamide and a spatula-tip full of dimethylaminopyridine in 150 ml of absolute dioxane for 24 hours. Toward the end of the reaction, the initially white suspension turns clear, and the mixture is mixed with 50 ml of water. The dioxane is distilled off, the white precipitate that is produced is filtered off by suction and washed with water, by which the first fraction product is obtained. The filtrate is extracted three times with 50 ml each of ethyl acetate, the combined organic phases are dried on sodium sulfate, filtered and concentrated by evaporation. By subsequent column chromatography (50 g of silica gel, mobile solvent: $CHCl_3$:MeOH=97:3), another fraction is obtained. Both fractions are dried at 50° C./50 mbar until a constant weight is reached, by which a total of 6.6 g (72% of theory) of colorless crystals is obtained on N-[2-(2-bromo-5-hydroxy-4-methoxyphenyl)ethyl]-N-[(4-hydroxyphenyl)methyl]-formamide with a melting point of 104–106° C.

TLC: $CHCl_3$:MeOH=9:1 $^1$H-NMR (DMSO; δ (ppm)): 2.56–2.78 (m, 2H, ArCH$_2$); 3.43–3.53 (m, 2H, CH$_2$N); 3.72 (s, 3H, $OCH_3$); 4.14 (dd, 2H, NCH$_2$Ph); 6.67–6.80, 7.00–7.11 (2*m, 6H, Ar, Ph); 9.30, 9.48 (2*s, 1H, CHO); $^{13}$C-NMR (DMSO; δ (ppm)): 32.6, 34.2 (2*t, ArCH$_2$); 41.5, 44.3 (2*t, CH$_2$N); 46.1, 50.4 (2*t, NCH$_2$Ph); 56.1 (q, $OCH_3$); 111.4, 111.6 (2*s, C-4); 115.1, 115.2 (2* d, C-6); 115.6, 115.7 (2*d, C-3'); 117.7, 118.0 (2*d, C-3); 126.8, 127.0 (2*s, C-5); 129.4 (d, C-2'); 130.0 (s, C-1'); 146.5, 146.6 (2* s, C-2); 147.5, 147.6 (2*s, C-1); 157.1, 157.5 (2*s, C-4'); 162.7, 163.0 (2*d, CHO).

Step 5: (4aα,8aα)-4a,5,9,10,11-Hexahydro-1-bromo-3-methoxy-6-oxo-6H-benzofuro[3a,3,2-ef]-[3]benzazepine-10-carboxyaldedyde

Step 6: (4aα,8aα)-4a,5,9,10,11-Hexahydro-1-bromo-3-methoxy-6H-benzofuro[3a,3,2-ef]-[3]benzazepin-6-ol

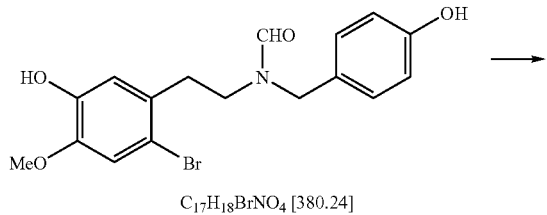

$C_{17}H_{18}BrNO_4$ [380.24]

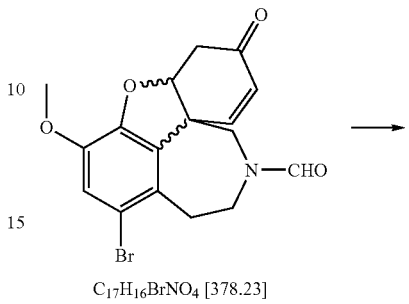

$C_{17}H_{16}BrNO_4$ [378.23]

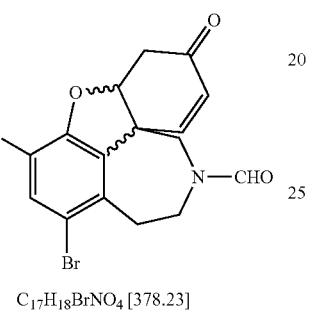

$C_{17}H_{16}BrNO_4$ [378.23]

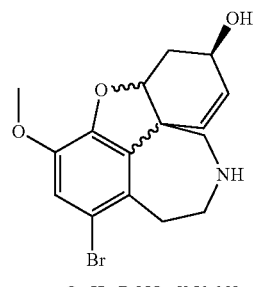

$C_{16}H_{18}BrNO_3$ [352.23]

A mixture of 13 g (39.5 mmol) of potassium hexacyanoferrate(III), 300 ml of chloroform and 50 ml of aqueous 10% potassium carbonate solution is heated to 60° C., mixed with 3 g (7.9 mMol) of N-[2-(2-bromo-5-hydroxy-4-methoxyphenyl)ethyl]-N-[(4-hydroyphenylyl)methyl]-formamide while being stirred vigorously and then mechanically stirred vigorously for another 10 minutes. Then, the brown solid that is produced is filtered off on Hyflo, rewashed three times with 30 ml each of chloroform and pressed out solid. The filtrate is then washed with about 150 ml of water, the washing phase is shaken back with 150 ml of chloroform, the combined organic phases are dried on magnesium sulfate, filtered and concentrated by evaporation. By purification on column chromatography (15 g of silica gel, mobile solvent: CHCl$_3$:MeOH=97:3), 580 mg (19% of theory) of colorless crystals with a melting point of 218–220° C. is obtained.

TLC: CHCl$_3$:MeOH=9:1 $^1$H-NMR (CDCl$_3$; δ (ppm)): 2.58–4.27 (m, 8H, H-5/5'/9/9'/11/11'/12/12'); 3.80 (s, 3H, OCH$_3$); 4.85 (dd, 1H, H-4a); 6.09 (dd, 1H, H-8); 6.53 (dd, 1H, H-7); 7.01 (s, 1H, H-2); 8.10, 8.30 (2*s, 1H, CHO$_{Conf. A/B}$); $^{13}$C-NMR (CDCl$_3$; δ (ppm)): 33.4, 35.3 (2*t, C-9$_{Conf. A/B}$); 37.2, 37.4 (2*t, C-5$_{Conf. A/B}$); 43.7 (t, C-11); 48.7, 49.0 (2*t, C-12$_{Conf. A/B}$); 50.9, 51.4 (2*s, C-8a$_{Conf. A/B}$); 56.2 (q, OCH$_3$); 83.8, 84.3 (2*s, C-4a$_{Conf. A/B}$); 115.3, 115.7 (2*s, C-1$_{Conf. A/B}$); 116.8, 117.0 (2*d, C-8$_{Conf. A/B}$); 127.6, 128.9 (2*s, C-12a$_{Conf. A/B}$); 128.0, 128.8 (2*d, C-7$_{Conf. A/B}$); 129.8, 130.8 (2*s, C-12b$_{Conf. A/B}$); 141.5, 141.7 (2*d, C-2$_{Conf. A/B}$); 143.8, 144.0 (2*s, C-3a$_{Conf. A/B}$); 146.8 (s, C-3); 161.7, 162.3 (2*d, CHO); 193.0, 193.4 (2*s, C-6); C$_{17}$H$_{16}$BrNO$_4$ (JOS 1526) 378.23 g/mol; Cld.: C 53.99 H 4.26 N 3.70 Fnd.: C 53.70 H 4.47 N 3.41

4 ml (4.00 mmol) of 1N L-selectride solution is added in drops at −12° C. under nitrogen to a solution of 500 mg (1.32 mmol) of (4aá,8aá)-4a,5,9,10,11-hexahydro-1-bromo-3-methoxy-6-oxo-6H-benzofuro[3a,3,2-ef][3]benzazepine-10-carboxaldehyde in 12 ml of absolute tetrahydrofuran, and the reaction mixture is then stirred for one hour at −10° C. Then, it is hydrolyzed with 3 ml of methanol, the solution is evaporated to the dry state, taken up in 50 ml of 2N hydrochloric acid and stirred vigorously for another hour. The aqueous solution is washed with 50 ml of ethyl acetate, the washing phase is shaken back with 20 ml of 2N hydrochloric acid, the combined aqueous phases are made basic with concentrated aqueous ammonia and extracted three times with 50 ml each of ethyl acetate. The combined organic phases are dried on magnesium sulfate, filtered and concentrated by evaporation, by which 380 mg (82% of theory) of light yellow crystals is obtained on (4aα,8aα)-4a,5,9,10,11-hexahydro-1-bromo-3-methoxy-6H-benzofuro[3a,3,2-ef][3][benzazepin-6-ol with a melting point of 132–136° C.

TLC: CHCl$_3$:MeOH=9:1 $^1$H-NMR (CDCl$_3$; δ (ppm)): 1.87 (ddd, 1H, H-5); 2.62 (ddd, 1H, H-5'); 2.68 (ddd, 1H, H-11); 2.78 (d, 1H, H-9, $^2$J$_{9/9'}$=12.6 Hz); 2.85 (ddd, 1H, H-11'); 2.98 (d, 1H, H-9', $^2$J$_{9/9'}$=12.6 Hz); 3.30 (ddd, 1H, H-12); 3.37 (ddd, 1H, H-12'); 3.80 (s, 3H, OCH$_3$); 4.08 (ddd, 1H, H-6); 4.50 (dd, 1H, H-4a); 6.08 (dd, 1H, H-8, $^3$J$_{7/8}$=10.2 Hz); 6.15 (d, 1H, H-7, $^3$J$_{7/8}$=10.2 Hz); 6.96 (s, 1H, H-2); $^{13}$C-NMR (CDCl$_3$; δ (ppm): 30.2 (t, C-5); 36.7 (t, C-9); 49.7 (t, C-11); 51.6 (s, C-8a); 56.0 (q, OCH$_3$); 57.3 (t, C-12); 62.0 (d, C-6); 85.5 (d, C-4a); 114.9 (s, C-1); 115.7 (d, C-8); 127.3 (d, C-2); 127.7 (d, C-7); 130.5 (s, C-12a); 134.2 (s, C-12b); 143.5 (s, C-3a); 145.4 (s, C-3)

Step 7: (4aα,8aα)-4a,5,9,10,11-Hexahydro-1-bromo-3-methoxy-10-methyl-6H-benzofuro[3a,3,2-ef]-[3]benzazepin-6-ol

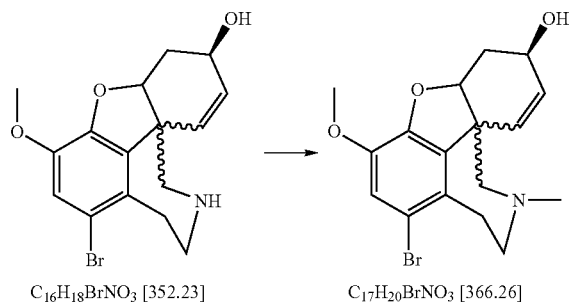

C₁₆H₁₈BrNO₃ [352.23]    C₁₇H₂₀BrNO₃ [366.26]

In succession, 1 ml of 35% aqueous formaldehyde solution and, in portions, 165 mg (2.63 mmol) of sodium cyanoborohydride are added while being stirred vigorously to a solution of 370 mg (1.05 mmol) of (4aα,8aα)-4a,5,9,10,11-hexahydro-1-bromo-3-methoxy-6H-benzofuro[3a,3,2-ef][3]benzazepin-6-ol in 12 ml of acetonitrile(and the reaction mixture is stirred vigorously at room temperature for one hour. The solution is then acidified with 2N hydrochloric acid, washed with 15 ml of dichloromethane, and the washing phase is shaken back with 15 ml of 2N hydrochloric acid. The combined organic phases are made basic with concentrated aqueous ammonia and extracted three times with 30 ml of dichloromethane each. The combined organic phases are dried on magnesium sulfate, filtered and concentrated by evaporation, by which 355 mg (92% of theory) of yellow crystals is obtained on (4aα,8aα)-4a,5,9,10,11-hexahydro-1-bromo-3-methoxy-10-methyl-6H-benzofuro[3a,3,2-ef][3]benzazepin-6-ol with a melting point of 158–161° C.

TLC: CHCl₃:MeOH=9:1 ¹H-NMR (CDCl₃; δ (ppm)): 1.91–2.04 (m, 1H, H-5); 2.27–2.48 (m, 2H, H-5'/11); 2.41 (s, 3H, NCH₃); 2.60–2.81 (m, 2H, H-9/11'); 2.92–3.16 (m, 2H, 9'/12); 3.34 (dd, ³J₁₁/₁₂'=6.37 Hz, ²J₁₂/₁₂'=16.48 Hz, 1H, H-12'); 4.13–4.25 (m, 1H, H-6); 4.58 (b, 1H, H-4a); 6.02 (dd, ³J₇/₈=10.17 Hz, ⁴J₆/₈=5.08 Hz, 1H, H-8); 6.18 (d, ³J₇/₈=10.17 Hz, 1H, H-7); 6.92 (s, 1H, H-2).

Step 8: (4aα,8aα)-4a,5,9,10,11-Hexahydro-3-methoxy-10-methyl-6H-benzofuro[3a,3,2-ef]-[3]benzazepin-6-ol A mixture that consists of 340 mg (0.93 mmol) of (4aα,8aα)-4a,5,9,10,11-hexahydro-1-bromo-3-methoxy-10-methyl-6H-benzofuro[3a,3,2-ef][3]benzazepin-6-ol and 722 mg (6.51 mmol) of calcium chloride in 40 ml of 50% ethanol is mixed with 1.4 g (22.32 mmol) of freshly activated zinc powders and refluxed for 5 hours. Then, the zinc is filtered out, it is rewashed with methanol, and the residual solution is concentrated by evaporation. The residue is taken up in 50 ml of 1N hydrochloric acid, washed with 30 ml of ethyl acetate, and the washing phase is shaken back with 20 ml of hydrochloric acid. The combined aqueous phases are made basic with concentrated aqueous ammonia and extracted three times with 50 ml each of ethyl acetate. The combined organic phases are dried on magnesium sulfate, filtered and concentrated by evaporation, by which 230 mg (86% of theory) of yellow crystals is obtained on (4aα,8aα)-4a,5,9,10,11-hexahydro-3-methoxy-10-methyl-6H-benzofuro[3a,3,2-ef][3]benzazepin-6-ol with a melting point of 152–155° C.

¹Zinc powder (Aldrich Company) mixed with 2N hydrochloric acid, thoroughly mixed, filtered off and first washed neutral with distilled water, then thoroughly rewashed with methanol TLC: EE:EtOH=9:1 (visible by oxidation in the iodine chamber); ¹H-NMR (CDCl₃; δ (ppm)): 1.90–2.04 (m, 1H, H-5); 2.26–2.46 (m, 2H, H-11/11'); 2.42 (s, 3H, NCH₃); 2.62–2.80 (m, 3H, H-5'/9/9'); 3.01–3.12 (m, 1H, H-12); 3.12–3.29 (m, 1H, H-12'); 3.83 (s, 3H, OCH₃); 4.12–4.22 (m, 1H, H-6); 4.57 (b, 1H, H-4a); 6.01 (ddd, ³J₇/₈=10.16 Hz, ⁴J₆/₈=5.18 Hz, ⁵J₇/₈=0.95 Hz; 1H, H-8); 6.22 (dd, ³J₇/₈=10.16 Hz, ⁴J₅/₇=1.09 Hz, 1H, H-7); 6.61 (d, ³J₁/₂=8.21 Hz, 1H, H-2); 6.66 (d, ³J₁/₂=8.21 Hz, 1H, H-1) ¹³C-NNR (CDCl₃; δ (ppm)): 30.0 (t, C-5); 34.5 (t, C-9); 48.9 (s, C-8a); 49.3 (q, NCH₃); 55.6 (q, OCH₃); 59.1 (t, C-11); 62.0 (d, C-6); 66.3 (t, C-12); 85.6 (d, C-4a); 111.1 (d, C-1); 121.5 (d, C-8); 126.5 (d, C-2); 128.3 (d, C-7); 130.9 (s, C-12a); 132.7 (s, C-12b); 142.9 (s, C-3a); 145.3 (s, C-3b)

EXAMPLE 2

(4aα,8aα)-4a,5,9,10,11-Hexahydro-1-bromo-6-[(4-bromophenyl)methyl]-3-methoxy-6H-benzofuro[3a,3,2-ef][3]benzazepin-6-ol

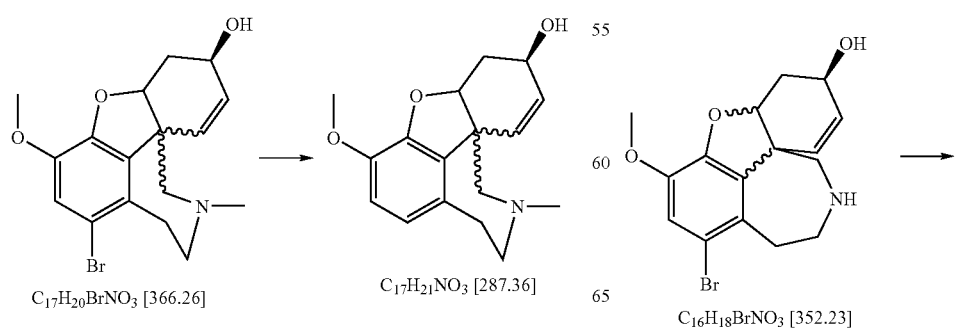

C₁₇H₂₀BrNO₃ [366.26]    C₁₇H₂₁NO₃ [287.36]    C₁₆H₁₈BrNO₃ [352.23]

-continued

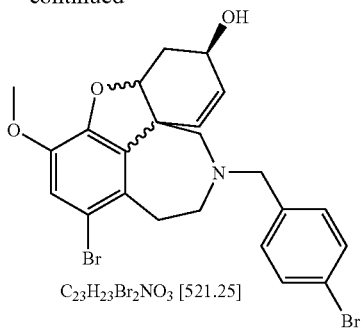

C₂₃H₂₃Br₂NO₃ [521.25]

A mixture of 23 mg (0.068 mmol) of (4aα,8aα)-4a,5,9,10,11-hexahydro-1-bromo-3-methoxy-6H-benzofuro[3a,3,2-ef][3]benzazepin-6-ol, 19 mg (0.136 mmol) of potassium carbonate and 12 mg (0.082 mmol) of sodium iodide is mixed in 20 ml of absolute acetone with 21 mg (0.082 mmol) of 4-bromobenzyl bromide and refluxed. After one hour, the reaction mixture is concentrated by evaporation, the residue is taken up in 10 ml of 2N hydrochloric acid, washed with ethyl acetate, made basic with concentrated aqueous ammonia and extracted three times with 5 ml each of ethyl acetate. The combined organic phases are washed once with saturated aqueous sodium chloride solution, dried (Na$_2$SO$_4$, activated carbon), filtered and concentrated by evaporation. Further purification is carried out via flash chromatography (15 g of silica gel; mobile solvent: CHCl$_3$→CHCl$_3$:MeOH=95:5), by which 10 mg (29% of theory) of oily substance on (4aα,8aα)-4a,5,9,10,11-hexahydro-1-bromo-6-[(4-bromophenyl)methyl]-3-methoxy-6H-benzofuro[3a,3,2-ef][3]benzazepin-6-ol is obtained.

TLC: CHCl$_3$:MeOH=9:1  $^1$H-NMR (CDCl$_3$; δ (ppm)): 1.78 (ddd, 1H, H-5); 1.98–2.31 (m, 4H, H-5'/9/11/11'); 2.70 (ddd, 1H, H-9'); 3.57 (ddd, 1H, H-12); 3.82 (s, 3H, OCH$_3$); 3.86 (ddd, 1H, H-12'); 4.15 (b, 1H, H-6); 4.42 (d, 1H, NCH$_2$); 4.65 (b, 1H, H-4a); 5.00 (d, 1H, NCH$_2$'); 5.91 (d, 1H, H-7); 6.06 (dd, 1H, H-8); 6.92 (s, 1H, H-2); 7.28 (d, 2H, Ph-2/6); 7.43 (d, 2H, Ph-3/5).

Diagrams for Examples 1 and 2

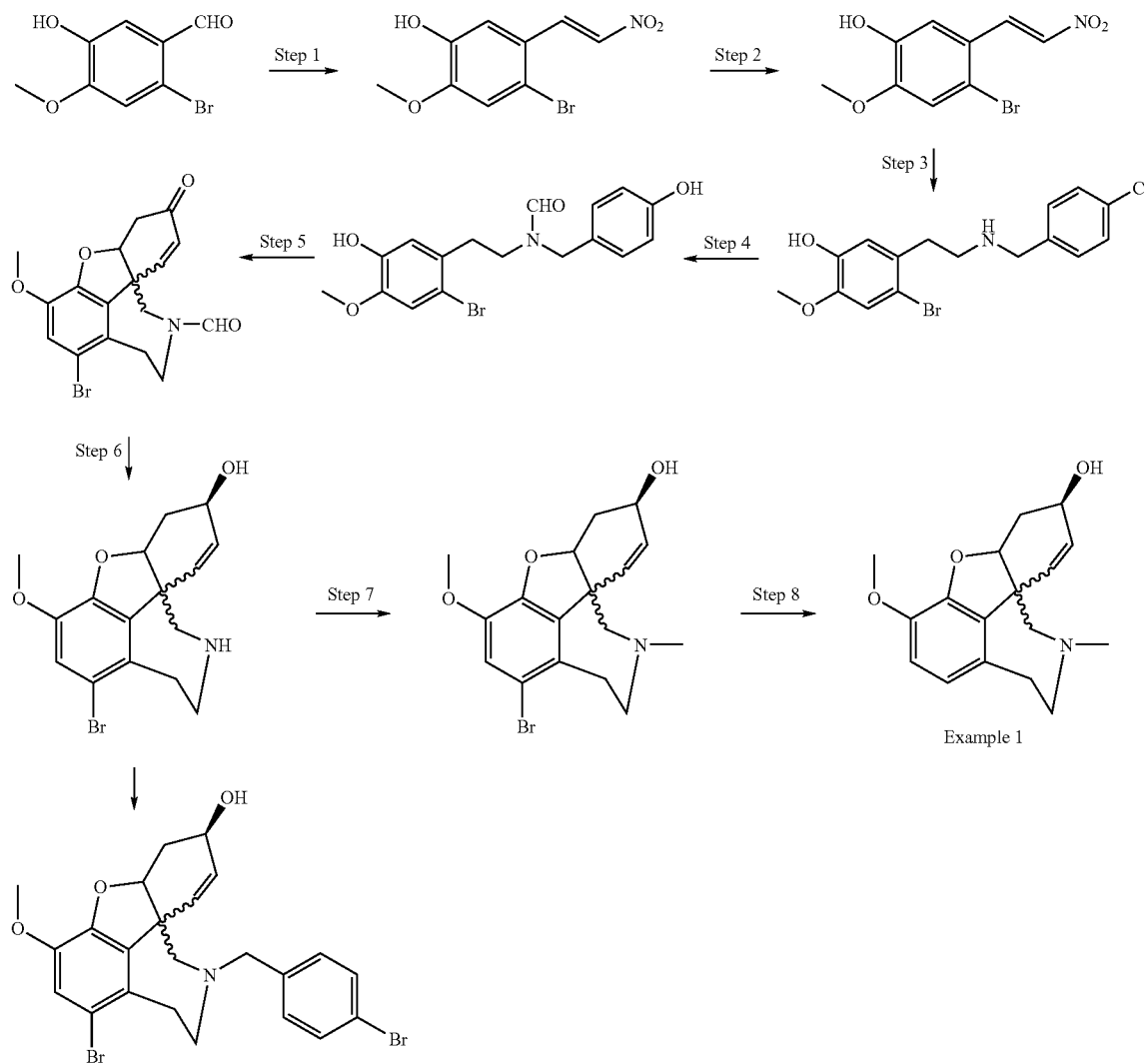

EXAMPLE 2

149

EXAMPLE 3

2-[4-[(4aS,6R,8aS)-6-Hydroxy-3-methoxy-5,6,9,10,11,12-hexahydro-4aH-benzofuro[3a,3,2-e,f][2]benzazepine-11-yl]butyl]-1,2-benzoisothiazol-3(2H)-one, 1,1-dioxide Tartrate, Dihydrate (SPH-1374)

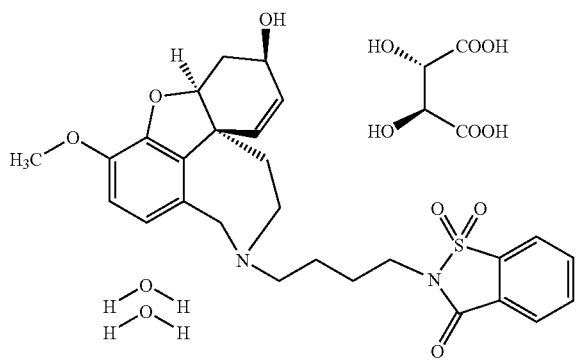

2-(6-Bromohexyl)-1,2-benzisothiazol-3(2H)-one-1,1-dioxide (2.33 g, 7.32 mmol), produced according to Hamor, G. H,; Rubessa, F.; Farmaco Ed. Sci. 1970, 25, 36–39, Norgalanthamine (2.00 g, 7.32 mmol) and N-ethyldiisopropylamine (2.84 g, 22.0 mmol) in absolute chloroform (20 ml) are stirred at boiling temperature for 24 hours.

The solvent is drawn off, and the residue is purified by column chromatography (150 g of silica gel, chloroform:methanol:ammonia:96.5:3:0.5), by which the product is obtained as a colorless foam (2.67 g, 5.23 mmol, 71.4%).

TLC: Chloroform:methanol:ammonia=89:10:1; Rf=0.5
$^1$H-NMR (CDCl$_3$): δ 8.05–7.72 (m, 4H), 6.63–6.55 (m, 2H), 6.10–5.90 (m, 2H), 4.56 (b, 1H), 4.15–4.01 (m, 2H), 3.84–3.70 (m, 6H), 3.42–3.04 (m, 2H), 2.71–2.35 (m, 4H), 2.10–1.72 (m, 4H), 1.65–1.40 (m, 2H); $^{13}$C-NMR (CDCl$_3$): δ 158.8 (s), 145.7 (s), 143.9 s), 137.5 (s), 134.6 (d), 134.1 (d), 133.0 (s), 129.4 (s), 127.4 (d), 127.2 (s), 126.8 (d), 124.9 (d), 121.8 (d), 120.7 (d), 111.0 (d), 88.5 (d), 61.9 (d), 57.5 (t), 55.7 (q), 51.4 (t), 50.5 (t), 48.3 (s), 39.1 (t), 32.9 (t), 29.8 (t), 26.0 (t), 24.5 (t)

The base (SPH-1369, 2.50 g, 4.90 mmol) and (+)-tartaric acid (0.80 g, 5.33 mmol, 1.09 equivalents) is heated in EtOH (95%, about 10 ml) until the solution turns clear (about 50° C.), and this solution is added still hot drop by drop within 5 minutes to absolute ether (about 200 ml) that is stirred with a magnet, whereby a white precipitate is produced. After standing overnight at room temperature, the crystals that are obtained are filtered off by suction and washed with absolute ether (3×50 ml), and the product is dried in a vacuum desiccator at room temperature/50 mbar on calcium chloride, whereby the tartrate dihydrate is obtained in the form of a colorless powder (3.184 g, 93.3% of theory). A sample quantity is dried at 2 mbar and 40° C. for 8 hours on phosphorus pentoxide.

150

EXAMPLE 4

2-[5-[(4aS,6R,8aS)-6-Hydroxy-3-methoxy-5,6,9,10,11,12-hexahydro-4aH-benzofuro[3a,3,2-e,f][2]benzazepine-11-yl]pentyl]-1,2-benzoisothiazol-3(2H)-one, 1,1-dioxide (SPH-1372)

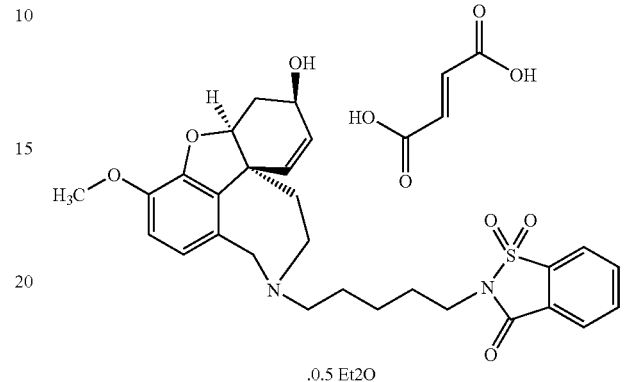

.0.5 Et2O 2-(5-Bromopentyl)-1,2-benzisothiazol-3(2H)-one-1,1-dioxide (1.66 g, 5.00 mmol), norgalanthamine (1.37 g, 5.00 mmol) and N-ethyldiisopropylamine (1.94 g, 15.0 mmol) in absolute chloroform (15 ml) are stirred for 24 hours at boiling temperature.

The solvent is drawn off, and the residue is purified by column chromatography (150 g of silica gel, chloroform:methanol:ammonia:96.5:3:0.5), by which the product is obtained as a colorless foam (2.09 g, 3.99 mmol, 79.7%).

TLC: Chloroform:methanol:ammonia=89:10:1; Rf=0.5
$^1$H-NMR (CDCl$_3$): δ 8.05–7.70 (m, 4H), 6.63–6.50 (m, 2H), 6.09–5.85 (m, 2H), 4.55 (b, 1H), 4.15–3.99 (m, 2H), 3.82–3.60 (m, 5H), 3.41–2.92 (m, 2H), 2.70–2.32 (m, 3H), 2.09–1.70 (m, 4H), 1.58–1.23 (m, 6H); $^{13}$C-NMR (CDCl$_3$): δ 158.7 (s), 145.6 (s), 143.8 (s), 137.5 (s), 134.5 (d), 134.1 (d), 133.0 (q), 129.4 (s), 127.3 (d), 127.2 (s), 126.8 (d), 124.8 (d), 121.8 (d), 120.7 (d), 111.0 (d), 88.5 (d), 61.8 (d), 57.5 (t), 55.7 (q), 51,4 (t), 51.0 (t), 48.2 (s), 39.1 (t), 32.8 (t), 29.8 (t), 28.1 (t), 26.6 (t), 24.3 (t), 20.3 (d)

Production of Fumarate (UJ-1682)

A hot (about 50° C.) solution of the base (1.686 g, 3.21 mmol) in EtOH (95%, 10 ml) is combined with saturated fumaric acid solution (10 ml, about 0.5 M in 95% ethanol), heated at about 60° C. until a clear solution is obtained, and this solution that is still hot is fed in drops within 5 minutes to absolute ether (about 200 ml) that is stirred with a magnet, whereby a white precipitate is produced. After standing overnight at room temperature, the crystals that are obtained are filtered off by suction and washed with absolute ether (3×50 ml), and the product is dried in a vacuum desiccator at room temperature/50 mbar on calcium chloride, whereby the fumarate is obtained in the form of a colorless powder (1.394 g, 67.7% of theory). A sample quantity is dried at 2 mbar and at 40° C. for 8 hours on phosphorus pentoxide. A second fraction is obtained from the mother liquor (=UJ-1682-1-2).

|  | $C_{27}H_{30}N_2O_6S \cdot C_4H_4O_4 \cdot 2\ H_2O$ (JOS 1659) (697.7) | | |
|---|---|---|---|
| Fnd. |  | C 56.18 | H 5.78 | N 4.23 |
| Cld. | a) | C 55.74 | H 5.81 | N 4.15 |
|  | b) | C 55.76 | H 5.79 | N 4.26 |

|  | $C_{28}H_{32}N_2O_6S \cdot C_4H_4O_4 \cdot \frac{1}{2}C_4H_{10}O$ (JOS 1657) (677.8) | | |
|---|---|---|---|
| Cld. | C 59.54 | H 6.21 | N 4.21 |
| Fnd. | C 59.49 | H 6.18 | N 4.20 |

EXAMPLE 5

2-[6-[(4aS,6R,8aS)-6-Hydroxy-3-methoxy-5,6,9,10,11,12-hexahydro-4aH-benzofuro[3a,3,2-e,f][2]benzazepine-11-yl]hexyl]-1,2-benzoisothiazol-3(2H)-one, 1,1-dioxide fumarate (SPH-1373)

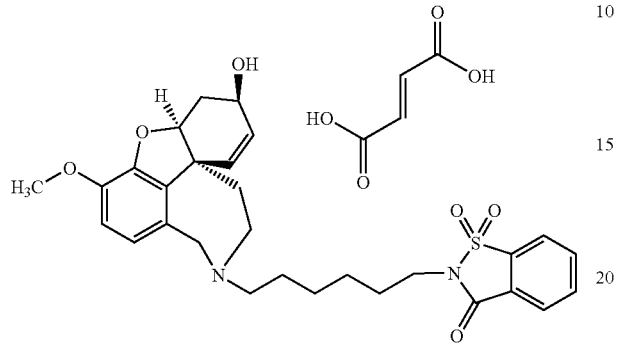

2-(6-Bromohexyl(-1,2-benzisothiazol-3(2H)-one-1,1-dioxide (1.50 g, 4.33 mmol), produced according to Kim, Sung-Kyu; Cho, Su-Dong; Moon, Jung-Kyen; Yoon, Yong-Jin. *J. Heterocycl. Chem.* (1996), 33(3), 615–618, norgalanthamine (1.18 g, 4.33 mmol) and N-ethyldiisopropylamine (1.68 g, 13.0 mmol) in absolute chloroform (15 ml) is stirred for 24 hours at boiling temperature. The solvent is drawn off, and the residue is purified by column chromatography (150 g of silica gel, chloroform:methanol:ammonia:96.5:3:0.5), by which the base is obtained as a colorless foam (1.91 g, 3.52 mmol, 81.4%).

TLC: Chloroform:methanol:ammonia=89:10:1; Rf=0.5
$^1$H NMR (CDCl$_3$): δ 8.08–7.72 (m, 4H), 6.68–6.55 m, 2H), 6.12–5.90 (m, 2H), 4.57 (b, 1), 4.16–4.01 (m, 2), 3.82–3.65 (m, 6H), 3.52–3.03 (m, 2H), 2.71–2.28 (m, 3H), 2.10–1.71 (t, 4H), 1.55–1.25 (m, 7H); 158.8 (s), 145.7 (s), 143.9 (s), 137.6 (s), 134.6 (d), 134.2 (d), 133.1 (s), 129.5 (s), 127.4 (d), 127.3 (s) 126.9 (d), 125.0 (d), 121.9 (d), 120.8 (d), 111.1 (d), 88.6 (d), 62.0 (d), 57.6 (t), 55.8 (q), 51.5 (t), 48.3 (t), 39.3 (t), 32.9 (t), 29.9 (t), 28.2 (t), 27.1 (t), 26.7 (t), 26.6 (t)

Production of Fumarate

A clear solution that is obtained by heating the base (1.33 g, 2.47 mmol) in fumaric acid solution (8 ml, saturated solution in 95% ethanol) to about 60° C. is added drop by drop within 5 minutes to absolute ether that is stirred with a magnet, whereby a white precipitate is produced. After standing overnight at room temperature, the crystals that are obtained are filtered off by suction and washed with absolute ether (3×50 ml), and the product is dried in a vacuum desiccator at room temperature/50 mbar on calcium chloride, whereby the fumarate is obtained in the form of a colorless powder (1.170 g, 72% of theory). A sample quantity is dried at 2 mbar and 40° C. for 8 hours on phosphorus pentoxide.

| C$_{29}$H$_{34}$N$_2$O$_6$S.C$_4$H$_4$O$_4$ (JOS 1658) | | | |
|---|---|---|---|
| Cld.: | C 60.54, | H 5.85, | N 4.28 |
| Fnd.: | C 60.49, | H 5.97, | N 4.22 |

EXAMPLE 6

Step 1: 2-(4-Bromobutyl)-5,6-dimethoxy-1-oxoindane-2-carboxylic acid methyl ester

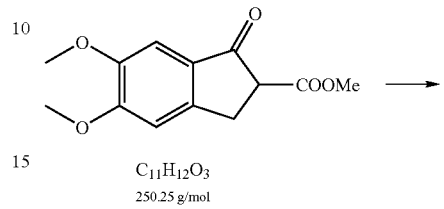

C$_{11}$H$_{12}$O$_3$
250.25 g/mol

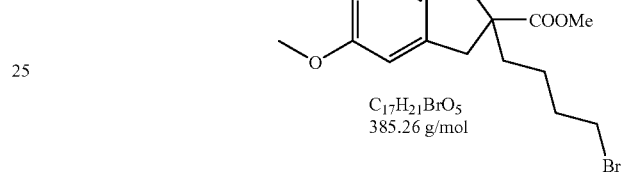

C$_{17}$H$_{21}$BrO$_5$
385.26 g/mol 5,6-Dimethoxy-1-oxoindane-2-carboxylic acid methyl ester (4.0 g, 16.0 mmol), produced according to Fukushi, Hideto; Mabuchi, Hiroshi; Itoh, Katsumi; Terashita, Zenichi; Nishikawa, Kohei; Sugihara, Hirosada; *Chem. Pharm. Bull.* 1994, 42(3), 541–550, is added in substance at room temperature to a suspension of sodium hydride (0.84 g, 17.6 mmol, 50% in white oil, released from white oil by digestion with absolute petroleum ether (3×50 ml) in absolute DMF, and the solution is stirred for 45 minutes at room temperature. Then, it is mixed with 1,4-dibromobutane (24.2 g, 112.0 mmol) and stirred for 18 hours at room temperature. It is dispersed between water and ether, the aqueous phase is extracted quantitatively with ether, the combined organic phases are washed with water (5×), saturated common salt solution (1×) and dried (sodium sulfate/activated carbon). Excess dibromoalkane under high vacuum is separated by bulb tube distillation (100° C./0.05 mbar) from the residue that is obtained after concentration by evaporation, and the residue that is obtained is recrystallized from boiling tert-butylmethyl ether (25 ml), by which the product is obtained in the form of colorless crystals (5.02 g, 13.0 mmol, 81.6%).

TLC: Petroleum ether:ethyl acetate=3:1; Rf=0.15 Melting point: 92–93° C. $^1$H NMR (CDCl$_3$): δ 7.13 (s, 1H), 6.88 (s, 1H), 3.94 (s, 3H), 3.87 (s, 3H), 3.65 (s, 3H), 3.58 (d, J=18.3 Hz, 1H), 3.33 (t, J=6.7 Hz, 2H), 2.97 (d, J=17.2 Hz, 1H), 2.20–1.99 (m, 1H), 1.95–1.73 (m, 3H), 1.53–1.26 (m, 2H); $^{13}$C NMR (CDCl$_3$): ≠7 200.7 (s), 171.6 (s), 156.1 (s), 149.7 (s), 148.5 (s), 127.7 (s), 107.1 (d), 104.8 (d), 60.6 (s), 56.2 (q), 56.0 (q), 52.6 (q), 36.3 (t), 33.6 (t), 33.2 (t), 32.6 (t), 23.1 (t)

Number, chemical displacement and multiplicity of the peaks found confirm the postulated structure

Step 2

2-(4-Bromobutyl)-5,6-dimethoxyindan-1-one

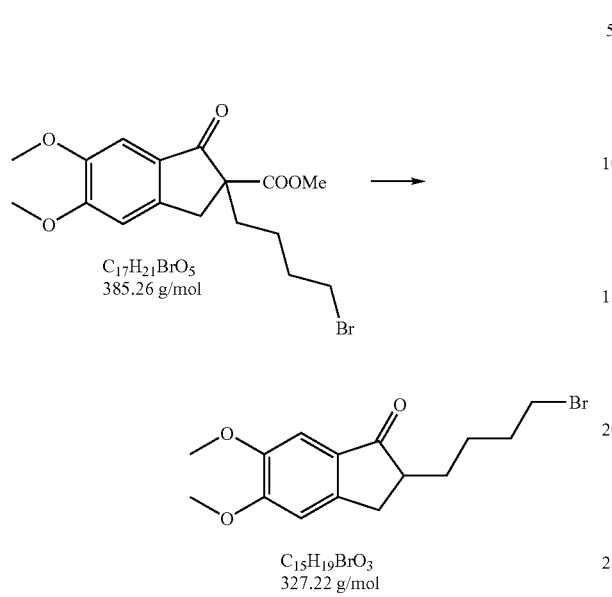

2-(4-Bromobutyl)-5,6-dimethoxy-1-oxoindane-2-carboxylic acid methyl ester (3.0 g, 7.79 mmol) is stirred in concentrated hydrochloric acid (10 ml) and acetic acid (30 ml) for 12 hours at 60° C. It is mixed with saturated sodium carbonate solution, neutralized with sodium carbonate and extracted quantitatively with ether, the combined organic phases are washed with saturated sodium carbonate solution (3×), water (1×), saturated common salt solution (1×), dried (sodium sulfate/activated carbon) and the residue that is obtained after concentration by evaporation is crystallized from tert-butylmethyl ether (10 ml). In this way, the product is obtained in the form of colorless crystals (1.85 g, 5.65 mmol, 72.5%).

TLC: Petroleum ether:ethyl acetate=3:1; Rf=0.2 Melting point: 72–73° C. $^1$H NMR (CDCl$_3$): δ 7.15 (s, 1H), 6.85 (s, 1H), 3.95 (s, 3H), 3.88 (s, 3H), 3.40 (t, J=6.8 Hz, 1H), 3.23 (dd, J=18.0 Hz, J=8.0 Hz, 1H), 2.78–2.57 (m, 2H), 2.00–1.72 (m, 3H), 1.65–1.35 (m, 3H); $^{13}$C NMR (CDCl$_3$): δ 207.1 (s), 155.5 (s), 149.4 (s), 148.8 (s), 129.3 (s), 107.3 (d), 104.3 (d), 56.1 (t), 56.0 (t), 47.4 (d), 33.5 (t), 32.6 (t), 32.5 (t), 30.6 (t), 25.8 (t)

Step 3

2-[4-(4aS,6R,8aS)-6-Hydroxy-3-methoxy-5,6,9,10,11,12-hexahydro-4aH-benzofuro[3a,3,2-e,f][2]benzazepine-11-yl]butyl]-5,6-dimethoxyindan-1-one

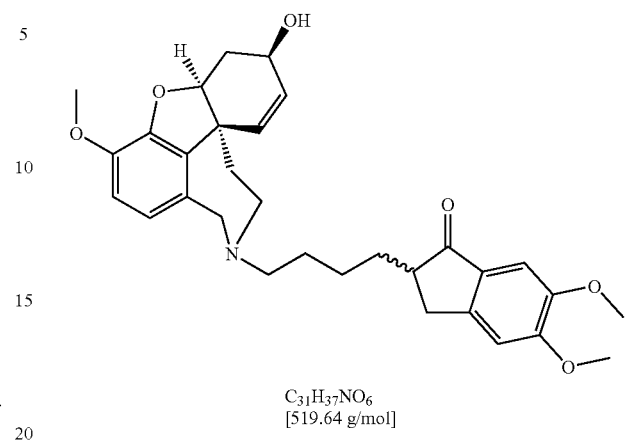

2-(4-Bromobutyl)-5,6-dimethoxyindan-1-one (1.0 g, 3.01 mmol), norgalanthamine (919 mg, 3.36 mmol) and potassium carbonate (1.26 g, 9.09 mmol, anhydrous, finely ground) are stirred at boiling temperature for 24 hours as in absolute acetonitrile (10 ml).

The reaction mixture is filtered, the solvent is drawn off, and the residue is purified by column chromatography (150 g of silica gel, chloroform:methanol:ammonia:96.5:3:0.5), by which the product is obtained as a colorless foam (1.21 g, 2.32 mmol, 77.6%).

TLC: Chloroform:methanol:ammonia:8.95:10:0.5, Rf=0.65 $^1$H-NMR (CDCl$_3$): δ 7.14 (s, 1H), 6.83 (s, 1H), 6.67–6.52 (m, 2H), 6.12–5.90 (m, 2H), 4.57 (b, 1H), 4.02–4.18 (m, 2H), 3.93 (s, 3H), 3.87 (s, 3H), 3.80 (s, 3H), 3.75 (d, J=13.7 Hz, 1H), 3.43–3.06 (m, 3H), 2.75–2.35 (m, 5H), 2.11–1.83 (m, 3H), 1.59–1.29 (m, 6H); $^{13}$C NMR (CDCl$_3$): δ 207.5 (s), 155.4 (5), 149.3 (s), 148.9 (s), 145.7 (s), 144.0 (s), 133.1 (s), 129.4 (s), 127.5 (d), 126.9 (d), 121.9 (d), 111.1 (d), 107.3 (d), 104.2 (d) 88.6 (d), 62.0 (d), 57.7 (t), 56.1 (q), 56.0 (q), 55.8 (q), 51.5 (t), 51.2 (t), 48.3 (t), 47.5 (d), 32.8 (t), 32.5 (t), 31.5 (t), 29.9 (t), 27.4 (t), 25.1 (t)

EXAMPLE 7

Step 1: 2-(5-Bromopentyl)-5,6-dimethoxy-1-oxoindane-2-carboxylic acid methyl ester

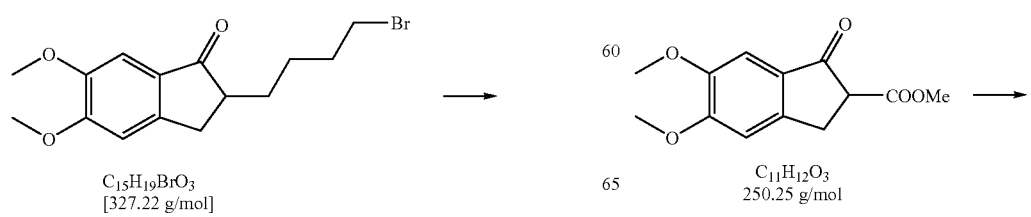

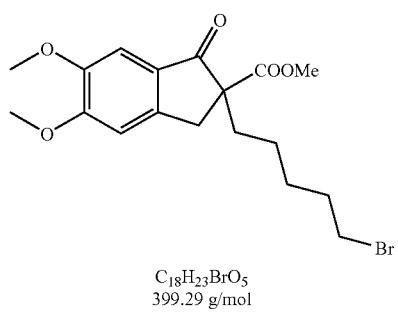

C₁₈H₂₃BrO₅
399.29 g/mol 5,6-Dimethoxy-1-oxoindane-2-carboxylic acid methyl ester (3.0 g, 12.0 mmol) is added in substance at room temperature to a suspension of sodium hydride (0.62 g, 13.2-mmol, 50% in white oil, released from white oil by digestion with absolute petroleum ether (3×50 ml)) in absolute DMF, and the solution is stirred for 45 minutes at room temperature. Then, it is mixed with 1,5-dibromopentane (19.3 g, 84.0 mmol) and stirred for 18 hours at room temperature. It is dispersed between water and ether, the aqueous phase is extracted quantitatively with ether, the combined organic phases are washed with water (5×), saturated common salt solution (1×) and dried (sodium sulfate/activated carbon). Excess dibromoalkane is separated under high vacuum by bulb tube distillation (100° C./0.05 mbar) from the residue that is obtained after concentration by evaporation, and the residue that is obtained is recrystallized from boiling tert-butylmethyl ether (20 ml), by which the product is obtained in the form of colorless crystals (3.75 g, 9.4 mmol, 78.3%).

TLC: Petroleum ether:ethyl acetate=3:1; Rf=0.15 Melting point: 108.5–110° C. ¹H NMR (CDCl₃): δ 7.15 (s, 1H), 6.89 (s, 1H), 3.96 (s, 3H), 3.89 (s, 3H), 3.67 (s, 3H), 3.60 (d, J=19.1 Hz, 1H), 3.35 (t, J=7.0 Hz, 2H), 2.96 (d, J=19.1 Hz, 1H), 2.20–1.15 (m, 8H); ¹³C NMR (CDCl₃): δ 200.9 (s), 171.8 (s), 156.1 (s), 149.7 (s), 148.4 (s), 127.9 (s), 107.1 (d), 104.9 (d), 60.8 (s), 56.2 (q), 56.1 (q), 52.6 (q), 36.4 (t), 34.5 (t), 33.5 (t), 32.3 (t), 28.3 (t), 26.9 (d), 23.7 (t)

Step 2

2-(5-Bromopentyl)-5,6-dimethoxyindan-1-one

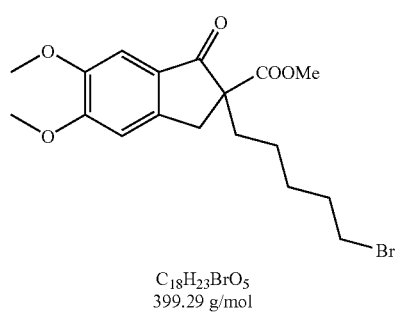

C₁₈H₂₃BrO₅
399.29 g/mol

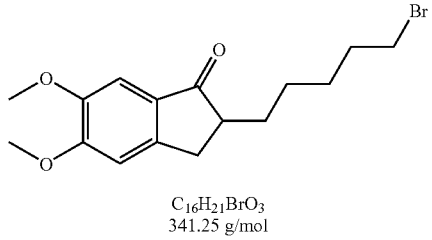

C₁₆H₂₁BrO₃
341.25 g/mol 2-(5-Bromopentyl)-5,6-dimethoxy-1-oxoindane-2-carboxylic acid methyl ester (3.0 g, 7.51 mmol) is stirred in concentrated hydrochloric acid (10 ml) and acetic acid (30 ml) for 12 hours at 60° C. It is mixed with saturated sodium carbonate solution, neutralized with sodium carbonate and extracted quantitatively with ether, the combined organic phases are washed with saturated sodium carbonate solution (3×), water (1×), saturated common salt solution (1×), dried (sodium sulfate/activated carbon), and the residue that is obtained after concentration by evaporation is crystallized from tert-butylmethyl ether (10 ml). In this way, the product is obtained in the form of colorless crystals (1.78 g, 5.22 mmol, 69.5%).

TLC: Petroleum ether:ethyl acetate=3:1; Rf=0.2 Melting point: 67.5–68.5° C. ¹H NMR (CDCl₃): δ 7.15 (s, 1H), 6.85 (s, 1H), 3.95 (s, 3H), 3.89 (s, 3H), 3.50 (t, J=7.0 Hz, 2H), 3.20 (dd, J=6.4 Hz, J=9.5 Hz, 1H), 2.72 (d, J=3.2 Hz, 1H), 2.60 (d, J=3.2 Hz, 1H), 2.00–1.65 (m, 3H), 1.55–1.35 (m, 5H); ¹³C NMR (CDCl₃): δ 207.4 (s), 155.5 (s), 149.4 (s), 148.8 (s), 129.4 (s), 107.4 (d), 104.3 (d), 56.2 (q), 56.0 (q), 47.5 (d), 44.9 (t), 32.5 (t), 32.3 (t), 31.4 (t), 26.8 (t), 26.5 (t)

Step 3

2-[5-[(4aS,6R,8aS)-6-Hydroxy-3-methoxy-5,6,9,10,11,12-hexahydro-4aH-benzofuro[3a,3,2-e,f][2]benzazepine-11-yl]pentyl]-5,6-dimethoxyindan-1-one
(SPH-1359)

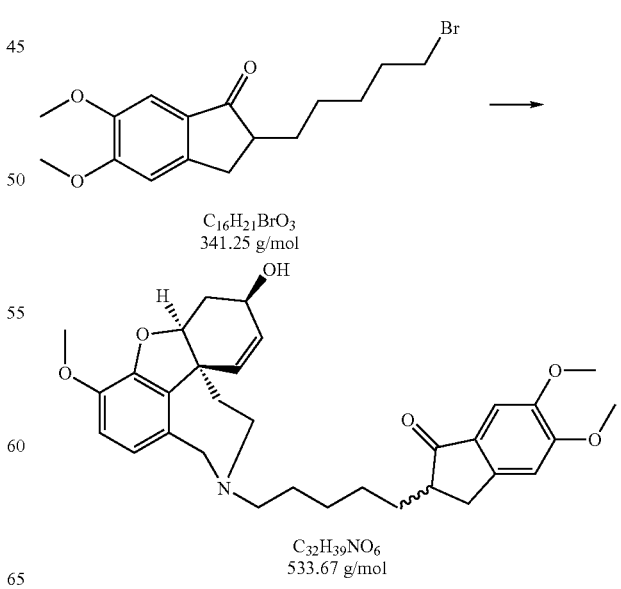

C₁₆H₂₁BrO₃
341.25 g/mol

C₃₂H₃₉NO₆
533.67 g/mol 2-(4-Bromopentyl)-5,6-dimethoxyindan-1-one (1.66 g, 4.86 mmol), norgalanthanamine (1.46 g, 5.35 mmol) and potassium carbonate (2.01 g, 14.6 mmol, anhydrous, finely ground) are stirred for 24 hours at boiling temperature as in absolute acetonitrile (10 ml).

The reaction mixture is filtered, the solvent is drawn off, and the residue is purified by column chromatography (150 g of silica gel, chloroform:methanol:ammonia:96.5:3:0.5), by which the product is obtained as a colorless foam (1.84 g, 2.32 mmol, 70.9%)

TLC: Chloroform:methanol:ammonia:89.5:10:0.5, Rf=0.65 $^1$H NMR (CDCl$_3$): δ 7.11 (s, 1H), 6.82 (s, 1H), 6.63–6.54 (m, 2H), 6.10–5.88 (m, 2H), 4.55 (b, 1H), 4.17–4.00 (m, 2H), 3.92 (s, 3H), 3.85 (s, 3H), 3.78 (s, 3l), 3.73 (d, J=13.7 Hz, 1H), 3.40–3.01 (m, 3l), 2.72–2.25 (m, 5H), 2.10–1.75 (m, 3H), 1.65–1.19 (m, 8H); $^{13}$C NMR (CDCl$_3$): δ 207.4 (s), 155.3 (s), 149.2 (s), 148.8 (5), 145.6 (s), 143.8 (s), 133.0 (s), 129.4 (s), 129.3 (s), 127.4 (d), 126.9 (d), 121.8 (d), 111.0 (d), 107.2 (d), 104.2 (d), 88.5 (d), 77.2 (d), 61.9 (d), 57.6 (t), 56.0 (q), 55.9 (q), 55.7 (q), 51.4 (t), 48.2 (s), 47.5 (d), 32.9 (t), 32.4 (t), 31.5 (t), 29.8 (t), 27.2 (t), 27.1 (t)

Production of Fumarate

A solution of the base (1.00, 1.874 mmol) in saturated fumaric acid solution (6 ml, about 0.5 M in 95% ethanol) is heated at about 60° C. until a clear solution is obtained, and this solution that is still hot is added drop by drop within 5 minutes to absolute ether (about 150 ml) that is stirred with a magnet, whereby a white precipitate is produced. After standing overnight at room temperature, the crystals that are obtained are filtered off by suction and washed with absolute ether (3×50 ml), and the product is dried in a vacuum desiccator at room temperature/50 mbar on calcium chloride, whereby the fumarate is obtained in the form of a colorless powder (0.694, 57.0% of theory). A sample quantity is dried at 2 mbar and 40° C. for 8 hours on phosphorus pentoxide. A second fraction is obtained from the mother liquor.

| $C_{32}H_{39}NO_6 \cdot C_4H_4O_4 \cdot \frac{1}{2} H_2O$ (658.7) | | | |
|---|---|---|---|
| Cld. | C 65.64 | H 6.73 | N 2.13 |
| Fnd.: | C 65.83 | H 6.72 | N 2.10 |

Formulas and Table for Examples 8–79

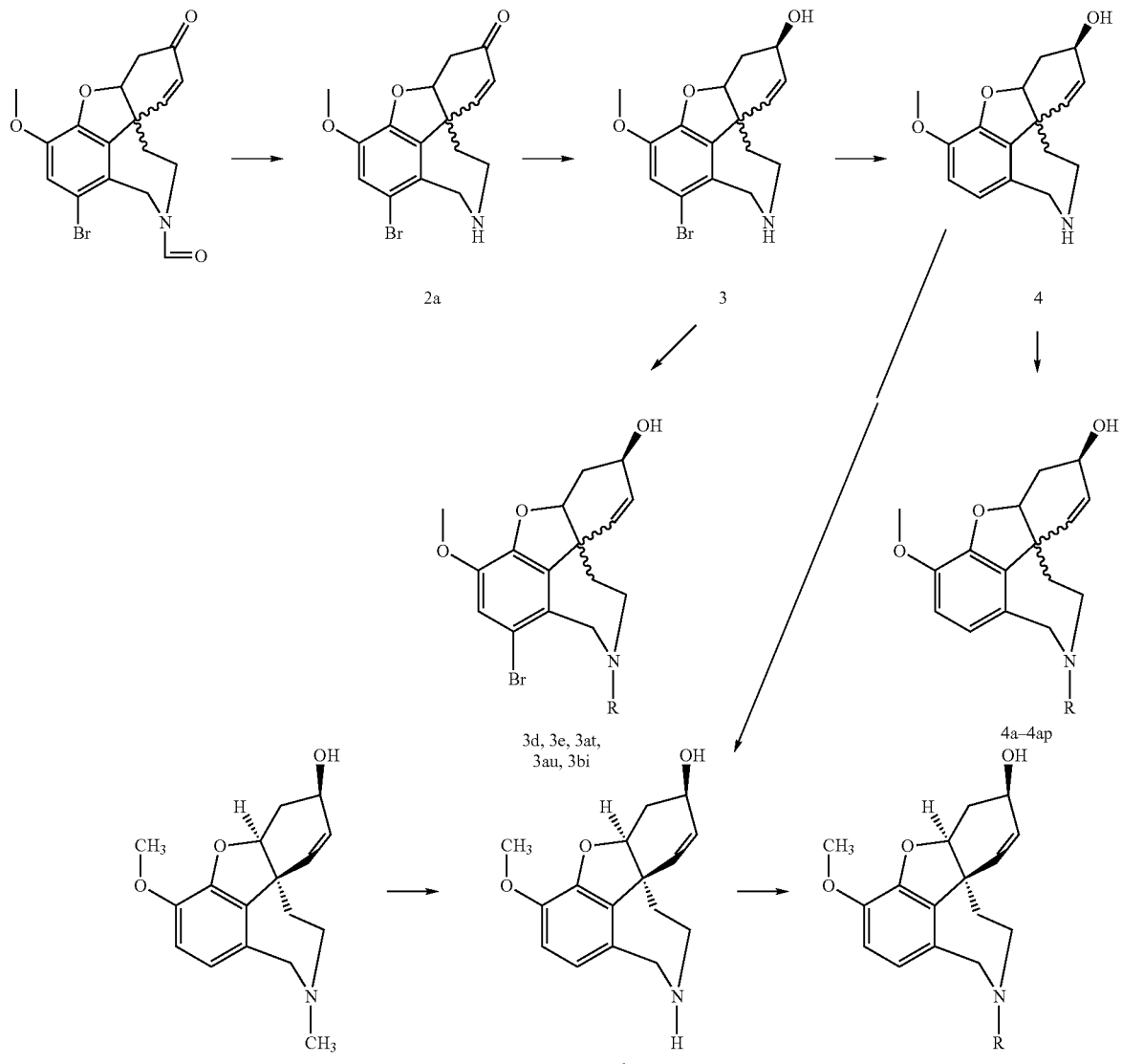

3d, 3e, 3at, 3au, 3bi

4a–4ap

8

8a–8ac: (+)-Galanthamin Derivate
9a–9e: (1)-Galanthamin Derivate

[Key:]
Galanthamin Derivate = galanthamine derivatives

| Beispiel | Nr. | SPH | BATCH LABCODE | R1 |
|---|---|---|---|---|
| 8 | 3bi | SPH-1218 | CB 30 | —C(SMe)=NCN |
| 9 | 4a | SPH-1229 | CB 52 | -pyrimidine-(2-yl) |
| 10 | 4b | SPH-1234 | CB 56 | -2-Cl-pyrimidine-(4-yl) |
| 11 | 4c | SPH-1245 | CB 59 | -2-NEt2-pyrimidine-(4yl) |
| 12 | 4d | SPH-1244 | CB 57 | -2-O(CH2)3NMe2-pyrimidine-(4-yl) |
| 13 | 4e | SPH-1230 | CB 53 | -4,6-Cl-1,3,5-triazine-(2-yl) |
| 14 | 4f | SPH-1243 | CB 58 | 4,6-di(NEt2)2-1,3,5-triazine-(2-yl) |
| 15 | 4g | SPH-1228 | CB 43 | -4,6-OPh-1,3,5-triazine-(2yl) |
| 16 | 4h | SPH-1233 | CB 51 | -4,6-di(O(CH2)2NH2-1,3,5-triazine-(2-yl) |
| 17 | 4i | SPH-1242 | CB 55 | 4,6-di(O(CH2)3NMe2-1,3,5-triazine-(2-yl) |
| 18 | 4j | SPH-1246 | MR 16 | —CO—CH2Cl |
| 19 | 4l | SPH-1214 | CB 34 | —CO—NHCH(Me)2 |
| 20 | 4m | SPH-1221 | CB 45 | —CO—NHC(Me)3 |
| 21 | 4n | SPH-1231 | CB 49 | —CONHEt |
| 22 | 4o | SPH-1222 | CB 46 | —CONH-cyclohexane |
| 23 | 4p | SPH-1215 | CB 33 | —CONHPh |
| 24 | 4q | SPH-1237 | CB 47 | —CONH-Ph(4-Cl) |
| 25 | 4r | SPH-1267 | CB 73 | —CO—NH—CH(Me)Ph,S—(–) |
| 26 | 4s | SPH-1232 | CB 50 | —CONH-2-naphthaline |
| 27 | 4t | SPH-1211 | CB 13 | —CSNHMe |
| 28 | 4u | SPH-1236 | CB 48 | —CSNHCH2CH=CH2 |
| 29 | 4v | SPH-1259 | HM 59 | —C(COOMe)=CHCOOMe |
| 30 | | SPH-1196 | TK 36-2 | —(CH2)3-(2-(4-F-phenyl)-2,5-diazabicyclo[2,2,1]heptane)-5-yl) |
| 31 | 4x | SPH-1219 | CB 36 | —CH=C(CN)2 |
| 32 | 4y | SPH-1278 | HM 60 | CH=C(COOMe)2 |
| 33 | 4z | SPH-1264 | HM 58 | —CH=CHCOCH2OEt |
| 34 | 4ac | SPH-1248 | MR 7 | —CH2—COOEt |
| 37 | 4af | SPH-1116 | Ja 6-2 | —(CH2)2—NH2 |
| 40 | 4ai | SPH-1217 | CB 28 | —(CH2)2—COOEt |
| 41 | 4aj | SPH-1277 | HM 57 | —(CH2)2—COOC(Me)3 |
| 42 | 4ak | SPH-1262 | MR 14 | —(CH2)2—CONHCHMe2 |
| 43 | 4ab | SPH-1102 | TK 72/5 | —CH2—CH=CH2 |
| 43 | 4al | SPH-1249 | MR 13 | —(CH2)2—CONHCMe3 |
| 44 | 4am | SPH-1216 | CB 35 | —(CH2)2—CN |
| 45 | 4an | SPH-1220 | CB 41 | —(CH2)3—OH |
| 46 | 4aa | SPH-1103 | TK 74/3 | -Bn |
| 46 | 4ao | SPH-1235 | CB 42 | —(CH2)3—NH2 |
| 47 | 4ap | SPH-1107 | TK 94/3 | —(CH2)3—N-piperidine |
| 48 | 8a | SPH-1280 | CB 98 | -Ph |
| 49 | 8b | SPH-1282 | CB 100 | -thiophene-2yl |
| 50 | 8c | SPH-1327 | WO 2 | -(N-benzoyl)-4-piperidine |
| 51 | 8e | SPH-1296 | CB 147 | —COOPh |
| 52 | 8f | SPH-1328 | CB 161 | —C(=S)OPb |
| 53 | 8g | SPH-1292 | CB 112 | -Fmoc |
| 54 | 8h | SPH-1326 | CB 171 | —CO—(CH2)2—CH=CH2 |
| 55 | 8i | SPH-1268 | CB 78 | —CONH2 |
| 56 | 8j | SPH-1287 | HM 109 | —CSNHMe |
| 57 | 8k | SPH-1269 | CB 85 | —CO—NHCH(Me)2 |
| 58 | 8l | SPH-1270 | CB 86 | —CO—NHC(Me)3 |
| 59 | 8m | SPH-1266 | CB 75 | —CONH-Ph(2-CF3) |
| 60 | 8n | SPH-1272 | CB 81 | —C(SMe)=NCN |
| 61 | 8o | SPH-1289 | HM 117 | —CH2-cyclopropane |
| 63 | 8r | SPH-1295 | BM 1 | —CH2—CN |
| 64 | 8s | SPH-1314 | DD 18 | —CH2—CO-(2-phenyl-2,5-diazabicyclo[2,2,1]heptane)-5-yl) |
| 65 | 8t | SPH-1311 | BM 4 | —(CH2)2—NH2 |
| 66 | 8u | SPH-1117 | Ro21 CB120 | —(CH2)2—N-morpholine |
| 67 | 8v | SPH-1329 | DD 26 | —(CH2)2-(2-phenyl-2,5-diazabicyolo[2,2,1]heptane)-5-yl) |
| 68 | 8w | SPH-1276 | CB 89 | —(CH2)2—COOH |
| 69 | 4ae | SPH-1096 | TK 81/3 | —(CH2)2—OH |
| 69 | 8x | SPH-1271 | CB 87 | —(CH2)2—COOC(Me)3 |
| 70 | 8z | SPH-1315 | | —(CH2)3—OH |
| 71 | 8aa | SPH-1213 | TK 96/3 | —(CH2)3—NMe2 |
| 72 | 4k | SPH-1104 | Ro 20 | CO(CH2)14Me |
| 72 | 8ab | SPH-1286 | HM 113 | —(CH2)3—N-piperidine |
| 73 | 4ad | SPH-1099 | TK 80-3 | —CH2—CN |
| 73 | Bac | SPH-1312 | DD 24 | —(CH2)3-(2-(4-F-phenyl)-2,5-diazabicyclo[2,2,1]heptane)-5-yl) |
| 74 | 4ag | SPH-1098 | Ro 11 | —(CH2)2—N-morpholine |
| 75 | 9a | SPH-1284 | DD 10 | —CO—NHCH(Me)2 |
| 76 | 9b | SPH-1283 | DD 9 | —CO—NHC(Me)3 |
| 77 | 9c | SPH-1118 | Ro 22 | —(CH2)2—N-morpholine |

-continued

| Beispiel Nr. | SPH | BATCH LABCODE | R1 |
|---|---|---|---|
| 78 | 9d | SPH-1330 | RMA-15 | —(CH2)3—NMe2 |
| 79 | 9e | SPH-1333 | RMA 14 | —(CH2)3—N-piperidine |

[Key:]
Beispiel = Example
—CONH-2-napthaline = —CONH-2-naphthalene

EXAMPLE 8

Step 1

(6R)-1-Bromo-3-methoxy-5,6,9,10,11,12-hexahydro-4aH-[1]benzofuro[3a,3,2-ef][2]benzazepin-6-one (2a)

Water (660 ml) and concentrated hydrochloric acid (400 ml) were added to a stirred solution of (6R)-5,6,9,10,11,12, 1-bromo-3-methoxy-6-oxo-4aH-hexahydro-benzofuro[3a,3, 2-ef][2]benzazepine-11(12H)-carboxaldehyde (2) (100.0 g, 0.26 mol) in toluene (2.6 l). The reaction mixture was refluxed for 48 hours while being stirred. The precipitate was filtered off and washed with water (3×500 ml). The phases of the hydrate were separated, and the organic phase was extracted with water (3×500 ml). The precipitate was heated with the combined, aqueous solutions of the hydrate and hot-filtered. The solution was set at pH=12 with 30% sodium hydroxide. The precipitate was filtered and dried (50° C./50 mbar) to obtain 64.5 g (70%) of title compound (2a) at about a melting point of 228–231° C. $^1$H-NMR (CDCl$_3$ δ 6.94 (dd, J$_1$=10.3, 1.9 Hz, 1H), 6.62 (s, 1H), 6.00 (d, J=10.5 Hz, 1H), 4.69 (m, 1H), 4.04 (d, J=15.9 Hz, 1H), 3.83 (d, J=15.9 Hz, 1H), 3.80 (s, 3H), 3.29 (m, 2H), 3.07 (d, J=1.9 Hz, 1H), 2.70 (dd, J$_1$=17.8 Hz, J$_2$=3.7 Hz, 1H), 2.16 (m, 1H), 1.80 (dt, J$_1$=14.0 Hz, J$_2$=2.9 Hz, 1H); $^{13}$C-NMR (CDCl$_3$) δ 194.3 (s), 146.9 (s), 143.8 (s), 135.3 (d), 130.6 (s), 129.3 (s), 126.9 (d), 121.9 (d), 111.8 (s), 87.9 (d), 56.3 (t), 55.9 (q), 51.8 (t), 49.0 (s), 37.2 (t), 33.0 (t). Anal. (C$_{16}$H$_{16}$BrNO$_3$.0.4 H$_2$O) C, H, N.

Step 2

(6R)-1-Bromo-3-methoxy-5,6,9,10,11,12-hexahydro-4aH-[1]benzofuro[3a,3,2-ef][2]benzazepin-6-ol (3)

An L-selectride solution (1 M, 276 ml, 0.276 mol) was added at −10° C. to a solution of (6R)-1-bromo-3-methoxy-5,6,9,10,11,12-hexahydro-4aH[1]benzofuro[3a,3,2-ef][2] benzazepin-6-one (2a) (64.5 g, 0.184 mol) in dry THF (1.3 l). After 30 minutes of stirring at −10 to −5° C., the reaction mixture was hydrolyzed with MeOH (80 ml) and concentrated by evaporation. The residue that was obtained was dissolved in 2N hydrochloric acid and stirred for 18 hours at room temperature. The solution was set at pH=9 with concentrated ammonia and extracted with EtOAc (3×500 ml), the combined, organic layers were washed with brine and dried (Na$_2$SO$_4$) to produce 55.9 g (90.6%) of the product. $^1$H-NMR (CDCl$_3$) δ 6.85 (s, 1H), 6.05 (m, 2H), 4.56 (b, 1H), 4.48 (d, J=14.7 Hz, 1H), 4.10 (m, 1H), 3.85 (d, J=14.7 Hz, 1H), 3.80 (s, 3H), 3.35–3.05 (m, 2H), 2.62 (m, 1H), 2.25 (m, 1H), 1.98 (d, J=13.2 Hz, 1H), 1.85–1.65 (m, 2H); $^{13}$C-NMR (CDCl$_3$) δ 145.8 (s), 144.0 (s), 134.1 (s), 131.6 (s), 127.9 (d), 126.8 (d), 115.5 (d), 113.0 (s), 88.4 (d), 61.7 (d), 56.0 (q), 52.7 (t), 49.3 (s), 46.6 (t), 29.7 (t).

Step 3

(6R)-3-Methoxy-5,6,9,10,11,12-hexahydro-4aH-[1]benzofuro[3a,3,2-ef][2]benzazepin-6-ol (=(+/−)norgalanthamine) (4)

Activated zinc (89.0 g, 1.36 mol) and calcium chloride (44.0 g, 0.40 mol) were added to a solution of (6R)-1-bromo-3-methoxy-5,6,9,10,11,12-hexahydro-4aH-[1]benzofuro[3a,3,2-ef][2]benzazepin-6-ol (3) (20.0 g, 56.8 mmol) in 50% EtOX (1000 ml). The reaction mixture was refluxed for 18 hours and filtered on Celite. The filtrate was concentrated by evaporation, the residue was diluted with 2N hydrochloric acid (500 ml) and extracted with EtOAc (3×400 ml). The pH of the aqueous phase was set at above 8.5 with concentrated ammonia and extracted with CH$_2$Cl$_2$ (3×100 ml) and with CH$_2$Cl$_2$:MeOH=9:1 (3×100 ml). The combined organic extracts were washed with brine (200 ml), dried (Na$_2$SO$_4$) and concentrated by evaporation to produce 12.3 g (79.0% of compound 4: $^1$H-NMR (CDCl$_3$) δ 6.62 (b, 2H), 6.02 (m, 2H), 4.61 (b, 1H), 4.14 (t, J=4.3 Hz, 1H), 3.98 (d, J=5.0 Hz, 2H), 3.83 (s, 3H), 3.30 (m, 1H), 2.69 (t, J=15.7, 1H), 2.10–1.63 (m, 4H); $^{13}$C-NMR (CDCl$_3$) δ 146.2 (s), 144.1 (s), 133.1 (s), 131.7 (s), 127.8 (d), 126.8 (d), 120.8 (d), 111.1 (d), 88.4 (d), 61.9 (d), 55.9 (q), 53.3 (t), 48.5 (s), 46.7 (t), 39.4 (t), 29.9 (t). Anal. (C$_{20}$H$_{26}$N$_2$O$_4$) C, H, N.

Step 4

Methyl(6R)-1-bromo-N$^{11}$-cyano-6-hydroxy-3-methoxy-5,6,9,10-tetrahydro-4aH[1]benzofuro[3a,3,2-ef] [2]benzazepine-11(12H)carboximidothioate (3bi)

0.21 g, 1.4 mmol) of N-cyanodithiocarbonimidic acid dimethyl ester (0.21 g, 1.4 mmol) was added to a solution of (+/−)-norgalanthamine (0.5 g, 1.4 mmol) in EtOH:DMF=4:1 (20 ml). The reaction mixture was refluxed for 4 days and concentrated by evaporation. The residue was crystallized in EtOH to produce 0.25 g (41.7%) of compound 3bi: $^1$H-NMR (CDCl$_3$) δ 6.90 (s, 1H), 6.05 (dd, J$_1$=10.3 Hz, J$_2$=5.0 Hz, 1H), 5.86 (d, J=10.3 Hz, 1H), 5.62 (d, J=16.5 Hz, 1H), 4.62 (b, 1H), 4.36 (d, J=16.5, 1H), 4.14 (m, 1H), 3.83 (s, 3H), 3.79 (m, 1H), 2.96 (d, J=15.3 Hz, 1H), 2.77 (s, 3H), 2.68 (m, 1H), 1.92 (m, 3H); $^{13}$C-NMR (CDCl$_3$) δ 146.3 (s), 145.0 (s), 132.7 (s), 129.0 (s), 125.4 (d), 125.2 (d), 125.2 (s), 116.0 (d), 114.3 (d), 88.0 (d), 61.3 (d), 56.1 (q), 55.0 (t), 49.6 (t), 48.6 (s), 29.4 (t), 16.1 (q). Anal. (C$_{19}$H$_{20}$BrN$_3$O$_3$S.0.85 EtOH) C, H, N.

EXAMPLE 9

(6R)-3-Methoxy-11-(2-pyrimidinyl)-5,6,9,10,11,12-hexahydro-4aH[1]benzofuro[3a,3,2-ef][2]benzazepin-6-ol (4a)

0.21 g, 1.8 mmol) of 2-chloropyrimidine and sodium bicarbonate (0.61 g, 7.2 mmol) were added to a solution of (+/−)-norgalanthamine (0.5 g 1.8 mmol) in EtOH (30 ml). The reaction mixture was refluxed for 2 days and concentrated. The residue was diluted with water (30 ml), and EtOAc (3×20 ml) was extracted. The combined, organic extracts were washed with common salt solution (20 ml), dried ($Na_2SO_4$) and concentrated by evaporation to produce 0.51 g (80.8%) of 4a: $^1$H-NMR (DMSO-d) δ 7.82 (d, J=4.0 Hz, 2H), 6.42 (d, J=12.0 Hz 1H), 6.23 (d, J=12.0 Hz, 1H), 6.03 (t, J=4.0 Hz, 1H), 5.83 (d, J=8.0 Hz, 1H), 5.54 (dd, $J_1$=8.0 Hz, $J_2$=3.0 Hz, 1H), 4.98 (d, J=14.0 Hz, 1H), 428 (d, J=16.0, 1H), 4.09 (b, 1H), 3.94 (d, J=14.0 Hz, 1H), 3.72 (m, 1H), 3.38 (s, 3H), 3.21 (t, J=14.0 Hz, 1H), 2.54 (d, J=12.0 Hz, 1H), 2.15 (m, 1H), 1.55 (m, 3H), $^{13}$C-NMR (DMSO-d) δ 159.5 (s), 156.7 (2), 145.5 (s), 1 142.8 (s), 131.6 (s), 128.9 (s), 126.8 (d), 126.1 (d), 120.8 (d) 109.9 (d), 108.8 (d), 86.8 (d), 61.3 (d), 54.8 (q), 50.2 (t), 47.3 (s), 47.4 (t), 34.6 (t), 29.2 (t). Anal. ($C_{20}H_{21}N_3O_3$.O.15 EtOH) C, H, N.

EXAMPLE 10

(6R)-11-(2-Chloro-4-pyrimidinyl)-3-methoxy-5,6,9,10,11,12-hexahydro-4aH-[1]benzofuro[3a,3,2-ef][2]benzazepin-6-ol (4b) was produced analogously to Example 9. Reaction time 40 hours, yield 0.62 g (88.6%). $^1$H-NMR ($CDCl_3$) δ 7.84 (d, J=4.0 Hz, 1H), 6.88 (d, J=12.0 Hz, 1H), 6.69 (d, J=12.0 Hz, 1H), 6.05 (b, 2H), 5.90 (d, J=4.0 Hz, 1H), 5.58 (b, 1H), 4.34 (m, 2H), 4.18 (b, 1H) 3.80 (s, 3H), 3.60 (t, J=16.0 Hz, 1H), 2.73 (d, J=16.0 Hz, 1H), 2.39 (m, 1H), 2.04 (d, J=18 Hz, 1H), 1.87 (m, 2H); $^{13}$C-NMR ($CDCl_3$) δ 160.5 (s), 158.4 (s), 157.0 (s), 145.0 (s), 144.1 (s), 132.2 (s), 128.2 (d), 127.8 (s), 126.6 (d), 126.1 (d), 111.0 (d), 107.1 (d), 88.1 (d), 61.6 (d), 55.8 (q), 53.8 (t), 48.3 (s), 46.0 (t), 34.9 (t), 29.6 (t).

EXAMPLE 11

(6R)-11-(2-Diethylamino)-4-pyrimidinyl)3-methoxy-5,6,9,10,11,12-hexahydro-4aH-[1]benzofuro]3a,3,2-ef][2]benzazepin-6-ol (4c)

0.1 g (1.30 mmol) of potassium hydroxide was added to a solution of compound 4b (0.5 g, 1.30 mmol) in diethylamine (6 ml, 57.6 mmol). The reaction mixture was refluxed for 22 hours and concentrated by evaporation. The residue was diluted with saturated solution of potassium carbonate (30 ml) and extracted with EtOAc (3×20 ml). The combined, organic phases were washed with common salt solution (20 ml), dried ($Na_2SO_4$) and concentrated by evaporation. Flash chromatography yielded 0.21 g (38.5%) of 4c. Below, only the different NMR signals are described: $^1$H-NMR ($CDCl_3$) δ 2.97 (d, J=16.0 Hz, 4H), 1.34 (m, 6H); $^{13}$C-NMR ($CDCl_3$) δ 36.3 (t), 14.0 (q).

EXAMPLE 12

(6R)-11-(2-(3-(Dimethylamino)propoxy)-4-pyrimidinyl)-3-methoxy-5,6,9,10,11,12-hexahydro-4aH-[1]benzofuro[3a,3,2-ef][2]benzazepin-6-ol (4d): The production was carried out analogously to Example 11. Reaction time 2 hours, yield 0.16 g (41.0%). Only the different NMR signals are described: $^1$H-NMR ($CDCl_3$) δ 4.34 (m, 2H), 2.28 (s, 6H), 2.00 (m, 4H); $^{13}$C-NMR ($CDCl_3$) 65.0 (t), 56.3 (t), 45.2 (q), 27.0 (t).

EXAMPLE 13

(6R)-11-(4,6-Dichloro-1,3,5-triazine-2-yl)-3-methoxy-5,6,9,10,11,12-hexahydro-4aH-[1]benzofuro[3a,3,2-ef][2]benzazepin-6-ol (4e): A solution of 2,4,6-trichloro-1,3,5-triazine (0.66 g, 3.7 mmol) in acetone (16 ml) was poured onto ice water (35 ml) and added in small portions at 0° C. to (+/−)-norgalanthamine (1.0 g, 3.7 mmol). After the addition of 2N-sodium hydroxide (2 ml), the reaction mixture was refluxed for 40 hours. The aqueous phase was extracted with EtOAc (3×30 ml). The combined, organic phases were washed with common salt solution (30 ml), dried ($Na_2SO_4$) and concentrated by evaporation, to produce 0.90 g (59.5%) of compound 4e: $^1$H-NMR ($CDCl_3$) δ 6.82 (d, J=10.0 Hz, 1H), 6.63 (d, J=10.0 Hz, 1H), 6.02 (b, 2H), 5.30 (d, J=11.0 Hz, 1H), 4.75 (d, J=16.0, 1H), 4.50 (b, 1H), 4.22 (d, J=11.0 Hz, 1H), 4.11 (b, 1H), 3.78 (s, 3H), 3.59 (m, 1H), 3.06 (m, 1H), 2.61 (d, J=16.0 Hz, 1H), 1.90 (m, 3H); $^{13}$C-NMR ($CDCl_3$) δ 207.0 (s) 171.2 (s), 163.7 (s), 146.2 (s), 143.9 (s), 132.3 (d), 129.5 (s), 127.6 (s), 126.7 (d), 121.5 (d), 110.8 (d), 88.0 (d), 61.7 (d), 55.7 (q), 51.8 (t), 48.2 (5), 43.4 (t), 35.9 (t), 29.7 (t).

Compounds 4f–4i contain the basic galanthamine skeleton, such as 4e, but are different in the nitrogen substituent. Since the proton and carbon signal of the galanthamine core are not significantly different, the NMR signals of the nitrogen substituent are relayed below.

EXAMPLE 14

(6R)-11-(4,6-Bis-(diethylamino-1,3,5-triazine-2-yl)-3-methoxy-5,6,9,10,11,12-hexahydro-4aH-[1]benzofuro[3a,3,2-ef][2]benzazepin-6-ol (4f): A solution of compound 4e (0.30 g, 0.71 mmol) in 40 ml of acetone was poured onto 100 ml of ice water, and at 0° C., a solution of diethylamine (5.7 ml, 54.7 mmol) in acetone (10 ml) was added. The reaction mixture was refluxed for 2 hours and then poured onto 200 ml of ice water. The aqueous phase was extracted with 3×100 ml of EtOAc. The combined organic phases were washed with common salt solution (100 ml), dried on sodium sulfate and concentrated by evaporation. Flash chromatography yielded 0.17 g (47.8%) of compound 4f: $^1$H-NMR ($CDCl_3$) δ 3.54 (m, 8H), 1.18 (m, 12H); $^{13}$C-NMR ($CDCl_3$) δ 41.7 (t), 13.4 (q).

EXAMPLE 15

(6R)-11-(4,6-Diphenoxy-1,3,5-triazine-2-yl)-3-methoxy-5,6,9,10,11,12-hexahydro-4aH-[1]benzofuro[3a,3,2-ef][2]benzazepin-6-ol (4 g): 6.5 g (18.3 mmol) of 2,4,6-triphenoxy-1,3,5-triazine was added to a solution of (+/−)-norgalanthamine (1.0 g, 3.74 mmol) in dioxane (60 ml). The reaction mixture was refluxed for 20 hours. The precipitate was filtered off and washed with dioxane. The filtrate was concentrated by evaporation, and flash chromatography yielded 0.91 g (45.9%) of compound 4g: $^1$H-NMR ($CDCl_3$) δ 7.42–7.03 (m, 10H); $^{13}$C-NMR ($CDCl_3$) δ 172.1 and 162.3 (s), 138.3 and 138.1 (d), 134.6 (d), 131.3 and 130.8 (d).

EXAMPLE 16

(6R)-11-(4,6-Bis-(2aminoethoxy)-1,3,5-triazine-2-yl)-3-methoxy-5,6,9,10,11,12-hexahydro-4aH-[1]benzofuro[3a,3,2-ef][2]benzazepin-6-ol (4H): The compound was produced according to the procedure indicated in Example 11, whereby the reaction time was 3 hours. 0.15 g (67.9%) of compound 4H was obtained. $^1$H-NMR (CDCl$_3$) δ 3.64 (m, 4H), 3.42 (m, 4H); $^{13}$C-NMR (CDCl$_3$) δ 61.3 (t), 42.1 (t).

EXAMPLE 17

(6R)-11-(4,6-Bis-(2-(dimethylamino)ethoxy)-1,3,5-triazine-2-yl)-3-methoxy-5,6,9,10,11,12-hexahydro-4aH-[1]benzofuro[3a,3,2-ef][2]benzazepin-6-ol (4i). According to the procedure indicated in Example 11, compound 4i was obtained at a reaction time of 3 hours in a yield of 0.16 g (59.5%): $^1$H-NMR (CDCl$_3$) δ 4.12 (q, J=6.0 Hz, 4H), 2.29 (d, J=4.0 Hz, 12H), 1.29 (m, 8H); $^{13}$C-NMR (CDCl$_3$) δ 65.6 (t), 56.0 (t), 45.2 (g), 29.2 (t).

EXAMPLE 18

2-Chloro-1-((6R)-6-hydroxy-3-methoxy-5,6,9,10-tetrahydro-4aH-[1]benzofuro[3a,3,2-ef][2]benzazepine-11(12H)-yl)-1-ethanone (4j): 0.82 g of chloroacetyl chloride (7.3 mmol) and 0.81 g (8.0 mmol) of triethylamine were added to a solution of (+/−)-norgalanthamine (2.0 g, 7.3 mmol) in dry TRF (100 ml). The reaction mixture was refluxed for 3 hours and concentrated by evaporation. The residue was diluted with 2N hydrochloric acid (100 ml) and extracted with EtOAc (3×75 ml). The aqueous phase was set at pH>8.5 with concentrated ammonia and extracted with 3×75 ml of CH$_2$Cl$_2$. The combined, organic phases were washed with common salt solution, dried on sodium sulfate and concentrated by evaporation. Flash chromatography yielded 0.20 g (7.7% of compound 4j): $^1$H-NMR (CDCl$_3$) δ 6.78 (b, 1H), 6.12 (m, 2H), 5.30 (d, J=11.0 Hz, 1H), 4.65 (m, 2H), 4.32–4.01 (m, 3H), 3.78 (s, 3H), 3.59 (m, 1H), 3.06 (m, 1H), 2.61 (d, J=16.0 Hz, 1H), 1.90 (m, 3H), $^{13}$C-NMR (CDCl$_3$) δ 166.0 (s) 146.2 (s), 144.9 (s), 132.3 (d), 128.3 (s), 127.3 (s), 126.0 (d), 120.2 (d), 111.2 (d), 88.2 (d), 61.7 (d), 55.8 (q), 52.8 (t), 48.1 (s), 45.5 (t), 41.4 (t), 35.4 (t), 29.6 (t).

EXAMPLE 19

(6R)-6-Hydroxy-N$^{11}$-isopropyl-3-methoxy-5,6,9,10-tetrahydro-4aH-[1]benzofuro[3a,3,2-ef][2]benzazepine-11(12H)carboxamide (4l): According to the procedure that is indicated in Example 11, 0.50 g of compound 4H was obtained at a reaction time of 4 hours with a melting point of 106–108° C.: 1H-NMR (CDCl$_3$) δ 6.68 (dd, J=10.3; 8.3 Hz, 2H), 6.00 (m, 2H), 4.59 (b, 1H), 4.47 (d, J=16.4 Hz, 1H), 4.31 (d, J=16.4 Hz, 1H), 4.16 (m, 1H), 3.86 (m, 1H), 3.83 (s, 3H), 3.36 (dt, J=12.6; 2.0 Hz, 1H), 2.69 (dd, J=15.7; 3.4 Hz, 1H), 2.28 (d, J=11.3 Hz, 1H), 2.02 (m, 1H), 1.88 (dd, J=12.3; 3.4 Hz, 1H), 1.77 m, 1H), 1.07 (dd, J=21.8; 6.4 Hz, 6H); $^{13}$C-NMR (CDCl$_3$) δ 156.4 (s), 146.8 (s), 144.5 (s), 132.4 (s), 129.0 (s), 127.9 (d), 126.4 (d), 120.1 (d), 111.0 (d), 88.3 (d), 61.7 (d), 55.8 (q), 51.5 (t), 48.3 (s), 45.4 (t), 42.4 (d), 36.4 (t), 29.7 (t), 23.3 (q), 23.1 (q). Anal. (C$_{20}$H$_{26}$N$_2$O$_4$), C, H, N.

Compounds 4m–4s contain the galanthamine skeleton such as 4l, but are different with respect to the nitrogen substituent. Since the proton and carbon signals of the galanthamine core do not differ from one another significantly, only the signals of the nitrogen substituent are relayed below.

EXAMPLE 20

(6R)-N$^{11}$-t-Butyl-6-hydroxy-3-methoxy-5,6,9,10-tetrahydro-4aH-[1]benzofuro[3a,3,2-ef][2]benzazepine-11(12H)-carboxamide (4m): Process according to Example 11, reaction time 3 hours, yield 0.57 g (85%); melting point 204–205° C.; $^1$H-NMR (CDCl$_3$) δ 1.24 (s, 9H); $^{13}$C-NMR (CDCl$_3$) 156.4 (s), 50.7 (s), 29.3 (q). Anal. (C$_{21}$H$_{28}$N$_2$O$_4$) C, H, N.

EXAMPLE 21

(6R)-N$^{11}$-Ethyl-6-hydroxy-3-methoxy-5,6,9,10-tetrahydro-4aH-[1]benzofuro[3a,3,2-ef][2]benzazepine-11(12H)-carboxamide (4n): Process according to Example 11, reaction time 3 hours, yield 0.61 g (98%); melting point 137–139° C.; $^1$H-NMR (CDCl$_3$) δ 3.14 (q, J=4.0 Hz, 2H), 1.04 (t, J=10 Hz, 3H); $^{13}$C-NMR (CDCl$_3$) δ 157.0 (s), 35.6 (t), 15.3 (q).

EXAMPLE 22

(6R)-N$^{11}$-Cyclohexyl-6-hydroxy-3-methoxy-5,6,9,10-tetrahydro-4aH-[1]benzofuro(3a,3,2-ef][2]benzazepine-11-(12H)-carboxamide (4o): Process according to Example 11, reaction time 5 hours, yield 0.56 g (79%); melting point 225–228° C.; $^1$H-NMR (CDCl$_3$) δ 1.24 (s, 9H); $^{13}$C-NMR (CDCl$_3$) δ 48.8 (d), 33.4 (t), 33.2 (t), 25.5 (t), 24.8 (t), 24.6 (t).

EXAMPLE 23

($^{6R}$)-6-Hydroxy-3-methoxy-N$^{11}$-phenyl-5,6,9,10-tetrahydro-4aH-[1]benzofuro[3a,3,2-ef][2]benzazepine-11-(12H)-carboxamide (4p): Process according to Example 11, reaction time 4 hours, yield 0.34 g (47%); melting point 198–199° C.; $^1$H-NMR (CDCl$_3$) δ 7.24 (m, 4H), 6.99 (q, J=4.2 Hz, 1H); $^{13}$C-NMR (CDCl$_3$) δ 154.5 (s), 138.7 (s), 128.7 (d), 122.9 (d), 119.7 (d), Anal. (C$_{23}$H$_{24}$N$_2$O$_4$, H$_2$O) C, H, N.

EXAMPLE 24

(6R)-N$^{11}$-4-Chlorophenyl-6-hydroxy-3-methoxy-5,6,9,10-tetrahydro-4aH-[1]benzofuro[3a,3,2-ef][2]benzazepine-11-(12H)-carboxamide (4q): Process according to Example 11, reaction time 5 hours, yield 0.16 g (21%); $^1$H-NMR (CDCl$_3$) δ 17.49–6.94 (m, 4H); $^{13}$C-NMR δ (CDCl$_3$) 154.1 (s), 139.1 (s), 123.4 (s), 122.9 (d), 119.7 (d).

EXAMPLE 25

(6R)-6-Hydroxy-3-methoxy-N$^{11}$-(S)-(−)α-methylbenzyl-5,6,9,10-tetrahydro-4aH-[1](benzofuro[3a,3,2-ef][2]benzazepine-11-(12H)-carboxamide (4r): Process according to Example 11, reaction time 6 hours, yield 0.66 g (58%); $^1$H-NMR (CDCl$_3$) δ 7.21 (d, J=6.0 Hz, 4H), 7.17 (m, 1H), 4.91 (m, 1H), 1.41 (dd, J=20.0; 12 Hz, 3H); $^{13}$C-NMR (CDCl$_3$) δ 156.6 and 165.4 (s), 144.5 (s), 128.3 and 128.1 (d), 126.5 and 126.4 (d), 125.9 and 125.5 (d), 46.1 (d), 22.9 and 22.6 (q).

EXAMPLE 26

(6R)-6-Hydroxy-3-methoxy-N$^{11}$-(S)-(−)α-methylbenzyl-5,6,9,10-tetrahydro-4aH-[1]benzofuro[3a,3,2-ef][2]benzazepine-11-(12H)-carboxamide (4s): Process according to Example 11, reaction time 6 hours, yield 0.66 g (58%); $^1$H-NMR (CDCl$_3$) δ 7.82 (d, J=8.0 Hz, 1H), 7.61 (d, J=6.0 Hz, 2H), 7.43 (m, 4H); $^{13}$C-NMR (CDCl$_3$) δ 155.4 (s), 134.0 (s), 133.6 (s), 132.5 (s), 128.6 (d), 127.9 (d), 125.9 (d), 125.7 (d), 125.6 (d), 125.6 (d), 121.1 (d).

EXAMPLE 27

(6R)-6-Hydroxy-3-methoxy-N$^{11}$-methyl-5,6,9,10-tetrahydro-4aH-[1]benzofuro[3a,3,2-ef][2]benzazepine-11-(12H)-carboxamide (4t): Process according to Example 11, reaction time 3 hours, yield 0.57 g (99%); melting point 219–221° C.; $^1$H-NMR (CDCl$_3$) δ 6.81 (d, J=8.3 Hz, 1H), 6.71 (d, J=8.1 Hz, 1H), 6.12 (d, J=10.3 Hz, 1H), 5.81 (dd, J=10.2; 4.4 Hz), 1H), 5.21 (d, J=15.8 Hz, 1H), 4.44 (s, 1H), 4.25 (d, J=5.5, 1H), 4.07 (b, 1H), 3.72 (s, 3H), 3.66 (m, 1H), 2.84 (d, J=3.4 Hz, 3H); 2.28 (d, J=11.2 Hz, 1H), 2.04 (d, J=20.1 Hz, 1H), 1.88 (d, J=12.1 Hz, 1H), 1.65 (d, J=13.9 Hz, 1H); $^{13}$C-NMR (CDCl$_3$) δ 182.2 (s), 147.2 (b), 144.9 (s), 132.4 (s), 128.2 (d), 126.6 (s), 126.2 (d), 120.5 (d), 111.3 (d), 88.3 (d), 61.7 (d), 55.9 (q), 53.7 (t), 50.5 (t), 48.2 (s), 35.6 (t), 32.9 (q) 29.7 (t). Anal. (C$_{18}$H$_{22}$N$_2$O$_3$S.O.05 CH$_3$C$_6$H$_5$) C, H, N.

EXAMPLE 28

(6R)-6-Hydroxy-3-methoxy-N$^{11}$-allyl-5,6,9,10-tetrahydro-4aH-[1]benzofuro[3a,3,2-ef][2]benzazepine-11-(12H)-carbothioamide (4u): Process according to Example 11, reaction time 5 hours, yield 0.47 g (70%); melting point 192–194° C.; same skeleton as 47, only the different NMR signals are relayed: $^1$H-NMR (CDCl$_3$) δ 6.85 (m, 1H), 5.13 (m, 2H), 4.14 (m, 2H); $^{13}$C-NMR (CDCl$_3$) δ 181.2 (s), 133.7 (d), 116.6 (t), 48.3 (t). Anal. (C$_{20}$H$_{24}$N$_2$O$_3$S) C, H, N.

EXAMPLE 29

((6R)-G-Hydroxy-3-methoxy-5,6,9,10-tetrahydro-4aH-[1]benzofuro[3a,3,2-ef][2]benzazepine-11-(12H)-yl-fumaric acid dimethyl ester (4v): Process according to Example 11. 0.37 g (2.61 mmol) of but-2-enedionic acid dimethyl ester was added to a solution of (+/−)-norgalanthamine (0.5 g, 1.74 mmol) in 40 ml of CH$_2$Cl$_2$, and it was stirred for 20 hours. The solvent was removed to obtain an oily product, whose flash chromatography yielded 0.28 g (39.1%) of 4v.

Melting point 112–115° C., $^1$H-NMR (CDCl$_3$) δ 6.63 (dd, J$_1$=12.6 Hz, J$_2$=8.1 Hz, 2H), 6.02 (dd, J$_1$=15.9 Hz, J$_2$=11.5 Hz, 2H), 4.77 (b, 1H), 4.59 (b, 1H), 4.22 (d, J=15.9, 1H), 4.13 (b, 1H), 3.92 (s, 3H), 3.83 (s, 3H), 3.72 (d, J=15.9 Hz, 1H), 3.59 (s, 3H); 3.46 (m, 1H), 3.19 (dt, J$_1$=15.1 Hz, J$_2$=3.1 Hz, 3H), 2.68 (dd, J$_1$=15.8 Hz, J$_2$=2.2 Hz, 1H), 2.00 (m, 1H), 1.54 (m, 1H); $^{13}$C-NMR (CDCl$_3$) δ 167.6 and 165.7 (s), 153.0 (s), 146.0 (s), 144.3 (s), 132.9 (s), 128.5 (d), 127.8 (d), 126.4 (d), 121.8 (d), 111.2 (d), 88.6 (d), 86.6 (d), 61.9 (d), 56.9 (t), 55.8 (q), 55.0 (q), 50.2 (q), 48.3 (s), 33.0 (t), 29.3 (t). Anal. (C$_{22}$H$_{25}$NO$_7$) C, H, N.

EXAMPLE 30

(6R)-11-(3-2-(4-Fluoro)phenyl-2,5-diazabicyclo[2.2.1]heptane-5-yl-propyl)-3-methoxy-5,6,9,10,11,12-hexahydro-4aH-[1]benzofuro[3a,3,2-ef][2]benzazepin-6-ol (4w): Process according to Example 11, reaction time 4 days, yield 0.14 g (63.0%); $^1$H-NMR (CDCl$_3$) δ 7.21 (m, 2H); 6.68 (m, 3H), 5.0 (s, 1H), 4.47 (d, J=14.0 Hz, 1H), 3.90 (m, 1H), 3.63 (m, 3H), 3.24 (m, 1H), 2.04 (m, 3H); $^{13}$C-NMR (CDCl$_3$) 168.0 and 167.6 (s), 146.4 (d), 144.1 (s), 127.7 and 127.5 (d), 112.5 and 112.4 (d), 67.0 (t), 57.0 and 56.8 (d), 56.8 and 56.6 (t), 51.8 and 51.6 (t), 36.6 (t); 33.7 and 33.6 (t).

EXAMPLE 31

2-((6R)-6-Hydroxy-3-methoxy-5,6,9,10-tetrahydro-4aH-[1]benzofuro[3a,3,2-ef][2]benzazepine-11(12H)-ylmethylene)-malononitrile (4x): Process according to Example 11, reaction time 6 hours, yield 0.41 g (64.8%); $^1$H-NMR (CDCl$_3$) δ 7.12 (m, 1H), 6.63 (dd, J$_1$=12.6 Hz, J$_2$=8.1 Hz, 2H), 6.02 (dd, J$_1$=15.9 Hz, J$_2$=11.5 Hz, 2H), 4.59 (b, 1H), 4.22 (d, J=15.9, 1H), 4.13 (b, 1H), 3.83 (s, 3H), 3.72 (d, J=15.9 Hz, 1H), 3.46 (m, 1H), 3.19 (dt, J$_1$=15.1 Hz, J$_2$=3.1 Hz, 3H), 2.68 (dd, J$_1$=15.8 Hz, J$_2$=2.2 Hz, 1H), 2.00 (m, 1H), 1.54 (m, 1H); $^{13}$C-NMR (CDCl$_3$) δ 157.2 and 156.8 (d), 146.0 (s), 144.3 (s), 132.9 (s), 128.5 (s), 127.8 (d), 126.4 (d), 124.2 (s), 121.8 (d), 116.8 and 116.5 (s), 115.0 and 114.7 (s), 111.2 (d), 88.6 (d), 61.9 (d), 56.9 (t), 55.8 (q), 48.3 (s), 33.0 (t), 29.8 (t).

EXAMPLE 32

2-((6R)-6-Hydroxy-3-methoxy-5,6,9,10-tetrahydro-4aH-[1]benzofuro[3a,3,2-ef][2]benzazepine-11(12H)-ylmethylene)-malonic acid diethyl ester (4y): Process according to Example 11, reaction time 21 hours, yield 0.46 g (63.3%), melting point 145–146° C., same skeleton as compound 4v, only the different NMR signals are described: $^1$H-NMR (CDCl$_3$) δ 6.83 (s, 1H), 3.43 (m, 6H); $^{13}$C-NMR (CDCl$_3$) δ 181.2 (s), 133.7 (d), 116.6 (t), 48.3 (t). Anal. (C$_{22}$H$_{25}$NO$_7$0.25 C$_6$H$_{14}$O) C, H, N.

EXAMPLE 33

3-((6R)-6-Hydroxy-3-methoxy-5,6,9,10-tetrahydro-4aH-[1]benzofuro[3a,3,2-ef][2]benzazepine-11(12H)-yl-acrylic acid ethyl ester (4z): Process according to Example 11, reaction time 20 hours, yield 0.30 g (46.2%), melting point 121–122° C., same skeleton as compound 4v, only the different NMR signals are described: $^1$H-NMR (CDCl$_3$) δ 7.40 (dd, J$_1$=16.0 Hz, J$_2$=2.0 Hz, 1H), 4.68 (d, J=16.0 Hz, 1H), 4.10 (m, 2H), 1.28 8m, 3H); $^{13}$C-NMR (CDCl$_3$) δ 169.3 and 167.8 (s), 161.1 (d), 97.5 (d), 59.0 (t), 14.5 and 14.3 (q).

Process E: A solution (+/−)-norgalanthamine (0.5 g, 1.83 mmol), 0.51 g (3.66 mmol) of potassium carbonate, (2.20 mmol) of sodium iodide and alkyl halide (2.20 mmol) in acetone (20 ml) were refluxed for 12 hours and concentrated by evaporation. The residue was dissolved in 30 ml of 2N hydrochloric acid and extracted with 1×20 ml of AcOEt. The aqueous solution was set at pH>8.5 with concentrated ammonia and extracted with AcOEt (3×20 ml). The combined, organic extracts were washed with common salt solution, dried (Na$_2$SO$_4$), concentrated by evaporation and purified by MPLC.

Compounds 4ab–4ah and 4an–4aq contain the basic galanthamine skeleton such as 4aa, but are different with respect to the nitrogen substituent. Since the proton and carbon signals of the galanthamine core are not essentially different from one another, only the NMR signals of the nitrogen substituent are relayed below.

EXAMPLE 34

Ethyl-2-((6R)-6-Hydroxy-3-methoxy-5,6,9,10-tetrahydro-4aH-[1]benzofuro[3a,3,2-ef][2]benzazepine-11(12H)- yl)acetate (4ac): According to process e with use of ethyl chloroacetate and a reaction time of 1 hour, 0.48 g of the compound (73%) was obtained; $^1$H-NMR (CDCl$_3$) δ 4.10 (m, 2H), 3.32 (s, 2H), 1.21 (t, J=7.3 Hz, 3H); $^{13}$C-NMR (CDCl$_3$) δ 170.7 (s), 60.4 (t), 58.0 (t), 14.1 (q).

EXAMPLE 35

Instructions:

Substitution in Position 1

Direct Introduction of New Substituents 3.2.1.1 [4aS-(4αa,6β,8aR*)]-4a,5,9,10,11,12-Hexahydro-1-(N,N-dimethylamino)-3-methoxy-11-methyl-6H-benzofuro[3a,3,2-ef][2]benzazepin-6-ol, 1-(N,N-dimethylamino)-galanthamine (MH-7)

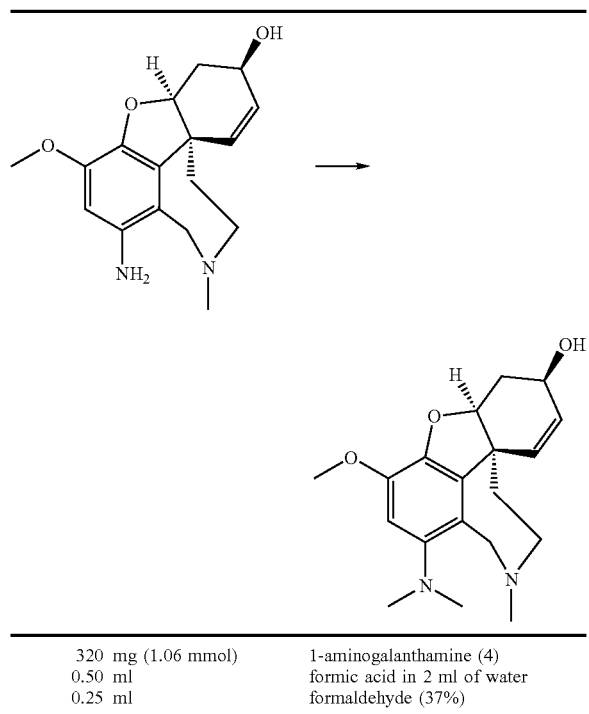

| 320 mg (1.06 mmol) | 1-aminogalanthamine (4) |
| 0.50 ml | formic acid in 2 ml of water |
| 0.25 ml | formaldehyde (37%) |

While being stirred with a magnet, all reactants, dissolved in 10 ml of water, were heated together to 70° C. After 4.5 hours, it was made basic with concentrated aqueous ammonia, whereby a white precipitate in yellow solution precipitated. The reaction mixture was exhaustively extracted with ethyl acetate, the combined organic phases were dried on sodium sulfate, filtered, and the solvent was drawn off.

The resulting substance mixture was separated on a silica gel column (CHCl$_3$:MeOH=1:1) and then distilled under high vacuum by means of a bulb tube.

Yield: 0.17 g (0.52 mmol=49% of theory) of a light yellow oil C$_{19}$H$_{26}$N$_2$O$_3$[330.43]TLC: R$_f$=0.49 (CHCl$_3$:MeOH=1:1) Boiling point: 180° C./0.01 Torr αD$^{20}$ [c=0.1, CHCl$_3$]=−156.36° FID Numbers: $^1$H:MHEMOF.016, $^{13}$C: MHEM1F.002, DEPT:MHEM2F.002 $^1$H-NMR (200 MHz, CDCl$_3$) δ 6.57 (s, 1H), 6.08 (dd, J=10.3, 1.0 Hz, 1H), 5.97 (dd, J=10.3, 4.8 Hz, 1H), 4.56 (bs, 1H), 4.45 (d, J=15.1 Hz, 1H), 4.12 (bs, 1H), 3.83 (s, 3H), 3.55 (d, J=15.1 Hz, 1H), 3.12 (td, J=13.1, 1.7 Hz, 1H), 2.97 (dt, J=14.1, 3.5 Hz, 1H), 2.72–2.53 (m, 1H), 2.58 (s, 6H), 2.44 (s, 3H), 2.12–1.98 (m, 2H), 1.62 (ddd, J=13.6, 3.8, 2.1 Hz, 1H); $^{13}$C-NMR (50 MHz, CDCl$_3$) δ 147.1 (s), 143.2 (s), 142.0 (s), 133.7 (s), 127.3 (d), 127.2 (d), 124.2 (s), 103.9 (d), 88.3 (d), 62.0 (d), 55.9 (q), 54.4 (t), 54.1 (t), 48.4 (s), 45.7 (q), 44.2 (q), 34.8 (t), 29.8 (t)

EXAMPLE 37

(4aS,6R,8aS)-11-(3-Aminoethyl)-3-methoxy-5,6,9,10,11,12-hexahydro-4aH-[1]benzofuro[3a,3,2-ef][2]benzazepin-6-ol (4af), Process F, reactant compound 4ad, reaction time 1 hour; yield 0.31 g (59.2%); melting point 47–51° C.; 1H-NMR (CDCl$_3$) δ 2.69 (m, 2H), 1.92 (b, 2H); $^{13}$C-NMR (CDCl$_3$) δ 51.9 (s), 38.0 (t).

EXAMPLE 40

Ethyl-3-((6R)-6-hydroxy-3-methoxy-5,6,9,10-tetrahydro-4aH-[1]benzofuro[3a,3,2-ef][2]benzazepine-11(12H)-yl)propanoate (4ai): Process B, reaction time 4 hours; yield 0.64 g (47.5%); $^1$H-NMR (CDCl$_3$) δ 4.15 (q, J=6.0 Hz, 2H), 2.81 (t, 7.0 Hz, 2H), 2.47 (t, J=7.0 Hz, 2H), 1.23 (t, J=6 Hz, 3H); $^{13}$C-NMR (CDCl$_3$) δ 172.4 (s), 60.3 (t), 57.3 (t), 32.9 (t), 14.1 (q).

EXAMPLE 41 t-Butyl-3-((6R)-6-Hydroxy-3-methoxy-5,6,9,10-tetrahydro-4aH-[1]benzofuro[3a,3,2-ef][2]benzazepine-11(12H)-yl)propanoate (4aj): Process B, reaction time 5 hours; yield 0.83 g (60.0%); $^1$H-NMR (CDCl$_3$) δ 2.82 (t, J=7.0 Hz, 2H), 2.40 (t, J=7.0 Hz, 2H), 1.43 (s, 9H); $^{13}$C-NMR (CDCl$_3$) δ 172.0 (s), 80.5 (s), 57.7 (t), 34.2 (t), 28.0 (q). Anal. (C$_{24}$H$_{33}$NO$_5$) C, H, N.

EXAMPLE 42

3-((6R)-6-Hydroxy-3-methoxy-5,6,9,10-tetrahydro-4aH-[1]benzofuro[3a,3,2-ef][2]benzazepine-11(12H)-yl)-N$^{11}$-isopropylpropanamide (4ak): Process B, reaction time 18 hours; yield 0.55 g (78.7%); $^1$H-NMR (CDCl$_3$) δ 3.81 (m, 1H), 2.79 (t, J=6Hz, 2H), 2.32 (t, J=6.0 Hz, 2H), 1.10 (t, J=12.0 Hz, 6H); $^{13}$C-NMR (CDCl$_3$) δ 171.4 (s), 56.9 (t), 40.7 (d), 33.2 (t), 22.7 (q).

EXAMPLE 43

3-((6R)-6-Hydroxy-3-methoxy-5,6,9,10-tetrahydro-4aH-[1]benzofuro[3a,3,2-ef][2]benzazepine-11(12H)-yl)-N1-t-butylpropanamide (4al): Process B, reaction time 24 hours; yield 0.37 g (51.2%); $^1$H-NMR (CDCl$_3$) δ 2.76 (t, 6.0 Hz, 2H), 2.29 (m, 2H), 1.28 (s, 9H); $^{13}$C-NMR (CDCl$_3$) δ 171.4 (s), 51.4 (t), 50.3 (s), 33.5 (t), 28.7 (q).

EXAMPLE 44

3-((6R)-6-Hydroxy-3-methoxy-5,6,9,10-tetrahydro-4aH-[1]benzofuro[3a,3,2-ef][2]benzazepine-11(12H)-yl)propanitrile (4am): Process B, reaction time 4 hours; yield 0.53 g (90.6%); $^1$H-NMR (CDCl$_3$) δ 2.82 (t, J=7.1 Hz, 2H), 2.47 (t, J=6.8 Hz, 2H); $^{13}$C-NMR (CDCl$_3$) δ 118.7 (s), 51.6 (t), 46.6 (t), 16.7 (t).

EXAMPLE 45

(6R)-11-(3-Hydroxypropyl)-3-methoxy-5,6,9,10,11,12-hexahydro-4aH-[1]benzofuro[3a,3,2-ef][2]benzazepin-6-ol (4an): Process F, reactant compound 4ai, reaction time 7 hours; yield 0.21 g (47.7%); $^1$H-NMR (CDCl$_3$) δ 3.77 (m, 2H), 2.72 (m, 2H), 2.02 (m, 2H); $^{13}$C-NMR (CDCl$_3$) δ 3.9 (t), 57.3 (t), 29.8 (t).

EXAMPLE 46

(6R)-11-(3-Aminopropyl)-3-methoxy-5,6,9,10-tetrahydro-4aH-[1]benzofuro[3a,3,2-ef][2]benzazepin-6-ol (4ao): Process F, reactant compound 4am, reaction time 1 hour; yield 78 mg (52.8%); $^1$H-NMR (CDCl$_3$) δ 3.22 (m, 2H), 2.68 (m, 2H), 1.72 (m, 2H); $^{13}$C-NMR (CDCl$_3$) δ 51.3 (t), 37.8 (t), 29.3 (t).

EXAMPLE 47

(6R)-11-(3-Piperidine-1-yl-propyl)-3-methoxy-5,6,9,10-hexahydro-4aH-[1]benzofuro[3a,3,2-ef][2]benzazepin-6-ol (4ap): Process e, reaction time 3 days; yield 0.36 g (53.2%); $^1$H-NMR (CDCl$_3$) δ 2.68 (m, 8H), 1.77 (m, 6H), 1.50 (m, 2H); $^{13}$C-NMR (CDCl$_3$) δ 57.4 (t), 44.1 (t), 49.2 (t), 24.7 (t), 23.4 (t), 23.3 (t).

EXAMPLE 48

Step 1

(4a,S,6R8aS)-3-Methoxy-5,6,9,10,11,12-hexahydro-4aH[1]benzofuro[3a,3,2-ef[2]benzazepin-6-ol, (−)-norgalanthamine (8)

Method 1:

A solution of 7.72 g (20.0 mmol) of (+)-O,O-di-p-toluoyl tartaric acid in 15 ml of methanol is added in drops to a solution of 10.92 g (40.0 mmol) of rac.norgalanthamine (4) in 40 ml of methanol, and it is then rewashed with 1 ml of methanol. The solution is mixed with a seed crystal (without a seed crystal, crystal formation can take several weeks), and it is allowed to stand for two days at 4° C. Then, it is thoroughly ground with a glass rod and allowed to stand for another two to five days at 4° C., whereby it is always thoroughly ground again with a glass rod. Then, the precipitated salt is suctioned off, rewashed three times with ice-cold methanol and taken up in 100 ml of water. The aqueous phase is made basic with concentrated aqueous ammonia and extracted three times with 60 ml each of ethyl acetate. The combined organic phases are washed once with saturated aqueous sodium chloride solution, dried (Na$_2$SO$_4$, activated carbon), filtered and concentrated by evaporation, by which 2.9 g (37.5% of theory) of colorless crystals is obtained on (−)-norgalanthamine (8).

Method 2:

m-CPBA (peroxide content 76%, 15.6 g 70 mmol) was added to a solution of galanthamine (1) (20.0 g, 70 mmol) in CH$_2$Cl$_2$ (350 ml), and the clear solution was stirred for 40 minutes at room temperature. In this stage, the conversion into the N-oxide was quantitative, as was found by HPLC. Then, a solution of FeSO$_4$.7H$_2$O (9.7 g 35 mmol) in MeOH (100 ml) was added. The mixture was stirred for 20 minutes, mixed with 2N hydrochloric acid (200 ml), the volatile portions (CH$_2$Cl$_2$ and MeOH) were evaporated at reduced pressure and then washed with ether (3×100 ml). The aqueous solution was set at pH>8.5 with concentrated ammonia and extracted with CH$_2$Cl$_2$ (3×100 ml) and with CH$_2$Cl$_2$:MeOH=9:1 (3×100 ml). The combined, organic extracts were washed with common salt solution (200 ml), dried on Na$_2$SO$_4$ and concentrated by evaporation to produce a crystalline product (18.2 g, 96%), which consisted of a 92:8 mixture of norgalanthamine and galanthamine. MPLC (CHCl$_3$:MeOH:Et$_3$N=98:1.25:0.5), 16.1 g (84.7%) of norgalanthamine (8): $^1$H-NMR (CDCl$_3$) δ 6.62 (b, 2H), 6.02 (m, 2H), 4.61 (b, 1H), 4.14 (t, J=4.3 Hz, 1H), 3.98 (d, J=5.0 Hz, 2H), 3.83 (s, 3H), 3.30 (m, 1H), 2.69 (d, J=15.7, 1H), 2.10–1.63 (m, 4H); $^{13}$C-NMR (CDCl$_3$ δ 146.2 (s), 144.1 (s), 133.1 (s), 131.7 (s), 127.8 (d), 126.8 (d), 120.8 (d), 111.1 (d), 88.4 (d), 61.9 (d), 55.9 (q), 53.3 (t), 48.5 (s), 46.7 (t), 39.4 (t), 29.9 (t).

Step 2

(4a,S,6R$_8$aS)-3-Methoxy-11-phenyl-5,6;9,10,11,12-hexahydro-4aH[1]benzofuro[3a,3,2-ef[2]benzazepin-6-ol (8a). 0.28 g of phenylboric acid (7.2 mmol), 0.6 ml of pyridine (7.2 mmol), 0.67 g of copper acetate (3.6 mmol) and one molecular sieve (1.0 g) were added to a solution of 1.0 g of compound 8 (−)-norgalanthamine in 50 ml of CH$_2$Cl$_2$. The reaction mixture was stirred at room temperature for 3 days. The precipitate was filtered off and washed with 3×10 ml of CH$_2$Cl$_2$. The filtrate was extracted 3× with 50 ml of dilute ammonia solution. The combined, aqueous phases were extracted with 3×50 ml of CH$_2$Cl$_2$, the organic phases were washed with common salt solution, dried on sodium sulfate and concentrated by evaporation. MPLC yielded 0.33 g (26.4%) of compound 8a. Melting point 178–180° C.;

$^1$H-NMR (CDCl$_3$) δ 7.18 (m, 2H), 6.82 (m, 3H), 6.67 (dd, J$_1$=33.8 Hz, J$_2$=7.6 Hz, 2H), 6.05 (b, 2H), 4.66 (b, 1H), 4.53 (m, 1H), 4.19 (d, J=15.3 Hz, 1H), 3.85 (s, 3H), 3.81 (d, J=15.3 Hz, 1H), 3.33 (m, 1H), 2.68 (m, 1H), 2.07 (m, 3H), 1.62 (m, 1H); $^{13}$C-NMR (CDCl$_3$ δ 158.2 (s), 145.9 (s), 144.5 (s), 133.0 (s), 129.4 (s), 128.9 (d), 128.1 (d), 126.9 (d), 126.1 (d), 121.1 (d), 116.0 (d), 111.4 (d), 88.6 (d), 61.9 (d), 57.0 (t), 55.9 (q), 50.6 (t), 48.2 (s), 32.8 (t), 29.9 (t). Anal. (C$_{22}$H$_{23}$NO$_3$.0.75 H$_2$O) C, H, N.

EXAMPLE 49

(4a,S,6R,8aS)-3-Methoxy-11-thiophenyl-5,6,9,10,11,12-hexahydro-4aH-[1]benzofuro[3a,3,2-ef][2]benzazepin-6-ol (8b). The compound was produced as in compound 8a, and the reaction time was 3 days, yield 0.14 g (28.0%). Only the NMR signals that are different from 8a are described: $^1$H-NMR (CDCl$_3$) 7.23 (m, 1H), 6.92 (t, J=3.0 Hz, 1H), 6.83 (d, J=2.7 Hz, 1H); $^{13}$C-NMR (CDCl$_3$ δ 145.7 (s), 127.6 (d), 126.2 (d), 125.0 (d). Anal. (C$_{20}$H$_{21}$NO$_3$S) C, H, N.

EXAMPLE 50

(4a,S,6R,8aS)-11-Benzoyl-piperidine-4-yl)-3-methoxy-5,6,9,10,11,12-hexahydro-4aH-[1]benzofuro[3a,3,2-ef][2]benzazepin-6-ol (8c). 1-Benzoyl-piperidin-4-one (0.34 g, 1.7 mmol), 0.47 g of titanium isopropylate (1.7 mmol) and 3.6 g (1.3 mmol) of compound 8 were melted for 30 minutes at 110° C. After cooling at room temperature, a solution of sodium cyanoborohydride (65 mg, 0.9 mmol) in dry EtOH (10 ml) was added, and the reaction mixture was stirred at room temperature for 24 An hours. After 2 ml of water was added, the precipitate was filtered off, the filtrate was concentrated by evaporation, and the residue was diluted with 20 ml of EtOAc and filtered again. The clear solution was concentrated by evaporation. MPLC yielded 0.24 g (38.8%) of compound 8c. $^1$H-NMR (CDCl$_3$) δ 7.52–7.31 (m, 5H), 6.65 (b, 2H), 6.08 (m, 2H), 4.64 (b, 1H), 4.22–3.90 (m, 4H), 3.82 (s, 3H), 3.37 (m, 2H), 3.01–2.62 (m, 5H), 2.10–1.82 (m, 5H), 1.67–1.42 (m, 2H); $^{13}$C-NMR (CDCl$_3$) 170.1 (s), 145.8 (s), 144.0 (s), 136.0 (s), 133.1 (s), 129.4 (d), 128.8 (d), 128.4 (d), 128.3 (d), 127.6 (d), 126.7 (d), 121.6 (d), 111.2 (d), 88.6 (d), 61.9 (d), 55.8 (q), 55.6 (t), 48.3 (t), 30.8 (t), 29.8 (t).

EXAMPLE 51

(4a,S,6R,8aS)-6-Hydroxy-3-methoxy-5,6,9,10-tetrahydro-4aH-[1]benzofuro[3a,3,2-ef][2]benzazepine-11(12H)-carboxylic acid phenyl ester (8e): 2.5 g of sodium bicarbonate (29.8 mmol) and 1.84 ml of phenyl chloroformate (14.6 mol) were added to a solution of 0.50 g of compound 8 (1.74 mmol) in 50 ml of CHCl$_3$. The mixture was vigorously stirred and refluxed for two hours and then diluted with water (30 ml). The phases were separated. The aqueous phase was extracted with 2×30 ml of CH$_2$Cl$_2$, and the combined organic phases were washed with 1N hydrochloric acid (30 ml), dried on sodium sulfate and concentrated by evaporation under reduced pressure to produce the crude product. MPLC (CH$_2$Cl$_2$:MeOH=99:1) yielded 0.58 g (84.2%) of compound 8e: $^1$H-NMR (CDCl$_3$) δ 7.51–7.04 (m, 5H), 6.82 (dd, J$_1$=24.0 Hz, J$_2$=6.0 Hz, 2H), 6.04 (b, 2H), 4.91 (b, 1H), 4.69 (d, J=6.0 Hz, 2H), 4.20 (b, 1H), 3.83 (s, 3H), 3.42 (m, 1H), 3.19 (m, 1H), 2.43–1.90 (m, 4H); $^{13}$C-NMR (CDCl$_3$) δ 151.3 (s), 146.6 (s), 145.7 (s), 130.5 (s), 130.1 (s), 129.4 (d), 129.3 (d), 125.9 (d), 125.3 (d), 125.0 (d), 121.6 (d), 111.9 (d), 88.3 (d), 62.8 (d), 57.7 (t), 55.9 (q), 53.4 (t), 49.3 (s), 43.3 (t), 32.7 (t).

EXAMPLE 52

(4a,S,6R,8aS)-6-hydroxy-3-methoxy-5,6,9,10-tetrahydro-4aH-[1]benzofuro[3a,3,2-ef][2]benzazepine-11(12H)-carbothionic acid-O-phenyl ester (8f): 0.24 ml of chlorothionoformate (1.74 mmol) was added to a solution of 0.50 g of compound 8 (1.74 mmol) in 25 ml of CHCl$_3$, and the reaction mixture was stirred for 1 hour under nitrogen. The solvent was separated to produce a colorless oil that was flash-chromatographed to produce 0.50 g (71.2%) of compound 8a: $^1$H-NMR (CDCl$_3$) δ 7.48–7.12 (m, 3H), 7.02 (d, J=6.0 Hz, 2H), 6.83 (m, 2H), 6.04 (b, 2H), 5.08 (m, 1H), 4.71 (d, J=26.0 Hz, 2H), 4.28 (m, 1H), 3.88 (s, 3H), 3.41 (m, 2H), 2.51–2.09 (m, 4H); $^{13}$C-NMR (CDCl$_3$) δ 187.5 and 187.4 (s), 153.8 and 153.7 (s), 146.7 and 146.6 (s), 145.8 and 145.7 (s), 131.3 and 130.6 (s), 130.2 and 129.5 (s), 129.2 and 129.1 (d), 126.0 and 125.9 (d), 125.0 and 124.9 (d), 122.7 and 122.6 (d), 121.6 and 120.4 (d), 115.3 (d), 112.0 (d), 84.4 and 84.2 (d), 63.1 and 62.9 (d), 55.9 (q), 51.5 (t), 49.5 and 49.3 (s), 47.8 (t), 36.9 (t), 33.1 (t).

EXAMPLE 53

(4a,S,6R,8aS)-6-hydroxy-3-methoxy-5,6,9,10-tetrahydro-4aH-[1]benzofuro[3a,3,2-ef][2]benzazepine-11(12H)-carboxylic acid-9-H-fluor-9-ylmethyl ester (8g): 0.5 g of 9-fluorenylmethyloxycarbonyl chloride (20 mmol) was added to a solution of 0.5 g of compound 8 (1.8 mmol) and 2.5 ml of triethylamine (1.8 mmol) in 20 ml of CH$_2$Cl$_2$, and it was stirred for 30 minutes at room temperature. The reaction mixture was concentrated by evaporation, the residue was diluted with 80 ml of 2N hydrochloric acid and extracted with 5×50 ml of CH$_2$Cl$_2$. The organic phases were combined, washed with common salt solution, dried on sodium sulfate and concentrated by evaporation to produce 0.88 g (99.2%) of compound 8g. Melting point 76–79° C.; α$_D$=–33.0°; $^1$H-NMR (CDCl$_3$) δ 1.72 (dd, J=13.5; 5.0 Hz, 1H), 1.80–2.10 (m, 2H), 2.69 (dd, J=13.5; 5.0 Hz, 1H), 3.20–3.45 (m, 2H), 3.85 (s, 3H), 3.95–4.35 (m, 3H), 4.40–4.52 (m, 2H), 5.78–6.05 (m, 2H), 6.22–6.82 (m, 2H), 7.19–7.82 (m, 8H); $^{13}$C-NMR (CDCl$_3$) δ 155.1 (s), 144.4 (s), 144.0 (s), 141.4 (s), 134.0 (s), 129.1 (s), 128.1 (s), 128.0 (d), 127.6 (d), 126.4 (d), 124.9 (d), 124.7 (d), 121.0 (d), 119.9 (d), 111.1 (d), 88.3 (d), 66.9 (t), 61.9 (d), 56.0 (q), 51.5 (t), 48.3 (s), 47.3 (d), 45.9 (t), 36.4 (t), 29.7 (t).

EXAMPLE 54

1-((4a,S,6R,8aS)-6-Hydroxy-3-methoxy-5,6,9,10-tetrahydro-4aH-[1]benzofuro[3a,3,2-ef][2]benzazepine-11 (12H)-yl)pent-4-en-1-one (8h): 0.97 ml (5.1 mmol) of pent-4-enoic anhydride was added at 0° C. to a solution of 1.0 g of compound 8 (3.7 mmol) and 0.51 ml (3.7 mmol) of triethylamine in 40 ml of CH$_2$Cl$_2$,MeOH=5:2, and it was stirred for 20 minutes. The reaction mixture was diluted with 20 ml of CH$_2$Cl$_2$, extracted with 2×20 ml of saturated sodium bicarbonate solution. The combined aqueous phases were extracted with 2×40 ml of CH$_2$Cl$_2$, the combined organic phases were washed with common salt solution, dried on sodium sulfate and concentrated by evaporation to produce 1.24 g (95.3%) of compound 8h: $^1$H-NMR (CDCl$_3$) δ 6.66 (b, 2H), 5.98 (m, 2H), 5.78 (m, 1H), 4.98 (m, 2H), 4.66 (d, J=12.8 Hz, 1H), 4.55 (s, 1H), 4.41 (d, J=16.5 Hz, 1H), 4.11 (b, 1H), 3.93 (m, 1H), 3.81 (s, 3H), 3.17 (t, J=17.7 Hz, 1H), 2.76–2.15 (m, 5H), 1.92 (m, 3H); $^{13}$C-NMR (CDCl$_3$) δ 171.7 (s), 146.8 (s), 144.6 (s), 137.3 (d), 132.4 (s), 128.1 (s), 128.0 (d), 126.3 (d), 120.3 (d), 114.9 (d), 111.0 (d), 88.2 (d), 61.7 (d), 55.8 (q), 52.7 (t), 48.2 (s), 44.6 (t), 35.7 (t), 33.2 (t), 29.7 (t), 28.8 (t).

EXAMPLE 55

1-((4a,S,6R,8aS)-6-Hydroxy-3-methoxy-5,6,9,10-tetrahydro-4aH-[1]benzofuro[3a,3,2-ef][2]benzazepine-11 (12H)-carboxamide (8i): the pH was set at 3 with 2N hydrochloric acid in a suspension of 0.5 g of compound 8 (1.8 mmol) in 25 ml of water, and 0.23 g (3.6 mmol) of sodium cyanide was added. The reaction mixture was stirred for 25 hours at room temperature, and then the pH was set at above 8.5 with concentrated ammonia and finally extracted with 3×20 ml of CH$_2$Cl$_2$. The combined, aqueous phases were extracted with common salt solution, dried on sodium sulfate and concentrated by evaporation. MPLC (CHCl$_3$:MeOH(NH$_3$)=95:5) yielded 0.38 g (66%) of compound 8i: $^1$H-NMR (CDCl$_3$) δ 6.67 (dd, J=12.8; 8.1 Hz, 2H), 6.00 (dd, J=15.1; 10.4 Hz, 2H), 4.68 (b, 1H), 4.51 (d, J=16.8 Hz, 1H), 4.31 (d, J=16.8 Hz, 1H), 4.11 (m, 1H), 3.81 (s, 3H), 3.35 (t, J=12.8 Hz, 1H), 2.67 (d, J=15.3 Hz, 1H), 2.41 (b, 1H), 1.97 (m, 2H), 1.72 (d, J=13.8 Hz, 1H); $^{13}$C-NMR (CDCl$_3$) δ 158.1 (s), 146.8 (s), 144.5 (s), 132.3 (s), 128.6 (s), 128.0 (d), 126.2 (d), 120.3 (d), 111.1 (d), 88.1 (d), 61.6 (d), 55.8 (q), 51.9 (t), 48.3 (s), 45.6 (t), 36.3 (t), 29.7 (t).

EXAMPLE 56

(4a,S,6R,8aS)-6-Hydroxy-3-methoxy-N$^{11}$-methyl-5,6,9,10-tetrahydro-4aH-[1]benzofuro[3a,3,2-ef][2]benzazepine-11(12H)-carbothioamide (8j): Process according to Example . . . , reaction time 4 hours, yield 1.02 g (88%);

melting point 229–230° C., $^1$H-NMR and $^{13}$C-NMR were identical to compound 4t. Anal. $C_{18}H_{22}N_2O_3S.O.2$ $CH_3C_6H_5$ C, H, N.

EXAMPLE 57

(4a,S,6R,8aS)-6-Hydroxy-N$^{11}$-isopropyl-3-methoxy-5,6, 9,10-tetrahydro-4aH-[1]benzofuro[3a,3,2-ef][2]benzazepine-11(12H)-carboxamide (8k): Process A, reaction time 3 hours, yield 1.86 g (71); $^1$H-NMR and $^{13}$H-NMR were identical to compound 4i.

EXAMPLE 58

(4a,S,6R,8aS)-N$^{11}$-t-Butyl-6-hydroxy-3-methoxy-5,6,9, 10-tetrahydro-4aH-[1]benzofuro[3a,3,2-ef][2]benzazepine-11(12H)-carboxamide (8l): Process A, reaction time 3 hours, yield 1.63 g (60%); melting point 106–108° C.; $^1$H-NMR and $^{13}$H-NMR were identical to compound 4m.

EXAMPLE 59

(4a,S,6R,8aS)-6-Hydroxy-3-methyl-N$^{11}$-2-trifluoromethyl-5,6,9,10-tetrahydro-4aH-[1]benzofuro[3a,3,2-ef][2] benzazepine-11(12H)-carboxamide (8m): Process A, reaction time 5 hours, yield 0.60 g (59%);

$^1$H-NMR (CDCl$_3$) δ 8.20 (t, J=8.0 Hz, 1H), 7.24 (m, 2H), 7.02 (m, 1H); $^{13}$C-NMR (CDCl$_3$) δ 153.6 (s), 137.6 (s), 127.6 (d); 126.1 (d), 123.0 and 117.8 (s), 122.3 (s), 119.8 (s), 111.3 (d).

EXAMPLE 60

Methyl-(4a,S,6R,8aS)-N$^{11}$-Cyano-6-hydroxy-=3-methoxy-5,6,9,10-tetrahydro-4aH-[1]benzofuro[3a,3,2-ef][2] benzazepine-11(12H)-carboximidothioate (8n). The compound was produced as described for compound 3bi. Reaction time 3 days, yield 0.90 g (33.2%); $^1$H-NMR (CDCl$_3$) δ 6.72 (m, 2H), 5.98 (d, J=10.2 Hz, 2H), 4.62 (m, 2H), 4.14 (b, 1H), 3.92 (d, J=11.8 Hz, 1H), 3.84 (s, 3H), 3.44 (m, 2H), 2.74 (s, 3H), 2.68 (m, 1H), 1.99 (m, 3H); $^{13}$C-NMR (CDCl$_3$) δ 146.2 (s), 144.9 (s), 131.7 (s), 128.7 (d), 125.8 (s), 125.5 (d), 121.8 (d), 111.2 (d), 88.1 (d), 61.6 (d), 55.8 (q), 51.2 (t), 49.7 (t), 47.9 (s), 29.6 (t), 16.1 (q).

EXAMPLE 61

(4a,S,6R,8aS)-11-(Cyclopropylmethyl)-3-methoxy-5,6,9, 10-tetrahydro-4aH-[1]benzofuro[3a,3,2-ef][2]benzazepin-6-ol (8o): Process according to Example E, reaction time 36 hours, yield 0.12 g (29.0%); same skeleton as 4aa, only the different NMR signals are described.

$^1$H-NMR (CDCl$_3$) δ 3.48 (t, J=8.0 Hz, 1H), 0.91 (m, 1H), 0.53 (d, J=12 Hz, 2H), 0.11 (d, J=6 Hz, 2H); $^{13}$C-NMR (CDCl$_3$) δ 57.2 (t), 9.8 (d), 4.7 (t), 4.1 (t).

EXAMPLE 63

3-((4a,S,6R,8aS)-6-Hydroxy-3-methoxy-5,6,9,10-tetrahydro-4aH-[1]benzofuro[3a,3,2-ef][2]benzazepine-11 (12H)-yl)ethanonitrile (8r): Process as in Example E, reaction time 2 hours, yield 1.67 g (61.1%); melting point 169–171° C.; $^1$H-NMR and $^{13}$C-NMR were identical to compound 4ad. Anal. ($C_{18}H_{20}N_2O_3.O..67 H_2O$) C, H, N.

EXAMPLE 64

1-(2-Phenyl-2,5-diazabicyclo[2.2.1]heptane-5-yl)-2-((4a, S,6R,8aS)-6-hydroxy-3-methoxy-5,6,9,10-tetrahydro-4aH-[1]benzofuro[3a,3,2-ef][2]benzazepine-11(12H)-yl)-1-ethanone (8s): Process as in Example E, reaction time 3 days, yield 0.68 g (37.8%); melting point 85–89° C.; α$_D$=–169.3°, same skeleton as 4aa, only different NMR signals are described: $^1$H-NMR (CDCl$_3$) δ 7.21 (m, 2H); 6.68 (m, 3H), 5.0 (s, 1H), 4.47 (d, J=14.0 Hz, 1H), 3.90 (m, 1H), 3.63 (m, 3H), 3.24 (m, 1H), 2.04 (m, 3H); $^{13}$C-NMR (CDCl$_3$) δ 168.0 and 167.6 (s), 146.4 (d), 144.1 (s), 127.7 (d), 127.5 (d), 112.5 (d), 112.4 (d), 67.0 (t), 57.0 and 56.8 (d), 56.8 and 56.6 (t), 51.8 and 51.6 (t), 36.6 (t); 33.7 and 33.6 (t). Anal. ($C_{29}H_{33}N_3O_4.O.33 H_2O$) C, H, N.

EXAMPLE 65

(4a,S,6R,8aS)-11-(3-Aminoethyl)-3-methoxy-5,6,9,10, 11,12-hexahydro-4aH-[1]benzofuro[3a,3,2-ef][2]benzazepin-6-ol (8t): Process according to Example F, reactant compound 8r; reaction time 18 hours, yield 1.01 g (66.1%); melting point 72–75° C.; α$_D$=–71.58°, $^1$H-NMR and $^{13}$C-NMR were identical to compound 4af. Anal. ($C_{18}H_{24}N_2O_3.0.65$ EtOH.0.05 $CH_2Cl_2$)) C, H, N.

EXAMPLE 66

(4a S,6R,8aS)-11-(2-Morpholine-4-yl-ethyl)-3-methoxy-5,6,9,10,11,12-hexahydro-4aH-[1]benzofuro[3a,3,2-ef][2] benzazepin-6-ol (8u): Process according to Example E, reaction time 2 days, yield 1.77 g (63.6%); melting point 101–104° C.; α$^D_{20}$=–110.9°, $^1$H-NMR and $^{13}$C-NMR were identical to compound 4ag. Anal. ($C_{22}H_{30}N_2O_4.0.15$ $CH_2Cl_2$) C, H, N.

EXAMPLE 67

(4a,S,6R,8aS)-11-(2-Phenyl-2,5-diazabicylo[2.2.1]heptane-5-yl-ethyl)-3-methoxy-5,6,9,10,11,12-hexahydro-4aH-[1]benzofuro[3a,3,2-ef][2]benzazepin-6-ol (8v): Process according to Example F, reactant compound 8s, reaction time 30 minutes, yield 0.26 g (50.8%); melting point 72–75° C.; α$^D_{20}$=–131.6°, $^1$H-NMR and $^{13}$C-NMR were identical to compound 4ah. Anal. ($C_{29}H_{35}N_3O_3.0.35$ $CH_2Cl_2.0.5$ Et$_3$N) C, H, N.

EXAMPLE 68

3-((4a,S,6R,8aS)-6-Hydroxy-3-methoxy-5,6,9,10-tetrahydro-4aH-[1]benzofuro[3a,3,2-ef][2]benzazepine-11 (12H)-yl)propanoic acid (8w): A solution of 8w (0.5 g, 1.25 mmol) was added to $CH_2Cl_2$ (20 ml) in trifluoroacetic acid (5 ml). The reaction mixture was stirred at room temperature for 2 hours and yielded a concentrate of 0.37 g (64.5%) of 8w: same skeleton as 4aa, only different NMR signals are described: $^1$H-NMR (CDCl$_3$) 8.95 (b, 1H), 2.82 (m, 2H), 2.25 (m, 2H).

EXAMPLE 69 t-Butyl-3-((4a,S,6R,8aS)-6-Hydroxy-3-methoxy-5,6,9, 10-tetrahydro-4aH-[1]benzofuro[3a,3,2-ef][2]benzazepine-11(12H)-propanoate (8x): Process B, reaction time 6 hours, yield 0.74 g (53.2%); $^1$H-NMR and $^{13}$C-NMR were identical to compound 4aj.

EXAMPLE 70

(4a,S,6R,8aS)-11-(3-Hydroxypropyl)-3-methoxy-5,6,9,10,11,12-hexahydro-4aH-[1]benzofuro[3a,3,2-ef][2]benzazepin-6-ol (8z): Process E, reaction time 4 days, yield 0.32 g (56.7%); $\alpha_D$=90.0°; $^1$H-NMR and $^{13}$C-NMR were identical to compound 4an.

EXAMPLE 71

(4a,S,6R,8aS)-11-((3-Dimethylamino)propyl-3-methoxy-5,6,9,10,11,12-hexahydro-4aH-[1]benzofuro[3a,3,2-ef][2]benzazepin-6-ol (8aa): Process E, reaction time 24 hours, yield 0.45 g (51.6%); same skeleton as 4aa, only the different NMR signals are described.

$^1$H-NMR (CDCl$_3$) δ 2.50 (m, 2H), 2.30 (m, 2H), 2.22 (s, 3H), 2.18 (s, 3H), 1.82 (m, 2H); $^{13}$C-NMR (CDCl$_3$) δ 55.6 (t), 53.4 (t), 45.0 (q); 25.3 (t).

EXAMPLE 72

(4a,S,6R,8aS)-3-Methoxy-11-(3-piperidine-1-yl-propyl)-5,6,9,10,11,12-hexahydro-4aH-[1]benzofuro[3a,3,2-ef][2]benzazepin-6-ol (8ab): Process E, reaction time 3 days, yield 1.77 g (54.7%); melting point 84–92° C.; $\alpha^D_{20}$=–50.64; $^1$H-NMR and $^{13}$C-NMR were identical to compound 4an. Anal. (C$_{24}$H$_{34}$N$_2$O$_3$. 3C$_4$H$_6$O$_6$) C, H, N.

EXAMPLE 73

(4a,S,6R,8aS)-11-(3-2-(4-Fluoro)phenyl-2,5-diazabicyclo[2.2.1]heptane-5-yl-propyl)-3-methoxy-5,6,9,10,11,12-hexahydro-4aH-[1]benzofuro[3a,3,2-ef][2]benzazepin-6-ol (8ac): Process E, reaction time 4 days, yield 1.77 g (59.3%); melting point 84–92° C.; $\alpha^{D20}$ =–50.64; $^1$H-NMR and $^{13}$C-NMR were identical to compound 4aq. Anal. (C$_{30}$H$_{36}$FN$_3$O$_3$.2CH$_2$Cl$_2$.2 Et$_3$N) C, H, N.

EXAMPLE 74

(4a,R,6S,8aR)-3-Methoxy-5,6,9,10,11,12-hexahydro-4aH-[1]benzofuro[3a,3,2-ef][2]benzazepin-6-ol, (+) norgalanthamine (9) was prepared and described for 8: yield 5.35 g (74.2%); $^1$H-NMR and $^{13}$C-NMR were identical to compound 8.

EXAMPLE 75

(4a,R,6S,8aR)-6-Hydroxy-N$^{11}$-isopropyl-3-methoxy-5,6,9,10-tetrahydro-4aH-[1]benzofuro[3a,3,2-ef][2]benzazepine-11(12H)-carboxamide (9a): Process A, reaction time 3 hours; yield 1.03 g (79%); $^1$H-NMR and $^{13}$C-NMR were identical to compound 4l.

EXAMPLE 76

(4a,R,6S,8aR)-N$^{11}$-t-Butyl-6-hydroxy-3-methoxy-5,6,9,10-tetrahydro-4aH-[1]benzofuro[3a,3,2-ef][2]benzazepine-i1(12H)-carboxamide (9b): Process A, reaction time 3 hours; yield 0.85 g (63%); $^1$H-NMR and $^{13}$C-NMR were identical to compound 4m.

EXAMPLE 77

(4a,R,6S,8aR)-3-Methoxy-11-(2-morpholine-4-yl-ethyl)-5,6,9,10,11,12-hexahydro-4aH-[1]benzofuro[3a,3,2-ef][2]benzazepin-6-ol (9c): Process E, reaction time 2 days; yield 0.12 g (53.2%); $^1$H-NMR and $^{13}$C-NMR were identical to compound 4ag.

EXAMPLE 78

(4a,R,6S,8aR)-11-((3-Dimethylamino)propyl)-3-methoxy-5,6,9,10,11,12-hexahydro-4aH-[1]benzofuro[3a,3,2-ef][2]benzazepin-6-ol (9d): Process E, reaction time 22 hours; yield 0.19 g (44.6%); $^1$H-NMR and $^{13}$C-NMR were identical to compound 8aa.

EXAMPLE 79

(4a,R,6S,8aR)-11-(3-Piperidine-1-yl-propyl)-3-methoxy-5,6,9,10,11,12-hexahydro-4aH-[1]benzofuro[3a,3,2-ef][2]benzazepin-6-ol (9e): Process E, reaction time 20 hours; yield 0.33 g (75.0%); $^1$H-NMR and $^{13}$C-NMR were identical to compound 4ap.

EXAMPLE 80

Step 1

2-Bromo-4-methoxy-5-(1-methylethoxy)benzaldehyde

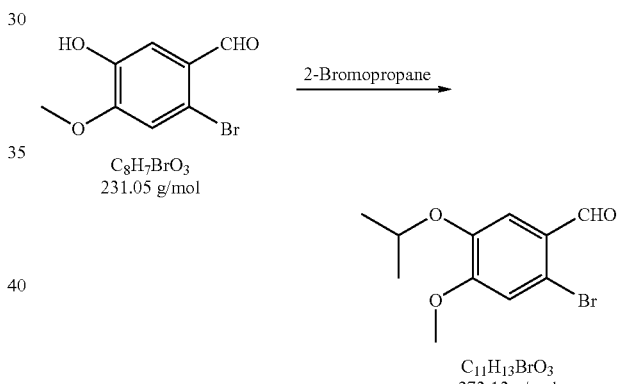

2-Bromo-5-hydroxy-4-methoxybenzaldehyde (100.0 g, 433 mmol), 2-bromopropane (160.0 g, 1.30 mol) and potassium carbonate (300 g, 2.16 mol, anhydrous, freshly ground) are stirred in acetonitrile (1200 ml) for 48 hours at 60° C.

The reaction mixture is filtered, the solvent is distilled off in a rotary evaporator, and the residue is dispersed between water (800 ml) and ether (800 ml). The aqueous phase is extracted with ether (2×300 ml), the combined organic phases are washed with water (2×500 ml) and saturated common salt solution (1×500 ml), dried (sodium sulfate/activated carbon), filtered, and the residue that is obtained after the solvent was distilled off is recrystallized from methanol (500 ml). In this way, the product is obtained in the form of pale rose-colored crystals (98.1 g, 83%).

Melting point: 75–76° C. TLC: Petroleum ether:ethyl acetate=3:1, Rf=0.75 $^1$H NMR (CDCl$_3$): δ 10.13 (s, 1H), 7.40 (s, 1H), 7.03 (s, 1H), 4.61 (septet, J=6.4 Hz, 1H), 3.92 (s, 3H), 1.38 (d, J=6.4 Hz 6H); $^{13}$C NMR (CDCl$_3$) δ 190.8 (d), 15.6 (s), 147.1 (s), 126.4 (s), 120.0 (s), 115.8 (d), 113.7 (d), 71.5 (d), 56.4 (q), 21.8 (q)

Step 2

2-Bromo-4-methoxy-5-(1-methylethoxy)benzenemethanol

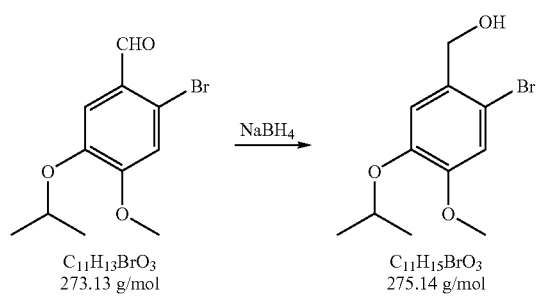

2-Bromo-4-methoxy-5-(1-methylethoxy)benzaldehyde (6.0 g, 22.0 mmol) is added in substance at 15° C. within 15 minutes to a suspension of sodium borohydride (1.67 g, 44.1 mmol) in anhydrous ethanol (60 ml), and the mixture is stirred for one hour at room temperature.

The residue that remains after the solvent is distilled off is dispersed between saturated sodium bicarbonate solution (60 ml) and ether (100 ml). The aqueous phase is extracted with ether (3×40 ml), the combined organic phases are washed with saturated sodium bicarbonate solution (1×100 ml), water (1×100 ml) and saturated common salt solution (1×100 ml), dried (sodium sulfate/activated carbon) and filtered. After the solvent is distilled off in a rotary evaporator, the product is obtained in the form of colorless crystals (5.575 g, 95).

Melting point: 67–69° C. TLC: Petroleum ether:ethyl acetate=4:1, Rf=0.25 $^1$H NMR (CDCl$_3$) δ 7.00 (s, 2H), 4.64 (s, 2H), 4.50 (septet, J=6.4 Hz, 1H), 3.85 (s, 3H), 2.05 (s, 1H), 1.34 (d, J=6.4 Hz, 6H); $^{13}$C NMR (CDCl$_3$) δ 150.1 (s), 146.5 (s), 131.8 (s), 116.1 (s), 115.9 (d), 112.6 (s), 71.7 (t), 64.3 (d), 56.0 (q), 21.8 (q) MT-44 JOS 1693 C$_{11}$H$_{15}$BrO$_3$ Cld.: C, 48.02; H, 5.50 Fnd.: C, 48.11: H, 5.29

Step 3

1-Bromo-2-(chloromethyl)-5-methoxy-4-(1-methylethoxy)-benzene

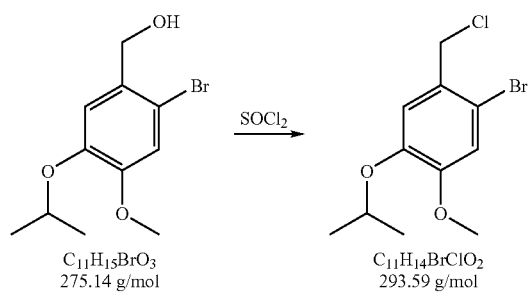

Thionyl chloride (20 ml) in absolute CH$_2$Cl$_2$ (10 ml) is added in drops within 10 minutes to 2-bromo-4-methoxy-5-(1-methylethoxy)benzenemethanol (5.63 g, 20.5 mmol) in absolute CH$_2$Cl$_2$ (60 ml), and it is stirred for 90 minutes at room temperature.

The residue that is obtained after solvent is removed in a rotary evaporator is dispersed between ether (100 ml) and saturated sodium bicarbonate solution (100 ml), the combined organic phases are washed with saturated sodium bicarbonate solution (2×100 ml), water (1×100 ml) and saturated common salt solution (1×100 ml), dried (sodium sulfate/activated carbon), filtered, and the solvent is distilled off in a rotary evaporator. In this way, the product is obtained in the form of colorless crystals (5.72 g, 95%).

Melting point: 68–70° C. TLC: Petroleum ether:ethyl acetate=3:1, Rf=0.9 $^1$H NMR (CDCl$_3$) δ 7.05 (s, 1H), 6.97 (s, 1H), 4.66 (s, 2H), 4.51 (septet, J=6.4Hz, 1H), 3.85 (s, 3H), 1.37 (d, J=6.4 Hz, 6H); $^{13}$C NMR (CDCl$_3$): δ 151.2 (s), 146.8 (s), 128.5 (s), 117.7 (s), 116.1 (d), 114.8 (s), 71.9 (t), 56.2 (d), 64.4 (q), 21.9 (q) MT-45 JOS 1760 C$_{14}$H$_{20}$O$_3$ Cld.: C, 71.16; H, 8.53 Fnd.: C, 70.90; H, 8.28

Step 4

1-[4-(1-Methylethoxy)phenyl]ethanone

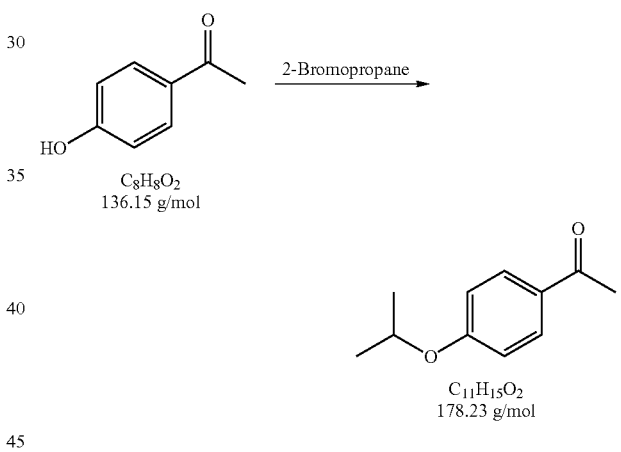

1-(4-Hydroxyphenyl)ethanone (12.7 g, 93.2 mmol), 2-bromopropane (57.3 g, 466 mmol) and potassium carbonate (62.2 g, 466 mmol, anhydrous, freshly ground) are stirred in absolute acetonitrile (150 ml) for 24 hours at 60° C.

The reaction mixture is filtered, the solvent is distilled off in a rotary evaporator, and the residue is dispersed between water (200 ml) and ether (200 ml). The aqueous phase is extracted with ether (2×80 ml), the combined organic phases are washed with water (2×100 ml) and saturated common salt solution (1×100 ml), dried (sodium sulfate/activated carbon) and filtered. In this way, after the solvent is distilled off, the product is obtained in the form of colorless crystals (16.8 g, 99%).

Melting point: 36–80° C. TLC: Petroleum ether:ethyl acetate=4:1, Rf=0.5 $^1$H NMR (CDCl$_3$) δ 7.82 (d, J=9.5 Hz, 2H), 6.88 (d, J=9.5 Hz, 2H), 4.63 (septet, J=6.4 Hz, 1H), 2.52 (s, 3H), 1.33 (d, J=6.4 Hz, 6H); $^{13}$C NMR (CDCl$_3$) δ 196.7 (s), 161.9 (s), 130.5 (d), 129.8 (s), 115.0 (d), 70.0 (d), 26.2 (q), 21.8 (q)

Step 5

2-Bromo-1-[4-(1-methylethoxy)phenyl]ethanone

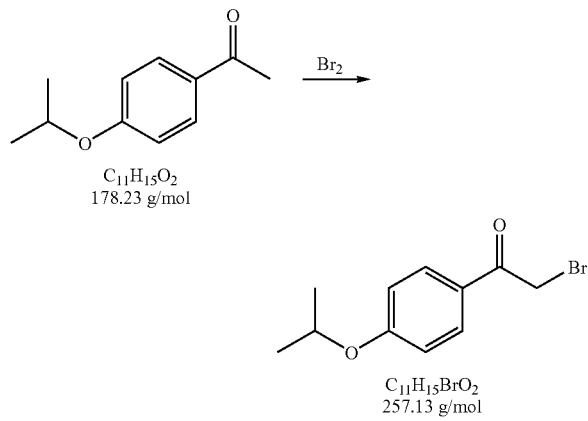

Bromine (11.7 g, 73.5 mmol) in absolute dioxane (70 ml)/absolute ether (100 ml) is added in drops within one hour to a solution of 1-[4-(1-methylethoxy)phenyl]ethanone (10.0 g, 56.0 mmol) in absolute dioxane (100 ml), and it is stirred for 2 hours at room temperature. The reaction mixture is mixed with sodium sulfite (5.0 g) in water (100 ml), the phases are separated, and the aqueous phase is extracted with ether (3×100 ml), the combined organic phases are washed with water (2×100 ml), saturated sodium bicarbonate solution (2×150 ml) and saturated common salt solution (1×200 ml), dried (sodium sulfate/activated carbon), filtered, and the residue that is obtained after the solvent is distilled off is crystallized under a mixture that consists of petroleum ether (25 ml) and cyclohexane (25 ml) at −20° C. In this way, the product is obtained in the form of colorless crystals that rapidly become dark in color (8.80 g, 59%).

Melting point: 36–37° C. TLC: Petroleum ether:ethyl acetate=4:1, Rf=0.7 $^1$H NMR (CDCl$_3$) δ 7.93 (d, J=9.5 Hz, 2H), 6.92 (d, J=9.5 Hz, 2H), 4.63 (septet, J=6.4 Hz, 1H), 4.40 (s, 2H), 1.35 (d, J=6.4 Hz, 6H); $^{13}$C NMR (CDCl$_3$) δ 189.8 (s), 162.7 (s), 131.4 (d), 126.4 (s), 115.3 (d), 70.3 (d), 30.7 (t), 21.9 (q)

Step 6

1-(2-Bromoethyl)-4-(1-methylethoxy)benzene

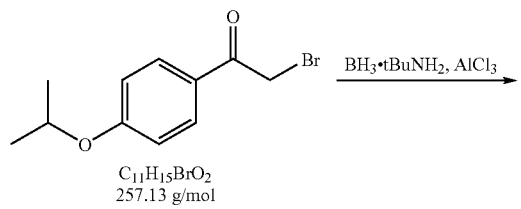

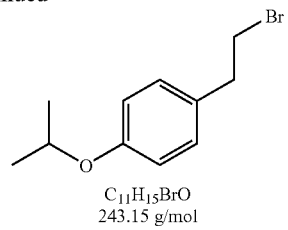

Tert-butylamine-borane complex (7.45 g, 85.0 mmol, pellets or powder) is added at 5° C. to a suspension of anhydrous aluminum chloride (5.70 g, 43.0 mmol) in absolute CH$_2$Cl$_2$ (100 ml). After 15 minutes, 2-bromo-1-[4-(1-methylethoxy)phenyl]-ethanone (7.30 g, 28.4 mmol) in anhydrous CH$_2$Cl$_2$ (50 ml) is added in drops within 30 minutes.

The mixture is stirred for three hours at room temperature, mixed with 0.1N hydrochloric acid (100 ml), and the aqueous phase is extracted with CH$_2$Cl$_2$ (2×30 ml). The combined organic phases are washed with 0.1N hydrochloric acid (2×50 ml), saturated sodium bicarbonate solution (2×50 ml) and saturated common salt solution (1×100 ml), dried (sodium sulfate/activated carbon), and the residue that is obtained after the solvent is concentrated by evaporation is purified by bulb tube distillation (0.05 mbar/80° C.), whereby the product is obtained as a colorless oil (5.81 g, 83%).

TLC: Petroleum ether, Rf=0.35 $^1$H NMR (CDCl$_3$) δ 7.18 (d, J=9.5 Hz, 2H), 6.87 (d, J=9.5 Hz, 2H), 4.53 (septet, J=6.4 Hz, 1H), 3.53 (t, J=6.9 Hz, 2H), 3.08 (t, J=6.9 Hz, 2H), 1.33 (d, J=6.4Hz, 6H); $^{13}$C NMR (CDCl$_3$) δ 156.7 (s), 130.7 (s), 129.5 (d), 115.8 (d), 69.8 (d), 38.5 (t), 33.2 (t), 21.9 (q) MT-35 JOS 1760 C$_{11}$H$_{15}$BrO Cld.: C, 54.34; H, 6.22 Fnd.: C, 54.34; H, 6.09

Step 7

2-[2-[4-(1-Methylethoxy)phenyl]ethyl]propanedioic acid dimethyl ester

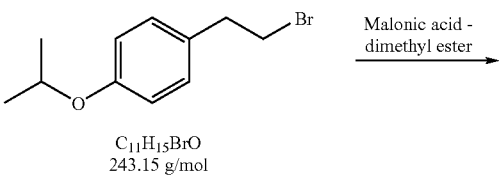

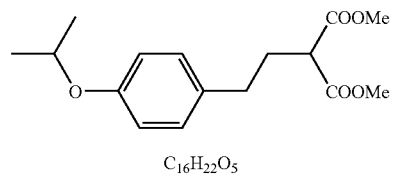

1-(2-Bromoethyl)-4-(1-methylethoxy)benzene (19.0 g, 78.1 mmol), malonic acid dimethyl ester (40.0 g, 300 mmol) and potassium carbonate (42.0 g, 300 mmol, anhydrous, freshly ground) in absolute DMF (400 ml) are stirred for 10 hours at 70° C.

The solvent is removed in a rotary evaporator, and the residue is dispersed between water (250 ml) and ether (250 ml). The aqueous phase is extracted with ether (1×100 ml), the combined organic phases are washed with water (3×200 ml) and saturated common salt solution (1×150 ml), dried (sodium sulfate/activated carbon) and excess malonic acid dimethyl ester is distilled off from the residue that is obtained after the solvent is removed from the rotary evaporator (160° C./15 mbar)

The crude product is purified by means of bulb tube distillation (140° C./0.001 mbar), by which the product is obtained as a colorless oil (18.9 g, 82%).

TLC: Petroleum ether:ethyl acetate=9:1, Rf=0.4 $^1$H NMR (CDCl$_3$) δ 7.08 (d, J=10 Hz, 2H), 6.81 (d, J=10 Hz, 2H), 4.50 (septet, J=6.5 Hz, 1H), 3.71 (s, 6H), 3.32 (t, J=75 Hz, 1H), 2.58 (t, J=7.5 Hz, 2H), 2.19 (q, J=7.5 Hz, 2H), 2.65–2.47 (m, 2H), 2.26–2.06 (m, 2H), 1.31 (d, J=6 Hz, 6H); $^{13}$C NMR (CDCl$_3$) δ 169.8 (s), 156.3 (s), 132.3 (s), 129.4 (d), 115.9 (d), 69.9 (d), 52.5 (q), 50.8 (d), 32.4 (t), 30.6 (t), 22.1 (q)

Step 8

2-[2-Bromo-4-methoxy-5-(1-methylethoxy)phenyl]methyl-2-[2-[4-(1-methylethoxy)phenyl]ethyl]propane-dioic acid methyl ester

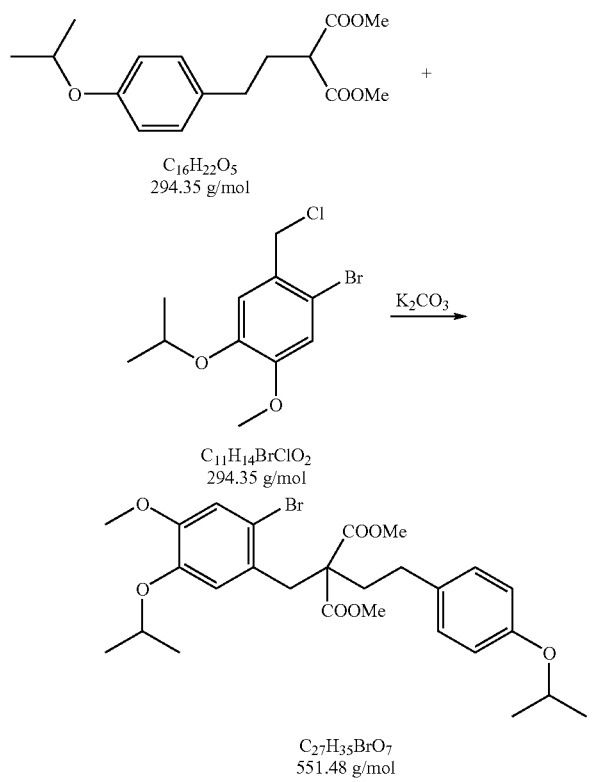

2-[2[4-(1-Methylethoxy)phenyl]ethyl]propanedioic acid dimethyl ester (18.9 g, 64.2 mmol), 1-bromo-2-(chloromethyl)-4-(1-methylethoxy)-5-methoxybenzene (18.9 g, 64.2 mmol) and potassium carbonate (45.0 g, 32 1 mmol, anhydrous, freshly ground) in absolute DMF (300 ml) are stirred for 12 hours at 60° C.

The residue that remains after the solvent is removed is dispersed between water (250 ml) and ether (250 ml). The aqueous phase is extracted with ether (1×100 ml), the combined organic phases are washed with water (3×200 ml) and saturated common salt solution (150 ml), dried (sodium sulfate/activated carbon), filtered, and the solvent is removed in a rotary evaporator.

After drying under high vacuum, the product is obtained as a colorless oil (33.7 g, 95%).

TLC: Petroleum ether:ethyl acetate=9:1, Rf=0.5 $^1$H NMR (CDCl$_3$) δ 7.04 (s, 1H), 7.01 (d, J=10 Hz, 2H), 6.79 (d, J=10 Hz, 2H), 6.73 (s, 1H); 4.47 (septet, J=6.5 Hz, 1H), 4.36 (septet, J=6.5 Hz, 1H), 3.80 (s, 3H), 3.72 (s, 6H), 3.48 (s, 2H), 2.65–2.47 (m, 2H), 2.26–2.06 (m, 2H), 1.31 (d, J=6.5 Hz, 12H); $^{13}$C NMR (CDCl$_3$) δ 171.4 (s), 156.1 (s), 149.8 (s), 146.2 (s), 133.0 (s), 129.3 (s), 129.1 (d), 118.2 (s), 116.2 (d), 116.0 (d), 115.8 (d), 69.7 (d), 58.7 (s), 55.9 (q), 52.3 (q), 37.4 (t), 34.5 (t), 29.9 (t), 21.95 (q), 21.9 (q) MT-54 JOS 1698 C$_{27}$H$_{35}$BrO$_7$ Cld.: C, 58.81; H, 6.40 Fnd.: C, 59.00: H, 6.26

Step 9

Alpha-[[2-bromo-4-methoxy-5-(1-methylethoxy)phenyl]methyl]-4-(1-methylethoxy)benzenebutanoic acid

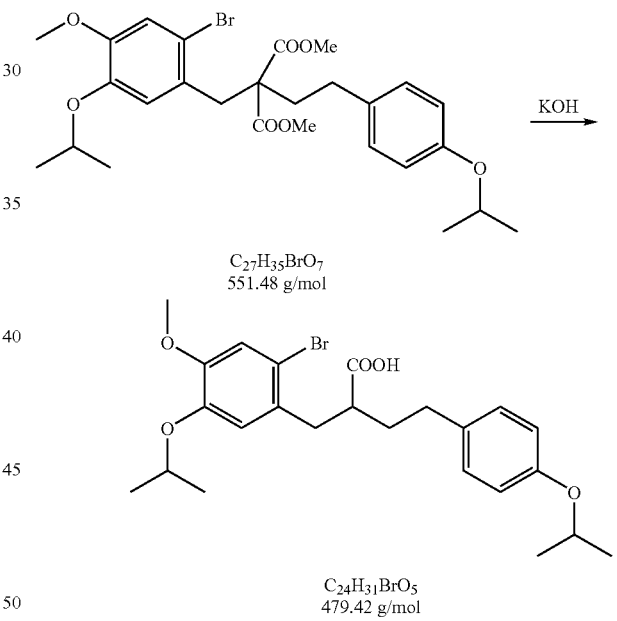

2-[2-Bromo-4-methoxy-5-(1-methylethoxy)phenyl]methyl-2-[2-[4-(1-methylethoxy)-phenyl]ethyl]propanedioic acid dimethyl ester (33.7 g, 61.1 mmol) and potassium hydroxide (17.5 g, 312 mmol) are stirred in ethanol (150 ml)/water (30 ml) for 12 hours at boiling temperature.

The reaction mixture is acidified with concentrated hydrochloric acid up to a pH of 1 and kept under ref lux for one hour.

The residue that remains after the solvent is removed is dispersed between water (250 ml) and ether (250 ml). The aqueous phase is extracted with ether (2×100 ml), the combined organic phases are washed neutral with water, washed with saturated common salt solution (150 ml), dried (sodium sulfate/activated carbon) and filtered. The residue that remains after the solvent is removed is decarboxylated in a bulb tube for 30 minutes at 140° C. and then distilled at 150° C./0.005 mbar. In this way, the product is obtained in the form of colorless crystals (27.5 g, 94%).

Melting point: 114–116° C. TLC: Chloroform:methanol=9:1, Rf=0.65 $^1$H NMR (DMSO-$d_6$) δ 7.09, (s, 1H), 7.01 (d, J=7.3 Hz, 2H), 6.80 (s, 1H), 6.78 (d, J=7.3 Hz, 2H), 4.69–4.37 (m, 2H), 372 (s, 3H), 3.00–2.33 (m, 5H), 1.99–1.58 (m, 2H), 1.18 (d, J=6.4 Hz, 12H); $^{13}$C NMR (DMSO$_6$): 176.0 (s), 155.6 (s), 149.3 (s), 145.8 (s), 133.1 (s), 130.3 (s), 129.1 (d), 118.1 (d), 116.0 (d), 115.5 (s), 114.1 (d), 70.6 (d), 69.0 (d), 55.8 (q), 44.9 (d), 33.5 (t), 31.9 (t), 21.85 (q), 21.8 (q) MT-100 JOS 1592 $C_{24}H_{31}BrO_5$ Cld.: C, 60.13; H, 6.52 Fnd.: C, 60.38; H, 6.55

Step 10

Alpha[[2-bromo-4-methoxy-5-(1-methylethoxy) phenyl]methyl]-4-(1-methylethoxy)benzenebutanoic acid amide

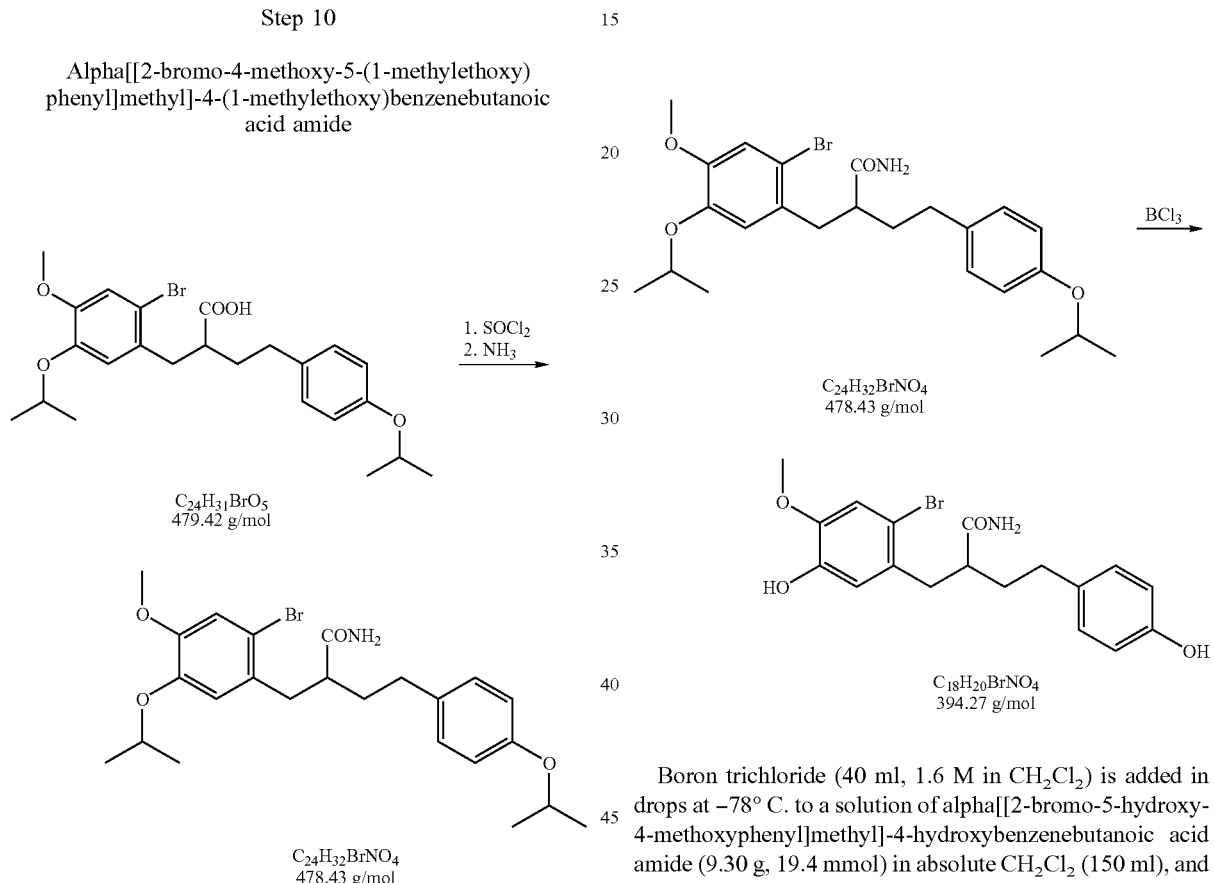

Thionyl chloride (50 ml) is added in drops at 0° C. within 15 minutes to alpha[[2-bromo-4-methoxy-5-(1-methylethoxy)phenyl]methyl]-4-(1-methylethoxy)-benzenebutanoic acid (10.0 g, 20.8 mmol) in CH$_2$Cl$_2$ (100 ml), and the mixture is stirred for two hours at this temperature.

The solvent is removed in a rotary evaporator, the residue is taken up in absolute formamide (15 ml) and mixed at 0° C. with ammonia in formamide (100 ml of a solution that is saturated at this temperature). The mixture is stirred for one hour at 0° C. and poured onto water (1500 ml).

The precipitated crystals are filtered off and digested with water (4×400 ml). In this way, the product is obtained in the form of colorless crystals (9.21 g, 92%).

Melting point: 154–156° C. TLC: CH$_2$:methanol=9:1, Rf=0.7 $^1$H NMR (DMSO-$d_6$) δ 7.32 (s, 1H), 7.08 (s, 1H), 7.02 (d, J=7.3 Hz, 2H), 6.83 (s, 1H), 6.80 (s, 1H), 6.78 (d, J=7.3 Hz, 2H), 4.68–4.32 (m, 2H), 3.77 (s, 3H), 3.39 (s, 3H), 3.00–2.62 (m, 2H), 2.00–1.58 (m, 2H), 1.18 (d, J=6.4 Hz, 12H); $^{13}$C NMR (DMSO-$d_6$): 175.8 (s), 155.5 (s), 149.1 (s), 145.8 (s), 133.5 (s), 130.9 (s), 129.9 (d), 118.1 (d), 115.8 (d), 115.5 (s), 114.1 (d), 70.9 (d), 69.0 (d), 55.8 (q), 45.9 (d), 34.2 (t), 32.1 (t), 21.85 (q), 21.8 (q) MT-112 JOS 1591 $C_{24}H_{32}BrNO_4$ Cld.: C, 60.25; H, 6.74; N, 2.93 Fnd.: C, 59.99; H, 6.56; N, 2.82

Step 11

Production of Alpha[[2-bromo-5-hydroxy-4-methoxyphenyl]methyl]-4-hydroxybenzenebutanoic acid amide Boron trichloride (40 ml, 1.6 M in CH$_2$Cl$_2$) is added in drops at –78° C. to a solution of alpha[[2-bromo-5-hydroxy-4-methoxyphenyl]methyl]-4-hydroxybenzenebutanoic acid amide (9.30 g, 19.4 mmol) in absolute CH$_2$Cl$_2$ (150 ml), and it is stirred for one hour at this temperature. Then, the mixture is heated to room temperature and stirred for two hours.

It is mixed with water (300 ml), and the organic solvent is distilled off in a rotary evaporator, whereby the crude product precipitates as crystals, the latter is filtered off and is digested with water (6×200 ml) and diisopropyl ether (2×40 ml). In this case, the product is obtained in the form of colorless crystals (6.76 g, 88%).

Melting point: 177–179° C. TLC: CH$_2$C$_2$: methanol=9:1, Rf=0.4 $^1$H NMR (DMSO-$d_6$) δ 9.18 (s, 2H), 7.18 (s, 1H), 7.04 (s, 1H), 6.97 (d, J=7.3 Hz, 2H), 6.72 (s, 1H), 6.65 (s, 1H), 6.66 (d, J=7.3 Hz, 2H), 3.77 (s, 3H), 3.48 (s, 3H), 2.92–2.38 (m, 4H); $^{13}$C NMR (DMSO-$d_6$) δ 175.6 (s), 155.5 (s), 147.0 (s), 145.8 (s), 131.3 (s), 129.9 (s), 129.8 (d), 117.9 (s), 115.8 (d), 115.0 (d), 11.9 (d), 56.0 (q), 48.1 (d), 37.6 (t), 37.0 (t) MT-114 JOS 1692 $C_{18}H_{20}BrNO_4$ Cld.: C, 54.84 H, 5.11; N, 3.55 Fnd.: C, 54.55; H, 4.90; N, 3.28

Step 12

1-Bromo-4a,5,9,10,11,12-hexahydro-3-methoxy-6-oxa-6H-benzo[a]cyclohepta[hi]benzofuran-11-carboxylic acid amide

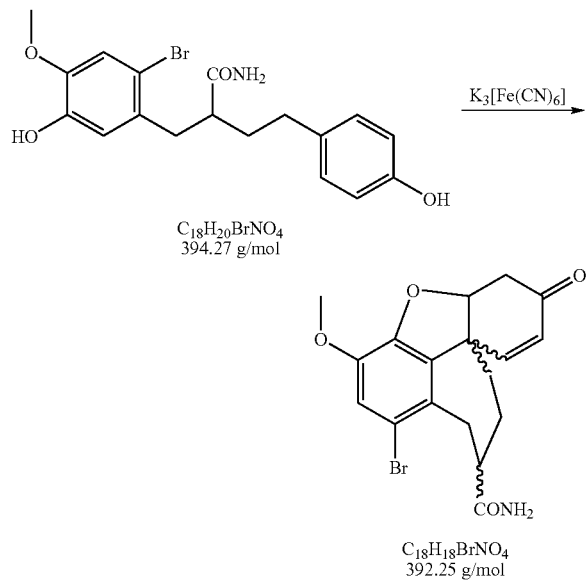

α-[[2-Bromo-5-hydroxy-4-methoxyphenyl]methyl]-4-hydroxybenzenebutanoic acid amide (3.00 g, 7.61 mmol) is suspended in chloroform (300 ml) and mixed with a solution of potassium hexacyanoferrate (III) (13.2 g, 40.0 mmol) in potassium carbonate solution (75 ml, ten percent).

The mixture is stirred vigorously at room temperature for 40 minutes and filtered on Hyflo. The aqueous phase is extracted with chloroform (3×50 ml), the combined organic phases are washed with water (2×200 ml) and saturated common salt solution (1×150 ml), dried (sodium sulfate/silica gel), filtered, and the crude product that is obtained after the solvent is concentrated by evaporation is purified by column chromatography (50 g of silica gel, ethyl acetate). In this way, the product is obtained in the form of colorless crystals (0.36 g, 12%).

TLC: Chloroform:methanol=9:1, Rf=0.4 and 0.5; $^1$H NMR (CDCl$_3$) δ 7.00 (s, 1H); 6.86 (dd, J=12 Hz, J=1 Hz, 1H), 6.06 (d, J=1 Hz, 1H), 5.02 (bs, 2H), 4.70 (s, 1H), 3.82 (s, 3H), 3.62 (d, J=16 Hz, 1H), 3.23 (dd, J=16 Hz, J=3 Hz, 1H), 3.08–2.89 (m, 1H), 2.77 (dd, J=16 Hz, J=6 Hz, 1H), 2.62–1.70 (m, 5H) $^{13}$C NMR (DMSO-d$_6$) δ 202.5 (s), 184.9 and 179.1 (s), 146.5 and 146.1 (d), 145.0 and 145.9 (s), 143.3 and 142.0 (s), 132.0 and 131.8 (s), 128.9 and 128.0 (s), 126.7 and 126.2 (d), 116.3 and 115.0 (s), 114.4 (d), 87.4 and 87.3 (d), 56.0 (q), 49.5 and 49.3 (s), 45.3 (d), 37.3 and 37.0 (t), 35.4 (t), 34.4 (t), 30.4 (t)

Deeper-Running Diastereomer $^1$H NMR (CDCl$_3$) δ 6.70–6.85 (m, 2H), 6.07–5.91 (m, 2H), 4.54 (s, 1H), 4.12 (s, 1H), 3.82 (s, 3H), 2.99 (s, 1H), 2.86 (t, J=15 Hz, 1H), 2.72 (d, J=16 Hz, 1H), 2.63 (dd, J=16 Hz, J=3 Hz, 1H), 2.30–1.60 (m, 9H); $^{13}$C NMR (CDCl$_3$) δ 146.4 (s), 143.9 (s), 133.7 (s), 128.5 (s), 128.1 (d), 127.5 (d), 123.3 (d), 111.7 (d), 88.9 (d), 62.4 (d), 56.3 (q), 52.8 (d), 48.3 (s), 45.1 (t), 35.8 (t), 35.6 (t), 30.4 (t) MT-115 JOS 1585 C$_{18}$H$_{18}$BrNO$_4$ Cld.: C, 55.12; H, 4.63; N, 3.57 Fnd.: C, 54.91; H, 4.66; N, 3.41

EXAMPLE 81

1-Bromo-4a,5,9,10,11,12-hexahydro-3-methoxy-6-hydroxy-6H-benzo[a]cyclohepta[hi]benzofuran-11-carboxylic acid amide

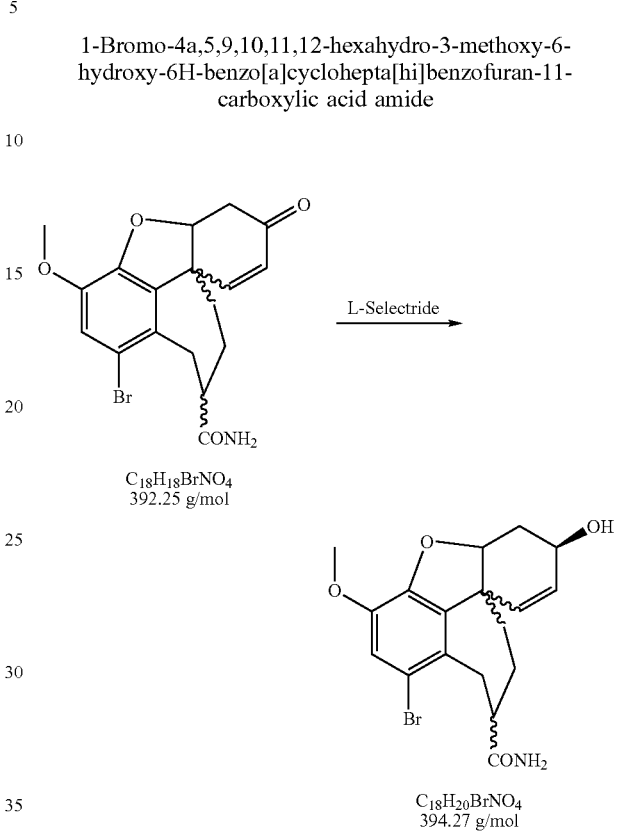

L-Selectride$^{(R)}$ (6.6 ml, 6.6 mmol, 1 M in THF) is added at 0° C. within is minutes to a suspension of 1-bromo-4a,5,9,10,11,12-hexahydro-3-methoxy-6-oxa-6H-benzo[a]cyclohepta[hi]benzofuran-11-carboxylic acid amide (860 mg, 2.19 mmol) in absolute THF (5 ml), and the mixture is stirred for 12 hours at room temperature. It is hydrolyzed with water (3 ml) and dispersed between water (10 ml) and ethyl acetate (10 ml), the aqueous phase is extracted with ethyl acetate (3×5 ml), the combined organic phases are washed with 1N hydrochloric acid (3×10 ml), water (2×10 ml), saturated sodium bicarbonate solution (1×10 ml) and saturated common salt solution (1×10 ml), dried (sodium sulfate/activated carbon), filtered, and the crude product that is obtained after the solvent is distilled off is purified by column chromatography (50 g of silica gel, ethyl acetate). In this way, the product is obtained in the form of colorless crystals (741 mg, 86%).

TLC: Chloroform:methanol=9:1, Rf=0.35 and 0.45 $^1$H NMR (CDCl$_3$) δ 6.92 (s, 1H), 6.10–5.89 (m, 2H), 5.82–5.53 (m, 2H), 4.54 (s, 1H), 4.13 (s, 1H), 3.81 (s, 3H), 3.51 (d, J=15 Hz, 1H), 3.05 (dd, J=17 Hz, J=6 Hz, 1H), 2.96–2.84 (m, 1H), 2.65 (d, J=16 Hz, 1H), 2.83 (dd, J=16 Hz, J=6 Hz, 1H), 2.44–1.40 (m, 9H); $^{13}$C NMR (CDCl$_3$) δ 177.7 and 175.2 (s), 145.3 (s), 145.7 (s), 144.2 (s), and 143.9 (s), 133.8 and 134.2 (s), 128.3 and 128.2 (d), 126.5 (d), 116.1 and 115.9 (s), 115.3 and 115.1 (d), 88.5 (d), 61.8 (d), 56.1 (q), 49.1 and 49.0 (s), 46.0 (d), 41.9 (t), 35.9 and 35.7 (t), 29.8 and 29.6 (t), 28.8 and 26.2 (t) MT-120 JOS 1710 C$_{18}$H$_{20}$BrNO$_4$ Cld.: C, 54.84; H, 5.11; N, 3.55 Fnd.: C, 54.84; H, 5.18; N, 3.43

EXAMPLE 82

11-Amino-1-bromo-4a,5,9,10,11,12-hexahydro-3-methoxy-6-hydroxy-6H-benzo[a]cyclohepta[hi]benzo-furan-6-ol (SPH-1459)

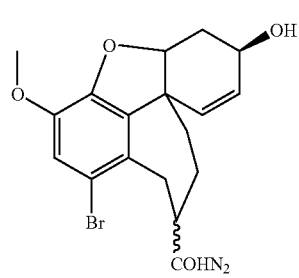

C$_{18}$H$_{20}$BrNO$_4$
394.27 g/mol

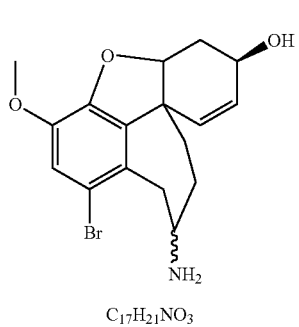

C$_{17}$H$_{21}$NO$_3$
367.27 g/mol

Bis(trifluoroacetoxy)iodobenzene (PIFA, 787 mg, 1.78 mmol) is dissolved in acetonitrile (3.5 ml, RPLC-quality) and mixed with water (3.5 ml, HPLC-quality). Then, 1-bromo-4a,5,9,10,11,12-hexahydro-3-methoxy-6-hydroxy-6H-benzo[a]cyclohepta[hi]benzofuran-11-carboxylic acid amide is added in substance within 2 hours, and the mixture is stirred for 24 hours at room temperature. The solvent is distilled off in a rotary evaporator, the residue is taken up in chloroform (5 ml), filtered, and purified by column chromatography (30 g of silica gel, chloroform:methanol:ammonia=96:3:1). In this way, the product is obtained in the form of colorless crystals (490 mg, 75%).

TLC: Chloroform:methanol=9:1, Rf=0.2 and 0.25 $^1$H NMR (MeOH-d$_4$) δ 7.07 (s, 1H), 6.12–5.87 (m, 2H), 5.82–5.53 (m, 2H), 4.53 (s, 1H), 4.14 (s, 1H), 3.80 (s, 3H), 3.59 (d, J=20 Hz, 1H), 3.14–2.92 (m, 1H), 2.47 (d, J=17 Hz, 1H), 2.16 (s, 3H), 2.01–2.62 (m, 2H); $^{13}$C NMR (MeOH-d$_4$) δ 148.3 and 148.2 (s), 146.5 and 146.1 (s), 135.8 (s), 129.9 and 129.3 (s), 128.5 and 127.9 (d), 125.9 and 123.9 (d), 118.4 and 118.1 (s), 116.9 and 116.0 (d), 118.4 and 118.0 (s), 116.8 and 116.0 (d), 89.0 and 88.9 (d), 62.4 and 62.3 (d), 57.2 (q), 50.6 and 50.4 (s), 49.8 (d), 38.5 (t), 36.0 and 33.0 (t), 31.8 and 31.0 (t), 31.4 and 28.3 (t); JOS 1707 C$_{17}$H$_{20}$BrNO$_3$*1 CHCl$_3$ Cld.: C, 44.52; H, 4.36; N, 2.88 Fnd.: C, 44.90; H, 4.30; N, 2.67

EXAMPLE 83

11-Amino-4a,5,9,10,11,12-hexahydro-3-methoxy-6-hydroxy-6H-benzo[a]cyclohepta[hi]benzofuran-6-ol

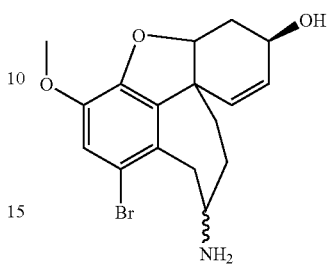

C$_{17}$H$_{21}$NO$_3$
367.27 g/mol

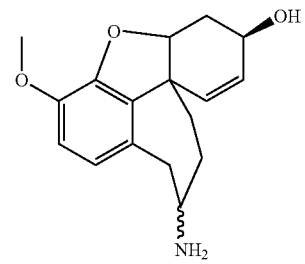

C$_{17}$H$_{21}$NO$_3$
287.36 g/mol

Production of the Copper-Zinc Alloy

Zinc powder (600 mg) and copper(I) iodide are reacted under argon in water (4 ml) and ethanol (4 ml) for 45 minutes in an ultrasonic bath, whereby a dark-black, fine-powder suspension is produced.

Debromination

11-Amino-1-bromo-4a,5,9,10,11,12-hexahydro-3-methoxy-6-hydroxy-6H-benzo[a]cyclohepta[hi]benzofuran-6-ol (80 mg, 0.22 mmol) and calcium chloride (300 mg, 2.7 mmol) are added in substance to the suspension that is produced, and the mixture is stirred for 12 hours at boiling temperature. It is mixed with concentrated aqueous ammonia solution (1 ml), the solvent is removed in a rotary evaporator, the residue is taken up in chloroform (15 ml), filtered, and the residue that is obtained after the filtrate is concentrated by evaporation in a rotary evaporator is purified by column chromatography (30 g of silica gel, chloroform:methanol:ammonia=96:3:1). In this way, the two optical isomers can be separated (10 mg, 0.04 mmol of isomer A: 26 mg, 0.09 mmol of isomer B; a total of 36 mg, 59%) and obtained as a colorless foam.

Higher-Running Diastereomer

1H NMR (CDCl$_3$) δ 6.73–6.62 (m, 2H), 6.05 (s, 2H), 4.62 (s, 1H), 4.14 (s, 1H), 3.82 (s, 3H), 3.57 (s, 1H), 3.22 (d, J=16 Hz, 1H), 2.83 (dd, J=16 Hz, J=6.5 Hz, 1H), 2.24–1.60 (m, 9H); $^{13}$C NMR (CDCl$_3$) δ 146.2 (s), 144.3 (s), 133.6 (s), 128.4 (s), 128.1 (d), 127.2 (d), 124.8 (d), 111.9 (d), 89.0 (d), 62.6 (d), 56.3 (q) 49.0 (s), 48.3 (d), 41.8 (t), 32.5 (t), 30.4 (t), 30.4 (t)

Deeper-Running Diastereomer $^1$H NMR (CDCl$_3$) δ 6.70–6.58 (m, 2H), 6.07–591 (m, 2H), 4.54 (s, 1H), 4.12 (s, 1H), 3.82 (s, 3H), 2.99 (s, 1H), 2.86 (t, J=15 Hz, 1H), 2.72 (d, J=16 Hz, 1H), 2.63 (dd, J=16 Hz, J=3 Hz, 1H), 2.30–1.60 (m, 9H); $^{13}$C NMR (CDCl$_3$) δ 146.4 (s), 143.9 (s), 133.7 (s), 128.5 (s), 128.1 (d), 127.5 (d), 123.3 (d), 111.7 (d), 88.9 (d), 62.4 (d), 56.3 (q), 52.8 (d), 48.3 (s), 45.1 (t), 35.8 (t), 35.6 (t), 30.4 (t).
Diagram for Example 83:
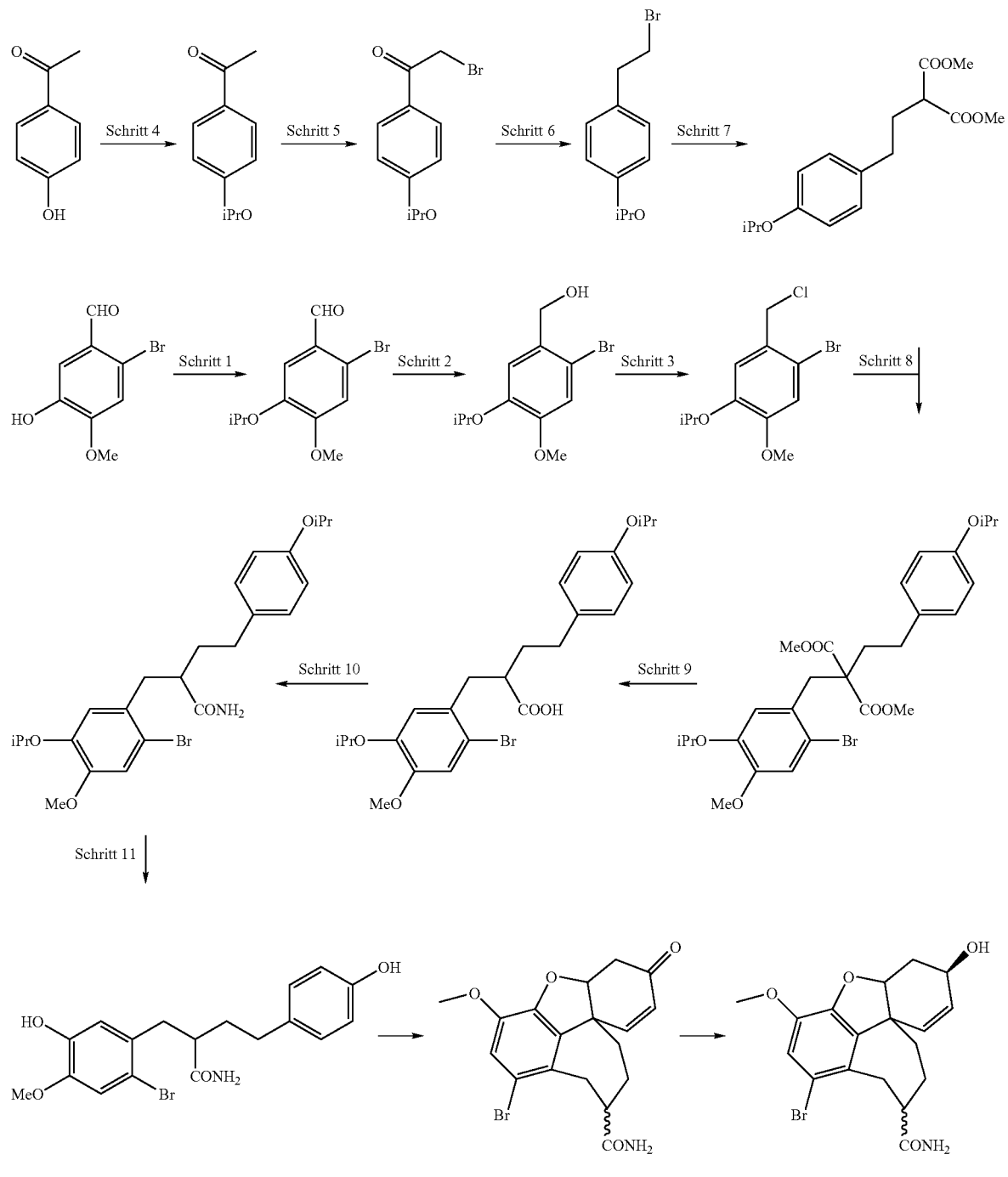

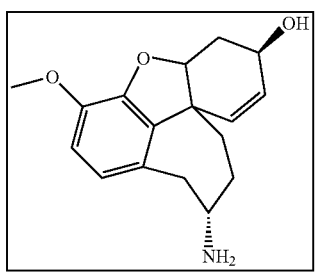

Beispiel 83

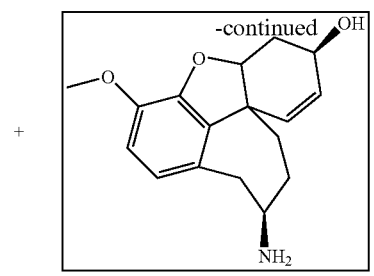

Beispiel 83

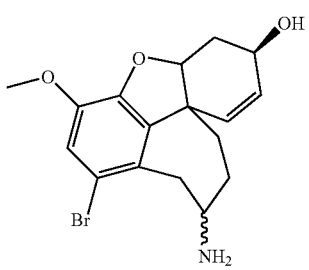

Beispiel 82

[Key:]
Schritt = Step
Beispiel = Example

EXAMPLE 84

Step 1

Condensation and Reduction: General Operating Instructions

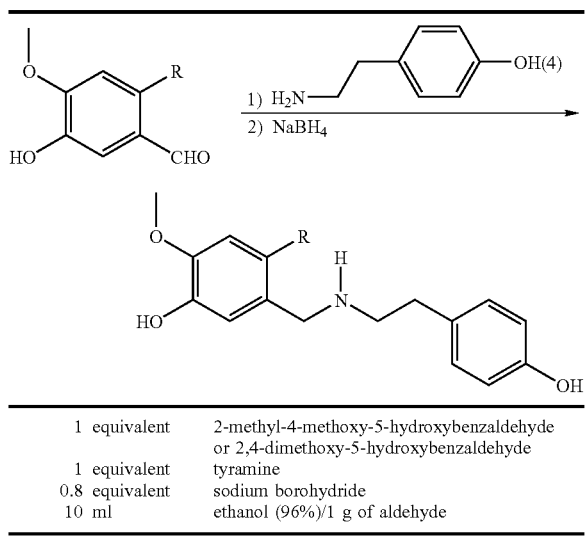

| 1 equivalent | 2-methyl-4-methoxy-5-hydroxybenzaldehyde or 2,4-dimethoxy-5-hydroxybenzaldehyde |
| 1 equivalent | tyramine |
| 0.8 equivalent | sodium borohydride |
| 10 ml | ethanol (96%)/1 g of aldehyde |

The educt was suspended in ethanol, and the tyramine was added while being stirred, then the reaction mixture was refluxed for 8.5 hours. Since the Schiff base (MH-16' or 34') that formed on the TLC plate breaks back down into the starting materials, the reaction progress was determined by reduction of a small sample with sodium borohydride, conventional working-up and application of the product obtained.

After 8.5 hours, the reaction mixture was cooled in an ice bath to 0° C., and the sodium borohydride, dissolved in 4 ml of water/1 g, was slowly added in drops, then stirred in an ice bath for 30 minutes. Then, it was poured onto 150 ml of ice/water/1 g of aldehyde while being stirred vigorously, the white precipitate that was produced was filtered off and dried in a vacuum drying oven. A second fraction of the product, which was collected and dried, was precipitated from the mother liquor.

EXAMPLE 84

Step 1a 5-(N-[2-[4-Hydroxyphenyl]ethyl]aminomethyl)-2-methoxy-4-methylphenol (MH-16)

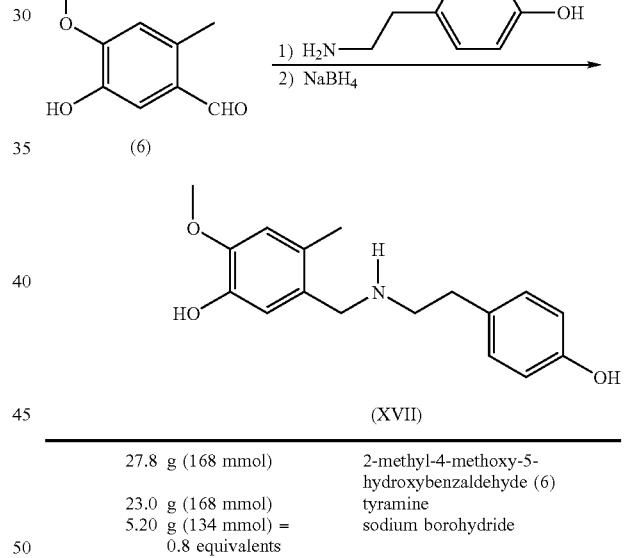

| 27.8 g (168 mmol) | 2-methyl-4-methoxy-5-hydroxybenzaldehyde (6) |
| 23.0 g (168 mmol) | tyramine |
| 5.20 g (134 mmol) = 0.8 equivalents | sodium borohydride |

Yield: 43.4 g (161 mmol=96% of theory) of a beige powder; $C_{17}H_{21}NO_3$[287.36] TLC: $R_f$=0.21 (CHCl$_3$: MeOH=9:1+1% concentrated NH$_4$OH) Melting point: 122–124° C.

|  | % C | % H | % N |
| --- | --- | --- | --- |
| Cld.: | 71.06 | 7.37 | 4.87 |
| Fnd.: | 71.07 | 7.41 | 4.86 |

$^1$H-NMR (200 MHz, DMSO-d$_6$) δ 6.90 (m, 2H), 6.67 (s, 1H), 6.62 (m, 2H), 6.55 (s, 1H); 3.72 (s, 3H); 3.51 (s, 2H); 2.73 (t, J=6.5 Hz, 2H); 2.60 (t, J=6.95 Hz, 2H); 2.10 (s, 3H); $^{13}$C-NMR (50 MHz, DMSO-d$_6$) δ 155.4 (s), 145.8 (s), 143.9 (s), 130.9 (s), 130.4 (s), 129.3 (d), 126.0 (s), 116.2 (d), 115.0 (d), 114.3 (d), 55.7 (q), 51.1 (t), 50.3 (t), 35.0 (t), 17.9 (q)

EXAMPLE 84

Step 1b 5-(N-[2-[4-Hydroxyphenyl]ethyl]aminomethyl)-2,4-dimethoxyphenol (MH-34)

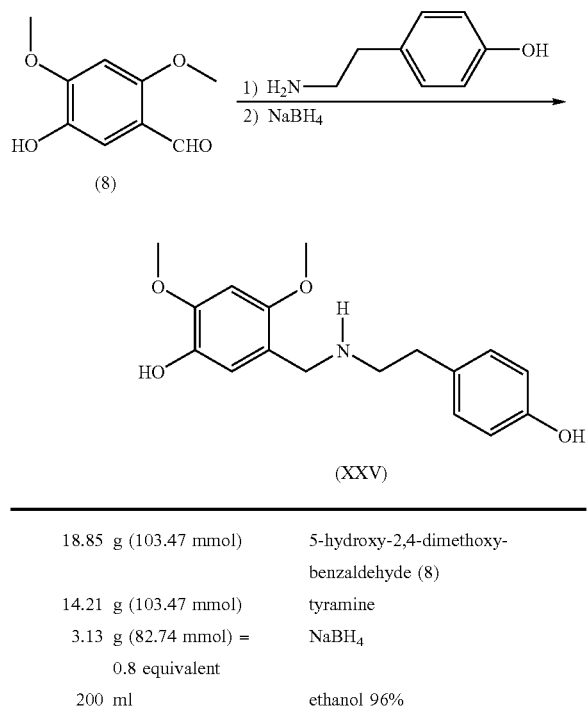

| 18.85 g (103.47 mmol) | 5-hydroxy-2,4-dimethoxy-benzaldehyde (8) |
| 14.21 g (103.47 mmol) | tyramine |
| 3.13 g (82.74 mmol) = 0.8 equivalent | $NaBH_4$ |
| 200 ml | ethanol 96% |

Yield: 28.1 g=92.63 mmol=89.5% of theory $C_{17}H_{21}NO_4$ [303.36] TLC: $R_f$=0.14 ($CHCl_3$:MeOH=9:1+1% concentrated $NH_4OH$) Melting point: 170–173° C. $C_{17}H_{21}NO_4$ [303.36] (contaminated with aliphatic substance; about $C_{15}H_{32}$, Schliffett)

|  | % C | % H | % N |
|---|---|---|---|
| Cld.: | 67.31 | 6.98 | 4.62 |
| Fnd.: | 68.10 | 7.04 | 4.66 |

$^1$H-NMR (200 MHz, DMSO-$d_6$) δ 6.95 (m, 2H), 6.70 (s, 1H), 6.64 (m, 2H), 6.57 (s, 1H), 3.75 (s, 3H), 3.66 (s, 3H), 3.52 (s, 2H), 2.59 (bs, 4H); $^{13}$C-NMR (50 MHz, DMSO-$d_6$) δ 155.3 (s), 149.9 (s), 146.3 (s), 139.7 (s), 130.4 (s), 129.3 (d), 120.4 (s), 116.6 (d), 115.0 (d), 98.4 (d), 56.0 (q+q), 50.6 (t), 47.1 (t), 35.0 (t)

EXAMPLE 84

Step 2

Formylation: General Operating Instructions

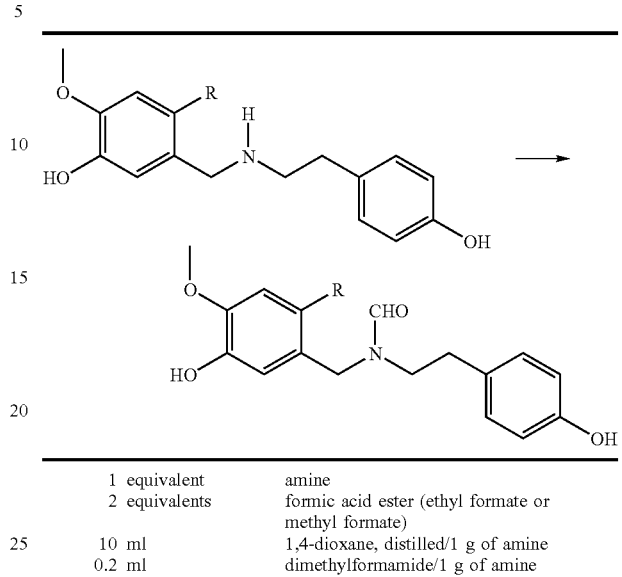

| 1 equivalent | amine |
| 2 equivalents | formic acid ester (ethyl formate or methyl formate) |
| 10 ml | 1,4-dioxane, distilled/1 g of amine |
| 0.2 ml | dimethylformamide/1 g of amine |

Catalytic Amount of Formic Acid

All reagents were refluxed together (formic acid optionally was added several times), and the reaction mixture was evaporated to the dry state in a vacuum after the end of the reaction. The solid residue was taken up in 10 ml of methanol/1 g of amine, and 50 ml of ice/water/1 g of amine was added in portions while being stirred, whereby the suspension of the intermediate product was converted under hydrolysis into the flocculent end product, which was suctioned off and dried.

EXAMPLE 84

Step 2a

N-((5-Hydroxy-4-methoxy-2-phenylmethyl)-N-(2-[4-hydroxyphenyl]ethyl)]formamide (MH-18)

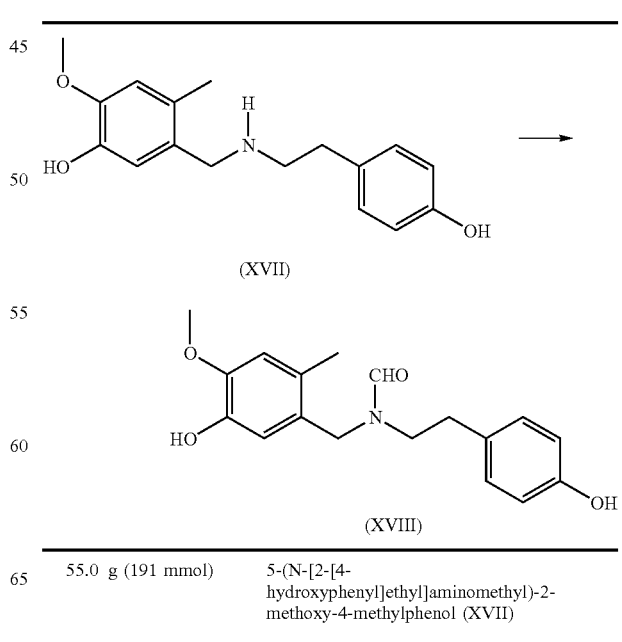

| 55.0 g (191 mmol) | 5-(N-[2-[4-hydroxyphenyl]ethyl]aminomethyl)-2-methoxy-4-methylphenol (XVII) |

-continued

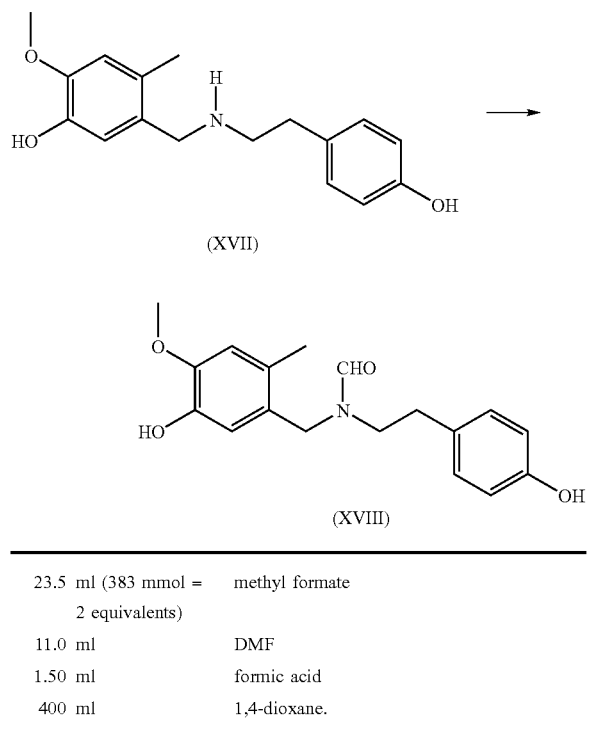

| 23.5 ml (383 mmol = 2 equivalents) | methyl formate |
| --- | --- |
| 11.0 ml | DMF |
| 1.50 ml | formic acid |
| 400 ml | 1,4-dioxane. |

The working-up is carried out after 7 hours.

Yield: 49.8 g (158 mmol=82.6% of theory) of a beige powder $C_{18}H_{21}NO_4$ [315.37] TLC: $R_f$=0.35 (CHCl$_3$: MeOH=9:1+1% concentrated NH$_4$OH) Melting point: 170–171° C.

| | % C | % H | % N |
| --- | --- | --- | --- |
| Cld.: | 68.55 | 6.71 | 4.44 |
| Fnd.: | 68.77 | 6.86 | 4.14 |

$^1$-NMR (200 MHz, DMSO-d$_6$) δ 9.20 (s, 1H), 8.74 (d, J=15.3 Ez, 1H), 8.19 (s, 0.5H), 7.88 (s, 0.5H), 7.00–6.87 (m, 2H), 6.74 (s, 1H), 6.72–6.56 (m, 2H), 6.59 (s, 1H), 4.31 (s, 1H), 4.23 (s, 1H), 3.73 (s, 3H), 3.21 (dd, J=15.3, 7.6 Hz, 2H), 2.60 (t, J=7.6 Hz, 2H), 2.12 (s, 3H); $^{13}$C-NMR (50 MHz, DMSO-d$_6$) δ 162.7 and 162.3 (d), 155.7 (s), 146.7 and 146.5 (s), 144.4 and 144.2 (s), 129.7 and 129.4 (d), 128.9 and 128.4 (s), 126.5 (s), 126.4 and 126.3 (s), 116.3 and 115.9 (d), 115.1 (d), 114.6 and 114.4 (s), 55.6 (q), 48.0 and 47.4 (t), 43.3 and 41.6 (t), 33.2 and 31.9 (t), 18.1 and 18.0 (q).

EXAMPLE 84

Step 2b

N-(2-(4-Hydroxyphenyl)ethyl)-N-((5-hydroxy-2,4-dimethoxyphenyl)methyl)-formamide (MH-35)

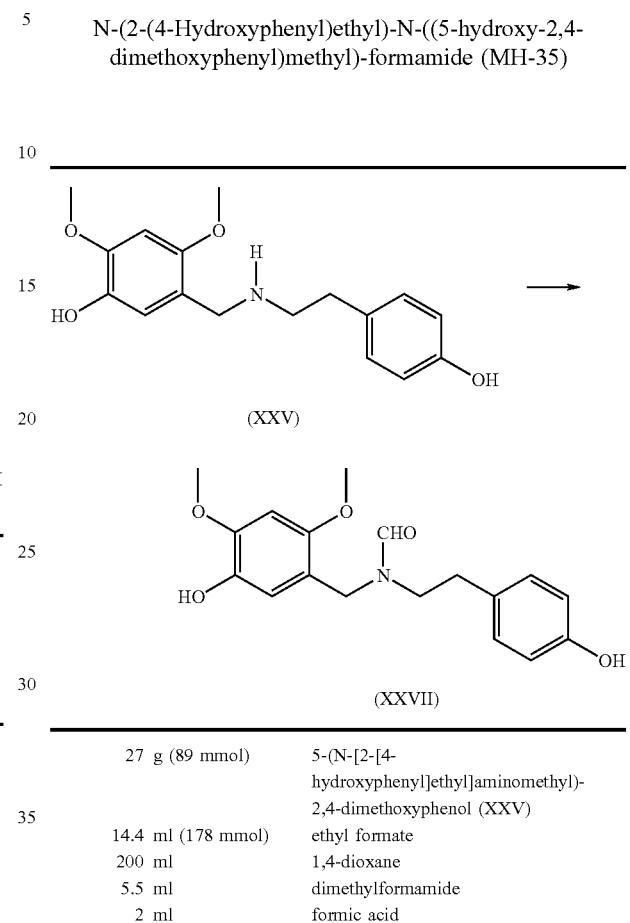

| 27 g (89 mmol) | 5-(N-[2-[4-hydroxyphenyl]ethyl]aminomethyl)-2,4-dimethoxyphenol (XXV) |
| --- | --- |
| 14.4 ml (178 mmol) | ethyl formate |
| 200 ml | 1,4-dioxane |
| 5.5 ml | dimethylformamide |
| 2 ml | formic acid |

The working-up was carried out after 24 hours, and the formic acid was added in 3 portions at intervals of several hours.

Yield: 26.13 g (78.85 mmol 88.6% of theory) of a beige powder $C_{18}H_{21}NO_5$ [331.37] TLC: $R_f$=0.53 (CHCl$_3$: MeOH=9:1+1% concentrated NH$_4$OH) Melting point: 130–132° C.

| | % C | % H | % N |
| --- | --- | --- | --- |
| Cld.: | 65.24 | 6.39 | 4.23 |
| Fnd.: | 64.97 | 6.40 | 4.18 |

$^1$H-NMR (200 MHz, DMSO-d$_6$) δ 9.18 (bs, 1H), 8.48 (d, J=7.4 Hz, 1H), 8.16 (s, 0.5H), 7.86 (s, 0.5H), 6.98–6.87 (m, 2H), 6.71–6.58 (m, 4H), 4.31 (s, 1H), 4.19 (s, 1H), 3.78 (s, 3H), 3.75 (s, 3H), 3.21 (dd, J=16.4, 7.7 Hz, 2H), 2.69–2.55 (m, 2H); $^{13}$C-NMR (50 MHz, DMSO-d$_6$) δ 162.7 and 162.5 (d), 155.7 and 155.6 (s), 150.6 and 150.3 (s), 146.7 and 147.3 (s), 140.1 and 139.9 (s), 129.6 and 129.3 (d), 129.0 and 128.4 (s), 116.8 and 116.4 (d), 116.2 and 115.9 (s), 115.1 (d), 98.5 and 98.4 (d), 56.3 and 56.2 (q), 55.9 (q), 47.9 and 45.2 (t), 43.0 and 38.3 (t), 33.4 and 31.9 (t)

EXAMPLE 84

Step 3

Phenolic Oxidative Coupling:
1-Methylgalanthamine (XV)

[(±)-(4aα,8aR*)]-4a,5,9,10,11,12-Hexahydro-3-methoxy-1-methyl-6-oxo-6H-benzofuro[3a,3,2-ef][2]benzazepine-11-carboxaldehyde, 1-Methyl-N-formylnarwedine (MH-19)

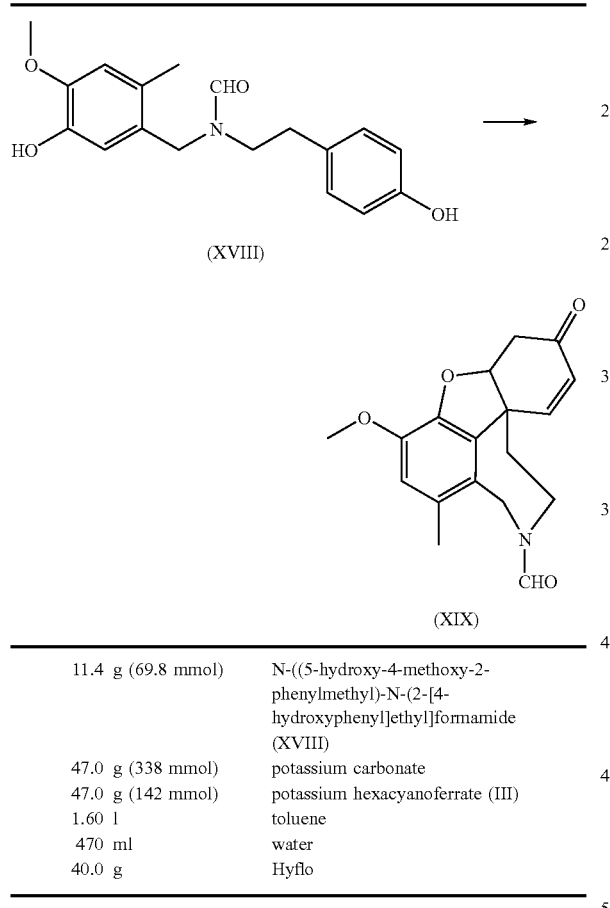

| 11.4 g (69.8 mmol) | N-((5-hydroxy-4-methoxy-2-phenylmethyl)-N-(2-[4-hydroxyphenyl]ethyl]formamide (XVIII) |
| --- | --- |
| 47.0 g (338 mmol) | potassium carbonate |
| 47.0 g (142 mmol) | potassium hexacyanoferrate (III) |
| 1.60 l | toluene |
| 470 ml | water |
| 40.0 g | Hyflo |

Potassium carbonate, potassium hexacyanoferrate (III), water and toluene were heated in a 4 liter-four-neck flask to 80° C., and then the educt was sprinkled while being mechanically stirred vigorously. The temperature was kept at 80° C. for 1 hour, then Hyflo was added and stirred for 10 more minutes. The reaction mixture was suctioned off, and the solid residue was rewashed 1× with water and 3× with hot toluene. The toluene phase was separated from the aqueous phase, and the latter was extracted with toluene. The organic phases were combined, the solvent was drawn off, and the product was dried in a vacuum drying oven.

Yield: 6.17 g (19.7 mmol=55.0% of theory) of a light yellow powder $C_{18}H_{19}NO_4$ [313.39] TLC: $R_f$=0.48 and 0.42 (2 rotamers) ($CHCl_3$:MeOH=9:1+1% concentrated $NH_4OH$) Melting point: Decomposition>215° C.

|  | % C | % H | % N |
| --- | --- | --- | --- |
| Cld.: | 69.00 | 6.11 | 4.47 |
| Fnd.: | 68.78 | 6.33 | 4.40 |

$^1$H-NMR (Mixture that consists of 2 rotamers, 200 MHz, DMSO-$d_6$): δ 8.18 (s, 0.2H), 8.10 (s, 0.8H), 7.25 (dd, J=10.4, 1.9 Hz, 0.8H), 7.15 (dd, J=10.4, 1.9 Hz, 0.2H), 6.73 (s, 0.2H), 6.69 (s, 0.8H), 5.95 (d, J=10.3 Hz, 0.8H), 5.93 (d, J=10.3 Hz, 0.2H), 5.14 (d, J=15.4 Hz, 0.8H), 4.83 (d, J=15.4 Hz, 0.2H), 4.67 (bs, 1H), 4.51 (d, J=15.4 Hz, 0.2H), 4.07 (d, J=15.4 Hz, 0.8H), 3.97 (bs, 1H), 3.78–3.60 (m, 4H), 3.07 (dd, J=17.4, 3.4 Hz, 1H), 2.78 (dd, J=17.4, 1.9 Hz, 1H), 2.33 (s, 3H), 2.30 (s, 0.8H), 2.22 (s, 0.2H), 1.86 (dt, J=13.5, 3.7 Hz, 1H); $^{13}$C-NMR (mixture that consists of 2 rotamers, 50 MHz, DMSO-$d_6$) δ 194.9 (s), 162.8 and 162.1 (d), 145.2 and 144.8 (d), 145.5 and 145.3 (s), 142.9 and 142.8 (s), 130.6 and 130.3 (s), 128.2 (s), 127.5 and 127.0 (s), 126.4 and 126.2 (d), 114.5 and 114.2 (d), 87.0 and 86.8 (d), 55.6 (q), 49.2 and 49.0 (s), 47.4 and 45.6 (t), 41.8 and 40.1 (t), 37.7 (t), 37.5 (t), 37.4 (t), 34.1 (t), 19.2 and 18.9 (q)

EXAMPLE 85

[(±)-(4aα,6β,8aR*)]-4a,5,9,10,11,12-Hexahydro-3-methoxy-1-methyl-6H-benzofuro[3a,3,2-ef][2]benzazepin-6-ol, 1-methyl-N-demethylgalanthamine (MH-20)

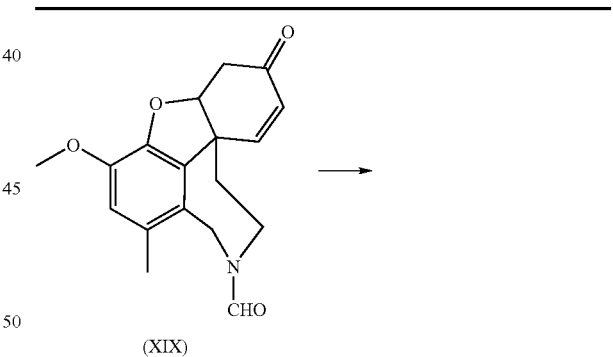

| 500 mg (1.60 mmol) | 1-Methyl-N-formylnarwedine (XIX) |
| --- | --- |

-continued

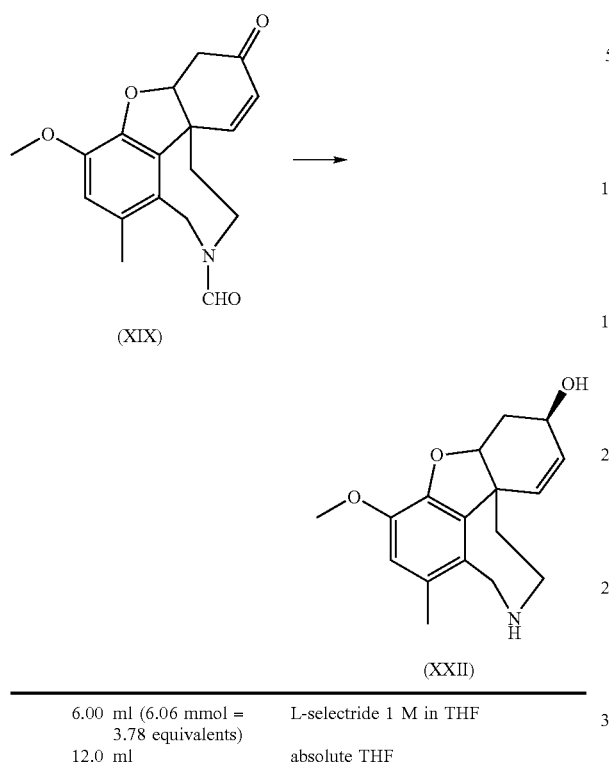

| 6.00 ml (6.06 mmol = 3.78 equivalents) | L-selectride 1 M in THF |
| 12.0 ml | absolute THF |

A suspension of finely ground educt in absolute THF was cooled to 0° C., and then L-selectride was added in drops, whereby a temperature increase of 5° C. was to be observed. At 0° C., it was stirred for 1 hour, whereby a clear solution formed. After 70 minutes, 5 drops of water and 1 ml of concentrated aqueous ammonia were added, stirred for 10 minutes, and then the reaction mixture was concentrated by evaporation by 50% in a vacuum. Then, 10 ml of ammonia were added once more, and the solution was extracted with methylene chloride. The combined organic phases were rewashed once with dilute ammonia solution, dried on sodium sulfate, filtered, and the solvent was drawn off. The luminous red oil that was produced was purified on a silica gel column.

Yield: 440 mg (1.53 mmol=96.0% of theory) of a colorless oil $C_{17}H_{21}NO_3$ [287.36] TLC: $R_f$=0.39 (CHCl$_3$:MeOH=9:1+1% NH OH) $C_{17}H_{21}NO_3 \times 0.8$ H$_2$O [301.76]

|  | % C | % H | % N |
| --- | --- | --- | --- |
| Cld.: | 67.66 | 7.55 | 4.64 |
| Fnd.: | 67.60 | 7.40 | 4.65 |

$^1$H-NMR (200 MHz, CDCl$_3$) δ 6.51 (s, 1H), 6.06 (d, J=10.2 Hz, 1H), 5.97 (dd, J=10.2, 4.5 Hz, 1H), 4.57 (bs, 1H), 4.27 (d, J=16.0 Hz, 1H), 4.11 (t, J=4.4 Hz, 1H), 3.80 (s, 3H), 3.77 (d, J=16.0 Hz, 1H), 3.40–3.10 (m, 2H), 2.65 (dd, J=15.6, 3.2 Hz, 1H), 2.23 (s, 3H), 1.99 (ddd, J=15.6, 4.9, 2.3 Hz, 1H), 1.89–1.63 (m, 2H); $^{13}$C-NMR (50 MHz, CDCl$_3$) δ 144.4 (s), 142.9 (s), 133.4 (s), 130.5 (s), 127.8 (s), 127.5 (d), 127.1 (d), 113.5 (d), 88.1 (d), 61.4 (d), 55.8 (q), 49.0 (s), 48.9 (t), 46.9 (t), 39.7 (t), 29.8 (t), 19.4 (q)

EXAMPLE 86

[(±)-(4aα,8aR*)]-4a,5,9,10,11,12-Hexahydro-3-methoxy-1,4'-dimethyl-spiro[-6H-benzofuro[3a,3,2-ef][2]benzazepine-6,2'-[1,3]-dioxolane]-11-carboxaldehyde, 1-Methyl-N-formyl-narwedine Ketal (MH-21)

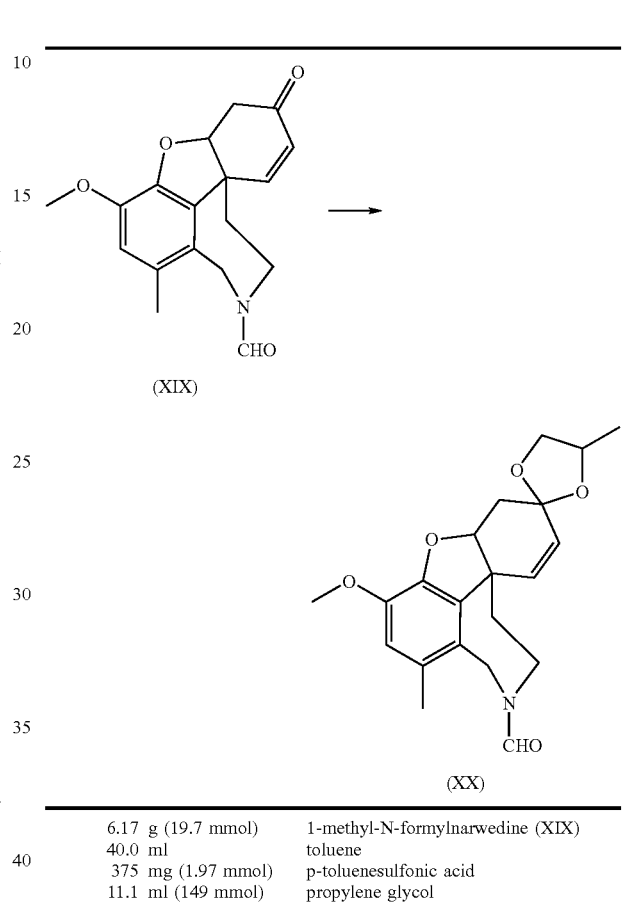

| 6.17 g (19.7 mmol) | 1-methyl-N-formylnarwedine (XIX) |
| 40.0 ml | toluene |
| 375 mg (1.97 mmol) | p-toluenesulfonic acid |
| 11.1 ml (149 mmol) | propylene glycol |

In a flask with a water separator, the educt was introduced into toluene, and ⅓ of the p-toluenesulfonic acid was added to ⅔ of propylene glycol. The reaction mixture was refluxed, and after 2 hours, the solution of the residual p-toluenesulfonic acid in propylene glycol was added in portions over 5 hours, then refluxed for another 6 hours. After the end of the reaction (HPLC study necessary, since TLC has little informational value), the toluene phase was separated, and the propylene glycol phase was exhaustively extracted with toluene. The collected toluene phases were extracted 2× with acetic acid (8% in water), 2× with saturated sodium bicarbonate solution and 2× with water, then the solvent was drawn off.

Yield: 5.34 g (14.38 mmol=73% of theory) of a beige foam $C_{21}H_{25}NO_5$ [371.44] TLC: $R_f$=0.71 (CHCl$_3$:MeOH=9:1) $C_{21}H_{25}NO_5 \times 0.85$ H$_2$O [386.74]

|  | % C | % H | % N |
| --- | --- | --- | --- |
| Cld.: | 65.22 | 6.96 | 3.62 |
| Fnd.: | 65.39 | 7.19 | 3.52 |

$^1$H-NMR (mixture that consists of diastereomers and rotamers, 200 MHz, CDCl$_3$) δ 8.14–8.01 (m, 1H), 7.30–7.09

(m, 2H), 6.51 (s, 1H), 6.22–5.97 (m, 1H), 5.85–5.61 (m, 1H), 5.38 and 4.77 (d, J=15.7 Hz, 1H), 4.49 (bs, 1H), 4.37–4.01 (m, 2H), 3.93–3.74 (m, 5H), 3.71–3.10 (m, 1H), 2.79–2.58 (m, 1H), 2.41 (s, 2H), 2.32 (d, J=10.2 Hz, 3H), 2.25–1.74 (m, 3H); $^{13}$C-NMR (mixture that consists of diastereomers and rotamers, 50 MHz, CDCl$_3$) δ 162.5 (d), 161.7 (d), 143.7 (s), 143.6 (s), 143.3 (d), 142.7 (d), 129.9 (s), 129.6 (s), 127.8 (d), 127.6 (d), 126.0 (s), 125.7 (s), 114.6 (d), 114.4 (d), 87.5 (d), 87.4 (d), 68.2 (d), 68.0 (t), 56.1 (q), 56.0 (q), 49.2 (s), 49.0 (s), 48.7 (t), 46.7 (t), 43.2 (t), 41.2 (t), 38.7 (t), 37.2 (t), 37.1 (t), 34.8 (t), 19.7 (q), 19.4 (q), 18.9 (q)

EXAMPLE 87

[(±)(4aα,8aR*)]-4a,5,9,10,11,12-Hexahydro-3-methoxy-1,11-dimethyl-6H-benzofuro[3a,3,2-ef][2]benzazepin-6-one, 1-methylnarwedine (MH-22)

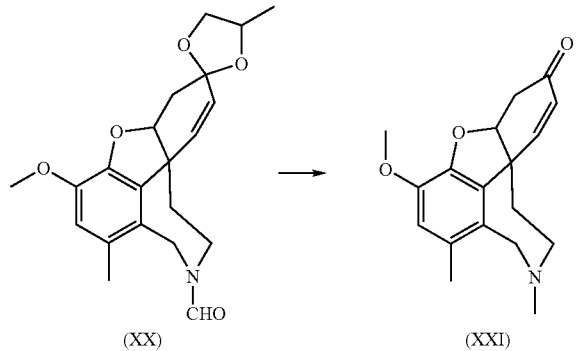

| 5.34 g (14.4 mmol) | 1-methyl-N-formylnarwedine ketal (XX) |
| 25.2 ml (25.2 mmol) = 1.75 equivalents | lithium aluminum hydride 1 M in THF |
| 20 ml | absolute THF |

1-Methyl-N-formylnarwedine (V) was dissolved in absolute THF, and lithium aluminum hydride was added in portions while being stirred. After 15 minutes, the reaction mixture was mixed with 10 ml of toluene, then hydrolyzed with 1.5 ml of water, and after 1.5 ml of sodium hydroxide solution (15% in water) was added, it was stirred for 15 minutes. After 1.5 g of Hyflo was added, it was refluxed for 1 hour, filtered off, the filter cake was boiled up 3× with 10 ml of toluene:THF=1:1 each and in each case suctioned off. The organic phases were evaporated to the dry state, taken up with 25 ml of 4N HCl and stirred for 25 minutes at 60° C., then exhaustively extracted with ethyl acetate. The collected organic phases were backwashed with dilute HCl. The collected acidic, aqueous phases were released by distillation of excess ethyl acetate, then made basic with concentrated aqueous ammonia and exhaustively extracted with chloroform. The collected chloroform phases were washed with saturated common salt solution, dried on sodium sulfate, filtered, and the solvent was drawn off. The purification was carried out by recrystallization from diisopropyl ether:ethyl acetate=9:1.

Yield: 4.01 g (13.36 mmol=93% of theory) of light yellow, very fine needles C$_{18}$H$_{21}$NO$_3$ [299.37] TLC: R$_f$=0.43 (CHCl$_3$:MeOH=95:5) Melting point: 121–122° C.

|  | % C | % H | % N |
|---|---|---|---|
| Cld.: | 72.22 | 7.07 | 4.68 |
| Fnd.: | 71.95 | 7.08 | 4.57 |

$^1$H-NMR (200 MHz, CDCl$_3$) δ 7.01 (dd, J=10.4, 1.6 Hz, 1H), 6.56 (s, 1H), 5.99 (d, J=10.4 Hz, 1H), 4.68–4.62 (m, 1H), 3.97 (d, J=15.7 Hz, 1H), 3.80 (s, 3H), 3.79 (d, J=15.7 Hz, 1H), 3.22–2.95 (m, 3H), 2.71 (dd, J=17.8, 3.7 Hz, 1H), 2.44 (s, 3H), 2.23 (s, 3H), 2.20–2.01 (m, 1H), 1.87 (dt, J=13.8, 3.4 Hz, 1H); $^{13}$C-NMR (50 MHz, CDCl$_3$) δ 194.4 (s), 145.2 (s), 142.9 (s), 131.0 (s), 128.9 (s), 126.8 (d+d+s), 114.3 (d), 87.7 (d), 55.9 (q), 55.8 (t), 54.1 (t), 48.9 (s), 43.5 (q), 37.1 (t), 33.4 (t), 19.4 (q)

EXAMPLE 88

[(±)-(4aα,6β,8aR*)]-4a,5,9,10,11,12-Hexahydro-3-methoxy-1,11-dimethyl-6H-benzofuro[3a,3,2-ef][2]benzazepin-6-ol, 1-Methylgalanthamine (MH-30)

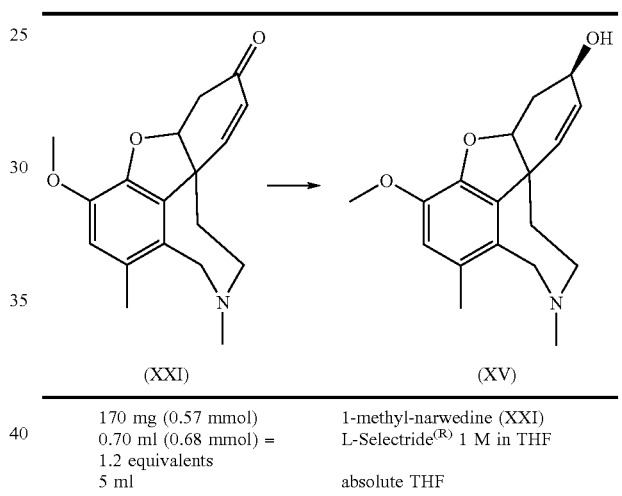

| 170 mg (0.57 mmol) | 1-methyl-narwedine (XXI) |
| 0.70 ml (0.68 mmol) = 1.2 equivalents | L-Selectride$^{(R)}$ 1 M in THF |
| 5 ml | absolute THF |

The educt was introduced into THF under N$_2$ atmosphere and cooled to −25° C., then L-Selectride was slowly added in drops. It was stirred for 30 minutes at −15° C., whereby the initial suspension was in a clear solution. Then, the reaction mixture was brought to room temperature over 1 hour, hydrolyzed with 5 drops of water, stirred for 30 minutes, 0.5 ml of concentrated aqueous NH$_4$OH was added, stirred for another 10 minutes, 2 ml of concentrated NH$_4$OH was added again and finally it was extracted with methylene chloride. The combined organic phases were washed with saturated common salt solution, dried on sodium sulfate, filtered, and the solvent was drawn off, whereby 350 mg of crude product was produced. This crude product was purified on a silica gel column (CHCl$_3$:MeOH=9:1), whereby a yellow oil was produced, which solidified by adding ether.

Yield: 120 mg (0.398 mmol 70% of theory) of a colorless powder C$_{18}$H$_{23}$NO$_3$ [301.39] TLC: R$_f$=0.43 (CHCl$_3$:MeOH=95:5), not to be separated from educt $^1$H-NMR (200 MHz, CDCl$_3$) δ 6.54 (s, 1H), 6.10 (dd, J=10.2, 1.2 Hz, 1H), 5.98 (dd, J=10.2, 4.7 Hz, 1H), 4.56 (bs, 1H), 4.12 (bs, 1H), 3.99 (d, J=15.6 Hz, 1H), 3.82 (s, 3H), 3.81 (d, J=15.6 Hz, 1H), 3.20 (ddd, J=14.2, 12.1, 2.1 Hz, 1H), 2.96 (dt, J=14.2, 3.4 Hz, 1H), 2.65 (ddd, J=15.7, 3.2, 1.5 Hz, 1H), 2.41 (s, 3H), 2.24 (s, 3H), 1.99 (ddd, J=15.5, 5.0, 2.5 Hz, 2H), 1.60

(ddd, J=13.7, 4.0, 2.4 Hz, 1H); $^{13}$C-NMR (50 MHz, CDCl$_3$) δ 144.0 (s), 143.0 (s), 133.4 (s), 128.9 (s), 127.4 (d+d), 127.0 (s), 126.6 (s), 113.6 (d), 88.3 (d), 61.9 (d), 55.7 (q), 55.4 (t), 53.8 (t), 48.2 (s), 42.7 (q), 33.8 (t), 29.8 (t), 19.4 (q)

Production of Hydrobromide:

The reaction solution is hydrolyzed with ethanol (about half the reaction volume), stirred for 30 minutes, then brought to pH≦1 with concentrated HBr and stirred overnight. The precipitate that is produced is suctioned off, washed with ethanol and dried.

Melting point: 246–250° C. (hydrobromide) C$_{18}$H$_{24}$NO$_3$Br×0.5 H$_2$O [391.30]

|  | % C | % H | % N |
|---|---|---|---|
| Cld.: | 55.25 | 6.44 | 3.58 |
| Fnd.: | 55.21 | 6.39 | 3.56 |

EXAMPLE 89

[(±)-(4aα,6α,8aR*)]-4a,5,9,10,11,12-Hexahydro-3-methoxy-1,11-dimethyl-6H-benzofuro[3a,3,2-ef][2]benzazepin-6-ol, 1-methylepigalanthamine (MH-31)

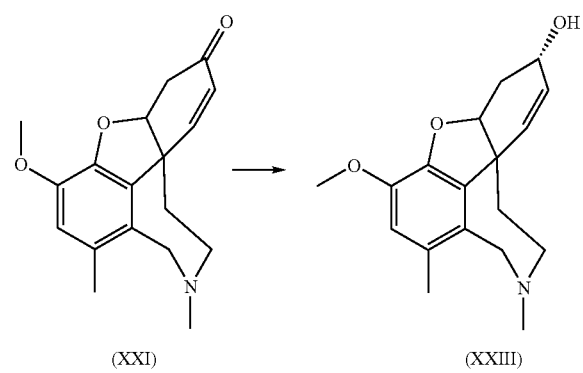

(XXI) → (XXIII)

| 2.00 g (6.68 mmol) | 1-methylnarwedine (XXI) |
| 150 ml | methanol |
| 2.50 g (6.68 mmol) | cerium trichloride heptahydrate |
| 0.50 g (13.4 minol) = 2 equivalents | NaBH$_4$ |

The educt was dissolved in methanol with heating and then cooled to 0° C., CeCl$_3$×7H$_2$O was added and stirred at 0° C. for about 30–60 minutes. Then, NaBH$_4$ was added in portions, it was stirred for another 2 hours at 0–5° C., whereby a precipitate formed. The reaction mixture was hydrolyzed with 5 ml of 2N HCl, methanol was distilled off in a vacuum, the residue was taken up with another 150 ml of 2N HCl, made basic with concentrated NH$_4$OH (violet precipitate), extracted with ethyl acetate, the collected organic phases were washed with saturated common salt solution, dried on sodium sulfate, filtered, and the solvent was drawn off. As a crude product, an isomer mixture of 1-methylepigalanthamine and 1-methylgalanthamine at a ratio of about 5:1 was produced, which could be separated by chromatography (silica gel, CHCl$_3$:MeOH=9:1+0.5% NH$_4$OH).

Yield: 1.34 g (4.45 mmol=66.6% of theory) of a colorless oil C$_{18}$H$_{23}$NO$_3$ [301.39] TLC: R$_f$=0.20 (CHCl$_3$:MeOH=9:1) $^1$H-NMR (200 MHz, CDCl$_3$) δ 6.51 (s, 1H), 6.10 (d, J=10.2 Hz, 1H), 5.79 (d, J=10.2 Hz, 1H), 4.69–4.56 (m, 1H), 4.55 (bs, 1H), 3.96 (d, J=15.3 Hz, 1H), 3.82 (s, 3H), 3.79 (d, J=15.3 Hz, 1H), 3.21 (td, J=13.1, 1.7 Hz, 1H), 2.97 (dt, J=14.1, 3.3 Hz, 1H), 2.75 (dddd, J=14.1, 5.3, 4.0, 1.2 Hz, 1H), 2.38 (s, 3H), 2.23 (s, 3H), 2.10 (dd, J=13.1, 3.2 Hz, 1H), 2.03 (bs, 1H), 1.69 (ddd, J=13.6, 10.7, 2.6 Hz, 2H); $^{13}$C-NMR (50 MHz, CDCl$_3$) δ 145.0 (s), 142.9 (s), 133.5 (s), 131.7 (d), 128.5 (s), 126.7 (d), 126.6 (s), 113.5 (d), 88.3 (d), 63.1 (d), 55.8 (q), 55.2 (t), 54.1 (t), 48.3 (s), 42.6 (q), 34.6 (t), 32.4 (t), 19.5 (q)

Production of Hydrobromide:

The 1-methylepigalanthamine that was obtained was taken up in ethanol and brought to pH≦1 with concentrated HBr. The hydrobromide was brought to crystallization under cold conditions and the precipitate that was produced was suctioned off, washed with cold ethanol and dried.

Melting point: 254–255° C. (hydrobromide) C$_{18}$H$_{24}$NO$_3$Br×0.5 H$_2$O [391.30]

|  | % C | % H | % N |
|---|---|---|---|
| Cld.: | 56.25 | 6.44 | 3.58 |
| Fnd.: | 56.28 | 6.21 | 3.57 |

EXAMPLE 90

[(±)-(4aα,6α,8aR*)]-4a,5,9,10,11,12-Hexahydro-3-methoxy-1-methyl-6H-benzofuro[3a,3,2-ef][2]benzazepin-6-ol, 1-Methyl-N-demethylepigalanthamine

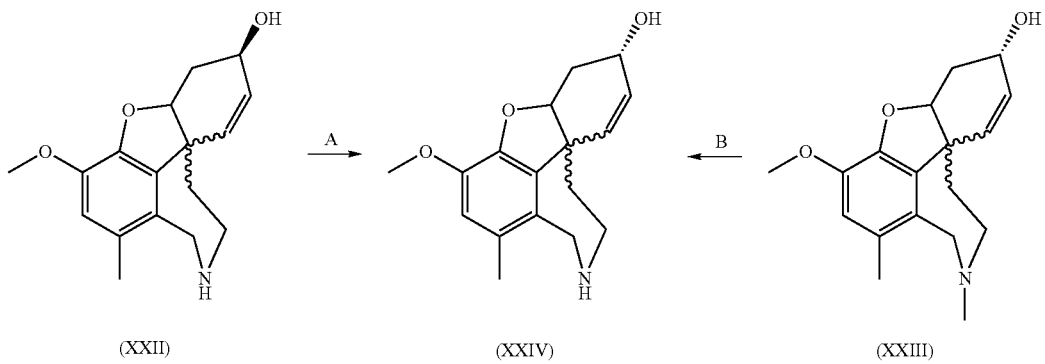

(XXII) →$^A$ (XXIV) ←$^B$ (XXIII)

Method A (Epimerization of 1-methyl-N-demethylgalanthamine (XXII))

Step 1 (Acetylation): [(±)-(4aα,6α,8aR*)-6-O-Acetyloxy-4a,5,9,10,11,12-hexahydro-3-methoxy-1-methyl-6H-benzofuro[3a,3,2-ef][2]benzazepine (MH-67)

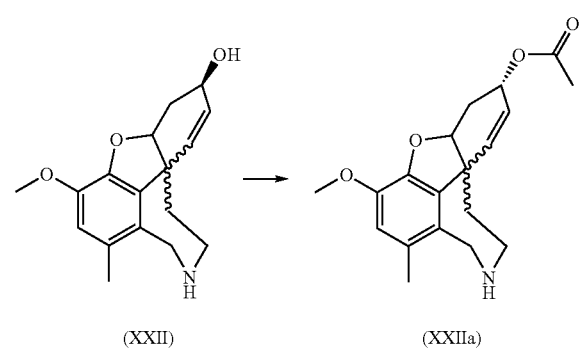

(XXII) → (XXIIa)

| 100 mg (0.35 mmol) | 1-methyl-N-demethylgalanthamine (XXII) |
| --- | --- |
| 0.50 ml (1.74 mmol) = 5 equivalents | N,N-dimethylformamide-bis(2,2-dimethylpropyl)-acetal |
| 0.10 ml (1.74 mmol) = 5 equivalents | glacial acetic acid |
| 12 ml | toluene |

The educt was heated in 10 ml of toluene under $N_2$ atmosphere to 80° C. and over 1 hour, a mixture that consists of N,N-dimethylformamide-bis-(2,2-dimethylpropyl)acetal and glacial acetic acid in 2 ml of toluene was added in drops. After 22 hours at 80° C., the cooled toluene phase was extracted 1× with water, then with 2N hydrochloric acid, the acidic aqueous phase was made basic with concentrated ammonia solution, it was extracted with ethyl acetate, the organic phases were washed with saturated common salt solution, dried on sodium sulfate, filtered, and the solvent was drawn off. The residue was purified by column chromatography.

(CHCl$_3$:MeOH=95:5). Yield: 45 mg (0.14 mmol=39% of theory) of a colorless oil C$_{19}$H$_{23}$NO$_4$ [329.40] TLC: R$_f$=0.20 (CHCl$_3$:MeOH=95:5) $^1$H-NMR (200 MHz, CDCl$_3$) δ 6.50 (s, 1H), 6.14 (d, J=10.2 Hz, 1H), 5.72 (d, J=10.2 Hz, 1H), 5.67–5.58 (m, 1H), 4.57 (bs, 1H), 4.24 (d, J=16.0 Hz, 1H), 3.83 (s, 3H), 3.75 (d, J=16.0 Hz, 1H), 3.40–3.09 (m, 2H), 2.90–2.70 (m, 1H), 2.23 (s, 3H), 2.07 (s, 3H), 2.01–1.73 (m, 3H); $^{13}$C-NMR (50 MHz, CDCl$_3$) δ 170.2 (s) 145.3 (s), 142.8 (s), 133.0 (s), 130.5 (s), 128.4 (d), 127.2 (d), 127.0 (s), 113.5 (d), 87.3 (d), 66.4 (d), 55.8 (q), 48.8 (s+t), 47.1 (t), 40.4 (t), 28.2 (t), 21.1 (q), 19.4 (q)

Step 2: Ester Hydrolysis (MH-78)

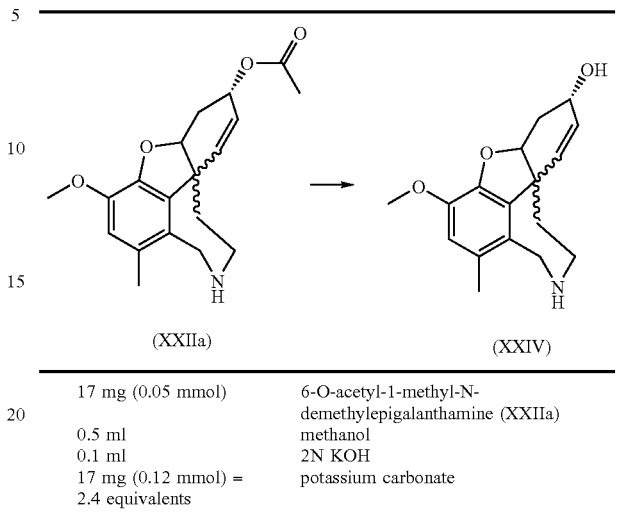

(XXIIa) → (XXIV)

| 17 mg (0.05 mmol) | 6-O-acetyl-1-methyl-N-demethylepigalanthamine (XXIIa) |
| --- | --- |
| 0.5 ml | methanol |
| 0.1 ml | 2N KOH |
| 17 mg (0.12 mmol) = 2.4 equivalents | potassium carbonate |

The reagents were stirred together at room temperature. After the end of the reaction, it was mixed with 1 ml of water, methanol was drawn off, it was acidified with 4 ml of 2N hydrochloric acid, the aqueous phase was washed with ethyl acetate, then made basic with concentrated aqueous ammonia solution and extracted with ethyl acetate. The organic phases were washed with saturated common salt solution, dried on sodium sulfate, filtered, and the solvent was drawn off.

C$_{17}$H$_{21}$NO$_3$ [287.36] TLC: R$_f$=0.07 (CHCl$_3$:MeOH=9:1)

Method B (Demethylation of 1-Methylepigalanthamine) (MH-94)

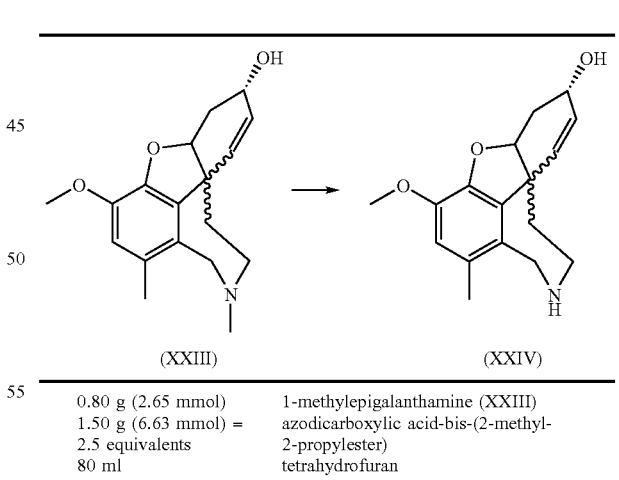

(XXIII) → (XXIV)

| 0.80 g (2.65 mmol) | 1-methylepigalanthamine (XXIII) |
| --- | --- |
| 1.50 g (6.63 mmol) = 2.5 equivalents | azodicarboxylic acid-bis-(2-methyl-2-propylester) |
| 80 ml | tetrahydrofuran |

The reagents were stirred together at room temperature for 24 hours, then the solvent was drawn off. The residue was taken up in trifluoroacetic acid in methylene chloride, stirred for 30 minutes, made basic in an ice bath with concentrated aqueous ammonia solution and extracted with methylene chloride. The organic phases were washed with saturated common salt solution, dried on sodium sulfate, filtered, and the solvent was removed. The crude product was purified by column chromatography (CHCl$_3$:MeOH=9:1).

Yield: 400 mg (1.39 mmol 53% of theory) of a colorless oil C$_{17}$H$_{21}$NO$_3$ [287.36] TLC: R$_f$=0.10 (CHCl$_3$:MeOH=9:1) $^1$H-NMR (200 MHz, CDCl$_3$) δ 6.50 (s, 1H), 6.08 (d, J=10.3 Hz, 1H), 5.80 (d, J=10.3 Hz, 1H), 4.70–4.62 (m, 1H), 4.57 (bs, 1H), 4.26 (d, J=15.7 Hz, 1H), 3.83 (s, 3H), 3.75 (d, J=15.7 Hz, 1H), 3.35–3.20 (m, 1H), 2.85–2.70 (m, 1H), 2.50–2.29 (m, 2H), 2.23 (s, 3H), 2.00–1.64 (m, 2H); $^{13}$C-NMR (50 MHz, CDCl$_3$) δ 145.4 (s), 142.9 (s), 133.5 (s), 131.6 (d), 130.7 (s), 127.2 (d), 126.8 (s), 113.3 (d), 88.2 (d), 63.1 (d), 55.9 (q), 48.9 (t), 48.8 (s), 47.2 (t), 32.2 (t), 28.2 (t), 19.5 (q)

General Operating Instructions for Quaternary 1-Methyl- and 1-Methylepi-galanthamine Derivatives (Examples 90–99)

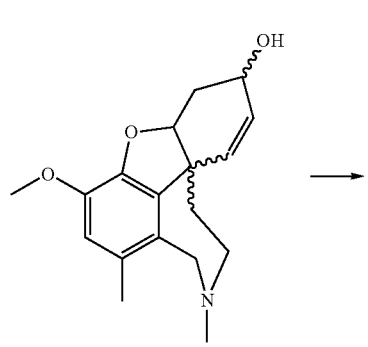

→

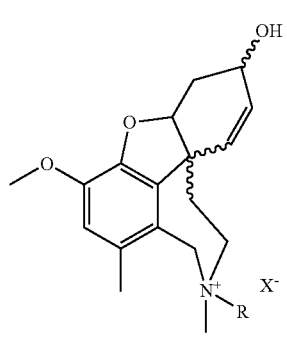

The educt was dissolved* in very little DMF, added to the alkyl halide, and the reaction mixture was heated (generally not above the boiling temperature of the alkyl halide, but at most 70° C.). By means of TLC, the end of the reaction was determined, then the reaction mixture was slowly added in drops to ether while being stirred (in many cases easily extrudes oil), the precipitate was suctioned off and washed with ether. For purification and for removing residual DMF, the precipitate was dissolved in ethanol and once more precipitated in ethyl acetate, then dried in a vacuum drying oven at 5° C.

With R=CH$_2$Cl, methylene chloride (p.A. 99.5%) is used as a solvent and reagent.

TLC: CHCl$_3$:MeOH=9:1, R$_f$ generally slightly over the starting value.

EXAMPLE 90

[(±)-(4aα,6β,8aR*)]-4a,5,9,10,11,12-Hexahydro-6-hydroxy-3-methoxy-1,11-dimethyl-11-(2-methyl-2-propenyl)-6H-benzofuro[3a,3,2-ef][2]benzazepinium, Chloride (MH-33)

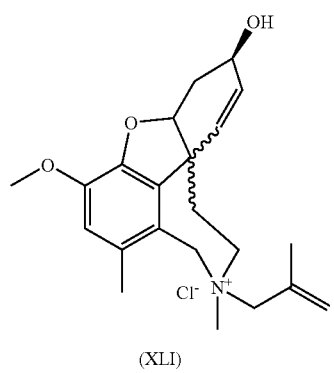

(XLI)

| | |
|---|---|
| 280 mg (0.94 mmol) | 1-methylgalanthamine (XV) |
| 0.30 ml (3.08 mmol) = 3 equivalents | 1-chloro-2-methylprop-2-ene |
| 5.00 ml | dimethylformamide |

The reaction was performed at 70° C. and worked up after 2 hours, by the reaction mixture having been added in drops to 25 ml of diethyl ether.

Yield: 270 mg (0.69 mmol=73% of theory) of a colorless powder C$_{22}$H$_{30}$ClNO$_3$ [391.94] TLC: R$_f$=0.10 (CHCl$_3$:MeOH=9:1) Melting point: 239–241° C. C$_{22}$H$_{30}$ClNO$_{3\times1.4}$ H$_2$O [417.14]

| | % C | % H | % N |
|---|---|---|---|
| Cld.: | 63.34 | 7.92 | 3.36 |
| Fnd.: | 63.22 | 7.85 | 3.59 |

$^{13}$C-NMR (50 MHz, DMSO-d$_6$) δ 144.6 (s), 134.2 (s), 133.5 (s), 131.1 (s), 130.9 (d), 127.5 (t), 124.9 (d), 115.9 (s), 114.4 (d), 86.3 (d), 73.0 (t), 60.8 (t), 59.4 (d), 55.5 (q), 46.3 (s), 43.0 (q), 31.1 (t), 23.8 (q), 18.9 (q)

EXAMPLE 91

[(±)-(4aα, 6β, 8aR*)]-4a,5,9,10,11,12-Hexahydro-6-hydroxy-3-methoxy-1,11-dimethyl-11-(2-propinyl)-6H-benzofuro[3a,3,2-ef][2]benzazepinium, bromide (MH-38)

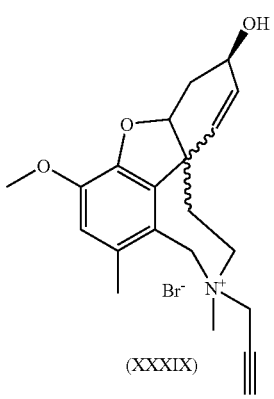

(XXXIX)

| 349 mg (1.16 mmol) | 1-methylgalanthamine (XV) |
| 0.13 ml (1.16 mmol) | 3-bromo-1-propine (propargyl bromide) |
| 4.00 ml | dimethylformamide |

The reaction was performed at 60° C. and worked up after 19 hours by the reaction mixture having been added in drops to 80 ml of diethyl ether.

Yield: 300 mg (0.71 mmol=62% of theory) of a beige powder; $C_{21}H_{26}BrNO_3$ [420.35] TLC: $R_f$=0.09 (CHCl$_3$: MeOH=9:1) Melting point: 216–218° C. $C_{21}H_{26}BrNO_{3\times 0.35}$ $H_2O\times 0.25$ $C_3H_7O$ [444.93]

|  | % C | % H | % N |
| --- | --- | --- | --- |
| Cld.: | 58.72 | 6.44 | 3.90 |
| Fnd.: | 58.70 | 6.37 | 3.94 |

$^{13}$C-NMR (50 MHz, DMSO-d$_6$) δ 144.8 (s), 144.7 (s), 133.4 (s), 131.0 (s), 125.2 (d), 115.3 (d), 114.5 (d), 86.2 (d), 83.7 (d), 72.6 (t), 60.6 (t), 59.7 (d), 55.6 (q), 46.2 (s), 43.0 (q), 31.0 (t), 18.8 (q)

EXAMPLE 92

(±)-(4aα, 6β,8aR*)]-4a,5,9,10,11,12-Hexahydro-6-hydroxy-3-methoxy-1,11-dimethyl-11-phenylmethyl-6H-benzofuro[3a,3,2-ef][2]benzazepinium, bromide (MH-39)

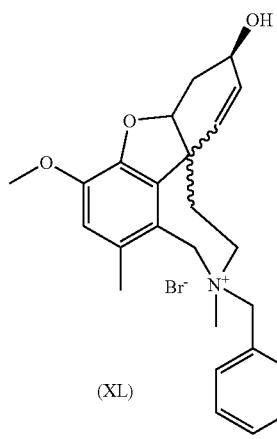

(XL)

| 242 mg (0.80 mmol) | 1-methylgalanthamine (XV) |
| 0.25 ml (1.01 mmol) = 1.4 equivalents | benzyl bromide |
| 4.00 ml | dimethylformamide |

The reaction was performed at 60° C. and worked up after 10 minutes.

Yield: 262 mg (0.55 mmol=69% of theory) of a beige powder $C_{25}H_{30}BrNO_3$ [472.42] TLC: $R_f$=0.08 (CHCl$_3$: MeOH=9:1) Melting point: 246–248° C.

|  | % C | % H | % N |
| --- | --- | --- | --- |
| Cld.: | 63.56 | 6.40 | 2.96 |
| Fnd.: | 63.35 | 6.34 | 2.93 |

$^{13}$C-NMR (50 MHz, DMSO-d$_6$) δ 144.7 (s), 133.4 (d), 130.7 (s), 130.4 (d), 129.0 (d), 128.1 (s), 114.5 (d), 86.3 (d), 59.7 (t), 59.5 (d), 55.6 (q), 46.2 (s), 18.6 (q)

EXAMPLE 93

[(±)-(4aα,6β,8aR*)]-4a,5,9,10,11,12-Hexahydro-6-hydroxy-3-methoxy-1,11,11-trimethyl-6H-benzofuro[3a,3,2-ef][2]benzazepinium, Iodide (MH-83)

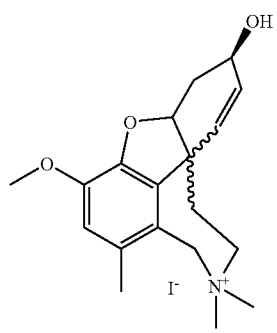

(XLII)

| 140 mg (0.46 mmol) | 1-methylgalanthamine (XV) |
| 198 mg (1.39 mmol) = | methyl iodide |

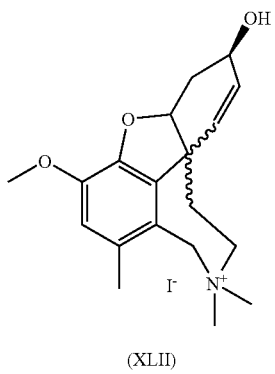

(XLII)

| 3 equivalents | |
| --- | --- |
| 4.00 ml | dimethylformamide |

The reaction was performed at 40° C. and worked up after 1.5 hours, by the reaction mixture having been added in drops to 30 ml of diethyl ether.

Yield: 146 mg (0.54 mmol=71% of theory) of a light brown powder $C_{19}H_{26}INO_3$ [443.32] TLC: $R_f$=0.05 (CHCl$_3$: MeOH=9:1) Melting point: 278–280° C. $C_{19}H_{26}INO_3 \times 0.3$ H$_2$O [448.72]

|  | % C | % H | % N |
| --- | --- | --- | --- |
| Cld.: | 50.86 | 5.97 | 3.12 |
| Fnd.: | 50.57 | 5.85 | 3.43 |

$^{13}$C-NMR (50 MHz, DMSO-d$_6$) δ 144.6 (s), 144.1 (s), 132.8 (s), 131.6 (s), 114.2 (d), 86.3 (d), 62.6 (t), 59.5 (d), 55.4 (q), 45.9 (s), 31.0 (t), 18.4 (q)

EXAMPLE 94

[(±)-(4aα,6β,8aR*)]-4a,5,9,10,11,12-Hexahydro-6-hydroxy-3-methoxy-1,11-dimethyl-11-(2-methyl-2-propenyl)-6H-benzofuro[3a,3,2-ef][2]benzazepinium, Chloride (MH-66)

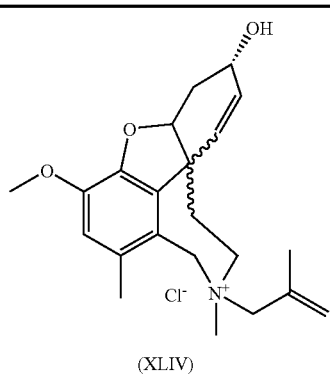

(XLIV)

| 150 mg (0.50 mmol) | 1-methylepigalanthamine (XXIII) |
| --- | --- |
| 45.0 mg (1.50 mmol) = | 1-chloro-2-methylprop-2-ene |
| 3 equivalents | |
| 4.00 ml | dimethylformamide |

The reaction was performed at 70° C. and worked up after 100 minutes, by the reaction mixture having been added in drops to 50 ml of diethyl ether.

Yield: 160 mg (0.41 mmol=82% of theory) of a colorless powder $C_{22}H_{30}$ ClNO$_3$ [391.94] TLC: $R_f$=0.09 (CHCl$_3$: MeOH=9:1) Melting point: 162–164° C. $C_{22}$ H$_3$ClNO$_{30} \times 0.7$ H$_2$O×0.15 C$_3$H$_7$NO [415.51]

|  | % C | % H | % N |
| --- | --- | --- | --- |
| Cld.: | 64.90 | 7.87 | 3.88 |
| Fnd.: | 64.77 | 7.68 | 3.95 |

$^{13}$C-NMR (50 MHz, DMSO-d$_6$) δ 144.7 (s), 134.2 (s), 134.1 (s), 131.1 (d), 127.5 (t), 114.4 (d), 87.3 (d), 73.0 (t), 60.7 (d), 59.4 (t), 55.6 (q), 46.3 (s), 23.8 (q), 18.9 (q)

EXAMPLE 95

[(±)-(4aα,6α,8aR*)]-4a,5,9,10,11,12-Hexahydro-6-hydroxy-3-methoxy-1,11-dimethyl-11-(2-propinyl)-6H-benzofuro[3a,3,2-ef][2]benzazepinium, bromide (MH-71)

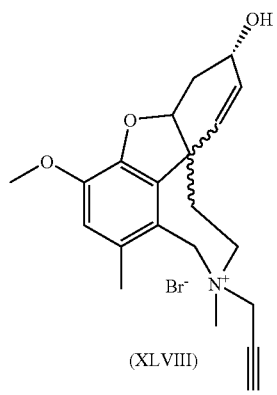

(XLVIII)

| 150 mg (0.50 mmol) | 1-methylepigalanthamine (XXIII) |
| --- | --- |
| 180 tag (1.50 mmol) = | 3-bromo-1-propine (propargyl |
| 3 equivalents | bromide) |
| 4.00 ml | dimethylformamide |

The reaction was performed at 70° C. and worked up after 2.5 hours, by the reaction mixture having been added in drops to 30 ml of diethyl ether.

Yield: 167 mg (0.40 mmol=82% of theory) of a light brown powder $C_{21}H_{26}BrNO_3$ [420.35] TLC: $R_f$=0.09 (CHCl$_3$:MeOH=9:1) Melting point: 158–162° C. $^{13}$C-NMR (50 MHz, DMSO-d$_6$) δ 144.8 (s), 133.9 (s), 131.2 (s), 114.5 (d), 87.2 (d), 83.7 (d), 72.6 (d), 55.6 (q), 46.3 (s), 31.9 (t), 18.8 (q)

EXAMPLE 96

[(±)-(4aα,6α,8aR*)]-4a,5,9,10,11,12-Hexahydro-6-hydroxy-3-methoxy-1,11-dimethyl-11-(2-propenyl)-6H-benzofuro[3a,3,2-ef][2]benzazepinium, bromide (MH-72)

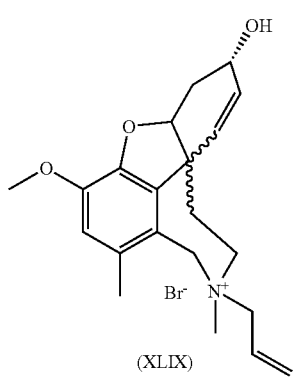

(XLIX)

| 150 mg (0.50 mmol) | 1-methylepigalanthamine (XXIII) |
| --- | --- |
| 0.13 ml (1.50 mmol) = 3 equivalents | 3-bromo-1-propene (allyl bromide) |
| 4.00 ml | dimethylformamide |

The reaction was performed at 60° C. and worked up after 2 hours.

Yield: 150 mg (0.36 mmol=64% of theory) of a light brown powder $C_{21}H_{28}BrNO_3$ [422.36] TLC: $R_f$=0.11 (CHCl$_3$:MeOH=9:1) Melting point: 140–145° C. $C_{21}H_{28}BrNO_3 \times 1H_2O \times 0.25\ C_3H_7NO$ [458.64]

|  | % C | % H | % N |
| --- | --- | --- | --- |
| Cld.: | 56.96 | 6.98 | 3.82 |
| Fnd.: | 56.69 | 6.65 | 4.05 |

$^{13}$C-NMR (50 MHz, DMSO-d$_6$) δ 144.7 (s), 134.5 (d), 134.0 (s), 131.1 (s), 128.3 (s), 126.1 (d), 115.3 (d), 114.4 (d), 87.2 (d), 60.7 (d), 59.8 (t), 55.6 (q), 46.3 (s), 31.5 (t), 18.8 (q)

EXAMPLE 97

[(±)-(4aα,6α,8aR*)]-4a,5,9,10,11,12-Hexahydro-6-hydroxy-3-methoxy-1,11-dimethyl-11-(4-(trifluoromethyl)phenylmethyl)-6H-benzofuro[3a,3,2-ef][2]benzazepinium, Bromide (MH-75)

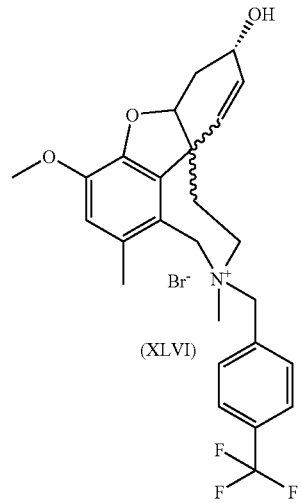

(XLVI)

| 150 mg (0.50 mmol) | 1-methylepigalanthamine (XXIII) |
| --- | --- |
| 357 mg (1.50 mmol) = 1.4 equivalents | 4-trifluoromethyl-benzyl bromide |
| 4.00 ml | dimethylformamide |

The reaction was performed at 70° C. and worked up after 1 hour.

Yield: 142 mg (0.26 mmol=53% of theory) of a light yellow powder $C_{26}H_{29}BrF_3NO_3$ [540.42] TLC: $R_f$=0.10 (CHCl$_3$:MeOH=9:1) Melting point: 178–182° C. $^{13}$C-NMR (50 MHz, DMSO-d$_6$) δ 144.8 (s), 134.4 (d+d), 134.2 (d) 132.6 (5), 131.2 (1), 130.9 (a), 130.3 (s), 126.6 (d), 125.8 (s), 121.2 (d), 114.5 (d), 87.3 (d), 60.8 (d), 55.6 (q), 46.3 (s), 34.3 (t), 18.7 (q)

EXAMPLE 98

[(±)-(4aα,6α,8aR*)]-4a,5,9,10,11,12-Hexahydro-6-hydroxy-3-methoxy-1,11-dimethyl-11-(phenylmethyl)-6H-benzofuro[3a,3,2-ef][2]benzazepinium, bromide (MH-76)

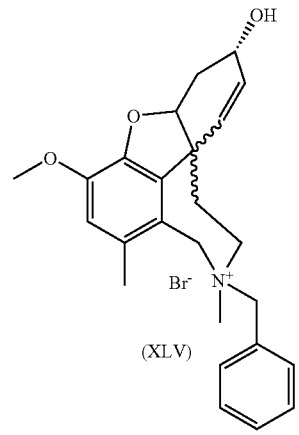

(XLV)

| 153 mg (0.51 mmol) | 1-methylepigalanthamine (XXIII) |
| --- | --- |
| 92 mg (0.51 mmol) | benzyl bromide |
| 4.00 ml | dimethylformamide |

The reaction was performed at 70° C. and worked up after 3 hours.

Yield: 150 mg (0.32 mmol=63% of theory) of a light brown powder $C_{25}H_{30}BrNO_3$ [472.42] TLC: $R_f$=0.11 (CHCl$_3$:MeOH=9:1) Melting point: 169–175° C. $^{13}$C-NMR (50 MHz, DMSO-d$_6$) δ 144.6 (s), 134.1 (s), 133.4 (d), 131.0 (s), 130.4 (d), 128.9 (d), 128.1 (s), 114.4 (d), 87.2 (d), 61.8 (d), 59.4 (t), 55.6 (q), 46.3 (s), 31.5 (t), 18.6 (q)

EXAMPLE 99

[(±)-(4aα,6α,8aR*)]-4a,5,9,10,11,12-Hexahydro-6-hydroxy-3-methoxy-1,11,11-trimethyl-6H-benzofuro[3a,3,2-ef][2]benzazepinium, Iodide (MH-81)

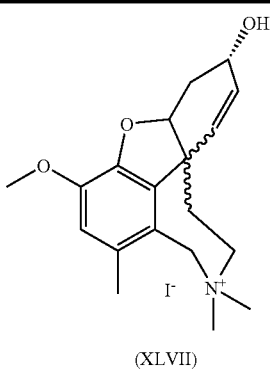

(XLVII)

| 210 mg (0.70 mmol) | 1-methylepigalanthamine (XXIII) |
| 290 mg (2.10 mmol) = 3 equivalents | methyl iodide |
| 4.00 ml | dimethylformamide |

The reaction was performed at 70° C. and worked up after 2 hours, by the reaction mixture having been added in drops to 30 ml of diethyl ether.

Yield: 240 mg (0.54 mmol=77% of theory) of a light-brown powder $C_{19}H_{26}INO_3$ [443.32] TLC: $R_f$=0.05 (CHCl$_3$:MeOH=9:1) Melting point: decomposition>280° C.

| | % C | % H | % N |
|---|---|---|---|
| Cld.: | 51.48 | 5.91 | 3.16 |
| Fnd.: | 51.25 | 5.75 | 3.32 |

$^{13}$C-NMR (50 MHz, DMSO-d$_6$) δ 144.7 (s), 133.6 (s), 131.1 (s), 114.4 (d), 87.1 (d), 62.2 (t), 60.7 (q), 55.5 (q), 48.4 (d), 46.2 (s), 31.5 (t), 18.9 (q)

| General Operating Instructions for the Production of Galanthamine-N-Oxides (Examples 100–101) | |
|---|---|
| 1 equivalent | galanthamine derivative |
| 1–1.5 equivalents | 3-chloroperbenzoic acid |
| 100 ml | chloroform/1 g of galanthamine derivative |
| 0.7 ml | H$_2$O$_2$ (35%)/1 g of galanthamine derivative |

The 3-chloroperbenzoic acid is dissolved in ⅓ chloroform, mixed with hydrogen peroxide and stirred for 2 minutes. Then, this solution is added to a solution of the galanthamine derivative in ⅔ chloroform, it is stirred for 15 minutes, concentrated by evaporation and purified by means of column chromatography (gradient: CHCl$_3$:MeOH=9:1→MeOH).

EXAMPLE 101

[4aS-(4aα,6α,8aR*)]-4a,5,9,10,11,12-Hexahydro-3-methoxy-11-methyl-6H-benzofuro[3a,3,2-ef][2]benzazepin-6-ol, 11-oxide, epigalanthamine-N-oxide (Pi-23)

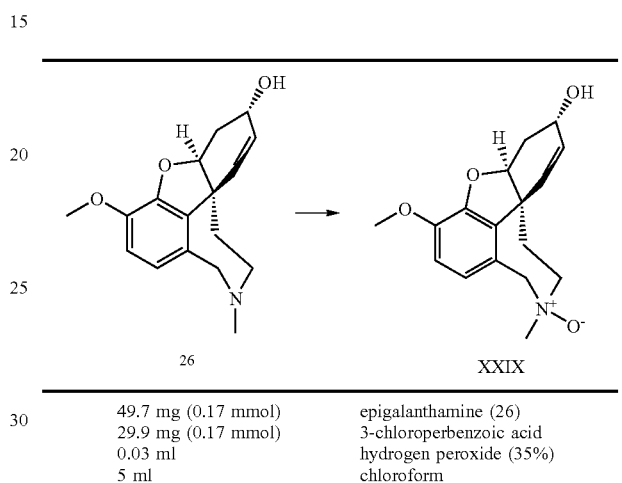

| 49.7 mg (0.17 mmol) | epigalanthamine (26) |
| 29.9 mg (0.17 mmol) | 3-chloroperbenzoic acid |
| 0.03 ml | hydrogen peroxide (35%) |
| 5 ml | chloroform |

Yield: 37 mg (71% of theory) $C_{17}H_{21}NO_4$ [303.36] TLC: $R_f$=0.05 (CHCl$_3$:MeOH=9:1) $^1$H-NMR (200 MHz, CDCl$_3$) δ 6.67 (s, 2H), 5.96 (bs, 2H), 4.78 (d, J=15.0 Hz, 1H), 4.67–4.50 (m, 2H), 4.26 (d, J=15.0 Hz, 1H), 3.83 (s, 3H), 3.67–3.41 (m, 2H), 3.41 (s, 2H), 2.96 (s, 3H), 2.77 (dt, J=13.1, 3.7 Hz, 1H), 2.05 (bs, 1H), 1.74 (t, J=11.3 Hz, 1H)

$^{13}$C-spectra could not be taken up because of the quick solvate formation and crystallization in chloroform, but the structural determination was made by x-ray crystallography.

General Operating Instructions for the Production of N-Substituted 1-Methylgalanthamine Derivatives (Examples 102–106)

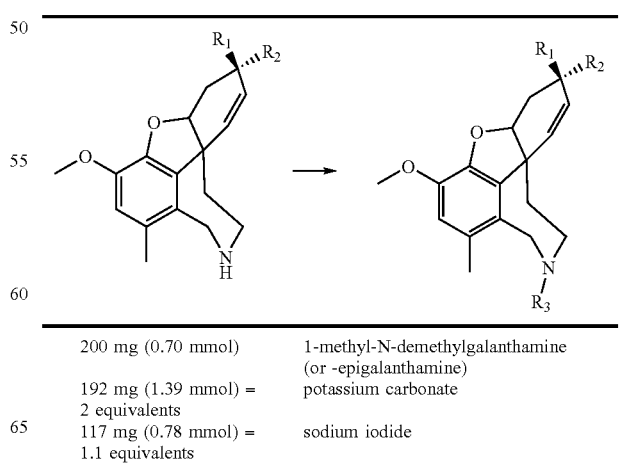

| 200 mg (0.70 mmol) | 1-methyl-N-demethylgalanthamine (or -epigalanthamine) |
| 192 mg (1.39 mmol) = 2 equivalents | potassium carbonate |
| 117 mg (0.78 mmol) = 1.1 equivalents | sodium iodide |

-continued

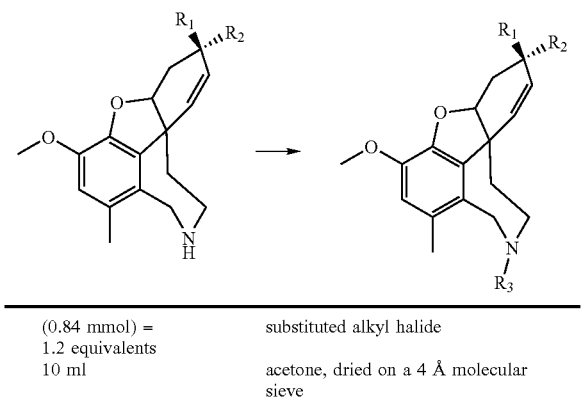

| (0.84 mmol) = 1.2 equivalents | substituted alkyl halide |
| --- | --- |
| 10 ml | acetone, dried on a 4 Å molecular sieve |

Sodium iodide, potassium carbonate and educt were thoroughly pulverized in a friction column, the mixture together with some glass pellets were introduced into the flask and suspended in absolute acetone. The substituted alkyl halide was added in measured quantities, and the reaction mixture was refluxed. After the end of the reaction, the reaction mixture was evaporated to the dry state in a vacuum, and the residue was taken up with 2N HCl, the aqueous phase was washed with ethyl acetate, then made basic with concentrated aqueous ammonia and in turn extracted with ethyl acetate. The collected organic phases were washed with saturated common salt solution, dried on sodium sulfate, filtered, and the solvent was drawn off. The crude product was purified on a silica gel column (mobile solvent: $CHCl_3$:MeOH 9:1+1% $NH_4OH$).

EXAMPLE 102

[(±)-(4aα,6β,8aR*)]-4a,5,9,10,11,12-Hexahydro-3-methoxy-1-methyl-11-(2-propenyl)-6H-benzofuro[3a,3,2-ef][2]benzazepin-6-ol, 1-Methyl-N-allylgalanthamine (MH-25)

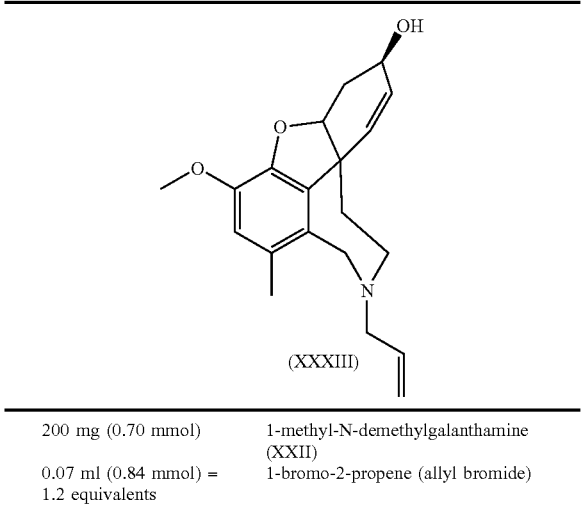

(XXXIII)

| 200 mg (0.70 mmol) | 1-methyl-N-demethylgalanthamine (XXII) |
| --- | --- |
| 0.07 ml (0.84 mmol) = 1.2 equivalents | 1-bromo-2-propene (allyl bromide) |

After 10 hours, the reaction was worked up.

Yield: 50 mg (0.15 mmol=22% of theory) of a yellow oil $C_{20}H_{25}NO_3$ [327.43] TLC: $R_f$=0.17 ($CHCl_3$:MeOH=9:1+1% $NH_4OH$) $C_{20}H_{25}NO_3 \times 0.8\ H_2O$ [341.83]

|  | % C | % H | % N |
| --- | --- | --- | --- |
| Cld.: | 70.27 | 7.84 | 4.10 |
| Fnd.: | 70.18 | 7.60 | 4.05 |

$^1$H-NMR (200 MHz, $CDCl_3$) δ 6.52 (s, 1H), 6.12 (d, J=10.3 Hz, 1H), 6.03–5.78 (m, 2H), 5.18 (bs, 1H), 5.11 (d, J=4.5 Hz, 1H), 4.57 (bs, 1H), 4.12 (bs, 1H), 4.09 (d, J=15.0 Hz, 1H), 3.81 (s, 3H), 3.78 (d, J=15.0 Hz, 1H), 3.32–3.02 (m, 4H), 2.72–2.58 (m, 1H), 2.21 (s, 3H), 2.07–1.89 (m, 2H), 1.57 (ddd, J=13.7, 3.4, 2.7 Hz, 1H); $^{13}$C-NMR (50 MHz, $CDCl_3$) δ 144.0 (s), 143.0 (s), 136.0 (d), 133.6 (s), 129.1 (s), 127.4 (d), 127.2 (d), 126.9 (s), 117.5 (t), 113.7 (d), 88.4 (d), 62.0 (d), 57.2 (t), 55.8 (q), 52.9 (t), 52.0 (t), 48.4 (s), 33.9 (t), 29.8 (t), 19.4 (q)

EXAMPLE 103

[(±)-(4aα,6β,8aR*)]-4a,5,9,10,11,12-Hexahydro-3-methoxy-1-methyl-11-(phenylmethyl)-6H-benzofuro[3a,3,2-ef][2]benzazepin-6-ol, 1-Methyl-N-benzylgalanthamine (MH-26)

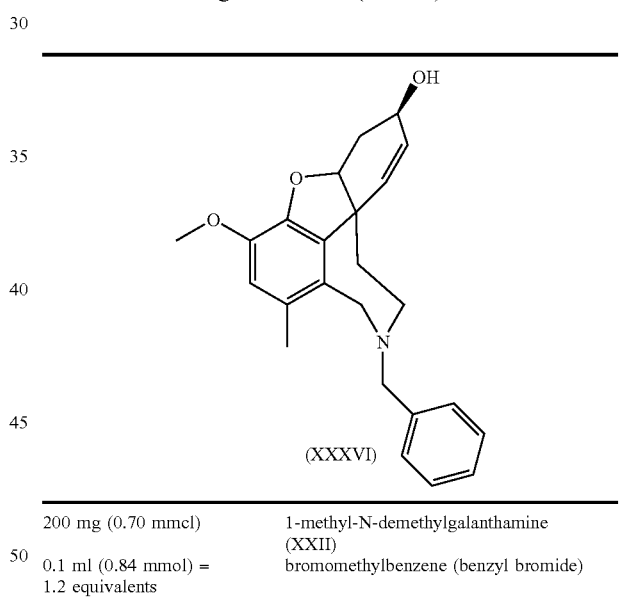

(XXXVI)

| 200 mg (0.70 mmol) | 1-methyl-N-demethylgalanthamine (XXII) |
| --- | --- |
| 0.1 ml (0.84 mmol) = 1.2 equivalents | bromomethylbenzene (benzyl bromide) |

After 24 hours, the reaction was worked up.

Yield: 140 mg (0.37 mmol=53% of theory) of a yellow oil; $C_{24}H_{27}NO_3$ [377.48] TLC: $R_f$=0.36 ($CHCl_3$:MeOH=9:1+1% $NH_4OH$) $^1$H-NMR (200 MHz, $CDCl_3$) δ 7.30 (m, 5H), 6.50 (s, 1H), 6.16 d, J=10.2 Hz, 1H), 5.99 (dd, J=10.2, 4.9 Hz, 1H), 4.61 (bs, 1H), 4.13 (bs, 1H, 4.00 (d, J=15.7 Hz, 1H), 3.82 (s, 3H), 3.81 (d, J=15.7 Hz, 1H), 3.69 (s, 2H), 3.34 (td, J=14.1, 12.4, 1.8 Hz, 1H), 3.13 (td, J=14.1, 3.5 Hz, 1H), 2.74–2.37 (m, 2H), 2.19–1.93 (m, 2H), 1.90 (s, 3H), 1.57 (dt, J=13.7, 3.0 Hz, 1H); $^{13}$C-NMR (50 MHz, $CDCl_3$) δ 143.9 (s), 143.0 (s), 138.9 (s), 133.6 (s), 129.2 (s), 128.7 (d), 128.2 (d), 127.4 (d), 127.3 (d) 127.2 (s), 126.9 (d), 113.7 (d), 88.4 (d), 62.0 (d), 57.4 (t), 55.8 (q), 52.4 (t), 52.2 (t), 48.5 (s), 33.7 (t), 29.8 (t), 19.1 (q)

EXAMPLE 104

[(±)-(4aα,6β,8aR*)]-4a,5,9,10,11,12-Hexahydro-3-methoxy-1-methyl-11-(2-(4-morpholinyl)ethyl)-6H-benzofuro[3a,3,2-ef][2]benzazepin-6-ol, 1-Methyl-N-morpholinoethyl-galanthamine (MH-28)

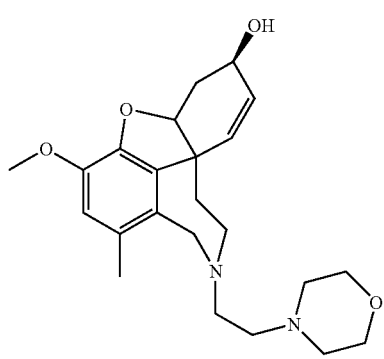

(XXXV)

| | |
|---|---|
| 200 mg (0.70 mmol) | 1-methyl-N-demethylgalanthamine (XXII) |
| 155 mg (0.84 mmol) = 1.2 equivalents | 4-(2-chloroethyl) morpholine hydrochloride |

After 24 hours, the reaction was worked up.

Yield: 210 mg (0.52 mmol=75% of theory) of a yellow oil $C_{23}H_{32}N_2O_4$ [400.52] TLC: $R_f$=0.51 (CHCl$_3$:MeOH=9:1+ 1% NH$_4$OH) $C_{23}H_{32}N_2O_4 \times 0.9$ H$_2$O [416.72]

| | % C | % H | % N |
|---|---|---|---|
| Cld.: | 66.29 | 8.17 | 6.72 |
| Fnd.: | 66.28 | 8.09 | 6.85 |

$^1$H-NMR (200 MHz, CDCl$_3$) δ 6.52 (s, 1H), 6.10 (d, J=10.3 Hz, 1H), 5.97 (dd, J=10.3, 4.8 Hz, 1H), 4.55 (bs, 1H), 4.13 (bs, 1H), 4.12 (d, J=15.9 Hz, 1H), 3.88 (d, J=15.9 Hz, 1H), 3.81 (s, 3H), 3.75–3.65 (m, 4H), 3.30 (ddd, J=14.3, 12.4, 2.0 Hz, 1H), 3.10 (dt, J=14.3, 3.3 Hz, 1H), 2.76–2.58 (m, 4H), 2.55–2.41 (m, 5H), 2.25 (s, 3H), 2.08–1.90 (m, 2H), 1.55 (dd, J=13.7, 2.8 Hz, 1H); $^{13}$C-NMR (50 MHz, CDCl$_3$) δ 144.1 (s), 143.0 (s), 133.5 (s), 128.9 (s), 127.4 (d), 127.1 (d), 126.9 (s), 113.7 (d), 88.4 (d), 66.7 (t+t), 66.6 (t), 61.9 (d), 57.1 (t), 55.8 (q), 54.0 (t+t), 53.4 (t), 52.0 (t), 48.4 (s), 33.4 (t), 29.8 (t), 19.4 (q)

EXAMPLE 105

[(±)-(4aα,6β,8aR*)]-4a,5,9,10,11,12-Hexahydro-3-methoxy-1-methyl-11-(3-(1-piperidinyl)propyl)-6H-benzofuro[3a,3,2-ef][2]benzazepin-6-ol, 1-Methyl-N-piperidinopropyl-galanthamine (MH-29)

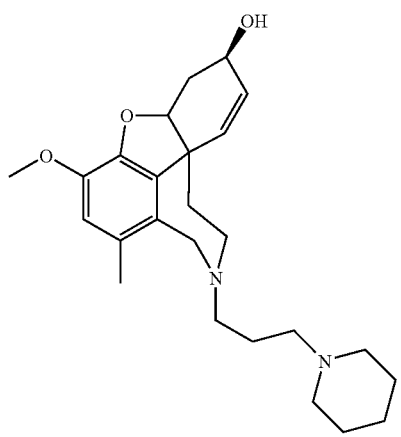

(XXXIV)

| | |
|---|---|
| 200 mg (0.70 mmol) | 1-methyl-N-demethylgalanthamine (XXII) |
| 166 mg (0.84 mmol) = 1.2 equivalents | 1-(3-chloropropyl)piperidine hydrochloride |

After 24 hours, the reaction was worked up.

Yield: 180 mg (0.44 mmol=63% of theory) of a yellow oil $C_{25}H_{36}N_2O_3$ [412.58] TLC: $R_f$=0.27 (CHCl$_3$:MeOH=9:1+ 1% NH$_4$OH) $C_{25}H_{36}N_2O_3 \times 0.50$ H$_2$O [421.58]

| | % C | % H | % N |
|---|---|---|---|
| Cld.: | 71.23 | 8.85 | 6.64 |
| Fnd.: | 71.33 | 8.97 | 6.60 |

$^1$H-NMR (200 MHz, CDCl$_3$) δ 6.52 (s, 1H), 6.10 (d, J=10.4 Hz, 1H), 5.96 (dd, J=10.4, 4.7 Hz, 1H), 4.55 (bs, 1H), 4.12 (bs, 1H), 4.08 (d, J=15.7 Hz, 1H), 3.83 (d, J=15.7 Hz, 1H), 3.81 (s, 3H), 3.24 (ddd, J=14.2, 12.2, 2.0 Hz, 1H), 3.07 (dt, J=14.2, 3.5 Hz, 1H), 2.71–2.13 (m, 10H), 2.24 (s, 3H), 2.07–1.88 (m, 2H), 1.77–1.35 (m, 9H); $^{13}$C-NMR (50 MHz, CDCl$_3$) δ 144.0 (s), 142.9 (s), 133.5 (s), 128.9 (s), 127.3 (d+d), 127.2 (d), 113.7 (d), 88.4 (d), 62.0 (d), 57.2 (t), 55.8 (q), 54.5 (t+t+t), 53.3 (t), 51.4 (t), 48.5 (s), 33.4 (t), 29.8 (t), 25.7 (t+t), 25.0 (t), 24.2 (t), 19.5 (q)

EXAMPLE 106

[(±)-(4aα,6α,8aR*)]-4a,5,9,10,11,12-Hexahydro-3-methoxy-1-methyl-11-(3-(1-piperidinyl)propyl)-6H-benzofuro[3a,3,2-ef][2]benzazepin-6-ol, 1-Methyl-N-piperidinopropyl-epigalanthamine (MH-117)

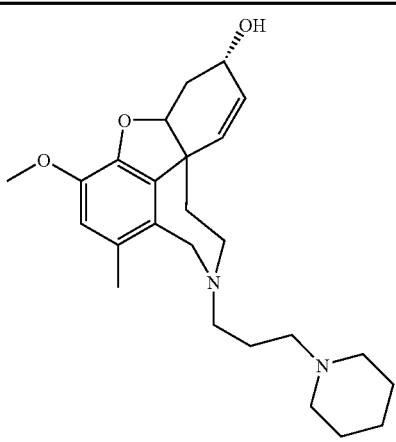

(XXXVII)

| 100 mg (0.35 mmol) | 1-methylepigalanthamine (XXIV) |
| 83 mg (0.42 mmol) = 1.2 equivalents | (1-(3-chloropropyl)piperidine hydrochloride |

After 28 hours, the reaction was worked up.

Yield: 60 mg (0.15 mmol=42% of theory) of a light yellow oil C$_{25}$H$_{36}$N$_2$O$_3$ [412.58] TLC: R$_f$=0.12 (CHCl$_3$:MeOH=9:1) $^1$H-NMR (200 MHz, CDCl$_3$) δ 6.50 (s, 1H), 6.10 (d, J=10.2 Hz, 1H), 5.78 (dd, J=10.2, 1H), 4.70–4.57 (m, 1H), 4.54 (bs, 1H), 4.05 (d, J=15.2 Hz, 1H), 3.82 (d, J=15.2 Hz, 1H), 3.82 (s, 3H), 3.25 (ddd, J=13.5, 12.8, 1.6 Hz, 1H), 3.09 (dt, J=13.5, 2.5 Hz, 1H), 2.75 (dt, J=13.7, 4.1 Hz, 1H), 2.56–2.27 (m, 8H), 2.23 (s, 3H), 2.08 (td, J=13.1, 4.0, 2H), 1.81–1.38 (m, 9H); $^{13}$C-NMR (50 MHz, CDCl$_3$) δ 144.9 (s), 142.7 (s), 133.4 (s) 131.3 (s), 128.3 (d+d), 127.0 (s), 113.3 (d), 88.1 (d), 63.0 (d), 57.2 (t), 55.7 (q), 54.4 (t+t+t), 53.1 (t), 51.6 (t), 48.4 (s), 33.1 (t), 29.5 (t), 25.6 (t+t), 24.8 (t), 24.1 (t), 19.5 (q)

General Operating Instructions for the Production of Galanthaminium Bromide Derivatives (Examples 107–109)

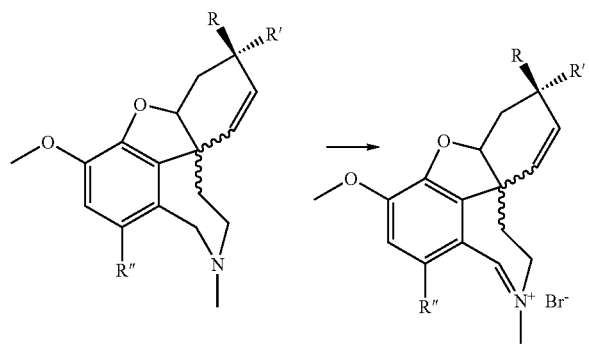

R, R' = H, OH

| 1 equivalent | a galanthamine derivative |
| 1 equivalent | N-bromosuccinimide |
| 50 ml | methylene chloride or chloroform, distilled via P$_2$O$_5$/1 g of a galanthamine derivative |

The educt is dissolved in a solvent, and N-bromosuccinimide is added while being stirred. A precipitate is immediately formed that is suctioned off after an appropriate length of time, washed and suctioned off in the dry state.

The products that are thus obtained are generally very pure, but the large amount of solvent rather than a small amount is important since otherwise succinimide is pulled into the substances and the latter are subsequently difficult to purify.

EXAMPLE 107

[4aS-(4aα,6β,8aR*)]-4a,5,9,10-Tetrahydro-6-hydroxy-3-methoxy-11-methyl-6H-benzofuro[3a,3,2-ef][2]benzazepinium, Bromide, Galanthaminium Bromide (MH-119)

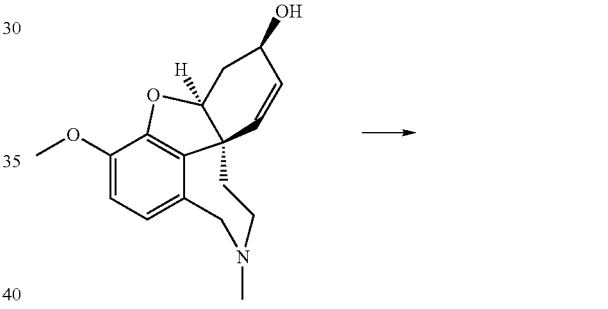

(1)

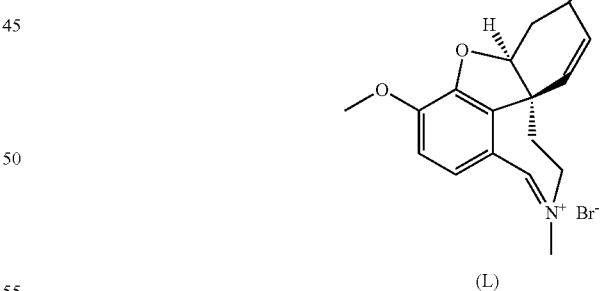

(L)

| 200 mg (0.7 mmol) | galanthamine (1) |
| 124 mg (0.7 mmol) | N-bromosuccinimide |
| 10 ml | methylene chloride or chloroform, distilled via P$_2$O$_5$ |

The precipitate that was produced was suctioned off after 10 minutes.

Yield: 230 mg (0.63 mmol=90% of theory) of a light yellow powder C$_{17}$H$_{20}$BrNO$_3$ [366.25] TLC: R$_f$=0.58 (CHCl$_3$:MeOH 9:1+1% NH$_4$OH) Melting point: 216–219° C. C$_{17}$H$_{20}$BrNO$_3$×0.1 HBr [374.34]

|  | % C | % H | % N |
|---|---|---|---|
| Cld.: | 54.55 | 5.41 | 3.74 |
| Fnd.: | 54.52 | 5.36 | 3.66 |

$^1$H-NMR (200 MHz, CDCl$_3$) δ 9.10 (s, 1H), 7.54 (d, J=8.5 Hz, 1H), 7.27 (d, J=8.5 Hz, 1H), 5.92 (dd, J=10.3, 4.5 Hz, 1H), 5.73 (d, J=10.3 Hz, 1H), 4.74 (s, 1H), 4.59 (s, 1H), 4.11 (s, 2H), 3.94 (s, 3H), 3.79 (s, 3H), 2.38 (d, J=15.3 Hz, 1H), 2.15 (m, 3H); $^{13}$C-NMR (50 MHz, CDCl$_3$) δ 167.3 (d), 151.3 (s), 146.2 (s), 136.9 (s), 133.0 (d), 129.8 (d), 126.4 (d), 115.0 (s), 112.9 (d), 87.0 (d), 58.9 (d), 56.4 (q), 54.0 (t), 51.5 (q), 45.9 (s), 31.1 (t), 29.7 (t)

EXAMPLE 108

[(±)-(4aα,6β,8aR*)]-4a,5,9,10-Tetrahydro-6-hydroxy-3-methoxy-1,11-dimethyl-6H-benzofuro[3a,3,2-ef][2]benzazepinium, Bromide, 1-methylgalanthaminium Bromide (Pi-8)

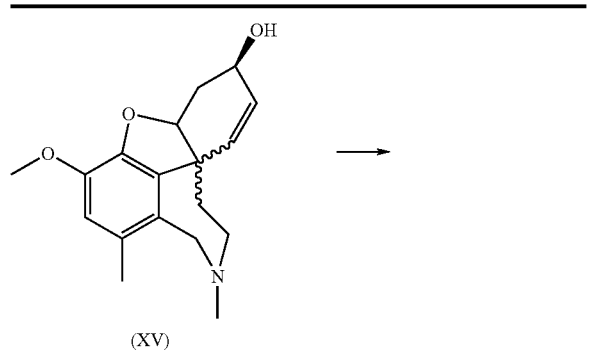

(XV)

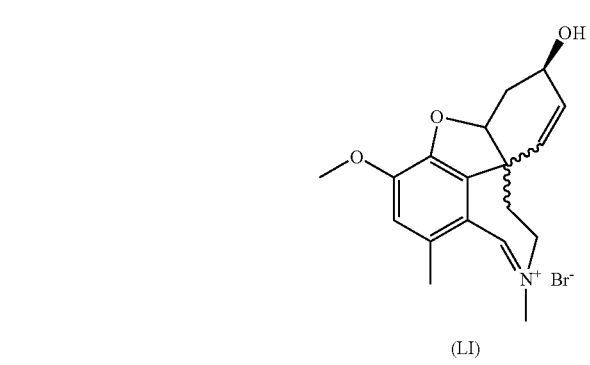

(LI)

| 200 mg (0.66 mmol) | 1-methylgalanthamine (XV) |
| 118 mg (0.66 mmol) | N-bromosuccinimide |
| 5 ml | chloroform |

After 5 minutes, an orange-yellow precipitate was produced, which was suctioned off after 15 minutes. The precipitate 162 mg) was washed twice with diethyl ether. The filtrate was concentrated by evaporation, taken up in a little ethanol and precipitated in diethyl ether (54 mg).

Yield: 216 mg (0.57 mmol 86% of theory) of an orange-yellow powder C$_{18}$H$_{22}$BrNO$_3$ [380.28] TLC: R$_f$=0.02 (CHCl$_3$:MeOH=9:1) Melting point: 223–226° C. C$_{18}$H$_{22}$BrBO$_3$×0.35 HBr [408.60]

|  | % C | % H | % N |
|---|---|---|---|
| Cld.: | 52.91 | 5.51 | 3.43 |
| Fnd.: | 52.99 | 5.52 | 3.48 |

$^1$H-NMR (200 MHz, DMSO-d$_6$) δ 9.06 (s, 1H), 7.04 (s, 1H), 5.81 (dd, J=10.1, 4.5 Hz, 1H), 5.54 (d, J=10.2 Hz, 1H), 4.74 (s, 1H), 4.17–3.95 (m, 4H), 3.91 (s, 3H), 3.86 (s, 3H), 2.53 (s, 3H), 2.40–1.96 (m, 4H); $^{13}$C-NMR (50 MHz, DMSO-d$_6$) δ 166.4 (d), 150.5 (s), 144.7 (s), 140.4 (s), 136.7 (s), 128.4 (d), 127.9 (d), 114.9 (d), 113.9 (s), 86.5 (d), 58.7 (d), 56.3 (q), 54.4 (t), 50.5 (q), 47.0 (s), 35.1 (t), 29.4 (t), 18.9 (q)

EXAMPLE 109

[4aS-(4aα,6a,8aR*)]-4a,5,9,10-Tetrahydro-6-hydroxy-3-methoxy-11-ethyl-6H-benzofuro[3a,3,2-ef][2]benzazepinium, bromide, epigalanthaminium bromide (Pi-13)

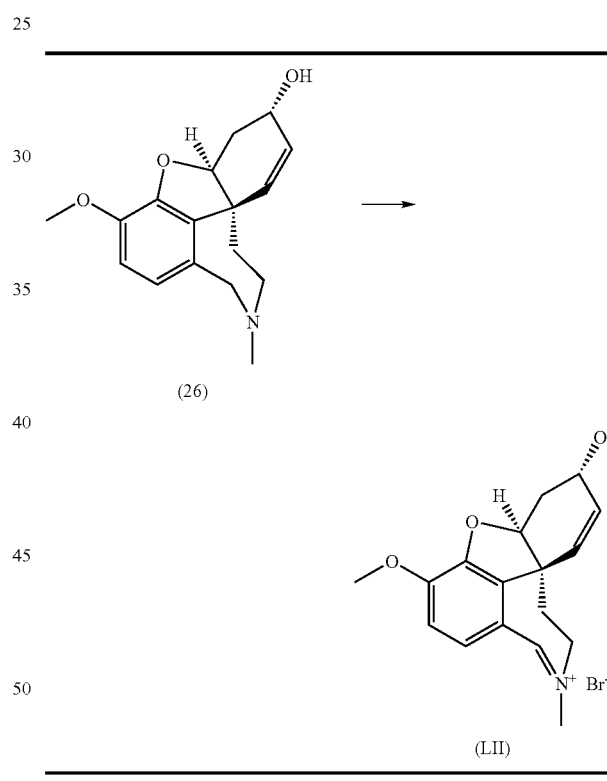

(26)

(LII)

| 0.78 g (2.71 mmol) | epigalanthamine (26) |
| 0.48 g (2.71 mmol) | N-bromosuccinimide |
| 6 ml | absolute chloroform |

After 3 minutes, a yellow precipitate was produced, which was suctioned off and washed twice with diethyl ether. A second fraction was obtained by concentration by evaporation of the filtrate and adding in drops of diethyl ether to a level of 60 ml. The second fraction was dissolved in a little ethanol for purification and added in drops to diethyl ether.

Yield: 0.91 g (2.48 mmol=92% of theory) C$_{17}$H$_{20}$BrO$_3$ [366.25] TLC: R$_f$=0.05 (CHCl$_3$:MeOH=9:1+1% NH$_4$OH) Melting point: 205–210° C. C$_{17}$H$_{20}$BrXO$_3$×0.3 HBr [390.52]

|  | % C | % H | % N |
|---|---|---|---|
| Cld.: | 52.28 | 5.24 | 3.59 |
| Fnd.: | 52.12 | 5.18 | 3.88 |

$^1$H-NMR (200 MHz, DMSO-$d_6$) δ 9.10 (s, 1H), 7.51 (d, J=11.5 Hz, 1H), 7.20 (d, J=11.5 Hz, 1H), 5.82 (d, J=12.7 Hz, 1H), 5.68 (d, J=12.7 Hz, 1H), 4.80 (bs, 1H), 4.40–4.21 (m, 1H), 4.21–4.04 (m, 2H), 3.94 (s, 3H), 3.77 (s, 3H), 2.60 (s, 1H), 2.30–2.10 (m, 2H), 1.81–1.60 (m, 1H); $^{13}$C-NMR (50 MHz, DMSO-$d_6$) δ 167.3 (d), 151.2 (s), 146.5 (s), 137.3 (s), 134.4 (d), 133.0 (d), 126.0 (d), 115.0 (s), 113.0 (d), 88.0 (d), 60.7 (d), 56.4 (q), 54.2 (t), 51.4 (q), 46.2 (s), 31.5 (t), 30.8 (t).

General Operating Instructions for the Production of Galanthamine-12-Carbonitrile Derivatives (Examples 110–113)

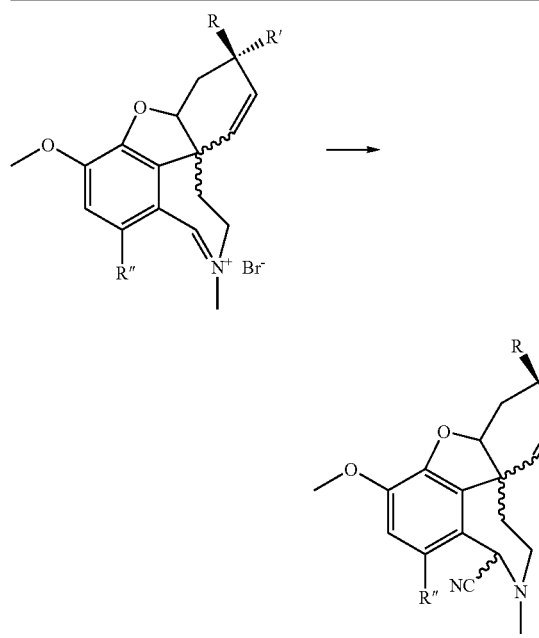

R, R' = H, OH

| 1 equivalent | a galanthaminium derivative |
| 3 equivalents | potassium cyanide |
| 30 ml | water/1 g of a galanthaminium derivative |
| 10 ml | diethyl ether/1 g of a galanthaminium derivative |

The educt was dissolved in a separatory funnel in water, and the solution was covered with a layer of ether, than solid potassium cyanide (freshly pulverized) was added thereto, whereby a white precipitate immediately formed in the aqueous phase. After about 2–3 minutes, the product was extracted by shaking in the ether phase. The aqueous phase was exhaustively extracted with ether and with sparingly soluble derivatives with chloroform, the organic phases were combined, washed with saturated aqueous common salt solution, dried on $Na_2SO_4$, filtered, and the solvent was drawn off. If necessary, the product that was obtained was purified on a silica gel column (mobile solvent: $CHCl_3$:MeOH=9:1, unless otherwise is indicated).

EXAMPLE 110

[4aS -(4aα,6β,8aR*)]-4a,5,9,10,11,12-Hexahydro-6-hydroxy-3-methoxy-11-methyl-6H-benzofuro[3a,3,2-ef][2]benzazepine-12-carbonitrile, Galanthamine-12-carbonitrile (MH-123)

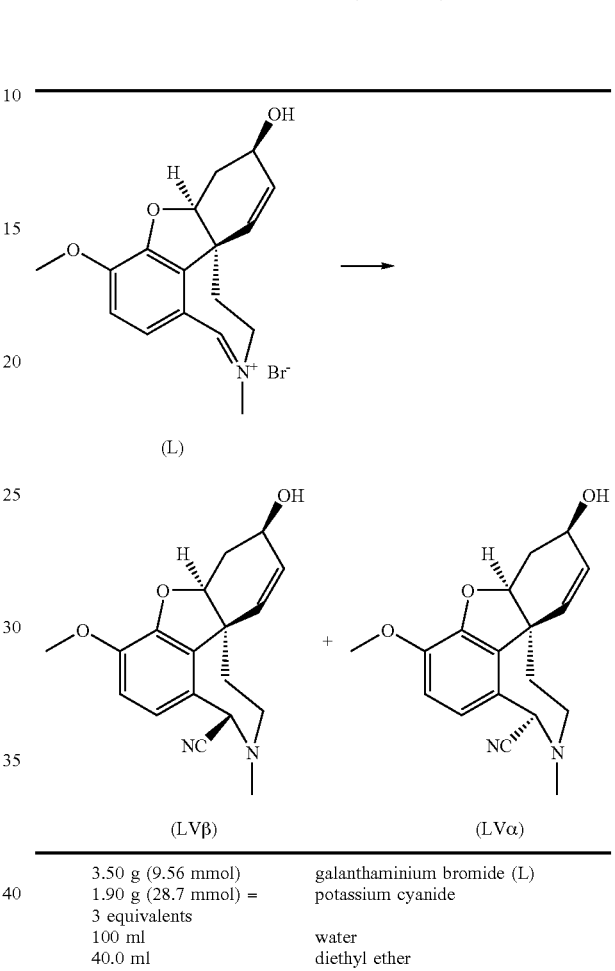

| 3.50 g (9.56 mmol) | galanthaminium bromide (L) |
| 1.90 g (28.7 mmol) = 3 equivalents | potassium cyanide |
| 100 ml | water |
| 40.0 ml | diethyl ether |

The reaction was performed according to the general operating instructions.

Raw yield>2 g

The oily raw mixture, consisting of an isomer ratio of about 9:1, was dissolved in as little ethanol as possible, and the main isomer was brought to crystallization while being stirred. The precipitate was suctioned off, washed with ethanol, and the filtrate was combined with the washing solution and concentrated by evaporation. The process was repeated until the main amount of pure main isomer was isolated.

Yield: 990 mg (3.28 mmol=34% of theory) of a white powder $C_{18}H_{20}N_2C_3$ [312.37]

A mixture that consists of two isomers (ratio 9:1) and galanthamine remains, and said mixture is produced during the isolation of the main isomer, which could be purified by columns. The isomer mixture is eluted again at a ratio of 9:1 from the column, since it is converted into one another on the column.

TLC: $R_f$=0.77 main isomer 0.63 Secondary isomer ($CHCl_3$:MeOH=9:1) Melting point: 151–155° C. $C_{18}H_{20}N_2O_3$×0.1 $H_2O$ [314.17]

| | % C | % H | % N |
|---|---|---|---|
| Cld.: | 68.82 | 6.48 | 8.92 |
| Fnd.: | 68.85 | 6.32 | 8.69 |

$^1$H-NMR (200 MHz, CDCl$_3$) δ 6.70 (s, 2H), 6.35 (d, J=10.2 Hz, 1H), 6.07 (dd, J=10.2, 5.3 Hz, 1H), 4.71 (s, 1H), 4.61 (m, 1H), 4.15 (dt, J=11.1, 5.0 Hz, 1H), 3.85 (s, 3H), 3.50 (dd, J=15.0, 13.6 Hz, 1H), 2.91 (dt, J=15.0, 3.2 Hz, 1H), 2.74–2.61 (m, 1H), 2.61 (s, 3H), 2.38 (d, J=11.4 Hz, 1H), 1.98–2.08 (m, 2H), 1.78 (ddd, J=13.7, 5.0, 1.2 Hz, 1H); $^{13}$C-NMR (50 MHz, CDCl$_3$) δ 146.7 (s), 145.6 (s), 132.9 (s), 128.2 (d), 126.9 (d), 124.2 (s), 122.5 (s), 111.6 (d), 88.9 (d), 61.6 (d+d), 55.9 (q), 49.9 (t), 48.1 (s), 46.1 (q), 36.4 (t), 29.7 (t)

EXAMPLE 111

[(±)-(4aα,6β,8aR*)]-4a,5,9,10,11,12-Hexahydro-6-hydroxy-3-methoxy-1,11-dimethyl-6H-benzofuro[3a,3,2-ef][2]benzazepine-12-carbonitrile, 1-methyl-galanthamine-12-carbonitrile (Pi-12)

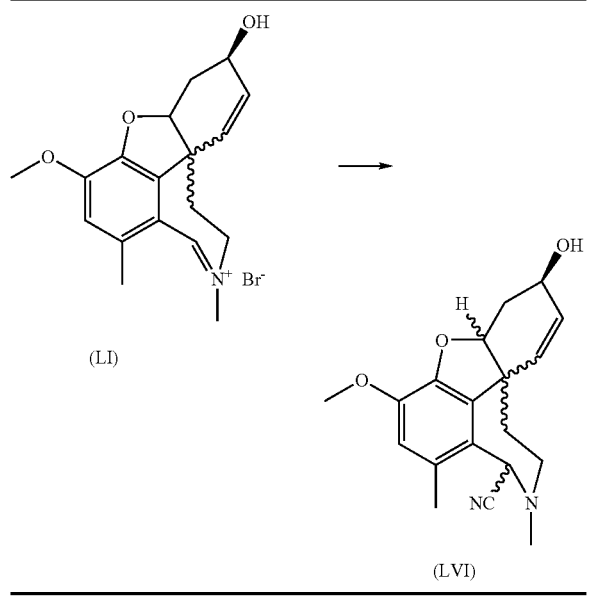

| 300 mg (0.79 mmol) | 1-methylgalanthaminium bromide (LI) |
| 154 mg (2.36 mmol) = 3 equivalentS | potassium cyanide |
| 20.0 ml | water |

205 mg of a white crude product was isolated.

An attempt was made to achieve column-chromatographic separation of the diastereomers with a pure ethyl acetate as a mobile solvent. In this case, however, no separation of the diastereomer mixture could be accomplished.

Yield: 151 mg (0.46 mmol=59% of theory) C$_{19}$H$_{22}$N$_2$O$_3$ [326.39] TLC: R$_f$=0.30/0.65 (diastereomer mixture; ethyl acetate) Melting point: 72–73° C. C$_{19}$H$_{22}$N$_2$O$_3$×0.5 H$_2$O [335.39]

| | % C | % H | % N |
|---|---|---|---|
| Cld.: | 68.04 | 6.91 | 8.35 |
| Fnd.: | 67.91 | 6.62 | 8.20 |

$^1$H-NMR (Mixture that consists of 2 isomers, 200 MHz, CDCl$_3$): δ 6.59 (s, 1H), 6.31 (d, J=8.9 Hz, 0.4H), 6.27 (d, J=8.9 Hz, 0.6H), 6.01 (dd, J=9.2, 5.0 Hz, 1H), 4.96 (s, 0.6H), 4.83 (s, 0.4H), 4.57 (bs, 0.6H), 4.50 (bs, 0.4H), 4.12 (dt, J=15.5, 4.9 Hz, 1H), 3.83 (s, 3H), 3.47 (ddd, J=13.9, 9.8, 3.4 Hz, 1H), 2.88 (dt, J=14.6, 3.8 Hz, 1H), 2.70 (bs, 1H), 2.62 (s, 1.8H), 2.60 (s, 1.2H), 2.31 (s, 3H), 2.10–1.92 (m, 2H), 1.87–1.68 (m, 1H); $^{13}$C-NMR (mixture that consists of 2 isomers, 100 MHz, CDCl$_3$): δ 145.5 (s), 145.4 (s), 145.3 (s), 144.8 (s), 135.7 (s), 133.6 (s), 129.7 (d), 129.3 (d), 129.6 (s), 128.7 (s), 128.4 (d), 127.7 (d), 122.9 (s), 122.8 (s), 116.7 (s), 115.3 (s), 114.5 (d), 114.4 (d), 89.4 (d), 88.9 (d), 62.3 (d), 62.2 (d), 57.9 (d), 56.6 (d), 56.5 (q), 56.3 (q), 51.0 (t), 50.3 (t), 49.0 (s), 47.9 (s), 47.2 (q), 47.2 (s), 36.8 (t), 33.7 (t), 30.2 (t), 20.3 (q), 19.3 (q).

EXAMPLE 112

[4aS-(4aα,6a,8aR*)]-4a,5,9,10,11,12-Hexahydro-6-hydroxy-3-methoxy-11-methyl-6H-benzofuro[3a,3,2-ef][2]benzazepine-12-carbonitrile, epigalanthamine-12-carbonitrile (Pi-14)

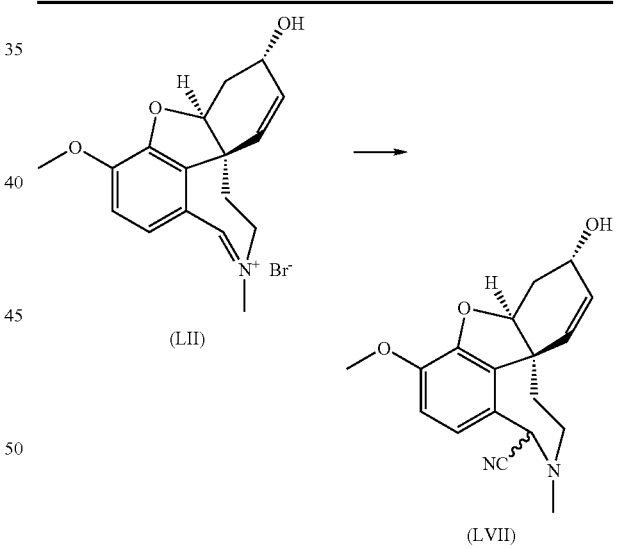

| 500 mg (1.37 mmol) | epigalanthaminium bromide (LII) |
| 270 mg (4.10 mmol) = 3 equivalents | potassium cyanide |
| 15.0 ml | water |

Yield: 0.33 g (1.06 mmol=77% of theory) C$_{18}$H$_{20}$N$_2$O$_3$ [312.37] TLC: R$_f$=0.75 (CHCl$_3$:MeOH=9:1) Melting point: 90–96° C.

$^1$H-NMR (Mixture that consists of 2 isomers, 200 MHz, CDCl$_3$): δ 6.92 (d, J=8.3 Hz, 0.3H), 6.72 (d, J=8.0 Hz, 0.3H), 6.68 (d, J=8.0 Hz, 0.7H), 6.62 (d, J=8.3 Hz, 0.7H), 6.31 (dt, J=10.5, 1.6 Hz, 0.7H), 6.03 (d, J=10.5 Hz, 0.3H), 5.85 (d, J=10.3 Hz, 1H), 5.22 (s, 0.3H), 4.64 (s, 0.7H), 4.58

(bs, 1H), 3.86 (s, 0.9H), 3.85 (s, 2.1H), 3.12 (dt, J=14.8, 3.2 Hz, 0.3H), 2.98–2.70 (m, 1.7H), 2.58 (s, 2.1H), 2.38 (s, 0.9H), 2.27–2.04 (m, 1.2H), 1.85 (dd, J=13.5, 4.2 Hz, 1.4H), 1.71 (ddd, J=13.5, 10.7, 2.5 Hz, 1.4H); $^{13}$C-NMR (mixture that consists of 2 isomers, 50 MHz, CDCl$_3$) δ 147.5 and 147.2 (s), 145.2 and 145.0 (s), 132.6 (s), 132.5 and 131.9 (d), 126.6 (d), 124.0 and 123.3 (s), 121.8 and 120.1 (d), 116.5 (s), 111.3 and 111.2 (d), 88.7 and 88.4 (d), 62.8 (d), 61.4 and 58.4 (d), 55.8 (q), 50.0 (t), 47.9 (s), 45.9 (q), 36.9 (t), 32.0 and 31.7 (t)

EXAMPLE 113

[(±)-(4aα,6α,8aR*)]-4a,5,9,10,11,12-Hexahydro-6-hydroxy-3-methoxy-1,11-dimethyl-6H-benzofuro[3a,3,2-ef][2]benzazepine-12-carbonitrile, 1-methyl-epigalanthamine-12-carbonitrile (Pi-19)

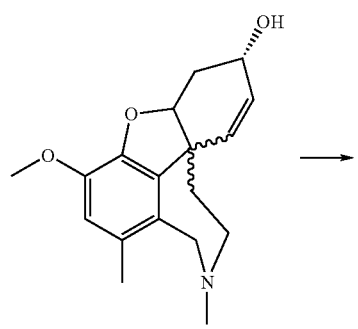

(XXIII)

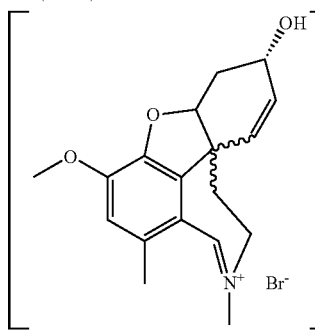

(LIII)

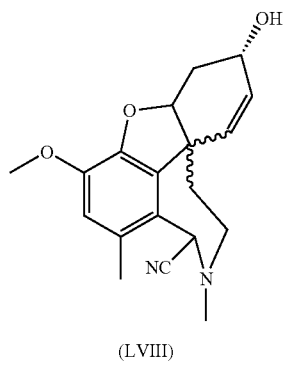

(LVIII)

1-Methylepigalanthaminium bromide was produced according to general operating instructions for the production of galanthaminium derivatives, whereby no precipitate formed, however. The reaction solution was therefore evaporated to the dry state, the remaining residue was taken up in ether, suctioned off and washed. The remaining crude product was used directly in the subsequent reaction according to NMR analysis.

| | |
|---|---|
| 500 mg (1.32 mmol) | 1-methylepigalanthaminium bromide (LIII) |
| 260 mg (3.96 mmol) = 3 equivalents | potassium cyanide |
| 50 ml | water |

The purification was carried out by means of column chromatography (CHCl$_3$:MeOH=9:1).

Yield: 220 mg (0.67 mmol=51% of theory) of a white foam C$_{19}$H$_{22}$N$_2$O$_3$ [326.39] TLC: R$_f$=0.70/0.60 (diastereomer mixture; CHCl$_3$:MeOH=9:1) $^1$H-NMR (Mixture that consists of 2 isomers, 200 MHz, CDCl$_3$): δ 6.57 (s, 1H), 6.26 (d, J=10.4 Hz, 1H), 5.82 (d, J=10.4 Hz, 1H), 4.94 and 4.82 (s, 1H), 4.74–4.55 (m, 1H), 4.50 and 4.45 (m, 1H), 3.87 and 3.84 (s, 3H), 3.55–3.32 (m, 1H), 3.05–2.68 (m, 2H), 2.58 and 2.57 (s, 3H), 2.33 and 2.30 (s, 3H), 2.23–2.07 (m, 1H), 1.93–1.63 (m, 2H); $^{13}$C-NMR (mixture that consists of 2 isomers, 50 MHz, CDCl$_3$) δ 146.0 (s), 145.8 (s), 144.5 (s), 144.1 (s), 135.0 (s), 133.0 (s), 132.2 (d), 131.7 (d), 129.5 (d), 128.5 (s), 127.6 (s), 127.1 (d), 122.4 (s), 122.2 (s), 116.4 (s), 114.8 (s), 113.9 (d), 113.8 (d), 88.5 (d), 88.4 (d), 63.0 (d), 62.6 (d) 57.2 (d), 56.4 (d), 56.0 (q), 55.8 (q), 50.7 (t), 50.0 (t), 48.4 (s), 47.3 (s), 46.7 (q), 36.9 (t), 34.1 (t), 31.7 (t), 19.8 (q) 18.8 (q)

General Operating Instructions for the Production of 12-Methylgalanthamine Derivatives (Examples 114–117)

R, R' = H, OH

| | |
|---|---|
| 1 equivalent | a galanthaminium derivative |
| 2–4 equivalents | methylmagnesium iodide (3 M in diethyl ether) |
| 20 ml | absolute diethyl ether/1 g of a galanthaminium derivative |

The entire amount of Grignard reagent was introduced under N$_2$ atmosphere, and then the solid galanthaminium derivative was added without solvent. After the length of time indicated in each case, diethyl ether was added and stirred for a specific length of time, whereby the solid material dissolved. Then, it was hydrolyzed with water, the reaction solution was made basic with concentrated ammonia and extracted with ethyl acetate. The organic phases

EXAMPLE 114

[4aS-(4aα,6β,8aR*)]-4a,5,9,10,11,12-Hexahydro-3-methoxy-11,12-dimethyl-6H-benzofuro[3a,3,2-ef][2]benzazepin-6-ol, 12-methylgalanthamine (Pi-4)

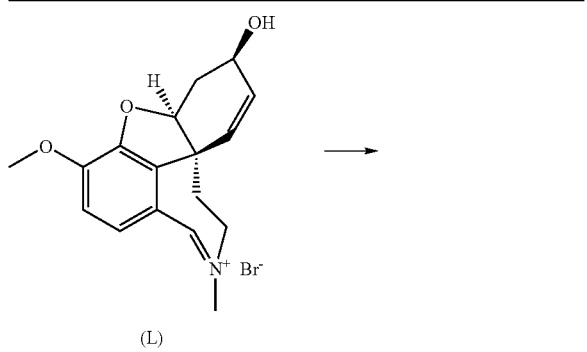

| | |
|---|---|
| 2.00 g (5.46 mmol) | galanthaminium bromide (L) |
| 6.70 ml (20.2 mmol) = 3.7 equivalents | methylmagnesium iodide (3 M in diethyl ether) |
| 40 ml | absolute diethyl ether |

After 40 minutes, the solvent was added and stirred for 5 hours, before it was hydrolyzed.

Yield: 760 mg (2.52 mmol=46% of theory) of a light yellow foam $C_{18}H_{23}NO_3$ [301.38] TLC: $R_f$=0.65 (CHCl$_3$:MeOH=9:1+1% NH$_4$OH) Melting point: 46–48° C. $^1$H-NMR (Mixture that consists of 2 isomers, 200 MHz, CDCl$_3$): δ 6.66 (d, J=8.3 Hz, 0.8H), 6.65 (s, 0.2H), 6.64 (s, 0.2H), 6.57 (d, J=8.3 Hz, 0.8H), 6.13 (d, J=10.1 Hz, 0.2H), 6.07 (d, J=10.1 Hz, 0.8H), 5.94 (dd, J=10.1, 4.4 Hz, 1H), 4.54 (bs, 1H), 4.26 (q, J=7.0 Hz, 0.2H), 4.08 (t, J=4.4 Hz, 1H), 3.88 (q, J=7.4 Hz, 0.8H), 3.80 (s, 0.6H), 3.78 (s, 2.4H), 3.62 (ddd, J=14.6, 13.2, 1.0 Hz, 0.8H), 3.45 (d, 14.2 Hz, 0.2H), 3.12 (dt, J=14.8, 3.3 Hz, 0.2H), 2.85 (td, J=15.5, 3.5 Hz, 0.8H), 2.76 (bs, 1H), 2.63 (d, J=15.6 Hz, 1H), 2.43 (s, 3H), 2.16 (d, J=2.7 Hz, 0.2H), 1.98 (dt, J=15.5, 2.3 Hz, 0.8H), 1.95 (dd, J=15.5, 2.3 Hz, 0.2H), 1.51 (d, J=7.3 Hz, 2.4H), 1.47 (d, J=7.3 Hz, 0.6H); $^{13}$C-NMR (mixture that consists of 2 isomers, 50 MHz, CDCl$_3$) δ 146.1 and 145.6 (s), 143.8 and 143.4 (s), 134.9 and 132.6 (s), 132.4 and 131.3 (s), 129.3 (d), 127.6 and 127.3 (d), 126.9 (d), 122.0 and 119.9 (d), 111.5 and 110.8 (d), 88.6 and 88.5 (d), 64.0 (d), 61.9 and 61.6 (d), 58.3 and 55.7 (q), 48.8 (s), 44.1 (t), 41.3 (q), 31.5 and 31.0 (t), 29.9 and 29.7 (t), 21.8 and 17.5 (q)

EXAMPLE 115

[4aS-(4a?,6?,8aR*,12R*)]-4a,5,9,10,11,12-Hexahydro-3-methoxy-11,12-dimethyl-6H-benzofuro[3a,3,2-ef]121benzazepin-6-ol, (=12-methylgalanthamine); (main isomer)

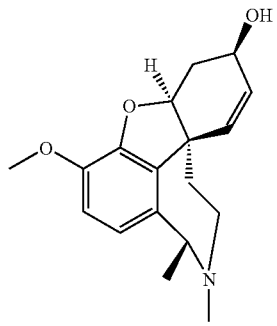

The isomer mixture was purified by column chromatography on silica gel (CHCl$_3$:MeOH=9:1+1% NH$_4$OH), whereby a pure isomer was obtained.

$^1$H-NMR (200 MHz, CDCl$_3$) δ 6.66 (d, J=8.3 Hz, 1H), 6.57 (d, J=8.3 Hz, 1H), 6.07 (d, J=10.1 Hz, 1H), 5.94 (dd, J=10.1, 4.4 Hz, 1H), 4.54 (bs, 1H), 4.08 (t, J=4.4 Hz, 1H), 3.88 (q, J=7.4 Hz, 1H), 3.78 (s, 3H), 3.62 (dd, J=14.6 (13.2 Hz, 1H), 2.85 (td, J=15.5, 3.5 Hz, 1H), 2.63 (d, J=15.6 Hz, 1H), 2.43 (s, 3H), 2.11 (dt, J=13.3, 2.4 Hz, 1H), 1.95 (ddd, J=16.5, 5.0, 1.8 Hz, 1H), 1.51 (d, J=7.3 Hz, 3H), 1.47 (dd, J=13.3 Hz, 1H); $^{13}$C-NMR (50 MHz, CDCl$_3$) δ 146.2 (s), 143.5 (s), 135.1 (s), 131.4 (s), 129.4 (d), 127.4 (d), 122.2 (d), 111.6 (d), 88.8 (d), 64.0 (d), 61.8 (d), 55.8 (q), 48.9 (s), 44.2 (t), 41.5 (q), 31.7 (t), 29.8 (t), 21.9 (q)

EXAMPLE 116

[(±)-(4aα,6β,8aR*)]-4a,9,10,11,12-Hexahydro-3-methoxy-6H-1,11,12-trimethyl-benzofuro[3a,3,2-ef][2]benzazepin-6-ol, 1,12-dimethylgalanthamine (Pi-21)

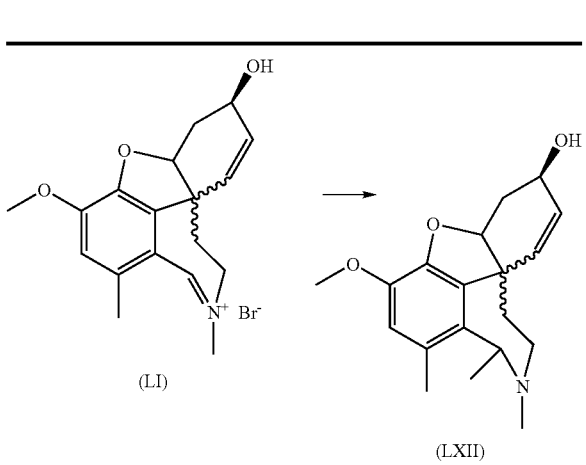

| | |
|---|---|
| 500 mg (1.31 mmol) | 1-triethylgalanthaminium bromide (LI) |
| 1.00 ml (3.00 mmol) = 2.3 equivalents | methylmagnesium iodide (3 M in diethyl ether) |
| 15 ml | absolute diethyl ether |

During the addition of educt, 5 ml of diethyl ether was added to keep the reaction mixture stirrable. After the addition of educt was completed (30 minutes), another 10 ml of diethyl ether was added. After 2.5 hours, the reaction mixture was hydrolyzed.

Yield: 73 mg (0.23 mmol=18% of theory) $C_{19}H_{25}NO_3$ [315.41] TLC: $R_f$=0.50 (CHCl$_3$:MeOH=9:1+1% NH$_4$OH) Melting point: 45–50° C. $^1$H-NMR (Mixture that consists of 2 isomers, 200 MHz, CDCl$_3$): δ 6.57 (s, 1H), 6.06 (d, J=10.2 Hz, 1H), 5.95 (dd, J=10.2, 4.5 Hz, 1H), 4.59–4.44 (m, 1H), 4.17–4.03 (m, 2H), 3.81 (s, 3H), 3.75–3.55 (m, 1H), 2.97–2.77 (m, 1H), 2.73–2.55 (m, 1H), 2.51 (s, 0.5H), 2.46 (s, 2.5H), 2.25 (s, 3H), 2.15–1.87 (m, 2H), 1.51 (d, J=7.3 Hz, 3H), 1.30–1.18 (m, 1H); $^{13}$C-NMR (mixture that consists of 2 isomers, 50 MHz, CDCl$_3$) δ 144.7 (s), 142.9 (s), 132.5 and 131.7 (s), 130.4 and 129.0 (s), 129.3 (d), 127.8 and 126.8 (s), 127.5 (d), 114.3 and 114.0 (d), 88.7 and 88.4 (d), 62.2 and 61.8 (d), 59.3 and 58.8 (d), 56.0 and 55.8 (q), 49.4 and 48.4 (s), 44.3 (t), 41.5 (q), 31.7 (t), 29.9 (t), 19.7 and 19.2 (q), 18.8 (q)

EXAMPLE 117

[4aS-(4aα,6a,8aR*)]-4a,5,9,10,11,12-Hexahydro-3-methoxy-11,12-dimethyl-6H-benzofuro[3a,3,2-ef][2]benzazepin-6-ol, 12-methylepigalanthamine (Pi-22)

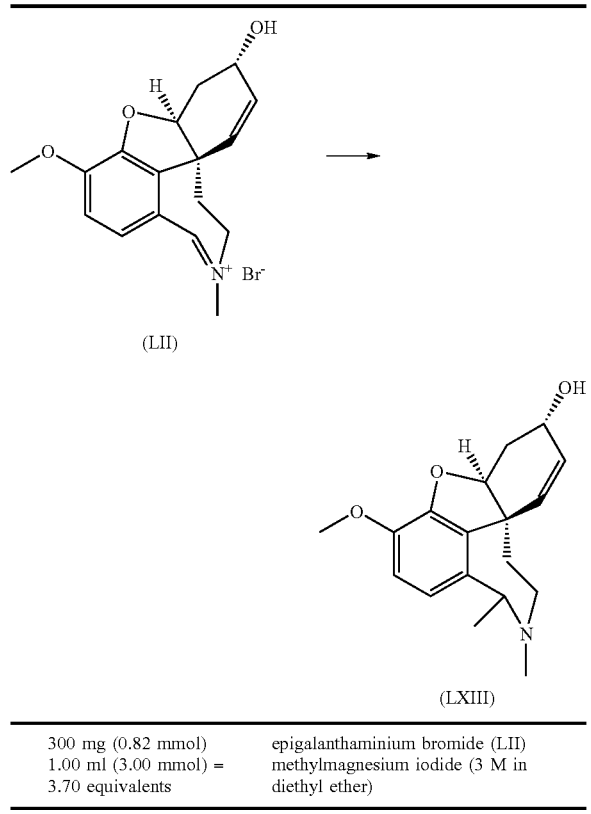

| 300 mg (0.82 mmol) | epigalanthaminium bromide (LII) |
| 1.00 ml (3.00 mmol) = 3.70 equivalents | methylmagnesium iodide (3 M in diethyl ether) |

The Grignard reagent was added over 30 minutes, then 5 ml of ether was added. After 20 minutes, another 15 ml of ether was added and hydrolyzed for 3 hours.

The purification was carried out by column chromatography (CHCl$_3$:MeOH=9:1).

Yield: 60 mg (0.20 mmol=24% of theory) $C_{18}H_{23}NO_3$ [301.39] TLC: $R_f$=0.78 (CHCl$_3$:MeOH=9:1+1% NH$_4$OH) $^1$H-NMR (200 MHz, CDCl$_3$) δ 6.65 (d, J=8.3 Hz, 1H), 6.53 (d, J=8.3 Hz, 1H), 6.04 (d, J=10.4 Hz, 1H), 5.76 (d, J=10.4 Hz, 1H), 4.70–4.57 (m, 1H), 4.54 (bs, 1H), 3.93–3.82 (m, 1H), 3.81 (s, 3H), 3.61 (t, J=13.6 Hz, 1H), 2.94–2.67 (m, 3H), 2.41 (s, 3H), 2.20 (td, J=13.2, 2.4 Hz, 1H), 1.69 (ddd, J=13.6, 10.6, 2.0 Hz, 1H), 1.52 (d, J=7.3 Hz, 3H), 1.59–1.44 (m, 1H); $^{13}$C-NMR (50 MHz, CDCl$_3$) δ 147.0 (s), 143.2 (s), 134.5 (s), 131.3 (d), 131.1 (s), 128.9 (d), 121.5 (d), 111.2 (d), 88.6 (d), 64.1 (d), 62.7 (d), 55.6 (q), 48.6 (s), 44.4 (t), 41.2 (q), 32.0 (t+t), 21.8 (q)

EXAMPLE 118

[4aS-(4αa,6β,8aR*)]-4a,5,9,10-Tetrahydro-6-hydroxy-3-methoxy-11-methyl-6H-benzofuro[3a,3,2-ef][2]benzazepin-12(l1H)-one (MH-128)

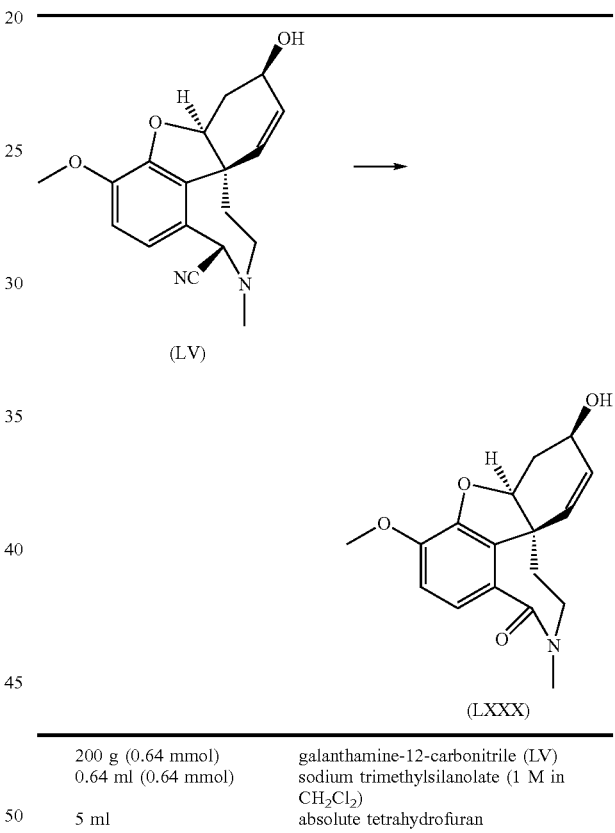

| 200 g (0.64 mmol) | galanthamine-12-carbonitrile (LV) |
| 0.64 ml (0.64 mmol) | sodium trimethylsilanolate (1 M in CH$_2$Cl$_2$) |
| 5 ml | absolute tetrahydrofuran |

The educts were stirred under N$_2$ atmosphere at room temperature for 72 hours, whereby a precipitate formed, which was suctioned off, washed with tetrahydrofuran and dried.

Yield: 177 mg (0.59 mmol=92% of theory) of a light yellow powder $C_{17}H_{19}NO_4$ [301.35] TLC: $R_f$=0.65 (CHCl$_3$:MeOH=9:1) Melting point: 251–255° C. $^1$H-NMR (200 MHz, CDCl$_3$) δ 7.49 (d, J=8.5 Hz, 1H), 6.89 (d, J=8.5 Hz, 1H), 5.87 (dd, J=9.8, 5.3 Hz, 1H), 5.53 (d, J=9.8 Hz, 1H), 4.74 (bs, 1H), 4.13 (dt, J=10.1, 4.8 Hz, 1H), 3.91 (s, 3H), 3.80 (dt, J=14.1, 2.1 Hz, 1H), 3.25–3.16 (m, 1H), 3.19 (s; 3H), 2.71 (dt, J=15.7, 1.7 HZ, 1H), 2.31 (dt, J=14.1, 3.9 Hz, 1H), 2.06 (ddd, J=15.7, 5.0, 2.3 Hz, 1H), 1.83 (dt, J=14.6, 2.5 Hz, 1H); $^{13}$C-NMR (50 MHz, CDCl$_3$) δ 168.3 (s), 146.9 (s), 145.1 (s), 131.7 (s), 131.6 (d), 125.2 (d), 124.4 (d), 123.4 (s), 111.9 (d), 89.2 (d), 61.0 (d)r 55.8 (q), 49.5 (t), 48.0 (s), 38.3 (t), 34.9 (q), 29.3 (t)

EXAMPLE 119

[4aS-(4aα,6β,8aR*)]-4a,5,9,10-Tetrahydro-3-methoxy-6H-benzofuro[3a,3,2-ef][2]benzazepin-6-ol, 11-oxide (MH-142)

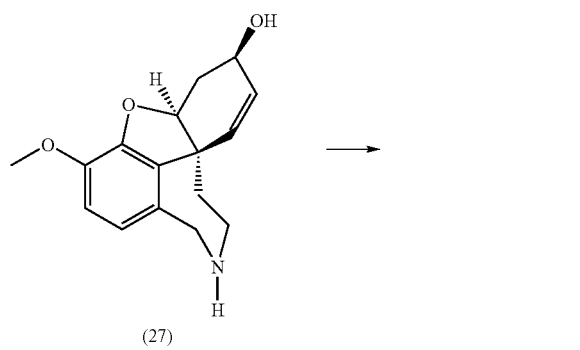

(27)

| | | |
|---|---|---|
| 4.25 g (15.55 mmol) | | demethylgalanthamine (27) |
| 85 mg (0.77 mmol) = 5% | | selenium dioxide |
| 70 ml | | 10% aqueous $H_2O_2$ solution (35%) in acetone (oxidation solution) |

Demethylgalanthamine was dissolved in the oxidation solution in an environment devoid of atmospheric humidity and cooled to 0° C. Then, $SeO_2$ was added, and it was stirred first for 20 minutes at 0° C. and then for 4 hours at room temperature, whereby a white precipitate settled out, which was suctioned off, washed with acetone and dried. The filtrate was mixed with water, the acetone was distilled off in a vacuum, and the remaining aqueous phase was extracted with methylene chloride. The collected organic phases were washed with saturated common salt solution, dried on sodium sulfate, filtered, and the solvent was drawn off. The oily residue was taken up in acetone, whereby a precipitate settled out, which could be obtained as a second fraction. By repeated concentration by evaporation of the filtrate and taking-up in acetone, other fractions were obtained.

Yield: 3.53 g (12.29 mmol=79% of theory) of a white powder $C_{16}H_{17}NO_4$ [287.31] TLC: $R_f$=0.42 ($CHCl_3$:MeOH=9:1+1% concentrated $NH_4OH$) Melting point: 232–233° C. ($CHCl_3$); release of a liquid starting from 215° C. $C_{16}H_{17}NO_4 \times 0.2$ H2O [290.91]

| | % C | % H | % N |
|---|---|---|---|
| Cld.: | 66.06 | 6.03 | 4.81 |
| Fnd.: | 66.11 | 6.05 | 4.73 |

$^1$H-NMR (200 MHz, DMSO-$d_6$) δ 7.82 (s, 1H), 6.90 (s, 2H), 5.81 (dd, J=10.1, 4.4 Hz, 1H), 5.54 (d, J=10.1 Hz, 1H), 4.64 (bs, 1H), 4.36 (d, J=5.5 Hz, 1H), 4.14–4.02 (m, 2H), 3.79 (s, 3H), 2.39–1.99 (m, 4H); $^{13}$C-NMR (50 MHz, DMSO-$d_6$) δ 146.1 (s), 144.6 (s), 134.6 (d), 131.8 (s), 128.3 (d), 127.6 (d), 122.4 (d), 118.3 (s), 112.6 (d), 86.7 (d), 61.8 (d) 59.1 (t), 55.7 (q), 45.3 (s), 34.2 (t), 29.7 (t)

EXAMPLE 119

[4aS-(4aα,6β,8aR*)]-4a,5,9,10,13,14a-Hexahydro-6-hydroxy-3-methoxy-6H,14H-benzofuro[3a,3,2-ef]isoxazolo[3,2-a][2]benzazepine-13(or 14)-carboxylic acid, methyl ester (MH-143)

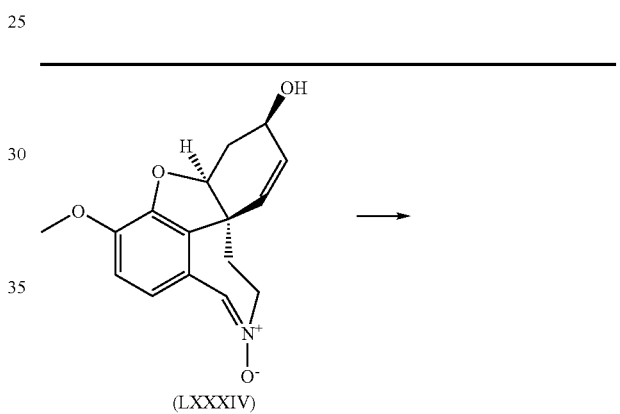

(LXXXIV)

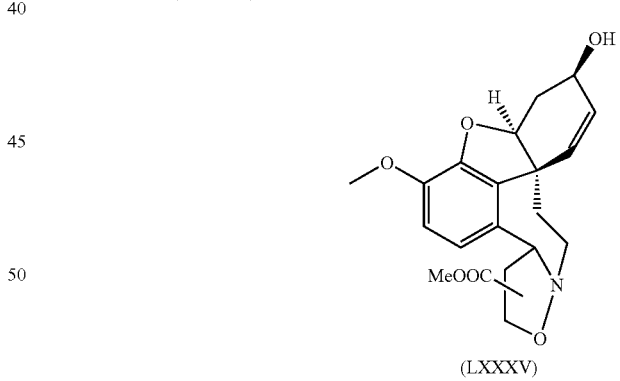

(LXXXV)

| | |
|---|---|
| 175 mg (0.61 mmol) | galanthamine nitrone (LXXXIV) |
| 0.05 ml (0.61 mmol) | acrylic acid methyl ester |
| 6 ml | absolute toluene |

The reagents were refluxed for 48 hours under argon atmosphere, then the solvent was drawn off. The residue was purified by column chromatography ($CHCl_3$:MeOH=9:1+1% concentrated $NH_4$ OH).

Yield: 225 mg (0.60 mmol 99% of theory) of a light brown, glass-like solidifying oil $C_{20}H_{23}NO_6$ [373.40] TLC: $R_f$=0.74 ($CHCl_3$:MeOH=9:1+1% concentrated $NH_4OH$) C20H23NO$_6 \times 0.5$ $H_2O$ [382.40]

|  | % C | % H | % N |
| --- | --- | --- | --- |
| Cld.: | 62.82 | 6.33 | 3.66 |
| Fnd.: | 62.88 | 6.17 | 3.65 |

Mixture that consists of stereoisomers and regioisomers. The more specific treatment of spectra is found in Chapter 2.2, Strukturaufklärungen [Structural Explanations].

EXAMPLE 120

[4aS-(4aα,6β,8aR*,14aS*)]-4a,5,9,10-Tetrahydro-6-hydroxy-3-methoxy-6H,14aH-benzofuro[3a,3,2-ef]isoxazolo[3,2-a][2]benzazepine-14-carboxylic acid, methyl ester (MH-145)

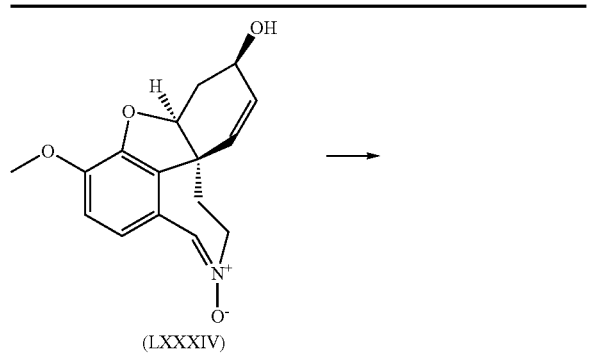

| 200 mg (0.70 mmol) | galanthamine nitrone (LXXXIV) |
| --- | --- |
| 0.06 ml (0.70 mmol) | acetylenecarboxylic acid methyl ester (propiolic acid methyl ester) |
| 5 ml | absolute toluene |

The reagents were refluxed for 10 minutes under argon atmosphere, whereby the solution was already colored orange during heating, then the solvent was drawn off. The residue was purified by column chromatography (CHCl$_3$:MeOH=9:1). The oily residue was recrystallized from ethanol, whereby yellow needles were obtained.

Yield: 261 mg (0.70 mmol=100% of theory) of light yellow needles C$_{20}$H$_{21}$NO$_6$ [371.39] TLC: R$_f$=0.73 (CHCl$_3$:MeOH=9:1) Melting point: 151–154° C.

|  | % C | % H | % N |
| --- | --- | --- | --- |
| Cld.: | 64.68 | 5.70 | 3.77 |
| Fnd.: | 64.59 | 5.89 | 3.67 |

$^1$H-NMR (200 MHz, CDCl$_3$) δ 7.54 (s, 1H), 6.96 (d, J=8.4 Hz, 1H), 6.74 (d, J=8.4 Hz, 1H), 5.96–5.77 (m, 2H), 5.67 (s, 1H), 4.55 (bs, 1H), 4.10 (bs, 1H), 3.85 (s, 3H), 3.68 (s, 3H), 3.59 (ddd, J=14.3, 6.8, 3.8 Hz, 1H), 3.30 (ddd, J=12.9, 9.3, 3.4 Hz, 1H), 2.64 (dd, J=15.7, 3.7 Hz, 1H), 2.15 (td, J=7.7, 3.4 Hz, 1H), 2.01 (ddd, J=15.6, 5.3, 1.9 Hz, 1H), 1.54 (ddd, J=15.6, 6.7, 3.5 Hz, 2H); $^{13}$C-NMR (50 MHz, CDCl$_3$) δ 163.9 (s), 154.6 (d), 146.8 (s), 145.1 (s), 133.3 (s), 130.3 (d), 126.9 (d), 125.3 (s), 123.3 (d), 111.3 (d), 109.9 (s), 89.1 (d), 68.7 (d), 61.4 (d), 55.8 (q), 52.4 (t), 51.4 (q), 47.2 (s), 29.2 (t), 28.0 (t)

EXAMPLE 121

[4aS-(4aα,6β,8aR*)]-4a,5,9,10,13,14a-Hexahydro-6-hydroxy-3-methoxy-6H,14H-benzofuro[3a,3,2-ef]isoxazolo[3,2-a][2]benzazepine-13 (or 14)-carbonitrile (MH-146)

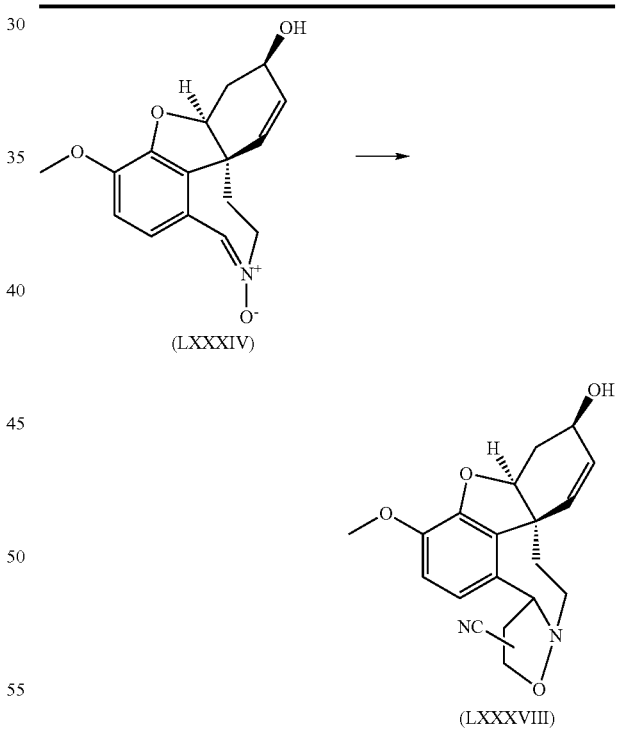

| 200 mg (0.70 mmol) | galanthamine nitrone (LXXXIV) |
| --- | --- |
| 0.05 ml (0.70 mmol) | acrylonitrile |
| 5 ml | absolute toluene |

The reagents were refluxed for 2 hours under argon atmosphere, then the solvent was drawn off. The residue was purified by column chromatography (CHCl$_3$:MeOH=9:1).

Yield: 230 mg (0.68 mmol=97% of theory) of a light yellow oil C$_{19}$H$_{20}$N$_2$O$_4$ [340.38] TLC: R$_f$=0.74 (CHCl$_3$:MeOH=9:1) C$_{19}$H$_{20}$N$_2$O$_4$×0.2 H$_2$O [343.98]

|       | % C   | % H  | % N  |
|-------|-------|------|------|
| Cld.: | 66.34 | 5.98 | 8.14 |
| Fnd.: | 66.22 | 6.03 | 7.86 |

Mixture that consists of 4 stereoisomers and regioisomers. The more specific treatment of spectra is found in Chapter 2.2, Strukturaufklärungen.

EXAMPLE 122

[4aS-(4aα,6β,8aR*,14aS*)]-4a,5,9,10,13,14a-Hexahydro-6-hydroxy-3-methoxy-6H,14aH-benzofuro[3a,3,2-ef]isoxazolo[3,2-a][2]benzazepine-6,13-diol, 13-acetate (MH-153)

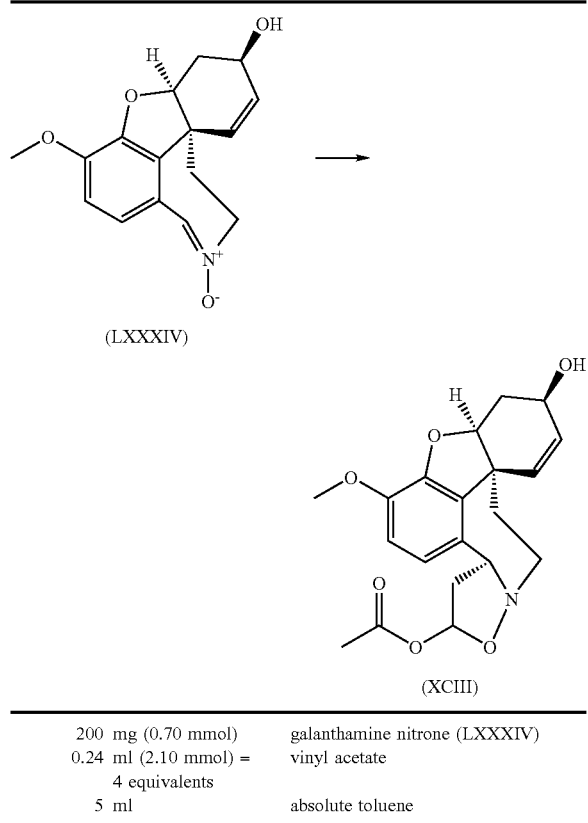

| 200 mg (0.70 mmol)     | galanthamine nitrone (LXXXIV) |
| 0.24 ml (2.10 mmol) = 4 equivalents | vinyl acetate |
| 5 ml                   | absolute toluene |

The reagents were refluxed for 4 days under $N_2$ atmosphere, whereby each day, 1 equivalent of vinyl acetate was added. The solvent was then drawn off, and the residue was purified by column chromatography ($CHCl_3$:MeOH=9:1). The purified oil was crystallized from methanol.

Yield: 256 mg (0.69 mmol=98% of theory) of beige crystals $C_{20}H_{23}NO_6$ [373.41] TLC: $R_f$=0.70 ($CHCl_3$:MeOH=9:1) Melting point: 132–134° C. $C_{20}H_{23}NO_6 \times 0.6 \, H_2O$ [384.21]

|       | % C   | % H  | % N  |
|-------|-------|------|------|
| Cld.: | 62.52 | 6.35 | 3.65 |
| Fnd.: | 62.59 | 6.12 | 3.61 |

$^1$H-NMR (Mixture that consists of 2 isomers, 200 MHz, $CDCl_3$): δ 6.76 and 6.73 (d, J=8.3 Hz, 1H), 6.68 and 6.60 (d, J=7.7 Hz, 1H), 6.36 (d, J=4.1 Hz, 1H), 6.30 (d, J=10.6 Hz, 1H), 6.08–5.91 (m, 1H), 4.60 and 4.50 (bs, 1H), 4.32 (dd, J=11.3, 5.6 Hz, 1H), 4.13 (bs, 1H), 3.84 (s, 3H), 3.80 (dd, J=19.1, 9.8 Hz, 1H), 3.22 (ddd, J=10.0, 6.8, 2.8 Hz, 1H), 2.92 (dd, J=12.3, 5.8 Hz, 1H), 2.78–2.57 (m, 2H), 2.09 (s, 3H), 2.07–1.79 (m, 2H); $^{13}$C-NMR (Mixture that consists of 2 isomers, 50 MHz, $CDCl_3$): δ 169.6 (s), 145.8 (s), 143.8 (s), 134.1 (s), 129.8 (d), 128.0 and 127.7 (d), 127.0 (s), 118.7 and 118.5 (d), 111.4 and 110.9 (d), 95.3 and 94.5 (d), 88.7 and 88.2 (d), 61.4 (d+d), 55.7 and 55.5 (q), 54.5 (t), 47.3 (s), 41.7 (t), 29.7 (t), 29.3 (t), 21.0 and 20.9 (q)

EXAMPLE 123

[4aS-(4aα,6β,8aR*,14aS*)]-4a,5,9,10-Tetrahydro-6-hydroxy-3-ethoxy-6H,14aH-benzofuro[3a,3,2-ef]isoxazolo[3,2-a][2]benzazepine-14-carbonitrile (MH-159)

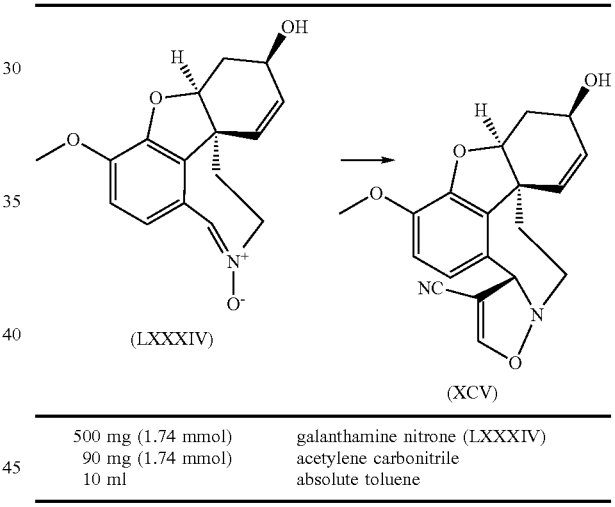

| 500 mg (1.74 mmol) | galanthamine nitrone (LXXXIV) |
| 90 mg (1.74 mmol)  | acetylene carbonitrile |
| 10 ml              | absolute toluene |

The reagents were stirred for 7 days under argon atmosphere at room temperature, whereby the solution was colored yellow, then the solvent was drawn off. The residue was crystallized from methanol, suctioned off, and washed with methanol. The filtrate was concentrated by evaporation and a second product fraction was obtained from the residue by column chromatography ($CHCl_3$:MeOH=9:1).

Yield: 570 mg (1.68 mmol=97% of theory) of colorless crystals $C_{19}H_{18}N_2O_4$ [338.37] TLC: $R_f$=0.60 ($CHCl_3$:MeOH=9:1) Melting point: 137–139° C.

|       | % C   | % H  | % N  |
|-------|-------|------|------|
| Cld.: | 67.45 | 5.36 | 8.28 |
| Fnd.: | 67.17 | 5.41 | 8.19 |

$^1$H-NMR (200 MHz, $CDCl_3$) δ 7.09 (d, J=8.6 Hz, 1H), 6.76 (d, J=8.6 Hz, 1H), 5.98 (s, 2H), 5.54 (s, 1H), 4.52 (bs, 1H), 4.11 (bs, 1H), 3.83 (s, 3H), 3.75–3.59 (m, 1H), 3.42–3.25 (m, 1H), 2.64 (dd, J=15.9, 3.2 Hz, 1H), 2.44 (d, J=11.5 Hz, 1H), 2.11–1.94 (m, 2H), 1.71–1.52 (m, 1H); $^{13}$C-NMR (50 MHz, CDCl$_3$) δ 156.5 (d), 147.1 (s), 145.5 (s), 132.7 (s), 129.6 (d), 127.9 (d), 123.8 (s), 120.8 (d), 114.0 (s), 111.7 (d), 88.9 (d), 88.6 (s), 68.4 (d), 61.3 (d), 55.9 (q), 52.5 (t), 47.2 (s), 29.3 (t), 28.3 (t)

EXAMPLE 125

Step 1

1-Bromo-5-methoxy-2-(2-methoxyethen-1-yl)-4-(1-methylethoxy)benzene

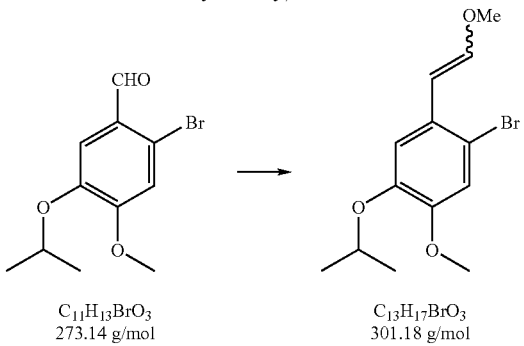

C$_{11}$H$_{13}$BrO$_3$
273.14 g/mol

C$_{13}$H$_{17}$BrO$_3$
301.18 g/mol

While being cooled with ice, potassium-tert-butylate (20.5 g, 183 mmol) is added to a suspension of (methoxymethyl)-triphenylphosphonium chloride (50.0 g, 152 mmol) in absolute THF (330 ml). After 15 minutes, 2-bromo-4-methoxy-5-(1-methylethoxy)benzaldehyde (33.1 g, 121 mmol) is added in portions.

After 15 minutes, the residue that is obtained after the solvent is removed in a rotary evaporator is dispersed between water (300 ml) and ether (300 ml). The organic phase is dried (sodium sulfate), filtered, and the residue that is obtained after concentration by evaporation (37.3 g) is purified by means of MPLC (petroleum ether:ethyl acetate=2:1, flow 70 ml/min). In this way, the product is obtained in the form of colorless crystals (32.5 g, 85%).

Melting point: 43–45° C. TLC: Petroleum ether:ethyl acetate=2:1 R$_f$=0.75 $^1$H: NMR (CDCl$_3$) δ 7.00 (s, 1H); 6.90 (s, 1H), 6.83 (d, J=12.7 Hz, 1H$_{trans}$), 6.13 (d, J=7.6 Hz, 1H$_{cis}$), 5.98 (d, J=12.7 Hz, 1H$_{trans}$), 5.50 (d, J=7.6 Hz, 1H$_{cis}$), 4.49 (septet, J=6.4 Hz, 1H), 3.81 (s, 3H), 3.74 (s, 3H$_{trans}$), 3.70 (s, 3H$_{cis}$), 1.35 (d, J=6.4 Hz, 6H); $^{13}$C-NMR (CDCl$_3$) δ 149.2 and 149.6 (s), 147.6 and 148.9 (s), 146.0 and 146.7 (d), 127.5 and 128.4 (s), 115.7 and 117.2 (d), 113.6 and 116.2 (d), 113.3 and 113.7 (s), 103.8 and 104.2 (d), 71.5 and 71.9 (d), 56.1 and 56.4 (q), 56.0 and 60.6 (q), 21.9 and 22.0 (q)

Step 2

2-Bromo-4-methoxy-5-(1-methylethoxy)benzene acetaldehyde

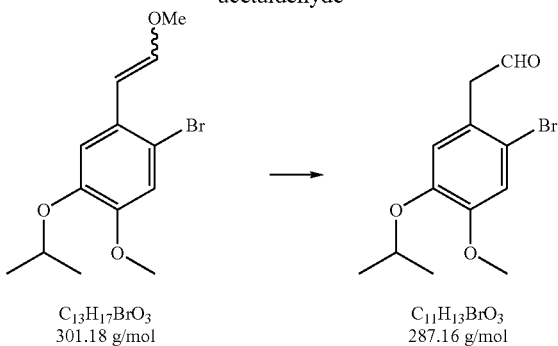

C$_{13}$H$_{17}$BrO$_3$
301.18 g/mol

C$_{11}$H$_{13}$BrO$_3$
287.16 g/mol

1-Bromo-5-methoxy-2-(2-methoxyethen-1-yl)-4-(1-methylethoxy)benzene (20.0 g, 66.4 mmol) is stirred in tetrahydrofuran (250 ml)/2N Hcl (10 ml) for three hours at boiling temperature.

After the solvent is drawn off in a rotary evaporator, the residue is dispersed between water (200 ml) and ether (200 ml), the aqueous phase is extracted with ether (3×100 ml), the combined organic phases are washed with water (4×150 ml), saturated sodium bicarbonate solution (2×200 ml) and saturated common salt solution (1×200 ml), dried (sodium sulfate/activated carbon) and filtered. After concentration by evaporation, the product is obtained as a yellow oil (18.7 g, 98%).

TLC: Petroleum ether:ethyl acetate=4:1, Rf=0.77 $^1$H: NMR (CDCl$_3$) δ 9.71 (t, J=1.71 Hz, 1H), 7.06 (s, 1H), 6.80 (s, 1H), 4.49 (septet, J=6.4 Hz, 1H), 3.90 (s, 3H), 3.73 (d, J=1.71 Hz, 2H), 1.35 (d, J=6.4 Hz, 6H); $^{13}$C NMR (CDCl$_3$) δ 191.8 (d), 146.6 (s), 145.1 (s), 125.4 (s), 118.1 (s), 115.8 (d), 113.7 (d), 71.5 (d), 56.4 (q), 49.8 (t), 21.8 (q)

Step 3

2-Bromo-4-methoxy-5-(1-methylethoxy)benzene ethanol

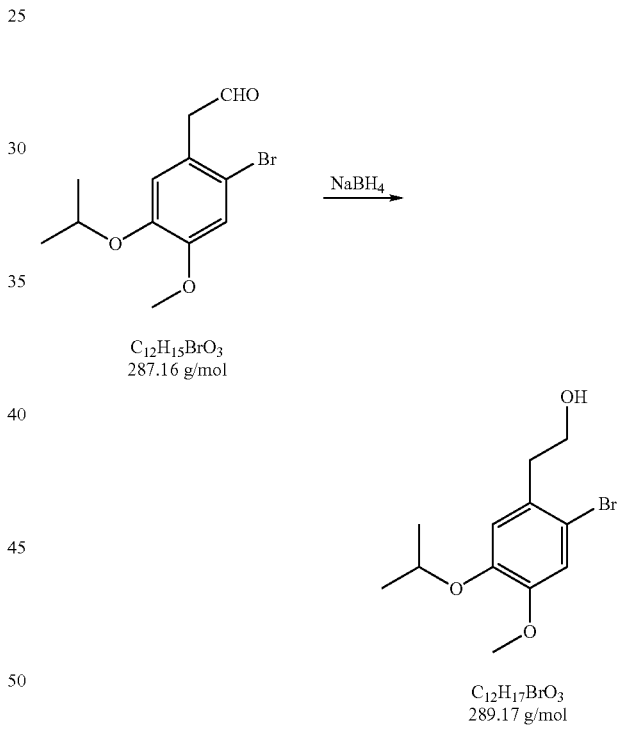

C$_{12}$H$_{15}$BrO$_3$
287.16 g/mol

C$_{12}$H$_{17}$BrO$_3$
289.17 g/mol

2-Bromo-5-(1-methylethoxy)-4-methoxybenzene acetaldehyde (2.60 g, 9.05 mmol) is added at 15° C. within 30 minutes to a suspension of sodium borohydride (0.341 g, 9.05 mmol) in absolute ethanol (40 ml), and it is stirred for two hours at this temperature.

The ethanol is removed in a rotary evaporator, and the residue is dispersed between saturated sodium bicarbonate solution (200 ml) and ether (200 ml). The aqueous phase is extracted with ether (3×50 ml). The combined organic phases are washed with water (3×200 ml) and saturated common salt solution (1×200 ml), dried (sodium sulfate/activated carbon), dried and filtered. After concentration by evaporation, the product is obtained in the form of colorless crystals (2.60 g, 99%).

TLC: PE:EE=9:1, 0.25 ¹H NMR (CDCl₃) δ 6.98 (s, 1H), 6.80 (s, 1H), 4.47 (septet, J=6.3 Hz, 1H), 3.82 (t, J=7.0 Hz, 2H), 3.80 (s, 3H), 2.90 (t, J=7.0 Hz, 2H), 1.32 (d, J=7.3 Hz, 6H); ¹³C NMR (CDCl₃) δ 149.7 (s), 146.4 (s), 129.6 (s), 118.5 (d), 116.3 (d), 114.8 (s), 71.8 (d), 62.2 (t), 56.1 (q), 38.8 (t), 21.9 (q) MT-163 JOS 1682 C₁₂H₁₇Br₃ Cld.: C, 49.84; H, 5.93 Fnd.: C, 49.69; H, 5.79.

Step 4

1-Bromo-2-(2-iodoethyl)-5-methoxy-4-(1-methylethoxy)benzene

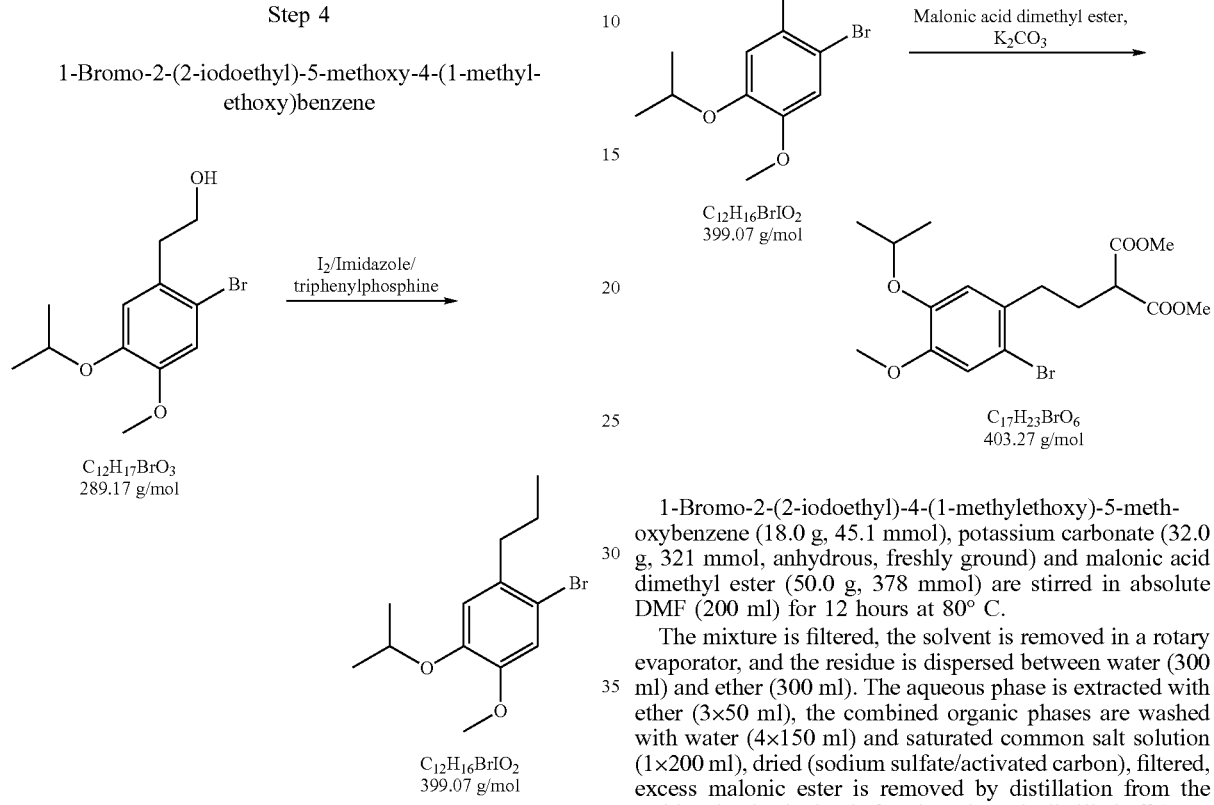

Triphenylphosphine (24.7 g, 94.0 mmol), imidazole (12.8 g, 188.0 mmol) and iodine (23.06 g 90.9 mmol) are stirred in absolute CH₂Cl₂ (150 ml) for one hour at 15° C.

2-Bromo-5-(1-methylethoxy)-4-methoxybenzene ethanol (18.0 g, 62.2 mmol) in absolute CH₂Cl₂ (100 ml) is added in drops at this temperature within 10 minutes, and the mixture is stirred for two hours at room temperature.

The mixture is filtered, and the filtrate is washed with water (1×200 ml). The aqueous phase is extracted with CH₂Cl₂ (2×50 ml), and the combined organic phases are washed with sodium thiosulfate solution (1×200 ml), water (1×200 ml), copper sulfate solution (1×200 ml), water (1×200 ml) and saturated common salt solution (1×200 ml), dried (sodium sulfate/activated carbon), filtered, and the solvent is removed is in a rotary evaporator.

After purification by column chromatography (1000 g of silica gel/petroleum ether:ethyl acetate=96:4), the product is obtained in the form of colorless needles (19.0 g, 77%).

¹H NMR (CDCl₃) δ 7.00 (s, 1H), 6.77 (s, 1H), 4.49 (septet, J=6.3 Hz, 1H), 3.81 (s, 3H), 3.39–3.24 (m, 2H), 3.24–3.09 (m, 2H), 1.36 (d, J=7.3 Hz, 6H); ¹³C NMR (CDCl₃) δ 150.0 (s), 146.5 (s), 131.7 (s), 118.0 (d), 116.3 (d), 114.3 (s), 71.8 (d), 56.1 (q), 40.0 (t), 22.0 (q), 4.2 (t) MT 164 JOS 1704 C₁₂H₁₆BrIO₂ Cld.: C, 36.12; H, 4.04 Fnd.: C, 36.38; H, 3.91

Step 5

2-[2-[2-Bromo-4-methoxy-5-(1-methylethoxy)phenyl]ethyl]-propanedioic acid dimethyl ester 1-Bromo-2-(2-iodoethyl)-4-(1-methylethoxy)-5-methoxybenzene (18.0 g, 45.1 mmol), potassium carbonate (32.0 g, 321 mmol, anhydrous, freshly ground) and malonic acid dimethyl ester (50.0 g, 378 mmol) are stirred in absolute DMF (200 ml) for 12 hours at 80° C.

The mixture is filtered, the solvent is removed in a rotary evaporator, and the residue is dispersed between water (300 ml) and ether (300 ml). The aqueous phase is extracted with ether (3×50 ml), the combined organic phases are washed with water (4×150 ml) and saturated common salt solution (1×200 ml), dried (sodium sulfate/activated carbon), filtered, excess malonic ester is removed by distillation from the residue that is obtained after the solvent is distilled off (160° C./15 mbar), and it is purified by means of bulb tube distillation (170° C./0.06 mbar), by which the product is obtained as a colorless oil (18.9 g, 72%).

¹H: NMR (CDCl₃) δ 6.99 (s, 1H), 6.73 (s, 1H), 4.49 (septet, J=6.3 Hz, 1H), 3.81 (s, 3H), 3.76 (s, 6H), 3.39 (t, J=7.9 Hz, 1H), 2.68 (t, J=7.9 Hz, 2H), 2.18 (q, J=7.9 Hz, 2H), 1.34 d, J=6.3 Hz, 6H); ¹³C NMR (CDCl₃) δ 169.6 (s), 149.7 (s), 146.6 (s), 131.7 (s), 117.8 (d), 116.3 (d), 114.6 (s), 71.8 (d), 56.2 (q) 52.5 (q), 50.9 (d), 33.1 (t), 29.0 (t), 22.0 (q) MT-165 JOS 1771 C₁₇H₂₃BrO₆ Cld.: C, 50.63; H, 5.75 Fnd.: C, 50.87; H, 5.62

Step 6

2-[2-[2-Bromo-4-methoxy-5-(1-methylethoxy)phenyl]ethyl]-2-[4-(1-methylethoxy)phenylmethyl]propanedioic acid methyl ester -continued

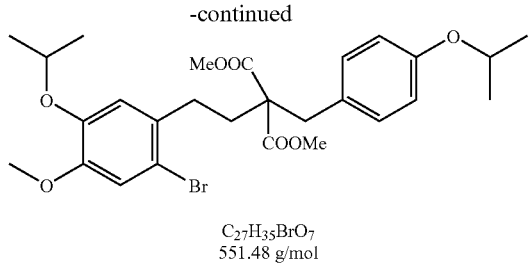

C₂₇H₃₅BrO₇
551.48 g/mol

1-Bromo-2-(2-iodoethyl)-4-(1-methylethoxy)-5-methoxybenzene (18.0 g, 45.1 mmol), potassium carbonate (32.0 g, 321 mmol, anhydrous, freshly ground) and (50.0 g, 378.4 mmol) of malonic acid dimethyl ester are stirred (200 ml) in anhydrous DMF for 12 hours at 80° C.

The mixture is filtered, the solvent is drawn off, and the residue is dispersed between 300 ml of water and 300 ml of ether. The aqueous phase is extracted three times with 50 ml each, the combined organic phases are washed four times with 150 ml of water each and once with 200 ml of saturated common salt solution, dried on sodium sulfate/activated carbon, filtered, and the solvent is drawn off. Excess malonic acid dimethyl ester is separated by distillation (160° C./15 mbar), and the residue is purified by means of bulb tube distillation (170° C. (0.06 mbar), by which the product is obtained in the form of a colorless oil (18.9 g, 72%).

MT 166 JOS 1694 C₂₇H₃₅BrO₇ Cld.: C, 58.81; H, 6.40 Fnd.: C, 59.03; H, 6.24.

Step 7

4-[2-Bromo-4-methoxy-5-(1-methylethoxy)]-α-[4-(1-methylethoxy)phenylmethyl]benzenebutanoic acid

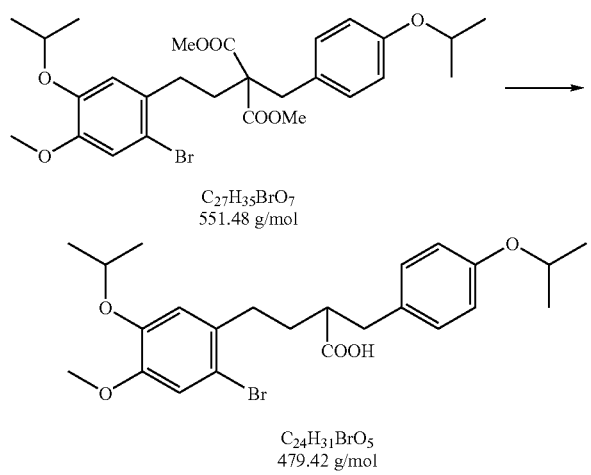

2-[2-[2-Bromo-5-(1-methylethoxy)-4-methoxyphenyl]ethyl]-2-[4-(1-methylethoxy)phenylmethyl]propanedioic acid dimethyl ester (18.1 g, 32.8 mmol) and potassium hydroxide (17.5 g, 312 mmol) are stirred in a mixture that consists of ethanol (100 ml) and water (20 ml) for 12 hours at boiling temperature.

The reaction mixture is acidified with concentrated hydrochloric acid to a pH of 1 and kept under reflux for one hour.

The residue that remains after the solvent is removed is dispersed between water (250 ml) and ether (250 ml). The aqueous phase is extracted with ether (2×100 ml), the combined, organic phases are washed neutral with water, washed with saturated common salt solution (150 ml) and dried (sodium sulfate/activated carbon). The residue that remains after the solvent is removed is decarboxylated in a bulb tube for 30 minutes at 160° C. under high vacuum and then distilled at 210° C./0.008 mbar. In this way, the product is obtained in the form of colorless crystals (13.3 g, 84%).

¹H: NMR (CDCl₃) δ 7.04 (d, J=9.5 Hz, 2H), 6.99 (s, 1H), 6.80 (d, J=9.5 Hz, 2H), 6.77 (s, 1H), 4.60–4.39 (m, 2H), 3.79 (s, 3H), 3.09–2.58 (m, 5H), 2.09–1.72 (m, 2H), 1.43–1.29 (m, 1H); ¹³C NMR (CDCl₃): 181.0 (s), 156.2 (s), 149.3 (s), 146.3 (s), 132.3 (s), 130.7 (s), 129.6 (d), 117.6 (d), 116.1 (d), 115.7 (d), 114.3 (s), 71.6 (d), 69.6 (d), 55.9 (q), 46.7 (d), 37.0 (t), 33.1 (t), 317 (t), 21.8 (q).

Step 8

4-[2-Bromo-4-methoxy-5-(1-methylethoxy)]-α-[4-(1-methylethoxy)phenylmethyl]benzenebutanoic acid amide

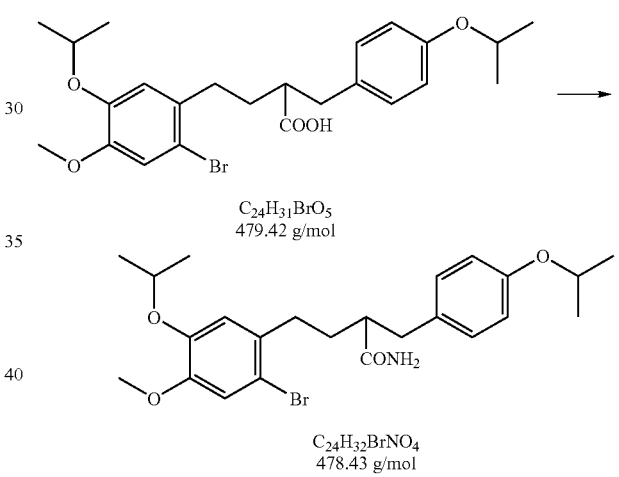

Oxalic acid dichloride (15 ml) is added in drops at 0° C. within 15 minutes to 4-[2-bromo-4-methoxy-5-(1-methylethoxy)]-α-[[4-(1-methylethoxy)-phenylmethyl]benzenebutanoic acid (24.0 g, 50.1 mmol) in absolute CH₂Cl₂ (200 ml), and the mixture is stirred for two hours at this temperature.

The solvent is removed in a rotary evaporator, the residue is taken up in absolute THF (100 ml), and ammonia is introduced at 0° C. for two hours. The mixture is stirred for one hour at 0° C. and poured onto water (1000 ml).

The precipitated crystals are filtered off and digested with water (4×500 ml). In this way, the product is obtained in the form of colorless crystals (19.9 g, 83%).

¹H NMR (CDCl₃) δ 7.04 (d, J=9.5 Hz, 2H), 6.96 (s, 1H), 6.72 (d, J=9.5 Hz, 2H), 6.70 (s, 1H), 6.00 (b, 1H), 5.55 (b, 1H), 4.60–4.30 (m, 2H), 3.77 (s, 3H), 2.96–2.52 (m, 4H), 2.51–2.28 (m, 1H), 2.03–1.60 (m, 2H), 1.36–1.20 (m, 12H); ¹³C NMR (CDCl₃): 1774, (s), 156.2 (s), 149.2 (s), 146.4 (s), 132.7 (s), 131.1 (d), 129.7 (d), 117.5 (d), 116.1 (d), 115.7 (d), 114.4 (d), 71.6 (d), 69.6 (d), 56.0 (q), 48.6 (d), 38.0 (t), 33.3 (t), 32.5 (t), 21.9 (q). MT-168 JOS 1770 C₂₄H₃₂BrNO₄ Cld.: C, 60.25; H, 6.74; N, 2.93 Fnd.: C, 60.15; H, 6.55; N, 2.77.

Step 9

4-(2-Bromo-5-hydroxy-4-methoxy)-α-(4-hydroxyphenylmethyl)-benzenebutanoic acid amide

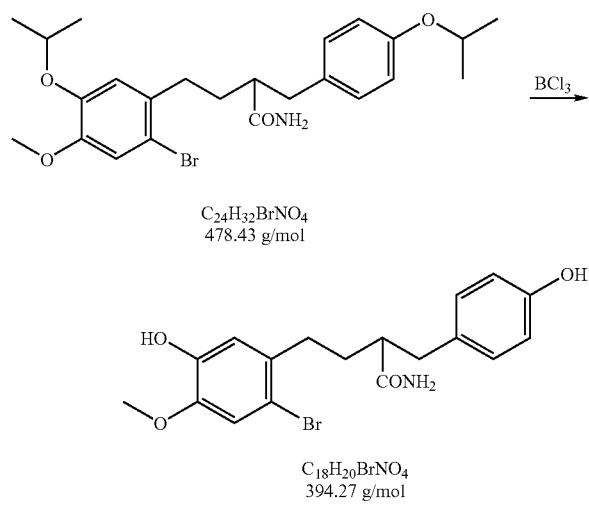

Boron trichloride (45 ml, 1.6 N in CH$_2$Cl$_2$) is added in drops at −78° C. to 4-[2-Bromo-4-methoxy-5-(1-methylethoxy)]-α-[4-(1-methylethoxy)-phenylmethyl]benzenebutanoic acid amide (10.0 g, 20.9 mmol) in absolute CH$_2$Cl$_2$ (150 ml), and it is stirred for one hour at this temperature. Then, the mixture is heated to room temperature and stirred for two hours.

It is mixed with water (400 ml), and the organic solvent is distilled off in a rotary evaporator, whereby the crude product precipitates as crystals, which is filtered off and is digested with water (6×200 ml) and diisopropyl ether (2×40 ml). In this case, the product is obtained in the form of colorless crystals (7.11 g, 86%).

MT 171 JOS 1714 C$_{18}$H$_{20}$BrNO$_4$·0.25 H$_2$O Cld.: C, 54.22; H, 5.18; N, 3.51 Fnd.: C, 54.05; H, 4.95; N, 3.54.

Step 10

1-Bromo-4a,5,9,10,11,12-hexahydro-3-methoxy-6-oxa-6H-benzo[a]cyclohepta[h]benzofuran-10-carboxylic acid amide (SPH-1478)

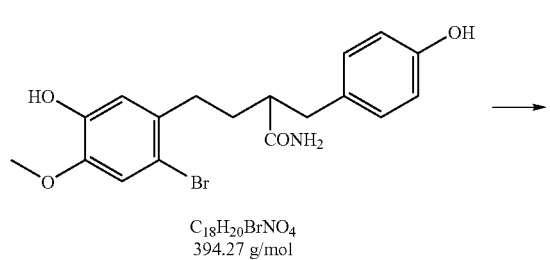

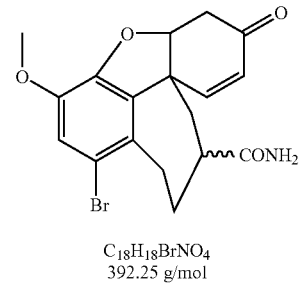

α-[[2-Bromo-5-hydroxy-4-methoxyphenyl]methyl]-4-hydroxybenzenebutanoic acid amide (3.00 g, 7.61 mmol) is suspended in chloroform (300 ml) and mixed with a solution of potassium hexacyanoferrate (III) (13.2 g, 40.0 mmol) in potassium carbonate solution (75 ml, ten percent).

The mixture is stirred vigorously at room temperature for 40 minutes and filtered on Hyflo. The aqueous phase is extracted with chloroform (2×50 ml), the combined organic phases are washed with water (2×200 ml) and saturated common salt solution (1×150 ml), dried (sodium sulfate/silica gel), and the crude product that is obtained after the solvent is concentrated by evaporation is purified via column chromatography (50 g of silica gel, ethyl acetate). In this way, the product is obtained in the form of colorless crystals (179 mg, 6%).

TLC: ethyl acetate, R$_f$=0.6 $^1$H NMR (CDCl$_3$) δ 6.95 (s, 1H), 6.71 (dd, J=12.1 Hz, J=2.0 Hz, 1H), 6.02 (d, J=12.1 Hz, 1H), 5.70 (b, 2H), 4.82 (s, 1H), 3.81 (s, 3H), 3.58 (dd, J=16.5 Hz, J=6.0 Hz, 1H), 3.13 (dd, J=6.0 Hz, J=16.5 Hz, 1H), 2.82–2.57 (m, 3H), 2.48–2.15 (m, 2H), 2.12–1.62 (m, 2H); $^{13}$C NMR (DMSO-d$_6$) δ 196.7 (s), 178.2 (s), 147.3 (d), 145.6 (s), 143.9 (s), 132.5 (s), 131.4 (s), 127.5 (d), 117.0 (s), 114.8 (d), 88.3 (d), 53.5 (q), 49.7 (s), 43.7 (d), 40.9 (t), 39.7 (t), 38.0 (t), 32.1 (t); $^{13}$C NMR (CDCl$_3$) δ 193.8 (s), 176.7 (s), 146.7 (d), 143.5 (s), 143.2 (s), 131.0 (s), 129.9 (s), 127.7 (d), 116.5 (s), 115.1 (d), 87.6 (d), 56.1 (q), 49.1 (s), 44.2 (d), 39.4 (t), 37.0 (t), 32.0 (t), 31.7 (t)

EXAMPLE 126

1-Bromo-4a,5,9,10,11,12-hexahydro-3-methoxy-6-hydroxy-6H-benzo[a]cyclohepta[hi]benzofuran-10-carboxylic acid amide (SPH-1479)

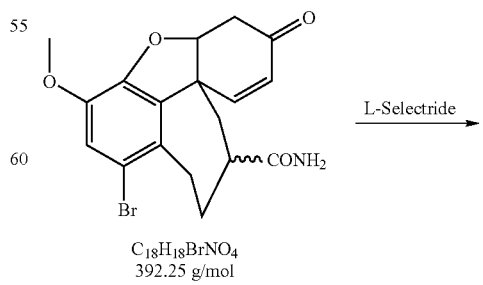

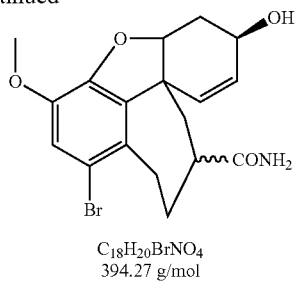

$C_{18}H_{20}BrNO_4$
394.27 g/mol

L-Selectride$^R$ (2.0 ml, 2.0 mmol, 1 M in THF) is added at 0° C. within 15 minutes to a suspension of 1-bromo-4a,5,9,10,11,12-hexahydro-3-methoxy-6-oxa-6H-benzo[a]cyclohepta[hi]benzofuran-1-carboxylic acid amide (160 mg, 0.41 mmol) in absolute THF (5 ml), and the mixture is stirred for 12 hours at room temperature. It is hydrolyzed with water (2 ml) and dispersed between water (10 ml) and ethyl acetate (10 ml), the aqueous phase is extracted with ethyl acetate (3×5 ml), the combined organic phases are washed with 1N hydrochloric acid (3×10 ml), water (2×10 ml), saturated sodium bicarbonate solution (1×10 ml) and saturated common salt solution (1×10 ml), dried (sodium sulfate/activated carbon), filtered, and the crude product that is obtained after the solvent is distilled off is purified by means of column chromatography (10 g of silica gel, ethyl acetate). In this way, the product is obtained in the form of colorless crystals (137 mg, 85%).

MT-194 JOS 1712 $C_{18}H_{20}BrNO_4$ Cld.: C, 54.84; H, 5.11; N, 3.55 Fnd.: C, 54.55; H, 5.22; N, 3.34 TLC: ethyl acetate, $R_f$-0.5 $^1$H NMR (MeOH-$d_4$) δ 6.99 (s, 1H), 6.03 (d, J=16.5 Hz, 1H), 5.94 (dd, J=16.5 Hz, J=5.9 Hz, 1H), 4.52 (s, 1H), 4.16 (s, 1H), 3.76 (s, 3H), 3.49 (dd, J=19.8 Hz, J=5.9 Hz, 1H), 2.90 (t, J=17.5 Hz, 1H), 2.77 (t, J=17.5 Hz, 1H), 2.46 (d, J=17.6 Hz, 1H), 2.29–2.10 (m, 2H), 1.98–1.53 (m, 3H); $^{13}$C NMR (MeOH-$d_4$) δ 181.6 (s), 148.1 (s), 145.4 (s), 135.4 (s), 132.3 (s), 129.5 (d), 128.7 (d), 117.8 (d), 115.4 (s), 89.0 (d), 70.3 (d), 62.6 (d), 57.2 (q), 45.7 (s), 42.5 (t), 33.5 (t), 33.1 (l), 31.9 (t)

Diagram for Examples 125 and 126

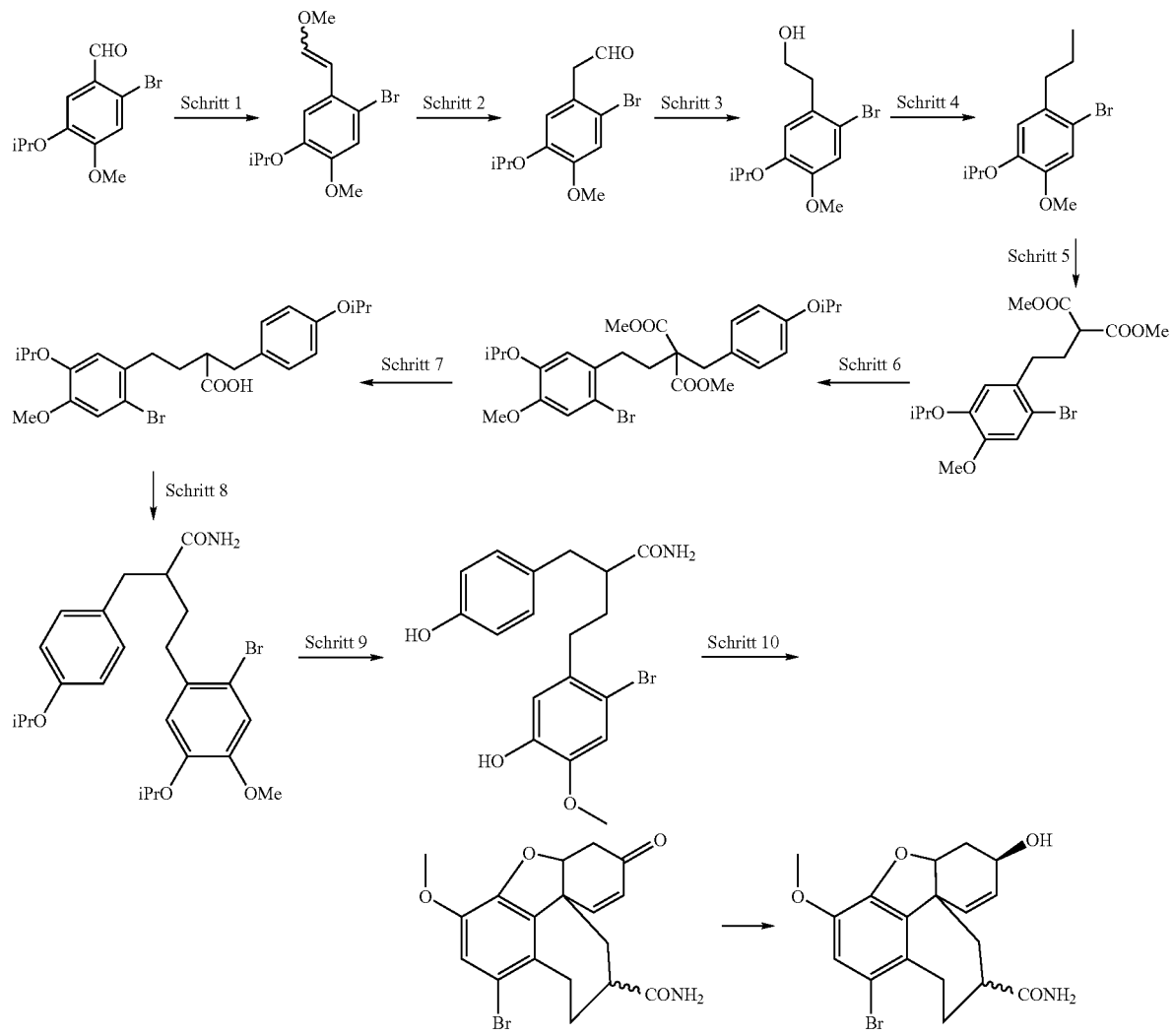

Biespiel 125  Biespiel 126

[Key:]
Schritt = Step
Biespiel = Example

EXAMPLE 127

Step 1

5-(6-Acetyloxy-1-oxohexyl)-5,6-dihydro-4H-pyrrolo[3,2,1-ij]quinolin-2(1H)-one

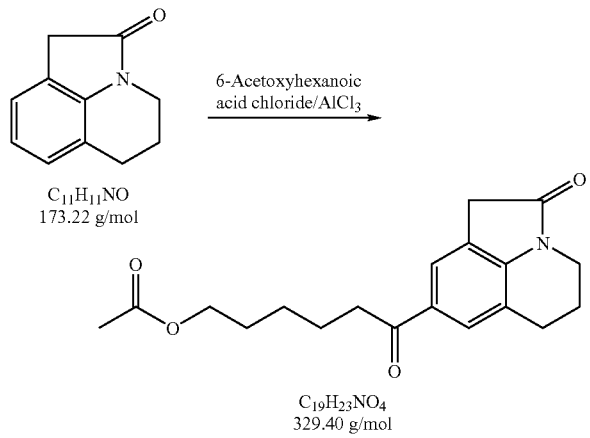

6-Acetyloxyhexanoic acid chloride (16.7 g, 86.6 mmol) in absolute $CH_2Cl_2$ (50 ml) is added in drops at 0° C. within 10 minutes to a suspension of anhydrous aluminum chloride (61.5 g, 461.6 mmol) in absolute $CH_2Cl_2$ (500 ml), and it is stirred for 15 minutes at this temperature. 5,6-Dihydro-4H-pyrrolo[3,2,1-ij]quinolin-2(1H)-one (10.0 g, 57.7 mmol) in absolute $CH_2Cl_2$ (100 ml) is added in drops within 15 minutes at 0° C., then it is heated to boiling temperature and stirred for 30 minutes. It is cooled to 0° C., hydrolyzed with ice and dispersed between water (300 ml) and $CH_2Cl_2$ (100 ml). The aqueous phase is extracted with $CH_2Cl_2$ (2×100 ml), the combined organic phases are washed with 2N hydrochloric acid (2×250 ml), water (2×250 ml), semi-concentrated aqueous $Na_2CO_3$ solution (2×250 ml), concentrated aqueous $Na_2CO_3$ solution (2×250 ml) and concentrated common salt solution (1×250 ml), dried (sodium sulfate/activated carbon), and the solvent is removed in a rotary evaporator.

After recrystallization from methanol (150 ml), the product is obtained in the form of light yellow crystals (14.3 g, 75.5%).

MT-304 JOS 1675 $C_{19}H_{23}N_4$ Cld.: C, 69.28; H, 7.04; N, 4.25 Fnd.: C, 69.27; H, 6.99; N, 4.25 $^1$H NMR (CDCl$_3$) δ 7.72 (s, 2H), 4.06 (t, J=6.5 Hz, 2H), 3.72 (t, J=5.7 Hz, 2H), 3.54 (s, 2H), 2.90 (t, J=7.0 Hz, 2H), 2.80 (t, J=6.0 Hz, 2H), 2.09–1.93 (m, 5H), 1.85–1.56 (m, 4H), 1.50–1.30 (m, 2H); $^{13}$C NMR (CDCl$_3$) δ 198.9 (s), 174.2 (s), 171.1 (s), 145.5 (s), 131.3 (s), 127.8 (d), 122.9 (s), 122.4 (d), 119.5 (s), 64.3 (t), 38.9 (t), 38.0 (t), 36.1 (t), 28.5 (t), 25.7 (t), 24.4 (t), 24.1 (t), 21.0 (q), 20.9 (t)

Step 2 5-(6-Hydroxy-1-oxohexyl)-5,6-dihydro-4H-pyrrolo[3,2,1-ij]quinolin-2(1H)-one

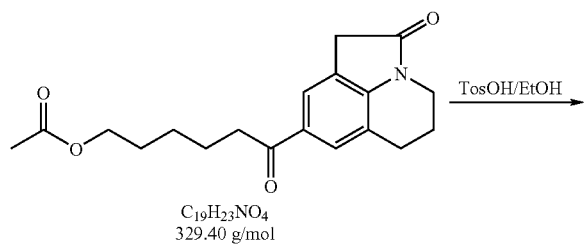

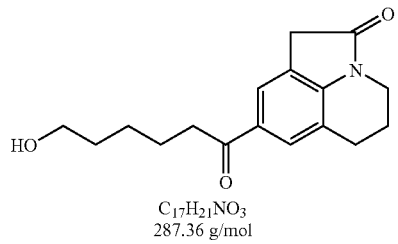

5-(6-Acetyloxy-1-oxohexyl)-5,6-dihydro-4H-pyrrolo[3,2,1-ij]quinolin-2(1H)-one (10.0 g, 30.6 mmol) is suspended in anhydrous ethanol (150 ml), mixed with catalyst amounts of 4-methylbenzenesulfonic acid monohydrate and stirred for five hours at boiling temperature. The solvent volume is concentrated by evaporation to one third, and the product is obtained in the form of light yellow needles (8.22 g, 93.5%) by crystallization at –20° C.

MT-305 JOS 1672 $C_{17}H_{21}NO_3$ Cld.: C, 71.06; H, 7.37; N, 4.87 Fnd.: C, 71.30; H, 7.37; N, 4.87 $^1$NMR (CDCl$_3$) δ 7.67 (s, 2H), 3.80–3.52 (m, 4H), 3.48 (s, 2H), 2.97–2.66 (m, 4H), 2.08–1.86 (Mn, 2H), 1.82–1.26 (m, 6H); $^{13}$C NMR (CDCl$_3$) δ 199.3 (s), 174.2 (s), 145.4 (s), 131.2 (s), 127.8 (d), 122.8 (s), 122.3 (d), 119.4 (s), 62.3 (t), 38.7 (t), 38.0 (t), 36.0 (t), 32.3 (t), 25.4 (t), 24.3 (t), 24.1 (t), 20.8 (t)

Step 3 5-(6-Iodo-1-oxohexyl)-5,6-dihydro-4H-pyrrolo[3,2,1-ij]quinolin-2(1H)-one

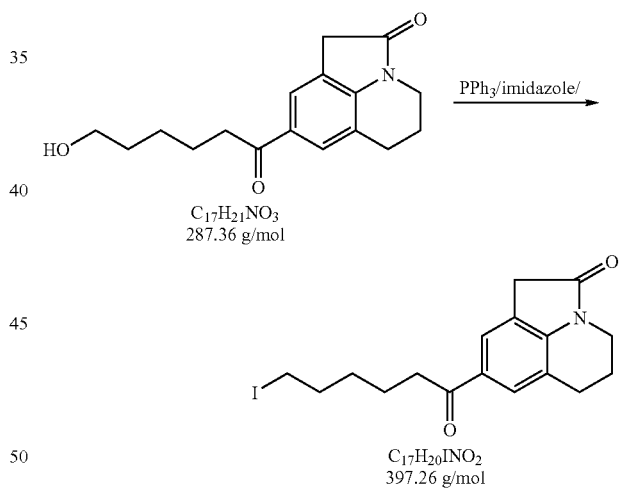

Triphenylphosphine (2.02 g, 7.74 mmol), iodine (3.08 g, 12.12 mmol) and imidazole (0.618 g, 9.08 mmol) are stirred in absolute $CH_2Cl_2$ (30 ml) for 30 minutes at 15° C.

5-(6-Hydroxy-1-oxohexyl)-5,6-dihydro-4H-pyrrolo[3,2,1-ij]quinolin-2(1H)-one (2.0 g, 6.96 mmol) in anhydrous $CH_2Cl_2$ (10 ml) is added in drops within 5 minutes at this temperature, then it is stirred for 40 minutes at room temperature.

It is mixed with semisaturated sodium sulfate solution (so ml), the phases are separated, the aqueous phase is extracted with $CH_2Cl_2$, the combined organic phases are washed with 2N hydrochloric acid (3×100 ml), water (2×100 ml), saturated sodium bicarbonate solution (2×100 ml) and saturated common salt solution (1×100 ml), dried (sodium sulfate/activated carbon), filtered, and the crude product that is obtained after the solvent is removed in a rotary evaporator is recrystallized from methanol (10 ml).

Variant A:

The residue is purified by column chromatography (100 g of silica gel, chloroform), by which the product is obtained in the form of light yellow crystals (2.44 g, 88.3%).

Variant B:

The residue is recrystallized one additional time from methanol (10 ml), by which the product is obtained in the form of light yellow crystals (2.28 g, 82.4%).

MT-308 JOS 1670 $C_{17}H_{20}INO_2$ Cld.: C, 51.40; H, 5.07; N, 5.53 Fnd.: C, 51.56; H, 4.97; N, 3.46 $^1$H NMR (CDCl$_3$) δ 7.70 (s, 2H), 3.72 (t, J=5.7 Hz, 2H), 3.52 (s, 2H), 3.18 (t, J=6.9 Hz, 2H), 2.91 (t, J=7.2 Hz, 2H), 2.80 (t, J=6.1 Hz, 2H), 2.12–1.61 (m, 6H), 1.57–1.36 (m, 2H); $^{13}$C NMR (CDCl$_3$) δ 198.7 (s), 174.1 (s), 145.5 (s), 131.2 (5), 127.8 (d), 122.9 (s), 122.3 (d), 119.4 (s), 38.8 (t), 37.9 (t), 36.0 (t), 33.2 (t), 30.1 (t), 24.0 (t), 23.3 (t), 20.9 (t), 6.6 (t)

Step 4 5-(6-Methylsulfonyloxy-1-oxohexyl)-5,6-dihydro-4H-pyrrolo[3,2,1-ij]quinolin-2(1H)-one

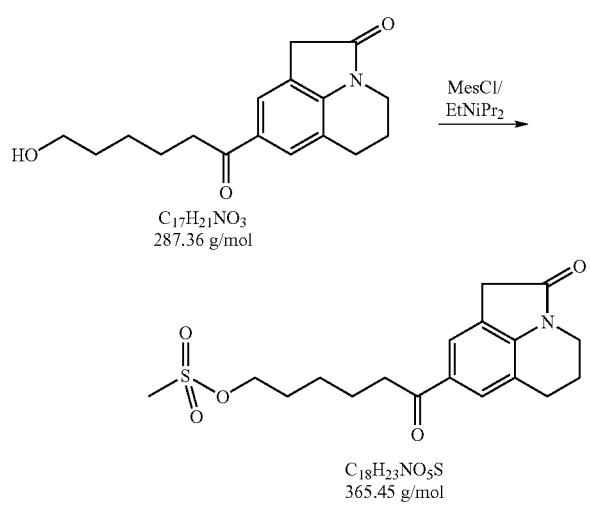

Methanesulfonic acid chloride (458 mg, 4.00 mmol) is added in drops within 5 minutes at 15° C. to 5-(6-hydroxy-1-oxohexyl)-5,6-dihydro-4H-pyrrolo[3,2,1-ij]quinolin-2 (1H)-one (1.0 g, 3.48 mmol) and N-ethyldiisopropylamine (560 mg, 4.35 mmol) in anhydrous CH$_2$Cl$_2$ (10 ml), and it is then stirred for two hours at room temperature.

It is mixed with water (20 ml), the phases are separated, the aqueous phase is extracted with CH$_2$Cl$_2$ (1×10 ml), the combined organic phases are washed with 2N hydrochloric acid (3×10 ml), water (2×10 ml), saturated sodium bicarbonate solution (2×10 ml) and saturated common salt solution (1×10 ml), dried (sodium sulfate/activated carbon), filtered, and the crude product that is obtained after the solvent is removed in a rotary evaporator is digested with diisopropyl ether (10 ml), by which the product is obtained in the form of light yellow crystals (1.17 g, 92.2%).

$^1$H NMR (CDCl$_3$) δ 7.70 (s, 2H), 4.22 (t, J=6.5 Hz, 2H), 3.71 (t, J=5.8 Hz, 2H), 3.52 (s, 2H), 2.99 (s, 3H), 2.92 (t, J=7.0 Hz, 2H), 2.80 (t, J=6.0 Hz, 2H), 2.17–1.92 (m, 5H), 1.90–1.64 (m, 4H), 1.60–1.37 (m, 2H); $^{13}$C NMR (CDCl$_3$) δ 198.7 (s), 174.2 (s), 145.6 (s), 131.2 (s), 127.8 (d), 123.0 (s), 122.4 (d), 119.5 (s), 69.8 (t), 38.8 (t), 37.8 (t), 37.3 (q), 36.1 (t), 28.9 (t), 25.1 (t), 24.3 (t), 23.7 (t), 20.9 (t)

Step 5

5-[6-[(4aS,6R,8aS)-4a,5,9,10,11,12-Hexahydro-6-hydroxy-3-methoxy-6H-benzofuro[3a,3,2-ef][2]benzazepine-11-yl]-1-oxohexyl]-5,6-dihydro-4H-pyrrolo [3,2,1-ij]quinolin-2-(1H)-one (SPH-1500)

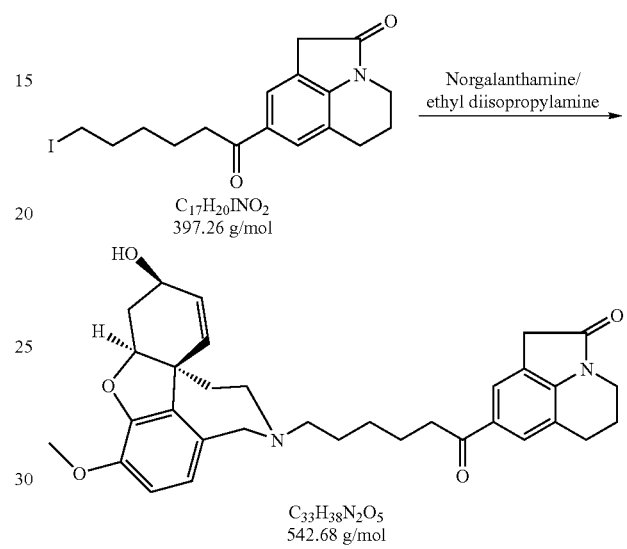

Norgalanthamine (1.13 g, 1.64 mmol), 5-(6-iodo-1-oxohexyl)-5,6-dihydro-4H-pyrrolo[3,2,1-ij]quinolin-2(1H)-one (1.50 g, 3.75 mmol) and N-ethyldiisopropylamine (1.46 g, 11.3 mmol) are stirred in absolute chloroform (20 ml) for 54 hours at boiling temperature.

The residue that is obtained after the solvent is removed in a rotary evaporator is purified by column chromatography (200 g of silica gel, chloroform:methanol:ammonia=96:3:1), by which the product is obtained as a light yellow foam (1.31 g, 64.3%).

$^1$H NMR (CDCl$_3$) δ 7.63 (s, 2H), 6.68–6.46 (m, 2H), 6.00 (d, J=10.3 Hz, 1H), 5.90 (dd, J=10.3 Hz, J=4.6 Hz, 1H), 4.51 (s, 1H), 4.19–3.96 (m, 2H), 3.75 (s, 1H), 3.73 (s, 3H), 3.70–3.58 (m, 2H), 3.44 (s, 2H), 3.35–2.98 (m, 2H), 2.96–6.67 (m, 4H), 2.66–2.29 (m, 4H), 2.15–1.84 (m, 4H), 1.82–1.11 (m, 6H); $^{13}$C NMR (CDCl$_3$) δ 199.1 (s), 174.1 (s), 145.6 (s), 145.3 (s), 143.8 (s), 133.0 (s), 131.2 (s), 129.3 (s), 127.7 (d), 127.4 (d), 126.8 (d), 122.8 (s), 122.3 (d), 121.7 (d), 119.4 (s), 111.0 (d), 88.5 (d), 61.8 (d), 57.6 (t), 55.7 (q), 51.4 (t), 51.2 (t), 48.2 (s), 38.7 (t), 38.0 (t), 36.0 (t), 32.8 (t), 29.8 (t), 27.1 (t), 26.9 (t), 24.3 (t), 24.2 (t), 20.8 (t)

Step 6

5-[6-[(4aS,6R,8aS)-4a,5,9,10,11,12-Hexahydro-6-hydroxy-3-methoxy-6H-benzofuro[3a,3,2-ef][2]benzazepine-11-yl]-1-oxohexyl]-5,6-dihydro-4H-pyrrolo [3,2,1-ij]quinolin-2(1H)-one Fumarate (SPH-1499)

The precipitation of the fumarate was carried out analogously to Example 4.

MT-311 JOS 1762 $C_{37}H_{42}N_2O_9$*$H_2O$ Cld.: C, 65.67; H, 6.55; N, 4.14 Fnd.: C, 65.93; H, 6.54; N, 4.03

EXAMPLE 128a

Step 1

2-[[4-(1-Methylethoxy)phenyl]methyl]propanedioic acid dimethyl ester

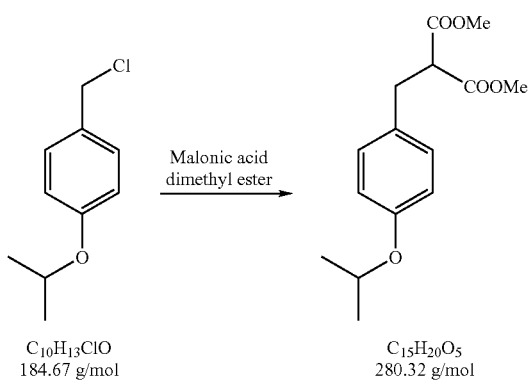

1-(Chloromethyl)-4-(1-methylethoxy)benzene (20.5 g, 111 mmol), malonic acid dimethyl ester (102.5 g, 776 mmol) and potassium carbonate (46.5 g, 332 mmol, anhydrous, freshly ground) are stirred in absolute DMF (250 ml) for 24 hours at 70° C.

The mixture is filtered, and the residue that is obtained after the filtrate is concentrated by evaporation in a rotary evaporator is dispersed between ether (250 ml) and water (250 ml). The organic phase is washed with water (3×200 ml) and saturated common salt solution (1×200 ml), dried (sodium sulfate/activated carbon), filtered, and the solvent is removed.

The excess malonic acid dimethyl ester is separated by vacuum distillation (85° C./15 mbar), and the crude product that remains in the residue is purified by bulb tube distillation (130° C./0.001 mbar). In this way, the product is obtained as a colorless oil (23.6 g, 78%).

MT-67 JOS 1774 $C_{15}H_{20}O_5$ Cld.: C, 64.27; H, 7.19 Fnd.: C, 64.28; H, 7.07

Step 2

4-(1-Methylethoxy)benzenepropanoic acid

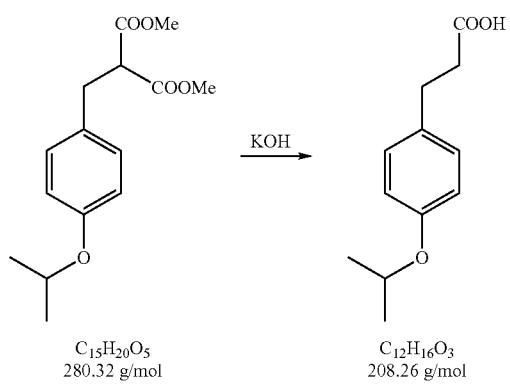

2-[[4-(1-Methylethoxy)phenyl]methyl]-propanedioic acid dimethyl ester (23.6 g, 84.2 mmol) is stirred into 2N potassium hydroxide solution (15 ml)/ethanol (25 ml) for 18 hours at boiling temperature.

The ethanol is distilled off in a rotary evaporator, the residue is brought to a pH of 1 with concentrated hydrochloric acid and extracted with ether (3×150 ml). The combined organic phases are washed with water (6×200 ml) and saturated common salt solution (200 ml), dried (sodium sulfate/activated carbon) and filtered. The residue that is obtained after concentration by evaporation in a rotary evaporator is decarboxylated in a bulb tube (140° C./0.08 mbar) and then distilled (155° C./0.08 mbar). In this way, the product is obtained in the form of colorless crystals (14.4 g, 82%).

$^1$H NMR (CDCl$_3$) δ 7.12 (d, J=9.5 Hz, 2H), 6.82 (d, J=9.5 Hz, 2H), 4.50 (septet, J=6.3 Hz, 1H), 2.89 (t, J=7.9 Hz, 2H), 2.63 (t, J=7.9 Hz, 2H), 1.32 (d, J=6.3 Hz, 6H); $^{13}$C NMR (CDCl$_3$) δ 178.8 (s), 156.4 (s), 132.1 (s), 129.2 (d), 116.0 (d), 69.9 (d), 35.8 (t), 29.7 (t), 22.1 (q)

Step 3

2-Bromo-4-methoxy-5-(1-methylethoxy)benzene acetonitrile

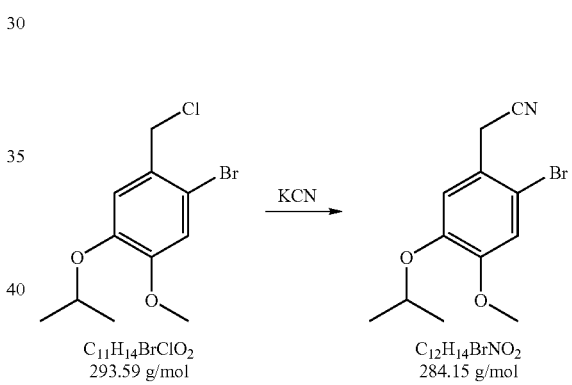

1-Bromo-2-(chloromethyl)-5-methoxy-4-(1-methylethoxy)benzene (7.00 g, 23.8 mmol) and potassium cyanide (1.70 g, 26.1 mmol, freshly ground) are stirred in absolute DMSO (70 ml) for 12 hours at room temperature.

The mixture is poured onto water (700 ml), the aqueous phase is extracted with ether (3×150 ml), the combined organic phases are washed with water (5×150 ml) and saturated common salt solution (1×200 ml), dried (sodium sulfate/activated carbon), filtered, and the residue that is obtained after concentration by evaporation is digested with diisopropyl ether (15 ml). In this way, the product is obtained in the form of colorless crystals (6.46 g, 95%).

MT-72 JOS 1695 $C_{12}H_{14}BrNO_2$ Cld.: C, 50.72; H, 4.97; N, 4.93 Fnd.: C, 50.73; H, 4.84; N, 4.89 $^1$H NMR (CDCl$_3$) δ 7.02 (s, 1H), 6.97 (s, 1H), 4.50 (septet, J=6.3 Hz, 1H), 3.81 (s, 3H), 3.72 (s, 2H), 1.36 (d, J=6.3 Hz, 6H); $^{13}$C NMR (CDCl$_3$) δ 150.8 (s), 147.1 (s), 12.1 5 (s), 117.3 (s), 116.7 (d), 116.3 (d), 113.9 (s), 72.1 (d), 56.2 (q), 24.2 (t), 21.9 (q)

Step 4

4-(1-Methylethoxy)benzenepropanoic acid-(1-methyl)ethyl ester

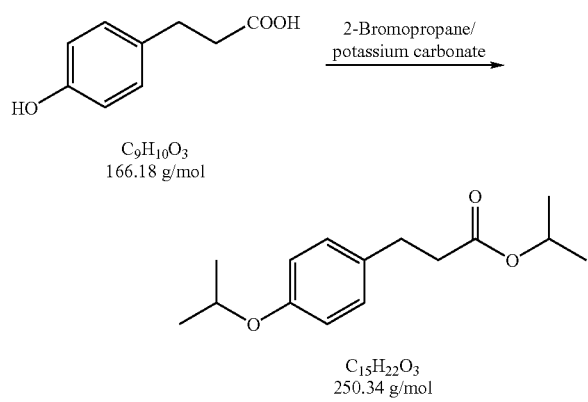

4-Hydroxybenzenepropanoic acid (50.0 g, 300 mmol), potassium carbonate (210 g, 1.5 mol, anhydrous, freshly ground) and 2-bromopropane (221 g, 1.8 mol) are stirred in absolute DMF (500 ml) for 24 hours at 60° C.

The solution is filtered, and the residue that is obtained after the concentration by evaporation in a rotary evaporator is dispersed between ether (500 ml) and 2N sodium hydroxide solution (500 ml). The organic phase is washed with 2N sodium hydroxide solution (2×200 ml), water (3×500 ml) and saturated common salt solution (200 ml), dried (sodium sulfate/activated carbon) and filtered. The residue that is obtained after the solvent is distilled off in a rotary evaporator is purified by bulb tube distillation (139–142° C./0.025 mbar), by which the product is obtained as a colorless oil (70.8 g, 94%).

MT-159 JOS 1768 $C_{15}H_{22}O_3$ Cld.: C, 71.97; H, 8.86 Fnd.: C, 71.84; H, 8.75 $^1$H NMR (CDCl$_3$) δ 7.10 (d, J=9.5 Hz, 2H), 6.81 (d, J=9.5 Hz, 2H), 4.99 (septet, J=6.3 Hz, 1H), 4.48 (septet, J=6.3 Hz, 1H), 2.87 (t, J=7.9 Hz, 2H), 2.54 (t, J=7.9 Hz, 2H), 1.20 (d, J=6.3 Hz, 6H), 1.31 (d, J=6.3 Hz, 6H); $^{13}$C NMR (CDCl$_3$) δ 172.4 (s), 156.2 (s), 132.4 (s), 129.1 (d), 115.8 (d), 69.7 (d), 67.4 (d), 36.4 (t), 30.1 (t), 22.0 (q) 21.7 (q)

Step 5

4-(1-Methylethoxy)benzenepropanol

1. From 4-(1-methylethoxy)benzenepropanoic acid

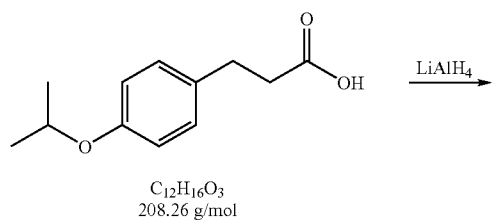

-continued

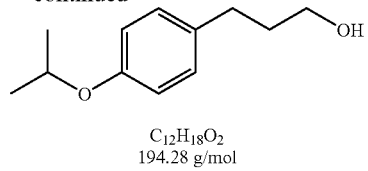

4-(1-Methylethoxy)benzenepropanoic acid (7.57 g, 36.3 mmol) in absolute THF (80 ml) is added in drops at 0° C. to a suspension of lithium aluminum hydride (4.17 g, 110 mmol) in absolute THF (80 ml) within 30 minutes, and it is stirred for 12 hours at room temperature. It is hydrolyzed with water (30 ml) and mixed with concentrated hydrochloric acid until the solution becomes clear, dispersed between water (30 ml) and ether (60 ml), the aqueous phase is extracted with ether (2×20 ml), the combined organic phases are washed with 2N hydrochloric acid (3×100 ml), water (1×100 ml), saturated sodium bicarbonate solution (2×100 ml) and saturated common salt solution (1×100 ml), dried (sodium sulfate/activated carbon) and filtered.

After the solvent is distilled off in a rotary evaporator, the product is obtained in the form of colorless crystals (6.84 g, 97%).

2. From 4-(1-Methylethoxy)benzenepropanoic acid-(1-methyl)ethyl ester

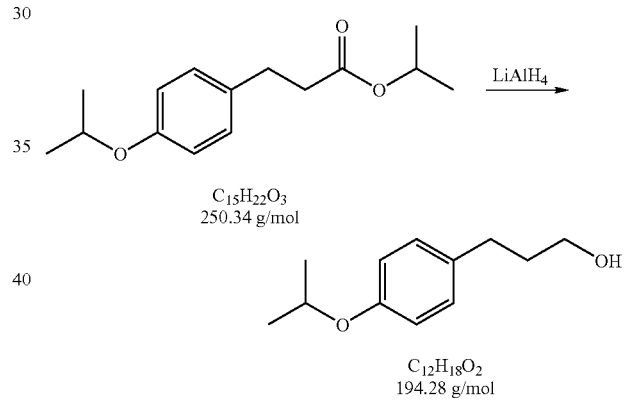

4-(1-Methylethoxy)benzenepropanoic acid-(1-methyl)ethyl ester (10.0 g, 39.9 mmol) in absolute THF (100 ml) is added in drops at 0° C. to a suspension of lithium aluminum hydride (3.04 g, 80 mmol) in absolute THF (100 ml) within 30 minutes, and it is stirred for 12 hours at room temperature.

It is hydrolyzed with water (30 ml) and mixed with concentrated hydrochloric acid, until the solution becomes clear, dispersed between water (30 ml) and ether (60 ml), the aqueous phase is extracted with ether (2×20 ml), the combined organic phases are washed with 2N hydrochloric acid (3×100 ml), water (1×100 ml), saturated sodium bicarbonate solution (2×100 ml) and saturated common salt solution (1×100 ml), dried (sodium sulfate/activated carbon) and filtered.

After the solvent is distilled off in a rotary evaporator, the product is obtained in the form of colorless crystals (7.04 g, 99%).

MT-89 JOS 1700 $C_{12}H_{18}O_2$ Cld.: C, 74.19; H, 9.34 Fnd.: C, 73.93; H, 9.07 $^1$H NMR (CDCl$_3$) δ 7.10 (d, J=9.5 Hz, 2H), 6.82 (d, J=9.5 Hz, 2H), 4.50 (septet, J=6.3 Hz, 1H), 3.68 (t, J=7.9 Hz, 2H), 2.66 (t, J=7.9 Hz, 2H), 2.0 (b, 1H), 1.93–1.78 (m, 2H), 1.32 (d, J=6.3 Hz, 6H); $^{13}$C NMR (CDCl$_3$) δ 155.9 (s), 133.7 (s), 129.2 (d), 115.9 (d), 69.9 (d), 62.0 (t), 34.3 (t), 31.1 (t), 22.0 (q)

Step 6

1-(3-Iodopropyl)-4-(1-methylethoxy)benzene

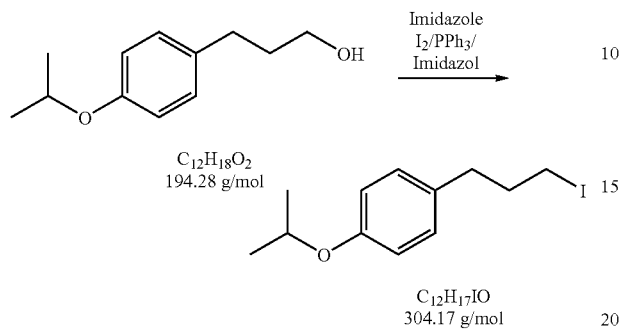

Triphenylphosphine (13.1 g, 49.9 mmol), iodine (19.9 g, 78.4 mmol) and imidazole (4.0 g, 58.8 mmol) are stirred in absolute CH$_2$Cl$_2$ (250 ml) for 20 minutes at room temperature. 4-(1-Methylethoxy)benzenepropanol (8.74 g, 45.0 mmol) in CH$_2$Cl$_2$ (100 ml) is added in drops at 15° C. and stirred for 12 hours at room temperature.

It is dispersed between water (300 ml) and CH$_2$Cl$_2$ (150 ml), the aqueous phase is extracted with CH$_2$Cl$_2$ (2×50 ml), the combined organic phases are washed with water (1×200 ml), semisaturated copper(II) sulfate solution (2×200 ml), water (1×200 ml), 10% sodium sulfite solution (1×200 ml), saturated common salt solution (1×200 ml), dried (sodium sulfate/activated carbon), filtered, and the residue that is obtained after concentration by evaporation in a rotary evaporator is taken up in diisopropyl ether (200 ml). The residue that is obtained from the filtrate after the solvent is drawn off in a rotary evaporator is filtered and purified by column chromatography (900 g of silica gel; petroleum ether:ethyl acetate=95:5). In this way, the product is obtained as a colorless oil (10.9 g, 79%).

MT-151 JOS 1755 C$_{12}$H$_{17}$IO Cld.: C, 47.39; H, 5.63 Fnd.: C, 47.37; H, 5.41 $^1$H NMR (CDCl$_3$) δ 7.11 (d, J=9.5 Hz, 2H), 6.82 (d, J=9.5 Hz, 2H), 4.53 (septet, J=6.3 Hz, 1H), 3.18 (t, J=7.9 Hz, 2H), 2.67 (t, J=7.9 Hz, 2H), 2.10 (quintet, J=7.9 Hz, 2H), 1.35 (d, J=6.3 Hz, 6H); $^{13}$C NMR (CDCl$_3$) δ 156.2 (s), 132.2 (s), 129.4 (d), 115.9 (d), 69.8 (d), 35.2 (t), 35.0 (t), 22.1 (q), 6.5 (t)

Step 7

α-[2-Bromo-4-methoxy-5-(1-methylethoxy)phenyl] 4-(1-methylethoxy)-benzenepentane nitrile

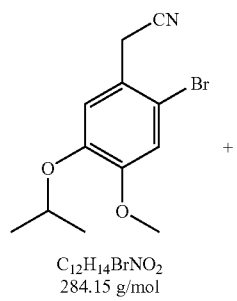

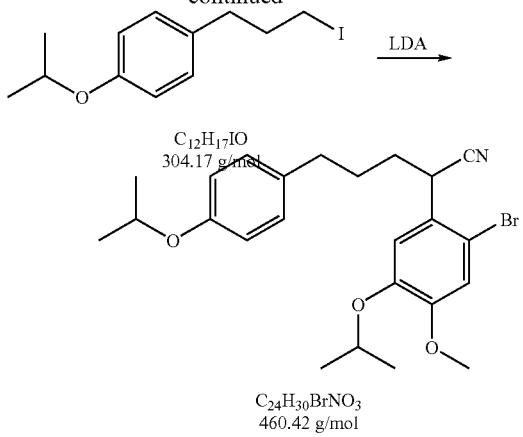

n-Butyllithium (12.7 ml, 27.5 mmol, 2.2 M in hexane) is added within 15 minutes at a temperature of −78° C. to a solution of diisopropylamine (3.55 g, 35.08 mmol) in absolute THF (50 ml), then the mixture is heated to −30° C. and stirred for 30 minutes at this temperature.

The solution is cooled to −78° C., mixed with 2-bromo-4-methoxy-5-(1-methylethoxy)-benzene acetonitrile (7.94 g, 27.9 mmol) in absolute THF (100 ml), stirred for 20 minutes at this temperature, heated to room temperature, and stirred for another hour. The mixture is cooled to −78° C., then 1-(3-iodopropyl)-4-(1-methylethoxy)benzene (8.50 g, 27.9 mmol) in absolute THF (50 ml) is added in drops with 15 minutes, and the mixture is stirred for 45 minutes.

It is mixed with saturated ammonium chloride solution (50 ml) and heated to room temperature. The residue that is obtained after concentration by evaporation is dispersed between 2N hydrochloric acid (200 ml) and ether (200 ml). The aqueous phase is extracted with ether (3×50 ml), the combined organic phases are washed with water (3×200 ml), saturated sodium bicarbonate solution (1×200 ml) and saturated common salt solution (1×200 ml), dried (sodium sulfate/activated carbon),filtered, and the residue that remains after the solvent is removed in a rotary evaporator is purified by column chromatography (1000 g of silica gel, petroleum ether:ethyl acetate=98:2). The product is thus obtained as a colorless oil (11.46 g, 71%).

MT-158 JOS 1699 C$_{24}$H$_{30}$BrNO$_3$ Cld.: C, 62.61; H, 6.57; N, 3.04 Fnd.: C, 62.32; H, 6.31; N, 2.97

Step 8

α-[2-Bromo-4-methoxy-5-(1-methylethoxy)phenyl]-4-(1-methylethoxy)-benzene pentanoic acid amide

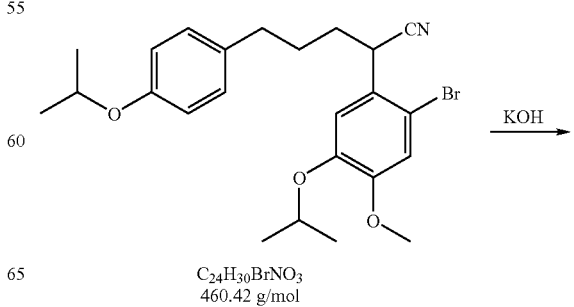

-continued

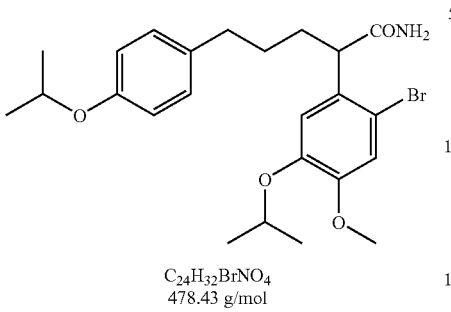

C$_{24}$H$_{32}$BrNO$_4$
478.43 g/mol

α-[2-Bromo-4-methoxy-5-(1-methylethoxy)phenyl]-4-(1-methylethoxy)benzene pentane nitrile (30.0 g, 65.2 mmol) in ethanol (600 ml) is mixed with potassium hydroxide (60.0 g, 1.07 mol) in water (100 ml) and stirred for 6 hours at boiling temperature.

The residue that is obtained after concentration by evaporation is dispersed between 2N hydrochloric acid (200 ml) and ether (300 ml). The aqueous phase is extracted with ether (3×75 ml). The combined organic phases are washed with water (3×200 ml), saturated sodium bicarbonate solution (1×200 ml) and saturated common salt solution (1×200 ml), dried (sodium sulfate/activated carbon), filtered, and the residue that remains after the solvent is removed is purified by column chromatography (1000 g of silica gel, petroleum ether:ether=1:2). The higher-running fraction is taken up in absolute CH$_2$Cl$_2$ (100 ml), mixed at 0° C. with oxalic acid chloride (3 ml) and a drop of DMF and stirred for two hours. The residue that is obtained after the solvent is drawn off in a rotary evaporator is suspended in absolute THF (100 ml), whereupon ammonia is introduced under the surface for two hours. The mixture is filtered, and the residue that is obtained after concentration by evaporation is dispersed between water (100 ml) and ether (100 ml). The aqueous phase is extracted with ether (3×50 ml), the combined organic phases are washed with water (3×200 ml) and saturated common salt solution (1×200 ml), dried (sodium sulfate/activated carbon), filtered, and the residue that is obtained after concentration by evaporation is combined with the deeper-running fraction that is obtained by column chromatography, crystallized under diisopropyl ether and digested with diisopropyl ether (100 ml). In this way, the product is obtained in the form of colorless crystals (26.0 g, 83.5%).

$^1$H NMR (CDCl$_3$) δ 7.01 (d, J=8.9 Hz, 2H), 6.98 (s, 1H), 6.92 (s, 1H), 6.75 (d, J=8.9 Hz, 2H), 5.98 (b, 1H), 5.52 (b, 1H), 4.47 (septet, J=6.3 Hz, 2H), 3.91 (t, J=7.0 Hz, 1H), 3.82 (s, 3H), 2.74–2.40 (m, 2H), 2.22–2.00 (m, 1H), 1.91–1.36 (m, 3H), 1.35–1.22 (m, 6H); $^{13}$C NMR (CDCl$_3$) δ 175.2 (s), 155.8 (s), 149.9 (s), 147.0 (s), 133.9 (s), 130.8 (s), 129.1 (d), 115.7 (d), 114.8 (d), 114.7 (d), 71.4 (d), 69.7 (d), 56.0 (q), 49.7 (d), 34.6 (t), 31.9 (t), 29.1 (t), 22.0 (q), 21.8 (q), 21.7 (q)

Step 9

α-[2-Bromo-5-hydroxy-4-methoxyphenyl]-4-hydroxybenzenepentanoic acid amide

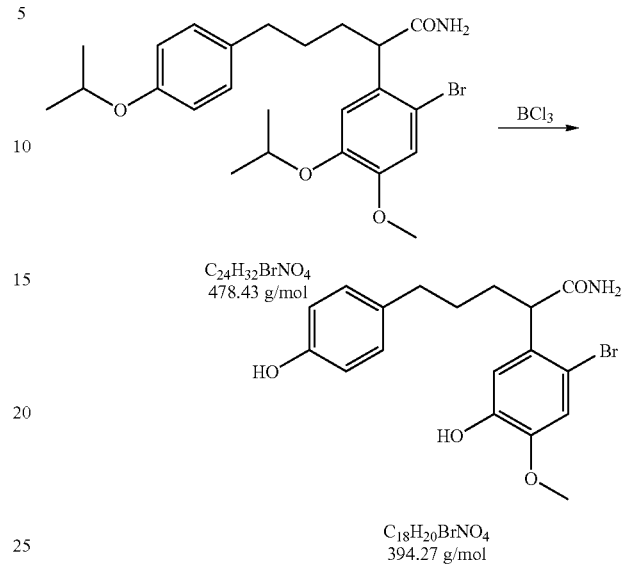

α-[2-Bromo-4-methoxy-5-[1-methylethoxy)phenyl]-4-(1-methylethoxy)benzenepentanoic acid amide (24.0 g, 50.2 mmol) in absolute CH$_2$Cl$_2$ (300 ml) is mixed at −78° C. with boron trichloride (150 ml, 150 mmol, 1 M in CH$_2$Cl$_2$) and stirred for four hours at room temperature.

Water (200 ml) is added in drops, and the organic phase is removed in a rotary evaporator. The precipitated crystals are digested with water (6×200 ml), by which the product is obtained in the form of colorless crystals (19.8 g, quant.).

MT-161 JOS 1713 C$_{18}$H$_{20}$BrNO$_4$ Cld.: C, 54.84; H, 5.11; N, 3.55 Fnd.: C, 54.56; H, 5.40; N, 3.25

Step 10

1-Bromo-4a,5,9,10,11,12-hexahydro-3-methoxy-6-oxa-6H-benzo[a]cyclohepta[hi]benzofuran-12-carboxylic Acid Amide (SPH-1484)

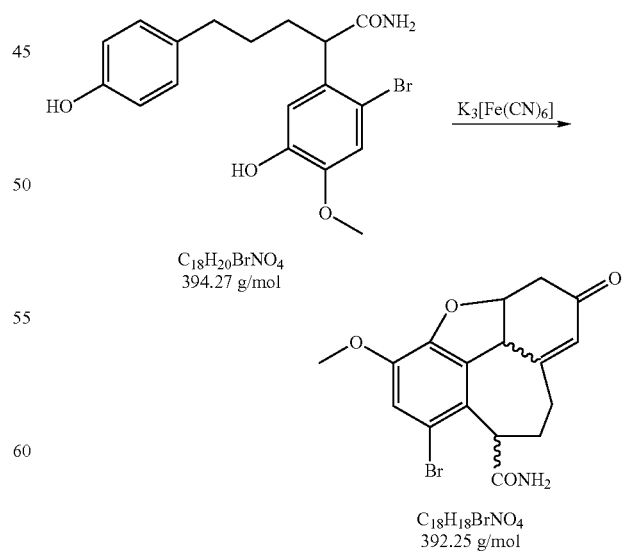

α-[2-Bromo-5-hydroxy-4-methoxyphenyl)-5-hydroxybenzenepentanoic acid amide (3.00 g, 7.61 mmol) is suspended in chloroform (300 ml) and mixed with a solution of potassium hexacyanoferrate(III) (13.2 g, 40.0 mmol) in potassium carbonate solution (75 ml, ten percent).

The mixture is vigorously stirred at room temperature for 40 minutes and filtered on Hyflo. The aqueous phase is extracted with chloroform (2×50 ml), the combined organic phases are washed with 2N hydrochloric acid (2×100 ml), water (2×200 ml) and saturated common salt solution (1×150 ml), dried (sodium sulfate/activated carbon), and the crude product that is obtained after concentration by evaporation of the solvent is purified via column chromatography (50 g of silica gel, ethyl acetate). In this way, the product is obtained as a mixture that consists of two diastereomeric enantiomer pairs, whereby the deeper-running is isomerized to the higher-running.

By column chromatography (chloroform:methanol=96:4), the enantiomer pair with the higher Rf-value is obtained in the form of colorless crystals (0.24 g, 8% of theory).

MT-162/OF JOS 1679 $C_{18}H_{18}BrNO_4$ Cld.: C, 55.12; H, 4.63; N, 3.57 Fnd.: C, 55.15; H, 4.71; N, 3.38 $^1$H NMR (DMSO-$d_6$) δ 7.57 (s, 1H), 7.48 (d, J=14.5 Hz, 1H), 7.14 (s, 2H), 5.89 (d, J=14.5 Hz, 1H), 4.66 (s, 1H), 4.32 (s, 1H), 4.01 (q, J=7.7 Hz, 1H), 3.78 (s, 3H), 3.02 (d, J=19.6 Hz, 1H), 2.79 (d, J=19.6 Hz, 1H), 2.52 (d, J=16.5 Hz, 1H), 2.16 (d, J=16.5 Hz, 1H), 1.96–1.67 (m, 2H), 1.14 (t, J=7.7 Hz, 1H) $^{13}$C NMR (DMSO-$d_6$) δ 195.6 (s), 174.6 (s), 149.5 (d), 147.9 (s), 144.4 (s), 133.6 (s), 130.6 (s), 126.5 (d), 117.5 (s), 117.1 (d), 88.4 (d), 56.8 (q), 52.1 (s), 51.6 (d), 37.9 (t), 36.6 (t), 33.3 (t), 21.5 (t)

EXAMPLE 128b (6R)-1-Bromo-4a,5,9,10,11,12-hexahydro-3-methoxy-6-hydroxy-6H-benzo[a]cyclohepta[hi]benzofuran-12-carboxylic Acid Amide (SPH-1483)

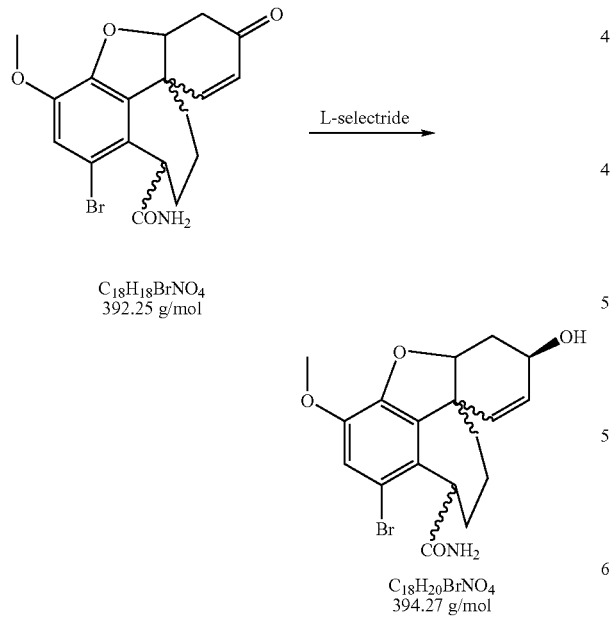

L-Selectride$^{(R)}$ (4.6 ml, 4.6 mmol, 1 M in THF) is added at 0° C. within 15 minutes to a suspension of 1-bromo-4a,5,9,10,11,12-hexahydro-3-methoxy-6-oxa-6H-benzo[a]cyclohepta[hi]benzofuran-12-carboxylic acid amide (600 mg, 1.52 mmol) in absolute THF (5 ml), and the mixture is stirred for 12 hours at room temperature. It is hydrolyzed with water (3 ml) and dispersed between water (10 ml) and ethyl acetate (10 ml), the aqueous phase is extracted with ethyl acetate (3×5 ml), the combined organic phases are washed with 1N hydrochloric acid (3×10 ml), water (2×10 ml), saturated sodium bicarbonate solution (1×10 ml) and saturated common salt solution (1×10 ml), dried (sodium sulfate/activated carbon), filtered, and the crude product that is obtained after the solvent is distilled off is purified by means of column chromatography (50 g of silica gel, ethyl acetate). In this way, the product is obtained in the form of colorless crystals (798 mg, 83%).

MT-169/OF JOS 1677 $C_{18}H_{20}BrNO_4$ Cld.: C, 54.84; H, 5.11; N, 3.55 Fnd.: C, 54.67; H, 5.10; N, 3.46 $^1$H NMR (CDCl$_3$/DMSO-$d_6$) δ 6.97 (s, 1H), 6.79 (b, 1H), 6.49 (b, 1H), 6.12 (d, J=11.4 Hz, 1H), 5.83 (dd, J=11.4 Hz, J=5.1 Hz, 1H), 4.42 (s, 1H), 4.31–4.21 (m, 1H), 3.78 (s, 3H), 3.42–3.18 (m, 2H), 2.68–2.29 (m, 2H), 2.14–1.38 (m, 5H); $^{13}$C NMR (CDCl$_3$/DMSO-$d_6$) δ 173.4 (s), 146.3 (s), 143.6 (s), 134.2 (s), 128.8 (d), 128.6 (d), 126.8 (s), 116.1 (s), 115.6 (d), 87.1 (d), 60.1 (q), 55.6 (d), 50.1 (s), 49.5 (d), 37.5 (t), 31.0 (t), 29.8 (t), 20.3 (t)

EXAMPLE 128c (6R)-10-Amino-1-bromo-4a,5,9,10,11,12-hexahydro-3-methoxy-6-hydroxy-6H-benzo[a]cyclohepta[hi]benzofuran-6-ol (SPH-1482)

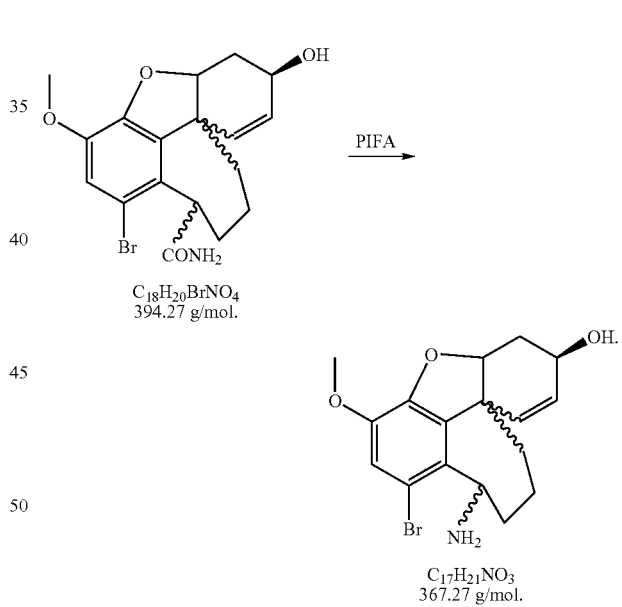

Bis(trifluoroacetoxy)iodobenzene (300 mg, 0.76 mmol) is dissolved in acetonitrile (1.5 ml, HPLC-quality) and mixed with water (1.5 ml, HPLC-quality). Then, (6R)-1-bromo-4a,5,9,10,11,12-hexahydro-3-methoxy-6-hydroxy-6H-benzo[a]cyclohepta[hi]benzofuran-12-carboxylic acid amide (338 mg, 0.76 mmol) is added in substance within 2 hours, and the mixture is stirred for 24 hours at room temperature. The solvent is distilled off in a rotary evaporator, the residue is taken up in chloroform (5 ml), filtered and purified by column chromatography (30 g of silica gel, chloroform methanol:ammonia=96:3:1). In this way, the product is obtained in the form of colorless crystals (161 mg, 58%).

MT-170 JOS 1705 $C_{17}H_{20}BrNO_3 \cdot 0.66$ $H_2O$ Cld.: C, 54.02; H, 5.68; N, 3.71 Fnd.: C, 53.96; H, 5.52; N, 3.60 $^1$H NMR (MeOH-d$_4$) δ 7.08 (s, 1H), 6.41 (d, J=14.5 Hz, 1H), 5.8883 (dd, J=14.5 Hz, J=5.1 Hz, 1H); 4.72 (s, 1H), 4.58 (s, 1H), 4.13 (t, J=3.6 Hz, 1H), 3.82 (s, 3H), 2.49 (d, J=17.2 Hz, 1H), 2.45–2.07 (m, 4H), 1.92–1.58 (m, 4H); $^{13}$C NMR (MeOH-d$_4$) δ 147.2 (s), 144.7 (s), 134.5 (s), 133.3 (s), 130.9 (d), 126.4 (d), 116.6 (d), 115.5 (s), 87.8 (d), 61.2 (d), 57.3 (q), 54.0 (d), 48.6 (s), 38.3 (t), 35.2 (t), 30.1 (t), 17.9 (t)

EXAMPLE 128d (6R)-10-Amino-4a,59,10,11,12-hexahydro-3-methoxy-6-hydroxy-6H-benzo[a]cyclohepta[hi]benzofuran-6-ol

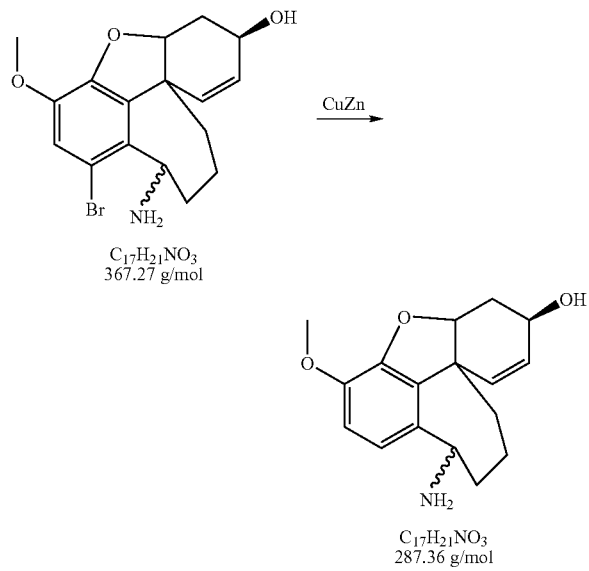

(6R)-10-Amino-1-bromo-4a,5,9,10,11,12-hexahydro-3-methoxy-6-hydroxy-6H-benzo[a]cyclohepta[hi]benzofuran-6-ol (70 mg, 0.19 mmol) and calcium chloride (300 mg, 2.7 mmol) are added in substance to a black suspension of zinc (production: zinc powder (500 mg) and copper(I) iodide (500 mg) are treated under argon in water (4 ml) and ethanol (4 ml) for 45 minutes in an ultrasound bath), and the mixture is stirred for 5 hours at boiling temperature. It is mixed with concentrated aqueous ammonia solution (1 ml), the solvent is removed in a rotary evaporator, the residue is taken up in chloroform (15 ml), filtered, and the residue that is obtained after the filtrate is concentrated by evaporation in a rotary evaporator is purified by column chromatography (30 g of silica gel, chloroform:methanol:ammonia=96:3:1). In this way, the product is obtained in the form of colorless crystals (42 mg, 78%).

$^1$H NMR (CDCl$_3$) δ 6.81–6.61 (m, 3H), 6.97 (dd, J=14 Hz, J=4 Hz, 1H), 4.44 (s, 1H), 4.30 (s, 1H), 4.24 (t, J=3 Hz, 1H), 3.85 (s, 3H), 2.63 (dd, J=17 Hz, J=6 Hz, 1H), 2.40 (q, J=15 Hz, 1H), 2.19–2.08 (m, 1H), 2.02 (dd, J=18 Hz, J=4 Hz, 1H) 1.97–1.52 (m, 9H) $^{13}$C NMR (CDCl$_3$) δ 145.4 (s), 143.2 (s), 134.1 (s), 132.6 (), 129.9 (d), 125.4 (d), 121.9 (d), 109.9 (d), 87.7 (d), 61.1 (d), 54.8 (q), 48.5 (s), 37.0 (t), 34.4 (t), 29.0 (t), 25.8 (t), 16.9 (t)

EXAMPLE 129

8-[6-[(4aS,6R,8aS)-4a,5,9,10,11,12-Hexahydro-6-hydroxy-3-methoxy-6H-benzofuro[3a,3,2-ef][2]benzazepine-11-yl]-1-oxohexyl]-1,2,5,6-tetrahydro-4H-pyrrolo[3,2,1-ij]quinolin-4-one (SPH-1516)

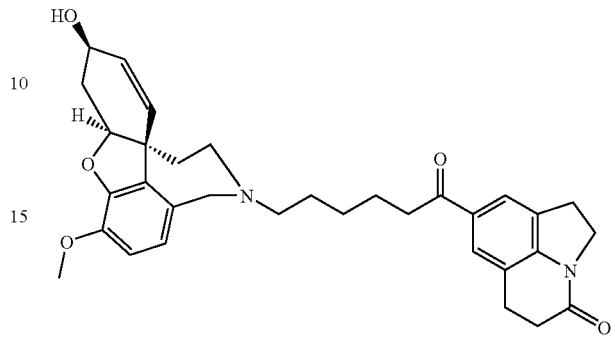

1. Synthesis in Solution:

Norgalanthamine (1.13 g, 4.13 mmol), 8-(6-iodo-1-oxohexyl)-1,2,5,6-tetrahydro-4H-pyrrolo[3,2,1-ij]quinolin-4-one (1.50 g, 3.75 mmol) and N-ethyldiisopropylamine (1.46 g, 11.3 mmol) are stirred in absolute chloroform (20 ml) for 54 hours at boiling temperature.

The residue that is obtained after the solvent is removed in a rotary evaporator is purified by column chromatography (200 g of silica gel, chloroform:methanol:ammonia=96:3:1), by which the product is obtained as a light yellow foam (1.87 g, 92%).

TLC: CHCl$_3$:MeOH:NH$_3$=89:10:1, R$_f$≈0.5 $^1$H NMR (CDCl$_3$) δ 7.62 (s, 1H), 7.67 (s, 1H), 6.68–6.43 (m, 2H), 6.00 (d, J=9.7 Hz, 1H), 5.93–5.81 (m, 1H), 4.51 (s, 1H), 4.22–3.91 (m, 4H), 3.92–3.64 (m, 4H), 3.48–2.28 (m, 13H), 2.20–1.12 (m, 10H); $^{13}$C NMR (CDCl$_3$) δ 198.7 (s), 167.5 (s), 145.5 (s), 145.1 (s), 143.7 (s), 132.8 (s), 132.6 (s), 129.1 (s), 128.9 (s), 127.2 (d), 126.7 (d), 126.3 (d), 123.6 (d), 121.6 (d), 119.3 (s), 110.8 (d), 88.3 (d), 61.6 (d), 57.4 (t), 55.6 (q), 51.2 (t), 51.0 (t), 48.1 (s), 45.4 (s), 38.0 (t), 32.6 (t), 31.1 (t), 29.7 (t), 27.0 (t), 26.8 (t), 24.2 (t), 23.9 (t)

Production of Fumarate (SPH-1519) Analogously to Example 4

MT-407 JOS 1761 $C_{37}H_{42}N_2O_2 \cdot H_2O$ Cld.: C, 65.67; H, 6.55; N, 4.14 Fnd.: C, 65.69; H, 6.49; N, 4.02

2. By Solid-Phase Synthesis 0.300 g (0.102 mmol) of norgalanthamine-6-yloxy)-1,5-dioxopentyloxymethyl-Merrifield resin is steeped in a 5-ml-polyethylene frit that is sealed on both sides for 30 minutes in 3 ml of dimethylformamide/acetone (1/1) and after filtering, it is suspended in a solution of 0.125 g (0.315 mmol) of 8-(6-iodo-1-oxohexyl)-1,2,5,6-tetrahydro-4H-pyrrolo[3,2,1-ij]quinolin-4-one and 54 µl (0.041 g, 0.315 mmol) of ethyldiisopropylamine in 3 ml of dimethylformamide/acetone (1/1).

The suspension is shaken at room temperature for 19 hours. A negative chloranil test indicates the complete conversion of the secondary amine. The resin is washed three times with dimethylformamide (2 minutes, 3 ml) and six times with tetrahydrofuran/methanol (4/1, 2 minutes, 3 ml). The resin is suspended below in a solution that consists of 0.113 g (0.63 mmol) of 30% sodium methanolate-methanol solution and 3.0 ml of tetrahydrofuran/methanol (4/1). After 15 hours, the solution is filtered off, and the resin is extracted six times with 3 ml each of dichloromethane.

The combined filtrates are neutralized with methanolic hydrochloric acid, diluted with 10 ml of dichloromethane, washed twice with 15 ml of saturated sodium chloride solution, dried on sodium sulfate, filtered and concentrated by evaporation in a rotary evaporator under reduced pressure. The crude product is separated by means of MPLC (200 g of silica gel, v=285 nm, chloroform/methanol/concentrated ammonia=96/3/1). After the concentration by evaporation, a yellow oil that crystallizes while standing is obtained: 0.043 g (0.041 g, 0.075 mmol, 74%) of yellowish crystals ($M_W$=542.7), HPLC, TLC identical to a reference sample:

TLC: $R_f$=0.55 (chloroform/methanol=8/2+2% concentrated ammonia); HPLC: $t_{Ref}$=13.7 minutes, 95.7% (Merck Purospher column, 4.0 mm×125 mm, RP-18e, 5.0 μm, 1 ml/min, 285 nm, acetonitrile/20 mmol of $Cl_3CCO_2H$ in $H_2O$ (5/95 v/v for 5 minutes, 5/95→60/40 v/v in 18 minutes (convex), 60/40 vv for 5 minutes).

EXAMPLE 130a (4aS, 6R,8aS)-4a,5,9,10,11,12-Hexahydro-3-methoxy-11-methyl-6H-benzofuro[3a,3,2-ef][2]benzazepin-6-ol, Galanthamine (ES 424)

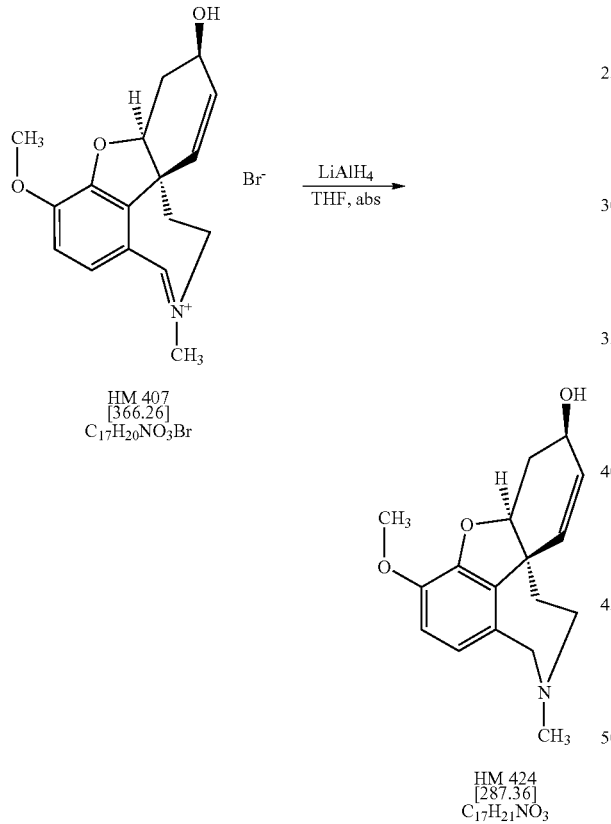

Lithium aluminum hydride (104 mg, 2.73 mmol) was added to a suspension of galanthaminium bromide HM 407 (1.0 g, 2.73 mmol) in absolute tetrahydrofuran (50 ml) and stirred for 3 hours at room temperature. Then, excess lithium aluminum hydride, annihilated with ethyl acetate, was added to water (49 mg, 2.73 mmol) to form a precipitate that could be filtered, and precipitated. The $Al_2O_3$ that was produced was filtered off, the filtrate was dried on sodium sulfate, and the solvent was removed in Rotavapor. 750 mg (96% of theory) of galanthamine was obtained as a white foam.

TLC: $CHCl_3$:MeOH/$NH_3$ (9:1) $^1$H NMR ($CDCl_3$) δ 6.66–6.58 (m, 2H), 6.08–5.94 (m, 2H), 4.58 (b, 1H), 4.15 (b, 1H), 4.06 (d, J=15.2 Hz, 1H), 3.78 (s, 3H), 3.66 (d, J=15.2 Hz, 1H), 3.25 (ddd, J=14.4, 2.2, 1.9 Hz, 1H), 3.05 (ddd, J=14.9, 3.1, 3.1 Hz, 1H), 2.68 (ddd, J=15.7, 1.8, 1.8, 1H), 2.40 (s, 3H), 2.15–1.90 (m, 2H), 1.55 (ddd, J=13.7, 4.1, 2.0 Hz, 1H); $^{13}$C NMR ($CDCl_3$) δ 145.8 (s), 144.1 (s), 133.1 (s), 129.2 (s), 127.6 (d), 126.8 (d), 122.1 (d), 111.1 (d), 88.7 (d), 62.0 (d), 60.4 (t), 55.8 (q), 53.7 (t), 48.2 (s), 41.9 (q), 33.4 (t), 29.9 (t)

EXAMPLE 130b (4aS,6R,8aS)-4a,5,9,10,11-Pentahydro-12-deutero-3-methoxy-11-methyl-6H-benzofuro[3a,3,2-ef][2]benzazepin-6-ol, (12-Deuterogalanthamine, SPH-1520)

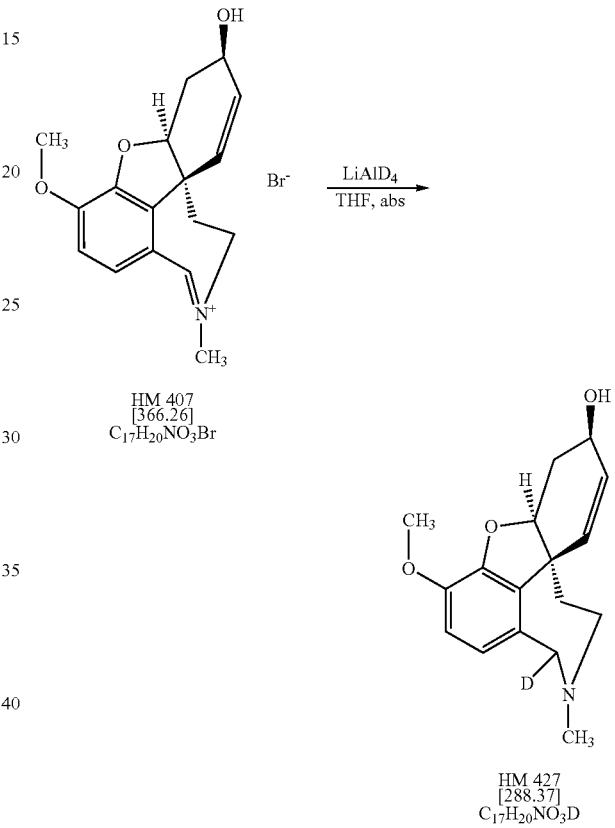

Lithium aluminum deuteride (28 mg, 0.68 mmol) was added to a suspension of galanthaminium bromide HM 407 (250 mg, 0.683 mmol) in absolute tetrahydrofuran (15 ml) and stirred for 3 hours at room. temperature. Then, excess lithium aluminum deuteride was destroyed with ethyl acetate and precipitated with deuterium oxide (12 mg, 0.68 mmol) of $Al_2O_3$. The $Al_2O_3$ that was produced was filtered off, the filtrate was dried on sodium sulfate, and the solvent was removed in Rotavapor. 100 mg (51% of theory) of HM 427 was obtained as a white foam.

TLC:$CHCl_3$:MeOH/$NH_3$ (9:1) $^1$H NMR ($CDCl_3$) δ 6.66–6.58 (m, 2H), 6.08–5.94 (m, 2H), 4.58 (b, 1H), 4.14 (b, 1H), 4.06 (d, J=15.2 Hz, 0.5H), 3.78 (s, 3H), 3.66 (d, J=15.2 Hz, 0.5H), 3.25 (ddd, J=14.4, 2.2, 1.9 Hz, 1H), 3.05 (ddd, J=14.9, 3.1, 3.1 Hz, 1H), 2.68 (ddd, J=15.7, 1.8, 1.8, 1H), 2.40 (s, 3H), 2.15–1.90 (m, 2H), 1.55 (ddd, J=13.7, 4.1, 2.0 Hz, 1H); $^{13}$C NMR ($CDCl_3$) δ 145.8 (s), 144.1 (s), 133.1 (s), 129.2 (s), 127.6 (d), 126.8 (d), 122.1 and 122.0 (d), 111.1 (d), 88.7 (d), 62.0 (d), 60.4 (t), 55.8 (q), 53.8 and 53.7 (t), 48.2 (s), 42.1 and 4.1.9 (q), 33.8 and 33.7 (t), 29.9 (t)

LC/MS:30*2.1 mm of Zorbax SB C18 3 μm, 40% MeOH for 2 minutes to 100% @10 minutes for 10 minutes;

remainder of H2O at 0.5 ml/minute, UV 210, 250, 280 and 310 nm, a single peak (RT about 6.0 minutes). PI-MS m/z 289 ([M+H]⁺), 271 ([M+H.H₂O]⁺). NI-MS m/z 287 ([M−H].), 269 ([M.H.H₂O]).

EXAMPLE 131

Norsanguinine (SPH-1486)

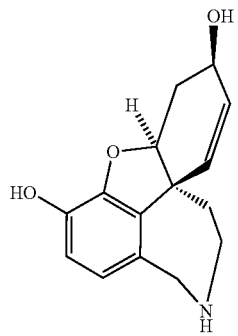

A solution of norgalanthamine (1.0 g, 3.66 mmol) in 40 ml of absolute THF is mixed at room temperature with 17 ml of L-selectride$^R$ (1 M in THF) and stirred for 24 hours at boiling temperature.

It is cooled to room temperature, mixed with ethyl acetate (20 ml), then with water (100 ml), and the phases are separated. The organic phase is extracted with water (4×20 ml), the combined aqueous phases are extracted with ethyl acetate (2×20 ml) and the residue that remains after concentration by evaporation is purified via column chromatography (100 g) of silica gel, chloroform:ammonia=90:9:1) and crystallized under acetone. In this way, the product is obtained in the form of colorless crystals (0.78 g, 82.3%).

$^1$H NMR (DMSO-d₆) δ 6.52–6.37 (m, 2H), 6.03 (d, J=10.3 Hz, 1H), 5.78 (dd, J=10.3 Hz, J=4.6 Hz, 1H), 4.43 (s, 1H), 4.09 (s, 1H), 3.90 (d, J=16 Hz, 1H), 3.71 (d, J=16 Hz, 1H), 3.25–2.92 (m, 2H), 2.24–2.90 (m, 2H), 2.39 (d, J=14 Hz, 2H); $^{13}$C NMR (DMSO-d₆) δ 145.6 (s), 140.4 (s), 133.0 (s), 132.3 (s), 127.7 (d), 127.6 (d), 119.6 (d), 114.8 (d), 86.5 (d), 60.1 (d), 53.1 (t), 48.3 (s), 46.6 (t), 40.2 (t), 30.8 (t)

EXAMPLE 132

(4a,S,6R,8aS)-4a,5,9,10,11,12-Hexahydro-3-methyl-6H-benzofuro[3a,3,2-ef][2]benzazepin-6-ol (SPH-1487)

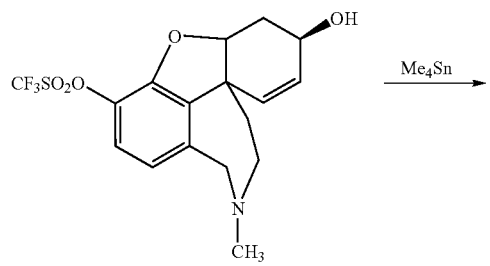

C₁₇H₁₈F₃NO₅S
405.4 g/mol

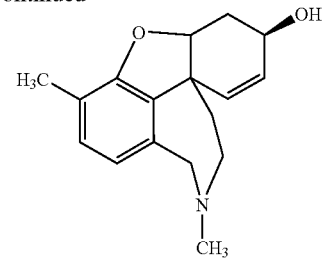

C₁₆H₁₉NO₂
271.36 g/mol (4aS,6R,8aS)-4a,5,9,10,11,12-Hexahydro-3-trifluoromethylsulfonyloxy-6H-benzofuro[3a,3,2-ef][2]benzazepin-6-ol (200 mg, 0.49 mmol), tetramethylstannane (106 mg, 0.59 mmol), anhydrous lithium chloride (62 mg, 1.47 mmol) and tetrakis triphenylphosphine palladium (28 mg, 0.025 mmol, 0.05 equivalent) are stirred in absolute DMF (3 ml) for 24 hours at 100° C. It is dispersed between water (20 ml) and ethyl acetate (30 ml), the aqueous phase is extracted with ethyl acetate (5×30 ml), the combined organic phases are washed with water (3×10 ml) and saturated common salt solution (15 ml), and the residue that is obtained after concentration by evaporation is purified by column chromatography (20 g of silica gel, chloroform:methanol:ammonia=96:3:1). In this way, the product is obtained in the form of colorless crystals (102 mg, 77%).

MT-298 JOS 1711 C₁₇H₂₁O₂*0.25 H₂O Cld.: C, 74.02; H, 7.86; N, 5.08 Fnd.: C, 73.77; H, 7.67; N, 5.04 $^1$H NMR (CDCl₃) δ 6.90 (d, J=7.0 Hz, 1H), 6.46 (d, J=7.0 Hz, 1H), 6.08 (d, J=11.5 Hz, 1H), 6.00 (dd, J=8.5 Hz, J=5.2 Hz, 1H), 4.54 (s, 1H), 4.13 (s, 1H), 4.11 (d, J=16.5 Hz, 1H), 3.70 (d, J=16.5 Hz, 1H), 3.30 (t, J=12.7 Hz, 1H), 3.08 (d, J=12.7 Hz), 2.66 (dd, J=15.2 Hz, J=5.0 Hz, 1H), 2.42 (s, 3H), 2.18 (s, 3H), 2.17–2.00 (m, 2H), 1.57 (dd, J=13.3 Hz, J=5.0 Hz, 1H); $^{13}$C NMR (CDCl₃) δ 156.4 (s), 135.3 (s), 131.6 (s), 130.1 (d), 127.7 (d), 127.6 (d), 122.0 (d), 119.8 (s), 88.1 (d), 62.7 (d), 61.3 (t), 54.2 (t), 48.5 (s), 42.4 (d), 33.9 (t), 30.4 (t), 15.3 (q).

EXAMPLE 136

SPH-1146 IK 66/1

(−) Cyclopropylmethylgalanthaminium bromide

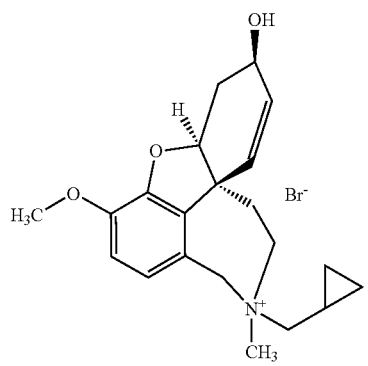

Production analogously to Examples 90–99, melting point 230–237° C.;

$a^D_{20}$=−110 (C=1.5 in water)

EXAMPLE 137

SPH-1149 HM 104

(−) (3-Methylbut-2-en-1-yl)-galanthaminium bromide

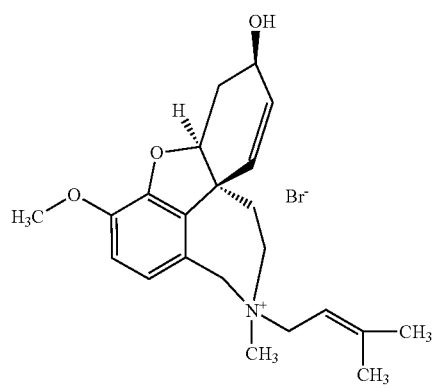

Production analogously to Examples 90–99, melting point 198–201° C.
$a^D_{20} = -118.2$ (1.5 in water)

EXAMPLE 138

SPH-1162 Cl 2-1 3au 3-((6R)-1-Bromo-6-hydroxy-3-methoxy-5,6,9,10-tetrahydro-4aH-[1]benzofuro[3a,3,2-ef][2]benzazepin-11(12H)-yl)propanoic acid ethyl ester

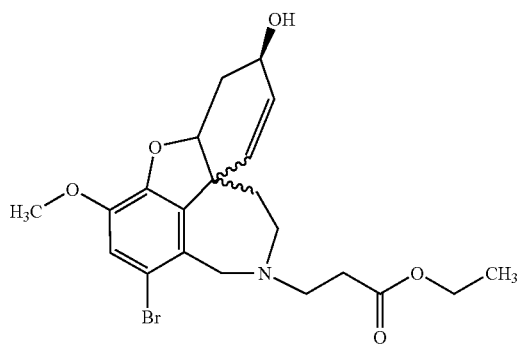

Production analogously to Example 143
Reaction time: 8 hours, yield: 80% colorless foam
Same skeleton as in Example 143, here only the signals that are different are indicated:
$^1$H NMR (CDCl$_3$) δ 4.13 (q, J=6.0 Hz, 2H), 2.85 (t, 7.0 Hz, 2H), 2.58 (t, J=7.0 Hz, 2H), 1.27 (t, J=6 Hz, 3H); $^{13}$C NMR (CDCl$_3$) δ 172.4 (s), 60.3 (t), 57.3 (t), 32.9 (t), 14.1 (q).

EXAMPLE 139

SPH-1184 LCz 225/1

(−)(4-Bromophenyl)methylgalanthaminium bromide hemihydrate

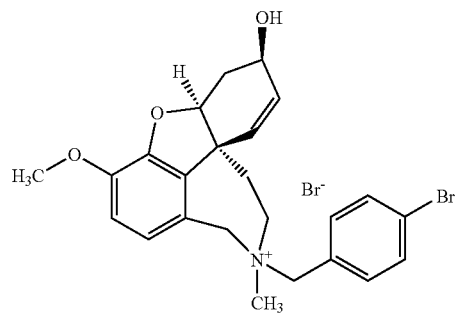

Production analogously to Examples 90–99,
Cld.: C52.77, H 5.17, N 2.56 Fnd.: C52.45, H 5.15, N 2.52

EXAMPLE 140

SPH-1191 LCz 205

(−)(3-Chloropropyl)-galanthaminium Bromide, 1.25 H$_2$O

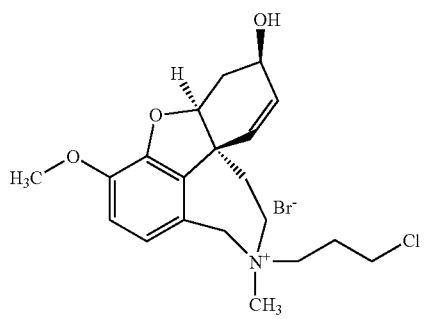

Production analogously to Examples 90–99,
Cld.: C51.40, H 6.36, N 3.00 Fnd.: C51.08, H 6.07, N 2.92

EXAMPLE 141

SPH-1208 CB 2

(6R)-1-Bromo-6-hydroxy-N$^{11}$-isopropyl-3-methoxy-5,6,9,10-tetrahydro-4aH-[1]benzofuro[3a,3,2-ef][2]benzazepine-11(12H)-carboxylic acid amide

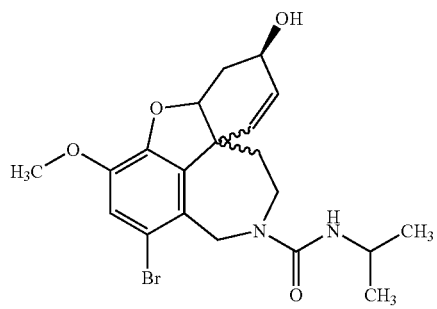

Production analogously to Example 142, yield: 96%;

¹H NMR (CDCl₃) δ 6.87 (s, 1H), 6.04 (dd, J=16.0; 10.0 Hz, 2H), 4.88 (d, J=18.0 Hz, 1H), 4.61 (m, 1H), 4.28 (d, J=18.0, 1H), 4.13 (b, 1H), 3.90 (m, 1H), 3.85 (s, 3H), 3.26 (t, J=12.0 Hz, 1H), 2.67 (dd, J=16.0; 3.0 Hz, 1H), 2.29 (d, J=10.0 Hz, 1H), 1.99 (m, 2H), 1.72 (d, J=17 Hz, 1H); 1.12 (dd, J=20.0; 5.0 Hz, 6H); ¹³C NMR (CDCl₃) δ 156.0 (s), 146.5 (s), 144.9 (s), 133.8 (s), 128.6 (d), 128.2 (s), 127.5 (s), 125.8 (d), 115.1 (d), 112.3 (d), 88.5 (d), 61.6 (d), 56.1 (q), 50.3 (t), 49.1 (s), 45.2 (t), 42.7 (d), 36.6 (t), 29.6 (t), 23.4 (q), 23.0 (q). Anal. [C₂₀H₂₅BrN₂O₄.0.3 H₂O] Cld.: C54.26 H 5.83 N 6.33 Fnd.: C54.28 H 5.79 N 6.14

EXAMPLE 142

SPH-1209 CB 5

(6R)-1-Bromo-6-hydroxy-3-methoxy-N¹¹-methyl-5,6,9,10-tetrahydro-4aH-[1]benzofuro[3a,3,2-ef][2]benzazepine-11(12H)-thiocarboxylic acid amide

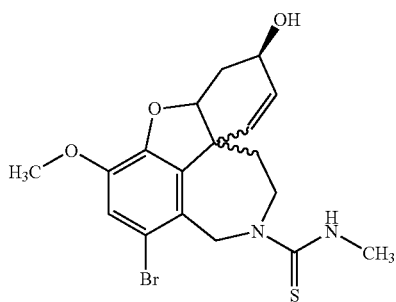

Methyl isothiocyanate (42.0 mg, 0.57 mmol) was added in drops to a stirred solution of bromonorgalanthamine (0.2 g, 0.57 mmol) in toluene (10 ml), and it was refluxed for three hours. After concentration by evaporation, the residue was taken up in 2N HCl (20 ml) and washed with AcOEt (1×10 ml). The aqueous solution was brought to a pH>8.5 with concentrated ammonia and extracted with AcOEt (3×10 ml). The combined organic phases were washed with saturated common salt solution, dried (Na₂SO₄) and concentrated by evaporation, by which the product was obtained in the form of colorless crystals with a melting point of 183–185° C. (0.22 g, 99%);

¹H NMR (CDCl₃) δ 7.35 (b, 1H), 6.89 (m, 1H), 6.10 (m, 2H), 5.50 (d, J=12.0 Hz, 1H), 5.11 (d, J=12.0 Hz, 1H), 4.69 (b, 1H), 4.52 (d, J=12.0 Hz, 1H), 4.17 (b, 1H), 3.85 (s, 3H), 3.60 (t, J=18.0 Hz, 1H), 3.10 (d, J=3.4 Hz, 3H), 2.72 (dd, J=18.8; 2.0 Hz, 1H), 2.13 (m, 2H), 1.79 (d, J=12.0 Hz, 1H); ¹³C-NMR (CDCl₃) δ 181.5 (s), 146.8 (s), 145.4 (s), 133.9 (s), 128.9 (d), 128.2 (s), 125.5 (d), 115.3 (d), 112.5 (d), 88.6 (d), 61.5 (d), 56.2 (q), 51.7 (t), 51.2 (t), 48.9 (s), 35.8 (t), 33.0 (q), 29.6 (t). Anal. (C₁₈H₂₁BrN₂O₃S.0.5 H₂O) Cld.: C 50.83 H 4.98 N 6.59 Fnd.: C 50.73 H 5.02 N 6.63

EXAMPLE 143

SPH-1210 CB 4

3-((6R)-1-Bromo-6-hydroxy-3-methoxy-5,6,9,10-tetrahydro-4aH-[1]benzofuro[3a,3,2-ef][2]benzazepine-11(12H)-yl)propanenitrile

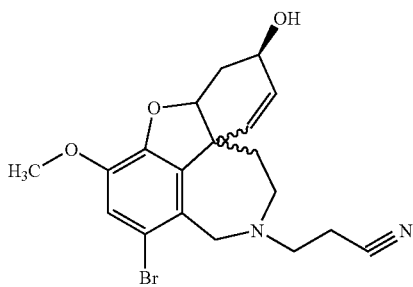

Acrylonitrile (0.05 ml, 0.85 mmol) and calcium chloride (200 mg, 1.80 mmol) were added to a solution of norgalanthamine (200 mg, 0.57 mmol) in 50% EtOH (20 ml), and the reaction was refluxed for 3 hours. The reaction was concentrated, the residue was taken up in 2N HCl (50 ml) and washed with EtOAc (3×25 ml, the organic phase was discarded). The aqueous solution was brought to pH>8.5 with concentrated NH₃ and extracted with methylene chloride (3×25 ml). The combined organic phases were washed with saturated sodium chloride solution (200 ml), dried (Na₂SO₄) and concentrated by evaporation, and the product, 220 mg (95.7%), was obtained as a colorless foam.

¹H NMR (CDCl₃) δ 6.90 (s, 1H), 6.04 (dd, J₁=16.0 Hz, J=10.0 Hz, 2H), 4.60 (b, 1H), 4.38 (d, J=16.0, 1H), 4.12 (b, 1H), 4.08 (d, J=16.0 Hz, 1H), 3.83 (s, 3H), 3.47 (t, J=10.0 Hz, 1H), 3.18 (d, J=18.0 Hz, 1H), 2.80 (t, J=10.0 Hz, 2H), 2.63 (m, 2H), 2.61 (m, 1H), 2.03 (m, 2H), 1.60 (d, J=10.0 Hz, 1H); ¹³C-NMR (CDCl₃) δ 145.6 (s), 144.5 (s), 134.1 (s), 128.4 (d), 127.1 (s), 126.1 (d), 118.6 (s), 115.8 (d), 114.3 (d), 88.7 (d), 61.7 (d), 56.1 (q), 54.9 (t), 52.0 (t), 48.9 (s), 47.2 (t), 33.3 (t), 29.7 (t), 16.8 (t). Anal. (C₁₉H₂₁BrN₂O₃) Cld.: C 56.31 H 5.22 N 6.91 Fnd.: C 56.53 H 5.44 N 6.64

EXAMPLE 144

SPH-1227

[4aS-(4aα,6α,8aR*)]-4a,5,9,10,11,12-Hexahydro-3-methoxy-11-methyl-6H-benzofuro[3a,3,2-ef][2]benzazepine-6-amine Step 1

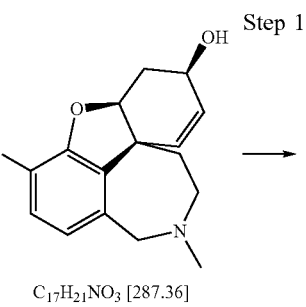

C₁₇H₂₁NO₃ [287.36]

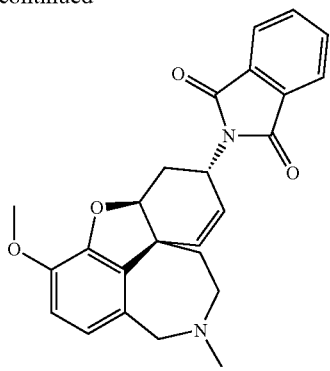

A solution of 300 mg (1.05 mmol) of galanthamine, 208 mg (1.20 mmol) of azadicarboxylic acid diethyl ester, 314 mg (1.20 mmol) of triphenylphosphine and 1.20 mmol of phthalimide in 30 ml of absolute tetrahydrofuran is stirred for 24 hours at room temperature. Then, the tetrahydrofuran is spun off, the residue is taken up in 30 ml of 2N hydrochloric acid, washed three times with 30 ml each of ethyl acetate and made basic with concentrated aqueous ammonia. Then, the solution is extracted three times with 30 ml each of ethyl acetate, the combined organic phases are washed once with saturated aqueous sodium chloride solution, dried ($Na_2SO_4$), filtered and concentrated by evaporation. The crude product is purified by FLC (15 g of silica gel, mobile solvent:$CHCl_3$:MeOH=97:3).

83% colorless crystals, melting point: 60–63° C. TLC: $CHCl_3$:MeOH=9:1

Step 2

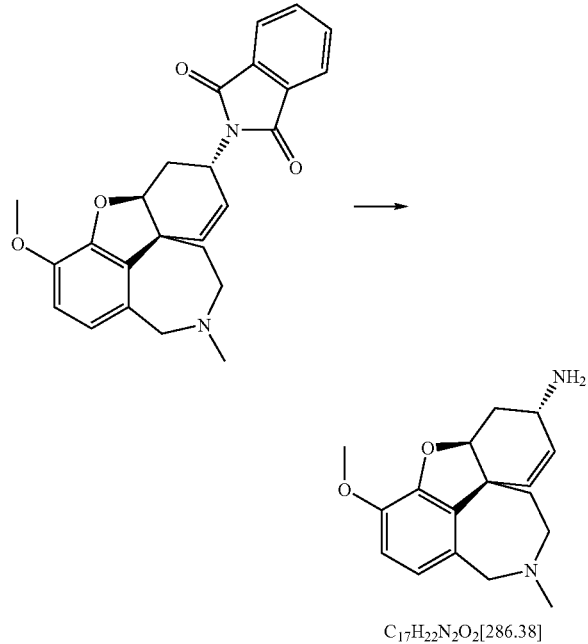

146 mg (1.44 mmol) of triethylamine and 162 mg (1.58 mmol) of 3-(dimethylamino)propylamine are added in drops to a solution, cooled to −5° C., of 0.72 mmol of educt in 5 ml of absolute methanol. Then, the reaction mixture is allowed to stir at room temperature for 24 hours, and then methanol, triethylamine and 3-(dimethylamino)propylamine are spun off. The crude product that is obtained is purified by FLC (15 g of silica gel, mobile solvent: $CHCl_3$:MeOH=9:1 with 0.5% concentrated aqueous ammonia), by which colorless crystals with a melting point of 119–121° C. with a rotation of $\alpha_D^{20}$ [c=0.1, $CHCl_3$]=−264° of product are obtained.

TLC: $CHCl_3$:MeOH=9:1 $^1$H NMR ($CDCl_3$) δ 1.56–1.89, m, 2H; 2.78, m, 1H; 3.02, m, 1H; 3.24, m, 1H; 3.48, m, 1H; 2.32, s, 1H; 3.83, s, 1H; 3.63, d, 1H; 4.07, d, 1H; 4.62, b, 1H; 4.98, b, 1H; 5.74, d, 1H; 6.11, d, 1H; 6.54, d, 1H; 6.64, d, 1H.

EXAMPLE 145

SPH-1273 CB 99

(4aS,6R,8aS)-11-Methyl-3-phenoxy-5,6,9,10,11,12-hexahydro-4aH-[1]benzofuro[3a,3,2-ef][2]benzazepin-6-ol

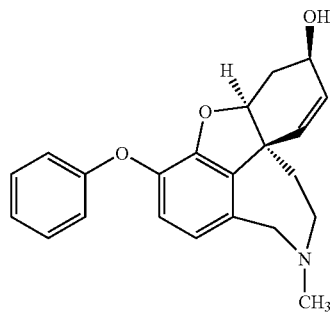

0.44 g (3.6 mmol) of benzeneboric acid, 2.5 ml (9 mmol) of triethylamine, 0.67 g (3.6 mmol) of copper(II) acetate and 1 g of molecular sieve (4 Å, crushed) were added to a solution of 1.0 g (3.6 mmol) of O-demethylgalanthamine in 50 ml of dichloromethane. The reaction mixture was stirred for 44 hours at room temperature. The solid was filtered off. The filtrate was extracted twice with 30 ml each of saturated sodium bicarbonate solution. The aqueous phase was re-extracted three times with 30 ml of methylene chloride in each case. The combined organic phases were dried on sodium sulfate, and the solvent was distilled off. The crude product (0.55 g, 43.7% of theory) was purified by means of column chromatography ($CHCl_3$:MeOH=95:5).

Yield: 0.3 g (23.8% of theory) TLC: $CHCl_3$: $CH_3OH$=9:1 CB 99: $^1$H NMR ($CDCl_3$) δ 7.29 (m, 2H), 7.04 (t, J=7.2 Hz, 1H), 6.89 (d, J=8.7 Hz, 2H), 6.73 (dd, $J_1$=31.6 Hz, $J_2$=8.7 Hz, 2H), 6.03 (m, 2H), 4.59 (s, 1H), 4.51 (b, 1H), 4.17 (d, J=15.3 Hz, 1H), 3.77 (d, J=15.3 Hz, 1H), 3.33 (t, J=13.0 Hz, 1H), 3.10 (d, J=14.5 Hz, 1H), 2.53 (m, 1H), 2.43 (s, 3H), 2.15 (m, 1H), 1.89 (m, 1H), 1.62 (d, J=13.8, 1H); $^{13}$C-NMR ($CDCl_3$) δ 157.3 (s), 148.1 (s), 139.6 (s), 134.2 (s), 129.6 (2*d), 128.1 (d), 126.2 (d), 122.8 (d), 122.7 (d), 120.2 (d), 116.8 (d), 88.7 (d), 61.7 (d), 59.9 (t), 53.2 (t), 48.1 (s), 41.2 (q), 32.8 (t), 29.7 (t). Anal. ($C_{22}H_{23}NO_3$*0.2 $CHCl_3$) Cld.: C 71.43 H 6.26 N 3.75 Fnd.: C 71.43 H 6.61 N 3.84

EXAMPLE 146

SPH-1288 HM 122.DD 13

(6R)-3,6-Dihydroxy-N[11]-isopropyl-5,6,9,10-tetrahydro-4aH-[1]benzofuro[3a,3,2-ef][2]benzazepine-11(12H)-carboxylic acid amide

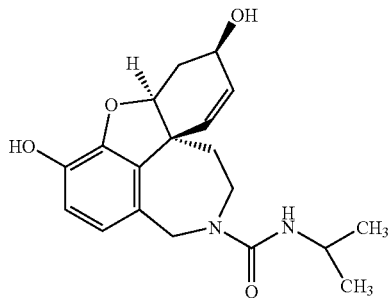

A solution of 0.42 ml (4.3 mmol) of boron tribromide in 4 ml of absolute dichloromethane was slowly added in drops under argon at −5° C. to a solution of 1.6 mmol of educt in 17 ml of absolute dichloromethane. After 3 hours of stirring at −5 to 0° C., the reaction mixture was poured onto 20 ml of water and saturated with sodium bicarbonate. The aqueous phase was extracted four times with 15 ml each of n-butanol, and the solvent was distilled off. The residue was purified by means of column chromatography (LM: $CHCl_3$:$CH_3OH$=97:3) and dried at 50° C./50 mbar.

$^1$H NMR ($CDCl_3$) δ 6.57 (dd, $J_1$=18.7 Hz, $J_2$=8.0 Hz, 2H) 5.94 (dd, $J_1$=21.4 Hz, $J_2$=10.4 Hz, 2H), 4.90 (dd, $J_1$=10.6 Hz, $J_2$=6.0 Hz, 1H), 4.36 (m, 3H), 3.85 (m, 1H), 3.33 (t, J=12.1 Hz, 1H), 2.93 (m, 1H), 2.25 (m, 1H), 1.87 (m, 2H), 1.24 (m, 1H), 1.06 (dd, $J_2$=21.3 Hz, $J_2$=6.5 Hz, 6H); $^{13}$C-NMR ($CDCl_3$) δ 156.7 (s), 146.5 (s), 141.0 (s), 131.5 (s), 130.1 (s), 128.1 (d), 127.1 (d), 120.1 (d), 115.5 (d), 88.2 (d), 51.6 (t), 48.0 (s), 45.9 (t), 42.8 (d), 42.0 (d), 36.8 (t), 34.2 (t), 23.5 (q), 23.1 (q). Anal. ($C_{19}H_{24}N_2O_4$.0.8 $CHCl_3$) (JOS 1622). Cld.: C 54.0 H 5.68 N 6.37 Fnd.: C 54.08 H 5.61 N 6.33

EXAMPLE 147

SPH-1302 HM 203

(4aα,6β,8aR*)-4a,5,9,10-Tetrahydro-6-hydroxy-3-methoxy-6H-benzofuro[3a,3,2-ef][2]benzazepine-11(12H)-carboxylic acid-1,1-dimethylethyl ester (8d)

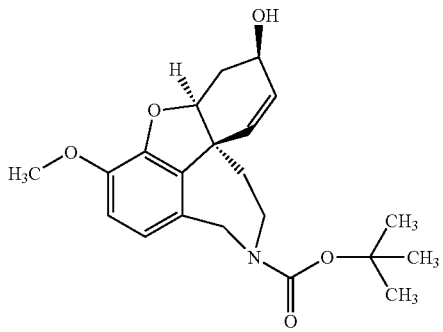

A solution of 9.00 g (41.30 mmol) of pyrocarbonic acid-di-tert-butyl ester in 150 ml of absolute tetrahydrofuran was added in drops while being cooled with ice to a solution of 12.0 g of a mixture of norgalanthamine and galanthamine at a ratio of 94:6 (corresponding to 41.3 mmol of norgalanthamine) and 7.10 g (70.2 mmol) of triethylamine in 400 ml of absolute tetrahydrofuran. After 10 minutes, the ice-cooling was removed, and it was stirred for 16 hours at room temperature. Then, the organic solvent was evaporated, the residue was taken up in ethyl acetate, and it was washed three times with 150 ml each of 1N aqueous hydrochloric acid, three times with 200 ml each of saturated sodium bicarbonate solution and twice with 200 ml each of saturated sodium chloride solution. The solvent was dried on sodium sulfate, concentrated by evaporation, and the crude product was purified by means of MPLC:mobile solvent:chloroform:methanol 99:1→90:10. 11.2 g of white foam was obtained at HM 203 (73% of theory).

TLC: $CHCl_3$:MeOH/$NH_3$ 9:1 $^1$H-NMR ($CDCl_3$, 200 MHz): 1.35–1.45 (m, 9H), 1.75 (m, 1H), 1.97 (m, 1H), 2.05 (m, 1H), 2.40 (m, 1H), 2.69 (b, 1H), 3.30 (b, 1H), 3.85 ($OCH_3$, s, 3H), 4.08–4.17 (m, 3H), 4.60 (b, 1H), 5.97–6.06 (m, 2H), 6.70–6.78 (m, 2H) Anal. ($C_{21}H_{27}NO_5$.0.4 MeOH) Cld.: C 66.54 H 7.46 N 3.63 Fnd.: C 66.59 H 7.59 N 3.47

EXAMPLE 149

SPH-1339 HM 264-1

(4aS,6R,8aS)-11-Propyl-3-methoxy-5,6,9,10,11,12-hexahydro-4aH-[1]benzofuro[3a,3,2-ef][2]benzazepin-6-ol

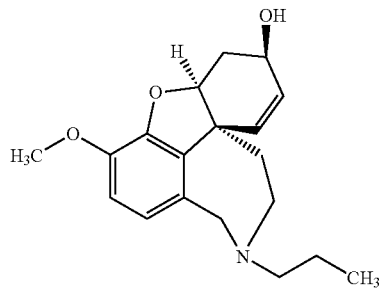

Method 1:

A solution of 250 mg (0.92 mmol) of (−)-norgalanthamine and 160 mg (2.76 mmol) of propanal in 20 ml of absolute acetonitrile were mixed in portions with 145 mg (2.3 mmol) of sodium cyanoborohydride and stirred for 12 hours at room temperature. Then, 145 mg (2.3 mmol) of sodium cyanoborohydride was repeatedly added in portions, and the reaction mixture was stirred for another 6 hours. After the solvent was evaporated, the working-up was carried out according to instructions A1. Further purification was carried out by means of MPLC (mobile solvent: chloroform:methanol/$NH_3$=95.5). 200 mg (70% of theory) of HM 264 was obtained.

TLC: $CHCl_3$:MeOH/$NH_3$ 9:1

Method 2:

A solution of 200 mg (0.73 mmol) of (−) norgalanthamine and 120 mg (1.46 mmol) of sodium acetate in 12 ml of water, 4 ml of absolute ethanol and 0.62 ml of glacial acetic acid was cooled to 0° C., mixed with 211 mg (3.65 mmol) of propanal and stirred for 5 minutes. Then, 138 mg (3.65 mmol) of sodium borohydride in 10 mg portions was added. After 20 minutes, another 211 mg (3.65 mmol) of propanal and 138 mg (3.65 mmol) of sodium borohydride were added and stirred for 30 minutes. Then, the reaction mixture was worked up as described in Instructions A1. 210 mg (91% of theory) of HM 264 was obtained.

TLC: CHCl$_3$:MeOH/NH$_3$ 9:1 $^1$H-NMR (CDCl$_3$, 200.13 MHz) δ 0.88 (t, J=7.2, 3H), 1.96–2.11 (m, 2H), 2.45 (sextet, J=7.8, J=4.6, J=5.0 Hz, 2H), 2.68 (ddd, J=15.7, J=1.8, J=1.8, 1H), 3.18 (ddd, J=14.9, J=3.1, J=3.1 Hz, 1H), 3.35 (ddd, J=14.4, J=2.2, J=1.9, 1H), 3.80 (d, J=15.3 Hz, 1H), 3.85 (s, 3H), 4.10 (d, J=15.3, 1H), 4.12 (b, 1H), 4.60 (b, 1H), 5.96–6.13 (m, 2H), 6.61 (d, J=8.2, 1H), 6.68 (d, J=8.2, 1H); $^{13}$C-NMR (CDCl$_3$, 50.32 MHz) δ 11.8 (q), 20.5 (t), 29.9 (t), 32.9 (t), 48.4 (s), 51.4 (t), 53.5 (t), 55.8 (q), 57.7 (t), 62.0 (d), 88.6 (d), 111.1 (d), 121.9 (d), 127.0 (d), 127.4 (d), 129.6 (s), 133.1 (s), 143.9 (s), 145.7 (s)

EXAMPLE 150

SPH-1340 HM 265-1

N-Demethyl-N-propargyl-galanthamine

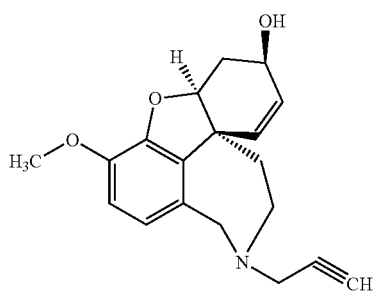

A solution that consists of 0.50 g (1.83 mmol) of (−)demethylgalanthamine, 0.51 g (3.66 mmol) of potassium carbonate and 0.55 g (3.66 mmol) of sodium iodide in 25 ml of dimethylformamide was mixed with 2.20 mmol of reagent and heated for six hours to 70–80° C. Then, the solvent was evaporated. The residue was taken up in 50–100 ml of 2N aqueous hydrochloric acid and washed twice with 40–70 ml each of ethyl acetate. Then, it was made basic with concentrated aqueous ammonia and extracted three times with 40–70 ml each of dichloromethane. The combined organic phases were washed twice with 40–70 ml each of saturated sodium chloride solution, dried on sodium sulfate, and the solvent was evaporated.

The further purification was carried out by means of MPLC (mobile solvent:chloroform:methanol/NH$_3$=95:5).

Yield: 0.26 g (46% of theory) of a colorless oil TLC: CHCl$_3$:MeOH/NH$_3$ 9:1 $^1$H-NMR (CDCl$_3$, 200.13 MHz) δ 1.53 (ddd, J=13.8, J=3.7, J=2.1, 1H), 1.89–2.09 (m, 4H), 2.27 (t, J=2.3, 2H), 2.65 (ddd, J=15.8, J=1.6, J=1.6, 1H), 3.15–3.43 (m, 2H), 3.79 (d, J=15.0 Hz, 1H), 3.85 (s, 3H), 4.11 (d, J=15.0 Hz, 1H), 4.13 (b, 1H), 4.58 (b, 1H), 5.91–6.09 (m, 2H), 6.63 (b, 2H); $^{13}$C-NMR (CDCl$_3$, 50.32 MHz) δ 29.9 (t), 34.5 (t), 44.2 (t), 48.0 (s), 51.5 (t), 55.8 (q), 58.2 (t), 61.9 (d), 72.8 (s), 79.4 (d), 88.6 (d), 111.3 (d), 122.0 (d), 126.8 (d), 127.6 (d), 128.7 (s) 132.9 (s), 144.1 (s), 145.8 (s)

EXAMPLE 151

SPH-1357 MF 8

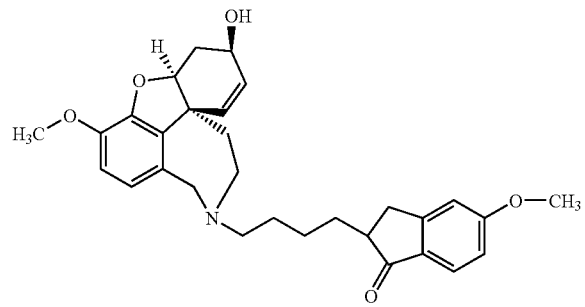

Production analogously to Example 6/step 3, but with use of 2-(4-bromobutyl)-5-methoxyindan-1-one, colorless foam.

$^1$H-NMR (ppm, CDCl$_3$) δ 7.65 (d, J=8.1 Hz, 1H), 6.87 (d, J=7.7 Hz, 2H), 6.62 (dd, J$_1$=12.9 Hz, J$_2$=8.4 Hz, 2H), 6.04 (m, 2H), 4.60 (b, 1H), 4.14 (m, 2H), 3.85 (s, 3H), 3.83 (s, 3H), 3.81 (m, 1H), 3.61 (d, J=6.24 Hz, 1H), 3.25 (m, 2H), 2.88 (d, J=15.1, 5H), 2.52 (b, 1H), 2.07 (m, 3H), 1.93 (m, 1H), 1.64–1.48 (m, 4H); $^{13}$C-NMR (ppm, CDCl$_3$): 207.0 (s), 165.3 (s), 162.5 (s), 156.6 (s), 145.8 (s), 144.1 (s), 133.1 (s), 129.5 (s), 127.6 (d), 126.9 (d), 122.0 (d), 115.2 (d), 111.2 (d), 109.6 (d), 88.7 (d), 62.0 (t), 57.6 (t), 55.9 (q), 55.8 (q), 51.5 (t), 48.4 (d), 47.6 (d), 32.8 (t), 31.5 (t), 29.9 (t), 29.6 (t), 27.4 (t), 25.1 (t).

EXAMPLE 155

SPH-1377 BK-34-2

2-[4-[(4aS,6R,8aS)-4a,5,9,10,11,12-Hexahydro-6-hydroxy-3-methoxy-6H-benzofuro[3a,3,2-ef][2]benzazepine-11-yl]butyl]-5-methoxyindan-1-one, fumarate

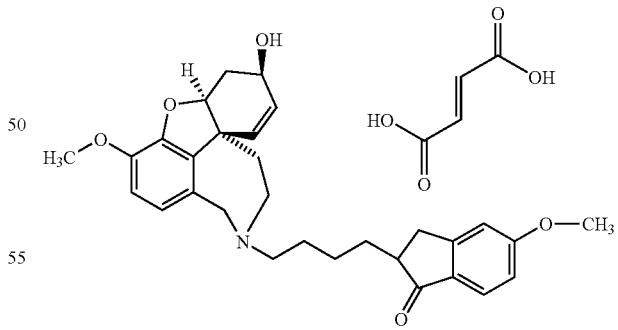

Production of Example 151 Analogously to Example 7/production of fumarate.

Melting point: 107–110° C. C$_{30}$H$_{35}$NO$_5$ 5/4C$_4$H$_4$O$_4$ 1 H$_2$O Cld.: C, 64.07 H, 6.44 N, 2.11 Fnd.: C, 64.26 H, 6.41 N, 2.23 $^1$H NMR (ppm, CDCl$_3$) δ 7.56 (d, J=10 Hz, 1H), 7.10 (s, 1H), 6.98 (d, J=10 Hz, 1H), 6.80 (m, 2H), 6.63 (s, 2H), 6.13 (d, J=12.0 Hz, 1H), 5.89 (m, 1H), 4.61 (s, 1H), 4.50 (d, J=8.0 Hz, 1H), 4.07 (b, 2H), 3.88 (s, 3H), 3.72 (s, 3H), 3.52 (t, J=12 Hz, 1H), 3.31 (m, 2H), 2.69 (m, 5H), 2.30 (d, J=12 Hz, 1H), 2.07 (m, 2H), 1.74 (m, 4H), 1.38 (m, 3H); $^{13}$C-NNR (ppm, CDCl$_3$): 206.3 (s), 166.9 (s), 165.3 (s), 157.2 (s), 146.3 (s), 144.6 (s), 133.1 (d), 129.7 (s), 129.4 (s), 126.4 (d), 125.1 (d), 122.5 (d), 115.8 (d), 112.7 (d), 110.3 (d), 86.8 (d), 65.3 (t), 60.0 (t), 56.1 (q), 55.8 (q), 51.1 (t), 47.5 (d), 46.9 (d), 32.5 (t), 32.5 (t), 31.9 (t), 31.2 (t), 30.8 (t), 24.9 (t), 24.2 (t).

EXAMPLE 157

SPH-1515

(4aS,6R,8aS)-3,6-Dihydroxy-5,6,9,10-tetrahydro-4aH-[1]benzofuro[3a,3,2-ef][2]benzazepine-11 (12H)-yl)carboxylic acid allyl ester (ML-7)

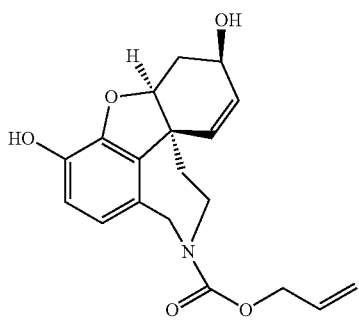

2.11 ml (1.538 g, 19.3 mmol) of triethylamine and 0.81 ml (0.693 g, 6.384 mmol) of trimethylsilyl chloride are sprayed under inert-gas atmosphere by means of a syringe through a septum into a suspension of 0.788 g (0.552 g, 2.13 mmol) of norsanguinine (HPLC purity 70%) and 10 ml of absolute dichloromethane, and the suspension is stirred for three hours at room temperature. In the meantime, a flocculent precipitate settles out. Then, 0.34 ml (0.385 g, 3.192 mmol) of allyl chloroformate is added while being cooled in an ice bath (exothermic). The reaction mixture is heated within two hours to room temperature while being stirred, by the ice bath being allowed to thaw. The reaction is halted by adding 13 ml of 2N hydrochloric acid, and the phases are separated. The organic phase is washed four times with 10 ml each of 2N hydrochloric acid and once with common salt solution, the combined aqueous phases are re-extracted once with 20 ml of dichloromethane. The combined organic phases are dried on sodium sulfate and filtered. After the solvent is distilled off in a rotary evaporator, the crude product (HPLC purity 87.5%) is purified by means of MPLC (50 g of silica gel, v=285 nm, chloroform/methanol=95/5). After concentration by evaporation and drying in a high vacuum, the product is obtained as a yellowish, highly viscous oil, which crystallizes during concentration by evaporation from dichloromethane. Yield: 0.443 g (1.29 mmol, 61%) of colorless crystalline solid, (M$_W$=343.4), TLC: R$_f$=0.55 (chloroform/methanol=9/1).

Melting point: 197–198° C. (dichloromethane). $^1$H-NMR: (200.13 MHz, CDCl$_3$, TMS) δ 7.66 (bs, 0.3H), 6.52–6.76 (m, 2H), 5.95 (bs, 2H), 5.72–5.90 (m, 1H), 5.06–5.36 (m, 2H), 4.90 (d, J=12.7 Hz, 0.5H), and 4.79 (d, J=12.7 Hz, 0.5H), 4.51 (bs, 3H), 4.00–4.41 (m, 3H), 3.22–3.53 (m, 1H), 3.13 (bs, 0.3H), 2.58 (bd, J=13.4 Hz, 1H), 1.63–2.10 (m, 3H), $^{13}$C-NMR. (50.32 MHz, CDCl$_3$, TMS), 6 155.4 and 155.2 (s), 145.4 (s), 140.6 (s), 132.7 and 132.6 (d), 131.9 and 131.7 (s), 128.3 (s), 127.1 (d), 127.0 (d), 121.6 and 121.1 (d), 117.4 and 116.8 (t), 115.8 and 115.7 (d), 87.7 (d), 66.1 and 65.9 (t), 61.8 (d), 51.9 and 51.5 (t), 48.4 (s), 45.9 and 45.4 (t), 37.0 and 36.0 (t), 29.5 (t).

Diagram for Examples 158 and 159

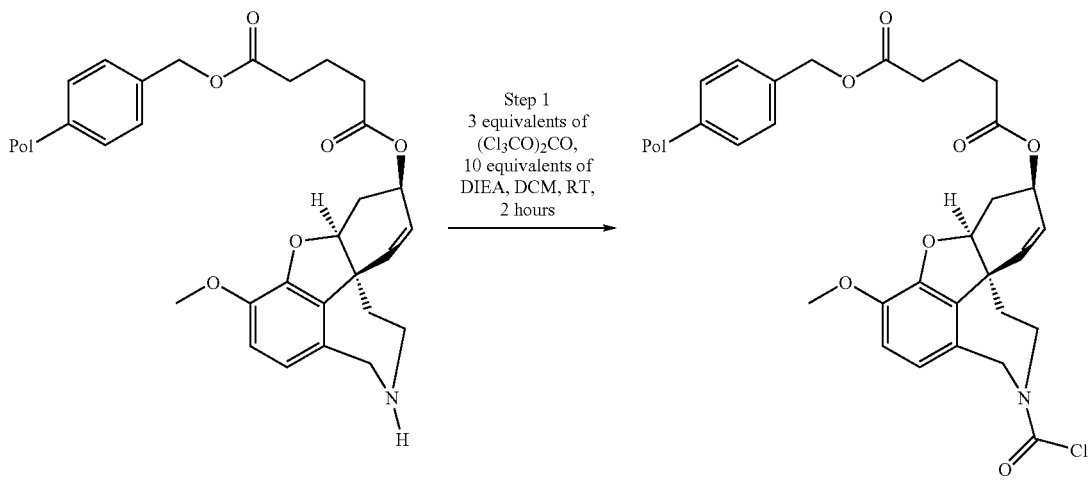

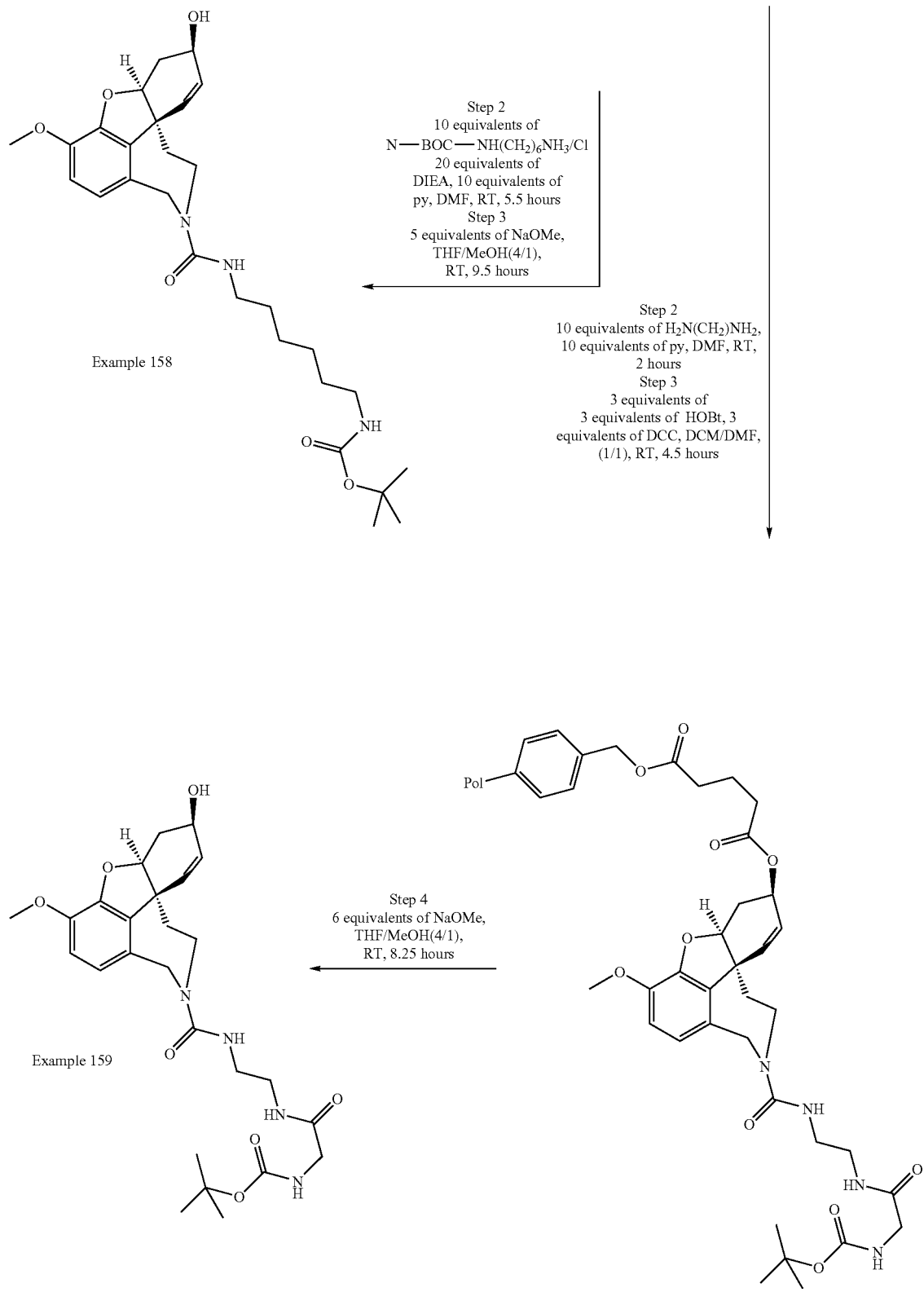

EXAMPLE 158

SPH-1522

(4aS,6R,8aS)-N[11]-(N-tert-Butoxycarbonyl-6-amino-hexyl)-6-hydroxy-3-methoxy-5,6,9,10-tetrahydro-4aH-[1]benzofuro-[3a,3,2-ef]-[2]benzazepine-11 (12H) Carboxamide (CK-52-6)

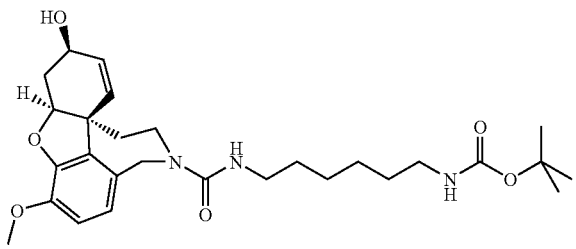

0.600 g (0.426 mmol) of N-tert-butoxycarbonylnorgalanthamine-6-yloxy-1,5-dioxopentyloxymethyl-Merrifield resin is steeped in a 10-ml-polyethylene frit that can be sealed on both sides for 30 minutes in a sufficient amount of dichloromethane and demasked analogously to the protection removal instructions to immobilize N-tert-butoxycarbonylnorgalanthamine (Example 147) and washed (in each case 6 ml of solvent). Then, the resin is reacted analogously to the above instructions with 730 μl (0.551 g, 4.260 mmol) of ethyldiisopropylamine and 0.379 g (1.278 mmol) of triphosgene in 6 ml of absolute dichloromethane. After the resin is washed and dried in a vacuum overnight, 0.653 g of N-chclorocarbonylnorgalanthamine-6-yloxy-1,5-dioxopentyloxymethyl-Merrifield resin is obtained.

After the resin (0.103 g, 0.065 mmol) is steeped and filtered. it is suspended in a solution that consists of 0.164 g (0.650 mmol) of N-tert-butoxycarbonyl-1,6-diaminohexanehydrochloride, 222 μl (0.168 g, 1.300 mmol) of ethyldiisopropylamine, 0.053 μl (0.051 g, 0.650 mmol) of pyridine and 2.0 ml of dimethylformamide (to dissolve the hydrochloride, the solution is heated beforehand). Then, the suspension is shaken at room temperature for 5.5 hours. The resin is washed three times with dimethylformamide (2 minutes, 1 ml) and six times with dichloromethane (2 minutes, 1 ml). After drying in a vacuum, the resin is shaken in 2 ml of tetrahydrofuran for 30 minutes, and after filtering, it is mixed with a solution that consists of 0.059 g (0.018 g, 0.325 mmol), 30% of sodium methanolate-methanol solution and 1.5 ml of tetrahydrofuran/methanol (4/1). After 9.5 hours of shaking at room temperature, the solution is filtered off, and the resin is extracted three times with 1.5 ml each of dichloromethane/methanol (1/1) and three times with 1.5 ml each of dichloromethane. The combined filtrates are neutralized with methanolic hydrochloric acid, diluted with 10 ml of dichloromethane, washed once with 15 ml of 2N hydrochloric acid and twice with 15 ml each of saturated sodium chloride solution, dried on sodium sulfate, filtered and concentrated by evaporation under reduced pressure in a rotary evaporator. The crude product (0.051 g) is separated by means of column chromatography (5 g of silica gel, chloroform/methanol=50/1).

After concentration by evaporation, a colorless oil is obtained.

Yield: 0.030 g (0.058 mmol, 89%), colorless oil ($M_W$=515.7) TLC: $R_f$=0.47 (chloroform/methanol=9/1) $^1$H-NMR: (200.13 MHz, CDCl$_3$, TMS) 6.73 (d, J=8.1 Hz, 1H), 6.66 (d, J=8.3 Hz, 1H), 5.90–6.07 (m, 2H), 4.23–4.70 (m, 5H), 4.13 (bs, 1H), 3.82 (s, 3H), 3.35 (t, J=13.5 Hz, 1.0 H), 2.96–3.20 (m, 4H), 2.67 (bd, J=15.7 Hz, 1H); 1.65–2.10 (m, 3H), 1.42 (s, 9H), 1.06–1.40 (m, 8H) $^{13}$C NMR: (50.32 MHz, CDCl$_3$, TMS) δ 157.2, 156.0, 147.0, 144.7, 132.5, 129.2, 128.1, 126.5, 120.2, 111.2, 88.4, 61.9, 55.9, 51.7, 48.5, 45.7, 42.1, 40.5, 39.3, 36.6, 30.0, 29.7, 28.4, 26.1, 23.5 HPLC: $t_{Ref}$=17.8 minutes, 98.7% (Merck Purospher column, 4.0 mm×125 mm, RP-18e, 5.0 μm, 1 ml/minute, 285 nm, acetonitrile/20 mmol of Cl$_3$CCO$_2$H in H$_2$O (20/80 for 5 minutes, 20/80→60/40 in 12 minutes, 60/40 for 5 minutes, v/v)

EXAMPLE 159

N-tert-Butyloxycarbonylglycine-[4-[(4aS,6R,8aS)-6-hydroxy-3-methoxy-5,6,9,10-tetrahydro-4aH-[1]benzofuro[3a,3,2-ef][2]benzazepine-11(12H)-yl]-3-aza-4-oxobutyl]amide (CK-58-2)

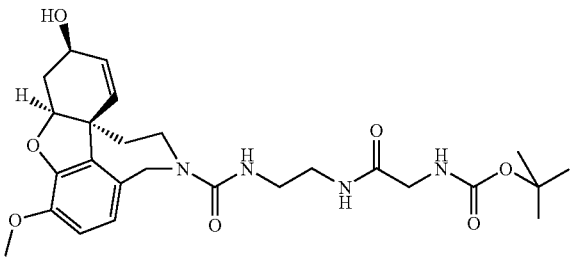

0.199 g (0.102 mmol) of norgalanathamine-6-yloxy-1,5-dioxopentyloxymethyl-Merrifield resin is steeped in a 5-ml-polyethylene frit that can be sealed on both sides for 30 minutes in 2 ml of dichloromethane, and after filtering, it is suspended in a solution of 120 μl (0.091 g, 0.700 mmol) of ethyldiisopropylamine in 1.5 ml of dichloromethane. Then, the suspension is mixed with a solution, cooled to 0° C., that consists of 0.062 g (0.210 mmol) of triphosgene and 0.5 ml of dichloromethane and shaken at room temperature for two hours. The resin is washed three times with dichloromethane (2 minutes, 2 ml) and three times with dimethylformamide (2 minutes, 2 ml). A solution that consists of 47 μl (0.042 g, 0.700 mmol) of ethylenediamine and 2.0 ml of dimethylformamide is subsequently added, and the suspension is shaken at room temperature. After three hours, the solution is filtered off, and the resin is washed six times with 2 ml each of dimethylformamide (2 minutes). (The Kaiser Test cannot be evaluated. The beads exhibit brown-red staining.) The resin is mixed with a solution that consists of 0.037 g (0.210 mmol) of N-BOC-glycine, 0.028 g (0.210 mmol) of 1-hydroxybenzotriazole and 1 ml of dimethylformamide, and the suspension is shaken for five minutes. Then, 0.043 g (0.210 mmol) of dicyclohexylcarbodiimide, dissolved in 1 ml of dichloromethane, is added. The suspension is shaken for three hours at room temperature, the resin is filtered, and it is washed three times with dimethylformamide (2 ml, 2 minutes) and six times with dichloromethane (2 ml, 2 minutes). After drying in a vacuum, 0.239 g of resin, which is shaken in tetrahydrofuran for 30 minutes, is obtained, and after filtering, it is mixed with a solution that consists of 0.076 g (0.023 g, 0.63 mmol) of 30% sodium methanolate-methanol solution and 2.0 ml of tetrahydrofuran/methanol (4/1). After 8.25 hours of shaking, the solution is filtered off, and the resin is extracted three times with 2 ml each of dichloromethane/methanol (1/1) and three times with 2 ml each of dichloromethane. The combined filtrates are neutralized with methanolic hydrochloric acid, diluted with 10 ml of dichloromethane, washed twice with 15 ml of saturated sodium chloride solution, dried on sodium sulfate, filtered and concentrated by evaporation in a rotary evaporator under reduced pressure. The crude product (0.064 g) is separated by means of column chromatography (5 g of silica gel, chloroform/methanol=25/1 15/1). After the concentration by evaporation, a colorless oil is obtained.

Yield: 0.030 g (0.025 g, 0.048 mmol, 47%), colorless oil ($M_W$=516.6) TLC: $R_f$=0.38 (chloroform/methanol=9/1) $^1$H-NMR: (200.13 MHz, CDCl$_3$, TMS) δ 6.90 (bs, 1H), 6.83 (d, J=8.1 Hz, 1H), 6.60–6.71 (m, 1H), 5.88–6.08 (m, 2H), 5.39 (bs, 1H), 5.19 (bs, 1H), 4.50–4.70 (m, 2H), 4.04–4.34 (m, 3H), 3.82 (s, 3H), 3.70 (d, J=6.1 Hz, 1H), 3.65 (d, J=5.6 Hz, 1H), 3.11–3.49 (m, 5H), 2.68 (d, J=15.9 Hz, 1H), 2.41 (d, J=10.9 Hz, 1H), 1.65–2.09 (m, 3H), 1.44 (s, 9H) HPLC: $t_{Ref}$=15.2 minutes, 82.3% (Merck Purospher column, 4.0 mm×125 mm, RP-18e, 5.0 μm, 1 ml/minute, 285 nm, MeOH/H$_2$O (5/95 for 5 minutes, 5/95→100/0 in 15 minutes (convex), 100/0 for 10 minutes, v/v) LC/MS: $t_{Ref}$=30.6 minutes, (Phenomenex Luna column, 3.0 mm×50 mm, RP-18, 3.0 μm, 0.8 ml/minute, methanol/H$_2$O (10/90 for 2 minutes, 10/90→100/0 in 15 minutes, 100/0 for 5 minutes, vv) APCI-PI-MS 517 (17), 499 (5), 461 (55), 443 (39), 417 (100), 399 (18), 274 (43), 256 (16)

EXAMPLE 160

SPH-1524

(4aS,6R,8aS)-6-(Benzoyloxy)-3-methoxy-5,6,9,10-tetrahydro-4aH-[1]benzofuro[3a,3,2-ef][2]benzazepine-11(12H)-yl)carboxylic Acid allyl ester (CK-65-1)

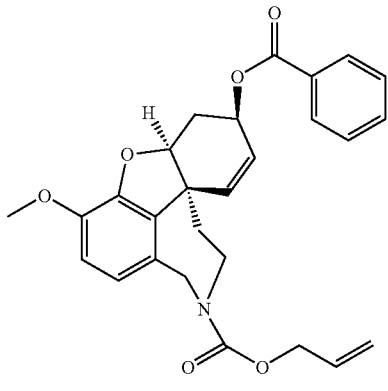

0.075 g (0.210 mmol) of N-allyloxycarbonylnorgalanthamine, 0.475 g (2.098 mmol) of benzoic acid anhydride and 0.013 g (0.105 mmol) of dimethylaminopyridine are introduced into 2 ml of dichloromethane and then mixed with 0.185 ml (0.136 g, 1.049 mmol) of ethyldiisopropylamine. After 13 hours at room temperature, the solution is taken up with 5 ml of saturated sodium bicarbonate solution, and extracted three times with 5 ml each of ethyl acetate. The combined organic extracts are washed with 10 ml of saturated sodium bicarbonate solution, twice with 10 ml of 2N hydrochloric acid and twice with 10 ml of saturated sodium chloride solution, dried on sodium sulfate, filtered and concentrated by evaporation in a rotary evaporator under reduced pressure. The residue is digested twice in each case with 10 ml of petroleum ether, and the solution is decanted off. The residue (0.100 g) is purified by column chromatography (10 g of silica gel, mobile solvent=petroleum ether/ethyl acetate=2/1).

Yield: 0.066 g (0.080 mmol, 68%), colorless foam ($M_W$=461.5) TLC: $R_f$=0.52 (ethyl acetate/petroleum ether=2/1) Melting point: 45–49° C. (ethyl acetate/petroleum ether=2/1) IR: KBr ν (cm$^{-1}$) 2946 (m), 1708 (s), 1509 (m), 1483 (m), 1276 (s), 1108 (m), 1056 (m), 714 (m) $^1$H-NMR: (200.13 MHz, CDCl$_3$, TMS) δ 8.06 (d, J=7.1 Hz, 1H), 7.29–7.61 (m, 3H), 6.59–6.84 (m, 2H), 6.28 (d, J=10.3 Hz, 5H), 6.07 (dd, J=5.0 Hz, J=10.2 Hz, 1H), 5.76–5.99 (m, 1H), 5.59 (t, J=4.4 Hz, 1H), 5.09–5.35 (m, 2H), 4.87 (dd, J=15.7 Hz, J=22.0 Hz, 1H), 4.05–4.70 (m, 5H), 3.89 (s, 3H), 3.29–3.60 (m, 1H), 2.81 (bd, J=16.1 Hz, 1H), 1.74–2.25 (m, 3H) $^{13}$C-NMR: (50.32 MHz, CDCl$_3$, TMS) δ 166.2 (s), 155.3 and 155.1 (s), 147.4 and 147.3 (s), 144.3 (s), 132.99 and 132.85 (d), 131.7 (d), 131.4 and 131.0 (s), 130.4 (s), 129.9 (d), 128.4 (d), 127.1 (d), 120.7 and 120.2 (d), 117.4 and 116.8 (t), 111.4 and 111.3 (d), 86 (d), 66.1 and 66.0 (t), 63.4 (d), 56.0 (q), 63 .8 (d), 51.9 and 51.4 (t), 48.3 (s), 45.8 and 45.4 (t), 37.9 and 37.0 (t), 27.8 (t)

Diagram for Examples 161 and 162

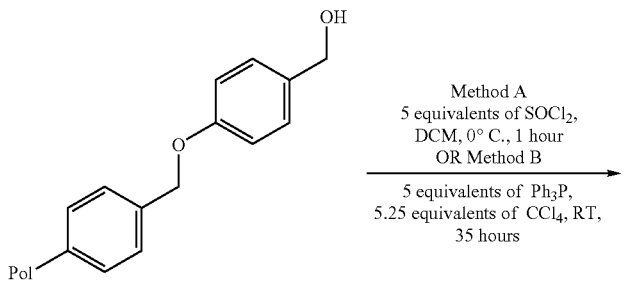

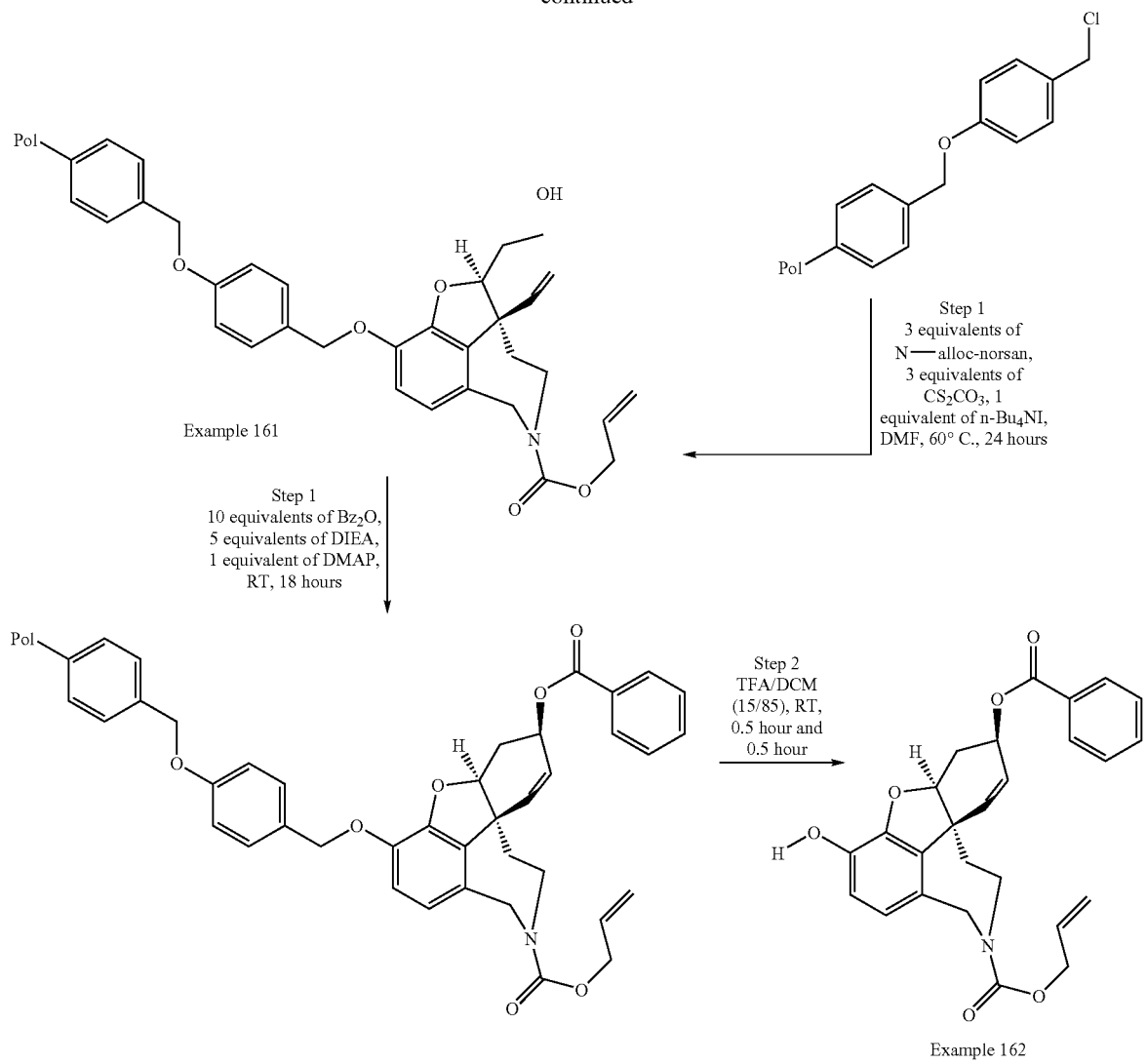
EXAMPLE 161
SPH-1525
Immobilization of (4aS,6R,8aS)-3,6-Dihydroxy-5,6,9,10-tetrahydro-4aH-[1]benzofuro[3a,3,2-ef]-[2]benzazepine-11(12H)-yl)carboxylic acid allyl ester on a para-hydroxymethylphenoxy-polystyrene resin (Wang resin)
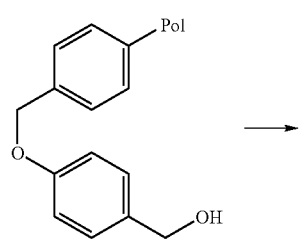
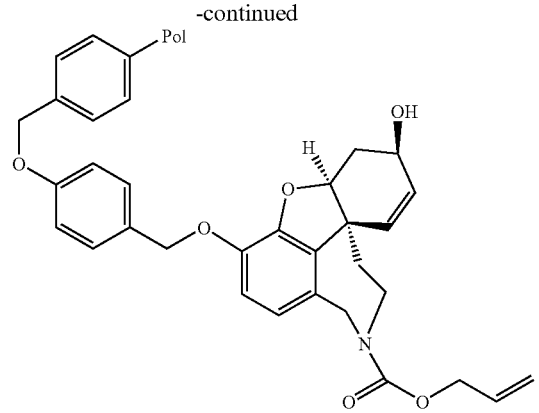
Method A (CK-63-2)
0.257 g (0.244 mmol) of Wang resin² is stirred under argon atmosphere in 3 ml of absolute dichloromethane for 15 minutes. Then, 86 µl (0.141 g, 1.19 mmol) of thionyl chloride is added in drops within five minutes at 0° C. The suspension is stirred at 0° C. for one hour. Then, the resin is moved to a polyethylene frit that can be sealed on both sides, and it is washed five times with dichloromethane (2 minutes, 2.5 ml), twice with methanol (2 minutes, 2.5 ml), once with dichloromethane (2 minutes, 2.5 ml) and once with diethyl ether (2 minutes, 2.5 ml). The resin is then dried in a vacuum on phosphorus pentoxide.

[2]P-Alkoxybenzyl alcohol resin, D-1250, Bachem Feinchemikalien AG

Step 1

0.2334 g of the chlorine-Wang resin that is thus produced, 0.232 g (0.713 mmol) of cesium carbonate, 0.088 g (0.238 mmol) of tetra-n-butylammonium iodide and 0.245 g (0.713 mmol) of N-alloc-norsanguinine are suspended in 3 ml of absolute dimethylformamide while being stirred. Then, the suspension is stirred for 24 hours at 60° C. After five hours, 1 ml of dimethylformamide is added to suspend the deposited precipitate. Then, the resin is moved to a polyethylene frit that can be sealed on both sides with dimethylformamide/water solution (2/1), and it is washed twice with dimethylformamide/water solution (2/1, 2 minutes, 2.5 ml), twice with dimethylformamide/water solution (1/2, 2 minutes, 2.5 ml), twice with methanol/water solution (1/1, 2 minutes, 2.5 ml), twice with methanol (2 minutes, 2.5 ml) and six times with dichloromethane (2 minutes, 2.5 ml).

Method B (CK-63-1)

0.121 ml (0.192 g, 1.247 mmol) of carbon tetrachloride is introduced into 2.0 ml of absolute dichloromethane at 0° C. While being stirred (KPG-stirrer), 0.311 g (1.188 mmol) of triphenylphosphine, dissolved in 1.0 ml of absolute dichloromethane, is added in drops within 15 minutes at 0° C. It is stirred for another ten minutes at 0° C. and then for another ten hours at room temperature, until triphenylphosphine can no longer be detected by thin-layer chromatography. 0.2506 g (0.238 mmol) of Wang resin[1] and 1.5 ml of dichloromethane are subsequently added, and the suspension is stirred for 35 hours at room temperature (300 s$^{-1}$). The working-up of the chlorinated Wang resin is carried out analogously to method A. After drying, 0.2403 g of chlorine-Wang resin, which is reacted analogously to step 1 above with the same amounts of cesium carbonate, tetra-n-butylammonium iodide and N-alloc-norsanguinine, is obtained.

[1]Zinc powder (Aldrich Company) mixed with 2N hydrochloric acid, thoroughly mixed, filtered off and first washed neutral with distilled water, then thoroughly rewashed with methanol

EXAMPLE 162

SPH-1526

Determination of Concentration, (4aS,6R,8aS)-6-(Benzoyloxy)-3-hydroxy-5,6,9,10-tetrahydro-4aH-[1]benzofuro[3a,3,2-ef][2]benzazepine-11(121)-yl) carboxylic acid allyl ester 1.1.1 Step 1 (CK-63-2)

To determine the concentration and to detect that the N-alloc-norsanguinine is bonded via the phenol function to the resin, the resin, which is obtained by method A and step 1, is mixed successively with a solution that consists of 0.537 g (2.375 mmol) of benzoic acid anhydride and 2 ml of dichloromethane and a solution that consists of 0.015 g (0.119 mmol) of dimethylaminopyridine, 0.203 ml (0.154 g, 1.188 mmol) of ethyldiisopropylamine and 0.5 ml of dichloromethane. Then, the suspension is shaken out at room temperature. After 18 hours, the resin is filtered off, washed six times with 2.5 ml each of dichloromethane (2 minutes) and once with 2.5 ml of diethyl ether (2 minutes) and dried in a vacuum on phosphorus pentoxide. 0.3085 g of substituted resin, which is suspended in absolute dichloromethane for 15 minutes and then is thoroughly filtered, is obtained.

Step 2

For cleavage, the resin is mixed with 2.5 ml of trifluoroacetic acid/dichloromethane solution (15/85), shaken for 30 minutes at room temperature, filtered and shaken again with 2.5 ml of trifluoroacetic acid/dichloromethane solution (15/85), filtered and finally extracted four times with 2.5 ml of dichloromethane in each case. The combined filtrates or extracts are taken up with 10 ml of distilled water and set at pH 6 with sodium bicarbonate. The phases are separated, and the aqueous phase is extracted three times with 10 ml of dichloromethane. The combined organic extracts are washed twice with 10 ml each of saturated sodium chloride solution, dried on sodium sulfate, filtered and concentrated. The purification of the crude product (0.078 g) is carried out by means of column chromatography (10 g of silica gel, ethyl acetate/petroleum ether=2/1). After concentration by evaporation and drying under high vacuum, 0.078 g of a colorless foam is obtained that is 95% pure according to HPLC analysis. The colorless foam can be purified by recrystallization from diethyl ether at −22° C. (deep freeze from the refrigerator).

Yield: 0.059 g (0.056, 0.0125 mmol, thus a concentration of 0.41 mmol/g, 61% of theoretical maximum concentration[2] is calculated), colorless foam ($M_W$=447.5) TLC: $R_f$=0.29 (ethyl acetate/petroleum ether=1/1) Melting point: 158–159° C. (diethyl ether) $^1$H-NMR: (200.13 MHz, $d_6$-DMSO) δ 7.99 (d, J=6.5 Hz, 2H), 7.38–7.71 (m, 3H), 6.39–6.63 (m, 3H), 5.73–6.17 (m, 2H), 5.47 (t, J=4.3 Hz, 1H), 5.04–5.33 (m, 2H), 4.00–4.72 (m, 6H), 2.60–2.89 (m, 1H), 2.55 (bd, J=18.6 Hz, 1H), 2.25 (bd, J=15.7 Hz, 1H), 1.70–1.93 (m, 2H) $^{13}$C-NMR: (50.32 MHz, $d_6$-DMSO) δ 165.4 (s), 154.6 and 154.4 (s), 146.3 (s), 141.3 (s), 133.5 (d), 133.3 (d), 133.2 (d), 131.8 (d), 131.5 (s, 130.2 (s), 129.5 (d), 128.6 (d), 128.0 (s), 122.2 (d), 120.4 and 120.0 (d), 117.0 and 116.1 (t), 115.0 (d), 84.7 (d), 65.2 and 65.0 (t), 63.8 (d), 51.0 and 50.5 (t), 48.0 (s), 45.1 and 44.7 (t), 37.3 and 36.4 (t), 27.4 (t) HPLC: $t_{Ref}$=21.41 minutes, 95.1% (Merck Purospher column, 4.0 mm×125 mm, RP-18e, 5 µm, 285 nm, 1 ml/minute, acetonitrile/20 mmol of $Cl_3CCO_2H$ in $H_2O$ (15/85 for 5 minutes, 15/85→60/40 in 12 minutes, 60/40 for 5 minutes, v/v)

[2] 0.67 mmol/g=0.95 mmol/g/(1 g+1 g * 0.95 mol/g * (447.5 g/mol −18 g/mol)/1000

(CK-63-1)

The resin, which is obtained by method B and step 1, is reacted analogously to step 1 with benzoic acid anhydride, and after drying under vacuum, 0.3004 g of the substituted resin is obtained. The cleavage of the product and the aqueous working-up are carried out analogously to step 2. After the concentration by evaporation and the drying in a vacuum, 0.070 g of crude product, which is purified by means of column chromatography (10 g of silica gel, ethyl acetate/petroleum ether=2/1), is obtained. After concentration by evaporation and drying under high vacuum, 0.051 g of a colorless foam, which is 93% pure according to HPLC analysis, is obtained.

Yield: 0.051 g (0.047 g, 0.0106 mmol, thus a concentration of 0.35 mmol/g, 52% of the theoretical maximum concentration[3], is calculated), colorless foam ($M_W$=447.5) HPLC: $t_{Ref}$=21.42 minutes, 92.7% (Merck Purospher column, 4.0 mm×125 mm, RP-18e, 5 μm, 285 nm, 1 ml minute, acetonitrile/20 mmol of $Cl_3CCO_2H$ in $H_2O$ (15/85 for 5 minutes, 15/85→60/40 in 12 minutes, 20 60/40 for 5 minutes, v/v)

[3] 0.67 mmol/g=0.95 mmol/g/(1 g+1 g * 0.95 mol/g * (447.5 g/mol −18 g/mol)/1000)

EXAMPLE 163

Synthesis of the Solid Phase/Manual

Diagram for Example 163

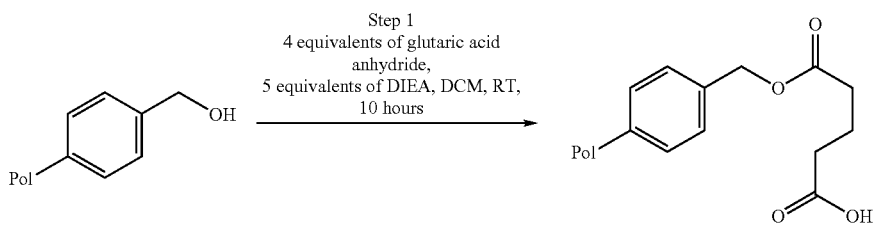

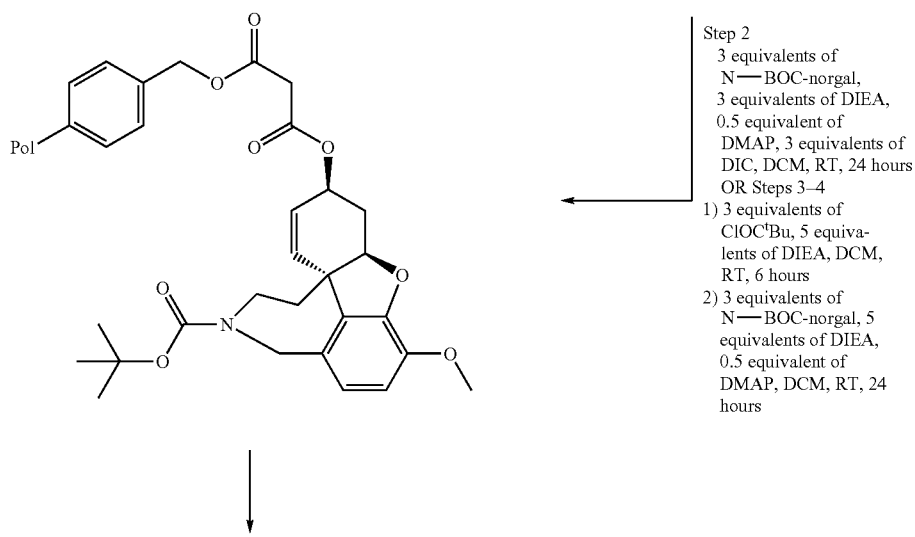

-continued

Step 5
TCA/DCM/anisole(25/70/5),
RT, 1.5 hours

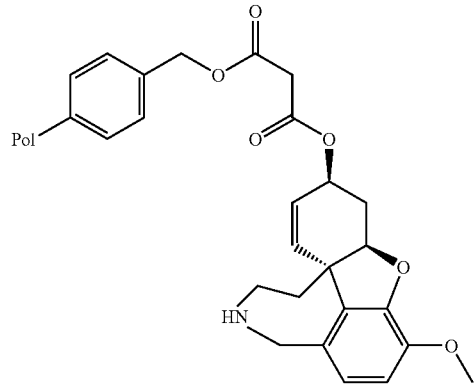

Steps 6–7
a) 25 equivalents of Ac2O, 15 equivalents of DIEA, DMF, RT, 9 hours
b) 0.3 M NaOMe THF/MeOH(4/1), RT, 8 hours

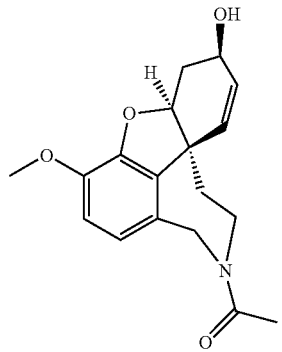

Steps 8–13
a) 3 equivalents of TBTU, 3 equivalents of Fmoc—Phe—OH,
  6 equivalents of DIEA, DMF, RT, 3 hours
b) Pip/DMF(2/8), RT, 2 and 10 minutes
c) 3 equivalents of TBTU, 3 equivalents of Fmoc—Phe—OH,
  6 equivalents of DIEA, DMF, RT, 0.5 hour
d) Pip/DMF(2/8), RT, 2 and 10 minutes
e) 3 equivalents of TBTU, 3 equivalents of p-MeO—C6H4—CO2H,
  6 equivalents of DIEA, DMF, RT, 12 hours
f) 0.5 M NaOMe, THF/MeOH(4/1), RT, 8 hours

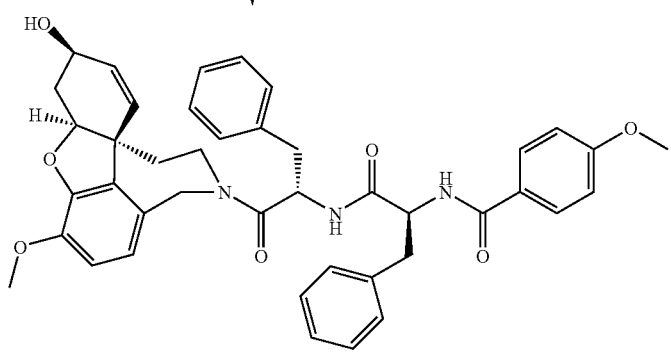

EXAMPLE 163

Steps 1–7

Immobilization of (4aR,6S,8aR)-3-Methoxy-5,6,9,10,11,12-hexahydro-4aH-[1]benzofuro[3a,3,2-ef][2]benazepin-6-ol on a Hydroxymethyl-Polystyrene Resin (Merrifield Resin)

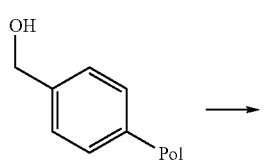

-continued

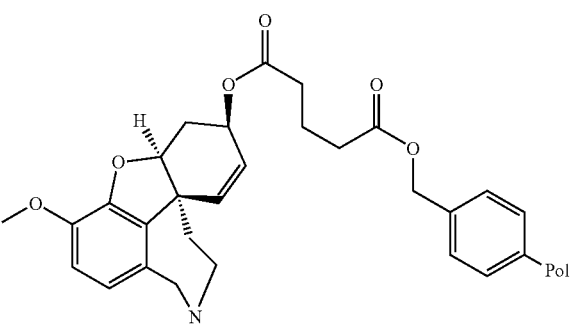

Method A (CK-41-1) Steps 1–2 and 5–7

5.000 g (5.2 mmol) of hydroxymethyl-Merrifield resin[4] is stirred in a three-neck glass reactor with a frit that is recessed in the bottom and a KPG stirrer in 60 ml of dichloromethane for one hour (300 s$^{-1}$). After filtering, the suspension is mixed with a solution of 2.373 g (20.8 mmol) of glutaric acid anhydride, 4.45 ml (3.362 g, 26.0 mmol) of ethyldiisopropylamine in 30 ml of absolute dichloromethane. The suspension is stirred at room temperature for ten hours, filtered, washed once with 50 ml of dichloromethane, once with 50 ml of methanol and three times with 50 of dichloromethane in each case. The resin is then dried in a vacuum.

[4]Hydroxymethyl resin, D-1160, Bachem Feinchemikalien AG 4.385 g of the 4-carboxy-1-oxobut-1-yloxymethyl-Merrifield resin that is thus produced is suspended for 30 minutes in 50 ml of absolute dichloromethane while being stirred, and it is filtered. Then, 4.569 g (12.23 mmol) of N-tert-butoxycarbonylnorgalanthamine and 0.249 g (2.04 mmol) of dimethylaminopyridine, both dissolved in 15 ml of dichloromethane, and 2.10 ml (1.582 g, 12.23 mmol) of ethyldiisopropylamine, dissolved in 5 ml of dichloromethane, are added. While being stirred, a solution that consists of 1.89 ml (1.544 g, 12.23 mmol) of diisopropylcarbodiimide and 5 ml of dichloromethane is added in drops within five minutes at room temperature. After 24 hours, the resin is filtered off, washed with 40 ml of methanol and filtered. Then, the resin is washed six times with 40 ml of dichloromethane in each case (5 minutes) and dried in a vacuum.

The resin is mixed with 42 ml of absolute dichloromethane and 3 ml of anisole and stirred for 30 minutes (150 s$^1$). Then, while being stirred (300 s$^1$), 15 ml of trifluoroacetic acid is added within 15 minutes. Then, the suspension is stirred for 60 minutes (150 s$^1$), filtered and washed with dichloromethane (2×40 ml, 5 minutes), with dichloromethane/dimethylformamide/triethylamine (5/4/1) (3×40 ml, 5 minutes) and finally with dichloromethane (5×40 ml, 5 minutes). After drying in a vacuum, 4.353 g of resin is obtained.

To determine the concentration, 0.2384 g of resin in 3 ml of dimethylformide is suspended in a polyethylene frit that can be sealed on both sides. After filtering, the resin is shaken in a solution that consists of 177 μl (0.191 g, 1.875 mmol) of acetic acid anhydride, 180 μl (0.136 g, 1.050 mmol) of ethyldiisopropylamine and 2 ml of dimethylformamide for nine hours at room temperature. After washing (dimethylformamide (3×2.5 ml, 2 minutes) and tetrahydrofuran/methanol (4/1) (5×2.5 ml, 2 minutes), the resin shows no reaction with the chloranil test. The polymer is suspended in a 0.3 M sodium methanolate solution in tetrahydrofuran/methanol (4/1). The resin is shaken for 8 hours at room temperature, filtered and extracted with methanol/dichloromethane (1/1, 3×2.5 ml) and with dichloromethane (3×2.5 ml). The combined filtrates are neutralized with methanolic hydrochloric acid. The solution is diluted with about 10 ml of dichloromethane, washed with 25 ml of saturated sodium bicarbonate solution, 1N hydrochloric acid and saturated sodium chloride solution in each case, dried on sodium sulfate, filtered and concentrated. The purification is carried out by means of column chromatography (10 g of silica gel, diethyl ether/ethanol=100/15). After concentration by evaporation and drying under high vacuum, 0.028 g of a yellowish foam, which contain 10% other contaminants according to HPLC analysis, is obtained.

Yield: 0.025 g (0.080 mmol. A concentration of 0.34 mmol/g, 45% of the theoretical maximum concentration[5] thus is calculated), yellowish foam ($M_W$=315.4) TLC: $R_f$=0.29 (diethyl ether/ethanol=100/15) IR: Kr v (cm$^{-1}$) 3551 (v), 3305 (bm), 2926 (m), 2864 (v), 1650 (m), 1615 (s), 1443 (m), 1257 (m), 1070 (m); $^1$H-NMR: (200.13 MHz, CDCl$_3$, TMS) δ 6.54–6.89 (m, 2H), 5.75–6.09 (m, 2H), 5.14–5.33 (m, 0.3H), 4.32–4.74 (m, 3.3H), 4.12 (bs, 1H), 3.86–4.00 (m, 0.3H), 3.81 and 3.79 (s, 3H), 3.56–3.76 (m, 0.8H), 3.23 (bt, J=12.6 Hz, 0.8H), 2.67 (bd, J=15.9 Hz, 1H), 2.38 (bs, 0.7H), 2.06 (m, 3H), 1.62–2.00 (m, 3H), HPLC: $t_{Ref}$=13.9 minutes, 89.8% (Merck Purospher column, 4.0 mm×125 mm, RP-18e, 5 μm, 285 nm, 1 ml/minute, acetonitrile/20 mmol of Cl$_3$CCO$_2$H in H$_2$O (05/95 for 5 minutes, 05/95→60/40 in 10 minutes, 10/40 for 10 minutes, v/v, pH 10)

[5]0.75 mmol/g=1.04 mmol/g/(1 g+1 g * 1.04 mol/g * (387.4 g/ml=18 g/mol)/1000)

Method B (CK-43-2), Steps 1 and 3–7

3.500 g (3.64 mmol) of hydroxymethyl-Merrifield resin[6] is reacted analogously to the method that is described under method A with 1.661 g (14.6 mmol) of glutaric acid anhydride, 3.15 ml (2.378 g, 18.39 mmol) of ethyldiisopropylamine and 0.044 g (0.364 mmol) of dimethylaminopyridine in 20 ml of absolute dichloromethane. After washing, the resin is stirred successively with a solution that consists of 3.15 ml (2.378 g, 18.39 mmol) of ethyldiisopropylamine, and 10 ml of absolute dichloromethane and with a solution that consists of 1.34 ml (1.317 g, 10.92 mmol) of pivaloyl chloride and for nine hours at room temperature. After washing (dichloromethane (4×30 ml, 5 minutes), tetrahydrofuran (30 ml, 5 minutes) and dichloromethane (2×30 ml, 5 minutes), the resin is successively treated with 4.061 g (10.87 mmol) of N-tert-butoxycarbonylnorgalanthamine and 0.222 g (1.82 mmol) of dimethylaminopyridine, both dissolved in 15 ml of dichloromethane, and 3.15 ml (2.378 g, 18.39 mmol) of ethyldiisopropylamine, dissolved in 15 ml of dichloromethane. After 24 hours at room temperature, the solution is filtered off, and the resin is mixed with 40 ml of a dry solution that consists of methanol and dichloromethane, and it is stirred for ten minutes at room temperature. After filtering, six cycles of washing with dichloromethane and drying in a vacuum, the resin is washed and dried with 40 ml of trifluoroacetic acid/dichloromethane/anisole (25/70/5) analogously to method A. 4.145 g of a yellow resin is obtained. 0.2214 g of the resin is reacted to determine the concentration analogously to the method, and it is purified. 0.024 g of a yellowish foam, which is 90% pure according to HPLC analysis, is obtained.

[6]Hydroxymethyl resin, D-1160, Bachem Feinchemikalien AG

Yield: 0.022 g (0.069 mmol. This corresponds to a concentration of 0.31 mmol/g, 41% of the theoretical maximum concentration). HPLC: $t_{Ref}$=14.4 minutes, 89.0% (Merck Purospher column, 4.0 mm×125 mm, RP-18e, 5 μm, 285 nm, 1 ml/minute, acetonitrile/20 mmol of Cl$_3$CCO$_2$H in H$_2$O (05/95 for 5 minutes, 05/95→60/40 in 10 minutes, 60/40 for 10 minutes, v/v, pH 10)

EXAMPLE 163

Steps 8–13

SPH-1528

1,2 N-P-METHOXYBENZOYL-PHENYLALA-
NYL-PHENYLALANINE-((4AS,6R,8AS)-6-HY-
DROZY-3-METHOXY-5,6,9,10-TETRAHYDRO-
4AH-[1]BENZOFURO[3A,3,2-EF][2]
BENZAZEPINE-11(12H)-YL)-AMIDE (CK-47-1)

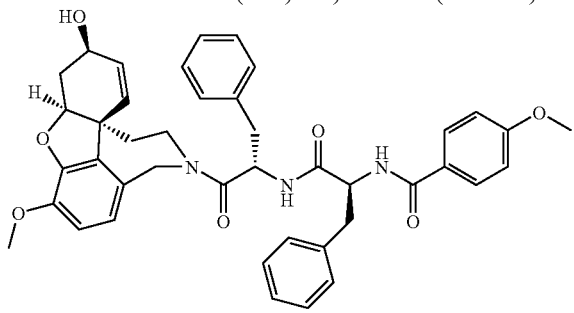

0.245 g (0.076 mmol) of N-tert-butoxycarbonylnorgalan-thamine-6-yloxy-1,5-dioxopentyloxymethyl-Merrifield resin is steeped twice in a 5-ml-polyethylene frit that is sealed on both sides for 15 minutes in 3 ml of dimethylformamide, and after filtering, it is suspended in a solution of 0.065 g (0.169 mmol) of Fmoc-phenylalanine and 0.062 g (0.169 mmol) of 2-(1H-benzotriazol-1-yl)-1,3,3-tetramethyluronium tetrafluoroborate in 1 ml of dimethylformamide each, and it is shaken for five minutes at room temperature. Then, 58 μl (0.044 g, 0.338 mmol) of ethyldiisopropylamine in 0.5 ml of dimethylformamide is added. The suspension is shaken at room temperature for 3 hours. The resin is washed six times with dimethylformamide (1 minute, 2.5 ml) and suspended in a 20% piperidine solution in dimethylformamide for two and ten minutes in each case at room temperature. After six washing cycles with dimethylformamide (1 minute, 2.5 ml), the resin is reacted analogously to the first peptide coupling step with 0.065 g (0.169 mmol) of Fmoc-phenylalanine and 0.062 g (0.169 mmol) of 2-(1H-benzotriazol-1-yl)-1,3,3-tetramethyluronium tetrafluoroborate in 1 ml of dimethylformamide in each case and 58 μl (0.044 g, 0.338 mmol) of ethyldiisopropylamine in 0.5 ml of dimethylformamide, washed with dimethylformamide, shaken in 20% piperidine-dimethylformamide solution and in turn washed six times with dimethylformamide (1 minute, 2.5 ml). Then, solutions of 0.065 g (0.169 mmol) of Fmoc-Phe-OH in 1 ml of dimethylformamide, 0.062 g (0.169 mmol) of 2-(1H-benzotriazol-1-yl)-1,1,3,3-tetramethyluronium tetrafluoroborate in 1 ml of dimethylformamide and 58 μl (0.044 g, 0.338 mmol) of ethyldiisopropylamine in 0.5 ml of dimethylformamide are added successively, and the suspension is shaken for 30 minutes at room temperature. The Kaiser test indicates complete reaction. Then, it is washed analogously to the above-described procedure, suspended in piperidine-dimethylformamide solution and washed in turn with dimethylformamide. After renewed successive addition of 0.026 g (0.169 mmol) of p-methoxybenzoic acid in 1 ml of dimethylformamide, 0.062 g (0.169 mmol) of 2-(1H-benzotriazol-1-yl)-1,1,3,3-tetramethyluronium tetrafluoroborate in 1 ml of dimethylformamide and 58 μl (0.044 g, 0.338 mmol) of ethyldiisopropylamine in 0.5 ml of dimethylformamide, the resin is shaken overnight, since the Kaiser test was not unambiguous after 30 minutes because of a green-bluish staining. The resin is filtered, washed three times with dimethylformamide, five times with dichloromethane and with methanol and then dried in a vacuum. The resin (0.251 g) is suspended for 30 minutes in THF, filtered and suspended in a solution that consists of 0.250 g (1.39 mmol) of 30% sodium methanolate-methanol solution and 2.5 ml of tetrahydrofuran/methanol (4/1). After eight hours, the solution is filtered off, and the resin is extracted six times with 3 ml of dichloromethane/methanol in each case. The combined filtrates are neutralized with 106 μl (0.158 g, 1.39 mmol) of trifluoroacetic acid, concentrated and separated with preparative thin-layer chromatography (silica gel, chloroform/methanol=100/5). The product-containing silica gel fraction is extracted with chloroform/methanol (9/1), and the combined extracts are filtered repeatedly with a filter (pore diameter 0.2 μm), concentrated by evaporation and dried in a vacuum.

Yield: 0.041 g (0.029 g, 0.041 mmol, 53%), rose-colored wax ($M_W$=701.8). The product contains a by-product (0.006 g, 0.008 mmol, 10%) that is a diastereomer of the main product according to LC/MS. TLC: $R_f$=0.43 (chloroform/methanol=20/1) HPLC: $t_{Ref}$=2.7 minutes, 70.4% (Phenomenex Luna column, 3.0 mm×50 mm, RP-18, 3.0 μm, 0.5 ml/minute, 285 nm, methanol/20 mmol of $Cl_3CCO_2H$ in $H_2O$ (30/70 v/v) LC/MS: $t_{Ref}$=30.6 minutes, 73%, (Phenomenex Luna column, 3.0 mm×50 mm, RP-18, 3.0 μm, 0.5 ml/minute, methanol/$H_2O$ (5/95 v/v for 2 minutes, 5/95→40/60 v/v in 15 minutes, 40/60 v/v for 5 minutes) APCI-PI-MS 702 (56), 421 (100), 274 (6), 256 (13) APCI-PI-MS 700 $t_{Ref}$=35.6 minutes, 8%, (diastereomeric by-product) APCI-PI-MS 702 (56), 421 (100), 274 (6), 256 (13) APCI-NI-MS 700

1.3

1.4 EXAMPLES 163–167

Synthesis on Robots 1.5

1.6 N-P-CARBOXYL-DIPEPTOYL-((4as,6R,8AS)-
6-HYDROXY-3-METHOXY-5,6,9,10-TETRAHY-
DRO-4AH-[1]BENZOFURO[3A,3,2-EF][2]BEN-
ZAZEPINE-11(12H)-YL)AMIDE (CK-59-1)

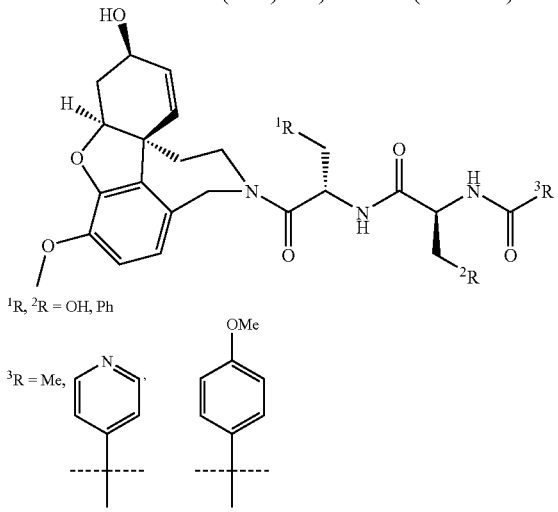

$^1R, ^2R$ = OH, Ph $^3R$ = Me,

In each case, 0.300 g (0.102 mmol) of norgalanthamine-6-yloxy-1,5-dioxopentyloxymethyl-Merrifield resin is introduced into polyethylene reactors with frits of a synthesis robot (Syro II MultiSynTech) and mixed with 3 ml of absolute dimethylformamide. After five minutes of standing, the suspensions are stirred at intervals for 25 minutes at 23° C. All subsequent operations are carried out at this temperature. Then, the resins are washed once with 3 ml of dimethylformamide and mixed successively with a solution that consists of 0.119 g (0.306 mmol) of Fmoc-phenylalanine or 0.117 g (0.306 mmol) of N-Fmoc-O-tert-butylserine and 1.5 ml of dimethylformamide and with a solution that consists of 0.112 g (0.306 mmol) of 2-(1H-benzotriazol-1-yl)-1,1,3,3-tetramethyluronium tetrafluoroborate and 1 ml of dimethylformamide. Then, the resin suspensions are stirred for five minutes. Then, 105 µl (0.079 g, 0.612 mmol) of ethyldiisopropylamine in 0.5 ml of dimethylformamide is added. The suspensions are stirred for 3 hours, suctioned off for two minutes and in each case mixed with a solution that consists of 241 µl (0.260 g, 2.550 mmol) of acetic anhydride, 437 µl (0.330 g, 2.550 mmol) of ethyldiiospropylamine and 3 ml of dimethylformamide. After 15 minutes of stirring and two minutes of filtering, the resins are washed six times with dimethylformamide (3 ml, 2 minutes), and suspended or stirred in a 20% piperidine solution in dimethylformamide for six and 15 minutes in each case. After six cycles of washing with dimethylformamide (2 minutes, 3 ml), the resins are reacted analogously to the first peptide coupling step with Fmoc-phenylalanine or N-Fmoc-O-tert-butylserine, the unreacted amine groups are masked with acetic anhydride, and the Fmoc-protective group is cleaved off with 20% piperidine-dimethylformide solution. It is then washed analogously to the above-described procedure, mixed with a solution that consists of 0.047 g (0.306 mmol) of p-methoxybenzoic acid or 0.038 g (0.306 mmol) of isonicotinic acid in 2.5 ml of dimethylformamide and stirred for five minutes. Then, in each case, solutions of 48 µl (0.039 g, 0.306 mmol) of diisopropylcarbodiimide 241 µl and 0.5 ml of 1,2-dichloroethane are added. It is stirred for three hours. The resins are filtered (2 minutes), washed three times with dimethylformamide (2 minutes, 3 ml), six times with dichloromethane (2 minutes, 3 ml), dried for ten minutes at 40° C., suctioned off and then dried in a vacuum on phosphorus pentoxide. The Kaiser test is negative in all resins (0.250 to 0.377 g).

The resins that contain O-tert-butyl-protected serine radicals are mixed successively with 1 ml of dichloromethane, 0.125 ml of phenol, 0.125 ml of anisole and 3.75 ml of trifluoroacetic acid, and it is stirred for three hours at room temperature. Then, the solutions are filtered off, and the resins are washed three times with dichloromethane (2 minutes, 3 ml), three times with dichloromethane/ethyldiisopropylamine (95/5, 2 minutes, 3 ml), three times with dichloromethane (2 minutes, 3 ml) in each case, and three times with tetrahydrofuran (2 minutes, 3 ml) and dried under reduced pressure.

The resins are transferred to 5-ml polyethylene frits that are sealed on both sides, suspended for 30 minutes in THF, filtered and suspended in a solution that consists of 0.092 g (0.028 g, 0.510 mmol) of 30% sodium methanolate-methanol solution and 3 ml of tetrahydrofuran/methanol (4/1). After six hours, the solution is filtered off, and the resin is extracted five times with 3 ml of tetrahydrofuran/methanol (4/1) in each case. The combined filtrates are neutralized with Dowex BOW (one spatula tip full) and $NaHCO_3$ (one spatula tip full). The suspensions are filtered on some Celite, and the filter Celite is flushed twice with 5 ml of dichloromethane. The filtrates are concentrated and purified with preparative thin-layer chromatography (mobile solvent: chloroform/methanol=(10/1) for CK-49-1-IPP-3, CK-59-MPP-1, CK-59-IPP-2, CK-59-AcPP-3, chloroform/methanol=(4/1) for CK-59-IPP-4 and chloroform/methanol=(6/1) for CK-59-MPP-5). The product-containing silica gel fractions are extracted with chloroform/methanol (9/1) and filtered. The extracts that are concentrated by evaporation are filtered repeatedly with a filter (pore diameter 0.2 µm), further concentrated by evaporation and dried in a vacuum.

HPLC: Phenomenex Synergi Polar-RP-column, 4.6 mm×150 mm, 4.0 µm, 1.0 ml/minute, methanol/20 mm of $Cl_3CCO_2H$ in $H_2O$ (20/80 for 5 minutes, 20/80→80/20 in 20 minutes, 80/20 for 10 minutes, v/v) LC/MS Phenomenex Luna column, 3.0 mm×50 mm, RP-18, 3.0 µm, 0.8 ml/minute, methanol/$H_2O$ (10/90 for 2 minutes, 10/90→100/0 in 15 minutes, 100/0 for 5 minutes, v/v)

| | | | Result | | |
|---|---|---|---|---|---|
| | Beispiel | SPH-Nummer | Aminosäure 1 und 2 | Carboxylrest 3 | $R_f$-Wert |
| CK-59-MPP-1-1 | 163 | SPH-1528 | Ph, Ph | 4-$MeOC_6H_4$ | 0.60 ($CHCl_3/CH_3OH$ = 10/1) |
| CK-59-MPP-1-2 | | | Ph, Ph | 4-$MeOC_6H_4$ | 0.45 ($CHCl_3/CH_3OH$ = 10/1) |
| CK-49-1-IPP-3-1 | 166 | SPH-1528 | Ph, Ph | p-$NC_5H_4$ | 0.40 ($CHCl_3/CH_3OH$ = 9/1) |
| CK-59-AcPP-3-1 | 164 | SPH-1528 | Ph, Ph | Me | 0.52 ($CHCl_3/CH_3OH$ = 10/1) |
| CK-59-AcPP-3-2 | | | Ph, Ph | Me | 0.43 ($CHCl_3/CH_3OH$ = 10/1) |
| CK-59-ISS-4-1 | 165 | SPH-1528 | OH, OH | p-$NC_5H_4$ | 0.22 ($CHCl_3/CH_3OH$ = 6/1) |
| CK-59-ISS-4-2 | | | OH, OH | p-$NC_5H_4$ | 0.17 ($CHCl_3/CH_3OH$ = 6/1) |
| CK-59-MSS-5-1 | 167 | SPH-1528 | OH, OH | 4-$MeOC_6H_4$ | 0.37 ($CHCl_3/CH_3OH$ = 6/1) |
| CK-59-MSS-5-2 | | | OH, OH | 4-$MeOC_6H_4$ | 0.27 ($CHCl_3/CH_3OH$ = 6/1) |

[Key to Table:]
Beispiel = Example
SPH-Nummer = SPH Number
Aminosäure 1 und 2 = Amino acid 1 and 2
Carboxylrest 3 = Carboxyl radical 3
$R_f$-Wert = $R_f$ value

| Beispiel | Code | HPLC ($t_{Ret}$, Reinheit) | LC/MS | Ausbeute und Bemerkung |
|---|---|---|---|---|
| 163 | CK-59-MPP-1-1 | 29.90 min (71 %) | $t_{Ret}$ = 10.90 min APCI, Neg 700 (100) APCI, Pos 702 (63), 684 (8), 421 (100), 274 (5), 256 (15) | 0.021 g (0.015 g, 0.021 mmol, 21%) |
|  | CK-59-MPP-1-2 | 29.35 min (24 %) | $t_{Ret}$ = 10.90 min APCI, Neg 700 (100), 682 (7), 606 (13) APCI, Pos 702 (63), 684 (26), 608 (28), 421 (100), 274 (11), 256 (19) | 0.014 g (0.003 g, 0.005 mmol, 5%); racemisiertes Produkt |
| 166 | CK-49-1-IPP-3-1 | 24.91 min (59 %) | $t_{Ret}$ = 20.22 min APCI, Neg 671 (100) APCI, Pos 673 (100), 655 (18), 421 (7), 274 (6), 256 (53) | 0.067 g (0.040 g, 0.059 mmol, 58%) |
| 164 | CK-59-AcPP-3-1 | 26.50 min (50 %) | $t_{Ret}$ = 10.08 min APCI, Neg 608 (100) APCI, Pos 610 (100), 592 (15), 421 (17), 274 (8), 256 (40) | 0.058 g (0.029 g, 0.048 mmol, 47%) |
|  | CK-59-AcPP-3-2 | 26.09 min (54%) | $t_{Ret}$ = 10.01 min APCI, Neg 608 (100) APCI, Pos 610 (100), 592 (24), 421 (20), 274 (18), 256 (69) | 0.019 g (0.011 mmol, 0.017 mmol, 17%); racemisiertes Produkt |
| 165 | CK-59-ISS-4-1 | 14.67 min (92%) | $t_{Ret}$ = 7.49 min APCI, Neg 551 (100), 533 (26), 521 (17), 491 (6) APCI, Pos 553 (100), 535 (36), 403 (6), 385 (9), 256 (100) | 0.009 g (0.008 g, 0.015 mmol, 15%) |
|  | CK-59-ISS-4-2 | 15.90 min (48%) | $t_{Ret}$ = 7.63 min APCI, Neg 551 (100), 533 (25), 521 (19), 491 (5) APCI, Pos 553 (100), 535 (70), 517 (7), 274 (9), 256 (57) | 0.004 g (0.002 g, 0.003 mmol, 3%); racemisiertes Produkt |
| 167 | CK-59-MSS-5-1 | 21.12 min (27%) und 21.57 min (26 %) | $t_{Ret}$ = 8.35 min APCI, Neg 580 (100), 562 (17), 550 (15), 520 (6) APCI, Pos 582 (49), 564 (43), 546 (67), 361 (100), 256 (55) $t_{Ret}$ = 8.49 min APCI, Neg 580 (100), 562 (21), 550 (16), 520 (9) APCI, Pos 582 (43), 564 (47), 546 (51), 361 (100), 256 (64) | 0.013 g (0.007 g, 0.012 mmol, 12%) racemisiertes Produkt |
|  | CK-59-MSS-5-2 | 21.27 min (10%) und 21.58 (15 %) | $t_{Ret}$ = 8.39 min APCI, Neg 580(100) $t_{Ret}$ = 8.64 min APCI, Neg 580 (100), 562 (35), 550 (14) APCI, Pos 582 (63), 564 (77), 546 (77), 361 (100), 256 (63) | 0.008 g (0.002 g, 0.003 mmol, 3%); racemisiertes Produkt |

[Key to Table:]
Beispiel = Example
HPLC ($t_{Ref}$, Reinheit) = HPLC ($t_{Ref}$, purity)
Ausbeute und Bemerkung = Yield and Remarks
racemisiertes Product = Racemized product

EXAMPLE 167b

SPH-1543

As a by-product, N-acetyl-phenylalanine-((4aS,6R,8aS)-6-hydroxy-3-methoxy-5,6,9,10-tetrahydro-4aH-[1]benzofuro-[3a,3,2-ef]-[2]benzazepine-11(12H)-yl)amide was obtained:

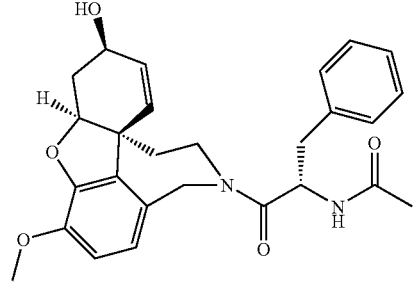

| Code | HPLC ($t_{Ref}$, Reinheit) | LC/MS und $R_f$-Wert | Ausbeute und Bemerkung |
|---|---|---|---|
| CK-59-IPP-2-1 | 23.49 min (67%) | $t_{Ref}$ = 9.37 min APCI, Neg 461 (100) ARCI, Pos 463 (100), 445 (8), 274 (17), 256 (31) 0.50 (CHCl$_3$/CH$_3$OH = 10/1) | 0.036 g (0.031 g, 0.077 mmol, 76%) |

-continued

| Code | HPLC ($t_{Ref}$, Reinheit) | LC/MS und $R_f$-Wert | Ausbeute und Bemerkung |
|---|---|---|---|
| CK-59-IPP-2-2 | 23.60 min (66%) | $t_{Ref}$ = 9.40 min<br>APCI, Neg<br>461 (100)<br>APCI, Pos<br>463 (100), 445 (17), 274 (32), 256 (60)<br>0.36 ($CHCl_3/CH_3OH$ = 10/1) | 0.012g (0.008 g, 0.17 mmol, 17%); racemisiertes Produkt |

[Key to Table:]
HPLC ($t_{Ref}$, Reinheit) = HPLC ($t_{Ref}$, purity)
LC/MS und $R_f$-Wert = LC/MS and $R_f$ value
Ausbeute und Bemerkung = Yield and remarks
racemisiertes Produkt = Racemized product

EXAMPLE 170

SPH-1371

(4aα,6b, 8aR* )-4a,5,9,10,111,12-Hexahydro-3-methoxy-11-[3-(1-piperidinyl)propyl]-6H-benzofuro[3a,3,2-ef][2]benzazepin-6-ol, Dihydrobromide, Dihydrate Production From the Free Base by Treatment With Hbr/EtOH $[a_D^{20}$=−92.5° (c 0.24, $H_2O$)

General Instructions—"Thiophene Derivatives" (Examples 171–172)

1.1 equivalents of norgalanthamine and 1 equivalent of the corresponding thienyl-halide were heated to reflux temperature together with 3 equivalents of fine-powder, anhydrous $K_2CO_3$ in dry acetonitrile (10% by weight of solution) for 24 hours. Complete conversion was examined by means of TLC.

After the solution was cooled, it was filtered, and the $K_2CO_3$ residue was washed several times with dry acetonitrile while being monitored by TLC. The crude product that was obtained after concentration by evaporation was purified by means of flash chromatography.

EXAMPLE 171

SPH-1490

6,7-Dihydro-5-(4-((4aS,6R,8aS)-6-hydroxy-3-methoxy-4a,5,9,10-tetrahydro-6H-benzofuro[3a,3,2-ef][2benzazepine-11(12H)-yl)-butyl)-benzo[b]thiophene-4(5H)-one $C_{28}H_{33}NO_4S$ (479.64)

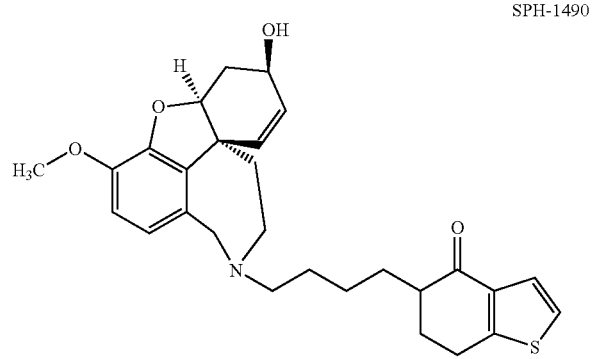

SPH-1490

| Norgalanthamine: | 500 mg (1.83 mmol) |
|---|---|
| 5 (4-bromobutyl)-6,7-dihydro-benzo[b]thiophene-4(5H)-one: | 479 mg (1.67 mmol) |
| $K_2CO_3$: | 693 mg (5.01 mmol) |
| about 4 ml of acetonitrile | |

Crude product: 450 mg Flash chromatography: Ethyl acetate:triethylamine=100:2 Yield: 440 mg (50%) of a light yellow powder $^1H$ (400 MHz, $CDCl_3$): δ 7.34 (d, J=5.26, 1H), 7.04 (d, J=5.26, 1H), 6.66 (d, J=8.18, 1H), 6.62 (d, J=8.18, 1H), 6.09 (m, 2H), 4.61 (m, 1H) 4.25–4.07 (m, 2H), 3.92–3.84 (m, 1H), 3.84–3.79 (m, 1H), 3.80 (s, 3H), 3.46–3.56 (m, 1H), 3.30–3.18 (m, 1H), 3.13–3.03 (m, 1H), 3.02–2.91 (m, 1H), 2.73–2.65(m, 1H), 2.64–2.47 (m, 2H), 2.45–2.36 (m, 1H), 2.32–2.23 (m, 1H), 2.11–1.83 (m, 4H), 1.63–1.09 (m, 6H) $^{13}C$ (100 MHz, $CDCl_3$): δ 195.2 (s), 154.8 (2*s), 145.8 (s), 144.4 (s), 136.8 (s), 132.9 (s), 127.9 (d), 126.4 (d), 125.1 (d), 123.2 (d), 122.4 (d), 111.3 (d), 88.6 (d), 61.9 (d), 58.1 (t), 55.9 (q), 51.4 (t), 51.3 (t), 48.2 (s), 46.2 (d), 29.9 (t), 29.5 (t), 28.9 (t), 28.8 (t), 28.5 (t), 24.8 (t), 24.2 (t)

EXAMPLE 172

SPH-1491

6,7-Dihydro-5-(5-((4aS,6R,8aS)-6-hydroxy-3-methoxy-4a,5,9,10-tetrahydro-6H-benzofuro[3a,3,2-ef][2]benzazepine-11(12H)-yl)-pentyl)-benzo[b]thiophen-4 (SH)-one $C_{29}H_{35}NO_4S$ (493.67)

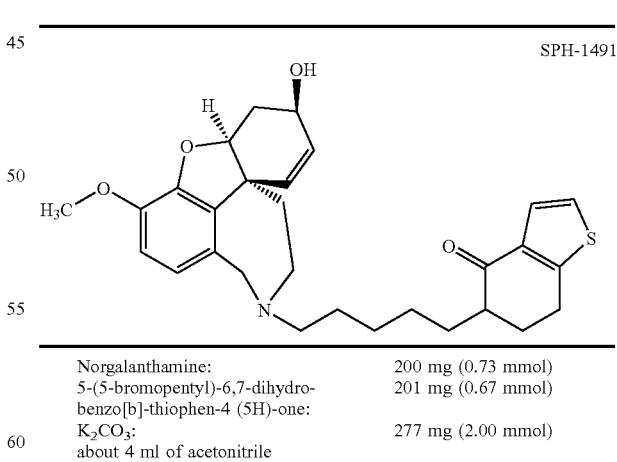

SPH-1491

| Norgalanthamine: | 200 mg (0.73 mmol) |
|---|---|
| 5-(5-bromopentyl)-6,7-dihydro-benzo[b]-thiophen-4 (5H)-one: | 201 mg (0.67 mmol) |
| $K_2CO_3$: | 277 mg (2.00 mmol) |
| about 4 ml of acetonitrile | |

Crude product: 430 mg Flash chromatography: ethyl acetate:triethylamine=100:2 Yield: 240 mg (66.3%) of a light yellow powder $^1H$ NMR (400 MHz, $CDCl_3$): δ 7.35 (d, J=5.2 Hz, 1H), 7.03 (d, J=5.2 Hz, 1H), 6.64 (d, J=8.1 Hz, 1H), 6.61 (d, J=8.1 Hz, 1H), 6.05 (d, J=10.2 Hz, 1H), 5.99

(dd, J=10.2, 4.6 Hz, 1H), 4.60 (m, 1H), 3.83 (d, J=15.2, 1H), 4.14–4.10 (m, 1H), 3.83 (d, J=15.2 Hz, 1H), 3.81 (s, 3H), 3.41–3.31 (m, 1H), 3.22–3.14 (m, 1H), 3.07 (dt, J=17.2, 5.2 Hz, 1H), 2.96 (ddd, J=17.2, 9.1, 4.7 Hz, 1H), 2.70–2.62 (m, 1H), 2.56–2.34 (m, 4H), 2.26 (m, 1H), 2.10–1.8 (m, 4H), 1.61–1.21 (m, 8H) $^{13}$C NMR: (100 MHz, CDCl$_3$): δ 195.7 (s), 155.1 (2*s), 146.2 (s), 144.5 (s), 137.3 (s), 133.5 (s), 128.0 (d), 127.3 (d), 125.5 (d), 123.6 (d), 122.5 (d), 111.5 (d), 89.1 (d), 62.5 (d), 58.1 (t), 56.3 (q), 51.3 (t), 48.8 (s), 46.7 (d), 33.2 (t), 30.3 (t), 30.0 (t), 29.9 (t), 29.4 (t), 27.8 (t), 27.6 (t), 27.5 (t), 24.6 (t)

General Instructions—"Azacycloalkyl Derivatives" (Examples 173–176)

One equivalent of norgalanthamine and 3 equivalents of the corresponding aminoalkyl halide was heated to reflux temperature together with 3 equivalents of fine-powder, dry K$_2$CO$_3$ in dry acetonitrile (about 10% by weight of solution) for 24 hours. Complete conversion was controlled by means of TLC.

After the solvent was distilled off, the remaining residue was dissolved in 2N HCl. After two extraction cycles with diethyl ether, it was made alkaline with 10% NaOH solution and extracted exhaustively with chloroform. After drying on Na$_2$SO$_4$, it was concentrated by evaporation and purified by means of flash chromatography (CHCl$_3$:MeOH:NH$_3$=10:1: 0.5). The indicated yields of the reactions relate to 500 mg (1.83 mmol) of norgalanthamine as a starting product and were determined according to flash chromatography.

EXAMPLE 173

SPH-1492

(4aS,6R,8aS)-3-Methoxy-11-(6-piperidin-1-yl-hexyl)-5,6,9,10,11,12-hexahydro-4aH-[1]benzofuro[3a,3,2-ef][2]benzazepin-6-ol $C_{27}H_{40}N_2O_3$ (440.63)

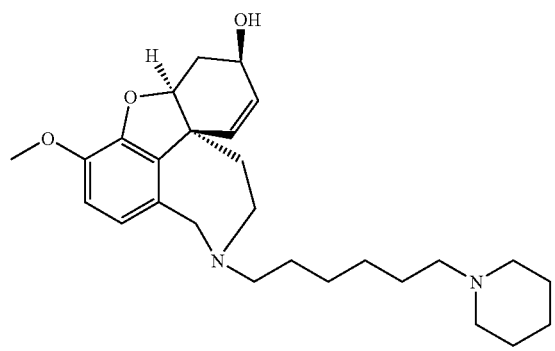

SPH-1492

Yield: 161 mg (20%) of a yellowish oil $^1$H (400 MHz, CDCl$_3$): δ 6.66 (d, J=8.0 Hz, 1H), 6.62 (d, J=8.0 Hz, 1H), 6.10 (d, J=10.0 Hz, 1H), 6.01 (dd, J=10.0, 5.4 Hz, 1H), 4.62 (m, 1H), 4.14 (m, 1H), 4.13 (d, J=15.6, 1H), 3.84 (s, 3H), 3.81 (d, J=15.6, 1H), 3.4–3.3 (m, 1H), 3.2–3.15 (m, 1H), 2.69 (ddt, J=15.7, 3.4, 1.6 Hz, 1H), 2.55–2.25 (m, 8H), 2.10–2.0 (m, 1H), 2.01 (ddd, J=12.9, 5.0, 2.6 Hz, 1H), 1.65–1.2 (m, 16H) $^{13}$C (100 MHz, CDCl$_3$): δ 146.2 (s), 144.4 (s), 133.6 (s), 129.9 (s), 127.9 (d), 127.4 (d), 122.4 (d), 111.5 (d), 89.1 (d), 62.5 (d), 59.9 (t), 58.1 (t), 56.3 (q) 54.9 (4*t), 51.9 (t), 48.8 (s), 33.3 (t), 30.3 (t), 28.0 (t), 27.9 (t), 27.8 (t), 27.1 (t), 26.2 (t), 24.8 (t)

EXAMPLE 174

SPH-1493

(4aS,6R,8aS)-3-Methoxy-11-(6-(4-methylpiperazine)-1-yl-hexyl)-5,6,9,10,11,12-hexahydro-4aH-[1]benzofuro[3a,3,2-ef][2]benzazepin-6-ol $C_{27}H_{41}N_3O_3$ (455.65)

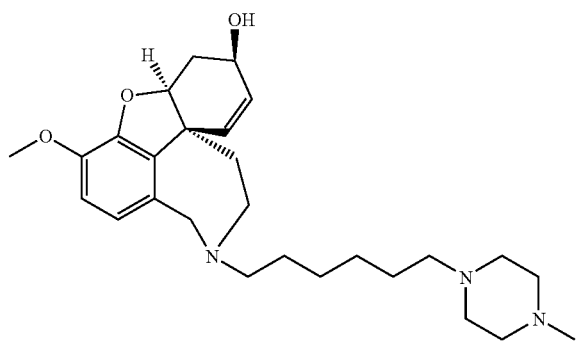

SPH-1493

Yield: 208 mg (25%) of a yellowish oil $^1$H (400 MHz, CDCl$_3$): δ 6.66 (d, J=8.18, 1H), 6.61 (d, J=8.18, 1H), 6.09 (d, J=10.23, 1H), 6.0 (dd, J=9.94, 4.97, 1H), 4.61 (m, 1H), 4.20–4.08 (m, 2H), 3.84 (s, 3H), 3.80 (d, J=15.8, 1H), 3.40–3.30 (m, 1H), 3.23–3.10 (m, 1H), 2.73–2.63 (m, 1H), 2.63–2.30 (m, 12H), 2.29 (s, 3H), 2.10–1.94 (m, 2H), 1.57–1.17 (m, 10H) $^{13}$C (100 MHz, CDCl$_3$): δ 146.2 (s), 144.4 (s), 133.6 (s), 129.9 (s), 127.9 (d), 127.4 (d), 122.4 (d), 111.5 (d), 89.1 (d), 62.5 (d), 59.1 (t), 58.2 (t), 56.3 (q), 55.5 (2*t), 53.6 (3*t), 51.9 (t), 48.8 (s), 46.5 (q), 33.3 (t), 30.4 (t), 27.98 (t), 27.83 (t), 27.74 (t), 27.23 (t)

EXAMPLE 175

SPH-1494

(4aS,6R,8aS)-3-Methoxy-11-(6-[4-hydroxypiperidine)-1-yl-hexyl)-5,6,9,10,11,12-hexahydro-4aH-[1]benzofuro[3a,3,2-ef][2]benzazepin-6-ol $C_{27}H_{40}N_2O_4$ (456.63)

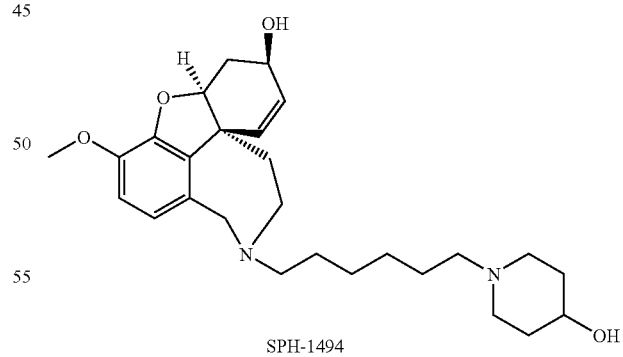

SPH-1494

Yield: 200 mg (24%) of a yellowish oil $^1$H (400 MHz, CDCl$_3$): δ 6.64 (d, J=8.1 Hz, 1H), 6.59 (d, J=8.1 Hz, 1H), 6.07 (d, J=10.2 Hz, 1H), 5.97 (dd, J=10.2, 4.9 Hz, 1H), 4.58 (m, 1H), 4.11 (m, 1H), 4.07 (m, 1H), 3.81 (s+m, 4H), 3.71–3.61 (m, 1H), 3.35 (m, 1H), 3.15 (m, 1H), 2.81–2.71 (m, 2H), 2.67 (d, J=15.4, 1H), 2.52–2.36 (m, 4H), 2.34–2.26 (m, 2H), 2.20–2.08 (m, 2H), 2.06–1.94 (m, 2H), 1.93–1.84 (m, 2H), 1.63–1.53 (m, 2H), 1.52–1.38 (m, 5H), 1.32–1.20 (m, 4H) $^{13}$C (100 MHz, CDCl$_3$): δ 146.2 (s), 144.5 (s), 133.6 (s), 129.9 (s), 127.9 (d), 127.4 (d), 122.4 (d), 111.5 (d), 89.1 (d), 62.5 (2*d), 58.9 (2*t), 58.2 (t), 56.3 (q), 51.9 (2*t), 51.3 (t), 48.8 (s), 34.6 (t), 33.4 (t), 30.4 (t), 28.0 (t), 27.8 (2*t), 27.7 (t), 27.3 (t)

EXAMPLE 176

SPH-1521

1-(6-((4aS,6R,8aS)-6-Hydroxy-3-methoxy-4a,5,9,10-tetrahydro-6H-benzofuro[3a,3,2-ef][2]benzazepine-11(12H)-yl)-hexyl)-piperidin-4-one $C_{27}H_{38}N_2O_4$ (454.61)

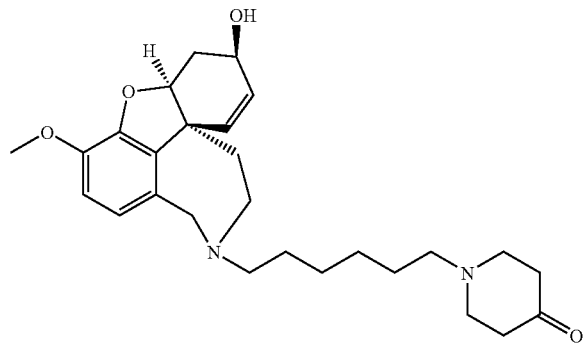

Yield. 125 mg (15%) of a yellowish oil $^1$H (400 MHz, CDCl$_3$): δ 6.65 (d, J=8.18 Hz, 1H), 6.60 (d, J=8.18 Hz, 1H), 6.07 (d, J=10.8 Hz, 1H), 5.99 (dd, J=10.8, 4.5 Hz, 1H), 4.60 (m, 1H), 4.18–4.08 (m, 2H), 3.82 (s, 3H), 3.79–3.76 (m, 1H), 3.40–3.30 (m, 1H), 3.22–3.10 (m, 1H), 2.74–2.68 (m, 4H), 2.67–2.62 (m, 1H), 2.53–2.34 (m, 8H), 2.09–1.93 (m, 2H), 1.57–1.42 (m, 6H), 1.37–1.21 (m, 4H) $^{13}$C (100 MHz, CDCl$_3$): δ 209.7 (s), 146.2 (s), 144.5 (s), 133.5 (s), 129.7 (s), 128.1 (d), 127.4 (d), 122.4 (d), 111.5 (d), 89.0 (d), 62.4 (d), 58.1 (2*t), 57.9 (2*t), 56.4 (q), 56.3 (t), 53.4 (t), 52.2 (t), 51.9 (t), 48.8 (s), 41.5 (t), 33.4 (t), 30.4 (t), 27.9 (t), 27.8 (t), 27.7 (t)

EXAMPLE 180

SPH-1363

(4aS,6R,8aS)-6-hydroxy-3-methoxy-S,6,9,10-tetrahydro-4aH-[1]benzofuro[3a,3,2-ef][2]benzazepine-11(12H)-yl)methyl-azodicarboxylic acid-di-tert-butyl ester (CK-24-2)

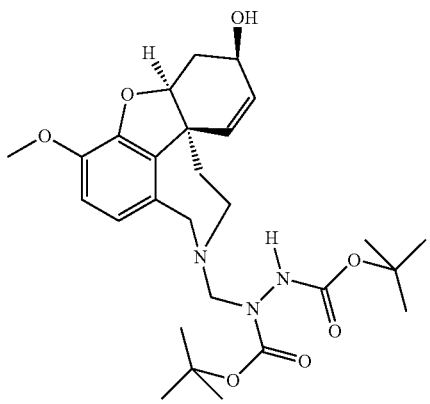

A solution that consists of 0.300 g (0.104 mmol) of galanthamine in 3 ml of dichloromethane is introduced at room temperature, mixed with 0.264 g (1.150 mmol) of di-tert-butylazodicarboxylate and stirred for four days at room temperature. After concentration by evaporation in a rotary evaporator, the residue (0.258 g) is purified by means of flash chromatography on silica gel (25 g, mobile solvent dichloromethane/petroleum ether=2/3+4% triethylamine). After drying under high vacuum, 0.292 g of a white foam is obtained.

Yield: 0.292 g (0.56 mmol, 54%), colorless foam, (M$_W$=517.6) TLC: R$_f$=0.71 (dichloromethane/methanol=9/1+2% concentrated NH$_3$ solution) Melting point: 59–62° C. (petroleum ether/dichloromethane=1/1+4% triethylamine) IR: KBr v (cm$^{-1}$) 3557 (v), 3340 (bm), 2932 (s), 2915 (s), 1726 (s), 1711 (s) $^1$H-NMR: (200.13 MHz, CDCl$_3$, TMS) δ 6.49–6.66 (m, 2H), 6.39 (s, 0.6 H), 5.84–6.06 (m, 2H), 4.52 (s, 1H), 4.35 (bs, 1H), 3.99–4.17 (m, 2H), 3.71–3.88 (m, 1H), 3.76 (s, 3H), 3.07–3.40 (m, 2H), 2.61 (bd, J=15.7 Hz, 1H), 2.40 (bd, J=11.8 Hz, 0.3H), 1.79–2.05 (m, 2H), 1.56–1.72 (m, 1H), 1.46 (s, 9H), 1.45 (s, 9H) $^{13}$C NMR: (50.32 MHz, CDCl$_3$, TMS) δ 156.7 (s), 155.9 (s), 145.9 (s), 144.0 (s), 132.8 (d), 129.8 (s), 127.6 (d), 126.7 (d), 121.5 (d), 111.1 (d), 88.5 (d), 68.9 (t), 62.4 (t), 61.8 (t), 61.8 (d) 56.6 (t), 55.8 (q), 49.7 (t), 48.1 (s), 35.2 (t), 29.8 (t), 14.32 (q), 14.26 (q) LC/MS: t$_{Ref}$=9.56 minutes, (Zorbax SB column, 2.1 mm×30 mm, RP-18, 3 µm, 0.5 ml/minute, methanol/H$_2$O (40/60→100/0 (v/v) in 2 minutes) APCI-PI-MS 518 (100), 500 (25), 462 (9), 285 (13), 274 (11), 256 (26) APCI NI-MS 516

EXAMPLE 181

SPH-1362

(4aS,6R,8aS)-6-Hydroxy-3-methoxy-5,6,9,10-tetrahydro-4aH-[1]benzofuro[3a,3,2-ef]2]benzazepine-11(12H)-yl)methyl-azodicarboxylic acid diethyl ester (CK-21-3)

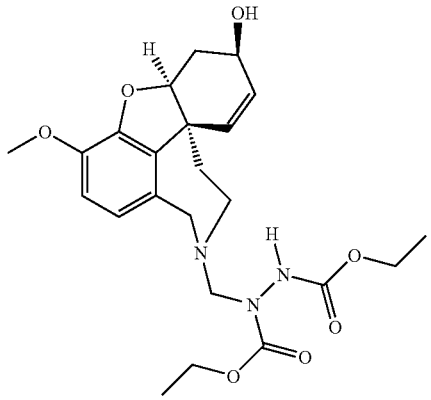

89 µl (0.100 g, 0.57 mmol) of diethylazodicarboxylate is added to a solution that consists of 0.150 g (0.52 mmol) of galanthamine in 2 ml of dichloromethane, and the solution is stirred for 72 hours at room temperature. After concentration by evaporation in a rotary evaporator, the residue (0.258 g) is purified by means of flash chromatography on silica gel (25 g, mobile solvent dichloromethane/petroleum ether=1/1+4% triethylamine). After drying under high vacuum, 0.168 g of a white foam is obtained.

Yield: 0.168 g (0.36 mmol, 70%), white foam, (M=461.6) TLC: R$_f$=0.66 (dichloromethane/methanol=9/1+2% concentrated NH$_3$ solution) Melting point: 40–42° C. (petroleum ether/dichloromethane=1/1+4% triethylamine) IR: KBr v (cm$^{-1}$) 3553 (v), 3305 (m), 2981 (s), 2935 (s), 1742 (s), 1722 (s) $^1$H-NMR (200.13 MHz, CDCl$_3$, TMS) δ 6.77 (bs, 1H), 6.64 (d, J=8.3 Hz, 1H), 6.58 (d, J=8.1 Hz, 1H), 5.84–6.06 (m, 2H), 4.53 (s, 1H), 3.98–4.23 (m, 6H), 3.69–3.87 (m, 1H), 3.76 (s, 3H), 3.01–3.42 (m, 2H), 2.66 (bd, J=15.7 Hz, 1H), 2.33 (bs, 0.2H), 1.65–1.77 (m, 2H), 1.35–1.47 (m, 1H), 1.09–1.35 (m, 6H) $^{13}$C-NMR: (50.32 MHz, CDCl$_3$, TMS) δ 155.1 (s), 145.9 (s), 143.9 (s), 132.8 (d), 130.2 (s), 127.5 (d), 126.9 (d), 121.4 (d), 111.1 (d), 81.2 (s), 80.9 (s), 69.5 (t), 61.9 (d), 56.8 (t), 55.8 (q), 49.8 (t), 48.1 (s), 35.6 (t), 29.8 (t), 28.1 (t), 28.0 (q) LC/MS: $t_{Ref}$=8.08 minutes, (Zorbax SB column, 2.1 mm×30 mm, RP-18, 3 μm, 0.5 ml/minute, methanol/H$_2$O (40/60→100/0 (v/v) in 2 minutes) APCI-PI-MS 462 (100), 444 (32), 286 (34), 274 (12), 256 (29) APCI-NI-MS 460

Process for Synthesis of Norgalanthamine

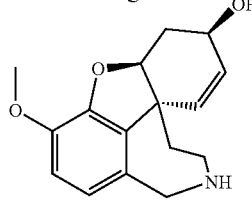

Method A 20 g (70 mmol) of galanthamine is reacted with 14.206 g (0.07 mol) of m-chloroperbenzoic acid (85%) in 350 ml of dichloromethane and subsequent addition of 9.730 g (35 mmol) of Fe(II)SO$_4$*7 H$_2$O in 100 ml of methanol. The reaction is terminated after 20 minutes with 200 ml of 2N hydrochloric acid. After the slightly volatile solvent is distilled off, after the acids and bases are separated and after the I e(OH)$_x$ precipitate is filtered off by means of a Hyflo nutsch, the filtrate is dried on Na$_2$SO$_4$, filtered and concentrated by evaporation. About 18 g of the crude product is obtained in the form of a yellow foam.

Working-up Variant 1 (CK-1-1)

The crude product (18.46 g) is taken up in about 200 ml of ethyl acetate/methanol/triethylamine (90/10/2) while being heated slightly. During cooling, I e(OH)$_x$ is again precipitated, which is filtered off. The purification is carried out by means of MPLC chromatography (silica gel, h=25 cm, d=3.6 cm, v=300 nm) with an altered mobile solvent mixture (ethyl acetate/methanol/triethylamine=95/5/2→90/10/2→80/20/2). The norgalanthamine content is only 68% according to an HPLC quantification (caffeine as an internal standard).

Yield: 10.34 g (38 mmol, 54%), yellowish, amorphous solid (M$_W$=273.3)

Working-up Variant 2 (CK-1-11)

The crude product (16.48 g) is dissolved in 100 ml of methanol, mixed with a solution that consists of 12.86 g (102 mmol) of oxalic acid dihydrate in 100 ml of methanol and carefully heated to homogenize the solution. Then, the solution is allowed to cool to room temperature and then to cool to about 5° C., the crystallized product is filtered off, and the precipitate is washed with methanol. The combined methanol solutions that are concentrated by evaporation are again subjected to recrystallization.

Yield: 16.108 g (43 mmol, 62%), colorless crystalline solid

Cld. for C$_{16}$H$_{19}$NO$_3$.C$_2$H$_2$O$_4$.0.5 H$_2$O
C, 58.06 H, 5.95 N, 3.76
Fnd. C, 57.91 H, 5.88 N, 3.69

Method B (CK-1-10)

2.000 g (6.96 mmol) of galanthamine and 0.981 g (10.44 mmol) of hydrogen peroxide-urea-adduct are stirred for two days in 25 ml of dichloromethane and 5 ml of methanol at room temperature, then mixed with 0.030 g of platinum/activated carbon and stirred for one hour at room temperature. When the catalyst is added, a strong gas development can be observed. Then, 0.967 g (3.48 mmol) of Fe(II)SO$_4$*7 H$_2$O in 5 ml of MeOH is added, and the brown suspension is vigorously stirred. The reaction is terminated after 20 minutes with 50 ml of saturated NaHCO$_3$ solution. The reaction solution is filtered by means of a Hyflo filter aid. The phases are separated, and the aqueous phase is extracted exhaustively with dichloromethane. The combined organic extracts are washed with saturated NaHCO$_3$ solution (50 ml) and with saturated NaCl solution (50 ml), dried on Na$_2$SO$_4$, filtered and concentrated by evaporation. The crude product (1.925 g) is dissolved in 10 ml of methanol, mixed with a solution that consists of 1.332 g (10.6 mmol) of oxalic acid dihydrate in 10 ml of methanol and carefully heated to homogenize the solution. Then, the solution is allowed to cool to room temperature and then to about 5° C., the crystallized product is filtered off, and the precipitate is washed with methanol. The combined methanol solutions that are concentrated by evaporation are again subjected to recrystallization.

Yield: 1.010 g (2.7 mmol, 39%), colorless crystalline solid (M$_W$=371.4), according to HPLC 97%

Method C:

Demethylation of Norgalanthamine by Means of Diethylazodicarboxylate (CK-1-7)

178 μl (0.199 g, 1.144 mmol) of diethylazodicarboxylate is added to a solution that consists of 0.300 g (1.04 mmol) of galanthamine in 3 ml of dichloromethane, and the solution is stirred for three days at room temperature. After concentration by evaporation in a rotary evaporator at 40° C., the residue is dissolved in 5 ml of ethanol and 5 ml of 4N hydrochloric acid and stirred at 80° C. for one and one-half hours. The reaction is cooled to room temperature, and the solution is diluted with 5 ml of water. The ethanol portion is distilled off in a rotary evaporator, and the aqueous phase is extracted three times with 10 ml of diethyl ether in each case. The aqueous phase is set at pH 10–11 by adding sodium carbonate and sodium hydroxide, and it is extracted four times with 20 ml of dichloromethane in each case. The combined phases are washed with 40 ml of saturated common salt solution and dried on Na$_2$SO$_4$. After filtering and concentration by evaporation, the residue (0.268 g) is purified by means of MPLC on silica gel (60 g, mobile solvent ethyl acetate/ethanol/triethylamine=19/1/0.4). After drying under high vacuum, 0.136 g of a yellowish foam is obtained.

Yield: 0.136 g (0.495 mmol, 48%), white-yellowish foam, (M$_W$=273.3), HPLC identical to a reference sample HPLC: $t_{Ref}$=3.79 minutes, 96.3% (Merck Purospher column, 4.0 mm×125 mm, RP-18e, 5 μm, 250 nm, 1 ml/minute, acetonitrile/20 mmol of trichloroacetic acid in H$_2$O (15/80 v/v)

Method D:

Demethylation of Norgalanthamine by Means of Di-tert-butylazodicarboxylate (CK-1-6)

0.300 g (1.04 mmol) of galanthamine and 0.264 g (1.144 mmol) of di-tert-butylazodicarboxylate in 3 ml of dichloromethane are reacted analogously to the above-described procedure for three days at room temperature, concentrated by evaporation and stirred in 5 ml of ethanol and 5 ml of 4N hydrochloric acid for 30 minutes at 80° C. The reaction is cooled to room temperature, and the solution is diluted with 5 ml of water. After the aqueous working-up, the residue (0.259 g) is purified by means of MPLC on silica gel (60 g, mobile solvent ethyl acetate/ethanol/triethylamine=19/1/0.4). After drying under high vacuum, 0.132 g of a white-yellowish foam is obtained.

Yield: 0.132 g (0.48 mmol, 46%), white-yellowish foam, ($M_W$=273.3), HPLC identical to a reference sample HPLC: $t_{Ref}$=3.74 minutes, 100% (Merck Purospher column, 4.0 mm×125 mm, RP-18e, 5 μm, 250 nm, 1 ml/minute, acetonitrile/20 mmol of trichloroacetic acid in $H_2O$ (15/80 v/v)

Method E:

Saponification of (4aS,6R,8aS)-3-Methoxy-12-trifluoroacetyl-5,6,9,10,11,12-hexahydro-4aH-[1]benzofuro[3a,3,2-ef][2]benzazepin-6-ol Method A (CK-40-2)

3.3 ml of a 0.25 M potassium hydroxide solution (0.045 g (0.81 mmol) in dioxane/methanol/water (10/2/5) is mixed with 0.100 g (0.27 mmol) of N-trifluoroacetylnorgalanthamine and stirred for one hour at room temperature. Then, the solution is diluted with 0.4 ml of 2N hydrochloric acid, and the volatile components are distilled off in a rotary evaporator. The residue is taken up with saturated sodium carbonate solution and extracted five times with dichloromethane. The combined extracts are washed with saturated sodium chloride solution, dried on sodium sulfate, filtered and concentrated by evaporation in a rotary evaporator under reduced pressure. 0.070 g of a white-yellowish foam with a purity of 95% (HPLC, caffeine as an internal standard) is obtained.

Yield: 0.070 g (0.067, 0.25 mmol, 91%), white-yellowish foam ($M_W$=273.3)

Method B (CK-40-3)

A solution that consists of 0.100 (0.27 mmol) of N-trifluoroacetylnorgalanthamine and 0.243 g (1.35 mmol) of 30% sodium methanolate-methanol solution in 3 ml of tetrahydrofuran/methanol (1/1) is stirred for three hours at room temperature. The solution is neutralized with 0.7 ml of 2N hydrochloric acid, and the solution is evaporated to the dry state, the residue is taken up with 25 ml of dichloromethane and washed with saturated sodium carbonate solution and with saturated sodium chloride solution, dried on sodium sulfate, filtered and concentrated by evaporation in a rotary evaporator under reduced pressure. After drying in a vacuum, a yellowish foam (0.067 g) with a purity of 76% (HPLC, caffeine as an internal standard) is obtained.

Yield: 0.067 g (0.051 g, 0.19 mmol, 69%), white-yellowish foam ($M_W$=273.3)

Method G:

Separation of (+) and (−) Isomers from rac.Norgalanthamine (4)

Production of (−) Norgalanthamine (8)

A solution of 7.72 g (20.0 mmol) of (+)-O,O-di-p-toluoyltartaric acid in 15 ml of methanol is added in drops to a solution of 10.92 g (40.0 mmol) of rac.norgalanthamine (4) in 40 ml of methanol and then rewashed with 1 ml of methanol. The solution is mixed with a seed crystal and allowed to stand for two days at 4° C. Then, a glass rod is passed vigorously through the solution, and it is allowed to stand for another two to five days at 4° C., whereby a glass rod is always passed vigorously through the solution again. Then, the precipitated salt is suctioned off, rewashed three times with ice-cold methanol and taken up in 100 ml of water. The aqueous phase is made basic with concentrated aqueous ammonia and extracted three times with 60 ml of ethyl acetate each. The combined organic phases are washed once with saturated aqueous-sodium chloride solution, dried ($Na_2SO_4$, activated carbon), filtered and concentrated by evaporation, by which 2.90 g (37.5% of theory) of colorless crystals with an angle of rotation of $\alpha_D^{22}$[$CHCl_3$]=−62.4 of (−) norgalanthamine (8) is obtained. The methanolic mother liquor is concentrated by evaporation, the residue is taken up in 100 ml of water and treated like the pure salt above, by which 4.1 g (53.1% of theory) of crude product can be recovered, which is used as follows for recovering (+) norgalanthamine.

Production of (+) Norgalanthamine

A solution of 2.9 g (7.5 mmol) of (−)-O,O-di-p-toluoyltartaric acid in 5.6 ml of methanol is added in drops to a solution of 4.1 g (15.0 mmol) of recovered norgalanthamine (this is concentrated in (+) isomers) in 21 ml of methanol, whereby it is rewashed with 0.5 ml of ethanol. The solution is mixed with a seed crystal and treated as in the recovery of (−) norgalanthamine, by which 3.0 g (39% of theory) of colorless crystals is obtained with an angle of rotation of $\alpha_D^{22}$ [$CHCl_3$]=+57.5° (+) norgalanthamine.

As an alternative, (+) norgalanthamine is also obtained by reaction of rac.norgalanthamine (4) with (−)-O,O-di-p-toluoyltartaric acid analogously to the above instructions with an angle of rotation of $\alpha_D^{22}$ [$CHCl_3$]=+60.5°.

EXAMPLE 182

SPH-1534

(4aS,6R,8aS)-6-Hydroxy-3-methoxy-5,6,9110-tetrahydro-4aH-[1]benzofuro]3a,3,2-ef][2]benzazepine-11(12H)-yl)carboxylic acid triisopropyl silyl ester (CK-9-2)

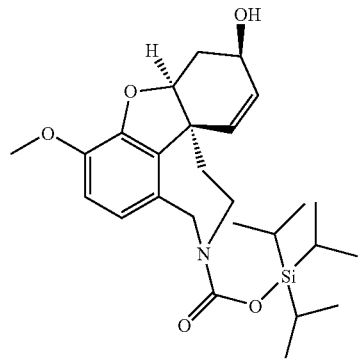

0.200 g (0.732 mmol) of norgalanthamine (68% (HPLC, CK-1-1)) and 0.47 ml (0.341 g, 3.37 mmol) of triethylamine are introduced at −80° C. in 6 ml of dichloromethane in a single-neck flask with a septum and a $CO_2$ tank, which is filled by evacuation and flushing with carbon dioxide. Then, the solution is cooled to the point that solid carbon dioxide precipitates in the reaction solution. After one and one-half hours at about −80 to −90° C., triisopropyl silyl chloride (0.155 ml, 0.141 g, 0.732 mmol) is added via a syringe. Then, the reaction solution is slowly heated overnight to room temperature. In this case, a colorless precipitate settles out. The reaction solution is taken up with 10 ml of 1N hydrochloric acid, the phases are separated, and the aqueous phase is extracted twice with 10 ml of dichloromethane. The combined organic phases are washed with 10 ml of 1N hydrochloric acid and with 10 ml of saturated common salt solution, dried on $Na_2SO_4$, filtered and concentrated by evaporation. The yellow viscous oil (0.315 g) is purified by means of column chromatography on silica gel with the mobile solvent petroleum ether/ethyl acetate. After concentration by evaporation, 0.208 g of the product is obtained in the form of a colorless foam.

Yield: 0.208 g (0.44 mmol, 60w), colorless foam, ($M_W$=473.7) TLC: $R_f$=0.35 (petroleum ether/ethyl acetate=1/1) Melting point: 53–54° C. (petroleum ether/ethyl acetate=(1/1) IR: KBr v ($cm^{-1}$) 3556 (m), 3454 (m), 2946 (s), 1679 (s) $^1$H-NMR (200.13 MHz, $CDCl_3$, TMS) δ

6.60–6.85 (m, 2H), 5.93–6.09 (m, 2H), 4.90 (d, J=15.3 Hz, 0.4H), 4.80 (d, J=15.7 Hz, 0.6H), 4.57 (s, 1H), 4.06–4.40 (m, 3H), 3.83 (s, 3H), 3.27–3.57 (m, 0.4H), 2.70 (bd, J=16.3 Hz, 1H), 2.41 20 (bd, J=11.0 Hz, 0.6H), 1.60–2.11 (m, 3H), 1.29 (bh, J=5.1 Hz, 3H), 1.05 (d, J=6.8 Hz, 8H), 0.98 (d, J=6.9 Hz, 10H) $^{13}$C-NMR: (50.32 MHz, CDCl$_3$, TMS) δ 154.4 and 153.9 (s), 146.5 and 146.2 (s), 144.3 and 144.1 (s), 132.2 and 131.8 (d), 129.4 and 129.2 (s), 127.9 (d), 126.5 (d), 121.6 and 120.9 (d), 111.1 and 110.9 (d), 88.2 (d), 61.8 (d), 55.8 and 55.7 (q), 52.5 and 51.7 (t), 48.3 (s), 46.4 and 45.8 (t), 37.3 and 36.1 (t), 29.7 (t), 17.77 17.75, 17.68 and 17.65 (q), 11.9 (d)

EXAMPLE 183

SPH-1535

(4aS,6R,8aS)-6-Hydroxy-3-methoxy-5,6,9,10-tetrahydro-4aH-[1]benzofuro[3a,3,2-ef][2]benzazepine-11(12H)-yl)carboxylic acid-tert-butyldiphenylsilyl ester

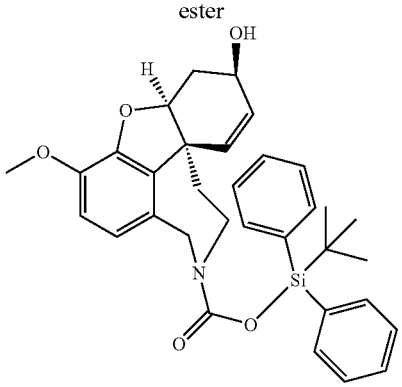

Analogously to the instructions for the N-triisopropylsilyloxycarbonylnorgalanthamine (TBDP-C$_1$), norgalanthamine (68% (HPLC, CK-1-1)) is reacted with 1 or 1.1 equivalents of tert-butyldiphenylsilyl chloride and 5 equivalents of triethylamine. Then, the reaction is terminated with water or dilute hydrochloric acid, the phases are separated, and the aqueous phase is extracted with dichloromethane. After drying with Na$_2$SO$_4$, filtering and concentration by evaporation, the amorphous foam is purified by means of column chromatography (silica gel, ethyl acetate/petroleum ether=1/1). A colorless foam is obtained.

| Conditions: | Aqueous Working-Up: | Yield (M$_W$ = 524.7): |
|---|---|---|
| CK-10-1 | 0.200 g (0.732 mmol) of norgalanthamine, 0.172 ml (0.181 g, 0.732 mmol) of TBDP-C1 | 10 ml of 1 N hydrochloric acid | 0.282 g (0.538 mmol, 73%) |
| CK-10-2 | 0.200 g (0.732 mmol) of norgalanthamine, 0.172 ml (0.181 g, 0.732 mmol) of TBDP-C1 | 10 ml of distilled water | 0.196 g (0.37 mmol, 51%) |
| CK-10-3 | 0.400 g (1.46 mmol) of norgalanthamine, 0.38 ml (0.398 g, 1.606 mmol) of TBDP-C1 | 20 ml of 0.3 M hydrochloric acid | 0.505 g (0.96 mmol, 66%) |

TLC: R$_f$=0.40 (petroleum ether/ethyl acetate=1/1) Melting point: 71–80° C. (petroleum ether/ethyl acetate=1/1) IR: KBr v (cm$^{-1}$) 3553 (m), 3454 (bm), 2932 (s), 1686 (s), 1625 (m) $^1$H-NMR: (200.13 MHz, CDCl$_3$, TMS) δ 7.20–7.68 (m, 10H), 6.56–6.77 (m, 2H), 4.83–5.03 (m, 1H), 5.03 (s, 1H), 4.02–4.40 (m, 3H), 3.83 (s, 3H), 3.63 (bt, J=13.1 Hz, 0.3H), 3.41 (bf, J=12.9 Hz, 0.7H), 2.70 (bt, J=15.6 Hz, 1H), 2.41 (bd, J=19.7 Hz, 1H), 1.78–2.10 (m, 2H), 1.54–1.76 (m, 1H), 1.05 (s, 9H) $^{13}$C-NMR: (50.32 MHz, CDCl$_3$, TMS) δ 153.7 and 153.2 (s), 146.6 and 146.1 (s), 144.4 and 144.2 (s), 135.0 and 134.7 (d), 132.4 and 132.3 (s), 132.4 (s), 132.3 and 131.8 (s), 129.7 and 129.6 (d), 129.2 and 129.0 (s), 126.5 (s), 121.8 and 121.2 (d), 111.1 and 110.9 (d), 88.3 and 88.1 (d), 61.8 (d), 55.9 (q), 52.7 and 51.8 (t), 48.3 (s), 46.5 and 46.1 (t), 37.4 and 35.8 (t), 29.7 (t), 27.0 and 26.9 (q), 19.1 and 18.9 (d)

EXAMPLE 184

SPH-1536

(4aS,6R,8aS)-3-Methoxy-12-trifluoroacetyl-5,6,9,10,11,12-hexahydro-4aH-[1]benzofuro[3a,3,2-ef]-[2] benzazepin-6-ol

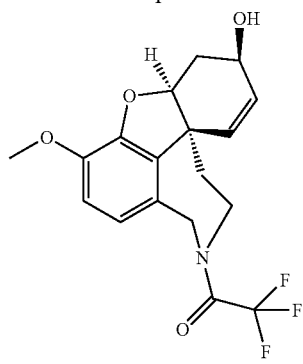

Method A (CK-32-1)

A solution that consists of 5 ml of dichloromethane and 4.6 ml (3.333 g, 32.9 mmol) of trifluoroacetic acid anhydride is added in drops at 0° C. within 15 minutes to a solution of 1.00 g (3.66 mmol) of norgalanthamine (68% (HPLC, CK-1-1)), 1.5 ml (1.095 g, 10.8 mmol) of triethylamine in 5 ml of absolute dichloromethane. Then, the solution is stirred for 1.75 hours at 0° C., and the reaction is then terminated by adding 5.5 ml of 2N hydrochloric acid. The phases are separated, and the aqueous phase is extracted three times with 20 ml of dichloromethane in each case. The combined organic phases are washed with 30 ml of saturated common salt solution, dried on Na$_2$SO$_4$, filtered and concentrated by evaporation. The crude product (0.866 g) is purified by means of MPLC (silica gel, h=25 cm, d=3.6 cm, v=300 nm, mobile solvent petroleum ether/ethyl acetate 2/1). After concentration by evaporation and drying in a vacuum, the product is obtained as a white-yellowish foam (0.866 g).

Yield: 0.866 g (1.95 mmol, 53a), white-yellowish foam, M$_W$=369.3.

Method B (CK-32-2)

2.52 g of norgalanthamine (≈90%, 2.268 g, 8.30 mmol) and 3.45 ml (2.520 g, 24.9 mmol) of triethylamine are dissolved in 20 ml of absolute dichloromethane. Then, a solution that consists of 1.211 ml (1.830 g, 8.71 mmol) of trifluoroacetic acid anhydride and 10 ml of dichloromethane is added in drops within 30 minutes at 0° C. It is heated to room temperature, additional trifluoroacetic acid anhydride (1.2 ml, 1.830 g, 8.71 mmol) is added in portions, and the reaction solution is stirred overnight. The solution is diluted with 120 ml of ethyl acetate and washed with 50 ml of 1N hydrochloric acid in each case, with 50 ml of saturated NaHCO$_3$ solution and twice with 50 ml of saturated common salt solution in each case, dried on Na$_2$SO$_4$ and filtered. After the concentration by evaporation, the residue is dissolved in 150 ml of dichloromethane, and 141.1 g of a 5% NH₃ solution is added. The two-phase solution is vigorously stirred at room temperature. After 30 minutes, the phases are separated, and the aqueous phase is extracted with dichloromethane (twice, 50 ml). The combined organic phases are washed with 1N hydrochloric acid (twice, 50 ml) and with saturated common salt solution (twice, 50 ml), dried on $Na_2SO_4$, filtered and concentrated by evaporation. The residue (2.77 g) is purified by means of MPLC (450 g of silica gel, v=300 nm, mobile solvent petroleum ether/ethyl acetate 1/1). After concentration by evaporation and drying in a vacuum, the product is obtained as a white-yellowish foam (2.6171 g).

Yield: 2.6171 g (7.09 mmol, 85%), white-yellowish foam ($M_W$=369.3) TLC: $R_f$=0.23 (petroleum ether/ethyl acetate=1/1) Melting point: 65–68° C. (petroleum ether/ethyl acetate=1/1) IR: KBr v (cm') 3546.3 (v), 3417 (bv), 2924 (m), 1690 (s) ¹H-NMR: (200.13 MHz, CDCl₃, TMS) δ 6.62–6.92 (m, 2H), 5.88–6.16 (m, 2H), 5.25 (d, J=15.2 Hz, 0.5H), 4.85 (d, J=16.6 Hz, 0.5H), 4.42–4.77 (m, 2H), 4.02–4.34 (m, 2H), 3.84 (s, 3H), 3.60–3.83 (m, 0.5H), 3.27–3.50 (m, 0.5H), 2.72 (d, J=16.0 Hz, 1.0H), 2.29 (bs, 0.7H), 1.80–2.13 (m, 3H) ¹³C-NMR: (50.32 MHz, CDCl₃, TMS) δ 156.1 (m), 146.4 and 146. (s), 144.8 and 144.7 (s), 132.0 (s), 128.8 and 128.5 (d), 126.6 and 126.1 (s), 125.7 and 125.3 (d), 120.9 and 119.1 (d), 121.9 (q, J=288 Hz), 111.3 (d), 88.1 and 88.0 (d), 61.6 (d), 55.8 (q), 52.6 and 51.8 (t), 47.9 (s), 46.5 and 46.3 (t), 38.4 and 35.4 (t), 29.64 and 29.58 (t)

EXAMPLE 185

SPH-1537

(4aS,6R,8aS)-6-Hydroxy-3-methoxy-5,6,9,10-tetrahydro-4aH-[1]benzofuro[3a,3,2-ef][2]benzazepine-11(12H)-yl)carboxylic acid allyl ester

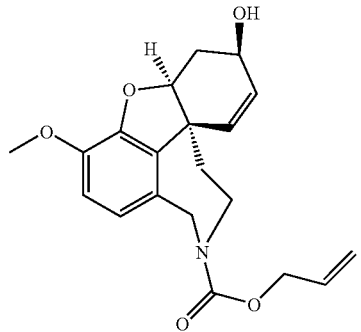

Variant A (CK-17-1)

3.000 g (11.0 mmol) of norgalanthamine is introduced at 0° C. into a solution that consists of 10 ml of absolute dichloromethane and 4.6 ml (3.333 g, 32.9 mmol) of triethylamine. At 0° C., a solution that consists of 1.454 g (12.1 mmol) of allyl chloroformate and 5 ml of absolute dichloromethane is added in drops within 20 minutes. The reaction solution is stirred overnight and in this case heated to room temperature. The reaction solution is taken up with 50 ml of 1N hydrochloric acid and 50 ml of dichloromethane. The phases are separated, and the aqueous phase is extracted three times with 50 ml of dichloromethane in each case. The combined organic phases are washed with 100 ml of saturated common salt solution, dried on $Na_2SO_4$, filtered and concentrated by evaporation. The crude product (3.2 g) is separated by means of MPLC (silica gel, h=25 cm, d=3.6 cm, v=300 nm, mobile solvent petroleum ether/ethyl acetate=2/1). After concentration by evaporation and drying in a vacuum, the product is obtained as a white-yellowish foam (2.594 g) and 0.232 g of a by-product, which was identified as N,O-diallyloxycarbonylnorgalanthamine.

Yield: 2.594 g (7.26 mmol, 66%) TLC: $R_f$=0.30 (petroleum ether/ethyl acetate=1/1) Melting point: 44–46° C. (petroleum ether/ethyl acetate=1/1) IR: KBr v (cm⁻¹) 3550 (m), 3458 (m), 1700 (s) ¹H-NMR: (200.13 MHz, CDCl₃, TMS) δ 6.62–6.86 (m, 2H), 5.95–6.09 (m, 2H), 5.76–5.94 (m, H), 5.10–5.33 (m, 2H), 4.93 and 4.83 (d and d, J=15.1 Hz, and J=15.7 Hz, 1H), 4.45–4.68 (m, 3H), 4.05–4.44 (m, 3H), 3.83 (s, 3H), 3.27–3.55 (m, 1H), 2.70 (bdd, J=15.1 Hz, and J=15.7 Hz, 1H), 2.26 (bs, 0.5H), 1.93–2.11 (m, 1H), 1.69–1.92 (m, 1H) ¹³C-NMR: (50.32 MHz, CDCl₃, TMS) δ 155.1 and 155.0 (s), 146.4 (s), 144.3 (s), 132.7 (d), 132.3 and 132.0 (s), 129.1 (s), 128.0 (d), 126.2 (d), 121.4 and 120.8 (d), 117.3 and 116.7 (t), 111.1 and 110.9 (d), 88.1 and 88.0 (d), 65.9 and 65.8 (t), 61.7 (d), 55.7 (q), 51.8 and 51.3 (t), 48.2 (s), 45.8 and 45.3 (t), 37.2 and 36.3 (t), 29.7 (t)

EXAMPLE 186

SPH-1538

(4aS,6R,8aS)-6-(2-Allyloxycarbonyloxy)-3-methoxy-5,6,9,10-tetrahydro-4aH-[1]benzofuro[3a,3,2-ef][2]benzazepine-11(12H)-yl)carboxylic acid allyl ester

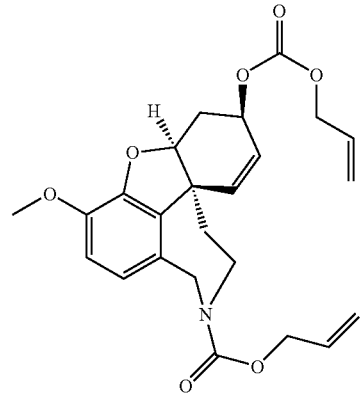

Colorless wax, ($M_W$=441.5) TLC: $R_f$=0.51 (petroleum ether/ethyl acetate=1/1) IR: KBr v (cm⁻¹) 2947 (m), 1739 (s), 1700 (s) ¹H-NMR: (200.13 MHz, CDCl₃, TMS) δ 6.56–6.81 (m, 2H), 6.22 (d, J=10.3 Hz, 1H), 5.73–6.04 (m, 3H), 5.08–5.40 (m, 5H), 4.90 (d, J=15.5 Hz, 0.5H), 4.80 (d, J=15.9 Hz, 0.5H), 4.44–4.64 (m, 5H), 4.04–4.43 (m, 2H), 3.82 (s, 3H), 3.24–3.54 (m, 1H), 2.78 (bd, J=16.4 Hz, 1H), 1.65–2.21 (m, 3H) ¹³C-NMR: (50.32 MHz, CDCl₃, TMS) δ 155.0 and 154.8 (s), 154.4 (s), 147.2 (s), 144.1 (s), 132.7 (d), 131.5 (d), 130.9 (s), 130.6 (d), 128.9 and 128.8 (s), 122.3 (d), 120.6 and 120.1 (d), 118.3 (t), 117.2 and 116.6 (t), 111.5 and 111.3 (d), 85.3 (d), 68.1 (t), 66.5 (d), 65.8 and 65.7 (t), 55.8 (q), 51.6 and 51.2 (t), 47.8 (s), 45.6 and 45.2 (t), 37.6 and 36.7 (t), 27.5 (t)

Variant B (CK-17-2)

1.000 g (3.66 mmol) of norgalanthamine (68% (HPLC, CK-1-1)), dissolved in 3 ml of absolute dichloromethane, and 0.441 g (3.66 mmol) of allyl chloroformate, dissolved in 2 ml of absolute dichloromethane, are reacted analogously to method A with 1.48 ml (1.448 g, 18.3 mmol) of pyridine. After aqueous working-up analogously to method A and column chromatography (50 g of silica gel, mobile solvent petroleum ether/ethyl acetate=2/1→1/1), 0.784 g of a colorless foam and 0.214 g of the same by-product are obtained.

Yield: 0.784 g (2.19 mmol, 60%)

EXAMPLE 187
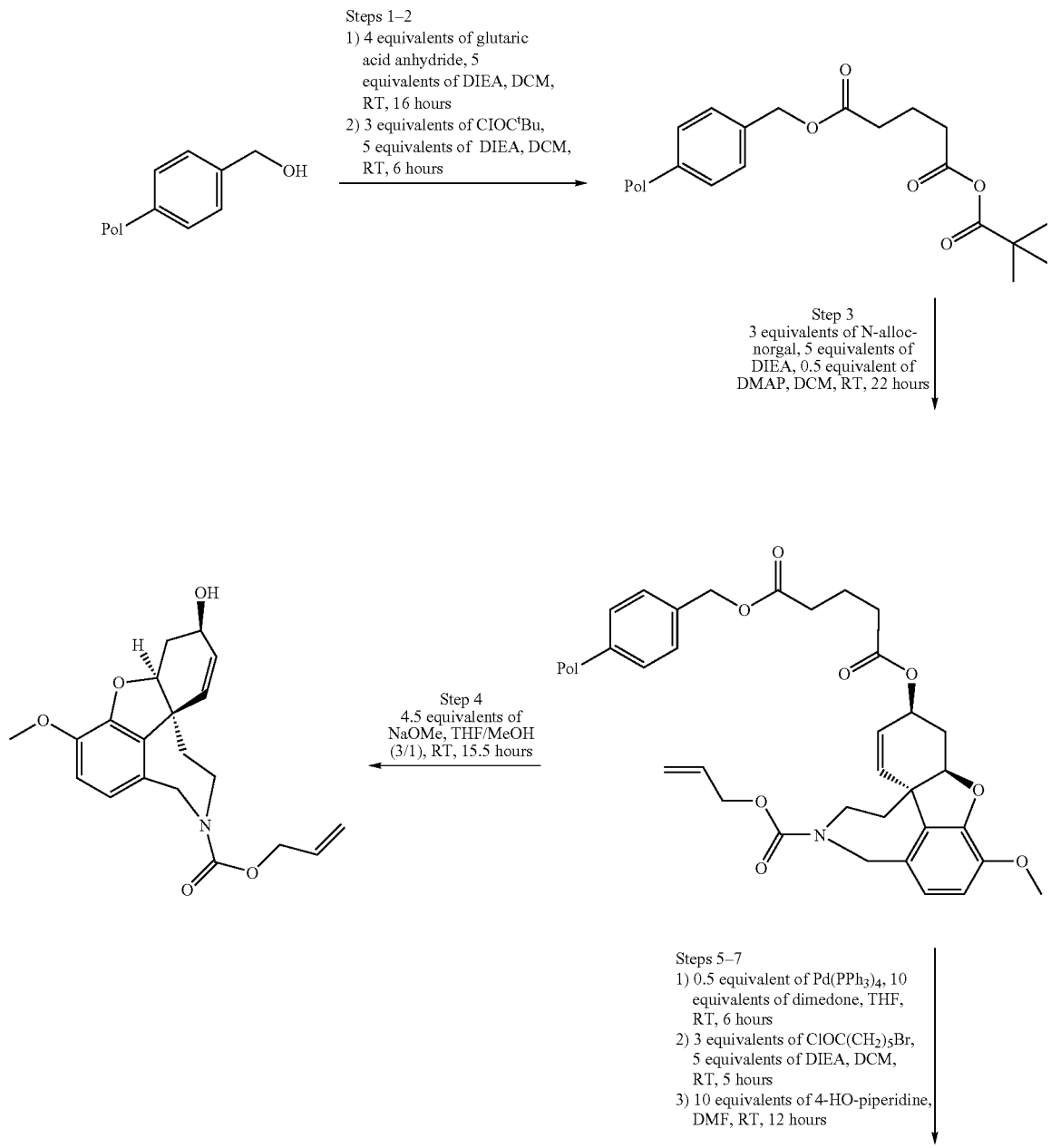

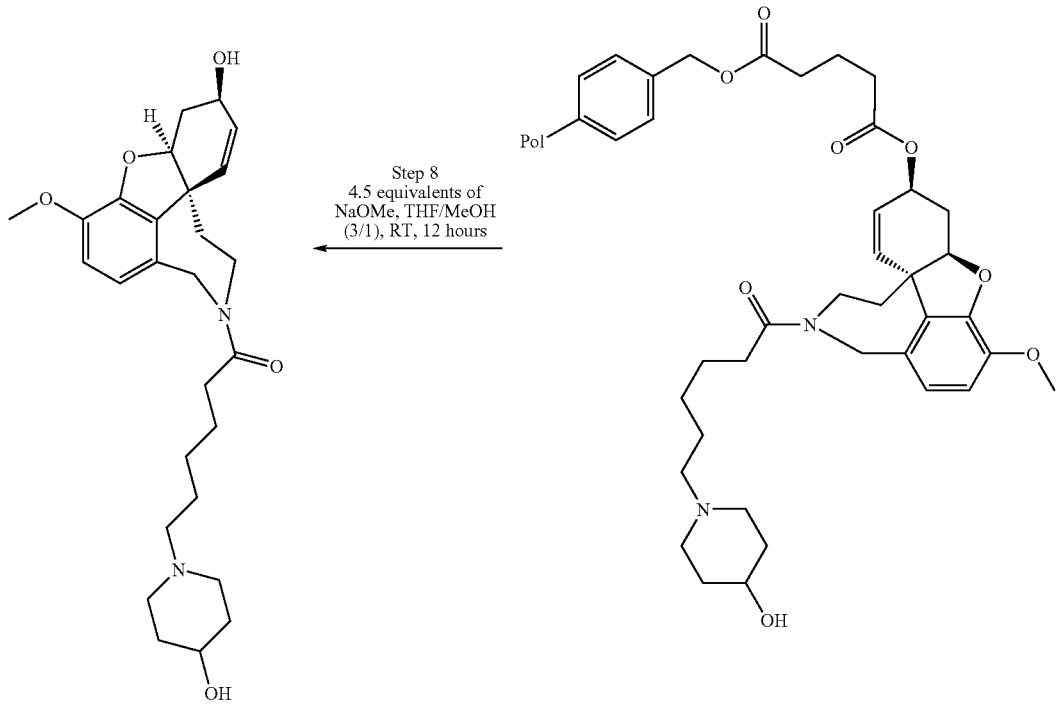

Example 187

Steps 1–4

Immobilization of (4aS,6R,8aS)-6-Hydroxy-3-methoxy-5,6,9,10-tetrahydro-4aH-[1]benzofuro-[3a,3,2-ef][2]benzoazepine-11(12H)-yl)carboxylic Acid Allyl Ester on a Hydroxymethyl-Polystyrene Resin (Merrifield Resin)

In a 5-ml-polyethylene frit that is sealed on both sides, 0.200 g (0.208 mmol) of hydroxymethylpolystyrene resin (1.04 mmol/g, Merrifield resin[3]) is suspended in 3 ml of dichloromethane, and it is shaken for 30 minutes at about 40× per minute. After filtering, 0.095 g (0.832 mmol) of glutaric acid anhydride, and 178 μl (0.134 g, 1.04 mmol) of ethyldiisopropylamine in 2 ml of dichloromethane are added, and the suspension is shaken for 16 hours at room temperature at about 40× per minute. The reaction solution is filtered off, and the resin is washed once with dichloromethane, once with methanol and five times with dichloromethane with 2.5 ml in each case. The resin is subsequently suspended in 77 μl (0.075 g, 0.624 mmol) of pivaloyl chloride, 178 μl (0.134 g, 1.04 mmol) of ethyldiisopropylamine in 1.75 ml of dichloromethane and shaken for six hours at room temperature. After filtering and washing with dichloromethane (1×2.5 ml), tetrahydrofuran (1×2.5 ml) and dichloromethane (5×2.5 ml), the resin is shaken in a solution that consists of 0.230 g (0.624 mmol) of N-allyloxycarbonylnorgalanthamine, 0.013 g (0.104 mmol) of 4-dimethylaminopyridine and 178 yl (0.134 g, 1.04 mmol) of ethyldiisopropylamine in 2 ml of dichloromethane at room temperature. After 22 hours, the reaction is terminated by filtering off the reaction solution, the resin is washed with dichloromethane (1×2.5 ml), with dimethylformamide (2×2.5 ml) and with dichloromethane (5×2.5 ml), dried, suctioned off and dried overnight in a vacuum at 30 to 50 mbar.

To determine the concentration, an aliquot of resin (0.262 g) in 2.5 ml of methanol/tetrahydrofuran (1/3) is steeped for 30 minutes, filtered and suspended in a solution of 0.168 g (0.933 mmol) of 30% sodium methanolate-methanol solution in 0.5 ml of methanol and 1.5 ml of tetrahydrofuran. The mixture is shaken for 15.5 hours at room temperature, filtered off, and the resin is extracted three times with methanol/dichloromethane (1/1, 2.5 ml) and three times with dichloromethane (2.5 ml). The combined filtrates are neutralized with 95 μl (0.067 g, 1.248 mmol) of trifluoroacetic acid and concentrated by evaporation in a rotary evaporator. The residue is purified by means of column chromatography (5 g of silica gel, mobile solvent petroleum ether/ethyl acetate=1/1). After concentration by evaporation and drying under high vacuum, 0.048 g of a colorless, vitreous solid is obtained.

Yield: 0.048 g (0.13 mmol, 65% relative to the degree of substitution of the hydroxymethyl resin), $^1$H-NMR spectrum identical to the starting material.

EXAMPLE 187

Steps 5–8

SPH-1539

1-(4aS,6R,8aS)-6-Hydroxy-3-methoxy-5,6,9,10-tetrahydro-4aH-[1]benzofuro[3a,3,2-ef]-[2]benzazepine-11(12H)-yl)-6-(4-hydroxy-1-piperidyl)hexan-1-one (CK-36-1)

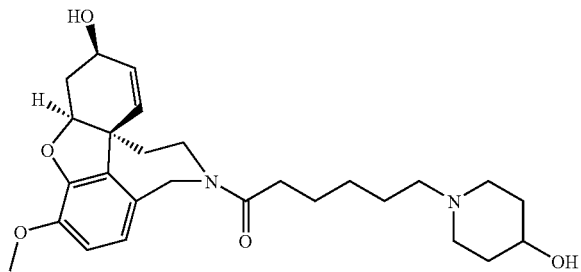

0.273 g of resin, produced from 0.200 g (0.208 mmol) of hydroxymethylpolystyrene resin[7] (1.04 mmol/g) according to the above-described method A, 0.120 g (0.104 mmol) of Pd(Ph$_3$ P)$_1$, and 0.292 g (2.08 mmol) of dimedone are shaken in 1.2 ml of tetrahydrofuran in a 5-ml-polyethylene frit that is sealed on both sides for six hours at room temperature at about 40× per minute. The resin is filtered and washed with dichloromethane (1×2.5 ml), with dichloromethane/methanol/ethyldiisopropylamine (5/4/1) (3×2.5 ml) and finally with dichloromethane (5×2.5 ml). The resin is subsequently mixed with a solution that consists of 96 µl (0.133 g, 0.624 mmol) of 6-bromocaproyl chloride and 178 µl (0.134 g, 1.04 mmol) of ethyldiisopropylamine in 2 ml of dichloromethane and shaken for five hours at room temperature. After washing with dimethylformamide (6×2.5 ml), the resin is shaken in a solution that consists of 0.210 g (2.08 mmol) of 4-hydroxypiperidine and 2 ml of dimethylformamide for twelve hours at room temperature. The resin is washed three times with 2.5 ml of dichloromethane in each case and three times with 2.5 ml of tetrahydrofuran in each case and subsequently suspended in a solution of 0.168 g (0.933 mmol) of 30% sodium methanolate-methanol solution in 0.5 ml of methanol and 1.5 ml of tetrahydrofuran. After twelve hours at room temperature, the resin is filtered and extracted with methanol/dichloromethane (1/1, 3×2.5 ml) and with dichloromethane (3×2.5 ml). The combined filtrates are neutralized with 95 µl (0.067 g, 1.248 mmol) of trifluoroacetic acid and concentrated by evaporation in a rotary evaporator at about 2 ml volumes. The crude product is purified by means of preparative thin-layer chromatography (PSC chromatoplate[8]$_1$ mobile solvent dichloromethane/methanol=9/1+3% triethylamine). Triethylammonium trifluoroacetate is then separated from the product fraction that is concentrated by evaporation by means of column filtration via aluminum oxide (pH 9–10, mobile solvent dichloromethane/methanol=20/1). After concentration by evaporation and drying under high vacuum, 0.012 g of the product is obtained in the form of a yellowish foam.

[7]Hydroxymethyl resin, D-1160, Bachem Feinchemikalien AG
[8]PSC chromatoplate by Merck, Art. No.: 113 895, 20×20 cm, 1 mm, silica gel 60 F$_{254}$ Yield: 0.012 g (0.025 mmol, 12% relative to the degree of substitution of the hydroxymethyl resin), white-brownish wax (M$_W$=470.6) TLC: R$_f$=0.32 (dichloromethane/methanol=8/2+2% triethylamine) HPLC: t$_{Ref}$=5.38 minutes, 98.6% (Waters Xterra column, 3.9 mm×100 mm, RP-18, 3.5 Jim, 250 nm, 1 ml/minute, acetonitrile/20 mmol of Na$_2$B$_4$O$_7$ in H$_2$O (20/80 v/v, pH 10) $^1$H-NMR: (200.13 MHz, CDCl$_3$, TMS) δ 6.81–6.88 and 6.61–6.71 (m, 2H), 5.90–6.10 (m, 2H), 4.52–4.75 (m, 2H), 4.51 (d, J=16.5 Hz, 1H), 4.15 (bs, 1H), 3.84 (s, 3H), 3.82 (s, 1H), 3.40–3.60 and 3.10–3.30 (m, 1H), 2.81–3.03 (m, 2H), 2.70 (bd, J=16.3 Hz, 1H), 2.33–2.62 (m, 4H), 1.15–2.30 (M, 21H) LC/MS: t$_{Ref}$=8.7 minutes, 98%, (Zorbax SB C 13-column, 2.1 mm×30 mm, RP-18, 3 µm, 0.5 ml/minute, Methanol/H$_2$O (40/60→100/0 (v/v) in 2 minutes); APCI-NI-MS 470

Diagram for Example 188

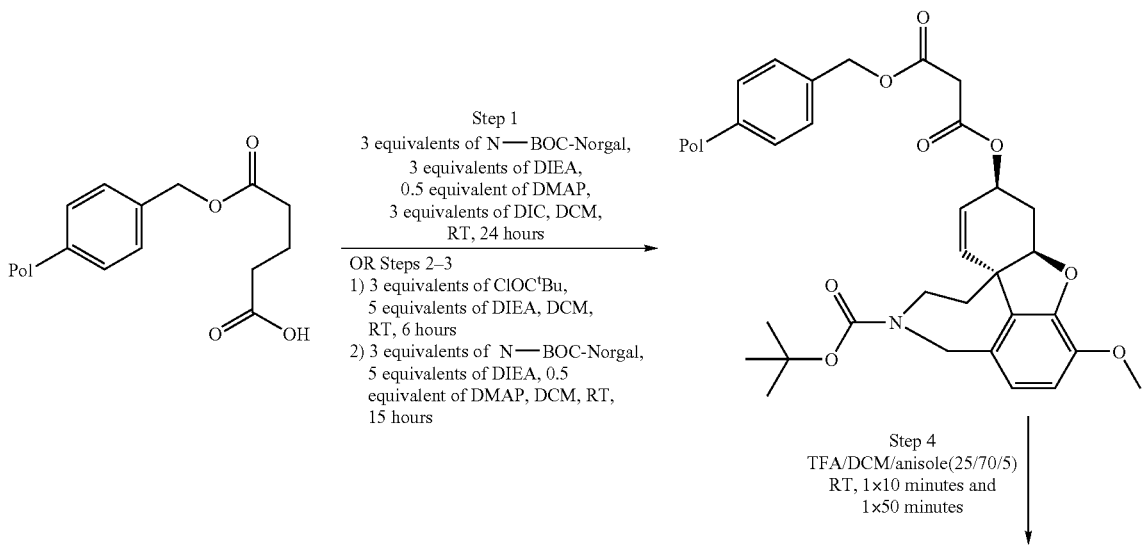

-continued

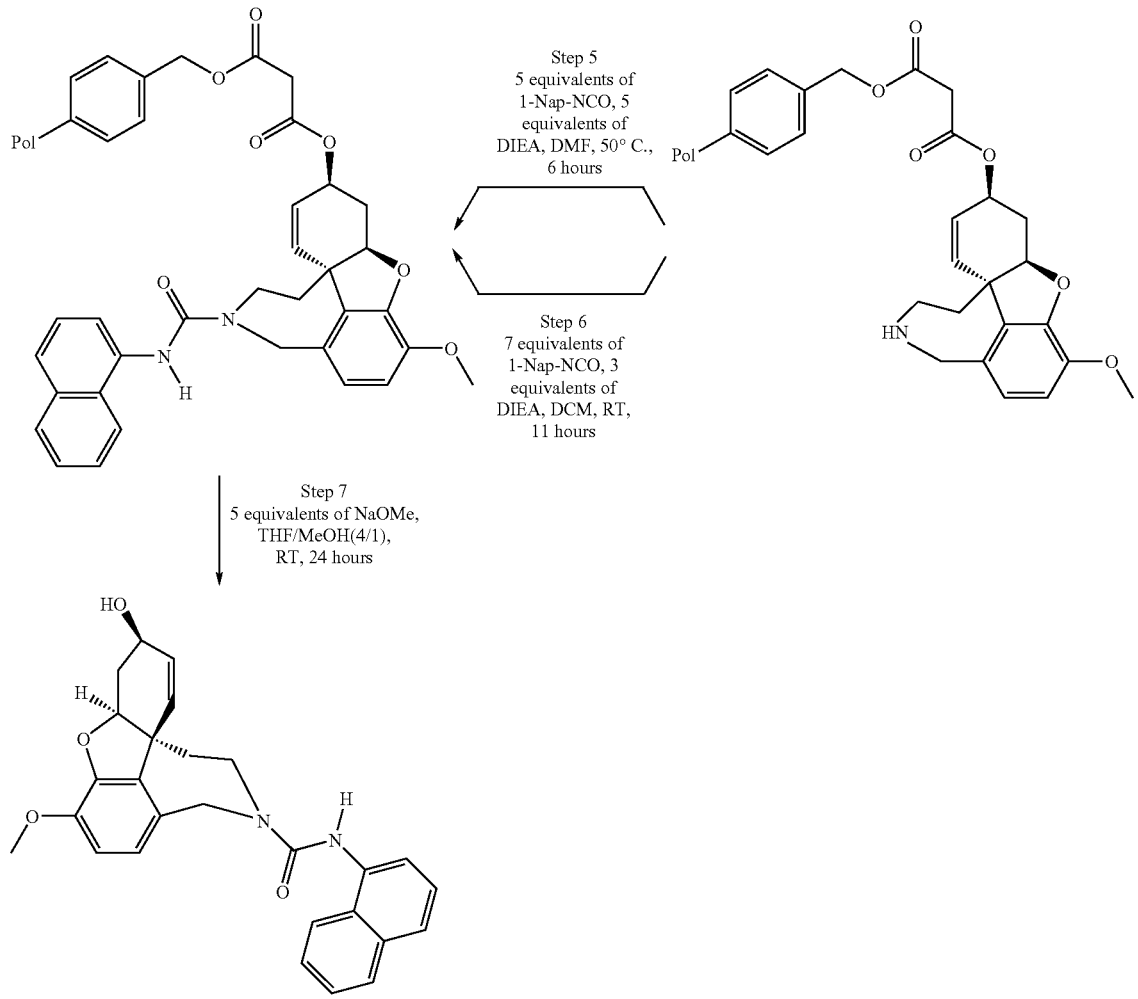

Step 5
5 equivalents of 1-Nap-NCO, 5 equivalents of DIEA, DMF, 50° C., 6 hours

Step 6
7 equivalents of 1-Nap-NCO, 3 equivalents of DIEA, DCM, RT, 11 hours

Step 7
5 equivalents of NaOMe, THF/MeOH(4/1), RT, 24 hours

EXAMPLE 188

Steps 1–7

SPH-1540

(4aS,6R,8aS)-6-Hydroxy-3-methoxy-N[11]-(1-naphthyl)-5,6,9,10-tetrahydro-4aH-[1]benzofuro-[3a,3,2-ef]-[2]benzazepine-11(12H)-carboxamide

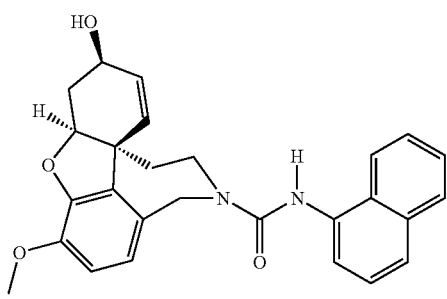

Variant A (CK-41-3), Steps 1, 4 and 6–7

0.228 g (0.212 mmol) of 4-carboxy-1-axobut-1-yloxymethyl-Merrifield resin is steeped in a 5-ml-polyethylene frit that is sealed on both sides for 30 minutes in 3 ml of dichloromethane, and after filtering, it is mixed in a solution of 0.234 g (0.628 mmol) of N-tert-butoxycarbonylnorgalanthamine, 0.013 g (0.105 mmol) of 4-dimethylaminopyridine and 108 µl (0.082 g, 0.628 mmol) of ethyldiisopropylamine in 1 ml of dichloromethane. Then, 97 µl (0.079 g, 0.628 mmol) of diisopropylcarbodiimide, dissolved in 1 ml of dichloromethane, is added, and the suspension is shaken for 24 hours at about 40× per minute at room temperature. After filtering, the resin is suspended for ten minutes in 2.5 ml of dichloromethane/methanol (1/1) while being shaken, filtered and washed with dichloromethane (5×2.5 ml). The resin is subsequently suspended once for ten minutes and once for 50 minutes in each case in 2.5 ml of a solution that consists of trifluoroacetic acid, dichloromethane, and anisole (25/70/5). After filtering, it is washed with dichloromethane (2×2.5 ml), with dichloromethane/methanol/triethylamine (5/4/1, 3×2.5 ml) and finally with dichloromethane (5×2.5 ml). The resin is shaken for eleven hours in a solution that consists of 0.208 µl (0.245 g, 1.45 mmol) of 1-naphthylisocyanate, 113 µl (0.085 g, 100.657 mmol) of ethyldiisopropylamine and 2 ml of dichloromethane at room temperature. After three cycles of washing in each case with dichloromethane (2.5 ml) and tetrahydrofuran (2.5 ml), the polymer is suspended in a solution of 1.88 g (1.045 mmol) of 30% sodium methanolate-methanol solution in 0.4 ml of methanol and 1.6 ml of tetrahydrofuran. After the resin was shaken for 24 hours at room temperature, the resin is filtered and extracted with methanol/dichloromethane (1/1, 3×2.5 ml) and with dichloromethane (3×2.5 ml). The combined filtrates are neutralized with concentrated hydrochloric acid. The suspension is filtered on a silica gel column (10 g, dichloromethane/methanol=9/1), and the filtrate is concentrated by evaporation in a rotary evaporator. The crude product is purified by means of preparative thin-layer chromatography (silica gel, mobile solvent dichloromethane/methanol=4//3). After concentration by evaporation and drying under high vacuum, 0.091 g of a yellowish foam is obtained. To remove triethylammonium salts, the residue is taken up in dichloromethane and extracted twice with 1N hydrochloric acid and once with saturated common salt solution, dried on $MgSO_4$, filtered and concentrated by evaporation.

Yield: 0.042 g (0.095 mmol, 45% relative to the degree of substitution of the 4-carboxy-1-oxobut-1-yloxymethyl-Merrifield resin), brown-yellowish wax ($M_W$=442.5) TLC: $R_f$=0.21 (dichloromethane/methanol=48/2) HPLC: $t_{Ref}$=5.15 minutes, 100% (Merck purospher column 4.0 mm×125 mm, RP-18e, 5 µm, 250 nm, 1 ml/minute, acetonitrile/20 mmol of $Cl_3CCO_2H$ in $H_2O$ (40/60 v/v) $^1$H-NMR: (200.13 MHz, $CDCl_3$, TMS) δ 7.71 (d, J=6.9 Hz, 1H), 7.20–7.66 (m, 6H), 6.85 (d, J=8.4 Hz, 1H), 6.63 (d, J=8.2 Hz, 1H), 5.96 (bs, 2H), 4.91 (d, J=16.7 Hz, 1H), 4.25–4.62 (m, 3H), 4.09 (bs, 1H), 3.78 (s, 3H), 3.25–3.50 (m, 2H), 2.55–2.67 (m, 1H), 1.87–2.04 (m, 2H), 1.60–1.75 (m, 1H) $^{13}$C-NMR: (50.32 MHz, $CDCl_3$, TMS) δ 155.7, 146.9, 144.6, 134.4, 133.8, 132.5, 129.0, 128.7, 128.1, 128.0, 126.3, 125.6, 125.5, 124.8, 122.1, 120.7, 111.0, 88.2, 62.9, 55.9, 51.8, 48.3, 46.1, 36.4, 29.7

Variant B, Steps 2–5 and 7

0.250 g (0.233 mmol) of 4-carboxy-1-oxobut-1-yloxymethyl-Merrifield resin is introduced into a frit reactor of synthesis robot (Syro II MultiSynTech). Then, the resin is steeped in a reactor for 30 minutes in dichloromethane, suctioned off, washed three times with dichloromethane and mixed successively with 0.150 g (1.163 mmol) of ethyldiisopropylamine in 1 ml of dichloromethane and 0.084 g (0.698 mmol) of pivaloyl chloride in 1.5 ml of dichloromethane. After six hours of stirring at 23° C., the solution is suctioned off, and the polymer is washed in each case with 3 ml of dichloromethane (6×2 minutes). After the addition of 0.260 g (0.698 mmol) of N-tert-butoxycarbonylnorgalanthamine, 0.014 g (0.116 mmol) of 4-dimethylaminopyridine and 0.150 g (1.163 mmol) of ethyldiisopropylamine in 2.5 ml of dichloromethane, the suspension is stirred at 23° C. for 15 hours. After suctioning off, the resin is stirred in 2.5 ml of dichloromethane/methanol (1/1) for ten minutes, suctioned off, washed three times with dichloromethane/methanol (1/1) (3 ml, 2 minutes) and five times with dichloromethane (3 ml, 2 minutes). The polymer is subsequently suspended once for ten minutes and once for 50 minutes in each case in 2.5 ml of a solution that consists of trifluoroacetic acid, dichloromethane and anisole (25/70/5). After suctioning off, it is washed with dichloromethane (3×3 ml), with dichloromethane/methanol/triethylamine (5/4/1, 3×3 ml) and finally with dichloromethane (5×) in each case for two minutes. Then, the residue is mixed with 0.197 g (1.163 mmol) of 1-naphthylisocyanate, 0.150 g (1.163 mmol) of ethyldiisopropylamine and 2.5 ml of dimethylformamide and stirred for six hours at 50° C. The reaction is terminated by the solution being suctioned off, the resin being washed with 3 ml of dichloromethane at 23° C. six times for two minutes in each case, and the resin being suctioned off in the dry state at 40° C. for ten minutes. For cleavage, the resin is transferred into a 5-ml-polyethylene frit that is sealed on both sides and steeped in 2.5 ml of tetrahydrofuran for 30 minutes. After filtering, the polymer is suspended in a solution that consists of 0.209 g (1.163 mmol) of 30% sodium methanolate-methanol solution in 0.75 ml of methanol and 1.25 ml of tetrahydrofuran, and it is shaken for 15 hours at about 40× per minute at room temperature. The resin is filtered and extracted three times with methanol/dichloromethane (1/1, 2.5 ml) and three times with dichloromethane (2.5 ml). The combined extracts are neutralized with concentrated hydrochloric acid, filtered and concentrated by evaporation. Then, the crude product is purified by means of column chromatography on 10 g of silica gel (mobile solvent dichloromethane/methanol=99/1). After concentration by evaporation and drying in a vacuum, 0.029 g of a rose-colored wax with a purity of 75% (HPLC), identical to the product that is produced according to method A, is obtained.

Yield: 0.029 g (0.021 g, 0.047 mmol, 20% relative to the degree of substitution of the 4-carboxy-1-oxobut-1-yloxymethyl-Merrifield resin) HPLC: $t_{Ref}$=14.32 minutes, 75% (Merck purospher column 4.0 mm×125 mm, RP-18e, 5 µm, 250 nm, 1 ml/minute, acetonitrile/20 mmol of $Cl_3CCO_2H$ in $H_2O$ (30/70 v/v)

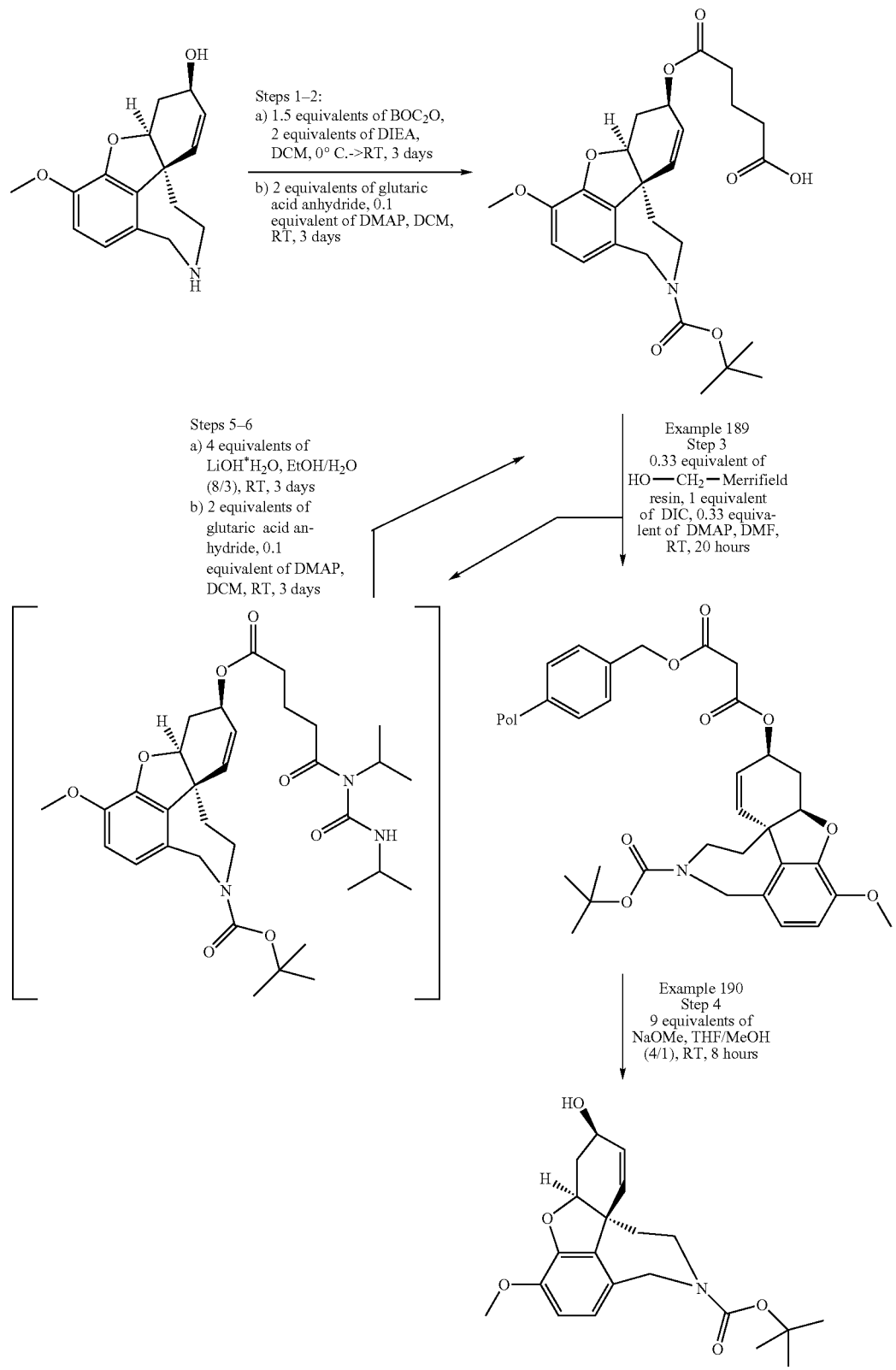
Diagram for Examples 189–190

EXAMPLE 189

PH-1541

Steps 1–2

(4aS,6R,8aS)-3-Methoxy-11-tert-butoxycarbonyl-5,6,9,10-tetrahydro-4aH-[l1benzofuro[3a,3,2-ef][2]benzazepine-6(12H)-yloxy)-5-oxopentanoic acid (CK-48-1)

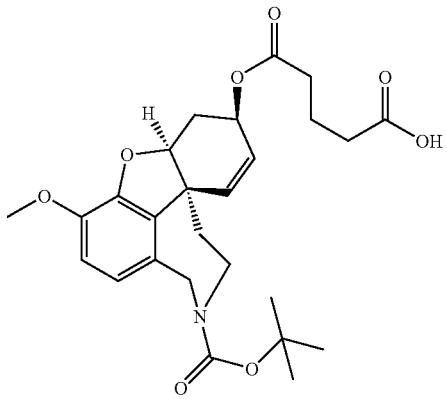

5.000 g (18.295 mmol) of norgalanthamine (98% (HPLC)) and 3.804 ml (2.777 g, 27.442 mmol) of triethylamine in 75 mil of absolute dichloromethane are introduced at 0° C. While being stirred, a solution that consists of 4.393 g (20.124 mmol) of di-tert-butyldicarbonate is added in drops within 15 minutes at 0° C. After 40 minutes at 0° C., the reaction solution is stirred for three days at room temperature. After two days, 1.598 g (7.318 mmol) of di-tert-butyldicarbonate and 1.27 ml (0.926 g, 9.147 mmol) of triethylamine are added again. The reaction solution is taken up with 150 ml of dichloromethane, and the organic phase is washed three times with 100 ml of 1N hydrochloric acid in each case, three times with 100 ml of a saturated NaHCO₃ solution in each case and twice with 100 ml of saturated common salt solution, dried on Na₂SO₄, filtered and concentrated by evaporation under reduced pressure. The residue (7.065 g, 18.9 mmol, 103% raw yield) is dissolved in 75 ml of absolute dichloromethane, and 4.175 g (36.590 mmol) of glutaric acid anhydride, 0.224 g (1.829 mmol) of 4-dimethylaminopyridine and 3.804 ml (2.777 g, 27.442 mmol) of triethylamine are added to this solution. The solution is stirred for three days at room temperature. The reaction is terminated by adding 200 ml of diethyl ether and 500 ml of aqueous ammonia solution (pH 10–11). The cloudy aqueous phase is separated (poor phase separation, addition of some methanol, optionally before the dichloromethane solution is distilled off) and extracted three times with 200 ml of diethyl ether and then set at pH 2 with concentrated hydrochloric acid. In this case, the cloudy solution becomes clear. The aqueous phase is extracted four times with 400 ml of dichloromethane in each case. The combined organic extracts are washed three times with 300 ml of distilled water in each case and twice with 300 ml of saturated common salt solution, dried on Na₂SO₄, filtered, mixed with 50 ml of diisopropyl ether and concentrated under reduced pressure until the product crystallizes out. The solution is allowed to stand for a little while and then the crystallized colorless solid is filtered off, which is dried in a vacuum.

Yield: 7.546 g (15.48 mmol, 84.6% over two stages), colorless crystalline solid, ($M_W$=487.6) TLC: $R_f$=0.45 (petroleum ether/ethyl acetate=1/2) $R_f$=0.28 (aluminum oxide, petroleum ether/ethyl acetate=1/2) Melting point: 159–163° C. (dichloromethane/diisopropyl ether=1/1) IR: KBr ν (cm⁻¹) 3245 (bs), 2978 (s), 1715 (s), 1683 (s) ¹H-NMR: (200.13 MHz, CDCl₃, TMS) δ 6.53–6.79 (m, 2H), 6.13–6.29 (m, 1H), 5.82–5.97 (m, 1H), 5.33 (1, J=4.9 Hz, 1.0 H), 4.87 (d, J=15.6 Hz, 0.3H), 4.67 (d, J=15.7 Hz, 0.7H), 4.53 (s, 1H), 3.99–4.38 (m, 2H), 3.83 (s, 3H), 3.19–3.50 (m, H), 2.68 (d, J=16.0 Hz, 1.0H), 2.40 (t, J=7.3 Hz, 2.0H), 2.39 (t, J=7.0 Hz, 2.0H), 2.01–2.17 (m, 1H), 1.93 (qui, J=7.1 Hz, 2.0H), 1.66–1.84 (m, 1H), 1.41 (s, 3H), 1.37 (s, 6H) ¹³C-NMR: (50.32 MHz, CDCl₃, TMS) δ 178.2 (s), 172.6 (s), 154.9 (s), 147.1 (s), 144.0 (s), 131.3 (s), 130.5 (d), 129.6 (s), 123.0 (d), 120.2 (d), 111.0 (d), 85.8 (d), 79.9 (s), 63.2 (d), 55.8 (q), 51.8 and 51.2 (t), 48.0 (s), 45.2 (t), 37.9 and 37.0 (t), 33.4 (t), 32.9 (t), 28.2 (q), 27.5 (t), 19.7 (t)

EXAMPLE 190

SPH-1542

(See Diagram, Step 3)

Immobilization of (4aS,6R,8aS)-6-Hydroxy-3-methoxy-5,6,9,10-tetrahydro-4aH-E[1]benzofuro-[3a,3,2-ef][2]benzoazepine-11(12H)-yl)carboxylic acid-tert-butyl ester on a Hydroxymethyl-Polystyrene Resin (Merrifield Resin) (CK-43-5)

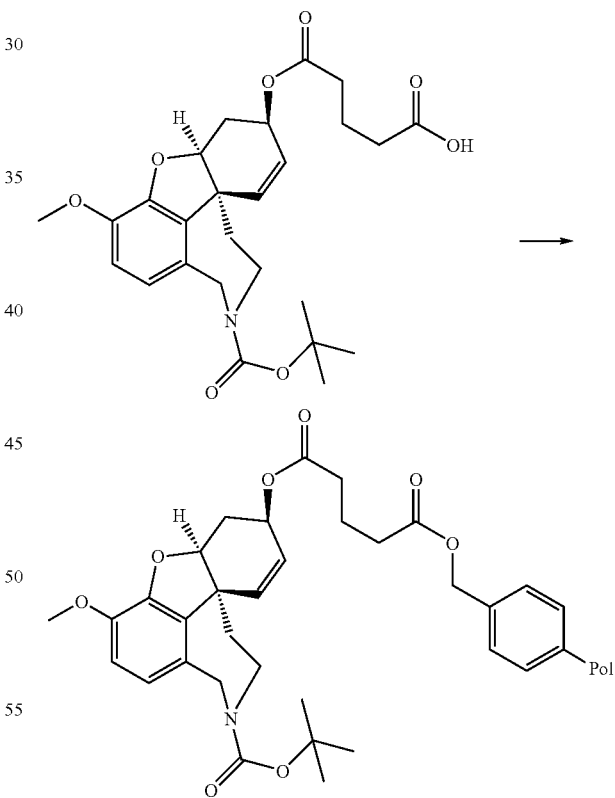

5.00 g (5.2 mmol) of hydroxymethylpolystyrene resin (1.04 mmol/g, Merrifield resin⁹) is stirred in a three-neck glass reactor with a frit that is recessed in the bottom and a KPG stirrer in 50 ml of dimethylformamide (300 s⁻¹) After filtering, a solution that consists of N-tert-butoxycarbonyl-norgalanthamine-6-yloxy-5-oxopentanoic acid (7.607 g, 15.6 mmol), 4-dimethylaminopyridine (0.635 g, 5.2 mmol) in 30 ml of absolute dimethylformamide is added to the resin. At room temperature, a solution that consists of diisopropylcarbodiimide (2.42 ml, 1.969 g, 15.6 mmol) and 10 ml of dimethylformamide is hen added in portions. After 20 hours of stirring at room temperature, it is filtered, the resin is washed six times with dichloromethane (40 ml, 5 minutes) and once with diethyl ether (40 ml, 5 minutes) and dried in a vacuum.

[9]Hydroxymethyl resin, D-1160, Bachem Feinchemikalien AG

To determine the concentration, an aliquot of resin (0.2465 g) in a polyethylene frit that can be sealed on both sides in 2.5 ml of methanol/tetrahydrofuran (1/4) is steeped for 30 minutes, filtered, and suspended in a solution of 0.280 g (1.56 mmol) of 30% sodium methanolate-methanol solution in 0.5 ml of methanol and 2 ml of tetrahydrofuran. The mixture is shaken for nine hours at room temperature, filtered off, and the resin is extracted three times with methanol/dichloromethane (1/1, 2.5 ml) and three times with dichloromethane (2.5 ml). The combined filtrates are neutralized with 119 μl (0.178 g, 1.56 mmol) of trifluoroacetic acid and concentrated by evaporation in a rotary evaporator. The residue is taken up in 30 ml of ethyl acetate, washed twice with saturated NaHCO$_3$ solution (10 ml), with distilled water (10 ml) and with saturated common salt solution (10 ml), dried on Na$_2$SO$_4$, filtered and concentrated by evaporation again. The residue (0.080 g) is purified by means of column chromatography (10 g of silica gel, mobile solvent petroleum ether/ethyl acetate=1/1→1/2). After concentration by evaporation and drying under high vacuum, 0.0661 g of a colorless, vitreous solid is obtained.

Yield: 0.0661 g (0.177 mmol. A concentration of 0.718 mmol/g, 103% of the theoretical maximum concentration[10] thus is calculated), $^1$H-NMR spectrum that is identical to the starting material; HPLC: $t_{Ref}$=9.18 minutes, 93.8% (270 nm), 97.7% (285 nm), (Phenomenex Luna column, 3.0 mm×50 mm, RP-18, 3.0 μm, 0.5 ml/minute, methanol/20 mmol of trichloroacetic acid in H$_2$O (50/50 v/v)

[10]=1.04 mmol/g/(1 g +1 g * 1.04 mol/g * (487.6 mol/g −18 mol/g) /1000)

Step 4

Recycling Excess (4aS,6R,8aS)-3-Methoxy-11-tert-butoxycarbonyl-5,6,9,10-tetrahydro-4aH-[1]benzofuro[3a,3,2-ef][2]benzazepine-6(12H)-yloxy)-5-oxopentanoic Acid from the Resin Immobilization (CK-51-1)

The filtrate of the reaction solution and the first five dichloromethane filtrates are combined and washed three times with 100 ml of 1N hydrochloric acid, three times with 100 ml of distilled water and twice with saturated sodium chloride solution, dried with Na$_2$SO$_4$, filtered and concentrated by evaporation. The amorphous residue (6.806 g) is suspended in 50 ml of ethanol and 30 ml of distilled water, then 1.97 g (46.9 mmol) of lithium hydroxide monohydrate is added. The suspension is stirred for three days at room temperature. The reaction solution is extracted three times with 100 ml of dichloromethane in each case, and the combined extracts are extracted in each case three times with 100 ml of 1N hydrochloric acid and twice with 100 ml of saturated common salt solution. After drying on Na$_2$SO$_4$, filtering and concentration by evaporation under reduced pressure, the organic phase produces 5.06 g of a colorless foam, which contains about 60% N-tert-butoxycarbonylnorgalanthamine according to HPLC. The residue is reacted analogously to the above-described procedure with 0.164 g (1.339 mmol) of dimethylaminopyridine, 3.056 g (26.78 mmol) of glutaric acid anhydride and 2.8 ml (2.033 g, 20.09 mmol) of triethylamine in 50 ml of dichloromethane. The reaction is terminated by the addition of 200 ml of diethyl ether and 250 ml of aqueous ammonia solution (pH 10–11). The cloudy, aqueous phase is separated and extracted twice with 200 ml of diethyl ether and then set to pH 2 with concentrated hydrochloric acid. The aqueous phase is extracted three times with 200 ml of dichloromethane in each case. The combined organic extracts are washed three times with 200 ml of distilled water in each case and twice with 200 ml of saturated common salt solution, dried on Na$_2$SO$_4$, filtered, concentrated by evaporation to about 50 ml, mixed with 50 ml of diisopropyl ether and further concentrated under reduced pressure until the product crystallizes out. The solution is allowed to stand for a little while, and then the crystallized colorless solid is filtered off, which is dried in a vacuum.

Yield: 4.909 g (10.07 mmol, 96.6% relative to the excess that is used in the immobilization) HPLC: $t_{Ref}$=13.9 minutes, 99.8%. (Merck Purospher column, 4.0 mm×125 mm, RP-18e, 5 μm, 285 nm, 1 ml/minute, acetonitrile/20 mmol of Cl$_3$CCO$_2$H in H$_2$O (40/60 v/v, pH 10)

EXAMPLE 192

Step 1

N-(Adamantan-1-yl)-6-bromohexanoic acid amide

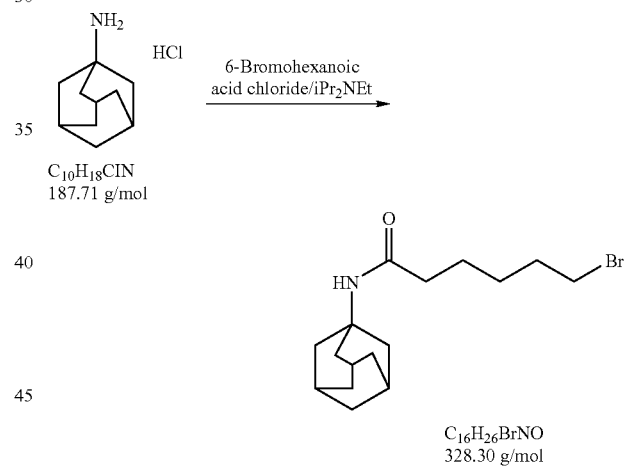

Adamantane-1-amine, hydrochloride (2.50 g, 13.3 mmol) and N-ethyldiisopropylamine (3.79 g, 29.3 mmol) are stirred in absolute CH$_2$Cl$_2$ (50 ml) for 15 minutes at room temperature. Then, 6-bromohexanoic acid chloride (3.13 g, 14.7 mmol) in CH$_2$Cl$_2$ (10 ml) is added in drops at 0° C. and stirred for one hour at room temperature.

It is extracted with 2N HCl (2×50 ml), water (1×50 ml), saturated sodium bicarbonate solution (2×50 ml) and saturated common salt solution (1×100 ml), dried (sodium sulfate/activated carbon), filtered, and the residue that is obtained after the solvent is removed in a rotary evaporator is recrystallized from petroleum ether (25 ml)/diisopropyl ether (25 ml), by which the product is obtained in the form of colorless crystals with a melting point of 73–75° C. (3.51 g, 80%). TLC: CHCl$_3$:MeOH=9:1, R$_f$=0.9 $^1$H NMR (CDCl$_3$) δ 5.43 (b, 1H), 3.33 (t, J=6.0 Hz, 2H), 2.21–1.15 (m, 23H); $^{13}$C NMR (CDCl$_3$) δ 171.6 (s), 51.4 (s), 41.3 (t), 37.0 (t), 36.1 (t), 33.5 (t), 32.2 (t), 29.1 (d), 27.4 (t), 24.6 (t)

Step 2

SPH-1517

N-(Adamantan-1-yl)-6-l(4aS,6R,8aS)-4a,5,9,10,11,12-hexahydro-6-hydroxy-3-methoxy-6H-benzofuro[3a,3,2-ef][2]benzazepine-11-yl]-bromohexanoic acid amide, fumarate

EXAMPLE 193

Step 1

2-(5-bromopentyl)-1H-benz[de]isoquinoline-1,3(2H)-dione

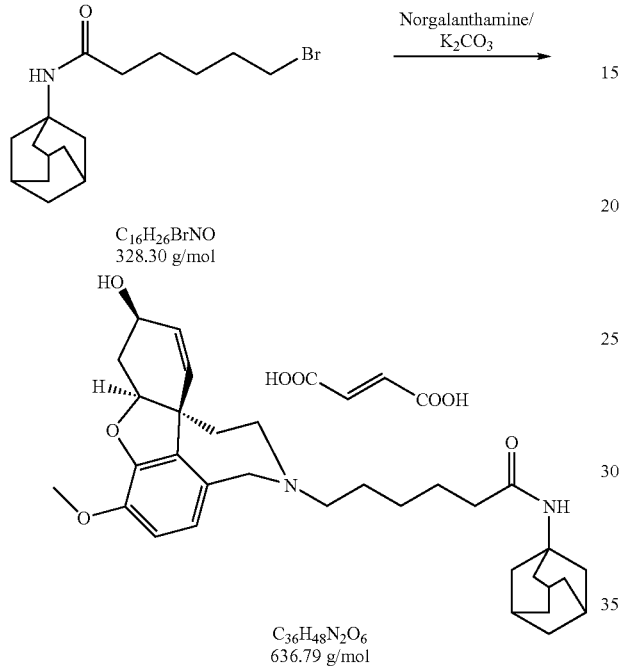

Norgalanthamine (1.00 g, 3.66 mmol), N-(adamantan-1-yl)-6-bromohexanoic acid amide (1.20 g, 3.66 mmol) and potassium carbonate (anhydrous, freshly ground, 1.52 g, 11.3 mmol) are stirred in absolute acetonitrile (10 ml) for 8 hours at boiling temperature.

The residue that is obtained after the solvent is removed in a rotary evaporator is purified by column chromatography (200 g of silica gel, chloroform:methanol:ammonia=96:3:1), by which the product is obtained as a light yellow foam (1.73 g, 91%).

The conversion into fumarate was carried out analogously to the production of MT-311 and MT-407 and yielded the product in the form of light yellow crystals with a melting point of 109–114° C.

TLC: $CHCl_3$:MeOH:$NH_3$=89:10:1, $R_f$=0.6 Microelement analysis (JOS 1763): $C_{37}N_{42}N_2O_9$*$H_2O$ Cld.: C, 66.03; H, 7.70; N, 4.28 Fnd.: C, 66.27; H, 7.61; N, 4.22 $^1H$ NMR (DMSO-$d_6$) δ=7.20 (b, 1H), 6.90–6.63 (m, 2H), 6.51 (s, 2H), 6.11 (d, J=10.2 Hz, 1H), 5.82 (dd, J=11.4 Hz, J=4.7 Hz, 1H), 4.56 (s, 1H), 4.41 (d, J=14.8 Hz, 1H), 4.22–3.86 (m, 2H), 3.76 (s, 3H), 3.62–3.12 (m, 3H), 2.81–2.47 (m, 3H), 2.44–1.04 (m, 26H); $^{13}C$ NMR (DMSO-$d_6$) δ 171.6 (s), 167.4 (s), 146.3 (s), 144.1 (5), 134.7 (d), 132.9 (s), 129.0 (d), 126.3 (d), 124.6 (s), 122.0 (d), 111.7 (d), 86.7 (d), 59.8 (d), 55.5 (q), 50.7 (t), 50.5 (t), 47.3 (s), 41.1 (t), 36.1 (t), 36.0 (s), 32.0 (t), 31.0 (t), 28.9 (d), 26.0 (t), 25.2 (t), 24.9 (t)

1H-Benz[de]isoquinoline-1,3(2H)-dione (10.0 g, 50.7 mmol) in DMF (50 ml) is slowly added in drops at room temperature to a suspension of sodium hydride (2.33 g, 55.8 mmol of a 55% dispersion, white oil is removed by washing with absolute petroleum ether) in absolute DMF (50 ml). It is stirred for 30 minutes, heated to 60° C., 1.5 dibromopentane (46.64 g, 202.8 mmol) is added once, and it is stirred for 12 hours at this temperature.

It is filtered, and the residue that is obtained after the solvent is removed in a rotary evaporator is dispersed between water (200 ml) and ether (200 ml). The aqueous phase is extracted with ether (3×50 ml), the combined organic phases are washed with water (3×200 ml), 2N NaOH (2×100 ml) and saturated common salt solution (1×200 ml), dried (sodium sulfate), and solvent is removed in a rotary evaporator. Excess dibromopentane is separated by distillation (100° C./20 mbar), the residue is recrystallized from methanol (200 ml), by which the product is obtained in the form of colorless crystals (15.45 g, 88%) of melting point 114–116° C.

TLC: Petroleum ether:ethyl acetate=4:1, $R_f$=0.35 $^1H$ NMR (CDCl$_3$) δ 8.48 (dd, J=7.0 Hz, J=1.3 Hz, 2H), 8.13 (dd, J=7.0 Hz, J=1.3 Hz, 2H), 8.48 (t, J=7.0 Hz, 2H), 4.21 (t, J=7.6 Hz, 2H), 3.89 (t, J=6.6 Hz, 2H), 1.89 (quintet, J=6.6 Hz, 2H), 1.79–1.43 (m, 4H); $^{13}C$ NMR (CDCl$_3$) δ 163.8 (5) 133.7 (d), 131.3 (s), 130.9 (d), 127.8 (s), 126.7 (d), 122.4 (d), 39.8 (t), 33.5 (t), 32.2 (t), 27.0 (t), 25.5 (t)

Step 2

SPH-1496

2-[5-[(4aS,6R,8aS)-4a,5,9,10,11,12-Hexahydro-6-hydroxy-3-methoxy-6H-benzofuro[3a,3,2-ef][2]benzazepine-11-yl]pentyl]-1H-benz[de]isoquinoline-1,3(2H)-dione, fumarate

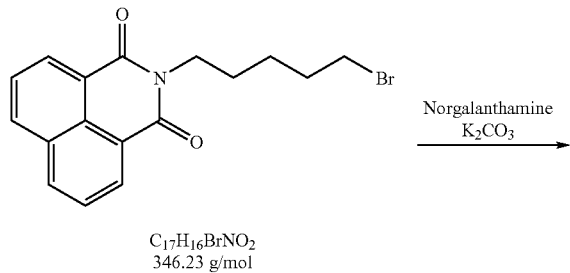

Norgalanthamine K$_2$CO$_3$

C$_{17}$H$_{16}$BrNO$_2$
346.23 g/mol

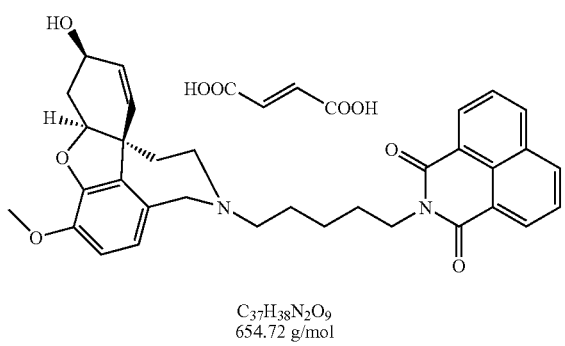

C$_{37}$H$_{38}$N$_2$O$_9$
654.72 g/mol

Norgalanthamine (1.00 g, 3.66 mmol), 2-(5-bromopentyl)-1H-benz[de]isoquinoline-1,3(2H)-dione (1.15 g, 3.33 mmol) and potassium carbonate (anhydrous, freshly ground, 1.15 g, 10.0 mmol) are stirred in absolute acetonitrile (10 ml) for 12 hours at boiling temperature.

The residue that is obtained after the solvent is removed in a rotary evaporator is purified by column chromatography (100 g of silica gel, chloroform:methanol:ammonia=96:3:1), by which the product is obtained as a light yellow foam (1.58 g, 88%).

The conversion into fumarate was carried out analogously to the production of MT-311 and MT-407 and yielded the product in the form of light yellow crystals with a melting point of 129–134° C.

TLC: CHCl$_3$:MeOH:KH$_3$=89:10:1, R$_f$=0.5 Microelement analysis (JOS 1790): C$_{37}$H$_{38}$N$_2$O$_9$*1.5H$_2$O Cld.: C, 65.19; H, 6.06; N, 4.11 Fnd.: C, 65.02; H, 5.82; N, 3.98 $^1$H NMR (DMSO d$_6$) δ 8.34 (d, J=7.0 Hz, 4H), 7.76 (d, J=7.0 Hz, 2H), 6.81–6.49 (m, 4H), 6.07 (d, J=11.4 Hz, 1H), 5.81 (dd, J=11.4 Hz, J=4.7 Hz, 1H), 4.49 (s, 1H), 4.29 (d, J=14.0 Hz, 1H), 4.16–3.74 (m, 4H), 3.70 (s, 3H), 3.43–3.01 (m, 2H), 2.50 (b, 2H), 2.27 (d, J=14.8 Hz, 1H), 2.12–1.88 (m, 2H), 1.78–1.12 (m, 8H); $^{13}$ NMR (DMSO-d$_6$) δ 167.3 (s), 163.3 (s), 146.2 (s), 143.8 (s) 134.7 (d), 134.2 (d), 132.8 (s), 131.2 (s), 130.6 (d), 128.7 (d), 127.2 (d), 127.1 (s), 126.5 (d), 126.1 (s), 121.9 (s), 121.6 (d), 111.5 (d), 86.7 (d) 59.8 (d), 56.0 (t), 55.5 (q), 50.7 (t), 50.2 (t), 47.4 (s), 39.5 (t), 32.2 (t)$_1$ 30.9 (t)$_1$ 27.3 (t), 25.3 (t), 24.1 (t)

EXAMPLE 194

Step 1

6-Bromo-1-(3,4-dimethoxyphenyl)-1-hexanone

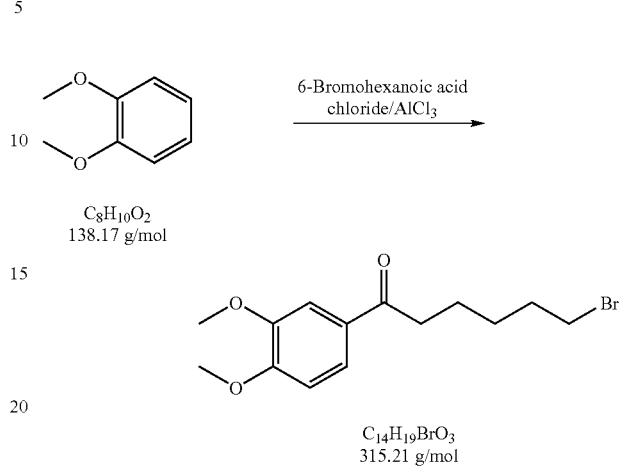

6-Bromohexanoic acid chloride/AlCl$_3$

C$_8$H$_{10}$O$_2$
138.17 g/mol

C$_{14}$H$_{19}$BrO$_3$
315.21 g/mol

6-Bromohexanoic acid chloride (4.9 g, 22.7 mmol) is added in drops within 10 minutes at a temperature of 0 to 5° C. to a mixture that consists of 1,2-dimethoxybenzene (3.10 g, 22.7 mmol) and aluminum chloride (3.0 g, 22.7 mmol) in absolute carbon disulfide (50 ml). It is heated within 30 minutes to 40° C., and it is stirred for one hour at this temperature. It is hydrolyzed with 2N hydrochloric acid (20 ml), dispersed between benzene (30 ml) and 2N hydrochloric acid (30 ml), and the aqueous phase is extracted with benzene (2×15 ml), the combined organic phases are washed with 2N hydrochloric acid (3×50 ml), water (1×50 ml), saturated sodium bicarbonate solution (3×50 ml), saturated common salt solution (1×50 ml), dried (sodium sulfate/activated carbon), filtered, and the residue that is obtained after concentration by evaporation in a rotary evaporator recrystallizes from pentane (35 ml), by which the product is obtained in the form of colorless crystals with a melting point of 44–45° C. (3.2 g, 44.7%).

TLC: Petroleum ether:ethyl acetate=4:1; R$_f$=0.85 $^1$H NMR (CDCl$_3$) δ 7.54 (dd, J=1.9 Hz, J=8.9 Hz, 1H), 7.51 (d, J=1.9 Hz, 1H), 6.89 (d, J=8.9 Hz, 1H), 3.97 (s, 6H), 3.40 (t, J=6.4 Hz, 2H), 2.92 (t, J=7.0 Hz, 2H), 1.90 (quintet, J=6.4 Hz, 2H), 1.73 (quintet, J=7.0 Hz, 2H), 1.63–1.48 (m, 2H); $^{13}$C NMR (CDCl$_3$) δ 198.6 (s), 153.2 (s), 149.0 (s), 130.2 (s), 122.6 (d), 110.1 (d), 110.0 (d), 56.0 (q), 55.9 (q), 37.7 (t), 33.6 (t), 32.6 (t), 27.9 (t), 23.6 (t)

Step 2

SPH-1497

1-(3,4-Dimethoxyphenyl)-6-[(4aS,6R,8aS)-4a,5,9,10,11,12-hexahydro-6-hydroxy-3-methoxy-6H-benzofuro[3a,3,2-ef][2]benzazepine-11-yl]hexan-1-one, fumarate

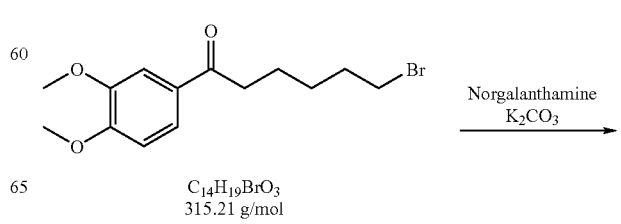

Norgalanthamine K$_2$CO$_3$

C$_{14}$H$_{19}$BrO$_3$
315.21 g/mol

-continued

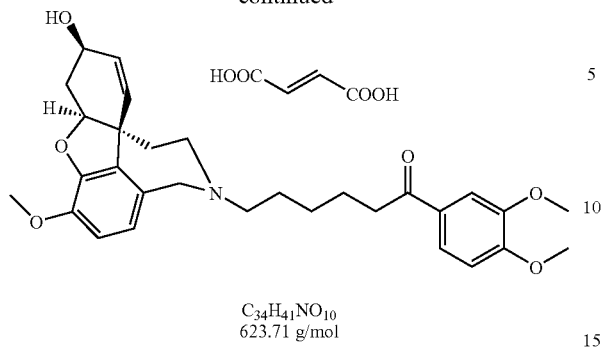

C₃₄H₄₁NO₁₀
623.71 g/mol

Norgalanthamine (1.00 g, 3.66 mmol), 6-bromo-1-(3,4-dimethoxyphenyl)-1-hexanone (1.15 g, 3.66 mmol) and potassium carbonate (anhydrous, freshly ground, 1.15 g, 10.0 mmol) is stirred in absolute acetonitrile (15 ml) for 12 hours at boiling temperature.

The residue that is obtained after the solvent is removed in a rotary evaporator is purified by column chromatography (100 g of silica gel, chloroform:methanol:ammonia=96:3:1), by which the product is obtained as a light yellow foam (1.70 g, 91%).

The conversion into fumarate was carried out according to standard instructions.

The conversion into fumarate was carried out analogously to the production of MT-311 and MT-407 and yielded the product in the form of light yellow crystals with a melting point of 88–94° C.

TLC: CHCl₃:MeOH:NH₃=89:10:1, $R_f$=0.5 Microelement analysis (JOS 1782): C₃₅H₄₃NO₁₀*0.5 H₂O Cld.: C, 65.00; H, 6.86; N, 2.17 Fnd.: C, 64.81; H, 6.64; N, 2.09 ¹H NMR (DMSO-d₆) δ 7.61 (d, J=8.9 Hz, 1H), 7.43 (s, 1H), 7.01 (d, J=8.9 Hz, 1H), 6.81–6.66 (m, 2H), 6.58 (s, 2H), 6.11 (d, J=11 Hz, 1H), 5.82 (dd, J=11 Hz, J=5 Hz, 1H), 4.61–4.33 (m, 2H), 4.20–3.92 (m, 2H), 3.84 (s, 3H), 3.80 (s, 3H), 3.72 (s, 3H), 3.62–3.12 (m, 2H), 3.10–2.81 (m, 2H), 2.78–2.43 (m, 3H), 2.39–1.86 (m, 5H), 1.78–1.40 (m, 5H), 1.38–1.14 (m, 2H); ¹³C NMR (DMSO-d₆) δ 198.5 (s), 167.2 (s), 153.0 (s), 148.6 (s), 146.3 (s), 144.2 (s), 134.6 (d), 132.9 (s), 129.7 (s), 129.0 (s), 126.2 (d), 124.0 (d), 122.7 (d), 122.1 (d), 111.7 (d), 110.9 (d), 110.2 (d), 86.6 (d), 65.0 (d), 59.8 (q), 55.8 (q), 55.5 (q), 50.8 (t), 50.4 (t), 47.3 (s), 37.2 (t), 31.9 (t), 31.0 (t), 26.1 (t), 24.7 (t), 23.8 (t), 15.2 (t)

The invention claimed is:

1. Compounds of formula I

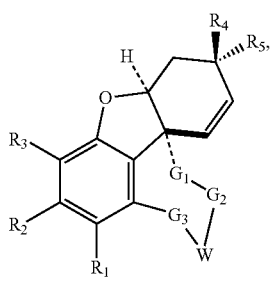

(I)

in which the substituents have the meanings that are explained below:

$R_1$ and $R_2$ are the same or different and mean:
a) hydrogen, F, Cl, Br, I, CN, NC, OH, SH, NO₂, SO₃H, PO₃H, NH₂, CF₃, OSO₂(CH₂)ₙCF₃, in which n is equal to 0, 1 or 2, —OSO₂-aryl, —OSO₂-vinyl or —OSO₂-ethinyl;

b) a $C_1$–$C_6$, optionally branched, optionally substituted alkyl, alkoxy, arylalkyl, arylalkoxy, cycloalkyl or cycloalkoxy group;

c) an amino group, which optionally is substituted by one or two identical or different $C_1$–$C_6$, optionally branched, optionally substituted alkyl, alkylcarbonyl, alkoxycarbonyl, arylalkyl, arylalkylcarbonyl, or arylalkoxycarbonyl groups or by a group that is selected from an optionally substituted pyrrolidine, piperidine, morpholine, thiomorpholine, piperazine, or homopiperazine radical;

d) a —COOH, —COOalkyl, —COOarylalkyl, —COamino group, which optionally is substituted as indicated under c), a COHalkyl group, or a COHarylalkyl group;

e) a —(CH₂)ₙX (in which X is Br, Cl, F or I), —(CH₂)ₙOH, —(CH₂)ₙCHO, —(CH₂)ₙCOOH, —(CH₂)ₙCN, —(CH₂)ₙNC, —(CH₂)ₙCOalkyl, or —(CH₂)ₙCOaryl group, in which n is 1–4;

f) a —(CH₂)ₙvinyl, —(CH₂)ₙethinyl, or —(CH₂)ₙcycloalkyl group in which n is 0, 1 or 2, wherein cycloalkyl is an aliphatic ring with 3 to 7 C atoms;

g) a $C_3$–$C_6$-substituted alkenyl group (optionally substituted with H, F, Br, Cl, CN, CO₂alkyl, COalkyl, COaryl); or h) a $C_3$–$C_6$-substituted alkinyl group (optionally substituted with H, F, Br, Cl, CN, CO₂alkyl, COalkyl, COaryl);

$R_3$ has the same meaning as $R_1$, $R_4$ and $R_5$ are either
a) both hydrogen, or
b) one of $R_4$ and $R_5$ is hydrogen, an alkyl, alkenyl, alkinyl, arylalkyl, arylalkenyl, or arylalkinyl group, and the other of $R_4$ and $R_5$ is i) OR₆, in which R₆ means hydrogen, a $C_1$–$C_{10}$, optionally branched or substituted alkyl group or cycloalkyl group, a $C_3$–$C_{10}$ substituted silyl group, or a $C_2$–$C_{10}$ alpha-alkoxyalkyl group;

$G_1$ is —CH₂—;
$G_2$ is —CH₂—;
$G_3$ is —CH₂—; and
W is:

N-Phenyl, optionally substituted with Fl, Br, Cl, $C_1$–$C_4$ alkyl, CO₂-alkyl, CN, CONH₂, or alkoxy; N-thien-2 or 3-yl; N-fur-2 or 3-yl; or an N-1,3,5-triazinyl, wherein the triazine radical can then be substituted with Cl, OR₆ or NR₇R₇, in which R₆ has the meaning indicated above and the two substituents R₇ are the same or different and are hydrogen, a $C_1$–$C_4$, optionally branched, alkyl group or cycloalkyl group, or substituents R₇ together are —(CH₂)ₙ—, in which n is 3 to 5.

2. The compound according to claim 1, wherein W is N-1,3,5-triazinyl, wherein the triazine radical can then be substituted with Cl, OR₆ or NR₇R₇, in which R₆ has the meaning indicated above and the two substituents R₇ are the same or different and are hydrogen, a $C_1$–$C_4$, optionally branched, alkyl group or cycloalkyl group, or substituents R₇ together are —(CH₂)ₙ—, in which n is 3 to 5.

3. The compound according to claim 1, wherein $R_3$ is OH or OCH₃.

4. The compound according to claim 1, wherein $R_3$ is OCH₃.

5. The compound according to claim 1, wherein $R_4$ is OH and $R_5$ is H.

6. The compound according to claim 1, wherein $R_3$ is OCH₃, $R_4$ is OH, $R_5$ is H, and W is N-1,3,5-triazinyl, wherein the triazine radical can then be substituted with Cl, OR₆ or NR₇R₇, in which R₆ has the meaning indicated above and the two substituents R₇ are the same or different and are hydrogen, a $C_1$–$C_4$, optionally branched, alkyl group or cycloalkyl group, or substituents $R_7$ together are —(CH$_2$)$_n$—, in which n is 3 to 5.

7. The compound according to claim 1, in which substituent $R_6$ is a triethylsilyl, trimethylsilyl, t-butyldimethylsilyl or dimethylphenylsilyl.

8. The compound according to claim 1, in which substituent $R_6$ is tetrahydropyranyl, tetrahydrofuranyl, methoxymethyl, ethoxymethyl, 2-methoxypropyl, ethoxyethyl, phenoxymethyl or 1-phenoxyethyl.

9. The compound according to claim 1, in which $R_5$ has a meaning other than hydrogen, and $R_4$ is OH.

10. A pharmaceutical composition comprising a pharmaceutically acceptable excipient and a therapeutically effective amount of a compound of formula I or a pharmaceutically acceptable salt thereof, the compound of formula I having the following formula:

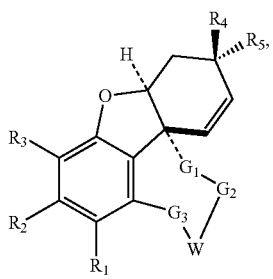
(I)

in which the substituents have the meanings that are explained below:

$R_1$ and $R_2$ are the same or different and mean:
a) hydrogen, F, Cl, Br, I, CN, NC, OH, SH, NO$_2$, SO$_3$H, PO$_3$H, NH$_2$, CF$_3$, OSO$_2$(CH$_2$)$_n$CF$_3$, in which n is equal to 0, 1 or 2, —OSO$_2$-aryl, —OSO$_2$-vinyl or —OSO$_2$-ethinyl;
b) a $C_1$–$C_6$, optionally branched, optionally substituted alkyl, alkoxy, arylalkyl, arylalkoxy, cycloalkyl or cycloalkoxy group;
c) an amino group, which optionally is substituted by one or two identical or different $C_1$–$C_6$, optionally branched, optionally substituted alkyl, alkylcarbonyl, alkoxycarbonyl, arylalkyl, arylalkylcarbonyl, or arylalkoxycarbonyl groups or by a group that is selected from an optionally substituted pyrrolidine, piperidine, morpholine, thiomorpholine, piperazine, or homopiperazine radical;
d) a —COOH, —COOalkyl, —COOarylalkyl, —CO-amino group, which optionally is substituted as indicated under c), a COHalkyl group, or a COHarylalkyl group;
e) a —(CH$_2$)$_n$X (in which X is Br, Cl, F or I), —(CH$_2$)$_n$OH, —(CH$_2$)$_n$CHO, —(CH$_2$)$_n$COOH, —(CH$_2$)$_n$CN, —(CH$_2$)$_n$NC, —(CH$_2$)$_n$COalkyl, or —(CH$_2$)$_n$COaryl group, in which n is 1–4;
f) a —(CH$_2$)$_n$vinyl, —(CH$_2$)$_n$ethinyl, or —(CH$_2$)$_n$cycloalkyl group in which n is 0, 1 or 2, wherein cycloalkyl is an aliphatic ring with 3 to 7 C atoms;
g) a $C_3$–$C_6$-substituted alkenyl group (optionally substituted with H, F, Br, Cl, CN, CO$_2$alkyl, COalkyl, COaryl); or
h) a $C_3$–$C_6$-substituted alkinyl group (optionally substituted with H, F, Br, Cl, CN, CO$_2$alkyl, COalkyl COaryl);

$R_3$ has the same meaning as $R_1$,
$R_4$ and $R_5$ are either a) both hydrogen, or
b) one of $R_4$ and $R_5$ is hydrogen, an alkyl, alkenyl, alkinyl, arylalkyl, arylalkenyl, or arylalkinyl group, and the other of and $R_4$ and $R_5$ is
i) OR$_6$, in which $R_6$ means hydrogen, a $C_1$–$C_{10}$, optionally branched or substituted alkyl group or cycloalkyl group, a $C_3$–$C_{10}$ substituted silyl group, or a $C_2$–$C_{10}$alpha-alkoxyalkyl group;

$G_1$ is —CH$_2$—;
$G_2$ is —CH$_2$—;
$G_3$ is —CH$_2$—; and
W is:
N-Phenyl, optionally substituted with Fl, Br, Cl, $C_1$–$C_4$ alkyl, CO$_2$-alkyl, CN, CONH$_2$, or alkoxy; N-thien-2 or 3-yl; N-fur-2 or 3-yl; or an N-1,3,5-triazinyl, wherein the triazine radical can then be substituted with Cl, OR$_6$ or NR$_7$R$_7$, in which $R_6$ has the meaning indicated above and the two substituents $R_7$ are the same or different and are hydrogen, a $C_1$–$C_4$, optionally branched, alkyl group or cycloalkyl group, or substituents $R_7$ together are —(CH$_2$)$_n$—, in which n is 3 to 5.

11. A method of preparing a pharmaceutical composition comprising:
providing a therapeutically effective amount of a compound of formula I or a pharmaceutically acceptable salt thereof; and
combining a pharmaceutically acceptable excipient with the therapeutically effective amount of the compound of formula I or a pharmaceutically acceptable salt thereof, the compound of formula I having the following formula:

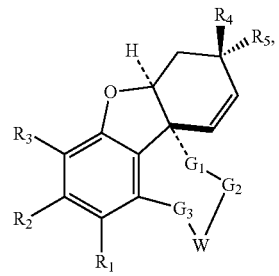
(I)

in which the substituents have the meanings that are explained below:

$R_1$ and $R_2$ are the same or different and mean:
a) hydrogen, F, Cl, Br, I, CN, NC, OH, SH, NO$_2$, SO$_3$H, PO$_3$H, NH$_2$, CF$_3$, OSO$_2$(CH$_2$)$_n$CF$_3$, in which n is equal to 0, 1 or 2, —OSO$_2$-aryl, —OSO$_2$-vinyl or —OSO$_2$-ethinyl;
b) a $C_1$–$C_6$, optionally branched, optionally substituted alkyl, alkoxy, arylalkyl, arylalkoxy, cycloalkyl or cycloalkoxy group;
c) an amino group, which optionally is substituted by one or two identical or different $C_1$–$C_6$, optionally branched, optionally substituted alkyl, alkylcarbonyl, alkoxycarbonyl, arylalkyl, arylalkylcarbonyl, or arylalkoxycarbonyl groups or by a group that is selected from an optionally substituted pyrrolidine, piperidine, morpholine, thiomorpholine, piperazine, or homopiperazine radical;
d) a —COOH, —COOalkyl, —COOarylalkyl, —CO-amino group, which optionally is substituted as indicated under c), a COHalkyl group, or a COHarylalkyl group;
e) a —(CH$_2$)$_n$X (in which X is Br, Cl, F or I), —(CH$_2$)$_n$OH, —(CH$_2$)$_n$CHO, —(CH$_2$)$_n$COOH, —(CH$_2$)$_n$CN, —(CH$_2$)$_n$NC, —(CH$_2$)$_n$COalkyl, or —(CH$_2$)$_n$COaryl group, in which n is 1–4;

f) a —(CH$_2$)$_n$vinyl, —(CH$_2$)$_n$ethinyl, or —(CH$_2$)$_n$cycloalkyl group in which n is 0, 1 or 2, wherein cycloalkyl is an aliphatic ring with 3 to 7 C atoms;
g) a C$_3$–C$_6$-substituted alkenyl group (optionally substituted with H, F, Br, Cl, CN, CO$_2$alkyl, COalkyl, COaryl); or
h) a C$_3$–C$_6$-substituted alkinyl group (optionally substituted with H, F, Br, Cl, CN, CO$_2$alkyl, COalkyl, COaryl);

R$_3$ has the same meaning as R$_1$,
R$_4$ and R$_5$ are either
a) both hydrogen, or
b) one of R$_4$ and R$_5$ is hydrogen, an alkyl, alkenyl, alkinyl, arylalkyl, arylalkenyl, or arylalkinyl group, and the other of R$_4$ and R$_5$ is
i) OR$_6$, in which R$_6$ means hydrogen, a C$_1$–C$_{10}$, optionally branched or substituted alkyl group or cycloalkyl group, a C$_3$–C$_{10}$ substituted silyl group, or a C$_2$–C$_{10}$ alpha-alkoxyalkyl group;

G$_1$ is —CH$_2$—;
G$_2$ is —CH$_2$—; —G$_3$ is CH$_2$—; and
W is:
N-Phenyl, optionally substituted with Fl, Br, Cl, C$_1$–C$_4$ alkyl, CO$_2$-alkyl, CN, CONH$_2$, or alkoxy; N-thien-2 or 3-yl; N-fur-2 or 3-yl; or an N-1,3,5-triazinyl, wherein the triazine radical can then be substituted with Cl, OR$_6$ or NR$_7$R$_7$, in which R$_6$ has the meaning indicated above and the two substituents R$_7$ are the same or different and are hydrogen, a C$_1$–C$_4$, optionally branched, alkyl group or cycloalkyl group, or substituents R$_7$ together are —(CH$_2$)$_n$—, in which n is 3 to 5.

12. A compound having the following structure:

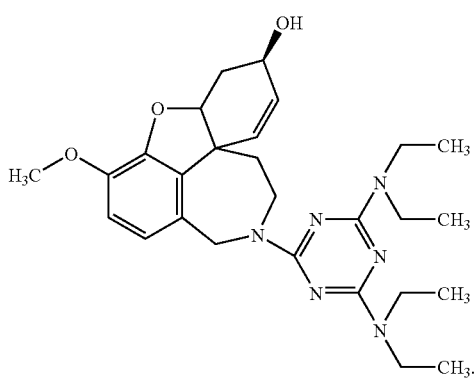

13. A pharmaceutical composition comprising a pharmaceutically acceptable excipient and a therapeutically effective amount of a compound having the following structure:

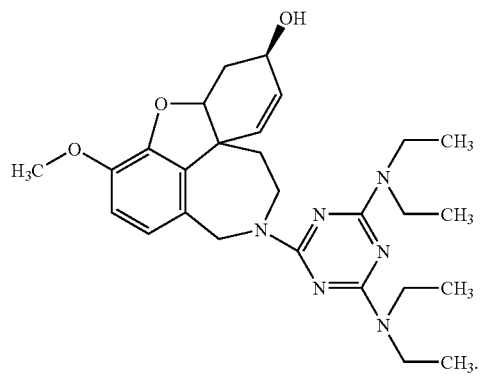

or a pharmaceutically acceptable salt thereof.

14. A method of preparing a pharmaceutical composition comprising:
providing a therapeutically effective amount of a compound having the following structure:

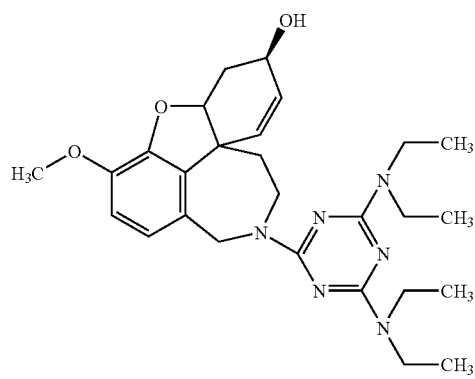

or a pharmaceutically acceptable salt thereof; and
combining a pharmaceutically acceptable excipient with the therapeutically effective amount of the compound or a pharmaceutically acceptable salt thereof.

* * * * *